US012571058B2

(12) United States Patent
Park

(10) Patent No.: US 12,571,058 B2
(45) **Date of Patent: *Mar. 10, 2026**

(54) BIOSENSORS FOR DETECTING AND/OR NEUTRALIZING BIOAVAILABLE URANIUM AND RELATED U-SENSITIVE GENETIC MOLECULAR COMPONENTS, GENE CASSETTES, VECTORS, GENETIC CIRCUITS, COMPOSITIONS, METHODS AND SYSTEMS

(71) Applicant: LAWRENCE LIVERMORE NATIONAL SECURITY, LLC, Livermore, CA (US)

(72) Inventor: Dan Mcfarland Park, Dublin, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 71 days.

This patent is subject to a terminal disclaimer.

(21) Appl. No.: 18/406,057

(22) Filed: Jan. 5, 2024

(65) Prior Publication Data

US 2024/0376556 A1 Nov. 14, 2024

Related U.S. Application Data

(63) Continuation of application No. 16/781,950, filed on Feb. 4, 2020, now Pat. No. 11,898,211.

(60) Provisional application No. 62/801,077, filed on Feb. 4, 2019.

(51) Int. Cl.
| | |
|---|---|
| *C12Q 1/6897* | (2018.01) |
| *C12N 1/20* | (2006.01) |
| *C12N 9/12* | (2006.01) |
| *C12N 15/52* | (2006.01) |
| *C12N 15/63* | (2006.01) |
| *C12N 15/74* | (2006.01) |
| *G21F 9/18* | (2006.01) |
| *G21F 9/30* | (2006.01) |

(52) U.S. Cl.
CPC ............. *C12Q 1/6897* (2013.01); *C12N 1/20* (2013.01); *C12N 9/12* (2013.01); *C12N 15/52* (2013.01); *C12N 15/635* (2013.01); *C12N 15/74* (2013.01); *C12Y 207/13003* (2013.01); *G21F 9/18* (2013.01); *G21F 9/30* (2013.01); *C12N 2830/002* (2013.01); *C12N 2830/55* (2013.01); *C12N 2840/002* (2013.01); *C12N 2840/105* (2013.01); *G01N 2520/00* (2013.01)

(58) Field of Classification Search
None
See application file for complete search history.

(56) References Cited

U.S. PATENT DOCUMENTS

| | | | |
|---|---|---|---|
| 8,697,388 B2 | 4/2014 | Hillson et al. | |
| 9,580,713 B2 | 2/2017 | Breaker et al. | |
| 11,608,536 B2 * | 3/2023 | Park .................. | G01N 33/84 |
| 11,898,211 B2 * | 2/2024 | Park .................. | C12N 15/52 |
| 12,297,513 B2 | 5/2025 | Park et al. | |
| 2005/0114923 A1 | 5/2005 | Blaylock et al. | |
| 2011/0117590 A1 | 5/2011 | Nathan et al. | |
| 2020/0248277 A1 | 8/2020 | Park | |
| 2020/0370135 A1 | 11/2020 | Park et al. | |
| 2023/0332251 A1 | 10/2023 | Park et al. | |

FOREIGN PATENT DOCUMENTS

| | | |
|---|---|---|
| WO | 2019/099934 A2 | 5/2019 |
| WO | 2020/163388 A1 | 8/2020 |

OTHER PUBLICATIONS

Ferla, M.P., et al., New rRNA gene-based phylogenies of the Alphaproteobacteria provide perspective on major groups, mitochondrial ancestry and phylogenetic instability. PLoS One, Dec. 2013. 8(12): p. e83383. 14 pages.
Fiebig, A., et al., Interaction specificity, toxicity and regulation of a paralogous set of ParE/RelE-family toxin-antitoxin systems. Mol Microbiol, 2010. 77(1): p. 236-51.
Finn, R.D., et al., The Pfam protein families database: towards a more sustainable future. Nucleic Acids Res, Published online Dec. 15, 2015. 44(D1): p. D279-D285.
Fisher et al., Transcriptional analysis of the major surface array gene of Caulobacter crescentus. J Bacterial, Oct. 1988. 170(10): p. 4706-4713.
Focazio, M.J., et al., The Chemical Quality of Self-Supplied Domestic Well Water in the United States. Groundwater Monitoring & Remediation, 2006. 26(3): p. 92-104.
Folliard, T., et al., Ribo-attenuators: novel elements for reliable and modular riboswitch engineering. Sci Rep, Published online Jul. 4, 2017. 7(1): p. 4599. 11 pages.
Francis, A.J., et al., XPS and XANES studies of uranium reduction by *Clostridium* sp. Environmental science & technology, 1994. 28(4): p. 636-639.
Gadd, G.M., Biosorption: critical review of scientific rationale, environmental importance and significance for pollution treatment. Journal of Chemical Technology and Biotechnology, Published online in Wiley Interscience Jul. 29, 2008. 84(1): p. 13-28.
Garst, A.D., A.L. Edwards, and R.T. Batey, Riboswitches: structures and mechanisms. Cold Spring Harb Perspect Biol, 2011. 3(6), a003533. 13 pages.
Goodrich, R., Lorega, G., LLNL Livermore Site and Site 300 Environmental Restoration Project Standard Operating Procedures (SOPs). Lawrence Livermore National Laboratory Livermore, Calif, Feb. 2016. (UCRL-MA-109115 Rev. 15). 694 pages.
Hallberg, Z.F., et al., Engineering and In Vivo Applications of Riboswitches. Annu Rev Biochem, Mar. 30, 2017. 86: p. 515-539.

(Continued)

*Primary Examiner* — Christian L Fronda

(74) *Attorney, Agent, or Firm* — Steinfl + Bruno LLP

(57) ABSTRACT

$UO_2F_2$ biosensors, and related U-sensing and/or F-sensing genetic molecular components, genetic circuits, compositions, methods and systems are described, which in several embodiments can be used to detect and/or neutralize uranium and in particular bioavailable $UO_2F_2$.

43 Claims, 81 Drawing Sheets

Specification includes a Sequence Listing.

(56) References Cited

OTHER PUBLICATIONS

Hierlemann, A. and H. Baltes, CMOS-based chemical microsensors. Analyst, 2003. 128(1): p. 15-28.

Hierlemann, A., et al., Microfabrication techniques for chemical/biosensors. Proceedings of the IEEE, 2003. 91(6): p. 839-863. 25 Pages.

Hillson, N.J., et al., Caulobacter crescentus as a whole-cell uranium biosensor. Applied and Environmental Microbiology, Dec. 2007. 73(23): p. 7615-7621.

Hoover, J., et al., Elevated Arsenic and Uranium Concentrations in Unregulated Water Sources on the Navajo Nation, USA. Exposure and Health, 2017: 9, 113-124. 12 pages.

Hsi, C.-K.D. and D. Langmuir, Adsorption of uranyl onto ferric oxyhydroxides: application of the surface complexation site-binding model. Geochimica et Cosmochimica Acta, 1985. 49(9): p. 1931-1941.

Hutcheson, S.W., et al., Enhancer-Binding Proteins HrpR and HrpS Interact to Regulate hrp-Encoded Type III Protein Secretion in Pseudomonas syringae Strains. Journal of Bacteriology, Oct. 2001. 183(19): p. 5589-5598.

Hwang, I.Y., et al., Engineered probiotic *Escherichia coli* can eliminate and prevent Pseudomonas aeruginosa gut infection in animal models. Nature Communications, Apr. 11, 2017. 8: p. 15028. 11 pages.

International Preliminary Report on Patentability for International application No. PCT/US2018/061667 filed on Nov. 16, 2018. Mailing date: May 19, 2020. 9 pages.

International Preliminary Report on Patentability for International Application No. PCT/US2020/016654 filed on Feb. 4, 2020, in the name of Lawrence Livermore National Security, LLC. Mailing date: Aug. 19, 2021. 9 Pages.

International Search Report and Written Opinion for International Appln No. PCT/US2020/016654 filed on Feb. 4, 2020 in the name of Lawrence Livermore National Security, LLC. Mailing date: Jun. 12, 2020. 14 pages.

International Search Report for International Application No. PCT/US2018/061667 filed on Nov. 16, 2018 on behalf of Lawrence Livermore National Security, LLC. Mail date: Jun. 26, 2019. 5 pages.

Istok, J., et al., In situ bioreduction of technetium and uranium in a nitrate-contaminated aquifer. Environmental Science & Technology, 2004. 38(2): p. 468-475.

Jin, Q., et al., Type III protein secretion in Pseudomonas syringae. Microbes and Infection, 2003. 5(4): p. 301-310.

Jonas, K., et al., Proteotoxic stress induces a cell-cycle arrest by stimulating Lon to degrade the replication initiator DnaA. Cell, Aug. 1, 2013. 154(3): p. 623-36.

Kabessa, Y., et al., Standoff detection of explosives and buried landmines using fluorescent bacterial sensor cells. Biosensors and Bioelectronics, 2016. 79: p. 784-788.

Karlin, S. and S.F. Altschul, Applications and statistics for multiple high-scoring segments in molecular sequences. Proceedings of the National Academy of Sciences, Jun. 1993. 90(12): p. 5873-5877.

Karlin, S. and S.F. Altschul, Methods for assessing the statistical significance of molecular sequence features by using general scoring schemes. Proceedings of the National Academy of Sciences, Mar. 1990. 87(6): p. 2264-2268.

Kazy, S.K., S.F. D'Souza, and P. Sar, Uranium and thorium sequestration by a *Pseudomonas* sp.: mechanism and chemical characterization. J Hazard Mater, 2009. 163(1): p. 65-72.

Kemp, R.S., Environmental Detection of Clandestine Nuclear Weapon Programs. Annual Review of Earth and Planetary Sciences, Jan. 11, 2016. 44(1): p. 17-35.

Kemp, R.S., Initial Analysis of the Detectability of UO2F2 Aerosols Produced by UF6 Released from Uranium Conversion Plants. Science & Global Security, 2008. 16(3): p. 115-125.

King, J.M., et al., Rapid, sensitive bioluminescent reporter technology for naphthalene exposure and biodegradation. Science, 1990. 249(4970): p. 778-81.

Kips, R.S. and M.J. Kristo, Investigation of chemical changes in uranium oxyfluoride particles using secondary ion mass spectrometry. Journal of Radioanalytical and Nuclear Chemistry, Published online Jul. 30, 2009. 282(3): p. 1031-1035.

Ko, W.-h. and F.K. Hora, Production of phospholipases by soil microorganisms. Soil Science, 1970. 110(5): p. 355-358.

Koch-Steindl, H. and G. Prohl, Considerations on the behaviour of long-lived radionuclides in the soil. Radiation and environmental biophysics, 2001. 40(2): p. 93-104.

Ku et al., "Notes on the use of propagation of error formulas". Journal of Research of the National Bureau of Standards, Oct.-Dec. 1966. 70C, No. 4, pp. 263-273.

Langmuir, D., Uranium solution-mineral equilibria at low temperatures with applications to sedimentary ore deposits. Geochimica et Cosmochimica Acta, 1978. 42(6, Part A): p. 547-569.

Law, G.T., et al., Uranium redox cycling in sediment and biomineral systems. Geomicrobiology Journal, 2011. 28(5-6): p. 497-506.

Lim, B.L., et al., Distribution and diversity of phytate-mineralizing bacteria. The ISME journal, 2007. 1(4): p. 321-330.

Lovley, D.R. and E. Phillips, Reduction of uranium by Desulfovibrio desulfuricans. Applied and Environmental Microbiology, Mar. 1992. 58(3): p. 850-856.

Lovley, D.R., D.E. Holmes, and K.P. Nevin, Dissimilatory fe (iii) and mn (iv) reduction. Advances in Microbial Physiology, 2004. 49: p. 219-286.

Lovley, D.R., et al., *Geobacter metallireducens* gen. nov. sp. nov., a microorganism capable of coupling the complete oxidation of organic compounds to the reduction of iron and other metals. Archives of microbiology, 1993. 159(4): p. 336-344.

Lovley et al., "Microbial reduction of uranium". Nature, Apr. 4, 1991. 350(6317). pp. 413-416.

MacAskie et al., Enzymically mediated bioprecipitation of uranium by a *Citrobacter* sp;: a concerted role for exocellular lipopolysaccharide and associated phosphatase in biomineral formation. Microbiology, 2000. 146(8): p. 1855-1867.

Macaskie, L.E., et al., Uranium Bioaccumulation by a *Citrobacter* sp. as a Result of Enzymically Mediated Growth of Polycrystalline HUO2 PO4. Science, Aug. 7, 1992: vol. 257, p. 782- 784. 4 pages.

Malakooti, J., S.P. Wang, and B. Ely, A consensus promoter sequence for Caulobacter crescentus genes involved in biosynthetic and housekeeping functions. J Bacteriol, Aug. 1995. 177(15): p. 4372-4276.

Markich, S.J., Uranium speciation and bioavailability in aquatic systems: an overview. The Scientific World Journal, Mar. 15, 2002. 2: p. 707-729.

Marsili, E., et al., Shewanella secretes flavins that mediate extracellular electron transfer. Proceedings of the National Academy of Sciences, Mar. 11, 2008. 105(10): p. 3968-3973.

Martinez, R.J., et al., Aerobic uranium (VI) bioprecipitation by metal-resistant bacteria isolated from radionuclide-and metal-contaminated subsurface soils. Environmental Microbiology, 2007. 9(12): p. 3122-3133.

2nd Restriction Requirement for U.S. Appl. No. 16/781,950, filed Feb. 4, 2020 on behalf of Lawrence Livermore National Security, LLC Mail Date: Jan. 11, 2023. 8 pages.

Andersen, J.B., et al., New unstable variants of green fluorescent protein for studies of transient gene expression in bacteria. Appl Environ Microbiol, Jun. 1998. 64(6): p. 2240-2246.

Anderson, R.T., et al., Stimulating the in situ activity of *Geobacter* species to remove uranium from the groundwater of a uranium-contaminated aquifer. Applied and Environmental Microbiology, Oct. 2003. 69(10): p. 5884-5891.

Arellano, B.H., et al., Identification of a dehydrogenase required for lactose metabolism in Caulobacter crescentus. Appl Environ Microbiol, May 2010. 76(9): p. 3004-3014.

Bailey, T.L. and C. Elkan, Fitting a mixture model by expectation maximization to discover motifs in biopolymers. Proc Int Conf Intell Syst Mol Biol, 1994. 2: p. 28-36.

Baker, J.L., et al., Widespread genetic switches and toxicity resistance proteins for fluoride. Science, Jan. 13, 2012. 335(6065): p. 233-235.

(56) References Cited

OTHER PUBLICATIONS

Bargar, J.R., et al., Uranium redox transition pathways in acetate-amended sediments. Proceedings of the National Academy of Sciences, Mar. 19, 2013. 110(12): p. 4506-4511.

Barrett, C. A.; Chouyyok, W.; Speakman, R. J.; Olsen, K. B.; Addleman, R. S., Rapid extraction and assay of uranium from environmental surface samples. Talanta, Oct. 2017, 173, 69-78.

Basnakova, G., et al., The use of *Escherichia coli* bearing a phoN gene for the removal of uranium and nickel from aqueous flows. Applied Microbiology and Biotechnology, 1998. 50(2): p. 266-272.

Beazley et al., "The effect of of pH and natural microbial phosphatase activity on the speciation of uraniumin subsurface soils". Geochemica et Cosmochimica Acta, 2011. 75(19): p. 5648-5663.

Begg, J.D., et al., Bioreduction behavior of U (VI) sorbed to sediments. Geomicrobiology Journal, 2011. 28(2): p. 160-171.

Belkin, S., et al., Remote detection of buried landmines using a bacterial sensor. Nat Biotechnol, Apr. 2017. 35(4): p. 308-310.

Bencheikh-Latmani, R. and J.O. Leckie, Association of uranyl with the cell wall of Pseudomonas fluorescens inhibits metabolism. Geochimica et Cosmochimica Acta, 2003. 67(21): p. 4057-4066.

Bereza-Malcolm, L.T., G. Mann, and A.E. Franks, Environmental Sensing of Heavy Metals Through Whole Cell Microbial Biosensors: A Synthetic Biology Approach. ACS Synth Biol, Oct. 9, 2014, 4, 535-546.

Bernier-Latmani et al., Non-uraninite products of microbial U (VI) reduction. Environmental science & technology, 2010. 44(24): p. 9456-9462.

Berset, Y., et al., Mechanistic Modeling of Genetic Circuits for ArsR Arsenic Regulation. ACS Synth Biol, Feb. 19, 2017. 6(5): p. 862-874.

Beveridge, T. and R. Murray, Sites of metal deposition in the cell wall of Bacillus subtilis. Journal of bacteriology, 1980. 141(2): p. 876-887.

Blanco, A.G., et al., Tandem DNA Recognition by PhoB, a Two-Component Signal Transduction Transcriptional Activator. Structure, May 2002. 10(5): p. 701-713.

Blondel, A. and H. Bedouelle, Engineering the quaternary structure of an exported protein with a leucine zipper. Protein Eng, 1991. 4(4): p. 457-61.

Bollmann, A., et al., Isolation and physiology of bacteria from contaminated subsurface sediments. Applied and Environmental Microbiology, Nov. 2010. 76(22): p. 7413-7419.

Bostick, W., et al., Sampling and characterization of aerosols formed in the atmospheric hydrolysis of UF/sub 6. 1983. 8 pages.

Breaker, R.R., New insight on the response of bacteria to fluoride. Caries Res, 2012. 46(1): p. 78-81.

Breaker, R.R., Riboswitches and the RNA world. Cold Spring Harb Perspect Biol, Feb. 10, 2012. 4(2), a003566, pp. 78-81. 15 pages.

Brewster, R.C., et al., The transcription factor titration effect dictates level of gene expression. Cell, Mar. 13, 2014. 156(6): p. 1312-23. 25 pages.

Britos, L., et al., Regulatory response to carbon starvation in Caulobacter crescentus. PLoS One, Apr. 11, 2011. 6(4): p. e18179. 19 pages.

Brutinel et al., "Shuttling happens: soluble flavin mediators of the extracellular electron transfer in Shewanella", Applied Microbiology and Biotechnology, 2012. 93(1): p. 41-48.

Buchler, N.E., U. Gerland, and T. Hwa, "On schemes of combinatorial transcription logic." Proceedings of the National Academy of Sciences, Apr. 29, 2003. 100(9): p. 5136-5141.

Buffi, N., et al., An automated microreactor for semi-continuous biosensor measurements. Lab Chip, 2016. 16(8): p. 1383-92.

Buttner, D. and U. Bonas, Who comes first? How plant pathogenic bacteria orchestrate type III secretion. Current Opinion in Microbiology, Mar. 9, 2006. 9(2): p. 193-200.

Cabantous et al., "A new protein-protein interaction sensor based on tripartite split-GFP association". Scientific reports, Oct. 4, 2013. 3: p. 2854. 9 pages.

Capra, E.J. and M.T. Laub, Evolution of two-component signal transduction systems. Annual Review of Microbiology, Online: Jun. 28, 2012. 66: p. 325-347.

Carey, M.F., C.L. Peterson, and S.T. Smale, The primer extension assay. Cold Spring Harbor Protocols, 2013. 2013(2): p. pdb. prot071902. 164-173.

Certification Statement and List—37 CFR 1.98(d)(1) filed in U.S. Appl. No. 18/406,057, filed Jan. 5, 2024 on behalf of Lawrence Livermore National Security, LLC. 1 page.

Cheng, P.-C., The contrast formation in optical microscopy, in Handbook of Biological Confocal Microscopy. 2006, Third edition, Springer. p. 162-206.

Choppin, G., J. Liljenzin, and J. Rydberg, "Chapter 22: Behavior of Radionuclides in the Environment". Radiochemistry and Nuclear Chemistry, 1995. 753-789.

Choudhary, S. and P. Sar, Uranium biomineralization by a metal resistant Pseudomonas aeruginosa strain isolated from contaminated mine waste. J Hazard Mater, Online: Nov. 9, 2010. 186(1): p. 336-343.

Christen, B., et al., High-throughput identification of protein localization dependency networks. Proc Natl Acad Sci U S A, Mar. 9, 2010. 107(10): p. 4681-4686.

Cormack, B.P., R.H. Valdivia, and S. Falkow, FACS—optimized mutants of the green fluorescent protein (GFP). Gene, 1996. 173(1): p. 33-38.

Da Silva Neto, J.F., R.F. Lourenco, and M.V. Marques, Global transcriptional response of Caulobacter crescentus to iron availability. BMC Genomics, 2013. 14: p. 549. 16 pages.

Dai, C. and S. Choi, Technology and Applications of Microbial Biosensor. Open Journal of Applied Biosensor, Online: Aug. 2013. 2(3), 83-93.

Datsenko, K.A. and B.L. Wanner, One-step inactivation of chromosomal genes in *Escherichia coli* K-12 using PCR products. Proc Natl Acad Sci U S A, Jun. 6, 2000. 97(12): p. 6640-6645.

Davis, J.A., et al., Approaches to surface complexation modeling of uranium (VI) adsorption on aquifer sediments. Geochimica et Cosmochimica Acta, 2004. 68(18): p. 3621-3641.

Di Bernardo, P.; Zanonato, P. L.; Benetollo, F.; Melchior, A.; Tolazzi, M.; Rao, L., Energetics and Structure of Uranium(VI)—Acetate Complexes in Dimethyl Sulfoxide. Inorg. Chem. Aug. 2012, 51 (16), 9045-9055.

Dove, S.L. and A. Hochschild, Conversion of the ω subunit of *Escherichia coli* RNA polymerase into a transcriptional activator or an activation target. Genes & Development, 1998. 12(5): p. 745-754.

Dworkin M, F.S., Rosenberg E, Schleifer KH, Stackebrandt E, The Prokaryotes: Proteobacteria: Alpha and Beta Subclasses. 2006. vol. 5: p. 15-18. 956 pages.

Evinger, M. and N. Agabian, Envelope-associated nucleoid from Caulobacter crescentus stalked and swarmer cells. J Bacteriol, 1977. 132(1): p. 294-301.

Ewing et al., "Environmental impact of the nuclear fuel cycle." Geological Society, London, Special Publications, 2004. 236(1); p. 7-23.

Shin, J. and V. Noireaux, An *E. coli* cell-free expression toolbox: application to synthetic gene circuits and artificial cells. ACS Synth Biol, Dec. 27, 2011. 1(1): p. 29-41.

Silva-Rocha, R. and V. de Lorenzo, Mining logic gates in prokaryotic transcriptional regulation networks. FEBS letters, 2008. 582(8): p. 1237-1244.

Siuda, W. and R. Chrost, Utilization of selected dissolved organic phosphorus compounds by bacteria in lake water under non-limiting orthophosphate conditions. Polish Journal of Environmental Studies, 2001. 10(6): p. 475-483.

Skerker, J.M., et al., Two-component signal transduction pathways regulating growth and cell cycle progression in a bacterium: a system-level analysis. PLoS Biol, Sep. 27, 2005. 3(10): p. e334, 1770-1788.

Smith, T.F. and M.S. Waterman, Comparison of biosequences. Advances in Applied Mathematics, 1981. 2(4): p. 482-489.

Speed, M. C.; Burkhart, B. W.; Picking, J. W.; Santangelo, T. J., An Archaeal Fluoride-Responsive Riboswitch Provides an Inducible

(56) References Cited

OTHER PUBLICATIONS

Expression System for Hyperthermophiles. Appl Environ Microbiol, (Posted online Jan. 19, 2018) Apr. 2018, 84 (7) e02306-17. 8 pages.

Stephens, C., et al., A cell cycle-regulated bacterial DNA methyltransferase is essential for viability. Proceedings of the National Academy of Sciences, Feb. 1996. 93(3): p. 1210-1214.

Stock, A.M., V.L. Robinson, and p. N. Goudreau, Two-component signal transduction. Annual Review of Biochemistry, 2000. 69(1): p. 183-215.

Stockbridge, R.B., et al., A family of fluoride-specific ion channels with dual-topology architecture. Elife, Aug. 27, 2013. 2: p. e01084. 14 pages.

Stockbridge, R.B., et al., Fluoride resistance and transport by riboswitch-controlled CLC antiporters. Proc Natl Acad Sci U S A, Sep. 18, 2012. 109(38): p. 15289-15294.

Suzuki, Y., et al., Flavin mononucleotide mediated electron pathway for microbial U (VI) reduction. Physical Chemistry Chemical Physics, 2010. 12(34): p. 10081-10087.

Thavarajah, W.; Silverman, A. D.; Verosloff, M. S.; Kelley-Loughnane, N.; Jewett, M. C.; Lucks, J. B., Point-of-Use Detection of Environmental Fluoride via a Cell-Free Riboswitch-Based Biosensor. ACS Synthetic Biology, Jan. 17, 2020, 9 (1), 10-18. 18 pages.

Thomas, R.A. and L. Macaskie, Biodegradation of tributyl phosphate by naturally occurring microbial isolates and coupling to the removal of uranium from aqueous solution. Environmental Science & Technology, 1996. 30(7): p. 2371-2375.

Tripet, B., et al., Engineering a de novo designed coiled-coil heterodimerization domain for the rapid detection, purification and characterization of recombinantly expressed peptides and proteins. Protein Eng, 1996. 9(11): 1029-1042).

Truffer, F., et al., Compact portable biosensor for arsenic detection in aqueous samples with *Escherichia coli* bioreporter cells. Rev Sci Instrum, Jan. 31, 2014. 85(1): p. 015120. 5 pages.

Utturkar, S.M., et al., Draft genome sequence for *Caulobacter* sp. strain OR37, a bacterium tolerant to heavy metals. Genome Announcements, May/Jun. 2013. 1(3): p. e00322-13. 2 pages.

VanEngelen, M.R., et al., UO(2) 2+ speciation determines uranium toxicity and bioaccumulation in an environmental *Pseudomonas* sp. isolate. Environ Toxicol Chem, 2010. 29(4): p. 763-769.

Von Canstein, H., et al., Secretion of flavins by *Shewanella* species and their role in extracellular electron transfer. Applied and Environmental Microbiology, Feb. 2008. 74(3): p. 615-623.

Wade, J.T., Where to begin? Mapping transcription start sites genome-wide in *Escherichia coli*. Journal of Bacteriology, (Online: Oct. 20, 2014) Jan. 2015. 197(1): p. 4-6.

Wang, B., et al., Engineering modular and orthogonal genetic logic gates for robust digital-like synthetic biology. Nature Communications, Oct. 18, 2011. 2: p. 508. 9 pages.

Wang, B., M. Barahona, and M. Buck, Engineering modular and tunable genetic amplifiers for scaling transcriptional signals in cascaded gene networks. Nucleic Acids Res, 2014. 42(14): p. 9484-92.

Weinberg, Z., et al., Comparative genomics reveals 104 candidate structured RNAs from bacteria, archaea, and their metagenomes. Genome Biol, 2010. 11(3): p. R31. 17 pages.

Wilkins, M., et al., The influence of microbial redox cycling on radionuclide mobility in the subsurface at a low-level radioactive waste storage site. Geobiology, 2007. 5(3): p. 293-301.

Williams et al., "Bioremediation of uranium-contaminated groundwater: a systems approach to subsurface biogeochemistry". Current Opinion in Biotechnology, 2013. 24(3): p. 489-497.

Williams, K.H., et al., Acetate availability and its influence on sustainable bioremediation of uranium-contaminated groundwater. Geomicrobiology Journal, 2011. 28(5-6): p. 519-539.

Wogman, N.A., Prospects for the introduction of wide area monitoring using environmental sampling for proliferation detection. Journal of Radioanalytical and Nuclear Chemistry, 2013. 296(2): p. 1071-1077.

Written Opinion for International Application No. PCT/US2018/061667 filed on Nov. 16, 2018 on behalf of Lawrence Livermore National Security, LLC. Mail date: Jun. 26, 2019. 7 pages.

Wu, Q., R.A. Sanford, and F.E. Loffler, Uranium (VI) reduction by Anaeromyxobacter dehalogenans strain 2CP-C. Applied and environmental microbiology, May 2006. 72(5): p. 3608-3614.

Wu, W.-M., et al., In situ bioreduction of uranium (VI) to submicromolar levels and reoxidation by dissolved oxygen. Environmental Science & Technology, 2007. 41(16): p. 5716-5723.

Yagi, K., Applications of whole-cell bacterial sensors in biotechnology and environmental science. Appl Microbiol Biotechnol, Online: Nov. 17, 2006. 73(6): p. 1251-1258.

Yung, M.C. and Y. Jiao, Biomineralization of uranium by PhoY phosphatase activity aids cell survival in Caulobacter crescentus. Applied and Environmental Microbiology, Online: May 25, 2014. 80(16): p. 4795-4804.

Yung, M.C., et al., Shotgun proteomic analysis unveils survival and detoxification strategies by Caulobacter crescentus during exposure to uranium, chromium, and cadmium. J Proteome Res, Feb. 21, 2014. 13(4): p. 1833-1847.

Zhao, B., et al., An excited state underlies gene regulation of a transcriptional riboswitch. Nat Chem Biol, Sep. 2017. 13(9): p. 968-974. 11 pages.

Zheng, J., Spectroscopy-based quantitative fluorescence resonance energy transfer analysis. Ion channels: methods and protocols, 2006: p. 65-77.

Zhou, B., et al., The global regulatory architecture of transcription during the Caulobacter cell cycle. PLoS Genet, Jan. 2015. 11(1): p. e1004831. 17 pages.

Zhou, L., et al., A protein engineered to bind uranyl selectively and with femtomolar affinity. Nat Chem, Online: Jan. 26, 2014. 6(3): p. 236-241.

Hu, P., et al., Whole-genome transcriptional analysis of heavy metal stresses in Caulobacter crescentus. Journal of Bacteriology, Dec. 2005. 187(24): p. 8437-8449.

Mascher, T., J.D. Helmann, and G. Unden, Stimulus perception in bacterial signaltransducing histidine kinases. Microbiology and Molecular Biology Reviews, Dec. 2006. 70(4): p. 910-938.

McGrath, P. T., et al., High-throughput identification of transcription start sites, conserved promoter motifs and predicted regulons. Nat Biotechnol, Published online Apr. 1, 2007. 25(5): p. 584-592.

Meisenzahl, Aimee C., et al., Isolation and characterization of a xylose-dependent promoter from Caulobacter crescentus. J Bacteriol; Feb. 1997. 179(3): p. 592-600.

Modell, J.W., A.C. Hopkins, and M.T. Laub, A DNA damage checkpoint in Caulobacter crescentus inhibits cell division through a direct interaction with FtsW. Genes Dev, 2011. 25(12): p. 1328-43.

Myers, E.W. and W. Miller, Optimal alignments in linear space. Computer applications in the biosciences: CABIOS, 1988. 4(1): p. 11-17.

Myers, W.L., A literature review on the chemical and physical properties of uranyl fluoride (UO sub 2 F sub 2 ). 1990: United States. 21 pages.

Needleman, S.B. and C.D. Wunsch, A general method applicable to the search for similarities in the amino acid sequence of two proteins. Journal of molecular biology, 1970. 48(3): p. 443-453.

Newsome, Laura et al., The biogeochemistry and bioremediation of uranium and other priority radionuclides. Chemical Geology, Online Nov. 6, 2013. 363: p. 164-184.

Nguyen, A.W. and P.S. Daugherty, Evolutionary optimization of fluorescent proteins for intracellular FRET. Nature Biotechnology, Mar. 2005. 23(3): p. 355-360.

Nolan, J. and K.A. Weber, Natural Uranium Contamination in Major U.S. Aquifers Linked to Nitrate. Environmental Science & Technology Letters, Jul. 31, 2015. 2(8): p. 215-220.

Nomellini, J.F., et al., S-Layer-mediated display of the immunoglobulin G-binding domain of streptococcal protein G on the surface of Caulobacter crescentus: development of an immunoactive reagent. Appl Environ Microbiol, May 2007. 73(10): p. 3245-3253.

Non-Final Office Action for U.S. Appl. No. 16/781,950, filed Feb. 4, 2020 on behalf of Lawrence Livermore National Security, LLC. Mail Date: Jun. 1, 2023. 22 pages.

(56)  References Cited

OTHER PUBLICATIONS

Non-Final Office Action for U.S. Appl. No. 18/186,095 on behalf of Lawrence Livermore National Security, LLC filed Mar. 17, 2023. Mailed on Sep. 4, 2024. 14 pages.

Notice of Allowance for U.S. Appl. No. 16/781,950, filed Feb. 4, 2020 on behalf of Lawrence Livermore National Security, LLC. Mail Date: Oct. 5, 2023. 8 pages.

Notice of Allowance issued for U.S. Appl. No. 16/764,824, filed May 15, 2020, on behalf of Lawrence Livermore National Security, LLC. Mail Date: Nov. 2, 2022. 26 Pages.

Nriagu, J.O., "Lead orthophosphates. I. Solubility and hydrolysis of secondary lead orthophosphate." Inorganic Chemistry, 1972. 11(10): p. 2499-2503.

Pabalan, R.T., et al., Uranium (VI) sorption onto selected mineral surfaces: Key geochemical parameters. 1996, American Chemical Society, Washington, DC (United States). pp. 99-130.

Pardoux, R., et al., Modulating uranium binding affinity in engineered calmodulin EF-hand peptides: effect of phosphorylation. PLoS One, Aug. 3, 2012. 7(8): p. e41922. 10 pages.

Park, D.M. and P.J. Kiley, The influence of repressor DNA binding site architecture on transcriptional control. MBio, Sep./Oct. 2014. 5(5): p. e01684-14. 11 pages.

Park, D.M. and Y. Jiao, Modulation of medium pH by Caulobacter crescentus facilitates recovery from uranium-induced growth arrest. Applied and environmental microbiology, Sep. 2014. 80(18): p. 5680-5688.

Park, D.M., et al., Bioadsorption of Rare Earth Elements through Cell Surface Display of Lanthanide Binding Tags. Environ Sci Technol, Feb. 2, 2016. 50(5): p. 2735-2742.

Park, D.M., et al., Identification of a U/Zn/Cu responsive global regulatory two-component system in Caulobacter crescentus. Mol Microbiol, 2017, 104[1], 46-64.

Park et al. "Combinatorial Sensor Design in Caulobacter crescentus for Selective Environmental Uranium Detection", ACS Synthetic Biology, Mar. 21, 2019. vol. 8, No. 4, pp. 807-817.

Park et al., Identification of a U/Zn/Cu responsive global regulatory two-component system in Caulobacter crescentus. Molecular Microbiol, Online Jan. 23, 2017, 104(1), 46-64.

Park et al. "The UzcRS two-component system in Caulobacter crescentus integrates regulatory input from diverse auxiliary regulators", Molecular Microbiology, Mar. 2019. vol. 111, No. 3, pp. 678-699.

Park, M., S.L. Tsai, and W. Chen, Microbial biosensors: engineered microorganisms as the sensing machinery. Sensors (Basel), May 6, 2013. 13(5): p. 5777-5795.

Pearson, W.R. and D.J. Lipman, Improved tools for biological sequence comparison. Proceedings of the National Academy of Sciences, Apr. 1988. 85(8): p. 2444-2448.

Periasamy, A., Fluorescence resonance energy transfer microscopy: a mini review. Journal of biomedical optics, Jul. 2001. 6(3): p. 287-291.

Poindexter, J.S., The caulobacters: ubiquitous unusual bacteria. Microbiological Reviews, Mar. 1981. 45(1): p. 123-179.

Powers, L.G., et al., Introduction of a plasmid-encoded phoA gene for constitutive overproduction of alkaline phosphatase in three subsurface Pseudomonas isolates. FEMS Microbiology Ecology, Online May 28, 2002. 41(2): p. 115-123.

Procaccini, A., et al., Dissecting the specificity of protein-protein interaction in bacterial two-component signaling: orphans and crosstalks. PloS one, May 9, 2011. 6(5): p. e19729. 9 pages.

Record for GenBank Accession No. AE005992.1, Caulobacter crescentus CB15, section 318 to 359 of the complete genome, 2002. 7 pages.

Ren, A., K.R. Rajashankar, and D.J. Patel, Fluoride ion encapsulation by Mg2+ ions and phosphates in a fluoride riboswitch. Nature, Jun. 7, 2012. 486(7401): p. 85-89. 6 pages.

Renninger, N., et al., Uranyl precipitation by Pseudomonas aeruginosa via controlled polyphosphate metabolism. Appl Environ Microbiol, Dec. 2004. 70(12): p. 7404-7412.

Response to Rule 312 Communication issued for U.S. Appl. No. 16/764,824, filed May 15, 2020, on behalf of Lawrence Livermore National Security, LLC. Mail Date Jan. 4, 2023. 2 Pages.

Restriction Requirement for U.S. Appl. No. 16/781,950, filed Feb. 4, 2020 on behalf of Lawrence Livermore National Security, LLC Mail Date: Jul. 5, 2022 7 pages.

Restriction Requirement for U.S. Appl. No. 18/406,057, filed Jan. 5, 2024 on behalf of Lawrence Livermore National Security, LLC. Mailed on Sep. 20, 2024. 8 pages.

Restriction Requirement for U.S. Appl. No. 18/186,095 on behalf of Lawrence Livermore National Security, LLC filed Mar. 17, 2023. Mailed on Apr. 12, 2024. 8 pages.

Restriction Requirement for U.S. Appl. No. 18/186,095 on behalf of Lawrence Livermore National Security, LLC filed Mar. 17, 2023. Mailed on Jun. 27, 2024. 7 pages.

Restriction Requirement issued for U.S. Appl. No. 16/764,824, filed May 15, 2020, on behalf of Lawrence Livermore National Security, LLC. Mail Date: Jul. 27, 2022. 8 Pages.

Richter, K., M. Schicklberger, and J. Gescher, Dissimilatory reduction of extracellular electron acceptors in anaerobic respiration. Applied and Environmental Microbiology, 2012. 78(4): p. 913-921.

Roggo, C. and J.R. van der Meer, Miniaturized and integrated whole cell living bacterial sensors in field applicable autonomous devices. Curr Opin Biotechnol, 2017. 45: p. 24-33.

Sanders, D., et al., Phosphorylation site of NtrC, a protein phosphatase whose covalent intermediate activates transcription. Journal of Bacteriology, Aug. 1992. 174(15): p. 5117-5122.

Sanders, D.A., et al., Identification of the site of phosphorylation of the chemotaxis response regulator protein, CheY. Journal of Biological Chemistry, Dec. 25, 1989. 264(36): p. 21770-21778.

Senko, J.M., et al., The effect of U (VI) bioreduction kinetics on subsequent reoxidation of biogenic U (IV). Geochimica et Cosmochimica Acta, Online Aug. 26, 2007. 71(19): p. 4644-4654.

Sharma, C.M., et al., The primary transcriptome of the major human pathogen Helicobacter pylori. Nature, Mar. 11, 2010. 464(7286): p. 250-255.

Shelobolina, E.S., et al., Isolation, characterization, and U (VI)-reducing potential of a facultatively anaerobic, acid-resistant Bacterium from Low-pH, nitrate- and U (VI)-contaminated subsurface sediment and description of Salmonella subterranea sp. nov. Applied and Environmental Microbiology, May 2004. 70(5): p. 2959-2965.

Sheng, L. and J.B. Fein, Uranium adsorption by Shewanella oneidensis MR-1 as a function of dissolved inorganic carbon concentration. Chemical Geology, 2013. 358: p. 15-22.

Notice of Allowance for U.S. Appl. No. 18/186,095 on behalf of Lawrence Livermore National Security, LLC filed Mar. 17, 2023. Mailed on Jan. 17, 2025. 10 pages.

* cited by examiner

A

P$_{phyt}$ sequence

CCCAAAGA GGGTGTGG CCCAAAGA GGGTGTGGA TTTCTCTTC GCGC
tandem repeat (TR)

CACCCGTT TCGTCAGCCGGACGTCAGGTCCAGACGGCTAAGC TAGC
DR1                    DR2
TGCGA     Regulator Direct Repeat

B

P$_{1361}$ sequence

ATGTTCAGCGCCTGGT TACCGGCGA TGGCGCGG TGTCAGCGT TCGG

GCGTTGCGATGCGTCAGGAGCGTGTCAGGATGCCTGTGGAAT CCTA
DR1                    DR2
AGCGC     Regulator Direct Repeat

C

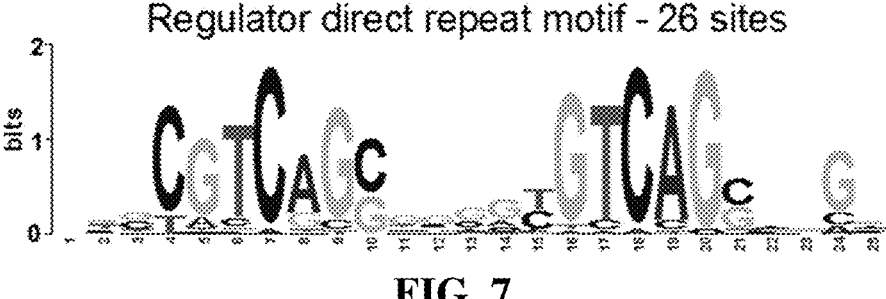

Regulator direct repeat motif - 26 sites

FIG. 7

A.    P<sub>phyt</sub> DNA sequence
CGGACGGTGACCGGCAAACCACCGCTGTCATGAATGCGTTTTGAAGCTTCGCCATAACGCGCCTTGGGTA
TCCGGTTCGGAACGCGGCGCTTTCGTTGACCTCTGGCCACGGAGAATTCTCCATCCCAAAGAGGGTGTGG
CCCAAAGAGGGTGTGGATTTCTCTTCGCGCCACCCGTTT*CGTCAGCCGGACGTCAGGT*CCAGACGGCTAA
GCTAGCTGC*ga*GAC*atg*AAAACGAG (SEQ ID NO:72)

B.    P<sub>phyt</sub> DR2 GTCA -> CAGT (mutation in bold)
CGGACGGTGACCGGCAAACCACCGCTGTCATGAATGCGTTTTGAAGCTTCGCCATAACGCGCCTTGGGTA
TCCGGTTCGGAACGCGGCGCTTTCGTTGACCTCTGGCCACGGAGAATTCTCCATCCCAAAGAGGGTGTGG
CCCAAAGAGGGTGTGGATTTCTCTTCGCGCCACCCGTTT*CGTCAGCCGGAC*CAGT*GGT*CCAGACGGCTAA
GCTAGCTGC*ga*GAC*atg*AAAACGAG (SEQ ID NO:73)

C.    P<sub>phyt</sub> DR1 GT -> CA (mutation in bold)
CGGACGGTGACCGGCAAACCACCGCTGTCATGAATGCGTTTTGAAGCTTCGCCATAACGCGCCTTGGGTA
TCCGGTTCGGAACGCGGCGCTTTCGTTGACCTCTGGCCACGGAGAATTCTCCATCCCAAAGAGGGTGTGG
CCCAAAGAGGGTGTGGATTTCTCTTCGCGCCACCCGTTT*CA**CAGCCGGACGTCAGGT*CCAGACGGCTAA
GCTAGCTGC*ga*GAC*atg*AAAACGAG (SEQ ID NO: 74)

D.    P<sub>phyt</sub> DR2 GT -> CA (mutation in bold)
CGGACGGTGACCGGCAAACCACCGCTGTCATGAATGCGTTTTGAAGCTTCGCCATAACGCGCCTTGGGTA
TCCGGTTCGGAACGCGGCGCTTTCGTTGACCTCTGGCCACGGAGAATTCTCCATCCCAAAGAGGGTGTGG
CCCAAAGAGGGTGTGGATTTCTCTTCGCGCCACCCGTTT*CGTCAGCCGGAC*CA*CAGGT*CCAGACGGCTAA
GCTAGCTGC*ga*GAC*atg*AAAACGAG (SEQ ID NO: 75)

E.    P<sub>phyt</sub> short
GGATTTCTCTTCGCGCCACCCGTTT*CGTCAGCCGGACGTCAGGT*CCAGACGGCTAAGCTAGCTGC*ga*GAC
*atg*AAAACGAG (SEQ ID NO:76)

FIG. 8

F.    P$_{1361}$ DNA sequence

GAACGATAGCGCCGCCTGCGAGCGCGACCTCAGGCCTCGGACGAAGCGCGTCCGGGGCCTTTTCTTGTCG
ATGTTCAGCGCCTGGTTACCGGCGATGGCGCGGTGTCAGCGTTCGGGCGTTGCGATG*CGTCAGGAGCGTG*
*TCAGGA*TGCCTGTGGAATCCTAAGCG*cCatg*ACCCAGTCCCGATCTTTCC (SEQ ID NO:77)

G.    P$_{1361}$ DR2 GTCA -> CAGT (mutation in bold)

GAACGATAGCGCCGCCTGCGAGCGCGACCTCAGGCCTCGGACGAAGCGCGTCCGGGGCCTTTTCTTGTCG
ATGTTCAGCGCCTGGTTACCGGCGATGGCGCGGTGTCAGCGTTCGGGCGTTGCGATG*CGTCAGGAGCGTC
AGT*GGA*TGCCTGTGGAATCCTAAGCG*cCatg*ACCCAGTCCCGATCTTTCC (SEQ ID NO:78)

H.    P$_{1361}$ DR2 GT -> CA (mutation in bold)

GAACGATAGCGCCGCCTGCGAGCGCGACCTCAGGCCTCGGACGAAGCGCGTCCGGGGCCTTTTCTTGTCG
ATGTTCAGCGCCTGGTTACCGGCGATGGCGCGGTGTCAGCGTTCGGGCGTTGCGATG*CGTCAGGAGCGTC
A*CAGGA*TGCCTGTGGAATCCTAAGCG*cCatg*ACCCAGTCCCGATCTTTCC (SEQ ID NO: 79)

I.    P$_{1361}$ short

GCGTTGCGATG*CGTCAGGAGCGTGTCAGGA*TGCCTGTGGAATCCTAAGCG*cCatg*ACCCAGTCCCGATCT
TCC (SEQ ID NO: 80)

FIG. 8 (cont.)

A
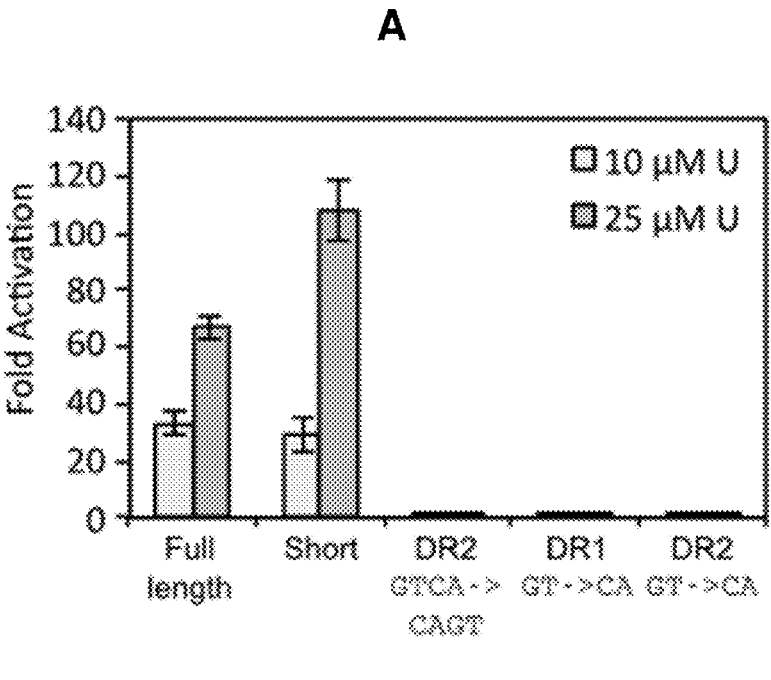
B
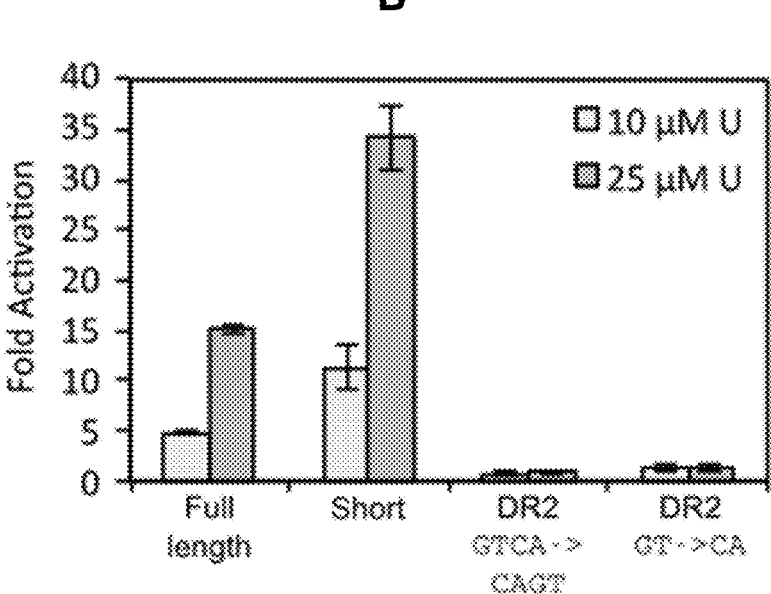
FIG. 9

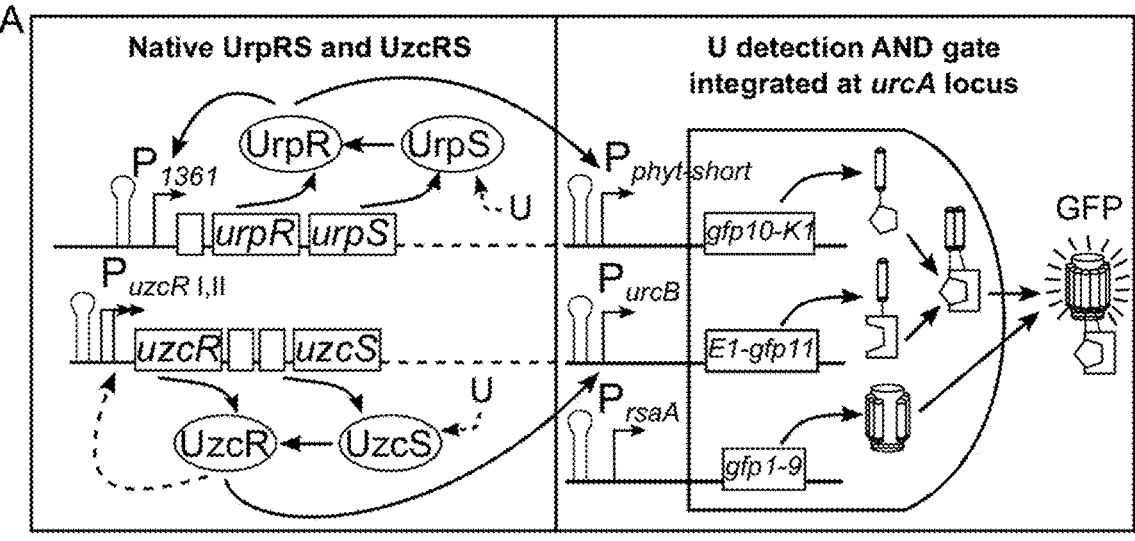
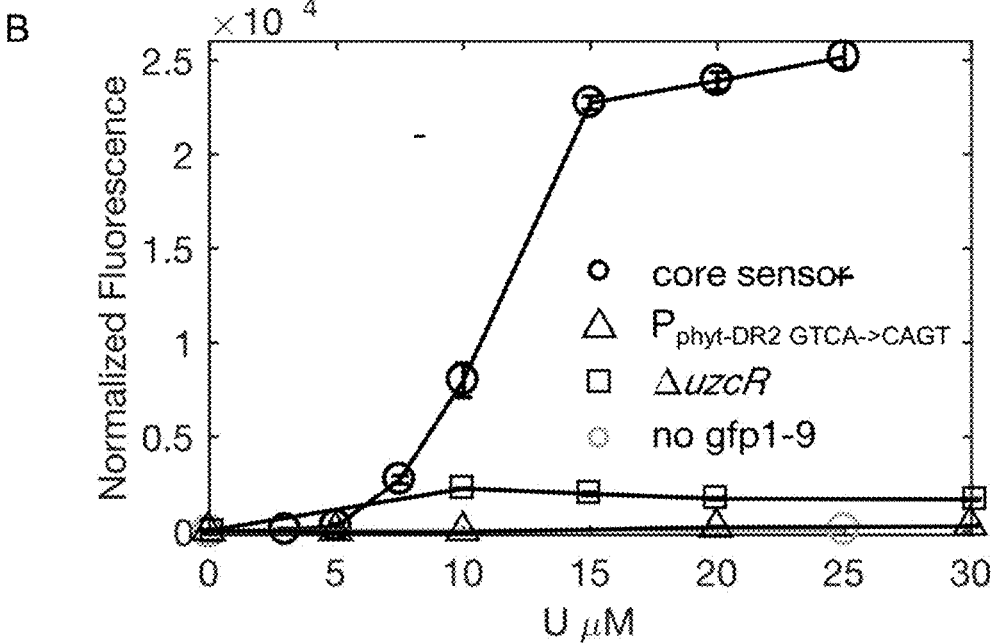
FIG. 14

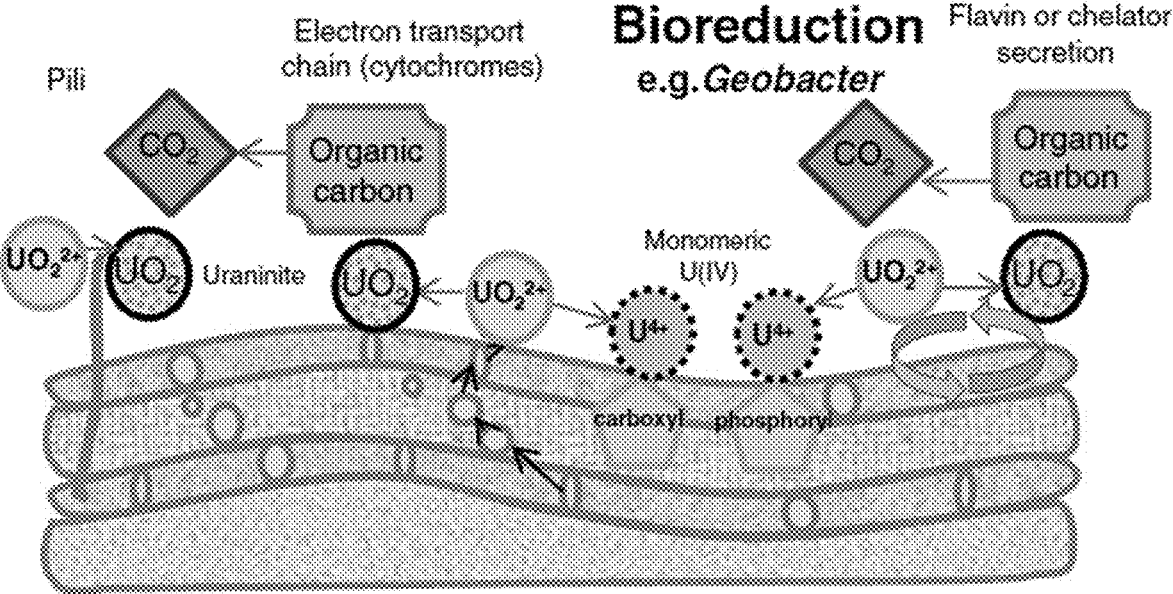
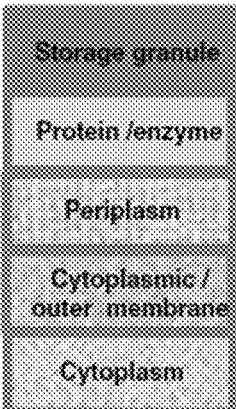
FIG. 16A

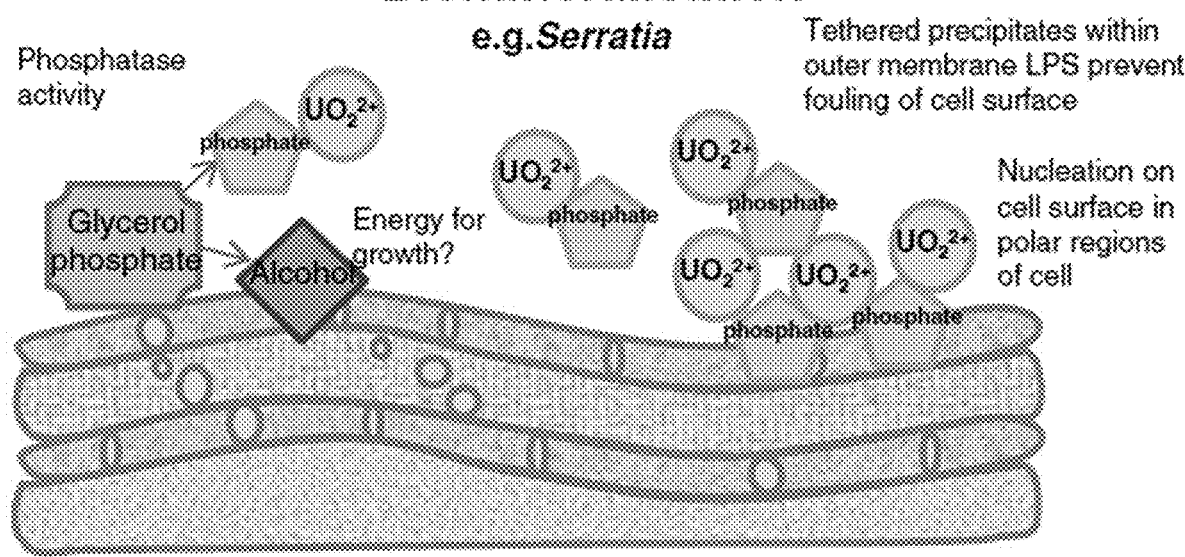
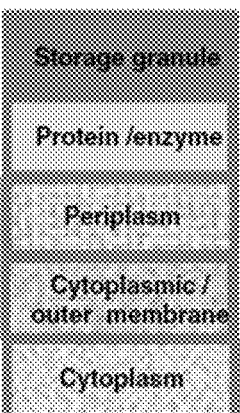
FIG. 16B

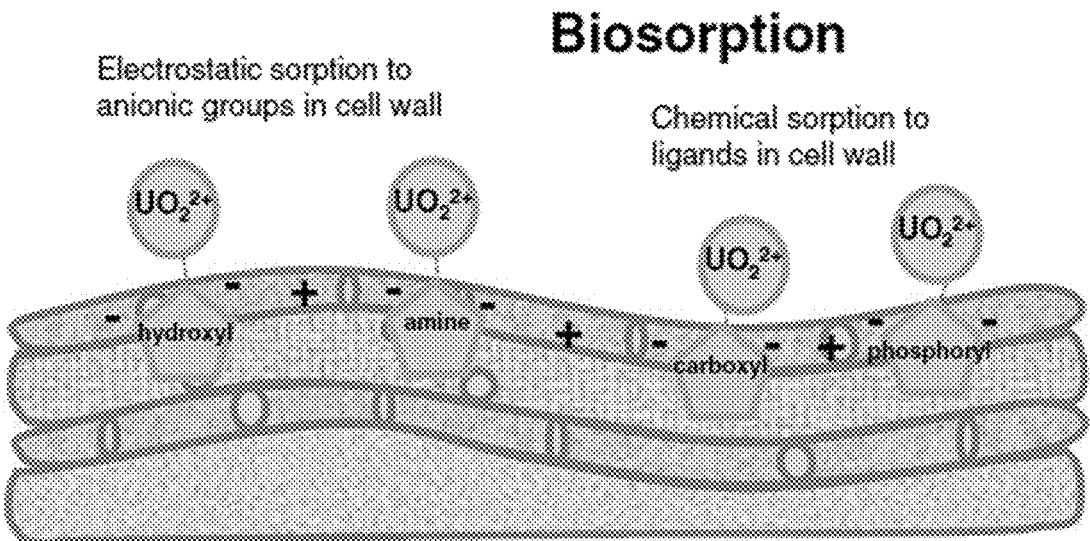
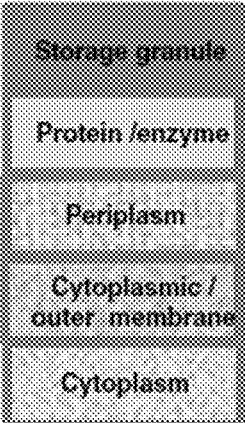
FIG. 16C

Bioaccumulation
e.g.*Pseudomonas*

Increased membrane permeability?

$UO_2^{2+}$

Interaction with negatively charged functional groups within the cell $UO_2^{2+}$ $UO_2^{2+}$ Active uptake of essential elements (or similar metals)

phosphate polyphosphate granule

Storage granule

Protein /enzyme

Periplasm

Cytoplasmic / outer membrane

Cytoplasm

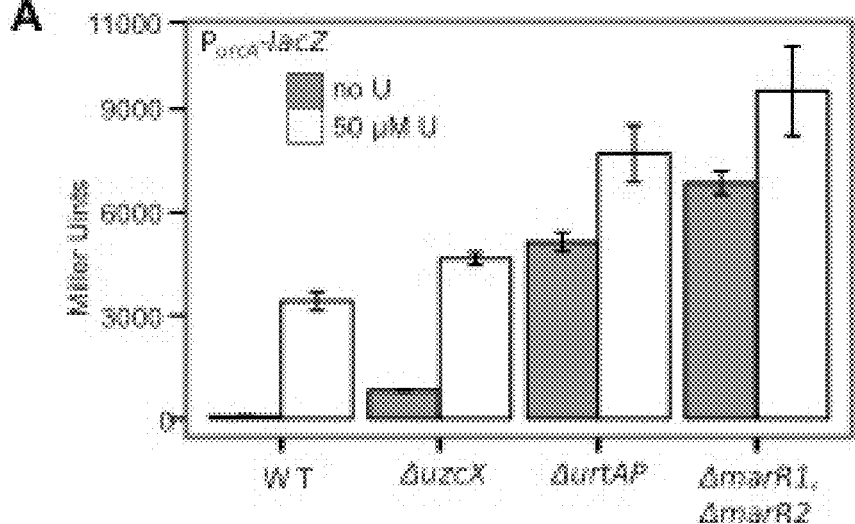
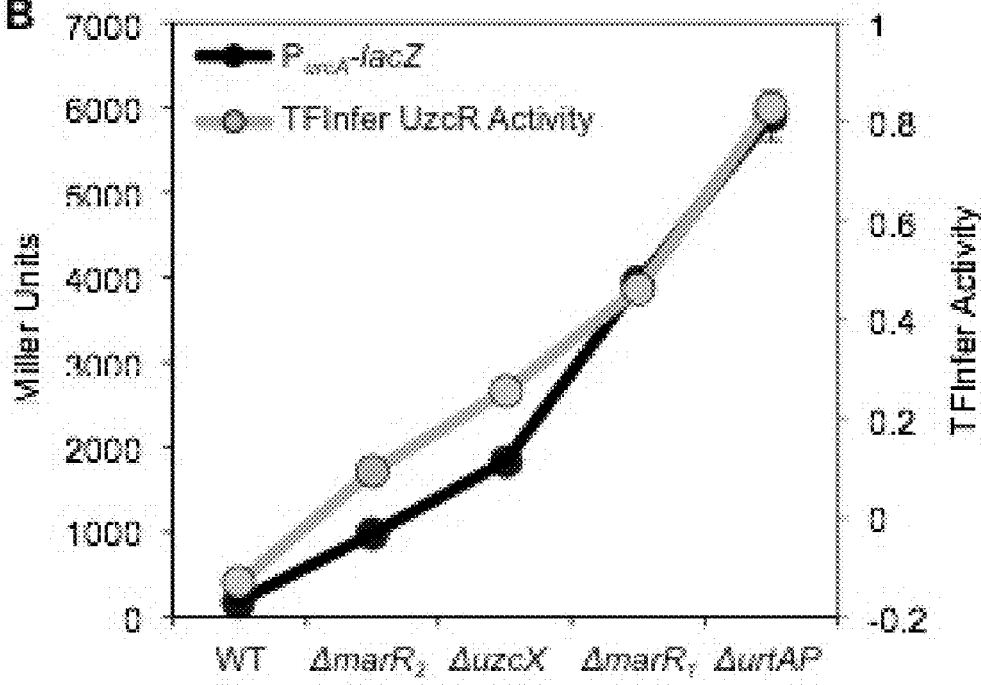
FIG. 27

Single Output UO$_2$F$_2$ Sensor Configurations
In-Series UO$_2$F$_2$ sensor
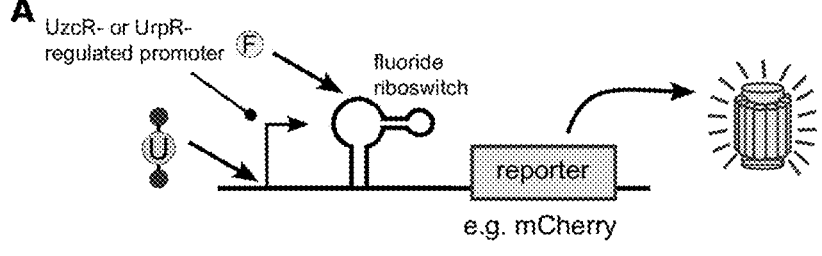
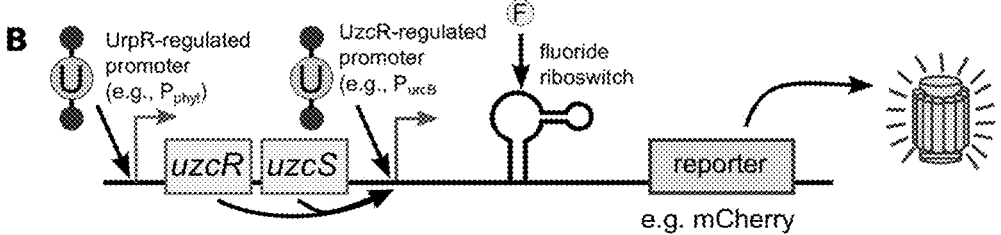
In-Parallel UO$_2$F$_2$ sensor
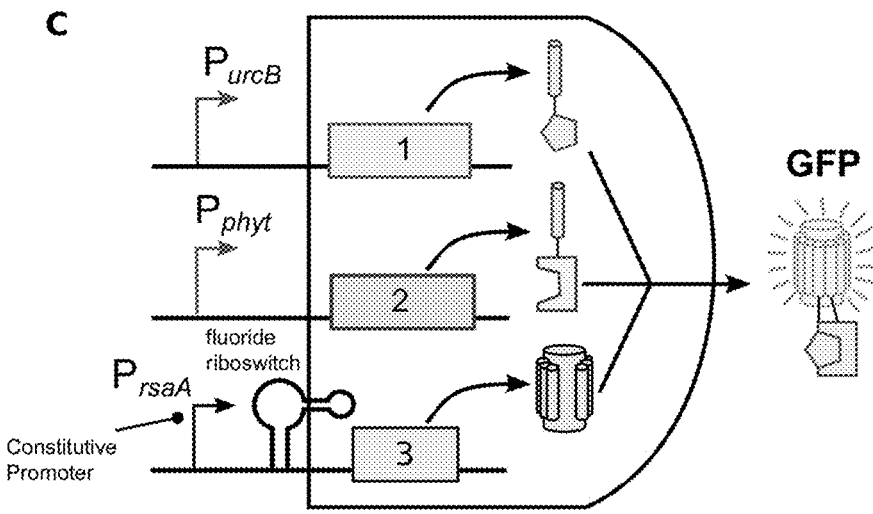
FIG. 46

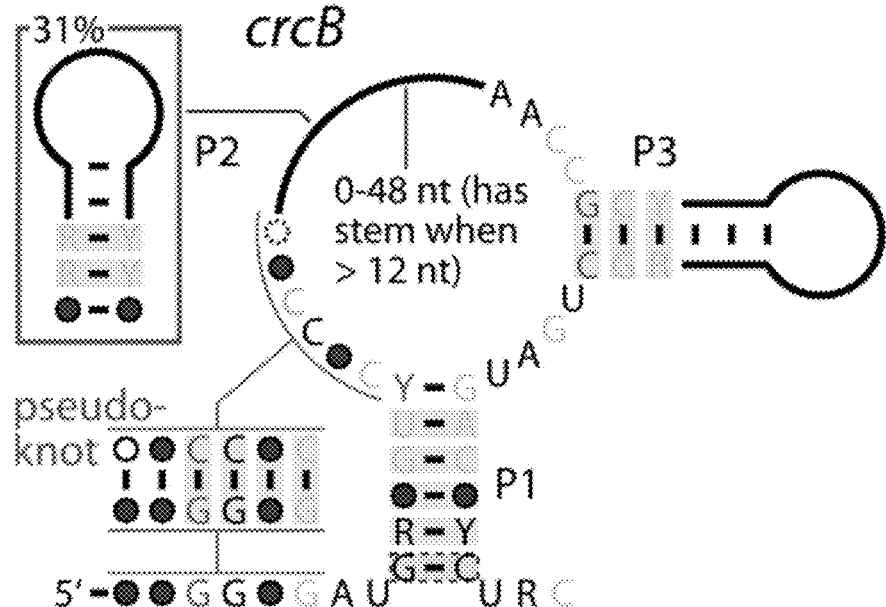
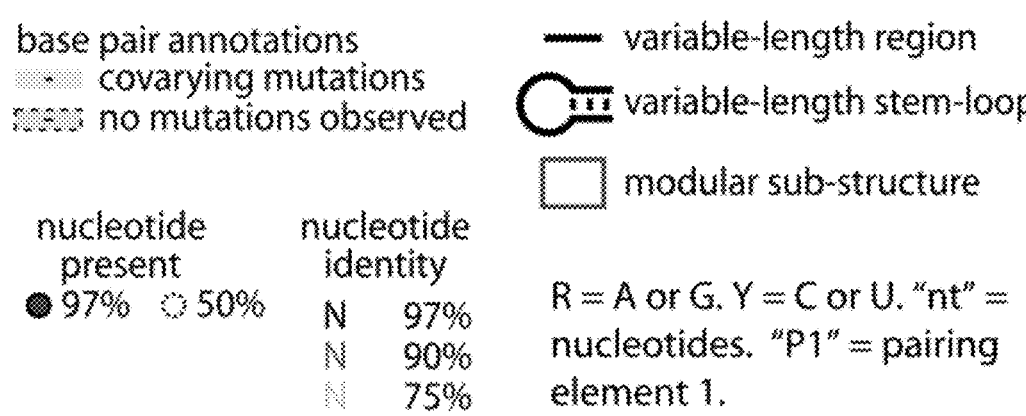
FIG. 48C
PRIOR ART

| 2. promoter | 1. fluoride riboswitch | 3. RBS | 4. portion of native *crcB* or *eric*<sup>F</sup> | 5. reporter |

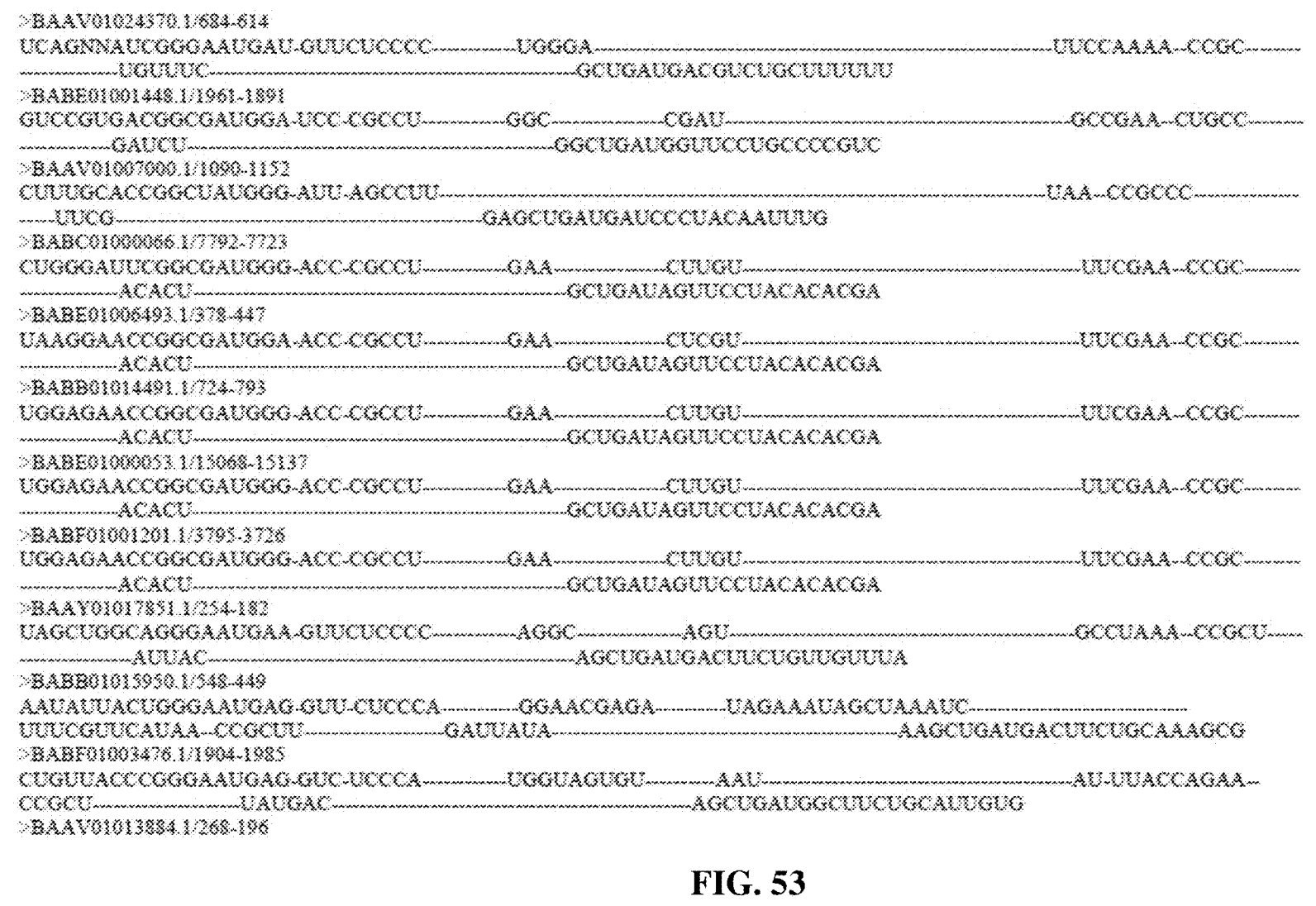

>BAAV01024570.1/683-614
UCAGNNAUCGGGAAUGAU-GUUCUCCCC------------UGGGA------------UUCCAAAA--CCGC------

GCCGUGACGGAUGGA-UCC-CGCCU-------GGC------------------------GCCGAA--CCGCC--
>BABE01001449.1/1961-1891
GUCCGUGACGGAUGGA-UCC-CGCCU----GHUUC--------------GCUGAUGACGUCGUGCUUUUUU

>BAAV01007900.1/1080-1152
CUUUGCACCGCGCUAUGCG-AUU-AGCCU----GAUCU----------------------GGCUGAUGGGUUCCUGCCGGUC

>BABC01000066.1/7792-7723
CUCGGAUUUCGCGGAUGCG-ACC-CGCCU------GAGCUGAUGAUCCUACAAUUG
ACACU

>BABE01006493.1/378-447
UAAGGAACCGGCGAUGGA-ACC-CGCCU----GAA-----------CUUGU------------UUCGAA--CCGC--
ACACU                                GCUGAUAGUUCCUACACACGA

>BABB01014401.1/724-793
UGGAGAACCGGCGAUGCG-ACC-CGCCU----GAA-----------CUCGU------------UUCGAA--CCGC--
ACACU                                GCUGAUAGUUCCUACACACGA

>BABE01000053.1/13066-13137
UGGAGAACCGGCGAUGCG-ACC-CGCCU----GAA-----------CUUGU------------UUCGAA--CCGC--
ACACU                                GCUGAUAGUUCCUACACACGA

>BABF01001201.1/5795-5728
UGGAGAACCGGCGAUGCG-ACC-CGCCU----GAA-----------CUUGU------------UUCGAA--CCGC--
ACACU                                GCUGAUAGUUCCUACACACGA

>BAAV01017851.1/254-183
UAGCUGGCAGGGAAUGAA-GUUCUCCCC------AGGC-----------AGU------------GCCUAAAA--CCGCU-
AUUAC                                AGCUGAUGGACUUCUGUUGUUUA

>BABB01015950.1/548-449
AAUAUUACUGGGAAUGAG-GUU-CUCCCA------GGAACGAGA-------UAGAAAUAGCUAAAUC------UAGAAAUAGCUAAAUC--
UUUCGUUCAUAA--CCGCCU------GAUUAUA---------------------------AGCUGAUGACUUCUGCAAAGCG

>BABF01005476.1/1904-1985
CUGUUACCCGGCAUGAG-GUC-UCCCA------UGGUAGUGU------AAU------------AU-UUACCAGAA--
CCGCU             UAUGAC--------------------------AGCUGAUGGCUUCUGCAUUGUG

>BAAV01013884.1/268-196

FIG. 53

Figure 53:
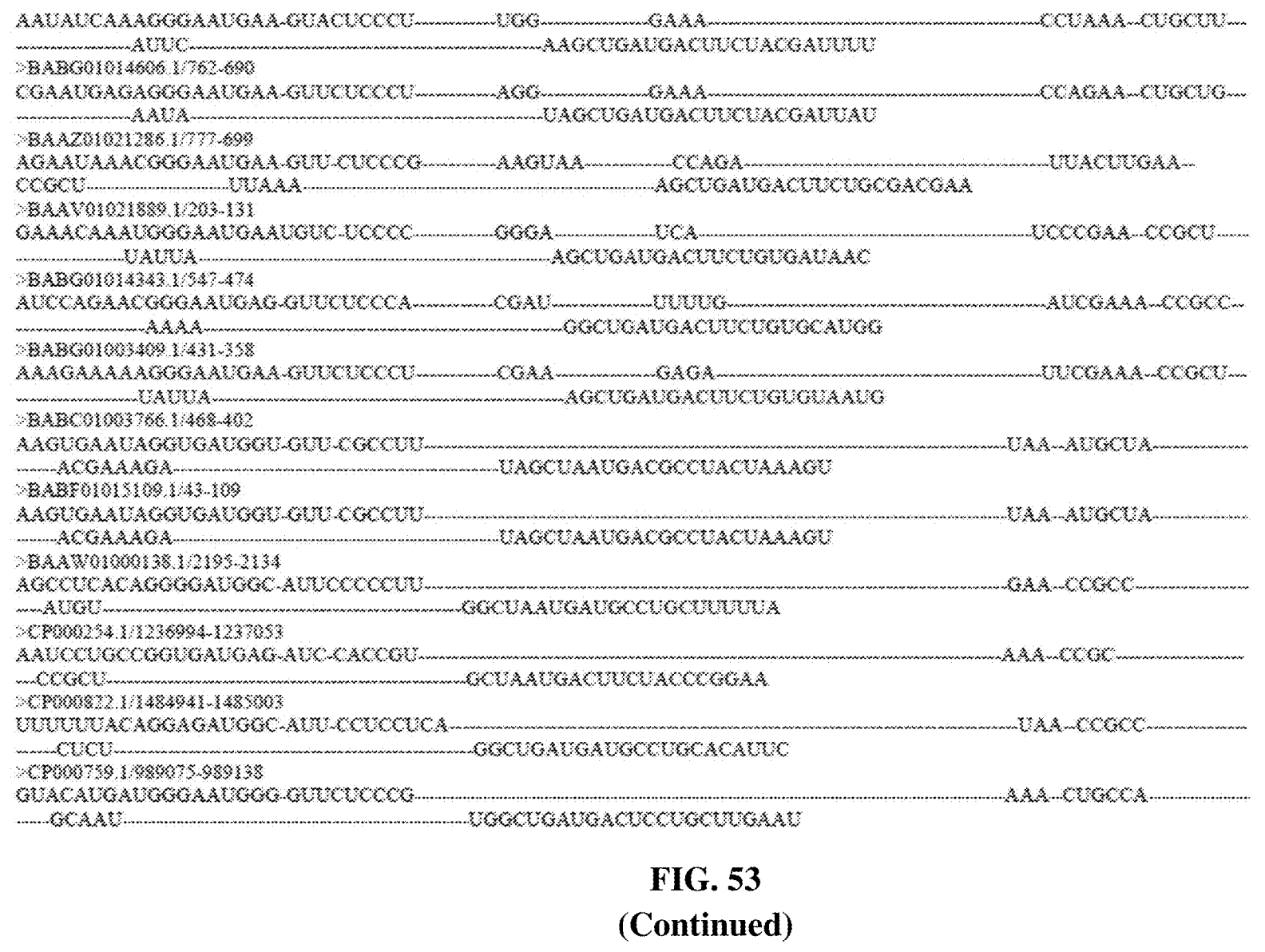

AAUAUCAAAGGGAAUGAA-GUACUCCCU------------UGG------------GAAA------------------CCUAAA--CGCCCU---
>BABG0101:4606.1/762-698  ------AUUC------------------AAGCUGAUGACUUCUAGGAUUUU

CGAAUCAGAGGGAAUCGAA-GUUCUCCCU------------AGC------------CAAA------------CCAGAA--CUGCUG---
>BAAZ01021286.1/777-699  ------AAUA------------------UAGCUGAUGACUUCUACGAUUAU

AGAAUAAACGGGAAUGAA-GUU-CUCCCG------------AAGUAA------CCAGA------------------UUACUUGAA---
>BAAV01021886.1/1203-131  CCGCU------UUAAA------------AGCUGAUGACUUCUGCGACCAA

GAAACAAAUGGGAAUGAA-UGUUC-UCCCC------------GGGA------UCA------------------UCCCGAA--CCGCU---
>BABG0101:1343.1/547-474  UAUUA------------------AGCUGAUGACUUCGUGAUAAC

AUCCAGAACCGGGAAUGAG-GUUCUCCCA------------CGAU------UUUUG------------------AUCGAAA--CCGCC---
>BABG0103:3409.1431-358  AAAA------------------GGCUGAUGACUUCUGUCCAUGG

AAAGAAAUAGGGAAUGAA-GUUCUCCCU------------CGAA------GAGA------------------UUCCAAA--CCGCU---
>BABG01003766.1/468-402  UAUUA------------------AGCUGAUGACUUCUGUGUAAUG

AAGUGAAUAGGGAUGUGU-GUU-CGCCCU------------UAGCUAAUGACGCCUACUAAAGU------------------UAA--AUGCUA---
>BABF0101:5109.143-109  ACGAAAGA

AAGUGAAUAGGUGAUGGU-GUU-CGCCCU------------UAGCUAAUGACGCCUACUAAAGU------------------UAA--AUGCUA---
>BAAV010000138.1/2193-214  ACGAAAGA

AGCCUCACAGCGGGAUGGC-AUUCCCCCCU------------GGCUAAUGAUGCCUGCCUUUUA------------------GAA--CCGCC---
>CP000254.1/1236994-1237053  AUGU

AAUCCCGCCGGUGAUGAG-AUUC-CACCCU------------GCUAAUGACUUCUACCGGAA------------------AAA--CCGC---
>CP000812.1/1484941-1485003  CCGCU

UUUUUCACAGGAGAUGGC-AUU-CCUCCUCA------------GGCUGAUGAUGGCCUUCACAUUC------------------UAA--CCGGC---
>CP000739.1:988075.989138  CUCU

GUUACAUGAUGGGAAUGGG-GUUCUCCCG------------UGGCUGAUGACUCCUGCUUGAAU------------------AAA--CUGCCA---
>  GCAAU

Figure 53:
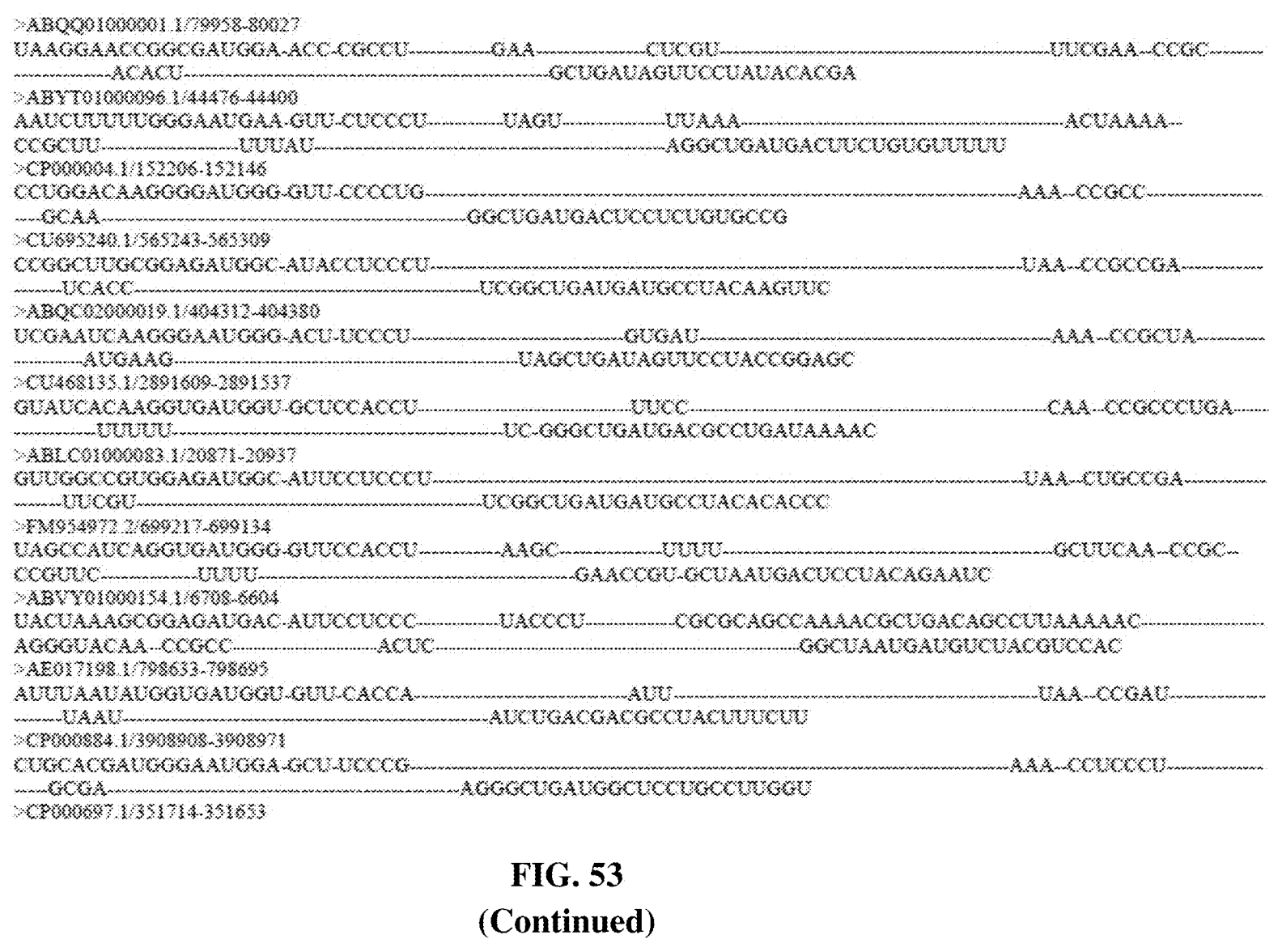

>ABQQ01000001.1/79958-80027
UAAGGGAACCCGCGAUGGA-ACC-CGCCU------GAA------CUCGU------------------CUCGU------UUUGAA--CCGC
------ACACU------------------------GCUGAUAGUUCCUAUACACGA

>ABYT01000096.1/44476-44400
AAUCUUUUGGGGAUGAA-GUU-CUCCCU-------UAGU-------UUAAA-----------------ACUAAAA--
CCGCU------UUUAU------------------AGGCUGAUGACUUCUGUGUUUUU

>CP000204.1/152206-152146
CCUGACAAGGGGAUGGG-GUU-CCCCUG-----------------------------------------AAA--CCGGC
---GCAA------------------GGCUGAUGACUCCUGUGCCG

>CU695240.1/363243-363309
CCGGCUUGCGGAGAUGGC-AUUACCUCCU-----------------------------------UAA--CCGCCGA
----UCACC------------------UCGGCUGAUGAUGCUUACAAGUUC

>ABQQ02000019.1/404312-404380
UCGAUCAAGGGGAUGGG-ACU-UCCCU------GUGAU-----------------------------AAA--CCGCUA
------AUCAAG------------------UAGGCUGAUAGUUCCUACCGGAGC

>CU468131.1/2391609-2391537
GUAUCACAAGGUGAUGGU-GCUCCACCU------UUCC-----------------------------CAA--CCGCCCUGA
------UUUU------------------UUC-CGGCUGAUGACGCCUGAUAAAAC

>ABLC01000003.1/20871-20957
GUUGGCCGUGGAGAUGGC-AUUCUCCCU------------------------------------------UAA--CUGCUGA
------UUCGU------------------UCGGCUGAUGAUGCCUACACACC

>FM954972.2/689217-689134
UAGGCACAUCAGGUGAUGGG-GUUCCACCU------AAGC------UUUU------------------GCUUCAA--CCGC
--CCGUUC------UUUU------------GAACCGU-GCUAAUGACUCCUACAGAAUC

>ABYT01000154.1/6708-6604
UACUAAAGGGGAACAUGAC-AUUCCUCCC------UACCCU--------------CGCGCGCAGCCAAACGCUGACAGCCUUAAAAC
AGGGUACAA--CCGC------ACUC------------------GGCUAAUGAUGUCUACGCCAC

>AE017198.1/798633-798695
AUUUAAUAUGGGUGAUGGU-GUU-CACCA------AUU------------------------------UAA--CCGAU
------UAAU------------------AUCUGACGACGCCUACUUUCUU

>CP000884.1/3908908-3908971
CUCCACGAUCGGAUGGA-GCUUCCCG----------------------------------------------AAA--CCUGCCU
---GCGA------------------AGGGCUGAUGGCUCCUGCCUUGGU

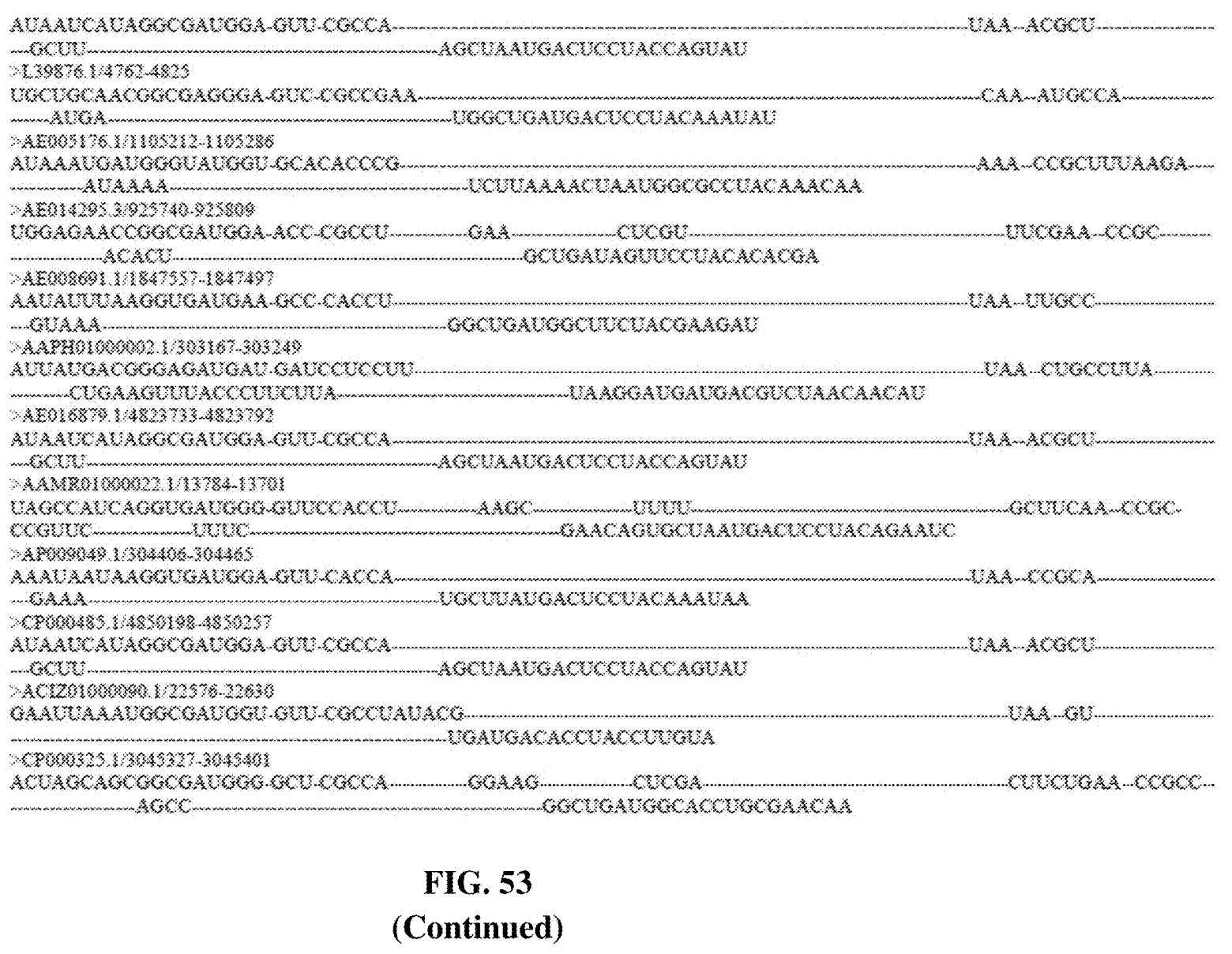

AUAAUCAUAGGCGAUGGA-GUU-CGCCA --------------------- UAA--ACGCU--------
-GCUU----------------------- AGCUAAUGACUCCUACCAGUAU

>L39876.1/4762-4825
UUCUCGCAACGGCGACGGA-GUU-CGCGAA-------------------- CAA--AUGCCA-------
------AUGA------------------ UGGCUGAUGACUCCUACCAAUAU

>AE005176.1/1118213-1105386
AUAAAUGCGGUAUGGU-GCACACCCU--------------- AAA--CCGUUUAACA---------
-----AUAAAA----------------- UCUUAAAACUAAUGCGCCUACCAACAA

>AE014295.3/925740-925809
UGGAGAACCGGCGAUGGA-ACC-CGCCU -------- GAA-------- CUCGU--------------
----ACACU------------------- GCUGAUAGUUCCUACACACGA

>AE008691.1/1847557-1847497
AAUAUUAAGGCGAUGGA-GCC-CACCU--------------------- UAA--UUUGCC-------
-GUAAA---------------------- GGCUGAUGGCUUCUUACGAAGAU

>AAPH01000002.1/303167-303249
AUUAUGACGGGAGAUGAU-GAUCCUCCU-------------- UAA--CUGCCUUA----------
----CUGAAGUUUACCCUUCUUA----- UAAUGAUGAUGACGUCUAACAACAU

>AE018879.1/4825733-4825792
AUAAUCAUAUAGGUGAUGGA-GUU-CGCCA --------------------- UAA--ACGCU--------
-CCUU----------------------- AGCUAAUGACUCCUACCAGUAU

>AAMR01000002.1/13784-13701
UAGCCAUCAGGGGAUGGG-GUUCC-ACCU -------- AGC--------- UUUU-----------------
-CCGUUC-------- UUUU -------- GAACAGUGCUAAUGACUCCUACAGAAUC

>AP009049.1/304406-304465
AAUAAUAAGGUGGAUGGA-GUU-CACCA --------------------- UAA--CCGCA--------
-CAAA----------------------- UGCUUAUGACUCCUACCAAAUAA

>CP000485.1/4830198-4830237
AUAAUCAUAGGCGAUGGA-GUU-CGCCA --------------------- UAA--ACGCU--------
-GCUU----------------------- AGCUAAUGACUCCUACCAGUAU

>ACIZ01000080.1/22576-22630
GAAUUAAAUGCCGAUGGU-GUU-CGCCUAUACG---------------- UAA--GU----------
-------------- UGAUGACACCUACCUGUA

>CP000325.1/3043227-3043401
ACUAUAGCGCGGCGAUGGG-GAUGGG-GCU-CGCCA -------- GGAAG-------- CUCGA-----------
------AGCC------------------ GGCUGAUGGCACCUGGCCUGCGAACAA ---- CUUCUGAA--CCGCC-----

FIG. 53
(Continued)

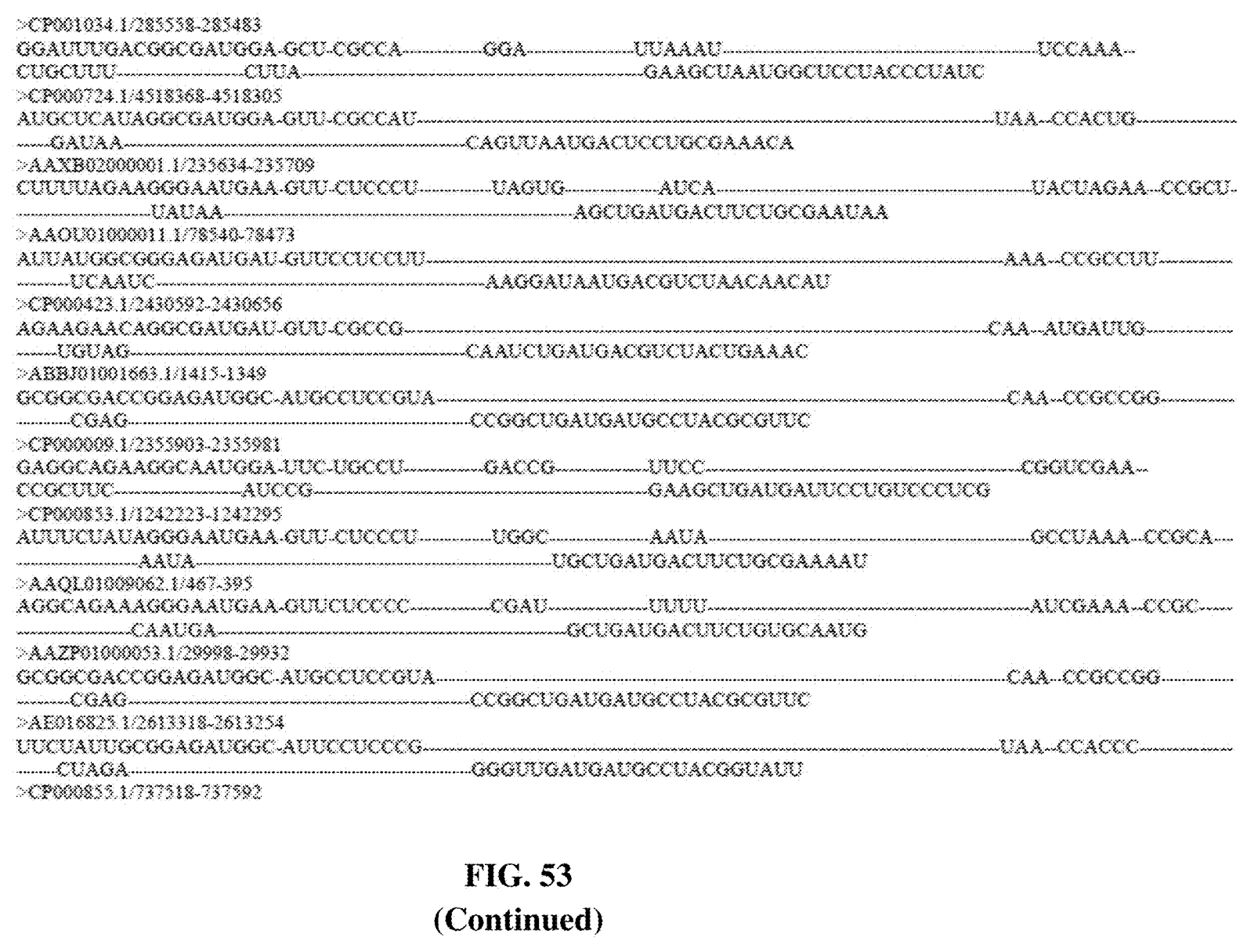

>CP001034.1/285558-285483
GGAUUGACGCGAUGGA_GCU_CGCCA----------GGA----------UUAAU----------UCCAAA--
>CP00724.1/451868-451805
CUGCUU--------------CUUA----------GAAGCUAAUGGCUCCUCUACCCUAUC
>CP00072.1/451868-451805
AUGCUCAUAGGCGAUGGA_GUU_CGCCAU----------CAGUUAAUGACUCCUCGCGAAACA----------UAA--CCACUG--
>AAXB02000001.1/235634-235709
CUUUUAGAAGGGAUUGAA_GUU_CUCCCU----------UAGUG----------AUCA----------UACUAGAA--CCGCU-
>AAQL01000011.1/78348-78473
AUUAUCGCGGCGAGAUGAU_GUUCCUCCUU----------AGCUGAUGAUGACUUCUGCGAAUAA
>CP00423.1/240682-240656
UCAAUC----------AAGGAUAAUGACGUCUACAACAU----------AAA--CCGCCUU--
>ABB01001663.1/1415-1349
AGAAGACAAGCGGAUGAU_GUU_CGCCG----------CAAUCUGAUGACGUCUACUGAAAC----------CAA--AUGAUUG--
>CP00809.1/2355983-2355981
UGUAG--------------------
>CP00809.1/2355983-2355981
GCGCGACCGGAGAUGGC-AUGCCUCCGUA----------CCGGCUGAUGAUGCCUACGCGUUC----------CAA--CCGCGG--
>CP00853.1/1242223-1242295
CGAG----------AUCCG----------GACCG----------UUCC----------CGGUCGAA-
>AAQL01009062.1/1467-395
CCGCUC----------AUCCG----------GAAGCUGAUGAUCCUGUCCCUCG
>AAZP01000053.1/29988-29993
AUUUCUUAAGGGAAUGAA_GUU_CUCCCU----------UGGC----------AAUA----------GCCUAAA--CCGGCA-
>AAZP01000053.1/29988-29993
AGGCGAGAAGGGGAUGAA_GUUCUCCCC----------UGCUGAUGACUUCUGCGAAAAU
>AE016823.1/2613318-2613254
CAAUGA----------CGAU----------UUUU----------AUCGAAA--CCGC--
>AE016823.1/2613318-2613254
GCGGCCAGACGCGGCAUGGC-AUGCCUCCGUA----------GCUGAUGACUUCUGUCGAAUG
>CP00853.1/737318-737592
CGAG----------CCGGUCGAUGAUGAUCCUACGCGUUU----------CAA--CCCCGG--
>CP00853.1/737318-737592
UUCCUAUUGCGGCGAGAUGGC-AUUUCUCCCG----------GGGUUGAUGAUGAUGCCUACGGUAUU----------UAA--CCACCC--
CUAGA----------

FIG. 53
(Continued)

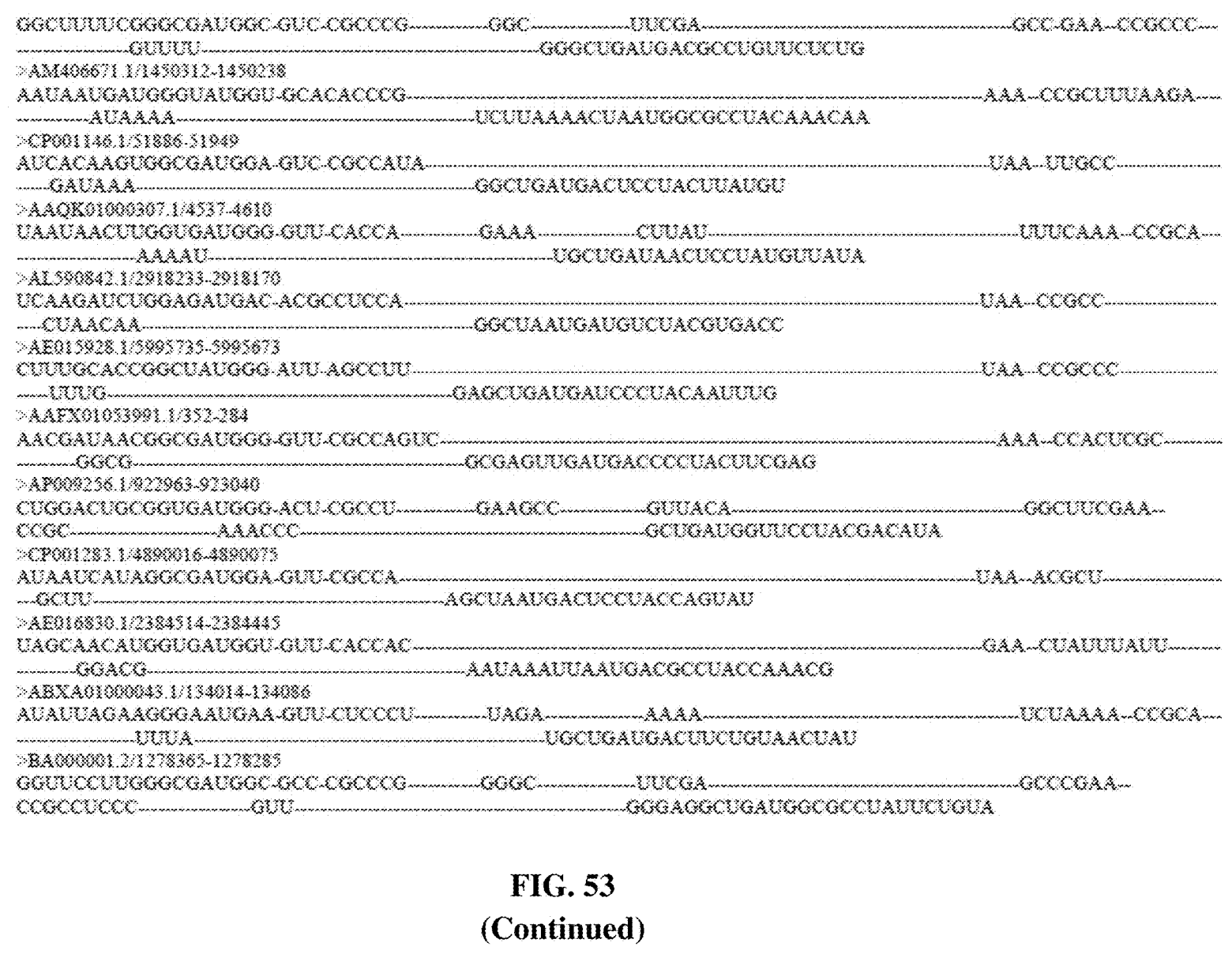

GGCUUUUCGGCGGAUGGC-GUC-CGCCCG---------GGC----------UUCGA----------------GCC-GAA--CCGCC---
----------------------GUUUU----------------------GGCGUGAUGAUGGCCGUUCUCUG
>AM406671.1/1450512-1450238
AAUAAUGAUGGGUAUGGU-GCACCCG----------------------AAA--CCGCUUUAAGA---
---------ATAAAA-----------------------------UCUUAAAACUAAUGCGCCUACAAACAA
>CP001146.1/51886-51949
AUCACAAGUGGCGAUGGA-GUC-CGCCAUA-------------------UAA--UUGCC---
----------GAUAAA--------------------------------GGCUGAUGACUCCUACUUAUGU
>AAQK01000307.1/4537-4610
UAAUAACUUCGUGAUGGG-GUU-CACCA----------GAAA-----CUUAU----------------UUUCAAA--CCGCA---
----------AAAAU----------------------------UGCUGAUAACUCCUAUGUUAUA
>AL590842.1/2918233-2918170
UCAAGAUUCUGGAGAUGAC-ACGCCUCCA-------------------UAA--CCGCC---
----------CUAACAA---------------------------GGCUAAUGAUGUCUACGUGAAC
>AE015928.1/3999725-3998873
CUUUGCACCGGCUAUGGG-AUU-AGCCUU-------------------UAA--CCGCC---
----------UUUG-----------------------------GAGCUGAUGAUCCUACAAUUG
>AAFX01103991.1/352-284
AACCGAUAACGGCGGAUGG-GUU-CGCCAGUC----------------AAA-CCACUCGC---
----------GGCG-------------------------GCGAGUUGAUGACCCUACUUCGAG
>AP009236.1/922963-923040
CUGGACUGCGGGUGGGC-ACU-CGCCU----------GAAGCC-----GUUACA----------------GGCUUCGAA---
----------AAACCC----------------------------GCUGAUGGUUCCUACGACAUA
>CP001283.1/4890816-4890875
AUAAUCAUAGGCGAUGGA-GUU-CGCCA-------------------UAA--ACGCU---
----------GCUU-----------------------------AGCUAAUGACUCCUACCAGUAU
>AE016830.1/2384514-2384445
UAGCAACAUGGCGAUGGU-GUU-CACCAC------------------GAA--CCAUUUAUU---
----------GGACG--------------------------AAUAAAUUAAUGAGCCUACCAAACG
>ABXA01000043.1/134014-134086
AUAUUAGAAGGCGAUGAA-GUU-CUCCCU----------UAGA------AAAA----------------UCUAAAA--CCGCA---
----------UUUA----------------------------UGCUGAUGACUUCUGUAACUAU
>BA000001.2/128365-128235
GGUUCCUUCGGGCGAUGGC-GCC-CGCCCG--------GGGC-------UUCGA----------------GCCCCGAA---
----------CCGCCUCCC-------GUU--------------GGGAGGCCUGAUGGGCGCCUAUUCUGUA

FIG. 53
(Continued)

Figure 53:
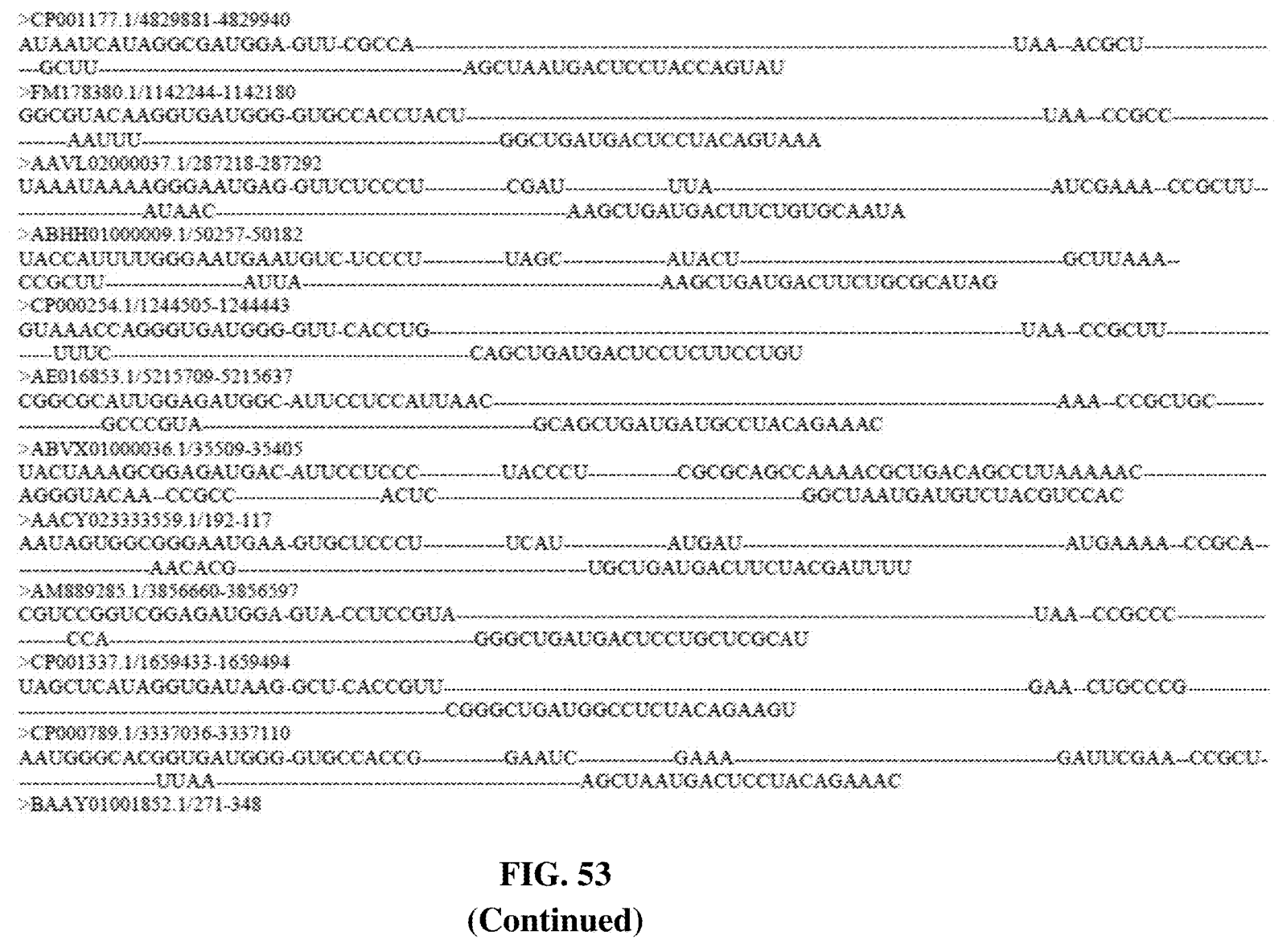

>CP001177.1/4826881-4829940
AUAAUCAUAGGCGGAUGGA-GUU-CGCCA----------AGCUAAUGACUCCUACCAGUAU-------------------UAA--ACGCU-----
--GCUU-

>FM178380.1/114234-114210
GGCGUACAAGGUGAUGGG-GUCGCCACUACU------------CGUCGAUGACUCCUACAGUAAA----------------UAA--CCGCC-----
--AAUUU

>AAVL02000037.1/287218-287293
UAAAUUAA-AAGGUGAUGAG-GUUCUCCCU--------CGAU--------UUA--------------------AUCGAAA--CCGCUU---
------AUAAC-------AAGCUGAUGACUUCUGUCGCAAUA

>ABHH01000009.1/50277-50182
UACCAUUUGGCGAAUGAUGUC-UCCCU--------UAGC------AUACU-----------------CCUUAAA------
--CCGCU--------AUUA--------AAGCUGAUGACUUCUGCGCAUAG

>CP000254.1/1244305-1244443
GUAAACCAGGGUGAUGGG-GUU-CACCUG--------------CAGCUGAUGAGACUCCUCUCUGU---------UAA--CCGCU-----
--UUC

>AE016853.1/5215709-5215637
CGGCCGCAUUGGAGAAUGGC-AUUCCUCCAUUAAC------------GCAGCUGAUGAUGCCUACAGAAAC---------AAA--CCCCGC-----
--GCCCGUA

>ABVX01000036.1/35589-35405
UACUUAAGCGGAUGAC-AUUUCCUCC--------UACCCU--------CGGCCAGCCAAAACCCUGACAGCCUUAAAAAC
AGGGUACAA--CCGCC--------ACUC--------------------GGCUAAUGAUGUCUACGUCCAC

>AACY023333359.1/192-117
AAUAGUGCGCGGAAUGAA-GUGCUCCCU---------UCAU--------AUGAU--------------AUGAAAA--CCGCA---
----AACACG---------UCCUGCAUUGACUUCUUACGAUUUU

>AM889285.1/3856660-3856597
CGUCCGGUCGGAUGAUGGA-GUA-CCUCCGUA------------------GGGGCUGAUGACUCCUGCUCGCAU---------UAA--CCGCC-----
--CCA

>CP001337.1/1659433-1659494
UAGCUCAUAAGUGAUGAG-GCU-CACCGUU-----------CGGGCCGAUGGCCCUUACAGAGU---------GAA--CUGCCCQ----

>CP000789.1/3357016-3357110
AAUGGGCACGGUGAUGCG-GUGCCACUG--------GAAUC--------GAAA-----------------GAUUGGAA--CCGCU---
----UUAA-------------AGCUAAUGACUCCUACAGAAAC

>BAAY01001852.1/271-348

Figure 53:
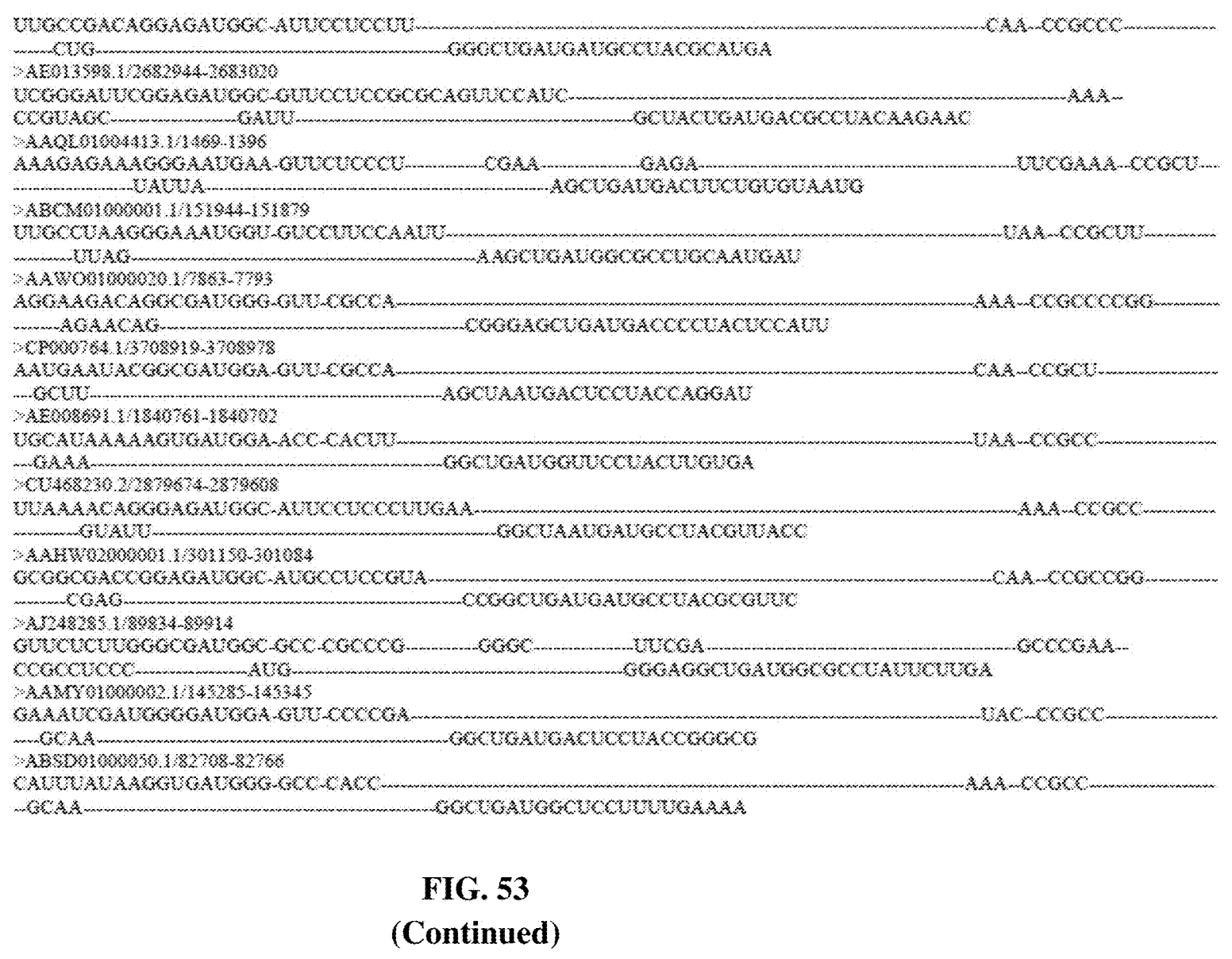

UUGCCGACAGGAGGAUGGC-AUUCUCUCCU----------------------------------------CAA-CCGCCC--------
----CUG--------------------------------GGCUGAUGAUGAUGCCUACCAUGA
>AE013598.1/2682944-2683020
UCCGGAUUCGGAGAUGGC-GUUCCUCCCGCGCAGUUCCAUC----------------------------------------AAA-
CCGUAGC----------GAUU---------------------------------GCUACUGAUGACGCCUACAAGAAC
>AAQL01004413.1/1469-1396
AAGGAGAAAGGGAUGAA-GUUCUCCCU----------CGAA----------GAGA-----------------UUCGAAA-CCGCU----
UAUUA--------------------------------AGCUGAUGACUUCUGUGUAAUG
>ABCM01008001.1/15194-15879
UUGCCUAAGGGAAUGHU-GUCCUUCCAAUU----------------------------------------UAA-CCGCUU----
----UAC--------------------------------AAGCUGAUGGCGCCUGCAAUGAU
>AAWO01008020.1/7803-7793
AGGAAGACAGGCCAUGKG-GUUCGCCA----------------------------------------AAA-CCGCCCCGG----
----AGAACAG--------------------------------CGGGAGCUGAUGACCCUACUCCAUU
>CP000784.1/3708919-3708978
AAUGAUACGGCGAUGGA-GUUUCGCCA----------------------------------------CAA-CCGCU----
----GCUU--------------------------------AGCUAAUGACUCCUACCAGGAU
>AE008691.1/1840761-1840702
UGCAUAAAAGUUGAUGGA-ACC-CACUU----------------------------------------UAA-CCGCC----
----GAAA--------------------------------GGCUGAUGGUUCUUACUUGUGA
>CU468230.2/3879674-3879608
UUAAAACAGCGAGAUGGC-AUUCCUCCCUUGAA----------------------------------------AAA-CCGCC----
----GUAUU--------------------------------GGCUAAUCAUGCCUACGUUACC
>AAHW02008001.1/301152-301084
GCCGGCCGGAGAUGGC-AUUCCUCCGUA----------------------------------------CAA-CCGCCGG----
----CGAG--------------------------------CCGGCUGAUGAUGCCUACGCGUUC
>AD246281.1/89834-89914
GUUCUUGGCGAUCGC-GCC-CGCCCG----------UUCGA----------GGGC-----------------GCCCGAA----
CCGCCUCC----------AUG--------------------------------GGGAGGCUGAUGGCGCCCAUUCUGA
>AAMY01008802.1/147285-145345
GAAUCGAUGGGGAUGGA-GUU-CCCGA----------------------------------------UAC-CCGCC--------
----GCAA--------------------------------GGCUGAUGACUCCUACCGGGCG
>ABSD01008050.1/82708-82766
CAUUUAUUAACGHUGAUGGC-GCC-CACC----------------------------------------AAA-CCGCC--------
----GCAA--------------------------------GGCUGAUGGCUCCUUUUGAAAA

UUGCAAUUACGGAAUGGU GUCCUUCCGAUU...............CAA-CCGAUUU.......

UUUCA................AAAGCUAAUGGCGCUACAAUAGA

>AAFX01046182.1/76-12
AACCCCAAGGGAAAUGGU-GUC-UUCCUUCGAC.........................AAA-CCGCU..........AACUGAUGACGGCCUUCAAAUCG
UGAA

>AAQL01000312.1/1870-1949
UAUUAACUUGGUGAUGGG-GUU-CACCA..........GAAA........CUUAU.........UUUCAAA-CCGC......
AAUU...............GCUGAUAACUCCUAGGUUAUA

>AAEW02000001.1/156146-156076
CAUGUUAACGGGAAUGGA GUUCUCCCGG...................................UAA-CCGCUG........
UCGAUUUUU.................CAGGCUGAUGACUCGGUAUGAGG

>ABCQ02000039.1/237860-237932
AUAAGUACCGGGAAUGAA-GUU-CUCCCU.........UAGU.........CUG...........ACUAGAA-CCGCU.......
UAUAA..............AGCUGAUGACUUCUGCAUUAUG

>CP001186.1/4973458-4973517
AUAAUUCAGAGGCGGAUGGA-GUU-CGCCA...................AGCUAAUGACUCCUACCAGUAU............UAA-CUGCU........
GCUU

>ABBM01000878.1/872-808
GCGGCGACCGGAGAUGGC-AUUGCCUUCCGUA.............CCGCUGAUGAUGGCCUAGCGGUUC.........CAA-CCGCCCG........
COAG

>CP001111.1/1611287-1611224
GGCGACGAUGGGGAUGGG-GCUUCCCCCGA.................ACGGCUGAUGGCUCCUGCCAAGAC........UAA-CCGGCCU.........
GAGA

>CP000679.1/782565-782843
GAAUAUGAGGCGGAUGGA-GUU-CGCCUU...................................CUUGUGGCUGAUUAACUCCUGUCCGUAU....AAA-UUGCCACAAG.....
AAUGAAAAUAC

>AL954242.1/1183968-1183902
AUAAUAAUUGCAAUGGC-AUUCCUUCCAU............GUUGGCUGAUGAUGGCCUAGGAUUGG...........UAA-CCGCCGC.......
AAUCU

>CP000318.2/204027-504091
AGCAACACAGGCGGAUUGGC-AUG-CGGCUU...........GCGCUGAUUAUGCCUACCUUCC.............GAA-CCGGC.......
CCCCGUCC

>CP000319.1/1049491-1049431
CUGGAAACAGGGAAUGGU-GUC-UCCCUU..........GGCUGAUGACUCCUGCUGACUG.............UCA-CCGCC.......
GACU

Figure 53:
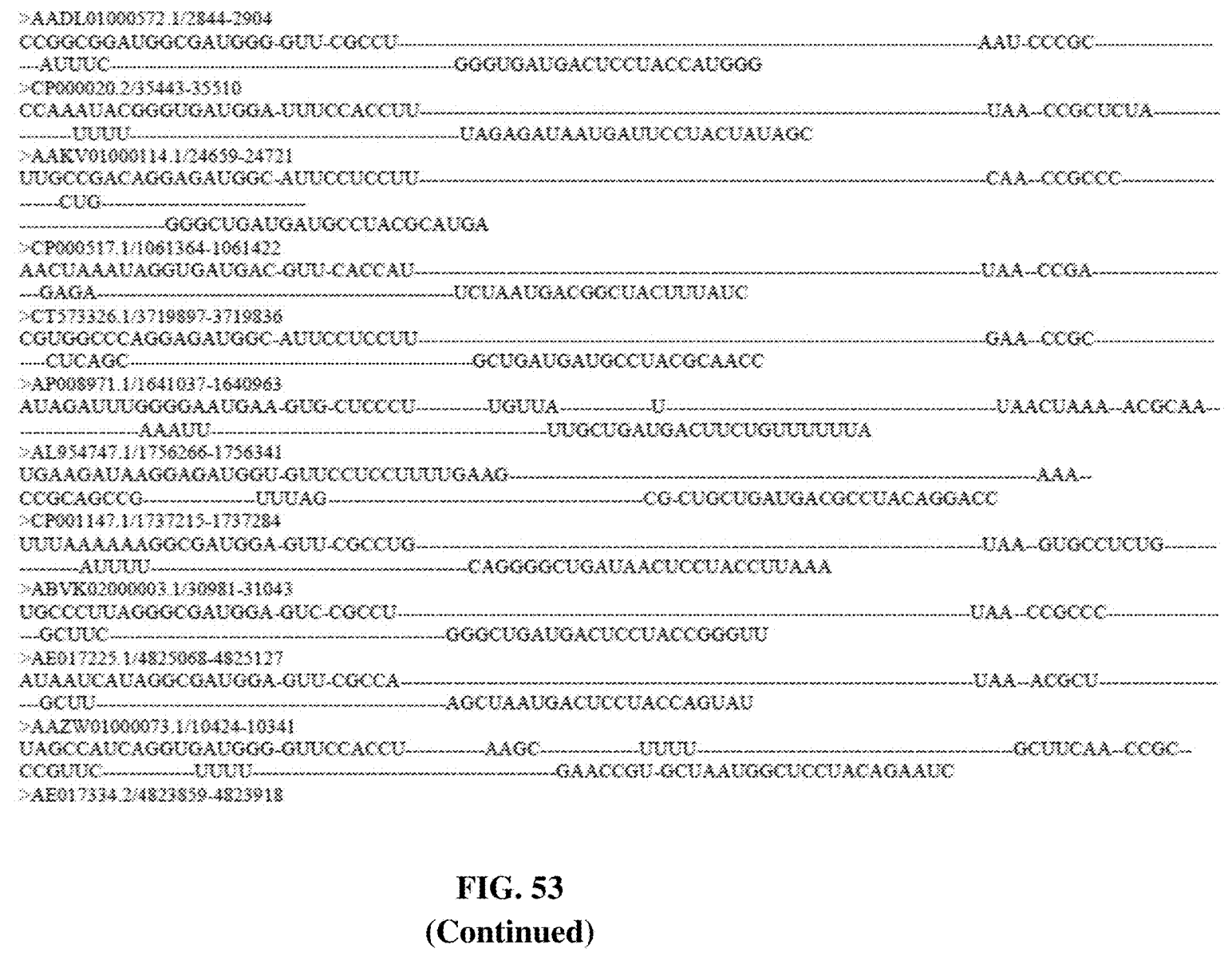

>AADL01000572.1/2844-2904
CCGGCGGAUGGGCGAUGGG-GUU-CGCCU----------GGGUGAUGGACUCCUACCAUGGG----------------AAU-CCCGC--------

>CP000820.2/3344-35310
-AUUUC----------------------------------------------------------------------------------------

>CCAAUACGGGUGAUCGA-UUUCCACCUU----------UAGAGAUAAUGAUUCCUACUAUAGC----------------UAA-CCGCUCUA----
-UUUU

>AAKV01000014.1/24659-24721
UUGCCGACAGGAGAUGGC-AUUCCUCCUU----------------------------------------------------CAA-CCGCC--------
-CUG

---------GGGCUGAUGAUGCCUACGCAUGA

>CP000517.1/10613X4-1061422
AACUAAAUAGGUGAUGAC-GUU-CACCAU----------UCUAAUGACGGCUACUUUAUC----------------UAA-CCGA--------
-GAGA

>CT573326.1/3719897-3719826
CGUGGCCCAGGAGAUGGC-AUUCCUCCUU----------GCUGAUGAUGCCUACGCAACC----------------GAA-CCGC--------
-CUCAGC

>AP008971.1/1641037-1640963
AUAGAUUUGGGGAAUGAA-GUG-CUCCCU----------UGUUA----------U----------------UAACUAAA-ACCCAA----
-AAUU                                       UUGCUGAUGACUCUGUUUUUUA

>AL954747.1/1756286-1756341
UGAACAUUAGGACGAUGGU-GUUCCUCUUUGAAG----------------------------------------------AAA-
CCGCAGCCG----------UUUAG----------CG-CUGCUGAUGACGCCUACAGGACC

>CP000147.1/1737215-1737284
UUUAAAAAGGCGAUGGA-GUU-CGCCUG----------CAGGGGCUGAUAAUCCUACCUUAAA----------------UAA-GUGCCUCUG-----
-AUUUU

>ABVX02000003.1/30981-31043
UGCCCUUAGGGCGAUGGA-GUC-CGCCU----------GGGCUGAUGACUCCUACGGGUU----------------UAA-CCGCC--------
-GCUUC

>AE017223.1/4835868-4825127
AUAAUCAUAGGCCGAUGGA-GUU-CCRCCA----------AGCUAAUGACUCCUACCAGUAU----------------UAA-ACGCU--------
-GCUU

>AAZW01000073.1/10424-10341
UAGCCAUCAGGUGAUGGG-GUUUCCACCU----------AAGC----------UUUU----------GCUUCAA-CCCGC--
CCGUUC----------UUUU----------GAACCGGU-GCUAAUGGCUCCUACAGAAUC

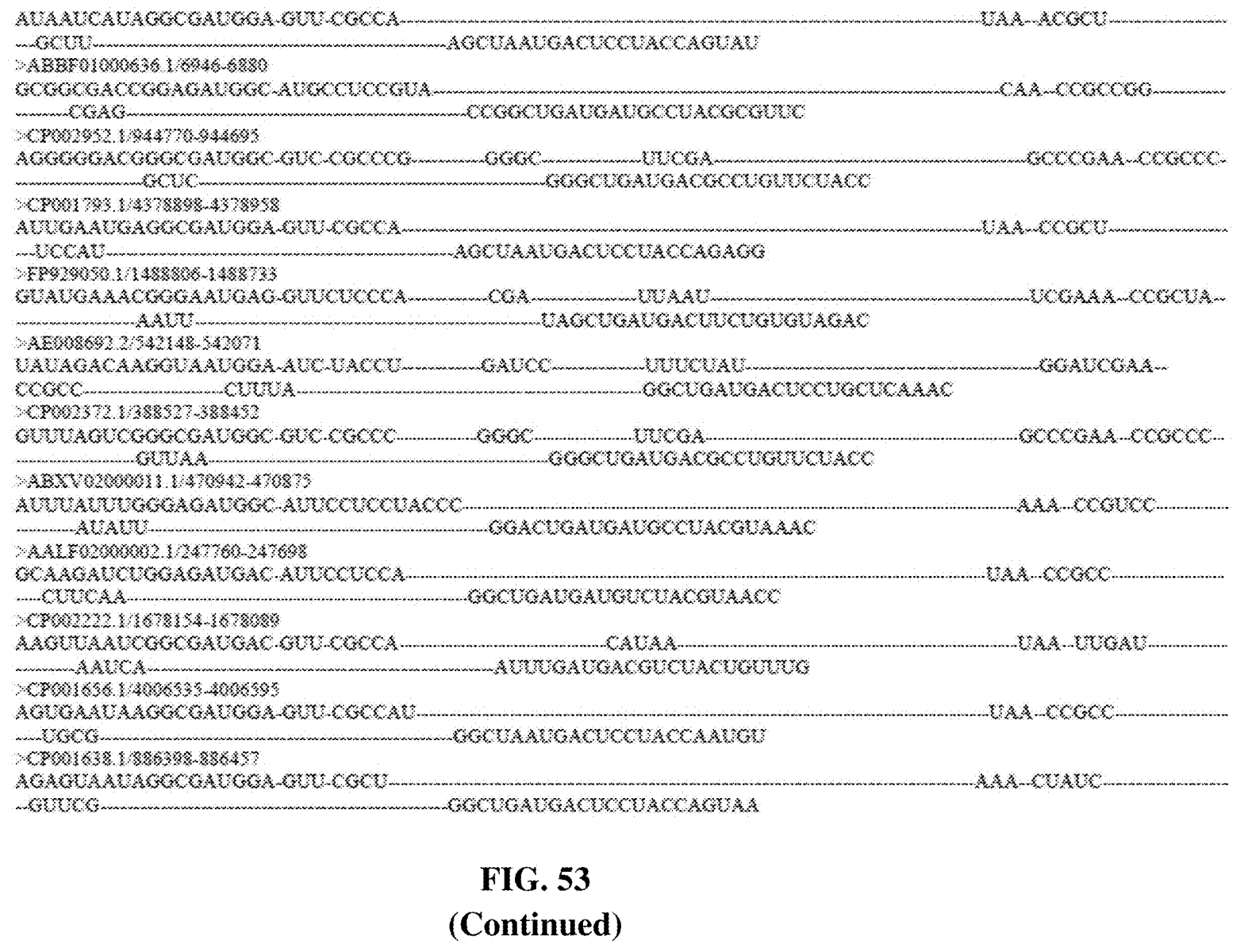

ATAAICATAGCCGAIGGA-GUU-CGCCA ------- AGUUAAUGACUCCUACCAGUAU ------- UAA--ACGCU-
-GCUU

>ABBF010006361 16946-6080
GCCGGCGACCGGCAGAUGGC-AUUCCUCCGUA ------- CCCGCCUGAUGAUGCCUACGCCUUC ------- CAA--CCGCCG-
-CGAG

>CP002953.1/944770-944695
ACGGCGGACGGGCGAUGGC-GUC-CGCCCG ----- -GCGC ------- GCCCGAA--CCGCCC-
-GCUC --------- GGGCUGAUGACCCUCGUUCUACC

>CP001793.1/4578898-4578958
AUUGAAUGAGCCGAUGGA-GUU-CGCCA ------- AGCUAAUGACUCCUACCAGAGG ------- UAA--CCGCU-
-UCCAU

>FP929050.1/1488806-1468733
GUAUGAAACGGGAGAUGAG-GUUCUCCCA ----- CGA-------------UU-AAU ------- UCGAAA--CCGCUA-
-AAUU -------- UAGCUGAUGAUCUCCGUGGUAGAC

>AEW08692.2/742148-542071
UAUAGAACAAGUUAUGGA-AUC-UACCU ------- GAUCC-------------UUUCUAU ------- GGAUCGAA--
-CCGCC ----CUUUA --------- GGCUGAUGAGACCCUGCUCAAAC

>CP002372.1/388527-38842
GUUUAGUCGGCCGAUGGC-GUC-CGCCC ----- -GGGC-------------UUCGA ------- GCCCGAA--CCGCCC-
-GUAA --------- GGGCUGAUGACCCCUGUUCUACC

>ABXV020000011 11470642-470875
AUUUAUUUGGGAGAUGGC-AUUCCUCCUACCC ------- CGACUGAUGAUGCCUACGUAAAC ------- AAA--CCGUCC-
-AUAUU

>AALF020000082.1/247760-247608
GCAAGAUUCGGGAGAUGAC-AUUCCCCCA ------- GGCUGAUGAUGUCUACGUAACC ------- UAA--CCGGC-
-CUCCAA

>CP002222.1/1678154-1678800
AAGUUAAUCGGCGAUGAC-GUU-CGCCA ------- CAUAA ------- UAA--UUGAU-
-AAUCA --------- AUUUGAUGACGCUUACUGUUUG

>CP001656.1/406535-406395
AGUUGAAUAAGGCGAUGGA-GUU-CGCCA ------- GGCUAAUGACUCCUACCAAUGU ------- UAA--CCGCC-
-UGCG

>CP001638.1/886398-886457
AGAGUAAUUAGGCCGAUGGA-GUU-CGCU ------- GGCUGAUGACUCCUACCAGUAA ------- AAA--CUAUC-
-GUUCG

FIG. 53
(Continued)

BIOSENSORS FOR DETECTING AND/OR NEUTRALIZING BIOAVAILABLE URANIUM AND RELATED U-SENSITIVE GENETIC MOLECULAR COMPONENTS, GENE CASSETTES, VECTORS, GENETIC CIRCUITS, COMPOSITIONS, METHODS AND SYSTEMS

CROSS REFERENCE TO RELATED APPLICATIONS

The present application is a continuation application of U.S. application Ser. No. 16/781,950 filed Feb. 4, 2020, which, in turn, claims priority to U.S. provisional application No. 62/801,077 entitled "Biosensors for detecting and/or Neutralizing Bioavailable Uranium and Related U-sensitive Genetic Molecular components, Gene Cassettes, Vectors, Genetic Circuits, Compositions, Methods and Systems" filed on Feb. 4, 2019, the disclosure of each of which is incorporated by reference in its entirety. The present application is further related to International Application Number PCT/US2020/016654 entitled "Biosensors for detecting and/or Neutralizing Bioavailable Uranium and Related U-sensitive Genetic Molecular components, Gene Cassettes, Vectors, Genetic Circuits, Compositions, Methods and Systems" filed on Feb. 4, 2020 herein incorporated by reference in its entirety. The present application is also related to International patent application PCT/US2018/061667, entitled "Biosensors for Detecting and/or Neutralizing Bioavailable Uranium And Related U-Sensitive Genetic Molecular Components, Gene Cassettes, Vectors, Genetic Circuits, Compositions, Methods And Systems" filed on Nov. 16, 2018 which claims priority to U.S. provisional application No. 62/587,753, entitled "Biosensors for Detecting and/or Neutralizing Bioavailable Uranium And Related U-Sensitive Genetic Molecular Components, Gene Cassettes, Vectors, Genetic Circuits, Compositions, Methods And Systems" filed on Nov. 17, 2017, the disclosure of each of which is incorporated by reference in its entirety.

STATEMENT OF GOVERNMENT GRANT

This United States Government has rights in this invention pursuant to Contract No. LDRD #16-LW-055 between the United States Department of Energy and Lawrence Livermore National Security, LLC, for the operation of Lawrence Livermore National Laboratory.

INCORPORATION BY REFERENCE STATEMENT FOR SEQUENCE LISTING

Further, the computer readable form of the sequence listing of the ASCII (XML) text file P2326-USC.xml, created on Apr. 4, 2025, with a size of 3,898,342 bytes measured on Windows Server 2019, is incorporated herein by reference in its entirety.

FIELD

The present disclosure relates to uranium (U) biosensors and related U-sensitive genetic molecular components, gene cassettes, vectors, genetic circuits, compositions, methods and systems. In particular, the present disclosure relates to U biosensors and related methods and systems to detect and/or neutralize bioavailable uranium and more particularly bioavailable uranyl oxycation.

BACKGROUND

Various methods and systems such as spectroscopy as well as antibodies and DNA enzymes are available to monitor environmental U concentrations which is important to minimize human exposure and inform remediation strategies.

In particular, detection of U in an environment in situ, and more particularly detection of bioavailable U that can transverse the cell membrane and exert toxicity, is an important part of an evaluation of the potential risk of environmental U exposure.

However, despite availability of various approaches, development of sensing technologies that provide sensitive, selective and/or cost-effective detection of bioavailable U is still challenging.

SUMMARY

Provided herein are U biosensors, and related U-sensing genetic molecular components, gene cassettes, genetic circuits, compositions, methods and systems which in several embodiments can be used to detect and/or neutralize uranium and in particular bioavailable $UF_6$, or its stable hydrolysis product $UO_2F_2$, which is typically produced in U enrichment operations.

According to a first aspect, a $UO_2F_2$-biosensor is described comprising a U-sensing genetic molecular component and an F-sensing riboswitch configured to report and/or neutralize uranium in presence of bioavailable Uranium and Fluoride, in a single output or dual output configuration. The $UO_2F_2$-biosensor comprises a genetically modified bacterial cell capable of natively and/or heterologously expressing histidine kinase 1363 herein also UrpS, and U sensitive transcriptional regulator 1362 herein also UrpR.

In the $UO_2F_2$-biosensor, the genetically modified bacterial cell is an engineered bacterial cell comprising a 1362 U-sensing reportable genetic molecular component and/or a 1362 U-sensing/U-neutralizing genetic molecular component, each comprising a U-sensitive promoter in a configuration wherein the U-sensitive promoter directly initiates expression of the 1362 U-sensing reportable molecular component and/or of the 1362U-neutralizing molecular component in presence of bioavailable U.

In the U-biosensor, the 1362 U-sensitive promoter comprises a 1362 (UrpR) binding site having a DNA sequence (SEQ ID NO: 1)
$N_1N_2N_3N_4N_5N_6N_7N_8N_9N_{10}N_{11}N_{12}N_{13}N_{14}N_{15}N_{16}N_{17}N_{18}$, wherein $N_1$ is C or T, preferably C;

$N_2$ is G or A, preferably G;

$N_3$ is T or C, preferably T;

$N_4$ is C;

$N_5$ is A or G, preferably A;

$N_6$ is G or C, preferably G;

$N_7$ C or G;

$N_8$ is any nucleotide;

$N_9$ is any nucleotide;

$N_{10}$ is any nucleotide;

$N_{11}$ is any nucleotide;

$N_{12}$ is T or C;

$N_{13}$ is G;

$N_{14}$ is T or C, preferably T;

3

$N_{15}$ is C;

$N_{16}$ is A or C, preferably A;

$N_{17}$ is G; and $N_{18}$ is C or G, and wherein $N_1$ to $N_{17}$ are selected independently.

In the $UO_2F_2$-biosensor, the genetically modified bacterial cell is an engineered bacterial cell further comprising an F-sensing riboswitch within at least one of the 1362 U-sensing reportable genetic molecular component wherein the 1362 U-sensing reportable genetic molecular component, is transcribed in presence of an effective amount of bioavailable fluoride, an F-sensing reportable genetic molecular component in a configuration wherein the F-sensing reportable genetic molecular component is transcribed in presence of an effective amount of bioavailable fluoride, and an F sensitive genetic circuit in which at least one molecular component is a reportable molecular component (and in particular one or more reportable genetic molecular component and/or one or more reportable cellular molecular component), the reportable molecular component expressed when the genetic circuit operates according to the circuit design in presence of bioavailable F.

In the $UO_2F_2$-biosensor comprising the F-sensing riboswitch within the 1362 U-sensing reportable genetic molecular component, the F-sensing riboswitch and the 1362 U-sensing reportable genetic molecular component are are in a single output configuration.

In the $UO_2F_2$-biosensor comprising the F-sensing reportable genetic molecular component and/or the F-sensing genetic circuit, the F-sensing riboswitch and the 1362 U-sensing reportable genetic molecular component are in a dual output configuration.

In some embodiments, the genetically modified bacteria are bacteria incapable of natively expressing the histidine kinase 1363 (UrpS) and the U-sensitive transcriptional regulator 1362 (UrpR) (e.g. *E. coli* bacteria). In those embodiments the bacterial cell is further engineered to include a 1362 U-sensing regulator genetic molecular component comprising an endogenous or exogenous gene encoding histidine kinase 1363 (UrpS), and an endogenous or exogenous gene encoding U-sensitive transcriptional regulator 1362 (UrpR) in a configuration wherein the a gene encoding histidine kinase 1363 (UrpS), and a gene encoding response regulator 1362 are expressed upon activation of a controllable promoter.

In some embodiments, the genetically modified bacteria are bacteria capable of natively expressing histidine kinase 1363 (UrpS), and U-sensitive transcriptional regulator 1362 (UrpR) (e.g. proteobacteria such as certain alpha proteobacteria, beta proteobacteria and/or gamma proteobacteria identifiable by a skilled person upon reading of the present disclosure). In some of those embodiments, the endogenous genes encoding the histidine kinase 1363, and the U-sensitive transcriptional regulator 1362 (UrpR), are knocked out and the genetically engineered bacterial cell is further engineered to include a 1362 U-sensing regulator genetic molecular component comprising an endogenous or exogenous gene encoding histidine kinase 1363 (UrpS), and an endogenous or exogenous gene encoding U-sensitive transcriptional regulator 1362 (UrpR) in a configuration wherein the a gene encoding histidine kinase 1363 (UrpS), and a gene encoding response regulator 1362 (UrpR) are expressed upon activation of a controllable promoter.

In some embodiments, the genetically modified bacteria are bacteria incapable of natively expressing an F-sensing riboswitch (e.g. *Caulobacter crescentus*) identifiable by a skilled person upon reading of the present disclosure). In some embodiments, the genetically modified bacteria are bacteria capable of natively expressing an F-sensing riboswitch (e.g. *Sphingomonas* sp. MM-1, and *Caulobacterales bacterium*) identifiable by a skilled person upon reading of the present disclosure). In some of those embodiments, the endogenous genes encoding the F-sensing riboswitch, are preferably knocked out.

According to a second aspect, a $UO_2F_2$-biosensor is described, comprising a U-sensitive F-sensitive genetic circuit wherein a U-sensing genetic molecular component and an F-sensing riboswitch are configured to report and/or neutralize uranium in presence of bioavailable Uranium and Fluoride, in a single output or dual output configurations.

The $UO_2F_2$ biosensor according to the second aspect comprises a genetically modified bacterial cell capable of natively and/or heterologously expressing histidine kinase 1363 (UrpS) and response regulator 1362 (UrpR). In the $UO_2F_2$-biosensor, the genetically modified bacterial cell is an engineered bacterial cell comprising a U-sensitive F-sensitive genetic circuit in which molecular components are connected one to another in accordance to a circuit design by activating, inhibiting, binding or converting reactions to form a fully connected network of interacting components. In the 1362 U-sensitive F-sensitive genetic circuit at least one molecular component is a 1362 U-sensing genetic molecular component in which a U-sensitive promoter is activated or repressed in presence of bioavailable U, the U sensitive promoter comprising a U-sensitive 1362 (UrpR) binding site having a DNA sequence (SEQ ID NO: 1)

$N_1N_2N_3N_4N_5N_6N_7N_8N_9N_{10}N_{11}N_{12}N_{13}N_{14}N_{15}N_{16}N_{17}N_{18}$, wherein $N_1$ is C or T, preferably C;

$N_2$ is G or A, preferably G;

$N_3$ is T or C, preferably T;

$N_4$ is C;

$N_5$ is A or G, preferably A;

$N_6$ is G or C, preferably G; $N_7$ C or G;

$N_8$ is any nucleotide;

$N_9$ is any nucleotide;

$N_{10}$ is any nucleotide;

$N_{11}$ is any nucleotide;

$N_{12}$ is T or C;

$N_{13}$ is G;

$N_{14}$ is T or C, preferably T;

$N_{15}$ is C;

$N_{16}$ is A or C, preferably A;

$N_{17}$ is G; and $N_{18}$ is C or G, and wherein $N_1$ to $N_{17}$ are selected independently.

In the U-sensitive F-sensitive genetic circuit, at least one molecular component is a reportable molecular component (and in particular one or more reportable genetic molecular component and/or one or more reportable cellular molecular component), and/or a U-neutralizing molecular component, (in particular one or more U-neutralizing genetic molecular component and/or one or more U-neutralizing cellular molecular component).

In the $UO_2F_2$-biosensor, the 1362 U-sensing F-sensing genetic circuit further comprises an F sensing riboswitch within at least one genetic molecular component of the molecular components of the U-sensitive F-sensitive genetic circuit, in a configuration wherein the at least one genetic molecular component is transcribed in presence of an effective amount of bioavailable fluoride.

In the $UO_2F_2$-biosensor, the at least one reportable molecular component and/or the U-neutralizing molecular component are expressed when the genetic circuit operates according to the circuit design in presence of an effective amount of bioavailable U and an effective amount of bioavailable F in a single output or dual output configurations.

In some embodiments, the genetically modified bacteria are bacteria not capable of natively expressing the histidine kinase 1363 (UrpS) and the U-sensitive transcriptional regulator 1362 (UrpR) (e.g. E. coli bacteria). In those embodiments, the bacterial cell is further engineered to include a 1362 U-sensing regulator genetic molecular component comprising an endogenous or exogenous gene encoding histidine kinase 1363 (UrpS), and an endogenous or exogenous gene encoding U-sensitive transcriptional regulator 1362 (UrpR) in a configuration wherein the a gene encoding histidine kinase 1363 (UrpR), and a gene encoding response regulator 1362 (UrpR) are expressed upon activation of a controllable promoter.

In some embodiments, the genetically modified bacteria are bacteria capable of natively expressing histidine kinase 1363 (UrpS), and U-sensitive transcriptional regulator 1362 (UrpR) (e.g. proteobacteria, such as certain alpha proteobacteria, beta proteobacteria and/or gamma proteobacteria identifiable by a skilled person upon reading of the present disclosure). In some of those embodiments, the endogenous genes encoding the histidine kinase 1363 (UrpS), and the U-sensitive transcriptional regulator 1362 (UrpR), can be preferably knocked out and the genetically engineered bacterial cell is further engineered to include a 1362 U-sensing regulator genetic molecular component comprising an endogenous or exogenous gene encoding histidine kinase 1363 (UrpS), and an endogenous or exogenous gene encoding U-sensitive transcriptional regulator 1362 in a configuration wherein the a gene encoding histidine kinase 1363 (UrpS), and a gene encoding response regulator 1362 (UrpR) are expressed upon activation of a controllable promoter.

In some embodiments, the genetically modified bacteria are bacteria incapable of natively expressing an F-sensing riboswitch (e.g. Caulobacter crescentus) identifiable by a skilled person upon reading of the present disclosure). In some embodiments, the genetically modified bacteria are bacteria capable of natively expressing an F-sensing riboswitch (e.g. Sphingomonas sp. MM-1, and Caulobacterales bacterium) identifiable by a skilled person upon reading of the present disclosure). In some of those embodiments, the endogenous genes encoding the F-sensing riboswitch, are preferably knocked out.

According to a third aspect, a $UO_2F_2$-biosensor is described, comprising a U-sensing genetic molecular component and an F-sensing riboswitch configured to report and/or neutralize uranium in presence of bioavailable Fluoride, in a single output or double output configuration.

The $UO_2F_2$ biosensor comprises a genetically modified bacterial cell capable of natively and/or heterologously expressing histidine kinase UzcS and U-sensitive transcriptional response regulator UzcR.

In the U-biosensors, the genetically modified bacterial cell is an engineered bacterial cell comprising a UzcR U-sensing reportable genetic molecular component and/or a UzcR U-sensing U-neutralizing genetic molecular component, each comprising a U-sensitive promoter in a configuration wherein the U-sensitive promoter directly initiates expression of the UzcR U-sensing reportable molecular component and/or of the UzcR U-sensing U-neutralizing molecular component in presence of bioavailable U.

In the U-biosensor, the U-sensitive promoter comprises an UzcR binding site having a DNA sequence:

(SEQ ID NO: 2)
$$CATTACN_7N_8N_9N_{10}N_{11}N_{12}TTAA$$

wherein $N_7$-$N_{12}$ is independently any nucleotide, and in some embodiments any one of $N_7$-$N_{11}$ can independently be A.

In the $UO_2F_2$-biosensor, the genetically modified bacterial cell is an engineered bacterial cell further comprising an F-sensing riboswitch within at least one of the UzcR U-sensing reportable genetic molecular component wherein the UzcR U-sensing reportable genetic molecular component, is transcribed in presence of an effective amount of bioavailable fluoride, an F-sensing reportable genetic molecular component in a configuration wherein the F-sensing reportable genetic molecular component is transcribed in presence of an effective amount of bioavailable fluoride, and an F sensitive genetic circuit in which at least one molecular component is a reportable molecular component (and in particular one or more reportable genetic molecular component and/or one or more reportable cellular molecular component), the reportable molecular component expressed when the genetic circuit operates according to the circuit design in presence of bioavailable F.

In the $UO_2F_2$-biosensor comprising the F-sensing riboswitch within the UzcR U-sensing reportable genetic molecular component, the F-sensing riboswitch and the UzcR U-sensing reportable genetic molecular component are in a single output configuration.

In the $UO_2F_2$-biosensor comprising the F-sensing reportable genetic molecular component and/or the F-sensing genetic circuit, the F-sensing riboswitch and the UzcR U-sensing reportable genetic molecular component are in a dual output configuration.

In some embodiments, the genetically modified bacteria are bacteria not capable of natively expressing the histidine kinase UzcS, and the U-sensitive transcriptional response regulator UzcR (e.g. E. coli bacteria), and the bacterial cell is further engineered to include a UzcR U-sensing regulator genetic molecular component comprising an endogenous or exogenous gene encoding the histidine kinase UzcS, and an endogenous or exogenous gene encoding the U-sensitive transcriptional response regulator UzcR, in a configuration wherein the gene encoding the histidine kinase UzcS, and the gene encoding the U-sensitive transcriptional response regulator UzcR, are expressed upon activation of a controllable promoter.

In some embodiments, the genetically modified bacteria are bacteria capable of natively expressing the histidine kinase UzcS, and the U-sensitive transcriptional response regulator UzcR (e.g. proteobacteria, such as certain alpha proteobacteria, beta proteobacteria and/or gamma proteobacteria identifiable by a skilled person upon reading of the present disclosure). In some of those embodiments, in the bacterial cell, the endogenous genes encoding the histidine kinase UzcS, and the U-sensitive transcriptional response regulator UzcR, can be preferably knocked out and the genetically engineered bacterial cell can be further engineered to include a UzcR U-sensing regulator genetic molecular component comprising an endogenous or exogenous gene encoding histidine kinase UzcS, and an endogenous or exogenous gene encoding U-sensitive transcriptional response regulator UzcR in a configuration wherein the a gene encoding histidine kinase UzcS, and a gene encoding response regulator UzcR are expressed upon activation of a controllable promoter.

In some embodiments, the genetically modified bacteria are bacteria incapable of natively expressing an F-sensing ribo-switch (e.g. *Caulobacter crescentus*) identifiable by a skilled person upon reading of the present disclosure). In some embodiments, the genetically modified bacteria are bacteria capable of natively expressing an F-sensing riboswitch (e.g. *Sphingomonas* sp. MM-1, and *Caulobacterales bacterium*) identifiable by a skilled person upon reading of the present disclosure). In some of those embodiments, the endogenous genes encoding the F-sensing riboswitch, are preferably knocked out.

According to a fourth aspect, a $UO_2F_2$-biosensor is described, comprising a U-sensitive F-sensitive genetic circuit wherein a UzcR U-sensing genetic molecular component and an F-sensing riboswitch are configured to report and/or neutralize uranium in presence of bioavailable Uranium and Fluoride, in a single output or dual output configurations.

The U biosensor comprises a genetically modified bacterial cell natively and/or heterologously expressing histidine kinase UzcS, and response regulator UzcR.

In the $UO_2F_2$-biosensor, the genetically modified bacterial cell is an engineered bacterial cell comprising a U-sensitive F-sensitive genetic circuit in which molecular components are connected one to another in accordance to a circuit design by activating, inhibiting, binding or converting reactions to form a fully connected network of interacting components. In the UzcR U-sensitive F-sensitive genetic circuit at least one molecular component is a UzcR U-sensing genetic molecular component in which a U-sensitive promoter is activated or repressed in presence of bioavailable U, the U sensitive promoter comprising a UzcR binding site having DNA sequence:

(SEQ ID NO: 2)
CATTACN₇N₈N₉N₁₀N₁₁N₁₂TTAA wherein $N_7$-$N_{12}$ is independently any nucleotide, and in some embodiments any one of $N_7$-$N_{11}$ can independently be A.

In the UzcR U-sensitive F-sensitive genetic circuit at least one molecular component is a reportable molecular component (and in particular one or more reportable genetic molecular component and/or one or more reportable cellular molecular component), and/or a U-neutralizing molecular component, (in particular one or more U-neutralizing genetic molecular component and/or one or more U-neutralizing cellular molecular component), In the $UO_2F_2$-biosensor the genetically modified bacterial cell further comprises an F-sensing riboswitch within at least one genetic molecular component of the molecular components of the U-sensitive F-sensitive genetic circuit in a configuration wherein the at least one genetic molecular component is transcribed in presence of an effective amount of bioavailable fluoride.

In the $UO_2F_2$-biosensor, the at least one reportable molecular component and/or the a U-neutralizing molecular component are expressed when the genetic circuit operates according to the circuit design in presence of an effective amount of bioavailable U and an effective amount of bio-available F in a single output or dual output configurations. In some embodiments, the genetically modified bacteria are bacteria not capable of natively expressing the histidine kinase UzcS, and the U-sensitive transcriptional response regulator UzcR (e.g. *E. coli* bacteria). In those embodiments, the bacterial cell is further engineered to include a UzcR U-sensing regulator genetic molecular component comprising an endogenous or exogenous gene encoding the histidine kinase UzcS, and an endogenous or exogenous gene encoding the U-sensitive transcriptional response regulator UzcR, in a configuration wherein the gene encoding the histidine kinase UzcS, and the gene encoding the U-sensitive transcriptional response regulator UzcR, are expressed upon activation of a controllable promoter.

In some embodiments, the genetically modified bacteria are capable of natively expressing the histidine kinase UzcS, and the U-sensitive transcriptional response regulator UzcR (e.g. proteobacteria, such as certain alpha proteobacteria, beta proteobacteria and/or gamma proteobacteria identifiable by a skilled person upon reading of the present disclosure). In some of those embodiments, in the bacterial cell, the endogenous genes encoding the histidine kinase UzcS, and the U-sensitive transcriptional response regulator UzcR, are knocked out. and the genetically engineered bacterial cell is further engineered to include a UzcR U-sensing regulator genetic molecular component comprising an endogenous or exogenous gene encoding histidine kinase UzcS, and an endogenous or exogenous gene encoding U-sensitive transcriptional response regulator UzcR in a configuration wherein the gene encoding histidine kinase UzcS, and a gene encoding response regulator UzcR are expressed upon activation of a controllable promoter.

In some embodiments, the genetically modified bacteria are bacteria incapable of natively expressing an F-sensing ribo-switch (e.g. *Caulobacter crescentus*) identifiable by a skilled person upon reading of the present disclosure). In some embodiments, the genetically modified bacteria are bacteria capable of natively expressing an F-sensing riboswitch (e.g. *Sphingomonas* sp. MM-1, and *Caulobacterales bacterium*) identifiable by a skilled person upon reading of the present disclosure). In some of those embodiments, the endogenous genes encoding the F-sensing riboswitch, are preferably knocked out.

According to a fifth aspect, a $UO_2F_2$-biosensor is described comprising a U-sensing genetic circuit and an F-sensing riboswitch configured to report and/or neutralize uranium in presence of bioavailable Uranium and Fluoride in a dual output configuration. The $UO_2F_2$-biosensor comprises a genetically modified bacterial cell capable of natively and/or heterologously expressing histidine kinase 1363 herein also UrpS, and U sensitive transcriptional regulator 1362 herein also UrpR and/or natively and/or heterologously expressing histidine kinase UzcS, and response regulator UzcS.

In the $UO_2F_2$-biosensor, the genetically modified bacterial cell is an engineered bacterial cell comprising a U-sensitive genetic circuit in which molecular components are connected one to another in accordance to a circuit design by activating, inhibiting, binding or converting reactions to form a fully connected network of interacting components. In the U-sensitive genetic circuit at least one molecular component is a U-sensing genetic molecular component in which a U-sensitive promoter is activated or repressed in presence of bioavailable U.

In the U-sensitive genetic circuit, when the cell is capable of natively and/or heterologously expressing histidine kinase 1363 herein also UrpS, and U sensitive transcriptional regulator 1362 herein also UrpR, at least one molecular component is a 1362 U-sensing genetic molecular component in which the U sensitive promoter comprises a U-sensitive 1362 (UrpR) binding site having a DNA sequence (SEQ ID NO: 1)

$$N_1N_2N_3N_4N_5N_6N_7N_8N_9N_{10}N_{11}N_{12}N_{13}N_{14}N_{15}N_{16}N_{17}N_{18},$$

wherein $N_1$ is C or T, preferably C;

$N_2$ is G or A, preferably G;

$N_3$ is T or C, preferably T;

$N_4$ is C;

$N_5$ is A or G, preferably A;

$N_6$ is G or C, preferably G; $N_7$ C or G;

$N_8$ is any nucleotide;

$N_9$ is any nucleotide;

$N_{10}$ is any nucleotide;

$N_{11}$ is any nucleotide;

$N_{12}$ is T or C;

$N_{13}$ is G;

$N_{14}$ is T or C, preferably T;

$N_{15}$ is C;

$N_{16}$ is A or C, preferably A;

$N_{17}$ is G; and $N_{18}$ is C or G, and wherein $N_1$ to $N_{17}$ are selected independently.

In addition or in the alternative, when the cell is natively and/or heterologously expressing histidine kinase UzcS, and response regulator UzcS, in the U-sensitive genetic circuit at least one molecular component is a UzcR U-sensing genetic molecular component in which a U-sensitive promoter is activated or repressed in presence of bioavailable U, the U sensitive promoter comprising a UzcR binding site having DNA sequence:

(SEQ ID NO: 2)

$$CATTACN_7N_8N_9N_{10}N_{11}N_{12}TTAA$$

wherein $N_7$-$N_{12}$ is independently any nucleotide, and in some embodiments any one of $N_7$-$N_{11}$ can independently be A.

In the U-sensitive genetic circuit, at least one molecular component is a reportable molecular component (and in particular one or more reportable genetic molecular component and/or one or more reportable cellular molecular component), and/or a U-neutralizing molecular component, (in particular one or more U-neutralizing genetic molecular component and/or one or more U-neutralizing cellular molecular component), the reportable molecular component and/or the a U-neutralizing molecular component expressed when the genetic circuit operates according to the circuit design in presence of bioavailable U.

In the $UO_2F_2$-biosensor the genetically modified bacterial cell is an engineered bacterial cell further comprising an F-sensing riboswitch within at least one of a genetic molecular component of an F sensitive genetic circuit in which at least one molecular component is a reportable molecular component (and in particular one or more reportable genetic molecular component and/or one or more reportable cellular molecular component), the reportable molecular component expressed when the genetic circuit operates according to the circuit design in presence of bioavailable F; and an F-sensing reportable genetic molecular component in a configuration wherein the F-sensing reportable genetic molecular component is transcribed in presence of an effective amount of bioavailable fluoride.

In the $UO_2F_2$-biosensor, the F-sensing reportable genetic molecular component and the F-sensing genetic circuit are in a dual output configuration with the U-sensing genetic circuit.

In some embodiments, the genetically modified bacteria are bacteria incapable of natively expressing the histidine kinase 1363 (UrpS) and the U-sensitive transcriptional regulator 1362 (UrpR) (e.g. *E. coli* bacteria). In those embodiments the bacterial cell is further engineered to include a U-sensing regulator genetic molecular component comprising an endogenous or exogenous gene encoding histidine kinase 1363 (UrpS), and an endogenous or exogenous gene encoding U-sensitive transcriptional regulator 1362 (UrpR) in a configuration wherein the a gene encoding histidine kinase 1363 (UrpS), and a gene encoding response regulator 1362 are expressed upon activation of a controllable promoter.

In some embodiments, the genetically modified bacteria are bacteria capable of natively expressing histidine kinase 1363 (UrpS), and U-sensitive transcriptional regulator 1362 (UrpR) (e.g. proteobacteria such as certain alpha proteobacteria, beta proteobacteria and/or gamma proteobacteria identifiable by a skilled person upon reading of the present disclosure). In some of those embodiments, the endogenous genes encoding the histidine kinase 1363, and the U-sensitive transcriptional regulator 1362 (UrpR), are knocked out and the genetically engineered bacterial cell is further engineered to include a U-sensing regulator genetic molecular component comprising an endogenous or exogenous gene encoding histidine kinase 1363 (UrpS), and an endogenous or exogenous gene encoding U-sensitive transcriptional regulator 1362 (UrpR) in a configuration wherein the a gene encoding histidine kinase 1363 (UrpS), and a gene encoding response regulator 1362 (UrpR) are expressed upon activation of a controllable promoter.

In some embodiments, the genetically modified bacteria are bacteria not capable of natively expressing the histidine kinase UzcS, and the U-sensitive transcriptional response regulator UzcR (e.g. *E. coli* bacteria), and the bacterial cell is further engineered to include a U-sensing regulator genetic molecular component comprising an endogenous or exogenous gene encoding the histidine kinase UzcS, and an endogenous or exogenous gene encoding the U-sensitive transcriptional response regulator UzcR, in a configuration wherein the gene encoding the histidine kinase UzcS, and the gene encoding the U-sensitive transcriptional response regulator UzcR, are expressed upon activation of a controllable promoter.

In some embodiments, the genetically modified bacteria are bacteria capable of natively expressing the histidine kinase UzcS, and the U-sensitive transcriptional response regulator UzcR (e.g. proteobacteria, such as certain alpha proteobacteria, beta proteobacteria and/or gamma proteobacteria identifiable by a skilled person upon reading of the present disclosure). In some of those embodiments, in the bacterial cell, the endogenous genes encoding the histidine kinase UzcS, and the U-sensitive transcriptional response regulator UzcR, can be preferably knocked out and the genetically engineered bacterial cell can be further engineered to include a U-sensing regulator genetic molecular component comprising an endogenous or exogenous gene encoding histidine kinase UzcS, and an endogenous or exogenous gene encoding U-sensitive transcriptional response regulator UzcR in a configuration wherein the a gene encoding histidine kinase UzcS, and a gene encoding response regulator UzcR are expressed upon activation of a controllable promoter.

In some embodiments, the genetically modified bacteria are bacteria incapable of natively expressing an F-sensing riboswitch (e.g. *Caulobacter crescentus*) identifiable by a skilled person upon reading of the present disclosure). In some embodiments, the genetically modified bacteria are bacteria capable of natively expressing an F-sensing riboswitch (e.g. *Sphingomonas* sp. MM-1, and *Caulobacterales bacterium*) identifiable by a skilled person upon reading of the present disclosure). In some of those embodiments, the endogenous genes encoding, encoding a fluoride efflux pump are preferably knocked out. In some embodiments of the $UO_2F_2$-biosensors according to the third a fourth and a fifth aspect wherein the $UO_2F_2$-biosensor comprises a U-sensing genetic molecular component in which a U-sensitive promoter comprising a UzcR binding site, the genetically modified bacterial cell is a bacterial cell capable of natively expressing MarR family repressors such as $marR_1$ (CCNA_03498) and $marR_2$ (CCNA_02298) genes (e.g. proteobacteria, such as certain alpha proteobacteria, beta proteobacteria and/or gamma proteobacteria identifiable by a skilled person upon reading of the present disclosure). In those embodiments, the bacterial cell is preferably further engineered to knock out at least one endogenous MarR family repressors such as $marR_1$ and $marR_2$ genes to provide an amplified $UO_2F_2$-biosensor configured to provide an amplified signal following activation of the $UO_2F_2$-sensitive genetic circuit.

In some preferred embodiments of the $UO_2F_2$-biosensor s according to the third a fourth aspect and a fifth aspect wherein the $UO_2F_2$-biosensor comprises a U-sensing genetic molecular component in which a U-sensitive promoter comprises a UzcR binding site, the $UO_2F_2$-biosensor or the U-sensitive F sensitive genetic circuit, further comprises an amplifier genetic molecular component comprising a U-sensitive promoter and UzcY and/or UzcZ in a configuration wherein the U-sensitive promoter directly initiates expression of the amplifier molecular component.

According to a sixth aspect, a method to provide a $UO_2F_2$-biosensor is described, the method comprising genetically engineering a bacterial cell capable of natively and/or heterologously expressing histidine kinase 1363 (UrpS) and/or histidine kinase UzcS, and U sensitive response regulator 1362 (UrpR) and/or U sensitive response regulator UzcR in combination with a heterologous F-sensing riboswitch, the genetically engineering performed by introducing into the cell one or more U-sensing genetic molecular components configured to report and/or neutralize U herein described, an F-sensitive riboswitch within the one or more U-sensing genetic molecular components configured to report U, an F-sensitive riboswitch within an F-sensing reportable genetic molecular component;

one or more genetic molecular components of an F sensitive genetic circuit described herein, and/or one or more genetic molecular components of the U-sensitive F-sensitive genetic circuits described herein, to provide a $UO_2F_2$-biosensor according to the first aspect, the second aspect, the third aspect the fourth aspect, and/or the fifth aspect herein described and optionally operatively connecting the $UO_2F_2$-biosensor so provided to an electronic signal transducer adapted to convert a $UO_2F_2$ biosensor reportable molecular component output into an electronic output.

In some embodiments wherein the bacterial cell is a cell incapable of natively expressing histidine kinase 1363 (UrpS) and response regulator 1362 (UrpR) and/or histidine kinase UzcS and response regulator UzcR, the method further comprises genetically engineering the cell to include a U-sensing regulator genetic molecular component comprising an endogenous or exogenous gene encoding histidine kinase 1363 (UrpS) and/or histidine kinase UzcS, and an endogenous or exogenous gene encoding U-sensitive transcriptional regulator 1362 (UrpR) and/or response regulator UzcR in a configuration wherein the a gene encoding histidine kinase 1363 (UrpS) and/or histidine kinase UzcS, and a gene encoding response regulator 1362 (UrpR) response regulator UzcR are expressed upon activation of a controllable promoter.

In some embodiments wherein the bacterial cell is a cell capable of natively expressing histidine kinase 1363 (UrpS) and response regulator 1362 (UrpR) and/or histidine kinase UzcS and response regulator UzcR (e.g. proteobacteria, such as certain alpha proteobacteria, beta proteobacteria and/or gamma proteobacteria identifiable by a skilled person upon reading of the present disclosure), the genetically engineering can preferably further comprises knocking out the natively expressed histidine kinase 1363 (UrpS) and response regulator 1362 (UrpR) and/or histidine kinase UzcS and response regulator UzcR of the bacterial cell, and introducing in the bacterial cell a U-sensing regulator component comprising an endogenous or exogenous gene encoding histidine kinase 1363 (UrpS) and/or histidine kinase UzcS, and an endogenous or exogenous gene encoding U-sensitive transcriptional regulator 1362 (UrpR) and/or response regulator UzcR in a configuration wherein the a gene encoding histidine kinase 1363 and/or histidine kinase UzcS, and a gene encoding response regulator 1362 (UrpR) response regulator UzcR are expressed upon activation of a controllable promoter.

In some embodiments, the genetically modified bacteria are bacteria incapable of natively expressing an F-sensing riboswitch (e.g. *Caulobacter crescentus*) identifiable by a skilled person upon reading of the present disclosure). In some embodiments, the genetically modified bacteria are bacteria capable of natively expressing an F-sensing riboswitch (e.g. *Sphingomonas* sp. MM-1, and *Caulobacterales bacterium*) identifiable by a skilled person upon reading of the present disclosure). In some of those embodiments, the endogenous genes encoding the F-sensing riboswitch, are preferably knocked out.

According to a seventh aspect a $UO_2F_2$-sensing gene cassette described. The $UO_2F_2$-sensing gene cassette comprises one or more U-sensing genetic molecular components herein described, one or more U-sensing regulator genetic molecular components herein described and/or one or more reportable genetic component herein described. The $UO_2F_2$-sensing gene cassette further comprises an F-sensitive riboswitch within the one or more U-sensing genetic molecular components configured to report U, within the one or more U-sensing regulator genetic molecular components and/or within an additional reportable genetic molecular component, in a configuration wherein the U-sensing genetic molecular components, the one or more U-sensing regulator genetic molecular components, and the additional reportable genetic molecular component are transcribed in presence of an effective amount of bioavailable fluoride. In some embodiments the U-sensing gene cassette is an expression cassette. In some embodiments, the gene cassette is comprised within a vector.

According to an eighth aspect a vector is described comprising a polynucleotide encoding for one or more U-sensing genetic molecular components herein described, one or more F-sensing genetic molecular components herein described, one or more U-sensing and/or F sensing regulator genetic molecular components herein described and/or one or more genetic molecular components of a $UO_2F_2$-biosensor herein described. The one or more vectors are configured to introduce one or more U-sensitive genetic molecular components, one or more F-sensing genetic molecular components and/or one or more genetic molecular components of a U-sensitive and/or F-sensitive genetic circuit into a bacterial cell of a plurality of bacterial cells.

According to a ninth aspect, a $UO_2F_2$-sensing system is described. The $UO_2F_2$ sensing system comprises one or more vectors herein described and/or a plurality of bacterial cells natively and/or heterologously expressing histidine kinase 1363 (UrpS) and response regulator 1362 (UrpR) and/or histidine kinase UzcS and response regulator UzcR in combination with one or more F-sensitive riboswitches.

In some embodiments wherein the bacterial cell is a cell incapable of natively expressing histidine kinase 1363 (UrpS) and response regulator 1362 (UrpR) and/or histidine kinase UzcS and response regulator UzcR, the bacterial cell is further genetically engineered to include a U-sensing regulator genetic molecular component comprising an endogenous or exogenous gene encoding histidine kinase 1363 (UrpS) and/or histidine kinase UzcS, and an endogenous or exogenous gene encoding U-sensitive transcriptional regulator 1362 (UrpR) and/or response regulator UzcR in a configuration wherein the a gene encoding histidine kinase 1363 (UrpS) and/or histidine kinase UzcS, and a gene encoding response regulator 1362 (UrpR) response regulator UzcR are expressed upon activation of a controllable promoter.

In some embodiments wherein the bacterial cell is a cell capable of natively expressing histidine kinase 1363 (UrpS) and response regulator 1362 (UrpR) and/or histidine kinase UzcS and response regulator UzcR (e.g. proteobacteria, such as alphaproteobacteria, beta proteobacteria and/or gamma proteobacteria), the bacterial cells is preferably further genetically engineered to comprises knocking out the natively expressed histidine kinase 1363 (UrpS) and response regulator 1362 (UrpR) and/or histidine kinase UzcS and response regulator UzcR of the bacterial cell, and introducing in the bacterial cell a U-sensing regulator component comprising an endogenous or exogenous gene encoding histidine kinase 1363 (UrpS) and/or histidine kinase UzcS, and an endogenous or exogenous gene encoding U-sensitive transcriptional regulator 1362 (UrpR) and/or response regulator UzcR in a configuration wherein the a gene encoding histidine kinase 1363 and/or histidine kinase UzcS, and a gene encoding response regulator 1362 (UrpR) response regulator UzcR are expressed upon activation of a controllable promoter.

In some embodiments, the genetically modified bacteria are bacteria incapable of natively expressing an F-sensing riboswitch (e.g. *Caulobacter crescentus*) identifiable by a skilled person upon reading of the present disclosure). In some embodiments, the genetically modified bacteria are bacteria capable of natively expressing an F-sensing riboswitch (e.g. *Sphingomonas* sp. MM-1, and *Caulobacterales bacterium*) identifiable by a skilled person upon reading of the present disclosure). In some of those embodiments, the endogenous genes encoding the F-sensing riboswitch, are preferably knocked out.

According to a tenth aspect, a $UO_2F_2$-sensing system is described. The system comprises one or more of the $UO_2F_2$ biosensors herein described operatively connected to an electronic signal transducer adapted to convert a U biosensor reportable molecular component output into an electronic output.

According to an eleventh aspect, a composition is described. The composition comprises one or more $UO_2F_2$ biosensors, $UO_2F_2$-sensing gene cassettes and/or vectors herein described together with a suitable vehicle.

According to a twelfth aspect, a system comprising an electronic signal transducer adapted to convert a $UO_2F_2$ biosensor reportable molecular component output into an electronic output is described. The system comprises an electronic signal transducer and one or more $UO_2F_2$ biosensors herein described operatively connected to the electronic signal transducer.

According to a thirteenth aspect, a method of detecting, reporting and/or neutralizing bioavailable $UO_2F_2$ is described. The method comprises:

contacting one or more $UO_2F_2$ biosensors herein described, or a system comprising an electronic transducer operatively connected to one or more $UO_2F_2$ biosensors herein described, with a target environment comprising one or more target ranges of U concentration in combination with one or more target F concentration for a time and under conditions to detect, report and/or neutralize bioavailable $UO_2F_2$ in the target environment.

According to a fourteenth aspect, one or more $UO_2F_2$-sensing genetic reportable components are also described, the $UO_2F_2$ sensing genetic reportable components comprising a U sensitive promoter comprising a U-sensitive 1362 (UrpR) binding site and/or a U sensitive promoter comprising a U sensitive UzcR binding site together with an F-sensing riboswitch, in a configuration wherein the U-sensitive promoter directly initiates expression of the U-sensing reportable molecular component and/or of the U-sensing U-neutralizing molecular component in presence of bioavailable U and the U-sensing reportable molecular component is transcribed in presence of an effective amount of bioavailable fluoride.

According to a fifteenth aspect, one or more U-sensitive and/or F sensitive genetic circuits are described wherein at least one molecular component is a U sensing genetic molecular component herein described and wherein at least one molecular component is a reportable molecular component, and/or a U-neutralizing molecular component (and in particular possibly one or more U-neutralizing genetic molecular components), The U-sensitive and/or F sensitive genetic circuits further comprises an F-sensing riboswitch within at least one of the genetic molecular components of the genetic circuit in a configuration wherein the at least one of genetic molecular components of the genetic circuit is transcribed in presence of an effective amount of bioavailable fluoride.

In the U-sensitive and/or F-sensitive genetic circuit the reportable molecular component and/or the U-neutralizing molecular component are expressed when the genetic circuit operates according to the circuit design in presence of bioavailable U and/or bioavailable Fluoride.

In particular, in several embodiments the biosensors and related genetic molecular components, genetic circuits, compositions, methods and systems herein described are configured for selective and sensitive detection, reporting and/or neutralizing $UO_2F_2$ a bioavailable environmental decomposition product of UF$_6$ and toxic form of U typically produced during enrichment operations.

The UO$_2$F$_2$ biosensors, and related genetic molecular components, genetic circuits, compositions, methods and systems herein described provide in several embodiments a selective, sensitive, portable, easy to use, high-throughput measurement and or neutralizing bioavailable UO$_2$F$_2$, with little or no sample preparation required.

The UO$_2$F$_2$ biosensors, and related genetic molecular components, genetic circuits, compositions, methods and systems herein described allow in several embodiments construction of consolidated bioremediators comprising bacterial systems that possess all the necessary components for deployment in environmental cleanup efforts, for example by coupling UO$_2$F$_2$ sensing with activation of one or more U-neutralizing components.

The UO$_2$F$_2$ biosensors, and related genetic molecular components, genetic circuits, compositions, methods and systems herein described allow in several embodiments detection, reporting and/or neutralization of U in its bioavailable form UO$_2$F$_2$ with low cost approaches as various proteobacterial cells, such as Caulobacter, can be inexpensively grown to high densities as will be understood by a skilled person.

The UO$_2$F$_2$ biosensors, and related genetic molecular components, genetic circuits, compositions, methods and systems herein described can be used in connection with various applications wherein detection and/or neutralizing of uranium is desired. For example, the UO$_2$F$_2$ biosensors, and related genetic molecular components, genetic circuits, compositions, methods and systems herein described can be used in biodefense and in particular to be used for non-proliferation purposes, in environmental monitoring and/or cleanup by regulatory agencies or communities, and in mining in particular for toxicology and safety concerns, as well as diagnostic applications. Additional exemplary applications include uses of the UO$_2$F$_2$ biosensors, and related genetic molecular components, genetic circuits, compositions, methods and systems herein described in several fields including basic biology research, applied biology, bio-engineering, medical diagnostics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 4 Panel C shows a schematic of a U-sensitive genetic circuit where a negative feedback loop was incorporated into the circuit, whereby UzcR represses its own expression from $P_{phyt}$ or $P_{1361}$. Specifically, an m_5 UzcR binding site was placed downstream of the $P_{phyt}$ or $P_{1361}$ transcription start site. This genetic circuit shows minimized basal expression of uzcRS, while maintaining strong responsiveness to U, and further shifted ratio of U response to that of Zn to 5.5 as shown in FIG. 5 Panel C.

FIG. 5 Panel A shows graphs reporting quantification of GFP fluorescence produced by *C. crescentus* NA1000 comprising the U-sensitive genetic circuit shown in FIG. 4 Panel A in response to exposure to 10 and 20 μM U (FIG. 5 Panel A left graph), 10, 20 and 40 μM Zn (FIG. 5 Panel A middle graph), or 80, 120 and 200 μM Cu (FIG. 5 Panel A right graph), from 0 to 4 hours after exposure. FIG. 5 Panel B shows graphs reporting quantification of GFP fluorescence produced by *C. crescentus* NA1000 comprising the U-sensitive genetic circuit shown in FIG. 4 Panel B in response to exposure to 10 and 20 μM U (FIG. 5 Panel B left graph), 10, 20 and 40 μM Zn (FIG. 5 Panel B middle graph), or 80, 120 and 200 μM Cu (FIG. 5 Panel B right graph), from 0 to 4 hours after exposure. FIG. 5 Panel C shows graphs reporting quantification of GFP fluorescence produced by *C. crescentus* NA1000 comprising the U-sensitive genetic circuit shown in FIG. 4 Panel C in response to exposure to 10 and 20 μM U (FIG. 5 Panel C left graph), 10, 20 and 40 μM Zn (FIG. 5 Panel C middle graph), or 80, 120 and 200 μM Cu (FIG. 5 Panel C right graph), from 0 to 4 hours after exposure. $P_{phyt}$ was used for the GFP fluorescence measurements shown in FIG. 5 Panels B-C. Experiments with U were performed in modified M5G medium (10 mM PIPES, pH 7, 1 mM NaCl, 1 mM KCl, 0.05% $NH_4Cl$, 0.01 mM Fe/EDTA, 0.2% glucose, 0.5 mM $MgSO_{4,}$ $_{0.5}$ mM $CaCl_2$)) supplemented with 5 mM glycerol-2-phosphate as the phosphate source (M5G-G2P). Cells were grown to mid-exponential phase in M5G-G2P media, washed once with fresh media, then resuspended in fresh media containing the indicated U concentration. Experiments with Zn and Cu were performed in PYE.

FIG. 6A shows a schematic of an exemplary 'in parallel' AND gate, comprised of an HRP AND gate system, in which hrpS is placed under the control of $P_{phyt}$ or $P_{1361}$ and hrpR is placed under the control of $P_{urcB}$, a promoter activated by UzcRS. In this U-sensitive genetic circuit, U exposure stimulates production of both HrpS and HrpR, leading to activation of $P_{hrPL}$ and expression of GFP. FIG. 6B shows a schematic of an exemplary 'in parallel' AND gate, comprised of a tripartite GFP system, in which gfp10 subunit is placed under the control of $P_{phyt}$ or $P_{1361}$, gfp11 is placed under the control of $P_{urcB}$, and gfp1-9 is placed under the control of the *Caulobacter* S layer promoter, $P_{rsaA}$, which is a strong, constitutive promoter [4]. This system requires expression of subunits gfp10, gfp11 and gfp1-9 for tripartite GFP reporter assembly and fluorescence. Gfp-10 is shown fused to K1 and gfp11 is shown fused to E1, wherein K1 and E1 are exemplary interacting protein partners comprised of oppositely charged coiled-coils [5]. When K1 and E1 interact, GFP10 and GFP11 self-associate with GFP1-9 to constitute a functional GFP reporter. Other exemplary embodiments of the genetic circuit shown in FIG. 6B comprise placement of gfp1-9 under the control of $P_{phyt}/P_{1361}$, or under the control of a different non-U-sensitive promoter, such as $P_{xyl}$ that is responsive to xylose [6]. In addition.

FIG. 7 shows schematics of regulatory sequences within $P_{phyt}$ (FIG. 7 Panel A), showing the sequence CCCAAAGAGGGTGTGGCCCAAAGAGGGTGTGGAT-TTCTCTTCGCGCCACCCGTTTCG TCAGCCGGAC-GTCAGGTCCAGACGGCTAAGCTAGCTGCGA (SEQ ID NO: 202) and $P_{1361}$ (FIG. 7 Panel B), showing the sequence ATGTTCAGCGCCTGGTTACCGGC-GATGGCGCGGTGTCAGCGTTCGGGCGTTGCGATG CGTCAGGAGCGTGTCAGGATGCCTGTGGAATCCT-AAGCGC (SEQ ID NO: 203) with arrows above nucleotides indicating putative transcription start sites. In FIG. 7 Panel C, a phylogenetic footprinting approach was used to construct a 1362 DNA-binding motif. An alignment of 26 $P_{phyt}$ or $P_{1361}$ DNA sequences from exemplary members of the subclass Caulobacteridae, Bradyrhizobiaceae, Sphingomonadaceae, Hyphomicrobiaceae, and Rhodobacteracea are indicated, with larger letters representing a higher level of consensus between aligned sequences.

FIG. 8 shows DNA sequences of full-length $P_{phyt}$ (Panel A), $P_{phyt}$ with a mutation of four nucleotides in the second direct repeat sequence (DR2, shown in bold, Panel B), $P_{phyt}$ with a mutation of two nucleotides in the first direct repeat sequence (DR1, shown in bold, Panel C), $P_{phyt}$ with a mutation of two nucleotides in the second direct repeat sequence (DR2, shown in bold, Panel D), a shortened $P_{phyt}$ ($P_{phyt}$ short, Panel E), full-length $P_{1361}$ (Panel F), $P_{1361}$ with a mutation of four nucleotides in the second direct repeat sequence (DR2, shown in bold, Panel G), $P_{1361}$ with a mutation of two nucleotides in the second direct repeat sequence (DR2, shown in bold, Panel H), and a shortened $P_{1361}$ ($P_{1361}$ short, Panel I). The sequence of the large tandem repeat (TR) in $P_{phyt}$ is shown in uppercase, underlined. The direct repeat sequence that is likely bound by the U-sensitive transcriptional response regulator 1362 is shown in uppercase, italic (with direct repeat sequences underlined). Putative Transcription start sites (based on RNA-seq data) are shown in lowercase, underlined.

FIG. 9 shows graphs reporting quantification of exemplary fluorescence levels of $P_{phyt}$-gfp (FIG. 9 Panel A) and $P_{1361}$-gfp (FIG. 9 Panel B) variants in response to U at 10 M or 25 M in the host organism *C. crescentus* NA1000. In FIG. 9 Panel A, fluorescence levels are shown for variants comprising full length $P_{phyt}$ promoter (Full length), a shortened $P_{phyt}$ (Short), $P_{phyt}$ with a mutation of four nucleotides in the second direct repeat sequence (DR2 GTCA→CAGT), $P_{phyt}$ with a mutation of two nucleotides in the first direct repeat sequence (DR1, GT→CA), and $P_{phyt}$ with a mutation of two nucleotides in the second direct repeat sequence (DR2, GT→CA). In FIG. 9 Panel B, fluorescence levels are shown for variants comprising full length $P_{1361}$ promoter (Full length), a shortened $P_{1361}$ (Short), $P_{1361}$ with a mutation of four nucleotides in the second direct repeat sequence (DR2 GTCA→CAGT), and $P_{1361}$ with a mutation of two nucleotides in the second direct repeat sequence (DR2, GT→CA). Cells were grown to mid-exponential phase in M5G-G2P media, washed once with fresh media, then resuspended in fresh media containing the indicated U concentration. Fluorescence was quantified following a two-hour exposure of cells to each U concentration and normalized to the $OD_{600}$.

FIG. 14 shows an exemplary embodiment of a U-responsive AND gate design. Panel A shows a schematic of an example of an 'in series' AND gate combined with an 'in parallel' AND gate in a U sensitive genetic circuit. In the exemplary combined circuit, the $P_{urcB}$ promoter in the exemplary 'in parallel' tripartite GFP AND gate is activated by UzcR, and expression of UzcR and UzcS is under transcriptional regulation of $P_{phyt}$ in an 'in series' AND gate. Grey arrows depict regulator modifications made to the base 'in parallel' AND gate to generate the combined 'in series', 'in parallel' AND gate circuit. In the tripartite GFP system, gfp10 subunit is placed under the control of $P_{phyt}$-short, gfp11 is placed under the control of $P_{urcB}$, and gfp1-9 is placed under the control of the *Caulobacter* S layer promoter, $P_{rsaA}$, which is a strong, constitutive promoter. [4] This genetic circuit was integrated into the chromosomal urcA locus and integrates regulatory input from the native, autoregulatory UzcRS and UrpRS TCS, depicted in the gray box. Panel B shows the fluorescence output profile of the core sensor and control variants lacking critical regulatory components over a range of U concentrations. Error bars represent the average of biological triplicates.

FIG. 16A is from Figure 2 of Newsome et al. (2014) [7] showing a schematic illustrating exemplary mechanisms of microbe-uranium interactions, such as bioreduction [10-13].

FIG. 16B is from Figure 2 of Newsome et al. (2014) [7] showing a schematic illustrating exemplary mechanisms of microbe-uranium interactions, such as biomineralisation [14-16].

FIG. 16C is from Figure 2 of Newsome et al. (2014) [7] showing a schematic illustrating exemplary mechanisms of microbe-uranium interactions, such as biosorption [17, 18].

In FIG. 17 Panels A and B, fluorescence levels are shown for wild type *C. crescentus* and strains deleted for CCNA_01362 (1362 response regulator) and CCNA_01363 (1363 histidine kinase). U induction of both $P_{phyt}$ and $P_{1361}$ is abolished by deletion of either CCNA_01362 (indicated by Δ CCNA_01362) or CCNA_01363 (indicated by Δ CCNA_01363), confirming that these genes encode the U sensitive transcriptional regulatory system required for U-responsive activation of the exemplary promoters $P_{phyt}$ and $P_{1361}$. Cells were grown to mid-exponential phase in M5G-G2P media, washed once with fresh media, then resuspended in fresh media containing the indicated U concentration. Fluorescence was quantified following a two-hour exposure of cells to each U concentration and normalized to the $OD_{600}$.

FIG. 17 Panel A shows a graph reporting exemplary quantification of GFP fluorescence produced by *C. crescentus* NA1000 comprising the U-sensitive genetic circuit shown in FIG. 6 Panel B upon exposure to U, Zn, Cu and Cd. In this circuit, the expression of gfp10-K1 is initiated by the shortened 1363/1362-regulated $P_{phyt}$ ($P_{phyt}$-short) and the expression of E1-gfp11 is initiated by the UzcRS-regulated promoter $P_{urcB}$. FIG. 17 Panel B shows a graph reporting exemplary quantification of GFP fluorescence produced by *C. crescentus* NA1000 comprising a control U-sensitive genetic circuit that incorporates input only from UzcRS. FIG. 17 demonstrates the enhanced selectivity of an exemplary 'in parallel' AND gate comprising two points of U-sensing by (1) 1363/1362 and (2) UzcRS two component systems. Cells were grown to mid-exponential phase in M5G-G2P media, washed once with fresh media, then resuspended in fresh media containing the indicated metal concentration. Fluorescence was quantified following a three-hour exposure of cells to each metal concentration and normalized to the $OD_{600}$.

FIG. 27 shows exemplary effect of UzcRS regulator mutants in minimal media and U induction and TFInfer activity of UzcR in negative regulator mutants according to some embodiments herein described. Panel (A): Genes containing transposon insertions that led to high basal $P_{urcA}$-lacZ activity were deleted and the resulting strains were transformed with plasmid-borne $P_{urcA}$-lacZ (pNJH123). Cells were grown to mid-exponential phase in M5G supplemented with glycerol-2-phosphate, washed once with fresh media, then resuspended in fresh media containing 50 M U. β-galactosidase assays were performed following 1 h exposure to U. Error bars represent the standard deviation of triplicate measurements. Panel (B): The activity of UzcRS was inferred from the log 2 fold change values for 37 UzcR regulon members determined in each mutant relative to WT. $P_{urcA-lacZ}$ expression data from FIG. 1A is plotted for comparison.

FIG. 37 Panel B shows the curves for the Corse Sensor, constitutive uzcY and $P_{phyt}$ uzcY. Fluorescence was quantified following a three-hour exposure to a range of metal concentrations. The data represent a zoomed in version of data depicted in FIG. 40 and FIG. 36C. Error bars represent the average of biological triplicates.

(FIG. 38 Panel A) Fluorescence output of the core sensor and control variants lacking critical regulatory components as a function of time in three distinct site 300 samples without nutrient supplementation. (FIG. 38 Panel B) Fluorescence output of the core sensor and a control strain lacking a UrpR binding site as a function of time in three distinct site 300 samples supplemented with glucose (0.2%), orthophosphate (1 mM), and ammonium chloride (0.05%). The plot legend is depicted below the plots.

FIG. 39 Panel A: Fluorescence output of the core sensor and control variants lacking critical regulatory components as a function of time in three distinct site 300 samples supplemented with glucose (0.2%), glycerol-2-phosphate (5 mM), and ammonium chloride (0.05%). Ground water samples from W-815-2621, W-812-01, and W-6C are referred to as 1, 2, and 3, respectively, in the text. The plot legend is depicted below the plots. FIG. 39 Panel B: The fluorescence of the core sensor and control variants was quantified six hours after exposure to site 300 samples supplemented with uranyl nitrate and the nutrients described in panel A. The x-axis concentrations represent the total U concentration in the ground water sample after addition of U in 1 M increments.

FIG. 46 shows a schematic representation of exemplary single output configurations of a $UO_2F_2$ biosensor herein described. In particular FIG. 46 Panel A describes a schematic of uranium- and fluoride-sensing components integrated in series. The promoter can be any UzcR- or UrpR-regulated promoter (defined in prior patent app) such that U-dependent transcription is initiated by UzcR or UrpR. In this circuit, transcription will be prematurely terminated by the fluoride sensing riboswitch in the absence of fluoride (i.e., not detectable output). Binding of fluoride to the riboswitch will mediate transcriptional read-through and ultimately, production of the reporter. FIG. 46 Panel B describes a schematic of uranium- and fluoride-sensing components integrated in series where U-dependent transcriptional activation requires the function of both UrpR and UzcR. This sensor will provide greater selectivity for uranium compared to the sensors described in panel A. However, in this configuration, the sensitivity for U would be limited by the UzcRS component. FIG. 46 Panel C describes a schematic of the integration of the fluoride riboswitch within the AND gate circuit such that expression of component three requires fluoride exposure. In this configuration, reconstitution of GFP fluorescence requires activation of the two uranium-responsive pathways and fluoride binding to the fluoride riboswitch. Transcription of component three can theoretically be controlled by any constitutive promoter. The assignment of each component with the given regulatory promoter is arbitrary and easily swapped. For example, the fluoride riboswitch could be used to control expression of component one or two.

FIG. 48C shows a schematic representation of a consensus secondary structure for F-sensing riboswitches in the sense of the disclosure from https://rfam.org/family/RF01734#tabview=tab0

FIG. 49 panel A reports results showing growth in *Caulobacter crescentus* WT at NaF concentrations above 4 mM and FIG. 49 panel B reports results showing growth in *Caulobacter crescentus* ΔcrcB at NaF concentrations above 126.5 μM.

FIG. 49 panel C reports results showing growth in *Caulobacter crescentus* WT at NaCl concentrations above 4 mM. FIG. 49 panel D reports results showing growth in *Caulobacter crescentus* ΔcrcB at NaCl concentrations above 4 mM.

FIG. 50 Panel A shows a schematic configuration of the exemplary construct used to perform the testing using β-galactosidase as a reporter. FIG. 50 Panel B shows a chart reporting the β-galactosidase activity for the *Sphingomonas* MM-1 in WT and the crcB deletion strain over a range of NaF concentrations FIG. 50 Panel C shows a chart reporting the β-galactosidase activity for the *Pseudomonas syringae* riboswitch in WT and the crcB deletion strain over a range of NaF concentrations and FIG. 50 Panel D shows a chart reporting the β-galactosidase activity for the *Sphingomonas* 67-36 riboswitch in WT and the crcB deletion strain over a range of NaF concentrations.

FIG. 51 Panel A shows a schematic representation of a construct wherein each of three tested riboswitches was included in construction between to the xylose inducible promoter (Pxyl) and the reporter mCherry. FIG. 51 Panel B shows a chart reporting the effect of xylose administration ad different concentration on promoter activity. FIG. 51 Panel C shows a chart reporting the effect of 200 uM xylose administration on mCherry expression in the constructs including each of the three riboswitches as indicated. FIG. 51 Panel D shows a chart reporting the effect of 2 mM xylose administration on mCherry expression in the constructs including each of the three riboswitches as indicated. FIG. 51 Panel E shows a chart reporting the effect of 200 uM xylose administration on mCherry expression in the constructs including the *Sphingomonas* MM-1 fluoride riboswitch in C. *Crescentus* WT and C. *Crescentus* with a crcB deletion. FIG. 51 Panel F shows a chart reporting the effect of 2 mM xylose administration on mCherry expression in the constructs including the *Sphingomonas* MM-1 fluoride riboswitch in C *Crescentus* WT and C. *Crescentus* with a crcB deletion.

FIG. 53 shows an alignment of RNA polynucleotides encoded by 287 sequences (SEQ ID NO: 1989-1998 and SEQ ID NO: 2232 to SEQ ID NO: 2508) from the 2017 exemplary F-sensing riboswitch sequences shown in Appendix I of U.S. provisional application No. 62/801,077 (SEQ ID NO: 205-1988 and SEQ ID NO: 1999-2231), wherein the nucleotide sequences shown are sequences forming a same structure in corresponding aligned sequences and the symbols "--" indicates gaps between the aligned sequences shown.

FIG. 55 Panel B shows fluoride detection performed with a uranyl fluoride sensing circuit constructed by combining the UrpRS-responsive Pphyt promoter with the MM-1 riboswitch. FIG. 55 Panel C shows the fluorescence of the uranyl fluoride sensing circuit in the presence of U alone, F alone, and both U and F. Tests-were performed with F–, added as NaF, and uranyl, added as uranyl nitrate.

APPENDIX I—U.S. Application No. 62/801,077

Figure 1:
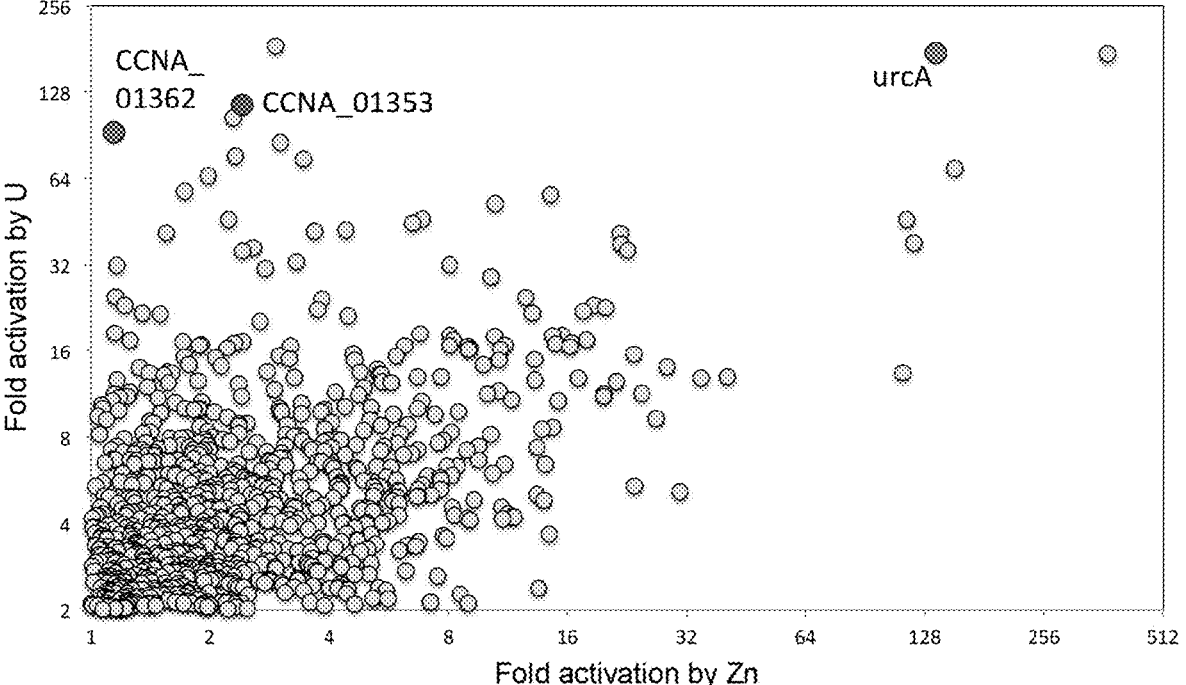
FIG. 1 shows a graph of pairwise comparison of fold-change in expression in Caulobacter crescentus of exemplary genes activated by Zn or U, analyzed using RNA-Seq. CCNA_01362 and CCNA_01353 (phytase) (dark grey data points shown as respectively labeled circles) are induced more than 100-fold by U but not induced by Zn. As such, the promoters regulating these genes, P$_{1361}$ and P$_{1353}$ (P$_{phyt}$) respectively, represent promising exemplary promoters for use in a whole-cell U biosensor. urcA (dark grey data point indicated as labeled circle), a gene regulated by UzcRS (FIG. 24A-C), is strongly induced by both U (FIG. 24A) and Zn (FIG. 23A).

Appendix I of U.S. provisional application No. 62/801, 077, which is incorporated into and constitute a part of this specification, illustrates one or more fluoride sensing riboswitch that can be used in any one of the $UO_2F_2$ biosensors of the present disclosure which are also reported in the enclosed Sequence Listing from SEQ ID NO: 205 to SEQ ID NO: 1988 and SEQ ID No: 1999 to SEQ ID NO: 2231. In particular the sequences from Appendix I U.S. provisional application No. 62/801,077, and the Sequences from SEQ ID NO: 205 to SEQ ID NO: 1988 and SEQ ID No: 1999 to SEQ ID NO: 2231 of the Sequence Listing of the instant application, are sequences from Rfam database reported with their related Genome file ID, bacteria and additional information concerning the position of the sequence in the genome of the bacteria as will be understood by a skilled person. Appendix I of U.S. provisional application No. 62/801,077 and the Sequence Listing enclosed herewith, together with the detailed description section, the Example section and the Drawings, serve to explain the principles and implementations of the disclosure. Other features, objects, and advantages will be apparent from the entire description and drawings, and from the claims.

DETAILED DESCRIPTION

Provided herein are $UO_2F_2$ biosensors and related U-sensing and/or F sensing genetic molecular components, genetic circuits, compositions, methods and systems which in several embodiments can be used to detect, report and/or neutralize U and in particular bioavailable Uranium which is produced in connection with enrichment programs $UO_2F_2$.

The term "bioavailable" as used herein refers to a molecule in particular a soluble molecule that is able to cross an organism's cellular membrane from the environment, or is otherwise able to exert a biological effect on an organism, if the organism has access to the molecule. In particular, with regard to a toxic molecule, a bioavailable toxic molecule is a toxic molecule that is able to exert toxicity on an organism contacted with the organism and/or with a toxic molecule sensing system of the organism. In some scenarios, the bioavailability can be inferred based on toxicity or activation of a tress response in an organism as will be understood by a skilled person. Thus, the term "bioavailable U" as used herein refers to a soluble molecular form of U that can cross an organism's cellular membrane from the surrounding environment or is otherwise able to exert a biological effect on an organism, e.g. following contact with the organism and/or with an organism U-sensing system.

In particular, the term "bioavailable uranium" comprises uranyl ion, which has a linear structure with short U—O bonds, indicative of the presence of multiple bonds between uranium and oxygen and can bind four or more ligands in an equatorial plane. The uranyl ion forms many complexes, particularly with ligands that have oxygen donor atoms. Complexes of the uranyl ion are important in the extraction of uranium from its ores and in nuclear fuel reprocessing. As would be understood by persons skilled in the art, 'naked' or 'uncomplexed' uranyl oxycation is a bioavailable form of U. In contrast, for example, uranyl oxycation complexed with inorganic phosphate is not considered to be bioavailable.

The term "uranyl oxycation" as used herein refers to the predominant form of U in oxygenated environments, comprising the +6 oxidation state ($UO_2^{+}$·), which has high chemical toxicity [24]. The US Environmental Protection Agency's maximum contaminant limit for U in drinking water is 30 μg/L (~0.13 μM), however, groundwater concentrations in the US frequently exceed this limit [25, 26].

The $UO_2F_2$ biosensors and related U-sensing and/or F-sensing genetic molecular component, gene cassettes, genetic circuits, compositions, methods and systems described herein can be used in several embodiments to detect and report and/or neutralize bioavailable U, and in particular $UO_2F_2$ which is a derivative of $UF_6$.

The term "$UF_6$" or "uranium hexafluoride" as used herein indicates is a compound used in the process of enriching uranium, which produces fuel for nuclear reactors and nuclear weapons. In particular Uranium hexafluoride ($UF_6$) is almost always produced as a precursor in any U-enrichment operation, is routinely released during the conversion process, and is not expected to occur naturally in the environment [27, 28] As such, environmental detection of $UF_6$—or the more stable hydrolysis product $UO_2F_2$, which is rapidly formed when atmospheric $UF_6$ reacts with water vapor [29]. does strongly suggest an enrichment program.

In particular, conversion facilities, which produce the $UF_6$ precursor that is almost always required for the production of highly enriched uranium, represent a likely source of leaked $UF_6$ as a consequence of the higher-than atmospheric pressures employed. [27, 28]

When gaseous $UF_6$ is released into the atmosphere, it is rapidly hydrolyzed by ambient moisture to form an $UO_2F_2$ aerosol (and HF gas) that is dispersed and ultimately deposited on vegetation, soil, or an aquatic system [29, 30]. $UO_2F_2$ is expected to have reasonable stability in the environment such that its detection may be feasible for months after release [27, 31].

$UO_2F_2$ aerosols, which are rapidly formed when atmospheric $UF_6$ reacts with water vapor [29], are expected to be deposited on vegetation, soil, or into aquatic systems [29, 30]. While $UO_2F_2$ aerosols are expected to have reasonable stability in low moisture environments [27, 31], $UO_2F_2$ exhibits relatively high solubility in aqueous environments (up to 2 M [32]);

A solution-based detection approach is therefore expected to be most relevant for $UO_2F_2$ monitoring in aquatic systems or when coupled with a sampling device that collects and solubilizes $UO_2F_2$ aerosols. Additionally, the rationale for separate uranium and fluoride detection components is supported by the solution chemistry of $UO_2F_2$ and prior studies on bacterial uranium interactions.

The physicochemical form, or speciation, of $UO_2F_2$, is dependent on the geochemical conditions [33, 34]. In particular, at pH below 5, the naked uranyl oxycation ($UO_2^{2+}$) and uranyl fluoride species ($UO_2F^+$, $UO_2F_2$, $UO_2F_3^-$) are expected to predominate [33]. At circumneutral (6.5-7.5) and alkaline pH, uranyl hydroxide and/or carbonate species are expected to predominate with concomitant formation of the anion, $F^-$ [33, 34]. Under those conditions, uranium and fluoride are expected to largely exist as separate species under geochemical conditions most relevant to aqueous environmental sampling (pH 6-8 range).

In addition, studies of bacterial uranium interactions suggest that cell surface functional groups could have a dissociative effect on uranyl fluoride species, yielding detectable forms of both components; cell surface functional groups have been shown to compete with environmental ligands (e.g., carbonate and citrate) for uranyl coordination, effectively freeing the coordinating ligand [35, 36].

Insoluble forms of uranyl—for example uranyl phosphate minerals formed when uranyl nitrate is added to solutions containing high orthophosphate levels—are not detected by the biosensor. This is an advantageous feature for environmental detection since natural U commonly occurs in the form of insoluble U minerals [37] and aqueous phosphate concentrations are typically very low (<10 ppb) [34].

$UO_2F_2$ biosensor herein described are bacteria-based $UO_2F_2$-sensor, which are engineered to comprise a fluoride-sensing riboswitch in combination a U-sensing genetic molecular components, U neutralizing genetic molecular component, reportable genetic molecular components, and/ or additional components possibly configured in genetic circuits directed to detect and/or neutralize U in presence of bioavailable Uranium and Fluoride.

In particular, the $UO_2F_2$ biosensors herein described are whole-cell biosensors comprising a genetically engineered bacterial cell.

The term "bacterial cell", bacteria" used herein interchangeably with the terms "cell" or "host" indicates a large domain of prokaryotic microorganisms. The term "prokaryotic" is used herein interchangeably with the terms "cell" or "host" and refers to a microbial species which contains no nucleus or other organelles in the cell. Exemplary prokaryotic cells include bacteria. Typically, a few micrometers in length, bacteria have a number of shapes, ranging from spheres to rods and spirals, and are present in several habitats, such as soil, water, acidic hot springs, radioactive waste, the deep portions of Earth's crust, as well as in symbiotic and parasitic relationships with plants and animals. Bacteria in the sense of the disclosure refers to several prokaryotic microbial species which comprise Gram-positive bacteria, Proteobacteria, Cyanobacteria, Spirochetes and related species, Planctomyces, *Bacteroides, Flavobacteria, Chlamydia*, Green sulfur bacteria, Green non-sulfur bacteria including anaerobic phototrophs, Radioresistant micrococci and related species, *Thermotoga* and Thermosipho thermophiles as would be understood by a skilled person. More specifically, the wording "Gram positive bacteria" refers to cocci, nonsporulating rods and sporulating rods, such as, for example, *Actinomyces, Bacillus, Clostridium, Corynebacterium, Erysipelothrix, Lactobacillus, Listeria, Mycobacterium, Myxococcus, Nocardia, Staphylococcus, Streptococcus* and *Streptomyces*.

The term "proteobacteria" as used herein refers to a major phylum of Gram-negative bacteria. Many move about using flagella, but some are nonmotile or rely on bacterial gliding. As understood by skilled persons, taxonomic classification as proteobacteria is determined primarily in terms of ribosomal RNA (rRNA) sequences. The Proteobacteria are divided into six classes, referred to by the Greek letters alpha through epsilon and the Acidithiobacillia and Oligoflexia, including alphaproteobacteria, betaproteobacteria and gammaproteobacteria as will be understood by a skilled person.

The term "alphaproteobacteria" as used herein refers to bacteria identifiable by those skilled in the art in the phylogenetic Class Alphaproteobacteri, in the Phylum Proteobacteria. As understood by those skilled in the art, Alphaproteobacteria is a diverse taxon and comprises several phototrophic genera, several genera metabolising C1-compounds (e.g., *Methylobacterium* spp.), symbionts of plants (e.g., *Rhizobium* spp.), endosymbionts of arthropods (*Wolbachia*) and intracellular pathogens (e.g. *Rickettsia*). As understood by those skilled in the art, taxonomic classification of alphaproteobacteria can be identified by reference to publicly available online databases such as the List of Prokaryotic names with Standing in Nomenclature (LPSN) and National Center for Biotechnology Information (NCBI) and the phylogeny is based on 16S rRNA-based LTP release 106 by "The All-Species Living Tree" Project. The Class Alphaproteobacteria is divided into three subclasses Magnetococcidae, Rickettsidae and Caulobacteridae [38]. In particular, the Caulobacteridae is a subclass composed of the orders Holosporales, Rhodospirillales, Sphingomonadales, Rhodobacterales, Caulobacterales, Rhizobhiales, Kiloniellales, Kordiimonadales, Parvularculales and Sneathiellales.

The term "betaproteobacteria" as used herein refers to a class of gram-negative bacteria, and one of the classes of the phylum Proteobacteria. [39] The Betaproteobacteria comprise more than 75 genera and 220 species of bacteria identifiable by persons skilled in the art. [40] Seven orders of betaproteobacteria have been described: Burkholderiales, Hydrogenophilales, Methylophilales, Neisseriales, Nitrosomonadales, Rhodocyclales, and Sulfuricellales. Examples of Betaproteobacteria genera comprise *Bordetella, Ralstonia, Neisseria* and *Nitrosomonas*, among others identifiable by skilled persons. While many Betaproteobacteria identifiable by skilled persons are found in environmental soil and water, others are obligate pathogens and can cause disease in a variety of hosts. Some members of betaproteobacteria can cause disease in various eukaryotic organisms. Several cause diseases in humans, such as members of the genus *Neisseria: N. gonorrhoeae* and *N. meningitides* which cause gonorrhea and meningitis respectively, as well as *Bordetella pertussis* which causes whooping cough. Other members infect plants, such as *Burkholderia cepacia* which causes bulb rot in onions as well as *Xylophilus ampelinus* which causes necrosis of grapevines. [40]

The term "gammaproteobacteria" as described herein refers to a class of gram-negative bacteria, and one of the classes of the phylum Proteobacteria. As would be identifiable by skilled persons, exemplary taxonomic orders, families and genera belonging to the class gammaproteobacteria comprise *Acidithiobacillus*, Xanthomonadales, Chromatiales, *Methylococcus, Beggiatoa*, Legionellales, *Ruthia, Vesicomyosocius, Thiomicrospira, Dichelobacter, Francisella*, Moraxellaceae, *Alcalinovorax, Saccharophagus, Reinekea*, Oceanospirillaceae, *Marinobacter*, Pseudomonadaceae, *Aeromonas*, Vibrionales, Pasteurellales, and Enterobacteriales among others. A number of bacteria have been described as members of gammaproteobacteria, but have not yet been assigned an order or family. These comprise bacteria of the genera *Alkalimarinus, Alkalimonas, Arenicella, Gallaecimonas, Ignatzschineria, Litorivivens, Marinicella, Methylohalomonas, Methylonatrum, Plasticicumulans, Pseudohongiella, Sedimenticola, Thiohalobacter, Thiohalomonas, Thiohalorhabdus, Thiolapillus*, and *Wohlfahrtiimonas* among others identifiable by skilled persons. Other examples of gammaproteobacteria genera comprise *Escherichia, Shigella, Salmonella, Yersinia, Buchnera, Haemophilus, Vibrio*, and *Pseudomonas*, among others identifiable by skilled persons. Some members of gammaproteobacterial are pathogenic in humans, for example some strains of the species *Salmonella* spp., *Yersinia pestis, Vibrio cholerae, Pseudomonas aeruginosa*, and *Escherichia coli*, among others identifiable by skilled persons. Some members of gammaproteobacteria are pathogenic in plants, such as *Xanthomonas axonopodis* pv. *citri, Pseudomonas syringae* pv. *actinidiae*, and *Xylella fastidiosa*, among others identifiable by skilled persons.

In some embodiments, the $UO_2F_2$ biosensors herein described are whole-cell biosensors comprising a genetically engineered alphaproteobacterial cell of the subclass Caulobacteridae. In particular in some embodiments, the U biosensors described herein can comprise a cell of any genus, species and/or strain of Caulobacteridae identifiable by those skilled in the art. Exemplary Caulobacteridae that can be used in U-biosensors herein described comprise species of the Families Bradyrhizobiaceae, Sphingomonadaceae, Caulobacteraceae, Hyphomicrobiaceae and Rhodobacteraceae which include species naturally comprising, as well as others identifiable by persons skilled in the art.

In particular, in some embodiments, $UO_2F_2$-biosensor s herein described can comprise species from the order Caulobacterales, the family Caulobacteraceae, the genus *Caulobacter* and the species *Caulobacter crescentus* which is described herein as one of the representative species of the subclass Caulobacteridae.

In some embodiments of the $UO_2F_2$-biosensors herein described, the bacterial cell of the U-biosensor is capable of natively and/or heterologously expressing a U-sensitive histidine kinase 1363, and cognate response regulator 1362.

The term "histidine kinase P1363" or "UrpS" as used herein refers to a histidine kinase having the amino acid sequence (SEQ ID NO: 3)
MSGGSLRWRLIVGGMLAILAALAVAWLAMTWLFERHIVRRETADLTR

AGQVLVAGLRLEPNGAPVIDATLSDPRLSKAAGGFYWQVSTTSGSER

SVSLWDQALKPPQTAPAEGWSSRIAAGPFDDRVLLVERSVRPDRDGP

AVLIQVASDEKVLRAARREFGRELAIFLGGLWAILSGAAALQVVLGL

-continued

SPLTRVRADLARLRKSPSARMSLDHPREIAPLAEAINALAEAREADL

ARARRRAGDLAHSLKTPLAALSAQSRRAREDGAVAAADGLDAAIASV

AAALEAELARARAAAAREAVFAAETAPLAVAERLVAVLERTADGERL

IFDIDVPADLKAPASEDVVTEMLGALIENAARHARRQVRISGAVVGQ

GAVLIVEDDGPGLDKGRAEAALARGARLDEAGPGHGLGLAIVRD LA

EASGAVLSMDRGDLGGLRAMVSWTAPGAGP, found in *C. crescentus* NA1000, or a sequence that when aligned with sequence SEQ ID NO: 3 has a BLAST score between 240 and 300, between 300 and 500, or preferably between 500 and 800, or more preferably over 800 but less than 100% homology or even more preferably having a BLAST Score of 851 and 100% homology with the sequence SEQ ID NO: 3.

The term "U sensitive response regulator 1362" or "response regulator 1362" or "UrpR" refers to a response regulator having amino acid sequence (SEQ ID NO: 4)
MMRALVVEDDPVVGPDLAKALSASGFVVDIARDGEDASFKGEVEDYA

LVVLDLGLPRLDGLSVLRRWRANDRAFPVLILSARGDWTEKVEGIEA

GADDYLAKPFEMGELLARARGLVRRAAGRTSPVIGAGRLALDTRRMS

ATLDGAPIRLSPLEFRLLDCLAHNPGRAVSAGELAEQLYGVADTADT

NAIEALVARLRRKIGADVIETR RGFGYLLAGGTA of *C. crescentus* NA1000 or a sequence that when aligned with sequence SEQ ID NO: 4 has a BLAST score between 200 and 250, or preferably between 250 and 300, or more preferably over 300 but less than 100% homology or even more preferably having a BLAST Score of 429 and 100% homology with the sequence SEQ ID NO: 4.

The term "BLAST" or "Basic Local Alignment Search Tool" is an algorithm for comparing primary biological sequence information, such as the amino-acid sequences of proteins or the nucleotides of DNA sequences. A BLAST search enables a researcher to compare a query sequence with a library or database of sequences, and identify library sequences that resemble the query sequence above a certain threshold. Accordingly, BLAST or Basis Local Alignment Search Tool uses statistical methods to compare a DNA or protein input sequence, also referred to as a query sequence to a database of nucleotide and protein (subject sequences) and returns sequences hits that have a level of similarity to the query sequence ranked based on the score.

The term "score" in the context of sequence alignments, indicates a numerical value that describes the overall quality of an alignment. Higher scores correspond to higher similarity and lower scores correspond to lower similarity. The score scale depends on the scoring system used for conducting the sequence alignment.

A BLAST score, also referred to as bit score or max score in the BLAST output is a normalized score with respect to the scoring system provided by the BLAST algorithm. The BLAST score defines the highest alignment score of a set of aligned segments from the same subject (database) sequences. The score is calculated from the sum of the match rewards and the mismatch, gap open an extend penalties independently for each segment. The BLAST score normally gives the same sorting order as the expect value (E value) in the BLAST alignment output.

A BLAST score can be obtained using BLAST software suite at the NCBI website and related references and in particular at the website https://blast.ncbi.nlm.nih.gov/Blast.cgi?PROGRAM=blastp&PAGE_TYPE=BlastSearch&LINK_LOC=blasthome at the date of filing of the present disclosure, as will be understood to a person skilled in the art.

In embodiments herein described the "histidine kinase P1363" or "UrpS" and the "response regulator 1362" or "UrpR" typically form a two-component system herein also indicated as "1363/1362 TCS", UrpRS TCS" or "UrpRS".

The term "two component system" as used herein refers to a stimulus-response coupling mechanism that allows organisms to sense and respond to changes in many different environmental conditions [41]. Two-component systems typically consist of a membrane-bound histidine kinase that senses a specific environmental stimulus and a corresponding response regulator that mediates the cellular response, mostly through differential expression of target genes [42]. Although two-component signaling systems are found in all domains of life, they are most common in bacteria, particularly in Gram-negative and cyanobacteria [43]. Two-component systems accomplish signal transduction through the phosphorylation of a response regulator (RR) by a histidine kinase (HK).

Histidine kinases are typically homodimeric transmembrane proteins containing a histidine phosphotransfer domain and an ATP binding domain. Response regulators can consist only of a receiver domain, but usually are multi-domain proteins with a receiver domain and at least one effector or output domain, often involved in DNA binding [43]. Upon detecting a particular change in the cellular environment, the HK performs an autophosphorylation reaction, transferring a phosphoryl group from adenosine triphosphate (ATP) to a specific histidine residue. The cognate response regulator (RR) then catalyzes the transfer of the phosphoryl group to an aspartate residue on the response regulator's receiver domain [44, 45]. This typically triggers a conformational change that activates the RR's effector domain, which in turn produces the cellular response to the signal, usually by activating or repressing expression of target genes [43].

Figure 3A:
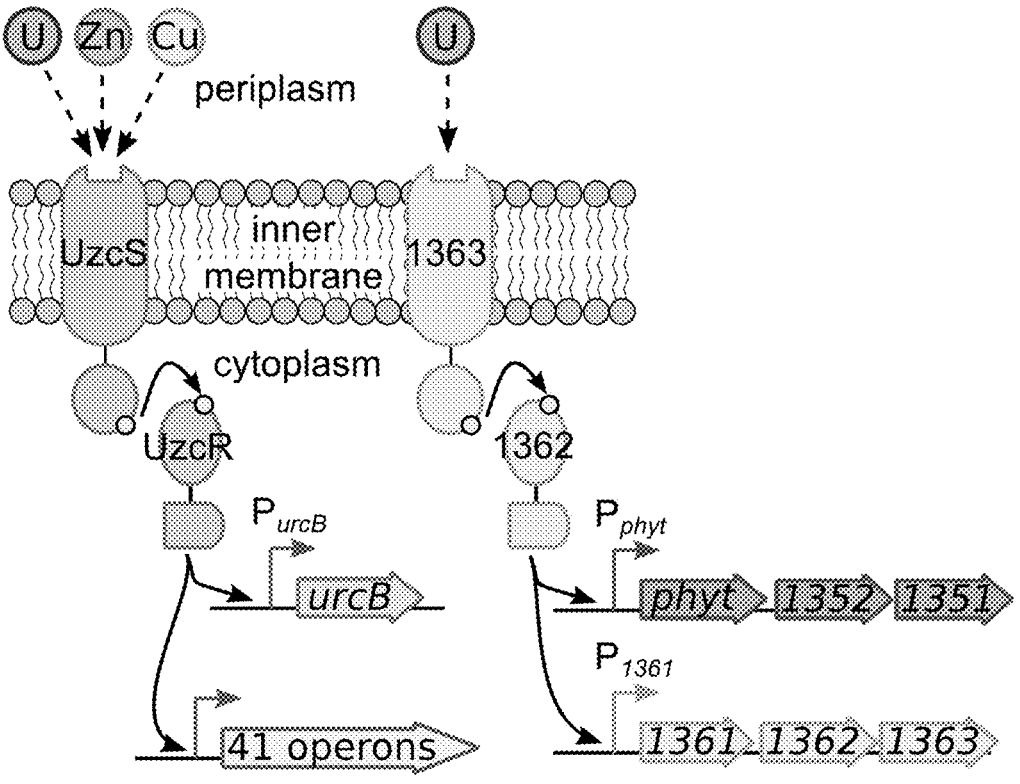
FIG. 3A shows schematics of two exemplary independent two component systems (TCS) that are sensitive to U in Caulobacter crescentus. Shown on the left side of FIG. 3A is a schematic of the putative mechanism of action of the UzcRS TCS, which was characterized as a transcriptional activator of at least 40 operons in response to U/Zn/Cu [3]. Shown on the right side of FIG. 3A is a schematic of the putative mechanism of action of the 1363/1362 TCS, wherein a histidine kinase 1363 (encoded by CCNA_01363) and a response regulator 1362 (encoded by CCNA_01362) activate promoters comprising the 1362 regulator direct repeat DNA binding site, e.g. P$_{phyt}$ and P$_{1361}$, in response to U. 1363 is membrane-bound and senses U either through a direct (U binding to 1363) or indirect mechanism. Upon U sensing, it is expected that 1363 autophosphorylates and then transphosphorylates 1362, activating 1362 for DNA binding of the 1362 direct repeat, e.g. in P$_{phyt}$ or P$_{1361}$. Possible additional stimuli for 1363/1362 remain unknown (indicated by the circled question mark).

An exemplary illustration of two-component system formed by the U-sensitive histidine kinase 1363 (UrpS) and the cognate response regulator 1362 (UrpR) is shown in the schematics of FIG. 3A.

Genes encoding histidine kinase 1363 (UrpS) and response regulator 1362 (UrpR) herein described are herein also indicated as 1363 gene or 1363 and 1362 gene or 1362, respectively as will be understood by a skilled person.

A representative example of histidine kinase P1363 (UrpS) and response regulator 1362 (UrpR) in a two component system herein described are provided by the histidine kinase encoded by 1363 gene CCNA_01363 in *Caulobacter crescentus* (SEQ ID NO:3), and the response regulator 1362 encoded by 1362 gene CCNA_01362 (SEQ ID NO:4), forming a two component systems respectively as will be understood by a skilled person.

In some embodiments the histidine kinase P1363 (UrpS) and response regulator p1362 (UrpR) can be heterologously expressed in the bacterial cell through genetic engineering of the cell performed to include in the cell a U-sensing regulator genetic molecular component comprising an endogenous or exogenous gene encoding histidine kinase 1363 (UrpS) and an endogenous or exogenous gene encoding U-sensitive transcriptional regulator 1362 (UrpR) in a configuration wherein the gene encoding histidine kinase 1363 and the gene encoding response regulator 1362 (UrpR) response regulator UzcR are expressed upon activation of a controllable promoter.

In some embodiments the histidine kinase P1363 (UrpS) and response regulator p1362 (UrpR) can be natively expressed in the bacterial cell. In particular in some embodiments, the host cell of the U-biosensors herein described is capable of natively expressing the proteins of the U-sensing two-component system 1363 (UrpS) and 1362 (UrpR) described herein. Those embodiments typically comprise certain proteobacterial cell such as alphaproteobacteria, betaproteobacteria or gammaproteobacteria comprising an endogenous 1363/1362 TCS (UrpRS) which can be identified and selected by methods to detect 1363 (UrpS) and/or 1362 (UrpR) genes in a candidate bacterial cell identifiable by a skilled person.

For example, presence of a 1363/1362 TCS or UrpRS in a proteobacterial cell can be identified by wet bench experiments, such as PCR, Southern blotting and additional techniques identifiable by a skilled person performed with histidine kinase P1363 (UrpS) and response regulator p1362 (UrpR) and/or fragments thereof used as primers or probes for the related detection, followed by isolation and sequencing of the identified 1363 gene and/or 1362 gene as will be understood by a skilled person.

In addition or in the alternative, presence of a 1363/1362 TCS (UrpRS) in a proteobacterial cell can be identified by performing a sequence alignment using BLASTP or PSI-BLAST or other alignment algorithms known to persons skilled in the art with the 1363 (UrpS) amino acid sequence of *C. crescentus* NA1000 (SEQ ID NO:3) and/or the 1362 (UrpR) protein sequence of *Caulobacter crescentus* NA1000 (SEQ ID NO:4) as a query sequence against protein sequences of a given proteobacterial cell, as would be understood by a skilled person.

In some embodiments, the U sensing bacterial cell can comprise proteobacteria capable of natively expressing a 1363 (UrpS) protein having 100% homology to 1363 (UrpS) protein of *C. crescentus* NA1000 (SEQ ID NO: 3), and/or having a BLAST Score of 851 when aligned with SEQ ID NO: 3, (herein also 1363/1362 Tier 1 proteobacteria or UrpRS Tier 1 proteobacteria) such as proteobacteria *C. crescentus* NA1000 and *C. crescentus* CB15.

In some embodiments, the U sensing bacterial cell can comprise proteobacteria capable of natively expressing 1363 (UrpS) proteins having a BLAST Score over 800 when aligned to 1363 (UrpS) protein of *C. crescentus* NA1000 (SEQ ID NO: 3) and with less than 100% homology to *C. crescentus* NA1000 1363) SEQ ID NO: 3, (herein also 1363/1362 Tier 2 proteobacteria or UrpRS Tier 2 proteobacteria) such as exemplary proteobacterium *C. crescentus* CB2 among others identifiable by persons skilled in the art.

In some embodiments, the U sensing bacterial cell can comprise proteobacteria capable of natively expressing 1363 (UrpS) proteins having a BLAST Score of 500-800 when aligned to 1363 (UrpS) protein of *C. crescentus* NA1000 (SEQ ID NO: 3) (herein also 1363/1362 Tier 3 or UrpRS Tier 3) such as proteobacteria *Caulobacter henricii, Caulobacter* sp. CCH5-E12, *Caulobacter* sp. OV484, *Caulobacter* sp. Root487D2Y, *Caulobacter* sp. Root1455, *Caulobacter* sp. 12-67-6, *Caulobacter* sp. Root487D2Y, *Caulobacter* sp. Root1455, *Caulobacter* sp. UNC358MFTsu5.1, *Caulobacter* sp. AP07 and *Caulobacter*, among others identifiable by persons skilled in the art.

In some embodiments, the U sensing bacterial cell can comprise proteobacteria capable of natively comprising a 1362 (UrpR) binding site (SEQ ID NO: 1) in a phytase or 1361 promoter, also referred to herein as "Pphyt" and "P1361", respectively (herein also indicated as 1363/1362 Tier 4 proteobacteria or UrpRS Tier 4 proteobacteria). Exemplary proteobacteria within these embodiments comprise *Caulobacter* sp. Root342, *Phenylobacterium* sp. Root700, *Caulobacter crescentus* NA1000, *Caulobacter* sp. Root1455, *Caulobacter* sp. Root487D2Y, *Paracoccus* sp. 228, Caulobacteraceae bacterium OTSz_A_272, Novosphingobium sp. AP12 PMI02, *Hyphomicrobium* sp. MCi, *Hyphomicrobium denitrificans*, *Brevundimonas* sp. Root1279 *Sphingopyxis* sp. Root1497, *Afipia* sp. P52-10, *Caulobacter* sp. Root342 *Hyphomicrobium denitrificans*, Sphingobium sp. YBL2, *Sphingobium baderi* LL03, Sphingobium indicum B90A, and *Roseovarius indicus* strain DSM 26383, among others identifiable by persons skilled in the art.

In some embodiments, the U sensing bacterial cell can comprise proteobacteria capable of natively expressing 1363 (UrpS) proteins having a BLAST Score of 300-500 when aligned to 1363 protein of *C. crescentus* NA1000 (SEQ ID NO: 3) (herein also indicated as 1363/1362 Tier 5 proteobacteria or UrpRS Tier 5 proteobacteria) such as exemplary proteobacteria *Phenylobacterium* sp. Root700, *Phenylobacterium* sp. Root700, *Caulobacter* sp. 39-67-4, *Sphingopyxis* sp. SCN 67-31, *Phenylobacterium* sp. SCN 70-31, *Sphingopyxis flava*, Caulobacteraceae bacterium OTSz_A_272, *Sphingobium baderi*, *Caulobacterales bacterium* 68-7, alpha proteobacterium U9-li, *Caulobacter* sp. 35-67-4, *Sphingopyxis granuli*, *Sphingopyxis macrogoltabida*, *Brevundimonas* sp. Root1279, *Sphingopyxis macrogoltabida*, *Brevundimonas* sp. Root1279, *Sphingopyxis macrogoltabida*, *Hyphomonas polymorpha*, *Porphyrobacter mercurialis*, Caulobacteraceae bacterium TH1-2, Hyphomonadaceae bacterium UKL13-1, *Sphingopyxis macrogoltabida*, *Porphyrobacter mercurialis*, and *Novosphingobium* sp. PASSN1, among others identifiable by persons skilled in the art.

In some embodiments, the U sensing bacterial cell can comprise proteobacteria capable of natively expressing 1363 (UrpS) proteins having a BLAST Score of 240-300 when aligned to 1363 protein of *C. crescentus* NA1000 (SEQ ID NO3), (herein indicated also as 1363/1362 Tier 6 proteobacteria or UrpRS Tier 6 proteobacteria) identifiable by persons skilled in the art.

In some embodiments, the U sensing bacterial cell can comprise proteobacteria capable of natively expressing 1363 proteins having a BLAST Score of 200-240 when aligned to 1363 protein of *C. crescentus* NA1000 (SEQ ID NO:3) (herein also indicated as 1363/1362 Tier 7 proteobacteria or UrpRS Tier 7 proteobacteria), identifiable by persons skilled in the art.

In some embodiments, the U sensing bacterial cell can comprise proteobacteria capable of natively expressing 1363 (UrpS) proteins having a BLAST Score of less than 200 when aligned to 1363 (UrpS) protein of *C. crescentus* NA1000 (SEQ ID NO: 3) (herein also indicated as 1363/1362 Tier 8 proteobacteria or UrpRS Tier 8 proteobacteria), identifiable by persons skilled in the art (herein also indicated as Tier 8 proteobacteria).

In embodiments of the U biosensor herein described wherein the host cell is a proteobacterial cell of any one of 1363/1362 Tiers 1 to 6 (UrpRS Tiers 1 to 6), the host proteobacterium can comprise a bacterial cell with a natively and/or heterologously expressed 1363/1362 TCS (UrpRS) endogenous to the host proteobacterium. In embodiments wherein the host cell is a bacterial cell other than proteobacteria or a proteobacteria of 1363/1362 Tiers 7 and 8, the host is engineered to include a heterologous 1363/1362 TCS system in a configuration capable of heterologous expression in the host bacteria as will be understood by a skilled person. In some embodiments wherein the host cell is a proteobacteria of 1363/1362 Tier 6, the host can be firstly tested for the presence of a natively expressed 1363/1362 TCS endogenous to the host proteobacteria according to procedure identifiable by a skilled person. The test can be performed by transforming the cell with a plasmid or other vector containing Pphyt or P1361-regulated gfp fusion and assaying the system for U-dependent induction of GFP as will be understood by a skilled person. If the host cell does not possess a natively expressed 1363/1362 TCS, the host can be engineered to include a heterologous 1363/1362 TCS system in a configuration capable of heterologous expression in the host bacteria.

In embodiments wherein a heterologous 1363/1362 TCS (UrpRS) is introduced into the host cell, the heterologous 1363/1362 TCS can be a 1363/1362 TCS system from a 1363/1362 Tier 1, a 1363/1362 Tier 2, a 1363/1362 Tier 3, a 1363/1362 Tier 4 or a 1363/1362 Tier 5 proteobacteria, and it is preferably a 1363/1362 TCS from a 1363/1362 Tier 2 proteobacteria and more preferably from a 1363/1362 Tier 1 proteobacteria. In those embodiments wherein a heterologous 1363/1362 TCS is introduced into a host cell, the native 1363/1362 TCS of the host cell is preferably knocked out, in particular in embodiments wherein the host organism is a proteobacteria of any one of 1363/1362 Tiers 1 to 6. The native 1363/1362 TCS of the host cell can be knocked out by deleting or inactivating the 1362 gene cluster only or by deleting or otherwise inactivating both the 1362 and 1363 gene clusters.

In some embodiments, $UO_2F_2$-biosensors herein described the proteobacterial cell is capable of natively and/or heterologously expressing a U-sensitive histidine kinase UzcS, and a transcriptional response regulator UzcR.

The term "histidine kinase UzcS", "UzcS" in the sense of the disclosure refers to a histidine kinase having the amino acid sequence:

(SEQ ID NO: 5)

MRLPRLLRTTPFRLTLLFLALFAAAASAFLGYIYVATAGEVNRRAQA

EISREFESLEAAYRQGGVDALNQTIVERATSERPFLYFLADKDGKRI

SGSIEESPVSGFTGDGPEWASFKVTETDLDGAEVKAAARGVQQRLDN

GEILFVGADVDASEAYVRKIVRALWGAGALVILLGMAGGVLISRNVS

RSMQGLVDVVNAVRGGDLHARARVRGTRDEYDELAEGLNDMLDRIER

LMGGLRHAGDAIAHDLRSPLTRLRARMEVALIDAENGKGDPVAALET

ALQDADGVLKTFNAVLAIARLQAAGSAPDQRQFDASELAGDMAELYE

LSCEDKGLDFKAEIVPALTIKGNREFLAQALANILDNAIKYTPEGGA

IMLRARRTSSGELEFSVTDTGPGVPEADRARVVQRFVRLENSRSEPG

AGLGLSLVSAVATSHGGRLELAEGPGEYNGMGPGLRVALVLPRVE.

or a sequence that when aligned with sequence SEQ ID NO: 5 has a BLAST score has a BLAST score greater than 300 and less than 500, or preferably greater than 500 and less than 767, or more preferably a BLAST score greater than 800 and a homology with SEQ ID NO: 5 less than 100%, or even more preferably BLAST score of 925 and an homology of 100% with SEQ ID NO: 5.

The term "transcriptional response regulator UzcR" or "UzcR' as used herein indicates a transcriptional regulator having the amino acid sequence:

(SEQ ID NO: 6)

```
MRILIIEDDLEAAGAMAHGLKEAGYDVAHAPDGEAGLAEAQKGGWDV

LVVDRMMPKMDGVTVVETLRREGDQTPVLFLSALGEVNDRVVGLKAG

ADDYLVKPYAFPELMARVEALSRRRETGAVATTLKVGELEMNLINRT

VHRQGKEIDLQPREFQLLEFMMRHAGQSVTRTMLLEKVWEYHFDPQT

NVIDVHISRLRSKIDKGFDRAM LQTVRGAGYRLDP.
``` or a sequence that when aligned with sequence SEQ ID NO: 6 has a BLAST score greater than 250 and less than 300, or preferably greater than 300 and less than 400, or more preferably a BLAST score greater than 400 and a homology with SEQ ID NO: 6 less than 100%, or even more preferably a BLAST score of 452 and an homology of 100% with SEQ ID NO: 6.

Figure 3B:
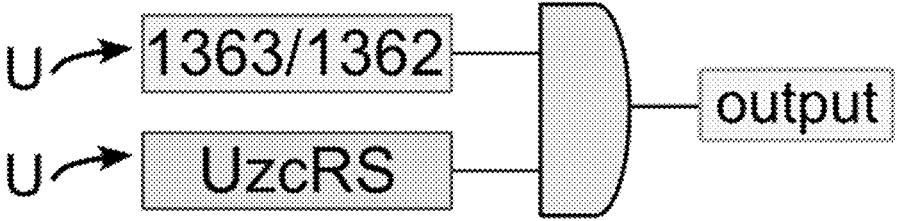
FIG. 3B shows a schematic of an exemplary U-sensitive AND gate that incorporates two independent points of uranyl sensing inputs (the two-component systems 1363/1362 AND UzcRS), which are both required to affect an output (such as a reportable molecular component and/or a U-neutralizing molecular component). The 1363/1362 two-component system is specifically activated by uranyl. The UzcRS two component system is activated for transcriptional regulation by uranyl, as well as zinc, copper and cadmium [3].

In $UO_2F_2$-biosensors herein described, the U-sensitive histidine kinase UzcS, and transcriptional response regulator UzcR form a two-component system in the sense of the disclosure, also referred to herein as "UzcRS two-component system" or "UzcRS TCS" which is similar to the 1363/1362 TCS system herein described and exemplified by the schematics of FIG. 3.

In particular, the term "UzcRS two component system" or UzcRS TCS" as used herein refers to a regulatory system responsible for U, Zn, and Cu-dependent regulation of numerous genes in *Caulobacter crescentus* [3]. The UzcRS two component system comprises an OmpR/PhoB family response regulator (RR) and a histidine kinase (HK) containing a 123 amino acid periplasmic domain, placing it in the periplasmic-sensing class of histidine kinases [42].

Genes encoding histidine kinase UzcS and response regulator UczR herein described are herein also indicated as UzcS gene or UzcS and UczR gene or UczR, respectively as will be understood by a skilled person.

A representative example of histidine kinase UzcS and transcriptional response regulator UzcR in a UzcRS two components system herein described are provided by histidine kinase encoded by UzcS gene CCNA_02842in *C. crescentus* NA1000 (SEQ ID NO: 5) and by a transcriptional response regulator, for example encoded by UzcR gene CCNZ_02485in *C. crescentus* NA1000 (SEQ ID NO: 6) as will be understood by a skilled person.

In some embodiments the histidine kinase UzcS and transcriptional response regulator UzcR can be heterologously expressed in the bacterial cell through genetic engineering of the cell performed to include in the cell a U-sensing regulator genetic molecular component comprising an endogenous or exogenous gene encoding histidine kinase UzcS and an endogenous or exogenous gene encoding U-sensitive transcriptional response regulator UzcR in a configuration wherein the gene encoding histidine kinase UzcS and the gene encoding response regulator UzcR are expressed upon activation of a controllable promoter.

In some embodiments the histidine kinase UzcS and transcriptional response regulator UzcR are natively expressed in the bacterial cell. In particular in some embodiments, the host cell of the U-biosensors herein described is capable of natively expressing the proteins of the U-sensing UzcS/UzcR TCS described herein. Those embodiments typically comprise certain proteobacterial cell such as alphaproteobacteria, betaproteobacteria or gammaproteobacteria comprising an endogenous UzcS/UzcR TCS which can be identified and selected by methods to detect UzcS and/or UzcR genes in a candidate bacterial cell identifiable by a skilled person.

For example, presence of a UzcS/UzcR TCS in a proteobacterial cell can be identified by wet bench experiments, such as PCR, Southern blotting and additional techniques identifiable by a skilled person performed with histidine kinase UzcS and response regulator UzcR and/or fragments thereof used as primers or probes for the related detection, followed by isolation and sequencing of the identified UzcS gene and/or UzcR gene as will be understood by a skilled person. The presence of an UzcS/UzcR TCS can also be identified by introducing in the cell a UzcR-regulated GFP fusion promoter and detecting GFP fluorescence thus testing for U-dependent fluorescence as will be understood by a skilled person.

In addition or in the alternative, a UzcS/UzcR TCS in a proteobacterial cell can be identified by performing a sequence alignment using BLASTP or PSI-BLAST or other alignment algorithms known to persons skilled in the art with the UzcS amino acid sequence of *C. crescentus* NA1000 (SEQ ID NO: 5) and/or the UzcR protein sequence of *Caulobacter crescentus* NA1000 (SEQ ID NO: 6) as a query sequence against protein sequences of a given proteobacterial cell, as would be understood by a skilled person.

In some embodiments, the U sensing bacterial cell can comprise proteobacteria capable of natively expressing UzcS proteins having 100% homology to UzcS protein of *C. crescentus* NA1000 (SEQ ID NO: 5) and a BLAST score of 925 when aligned to sequence SEQ ID NO: 5 (herein also indicated as UzcS/UzcR Tier 1 proteobacteria).

In some embodiments, the U sensing bacterial cell can comprise proteobacteria capable of natively expressing UzcS proteins having a homology of less than 100% to UzcS protein of *C. crescentus* NA1000 (SEQ ID NO: 5) and a BLAST score greater than 800 when aligned to sequence SEQ ID NO: 5 (herein also indicated as UzcRS Tier 2 proteobacteria).

In some embodiments, the U sensing bacterial cell can comprise proteobacteria capable of natively expressing UzcS proteins a BLAST score greater than 767 and lower than 800 when aligned to sequence SEQ ID NO: 5 (herein also indicated as UzcRS Tier 3 proteobacteria).

In some embodiments, the U sensing bacterial cell can comprise proteobacteria capable of natively expressing UzcS proteins having a BLAST score greater than 500 and less than 767 when aligned to sequence SEQ ID NO: 5 (herein also indicated as UzcRS Tier 4 proteobacteria).

In some embodiments, the U sensing bacterial cell can comprise proteobacteria capable of natively expressing UzcS proteins having a BLAST score greater than 300 and less than 500 when aligned to sequence SEQ ID NO: 5 (herein also indicated as UzcRS Tier 5 proteobacteria).

In some embodiments, the U sensing bacterial cell can comprise proteobacteria capable of natively expressing UzcS proteins having a BLAST score greater than 250 and less than 300 when aligned to sequence SEQ ID NO: 5 (herein also indicated as UzcRS Tier 6 proteobacteria).

In some embodiments, the U sensing bacterial cell can comprise proteobacteria capable of natively expressing UzcS proteins having a BLAST score greater than 200 and less than 250 when aligned to sequence SEQ ID NO: 5 (herein also indicated as UzcRS Tier 7 proteobacteria).

In some embodiments, the U sensing bacterial cell can comprise proteobacteria capable of natively expressing UzcS proteins having a BLAST score less than 200 when aligned to sequence SEQ ID NO: 5 (herein also indicated as UzcRS Tier 8 proteobacteria).

In embodiments of the U biosensor herein described wherein the host cell is a proteobacterial cell of any one of UzcRS Tiers 1 to 6, the host proteobacterium can comprise a bacterial cell with a natively and/or heterologously expressed UzcRS TCS endogenous to the host proteobacterium. In embodiments wherein the host cell is a bacterial cell other than proteobacteria or a proteobacteria of UzcRS Tiers 7 and 8, the host is engineered to include a heterologous UzcRS TCS system in a configuration capable of heterologous expression in the host bacteria as will be understood by a skilled person.

In embodiments wherein a heterologous UzcRS TCS is introduced into the host cell, the heterologous UzcRS TCS can be a UzcRS TCS system from a 1363/1362 Tier 1, a UzcRS Tier 2, a UzcRS Tier 3, a UzcRS Tier 4 or a UzcRS Tier 5 proteobacteria, and it is preferably a UzcRS TCS from a UzcRS Tier 2 proteobacteria and more preferably UzcRS TCS from a UzcRS Tier 1 proteobacteria. In those embodiments wherein a heterologous UzcRS TCS is introduced into a host cell, the native UzcRS TCS of the host cell is preferably knocked out, in particular in embodiments wherein the host organism is a proteobacteria of any one of UzcRS Tiers 1 to 6. The native UzcRS TCS of the host cell can be knocked out by deleting or otherwise inactivating the UzcR gene cluster only or by deleting or otherwise inactivating both the UzcR and UzcS gene clusters according to techniques identifiable by a skilled person (e.g. by microdeletion, clean deletion via double recombination, recombineering (e.g., Wanner method [46]) insertional inactivation, CRISPRi, CRISPR-mediate recombination, transposon insertion, mutational inactivation, methylation and/or epigenetic inactivation as well as other techniques identifiable by a skilled person).

In some embodiments of the $UO_2F_2$-biosensors herein described, a bacterial cell capable of natively and/or heterologously expressing histidine kinase 1363, and transcriptional response regulator 1362, and/or capable of natively and/or heterologously expressing a U-sensitive histidine kinase UzcS, and a transcriptional response regulator UzcR, is genetically engineered to include a U-sensitive genetic molecular component configured to report and/or neutralize U.

The term "molecular component" as used herein indicates a chemical compound comprised in a cellular environment. Exemplary molecular components thus comprise polynucleotides, such as ribonucleic acids or deoxyribonucleic acids, polypeptides, polysaccharides, lipids, amino acids, peptides, sugars and/or other small or large molecules and/or polymers that can be found in a cellular environment.

The term "genetic molecular component" as used herein indicates a molecular unit formed by a gene, an RNA transcribed from the gene or a portion thereof and optionally a polypeptide or a protein translated from the transcribed RNA.

In embodiments herein described, a genetic molecular component comprises a promoter operatively connected to the gene of the genetic molecular component, so that the promoter is configured to initiate transcription of said gene. As would be understood by those skilled in the art, promoters are typically located adjacent to the transcription start sites of genes, on the same strand and upstream on a DNA sequence (towards the 5' region of the sense strand), and for transcription to occur, the enzyme that synthesizes RNA, known as RNA polymerase, attaches to the promoter. Promoters contain DNA sequences identifiable by those skilled in the art and described herein, such as those that provide binding sites for RNA polymerase and also for proteins that function as transcription regulatory factors that can either activate or repress gene transcription.

The term "transcription regulatory factor" or "transcription factor" as used herein refers to any type of factors that can function by acting on a regulatory DNA element such as a promoter or enhancer sequence. The transcription regulatory factors can be broadly classified into a transcription repression factor (also referred to as "repressor") and a transcription activation factor (also referred to as "activator"). The transcription repression factor acts on a regulatory DNA element to repress the transcription of a gene, thereby reducing the expression level of the gene. The transcription activation factor acts on a regulatory DNA element to promote the transcription of a gene, thereby increasing the expression level of the gene. Both the transcription repression factors and the transcription activation factors can be used as one or more components in the gene circuits herein described. In particular, a transcription regulatory factor has typically at least one DNA-binding domain that can bind to a specific sequence of enhancer or promoter sequences.

Some transcription factors bind to a DNA promoter sequence near the transcription start site and help form the transcription initiation complex. Other transcription factors bind to other regulatory sequences, such as enhancer sequences, and can either stimulate or repress transcription of the related gene. Examples of specific transcription repression factors include TetR, LacI, LambdaCI, PhlF, SrpR, QacI, BetR, LmrA, AmeR, LitR, met, and others identifiable by a skilled person, as well as homologues of known repression factors, that function in both prokaryotic and eukaryotic systems. Examples of transcription activation factors include AraC, LasR, LuxR, IpgC, MxiE, Gal4, GCN4, GR, SPi, CREB, and additional activation factors identifiably by a skilled person as well as homologues of known activation factors that function in both prokarayotic and eukaryotic systems also identifiable by a skilled person. Exemplary inducible regulators that can be used in *Caulobacter* comprise VanR (regulated by vanillate) and XylR (regulated by xylose), as well as others identifiable by those skilled in the art.

A gene comprised in a genetic molecular component is a polynucleotide that can be transcribed to provide an RNA and typically comprises coding regions as well as one or more regulatory sequence regions which is a segment of a nucleic acid molecule which is capable of increasing or decreasing transcription or translation of the gene within an organism either in vitro or in vivo. In particular coding regions of a gene herein described can comprise one or more protein coding regions which when transcribed and translated produce a polypeptide, or if RNA is the final product only a functional RNA sequence that is not meant to be translated. Regulatory regions of a gene herein described comprise promoters, transcription factor binding sites, operators, activator binding sites, repressor binding sites, enhancers, protein-protein binding domains, RNA binding domains, DNA binding domains, silencers, insulators and additional regulatory regions that can alter gene expression in response to stimuli as will be recognized by a person skilled in the art.

An RNA of a genetic molecular component comprises any RNA that can be transcribed from a gene, such as a messenger ribonucleic acid (mRNA), short interfering ribonucleic acid, and ribonucleic acid capable of acting as regulating factors in the cell. mRNA comprised in a genetic molecular component comprise regions coding for the protein as well as regulatory regions e.g. ribosome binding site domains ("RBS"), which is a segment of the upstream (5') part of an mRNA molecule to which the ribosomal machinery of a cell binds to position the message correctly for the initiation of translation. RBSs control the accuracy and efficiency with which the translation of mRNA begins. mRNA can have additional control elements encoded, such as riboregulator sequences or other sequences that form hairpins, thereby blocking the access of the ribosome to the Shine-Delgarno sequence and requiring an external source, such as an activating RNA, to obtain access to the Shine-Delgarno sequence. Other RNAs that serve regulatory roles that can comprise the genetic molecular component include riboswitches, aptamers (e.g. malachite green, Spinach), aptazymes, guide CRISPR RNAs, and other RNAs known to those skilled in the art.

A protein comprised in a molecular component can be proteins with activating, inhibiting, binding, converting, or reporting functions. Proteins that have activating or inhibiting functions typically act on operator sites encoded on DNA, but can also act on other molecular components. Proteins that have binding functions typically act on other proteins, but can also act on other molecular components. Proteins that have converting functions typically act on small molecules, and convert small molecules from one small molecule to another by conducting a chemical or enzymatic reaction. Proteins with converting functions can also act on other molecular components. Proteins with reporting functions have the ability to be easily detectable by commonly used detection methods (absorbance, fluorescence, for example), or otherwise cause a reaction on another molecular component that causes easy detection by a secondary assay (e.g. adjusts the level of a metabolite that can then be assayed for). The activating, inhibiting binding, converting, or reporting functions of a protein typically form the interactions between genetic components of a genetic circuit. Exemplary proteins that can be comprised in a genetic molecular component comprise monomeric proteins and multimeric proteins, proteins with tertiary or quaternary structure, proteins with linkers, proteins with non-natural amino acids, proteins with different binding domains, and other proteins known to those skilled in the art. Specific exemplary proteins include TetR, LacI, LambdaCI, PhlF, SrpR, QacI, BetR, LmrA, AmeR, LitR, met, AraC, LasR, LuxR, IpgC, MxiE, Gal4, GCN4, GR, SPi, CREB, and others known to a skilled person in the art.

A "U-sensing genetic molecular component" or "U-sensitive genetic molecular component" as used herein indicates a genetic molecular component wherein the gene of the genetic molecular component is under control of a U-sensing or U-sensitive promoter.

In particular, in some embodiments herein described, wherein the host cell is capable of natively and/or heterologously expressing the histidine kinase P1363 and response regulator p1362, at least one U-sensitive promoter comprises a U-sensitive 1362 binding site having a DNA sequence $$N_1N_2N_3N_4N_5N_6N_7N_8N_9N_{10}N_{11}N_{12}N_{13}N_{14}N_{15}N_{16}N_{17}N_{18},$$
(SEQ ID NO: 1)

wherein $N_1$ is C or T, preferably C;
$N_2$ is G or A, preferably G;
$N_3$ is T or C, preferably T;
$N_4$ is C; $N_5$ is A or G, preferably A;
$N_6$ is G or C, preferably G;
$N_7$ C or G;
$N_8$ is any nucleotide;
$N_9$ is any nucleotide;

$N_{10}$ is any nucleotide;
$N_{11}$ is any nucleotide;
$N_{12}$ is T or C;
$N_{13}$ is G;
$N_{14}$ is T or C, preferably T;
$N_{15}$ is C;
$N_{16}$ is A or C, preferably A;
$N_{17}$ is G; and
$N_{18}$ is C or G
and wherein $N_1$ to $N_{17}$ are selected independently.

In some embodiments of the U-sensing promoter comprising SEQ ID NO: 1, nucleotide $N_1$ of the regulator direct repeat is in a position from about 16 nucleotides downstream of the transcription start site of the genetic molecular component as described herein to about 40 nucleotides upstream of the transcription start site of the genetic molecular component or genetic molecular component.

In some embodiments, the U-sensitive promoter further comprises nucleotides $N_{19}N_{20}N_{21}$ (SEQ ID NO: 83), downstream of SEQ ID NO: 1 wherein each of $N_{19}$ to $N_{21}$ can independently be any nucleotide, and therefore $N_{19}$ is any nucleotide $N_{20}$ is any nucleotide; and $N_{21}$ is G.

In some embodiments of the U biosensors described herein, the 1362 binding site has a DNA sequence CGTCAGCNNNNTGTCAGC (SEQ ID NO:7), CGTCAGGNNNNTGTCAGG (SEQ ID NO: 8), CGTCAGCNNNNTGTCAGG (SEQ ID NO:9), CGTCAGCNNNNCGTCAGG (SEQ ID NO: 10), TGTCAGCNNNNTGTCAGC (SEQ ID NO: 11), CGCCTGCNNNNCGTCAGC (SEQ ID NO: 12), CGTCAGGNNNNCGTCAGC (SEQ ID NO: 13), CGTCAGCNNNNTGTCAGC (SEQ ID NO: 14), TGTCAGGNNNNTGTCAGC (SEQ ID NO: 15), CGTCAGCNNNNCGTCAGT (SEQ ID NO: 16), CCGCGGGNNNNTGTCAGG (SEQ ID NO: 17), CGTCGGGNNNNAGACCGG (SEQ ID NO: 18), CGTCCGGNNNNCGTCAGA (SEQ ID NO: 19), CAACGCCNNNNCGTCAGC (SEQ ID NO: 20), CATCAGGNNNNCGTCAGC (SEQ ID NO: 21), CGCAGGGNNNNTGCAAGC (SEQ ID NO: 22), CATCAGCNNNNCGTCAGC (SEQ ID NO: 23), CGT-CATCNNNNTGTCACG (SEQ ID NO: 24), CGTCAGCNNNNCATCAGC (SEQ ID NO: 25), CTTCGCGNNNNCGTCCGG (SEQ ID NO: 26), CGTCAGGNNNNGGTCAGG (SEQ ID NO: 27), or TGTCAGCNNNNATCCTGC (SEQ ID NO: 28), wherein N can be any nucleotide.

In some embodiments, wherein the U-biosensor comprises a genetically engineered proteobacterial cell capable of natively and/or heterologously expressing histidine kinase UzcS, and U-sensitive transcriptional response regulator UzcR, at least one U-sensitive promoter comprises a UzcR binding site with an m_5 site configured for binding UzcR, having a DNA sequence:

$$CATTACN_7N_8N_9N_{10}N_{11}N_{12}TTAA$$
(SEQ ID NO: 2)

wherein $N_7$-$N_{12}$ is independently any nucleotide, and in some embodiments $N_7$-$N_{11}$ can independently be A. In an embodiment, each of $N_7$-$N_{12}$ can be A.

In some embodiments, in the proteobacterial cell, the endogenous genes encoding the histidine kinase UzcS, and the U-sensitive transcriptional response regulator UzcR, are knocked out and the genetically engineered proteobacterial cell is further engineered to include a U-sensing regulator genetic molecular component comprising an endogenous or exogenous gene encoding histidine kinase UzcS, and an endogenous or exogenous gene encoding U-sensitive transcriptional response regulator UzcR in a configuration wherein the a gene encoding histidine kinase UzcS, and a gene encoding response regulator UzcR are expressed upon activation of a controllable promoter.

In some embodiments, the U-sensitive promoter comprises a UzcR binding site can be either a constitutively active promoter or an inducible promoter. In preferred embodiments, the promoter is constitutively active.

The term "m_5 site" or ""UczR binding site" as used herein refers to a semi-palindromic consensus DNA binding site of sequence $CATTACN_7N_8N_9N_{10}N_{11}N_{12}TTAA$ (SEQ ID NO:2) [3], wherein $N_7$-$N_{12}$ is independently any nucleotide, and in some embodiments any one of $N_7$-$N_{11}$ can independently be A. One UzcR dimer likely to binds one m_5 site [3]. For example, a variant of an m_5 site wherein CATTAC (SEQ ID NO:29) is mutated to CAATAG (SEQ ID NO:30) is not bound by UzcR and a variant of an m_5 site wherein TTAA (SEQ ID NO:31) is mutated to TAAT (SEQ ID NO:32) is no longer activated by UzcR [3].

In embodiments herein described, UzcRS-regulated promoters comprise those having naturally-occurring m_5 sites or m_5 sites that are introduced into a promoter through genetic engineering. Accordingly, UzcRS-regulated promoters comprise DNA sequence elements required for RNA Polymerase binding, as well as one or more m_5 sites, such that the promoter is configured to be regulated by the UzcRS two-component system. Similar to promoters comprising 1362 binding sites, in UzcRS-regulated promoters, the σ-RNAP biding sites typically have low sequence homology to the canonical $\sigma^{73}$-RNAP −10 and −35 hexamer sequences. Accordingly, typically transcriptional activation of native UzcRS-regulated promoters occurs through binding of UzcR to the promoter, consistent with little observed transcriptional activation in absence of UzcR.

In some embodiments, an UzcRS-regulated promoter can comprise 1-3 copies of the m_5 site. In particular, in some embodiments, when one or more m_5 sites are located at a position from about −50 to about −100 upstream of the TSS, preferably at a position −52/53 or −62/63 upstream of the TSS, considering the first nucleotide of Seq ID NO: 2 as the first nucleotide of the m_5 site upstream from the TSS (see the position of the first nucleotide (C on the 5' end) of the binding site in FIG. 25 A) wherein the m_5 site is configured for activation of the UzcRS-regulated promoter (see e.g. configurations of FIG. 25B); [3]). In some embodiments, one or more m_5 sites are located at a position 52 to 53 bp upstream of the TSS or at a position 62 or −63 bp upstream of the TSS considering the first nucleotide of Seq ID NO: 2 as the first nucleotide of the m_5 site upstream from the TSS (see the position of the first nucleotide (C on the 5' end) of the binding site in FIG. 25 A) wherein the m_5 site is configured for activation of the UzcRS-regulated promoter (see e.g. FIG. 25 B).

Figure 25:
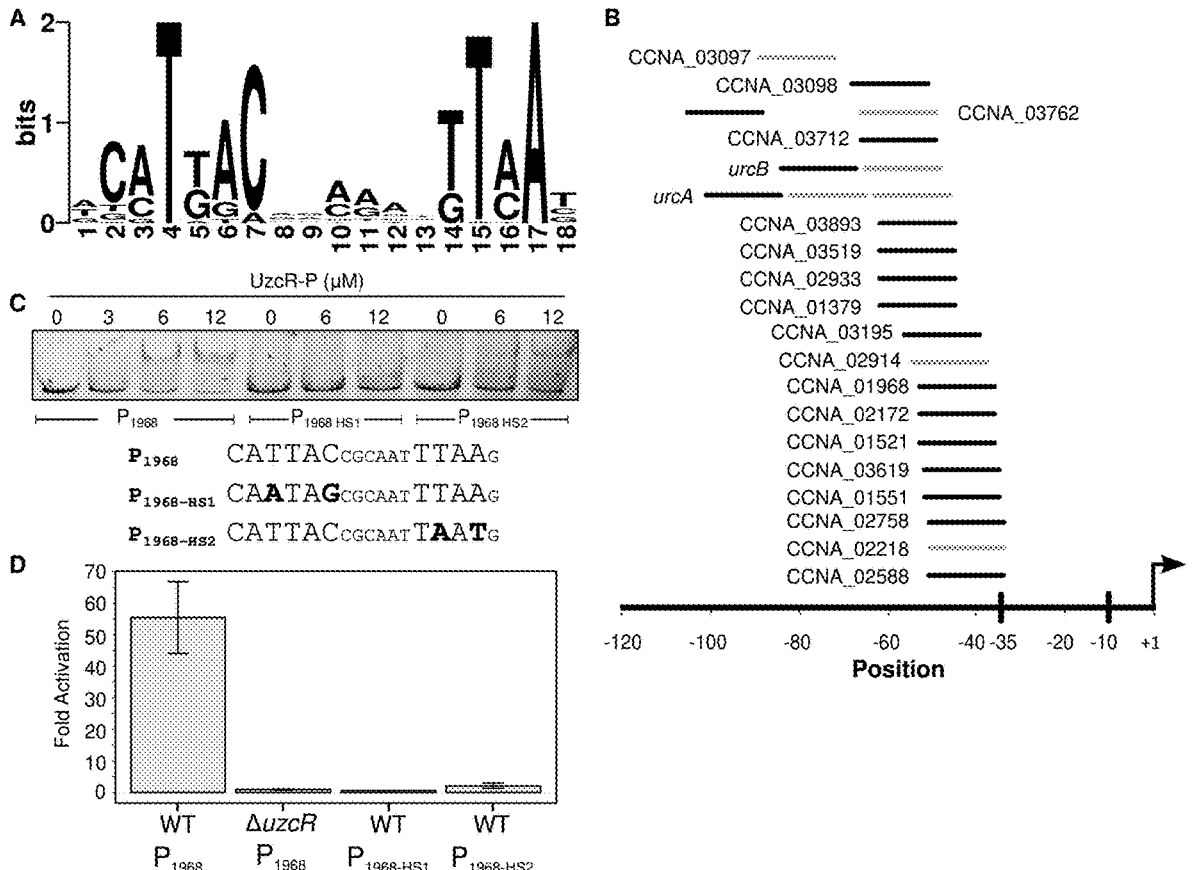
FIG. 25 shows an exemplary identification of the UzcR sequence recognition motif in some embodiments herein described. Panel (A): The 18-bp UzcR (m_5) sequence logo was constructed from the alignment of 49 UzcR boxes identified within the sequence regions bound by UzcR in vivo using MEME [21]. The sequence conservation (bits) is depicted by the height of the letters with the relative frequency of each base depicted by its relative height. Panel (B): Location of the predicted UzcR binding sites with respect to the previously determined Transcription Start Site (TSS) [22] for the directly activated operons. For urcA and urcB, the approximate TSSs as determined by tiled microarray analysis [23] were used. Note that multiple copies of the m_5 motif were found within some binding regions. For urcA and urcB, the approximate TSSs as determined by tiled microarray analysis [23] were used. The length of the line is representative of the length of the binding site with the line color denoting a directional orientation on the coding strand (black) or noncoding strand (gray). Panel (C): EMSA assays of UzcR-P binding to wild type and mutant $P_{1968}$ fragments. Each UzcR half site was individually eliminated by mutation away from consensus (bolded nucleotides). The Assays were performed with 5' 6-FAM-labeled DNA and UzcR-P, generated by phosphorylation of UzcR with carbamoyl phosphate. The concentrations indicate the total UzcR-P used in the assay and arrow depicts the shifted complex. A representative example of three biological replicates is depicted Panel (D): Effects of mutations in each UzcR half site on CCNA_01968 promoter activity in wild type and ΔuzcR backgrounds. Promoter-gfpmut3 fusions with the wild type and mutant $P_{1968}$ fragments described in Panel (B) were constructed and fluorescence was quantified following a two-hour treatment with or without M Zn using a Biotek plate reader (ex: 480/em: 516). The fluorescence signal was normalized to the $OD_{600}$ and fold activation was calculated by dividing the normalized fluorescence in the presence of Zn by the fluorescence in the uninduced condition. Error bars represent that standard deviation calculated using a formula for propagation of standard error [20] This figure is taken from the Appendix B of U.S. provisional application No. 62/587,753 the disclosure of which is incorporated herein by reference in its entirety.

In some embodiments, one or more m_5 sites are located at a position within 100 nucleotides upstream of the TSS considering the first nucleotide of Seq ID NO: 2 as the first nucleotide of the m_5 site upstream from the TSS (see the position of the first nucleotide (C on the 5' end) of the binding site in FIG. 25 A). In some embodiments, when one or more m_5 sites are located at a position from about −49 upstream of the TSS to +25 downstream of the TSS, in particular, −33 upstream of the TSS to +15 nt downstream of the TSS, the m_5 site is configured for repression of the UzcRS-regulated promoter.

In some embodiments herein described, the U-sensitive promoter is configured such that upon binding of the response regulator UzcR to the m_5 site, the U-sensitive promoter is activated and transcription of a gene operatively connected to the U-sensitive promoter within the related genetic molecular component is initiated.

In other embodiments, the U-sensitive promoter is configured such that upon binding of the U-sensitive transcriptional regulator to the U-sensitive transcriptional UzcR binding site, the U-sensitive promoter is repressed and transcription of a gene operatively connected to the U-sensitive promoter within the related U-sensing genetic molecular component is not initiated. In particular, in some embodiments one or more m_5 sites are located at a position −49 to +25 bp from the TSS considering the first nucleotide of Seq ID NO: 2 as the first nucleotide of the m_5 site upstream from the TSS The approximate range is −49 to +25 bp from the TSS (see the position of the first nucleotide (C on the 5' end) of the binding site (FIG. 25A).

For example, in an exemplary embodiment wherein a promoter is repressed by UzcR, a m_5 site is engineered downstream of a transcription start site of a U-sensitive promoter such as a $P_{1361}$ promoter or $P_{phyt}$ promoter (see Example 2). In these exemplary embodiments, insertion of a m_5 site downstream of the TSS of e.g. $P_{phyt}$ minimizes activation of $P_{phyt}$ in both the presence and absence of U. As would be understood by skilled persons, the latter is preferable as it minimizes UzcRS expression levels when no U is present, minimizing cross-reactivity with Zn and Cu.

Examples of promoters regulated by UzcRS comprise $P_{urcA}$, $P_{urcB}$, $P_{1968}$, and others identifiable by those skilled in the art, such as those described in Park et al., 2017 [3] herein incorporated by reference in its entirety (see also Example 11).

In several embodiments, one or more U-sensing promoters herein described are comprised within a U sensing genetic molecular component which is a genetically engineered polynucleotide construct configured to regulate expression of one or more RNA and/or protein-encoding genes through the one or more U-sensing promoter.

In some embodiments, the U-sensitive promoter includes a 1362 binding site functioning as a binding site for natively expressed U-sensitive transcriptional regulator 1362 and/or a UzcR binding site for natively expressed UzcR. In some embodiments of the U-biosensors herein described, the histidine kinase 1363, and U-sensitive transcriptional regulator 1362 are therefore encoded respectively by 1363 and 1362 genes natively encoded in the genome of the proteobacterial cell and the encoded 1363 and 1362 proteins can be natively expressed in the proteobacterial cell. Similarly, in some embodiments of the U-biosensors herein described, the histidine kinase UzcR, and U-sensitive transcriptional regulator UzcS are therefore encoded respectively by uczR and uczS genes natively encoded in the genome of the proteobacterial cell and the encoded UczR and UczS proteins are natively expressed in the proteobacterial cell.

In other embodiments of $UO_2F_2$-biosensors herein described, 1363 and 1362 genes and/or the uczR and uczS genes are introduced into the proteobacterial cell of (e.g. a species of the subclass Caulobacteridae) within one or more U-sensing regulator genetic molecular components configured to express the proteins 1363 and 1362 and/or UczR and UczS proteins upon activation of a controllable promoter.

In those embodiments, the genetic molecular components comprise the 1363 1362, uczR and/or uczS genes together with one or more regulatory regions configured to directly initiate expression of operatively connected 1363 and 1362 genes and/or operatively connected uczR and uczS genes. In some embodiments, a genetic molecular component introduced into the proteobacterial cell can comprise 1363 and 1362 genes and/or uczR and uczS genes in a same genetic molecular component, while in other embodiments the 1363 gene, the 1362 gene, the uczR gene and/or the uczS gene are comprised in different genetic molecular components. In some embodiments, the one or more regulatory regions operatively connected to the 1363 and/or 1362 genes and/or to the uczR and uczS genes, can comprise any promoter identifiable by skilled persons that is capable of initiating gene expression in a Caulobacteridae cell. Exemplary promoters that can be used to express 1363 and/or 1362 in Caulobacteridae comprise inducible promoter systems such as VanR (regulated by vanillate) and XylR (regulated by xylose), as well as others identifiable by those skilled in the art. In some embodiments, any constitutive promoter identifiable by those skilled in the art that has been characterized as functional to express an operatively linked gene of interest in a proteobacterial species of interest can be used to express 1363 and 1362 and/or uczR and uczS genes in the proteobacterial species of interest.

In some embodiments of the $UO_2F_2$ biosensors described herein wherein one or more genetic molecular components comprising a 1363 gene, 1362 gene, a uzcS and/or uzcR genes are introduced into a proteobacterial cell, the proteobacterial cell is further genetically engineered so that expression of its native a 1363 gene, 1362 gene, a uzcS and/or uzcR gene is inactivated by gene knockout.

In some embodiments, in the proteobacterial cell, the endogenous genes encoding histidine kinas 1363, transcriptional regulator 1362, histidine kinase UzcS, and/or the U-sensitive transcriptional regulator UzcR are knocked out and the genetically engineered proteobacterial cell is further engineered to include a U-sensing regulator component comprising a gene encoding histidine kinase UzcS, and a gene encoding response regulator UzcR in a configuration wherein the a gene encoding histidine kinase UzcS, and a gene encoding response regulator UzcR are expressed upon activation of a controllable promoter.

In some embodiments, the promoter controlling the expression of the heterologous 1363 gene, the 1362 gene, the UczR gene and/or the UczS gene can be either a constitutively active promoter or an inducible promoter. In preferred embodiments, the promoter is constitutively active.

In some embodiments of the $UO_2F_2$ biosensors described herein wherein one or more genetic molecular components comprising the 1363 and/or 1362 genes and/or the uczR and/or uczS genes are introduced into a proteobacterial cell, the proteobacterial cell is further genetically engineered so that expression of the host endogenous 1363 gene, 1362 gene, uczR gene and/or uczS gene is inactivated by gene knockout. Methods for performing genetic knockout are identifiable by persons skilled in the art, such as gene targeting using techniques such as homologous recombination, or transposon-mediated mutagenesis, or gene editing techniques such as those using CRISPR/Cas9 among others known to those skilled in the art.

In several embodiments, the U sensing genetic molecular component herein described is a genetically engineered polynucleotide construct configured to regulate expression of one or more RNA and/or protein-encoding genes through one or more U-sensing promoter.

In some embodiments herein described, the U-sensitive promoter is configured such that upon binding of the U-sensitive transcriptional regulator 1362 or UzcR to the U-sensitive corresponding binding site, the U-sensitive promoter is activated and transcription of a gene operatively connected to the U-sensitive promoter within the related genetic molecular component is initiated.

In particular, in some embodiments, when the U-sensing promoter comprises a 1362 binding site is located in a position wherein nucleotide $N_{18}$ of the regulator direct repeat (SEQ ID NO: 1) is from about 17 nucleotides upstream of the transcription start site of the genetic molecular component to about 40 nucleotides upstream of the transcription start site of the genetic molecular component, the regulator direct repeat is configured to function as a transcriptional activator binding site.

In other embodiments, the U-sensitive promoter is configured such that upon binding of the U-sensitive transcriptional regulator to the U-sensitive transcriptional 1362 binding site, the U-sensitive promoter is repressed and transcription of a gene operatively connected to the U-sensitive promoter within the related U-sensing genetic molecular component is not initiated.

In particular, in some embodiments, when the U-sensing promoter comprises a 1362 binding site, the 1362 binding site can be located in a position wherein nucleotide $N_1$ of the regulator direct repeat (SEQ ID NO:1) is from about 16 nucleotides downstream of the transcription start site of the genetic molecular component to about 16 nucleotides upstream of the transcription start site of the genetic molecular component or genetic molecular component, the 1362 binding site configured to function as a transcriptional repressor binding site. As would be understood by those skilled in the art, typically, within a given promoter polynucleotide sequence, substitution of a regulator repeat binding site polynucleotide sequence described herein for a promoter polynucleotide sequence comprising a –35 and/or a –10 hexamer sequence of the promoter, or one or more nucleotides at the transcriptional start site or downstream of the transcriptional start site, is expected to provide a promoter comprising a 1362 binding site configured to repress transcription of the promoter.

In preferred embodiments of the U-sensitive genetic molecular component described herein comprising the 1362 binding site, the regulator direct repeat is located in a position wherein nucleotide $N_{18}$ of the regulator direct repeat (SEQ ID NO:1) is from about 17 nucleotides upstream of the transcription start site of the U-sensing genetic molecular component to about 40 nucleotides upstream of the transcription start site of the genetic molecular component or genetic molecular component, such that the regulator direct repeat is configured to function as a transcriptional activator binding site As understood by those skilled in the art, positions in the promoter are designated relative to the transcriptional start site, where transcription of DNA begins for the gene of interest. Positions upstream (towards the 5' end of the promoter) are negative numbers counting back from –1, for example –10 is a position 10 base pairs upstream of the transcription start site.

The term "transcription start site" or "TSS" as used herein refers to the location where transcription starts at the 5' end of an encoded gene sequence. The location of the transcription start site is typically referred to as +1 relative to the 3' end of a promoter operatively connected to the gene. As would be understood by persons skilled in the art, a putative transcription start site can be detected using techniques such as differential RNA-seq (dRNA-seq) [47], which can differentially detect primary transcripts having triphosphorylated 5' ends, and processed RNAs which do not. Additional techniques to detect transcription start sites known in the art comprise bioinformatic analysis to identify enrichment of promoter elements upstream of a putative transcriptional start site, and experimental validation of selected putative transcription start sites, for example using primer extension methods [48], or by using Northern blots to detect the associated RNAs, among other techniques identifiable by those skilled in the art [49].

In some exemplary embodiments of the U biosensors described herein, the U-sensitive promoter comprising the 1362 binding site is a $P_{1361}$ promoter. The term "$P_{1361}$ promoter" as used herein refers to the promoter that natively regulates expression of an operon comprising CCNA_01361, CCNA_1362 and CCNA_1363 genes in *Caulobacter crescentus*. The DNA sequence of $P_{1361}$ is shown in Table 4.

In some exemplary embodiments of the U biosensors described herein, the U-sensitive promoter comprising the 1362 binding site is a $P_{phyt}$ promoter. The term "$P_{phyt}$ promoter" as used herein refers to the promoter that natively regulates expression of an operon comprising CCNA_01353, CCNA_01352_, and CCNA_01351 genes in *Caulobacter crescentus*. The DNA sequence of $P_{phyt}$ is shown in Table 4. As understood by those skilled in the art, *Caulobacter crescentus* (Poindexter 1964) refers to a Gram-negative, oligotrophic bacterium widely distributed in fresh water lakes and streams. *Caulobacter* is an obligate aerobe with a ubiquitous presence in aqueous environments where it is well-adapted to life under low-nutrient conditions [50]. *Caulobacter* species tolerate high concentrations of U [51, 52], are found in U-contaminated sites [53], and can mineralize U through the formation of uranyl phosphate precipitates [54]. Multi-omics studies to elucidate the U stress response pathways in *C. crescentus* have revealed many highly-induced genes that are not induced by Cd, Cr, Pb or Se [51].

In some embodiments, the U-sensitive promoter is a UzcRS-regulated promoters comprising DNA sequence elements required for RNA Polymerase binding, as well as one or more sequence elements for binding UzcR known as an m_5 site [3], as understood by those skilled in the art and herein also identified as UczR binding site. Examples of promoters regulated by UzcRS comprise $P_{urcA}$, $P_{urcB}$, $P_{1968}$, and others identifiable by those skilled in the art, such as those described in Park et al., 2017 [3].

In embodiments herein described, UzcRS-regulated promoters comprise those having naturally-occurring m_5 sites or m_5 sites that are introduced into a promoter through genetic engineering. Accordingly, UzcRS-regulated promoters comprise DNA sequence elements required for RNA Polymerase binding, as well as one or more m_5 sites, such that the promoter is configured to be regulated by the UzcRS two-component system. Similar to promoters comprising 1362 binding sites, in UzcRS-regulated promoters, the σ-RNAP biding sites typically have low sequence homology to the canonical $σ^{73}$-RNAP −10 and −35 hexamer sequences. Accordingly, typically transcriptional activation of native UzcRS-regulated promoters occurs through binding of UzcR to the promoter, consistent with little observed transcriptional activation in absence of UzcR.

In some embodiments, an UzcRS-regulated promoter can comprise 1-3 copies of the m_5 site. In particular, in some embodiments, when one or more m_5 sites are located at a position from about −34 to about −100 upstream of the TSS, preferably at a position −43 to −53 upstream of the TSS, the m_5 site is configured for activation of the UzcRS-regulated promoter [3]. In other embodiments, when one or more m_5 sites are located at a position from about −33 upstream of the TSS to +15 nt downstream of the TSS, the m_5 site is configured for repression of the UzcRS-regulated promoter.

Accordingly, in some embodiments described herein, a promoter can be either activated or repressed by UzcR. For example, in an exemplary embodiment wherein a promoter is repressed by UzcR, a m_5 site is engineered downstream of a transcription start site of a U-sensitive promoter such as a $P_{1361}$ promoter or $P_{phyt}$ promoter (see Example 2). In these exemplary embodiments, insertion of a m_5 site downstream of the TSS of e.g. $P_{phyt}$ minimizes activation of $P_{phyt}$ in both the presence and absence of U. As would be understood by skilled persons, the latter is preferable as it minimizes UzcRS expression levels when no U is present, minimizing cross-reactivity with Zn and Cu.

In some embodiments, the U-sensitive promoter can be a promoter genetically engineered to comprise the U-sensitive 1362 binding site. In some exemplary embodiments, it is expected that a promoter can be engineered comprising a U-sensitive 1362 binding site having $N_{18}$ of SEQ ID NO:1 at a position of about −40 to −42 upstream of the transcription start site, as in exemplary promoters $P_{1361}$ and $P_{phyt}$ (see e.g. FIG. 7).

The U-sensitive promoters described herein can further comprise a holo-RNA Polymerase (RNAP) binding site. As understood by those skilled in the art, promoters in bacteria, such as members of Caulobacteridae require DNA sequence elements for σ-RNAP binding for initiation of transcription. In particular, in Caulobacteridae promoters comprising the 1362 binding site such as exemplary promoters $P_{1361}$ and $P_{phyt}$, the σ-RNAP biding site typically have low sequence homology to the canonical $σ^{73}$-RNAP −10 and −35 hexamer sequences. As such, activation of a promoter comprising a 1362 binding site at a position configured for transcriptional activation (e.g. wherein nucleotide $N_{18}$ of the regulator direct repeat is located about −17 to about −40 upstream of the TSS), such as exemplary promoters $P_{1361}$ and $P_{phyt}$, σ-RNAP binding likely requires binding of the U-responsive transcriptional factor to the 1362 binding site, consistent with the observed low level of transcriptional activation in absence of U (see Examples section).

The term "holoenzyme" as used herein refers to enzymes that contain multiple protein subunits, such as RNA polymerases, wherein the holoenzyme is a complete complex containing all the subunits needed for activity. The term "holoenzyme" can also refer to an enzyme together with one or more cofactors required for activity. For example, in bacteria, a promoter is recognized by RNA polymerase (RNAP) and an associated sigma factor, and the complex is referred to as an "RNAP holoenzyme" or "holo-RNAP". An example of a RNAP holoenzyme in Caulobacteridae is RNAP holoenzyme containing $σ^{-73}$.

Figure 2:
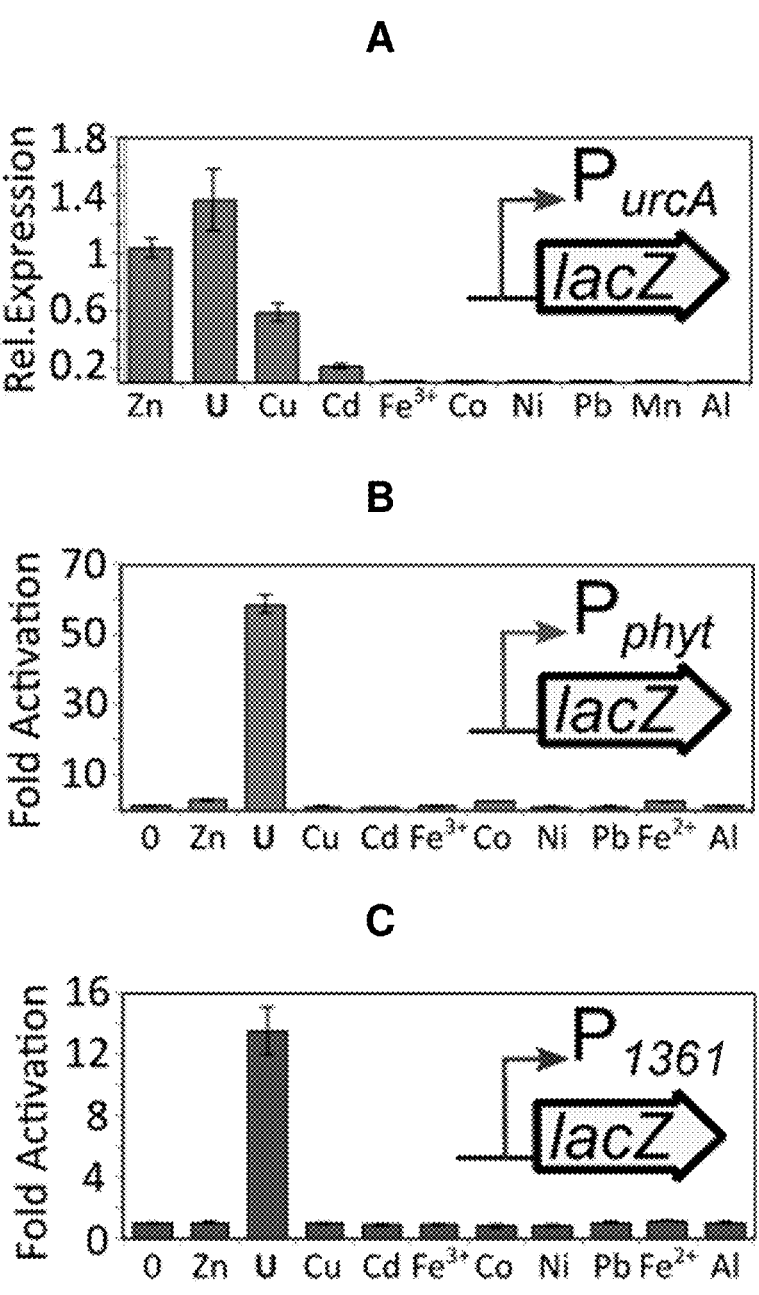
FIG. 2 shows graphs reporting determination of metal specificity of native U-responsive promoters in Caulobacter crescentus. The metal specificity of chromosomal P$_{urcA}$-lacZ (Panel A), P$_{phyt}$-lacZ (Panel B), and P$_{1361}$-lacZ (Panel C) was determined by treating mid-exponential phase cells with a range of concentrations of various metal salts for two hours before determining β-galactosidase activity using the method of Miller [1]. Cell growth was performed in peptone yeast extract (PYE) media supplemented with 50 mM MES pH 6.1. For Panel A, the relative expression was determined by normalizing the β-galactosidase activity observed by treatment with each metal to that of Zn. For Panels A and B, fold activation was calculated by dividing the activity with no added metal from the activity following metal exposure. Error bars represent the standard deviation calculated using a formula for propagation of standard error [2]. See FIG. 23 for more comprehensive metal specificity plot for P$_{urcA}$-lacZ.

The $UO_2F_2$ biosensors comprising the U-sensitive molecular component and/or U-sensitive genetic circuits comprising 1363/1362 TCS and/or UczRS TCS described herein in several embodiments can show improved selectivity for U compared to those previously described, such as in Hillson et al., 2007 [55], as illustrated in the Examples. As shown in FIGS. 1 and 2, the previously unknown exemplary U-responsive *Caulobacter crescentus* promoters $P_{1361}$ and $P_{phyt}$ show highly selective gene expression upregulation in response to U, in contrast to *Caulobacter crescentus* promoter $P_{urcA}$ [55], which also shows upregulation of gene expression in response to other metals such as Zn, Cu and Cd. Accordingly, a U-sensitive promoter, such as a $P_{1361}$ or a $P_{phyt}$ promoter, or a U-sensitive promoter genetically engineered to comprise the U-sensitive 1362 binding site can be used as a stand-alone selective U-sensing promoter.

In a U-sensitive genetic molecular component herein described, the U-Sensing promoter of the present disclosure directly or indirectly controls the expression of a reportable molecular component and/or a U-neutralizing molecular component.

The term "reportable molecular component" as used herein indicates a molecular component capable of detection in one or more systems and/or environments. The terms "detect" or "detection" as used herein indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

In some embodiments, the reportable molecular component can be a molecular component linked to or comprising a label wherein the term label refers to a compound capable of emitting a labeling signal, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence.

In embodiments of the U-sensitive genetic molecular component described herein, the genetic molecular component comprises a "reporter gene", which can be any genetically-encoded reportable molecular component.

As would be understood by persons skilled in the art, the terms "genetically-encoded reportable molecular component", "reportable genetic molecular component", "genetically encoded reporter" or "reporter gene" comprises polynucleotide-encoded RNA and/or proteins having reportable characteristics identifiable by those skilled in the art and as described herein. Using genetic engineering techniques known to those skilled in the art, a reporter gene can be placed under the regulatory control of a promoter, and expression of the genetically-encoded reportable molecular component thereby serves as an indication of activation of the promoter in a host organism comprising the reporter gene. A reporter gene can be fused to another gene under the regulatory control of the promoter, such as a gene encoding a protein natively regulated by the promoter, so that the promoter regulates the expression of a fusion gene encoding a fusion protein comprised of the natively regulated protein covalently linked to the reportable molecular component. As would be understood by those skilled in the art, it is typical to use a reporter gene that is not natively expressed in the host organism, since the expression of the genetically-encoded reportable molecular component is used as a marker of activation of the promoter in the host organism. Exemplary genetically encoded reportable molecular components comprise fluorescent proteins such as green fluorescent protein (GFP) from *Aequorea victoria* or *Renilla reniformis*, red fluorescent protein from *Discosoma* species (dsRED), and variants thereof, beta galactosidase encoded by lacZ gene, luciferase and others identifiable to those skilled in the art. In exemplary embodiments described herein, exemplary reporters comprise a fluorescent protein which is a mutant variant of GFP referred to as 'gfpmut3' [56].

In some embodiments, the $UO_2F_2$-biosensors comprising U-sensitive genetic molecular components and/or U-sensitive genetic circuits described herein are configured to produce a U-neutralizing molecular component in presence of U.

The term "U-neutralizing molecular component" as used herein refers to any component capable of decreasing the bioavailable U concentration.

In some embodiments, the U-neutralizing molecular component is a U-neutralizing genetic molecular component comprising a "U-neutralizing gene". The term "U-neutralizing genetic molecular component" as used herein refers to a genetic molecular component in which the gene of the genetic molecular component is a U-neutralizing gene and wherein polynucleotide-encoded RNA and/or proteins have U-neutralizing characteristics identifiable by those skilled in the art upon reading of the present disclosure, such as proteins having enzymatic functions capable of allowing bioreduction, biomineralization, biosorption, or bioaccumulation of bioavailable U, as described herein.

The term "bioreduction" as used herein refers to altering the redox state of uranium from aqueous U (VI) to insoluble U (IV). As would be understood by persons skilled in the art, in the absence of oxygen, some bacteria are able to respire different electron acceptors to gain energy for metabolism. As anoxia progresses, the most energetically favorable electron acceptors are used in sequence, starting with the reduction of nitrate, then proceeding through Mn(IV), Fe(III) and sulfate, and finally the reduction of carbon dioxide to produce methane. At circumneutral pH, U(VI) has a similar redox couple to Fe(III), and natively Fe(III)-reducing bacteria are able to respire U(VI) as an alternative electron acceptor, reducing it to insoluble U(IV) [12]. Other groups natively capable of U(VI) reduction comprise bacteria such as sulfate-reducing bacteria [57], fermentative bacteria [58], acid-tolerant bacteria [59] and myxobacteria [60]. In some embodiments where a bioreduction component is comprised in the U-biosensor herein described, the host cell is preferably selected among cells natively expressing the components required to perform uranium bioreduction, which can be engineered to include one or more U-sensing genetic molecular component and/or other components of the U-sensing genetic circuit herein described. In other embodiments, a host cell can be *E. coli* or other facultative anaerobe genetically engineered to include one or more U-sensing genetic molecular component and/or other components of the U-sensing genetic circuit herein described as well as genetic molecular components required to perform U-bioreduction as will be understood by a skilled person Accordingly, in some embodiments uranium bioreduction can be used as a bioremediation technique, stimulated by adding an electron donor to promote enzymatic reduction of aqueous U(VI) to insoluble U(IV) [61-66]. Enzymatic reduction of U(VI) can be catalyzed using U-neutralizing genes such as those expressing cytochrome c [57, 67, 68]. In addition, chelators can be used to solubilize U(VI) and/or electron shuttles to mediate extracellular electron transfer, such as U-neutralizing genes expressing flavin mononucleotide or riboflavin [11, 69-72]. Therefore, in some embodiments of the U biosensors described herein, exemplary U-neutralizing genes comprise cytochrome c genes, flavin mononucleotide genes, or riboflavin genes which can be natively expressed in suitable host possibly further engineered to include one or more U-sensing genetic molecular components and/or U-sensing genetic circuit herein described.

The terms "biomineralization" and "bioprecipitation" as used herein refers to a process by which metals precipitate with microbially generated ligands such as sulfide or phosphate, or as carbonates or hydroxides in response to localized alkaline conditions at the cell surface. Thereafter, the uranium precipitate can be removed. In some embodiments. In some embodiments, the U can be comprised into a stable mineral that sediment out and not be re-leached over time. In addition or in the alternative U-removal can be performed by some form of on-site filtration identifiable by a skilled person. In particular, sequestration of uranium as insoluble uranyl U(VI) phosphate biominerals can be used for in situ biomineralization for sites where bioreduction may not be feasible due to high nitrate concentrations or where there is risk of reoxidation reoccurring, e.g., in sites comprising carbonate [73, 74].

Accordingly, in some embodiments, the $UO_2F_2$-biosensors described herein can be engineered to catalyze precipitation of uranium such as uranyl phosphates. For example, bacteria can be engineered to precipitate uranyl phosphates [75] by expressing U-neutralizing genes such as acid-phosphatase genes [76] or alkaline-phosphatase genes [77] or phytase genes. In some embodiments, an exogenous source of phosphate can be added such as glycerol phosphate [16] or tributylphosphate [78]. Therefore, in some embodiments of the U biosensors described herein, exemplary U-neutralizing genes comprise acid-phosphatase genes, or alkaline-phosphatase genes. In an exemplary embodiment, the U-neutralizing gene is phoY, encoding an alkaline phosphatase that has been shown to allow the coupling of release of inorganic phosphorus (Pi) from organophosphates with U-Pi precipitation in *Caulobacter crescentus* [54], or phytase, that can be used to liberate phosphate from phytate, an environmental source of phosphate (see Example 10). In some embodiments, Pphyt or P1361 can be used to drive expression of an alkaline phosphatase. In some embodiments, the U-biosensors described herein can be engineered to comprise additional genetic molecular components configured to express one or more genes encoding proteins having enzymatic functions to catalyze release of inorganic phosphate from organophosphates (via hydrolytic cleavage catalyzed by phosphatases), inorganic phosphite (via enzymatic oxidation) and phosphonates (via cleavage catalyzed by C-P lyases), or from nucleic acids [79], phytate [80] or phospholipids [81].

The term "bioaccumulation" as used herein refers to accumulation of metals such as uranium in bacteria. For example, intracellular uranium accumulation occurs as uranyl phosphates in bacteria such as *Pseudomonas* species (Kazy et al., 2009; [82], VanEngelen et al., 2010; [83], Choudhary and Sar, 2011, [84]). In particular, overexpression of the polyphosphate kinase gene (ppk) encoding the PPK enzyme can be used to produce high levels of polyphosphate, a phosphate polymer with chain lengths of two to a few hundred, to allow precipitation of uranyl phosphate at the cell membrane [85]). Accordingly, in some embodiments of the U biosensors described herein, exemplary U-neutralizing genes comprise ppk genes.

The terms "biosorption" or "bioadsorption" as used herein refers to the passive uptake of uranium to the surface of microbial cells, wherein bacterial cell envelopes possess an electronegative charge, so are able to attract metal cations which sorb to the surface. In some embodiments of the U biosensors described herein, exemplary U-neutralizing genes comprise genes encoding proteins configured to bind U to the cell surface of the U biosensor. In an exemplary embodiment, the U-neutralizing gene is an ompA-SUP fusion gene encoding a rationally engineered super uranyl binding protein (SUP) having femtomolar affinity [86](see Example 10). The encoded ompA fusion is configured to anchor SUP to the outer membrane, allowing adsorption of U to the cell surface. In other exemplary embodiments, the U-neutralizing gene is a fusion gene comprising the ompA protein fused to a Calmodulin EF-Hand Peptide (CaM) [87] that has been engineered for high U selectivity. In other exemplary embodiments, the U-neutralizing gene is a fusion gene comprising the Calmodulin EF-Hand Peptides (CaM) or SUP fused with the rsaA (S-layer) gene (see Example 10), for example using the method outline in Nomellini [88]. Accordingly, in some embodiments, proteobacteria can be engineered to provide U biosensors comprising U-neutralizing components configured to produce a U biosorption output, following a methodology such as has been used in *Caulobacter* for rare earth element adsorption [89].

Accordingly, $UO_2F_2$-biosensors comprising U-neutralizing molecular components described herein can be used in several embodiments for U bioremediation.

The term "bioremediation" as used herein refers to a waste management technique that involves the use of organisms to neutralize pollutants from a contaminated site. Bioremediation can be performed in situ or ex situ. In situ bioremediation involves treating the contaminated material at the site, while ex situ involves the removal of the contaminated material to be treated elsewhere.

Figure 15:
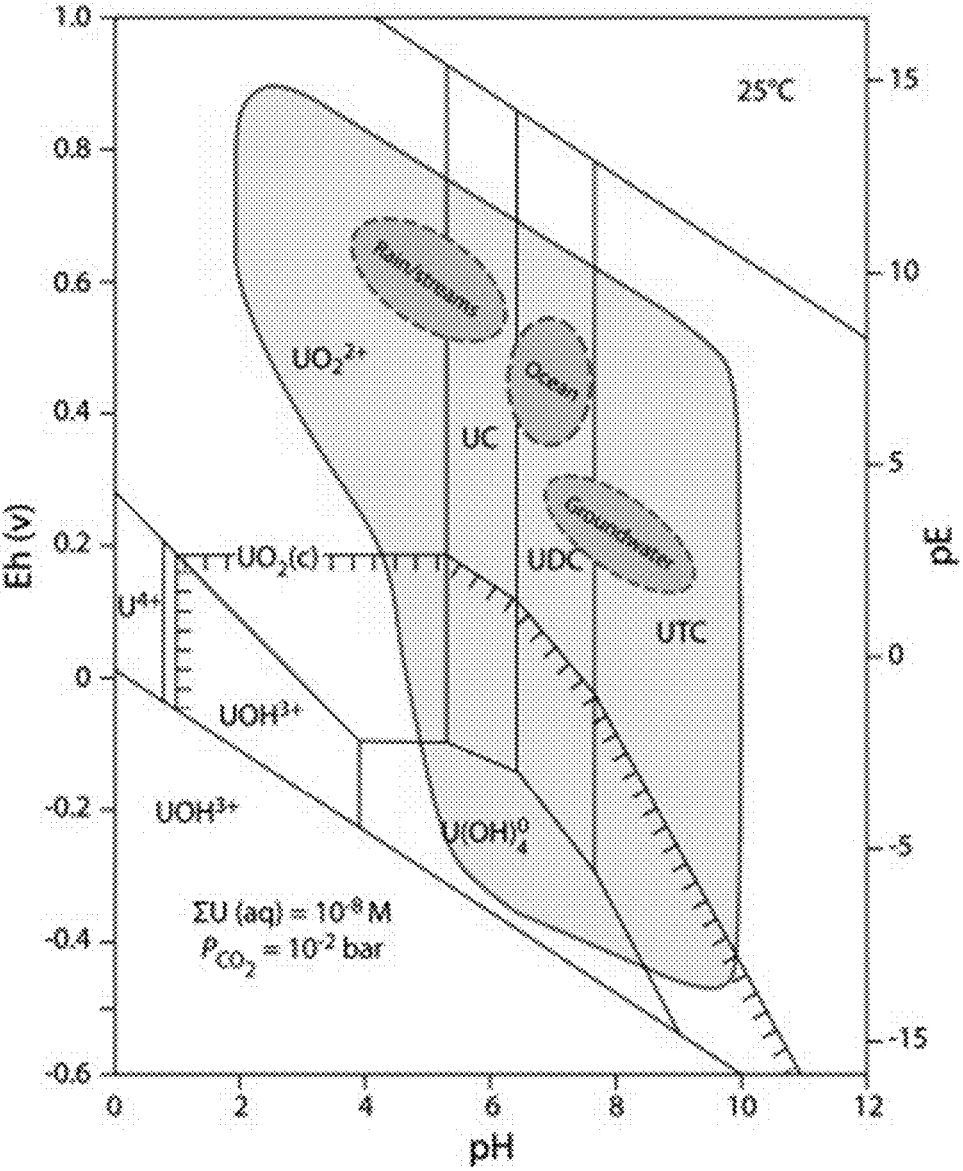
FIG. 15 is FIG. 1 from Newsome et al. (2014) [7] showing an exemplary Eh-pH diagram (which maps out possible stable (equilibrium) phases of an aqueous electrochemical system) for aqueous species in the U—$O_2$—$CO_2$—$H_2O$ system in pure water at 25° C. and 1 bar total pressure for $\Sigma U=10^{-8}$ M and a typical groundwater C02 pressure of $PCO_2=10^{-2.0}$ bar [8]. UC, UDC and UTC represent the aqueous complexes $UO_2CO_3^0$, $UO_2(CO_3)_2^{2-}$ and $UO_2(CO_3)_3^{4-}$. The position of the $UO_{2(c)}$ solid solution boundary for $\Sigma U=10^{-8}$ M is stippled. The shaded area represents the range of conditions of common natural waters [9] as presented in Newsome et al., (2014) [7].
Figure 16D:
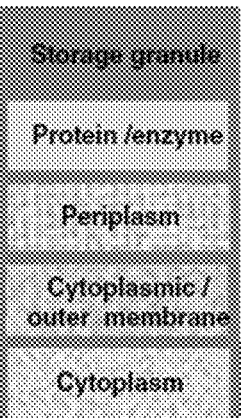
FIG. 16D is from Figure 2 of Newsome et al. (2014) [7] showing a schematic illustrating exemplary mechanisms of microbe-uranium interactions, such as bioaccumulation [19] as presented in Newsome et al., (2014) [7].

As would be understood by persons skilled in the art, mobility of uranium in the environment depends on its speciation and redox state (e.g., see FIG. 15). It is present as mobile U(VI) in oxidizing conditions, predominantly as the uranyl ion ($UO_2^{2+}$) or hydroxyl complexes below ~pH 6.5, or as uranyl carbonate complexes at higher pH [90]. In the absence of carbonate, the uranyl ion and its complexes sorb strongly onto the surface of iron oxides and organics [73, 91, 92] and onto the edge sites of clay minerals [93, 94]. Sorption decreases in the presence of complexing ligands such as humic and fulvic acids, and in the presence of competing cations such as $Ca^{2+}$ and $Mg^{2+}$ [95]. Under reducing conditions, relatively insoluble and immobile U(IV) predominates, typically as the mineral uraninite, or as other U(IV) minerals [10, 96].

Biogeochemical interactions play a key role in controlling the speciation and mobility of uranium, through direct metabolic processes such as microbial respiration, or indirectly by changing ambient redox/pH conditions, producing ligands or new biominerals, or altering mineral surfaces. In addition to controlling uranium mobility via "natural attenuation", these biogeochemical processes can be stimulated to accelerate clean-up of contaminated environments through bioremediation.

Preventing uncontrolled dispersion and transport of uranium in groundwater is a primary remediation goal at contaminated sites. Accordingly, stimulating bacterial interactions to fix aqueous uranium into insoluble minerals in situ can provide a relatively inexpensive and non-intrusive solution to remediating uranium contamination. Exemplary mechanisms of different microbe-uranium interactions are illustrated in FIGS. 16A-D, comprising bioreduction, biomineralization, biosorption, and bioaccumulation [7], among other identifiable by those skilled in the art.

In embodiments of the $UO_2F_2$-biosensors described herein configured to have a U-neutralizing molecular component output to perform a U bioremediation function in response to bioavailable U, the preferred U-neutralizing molecular component output is a U-neutralizing molecular component having a U biomineralization function.

In some embodiments of a U-sensing genetic molecular component, the reporter gene or U-neutralization gene is contiguous with the U-sensitive promoter, wherein the 5' end of the reporter gene is immediately adjacent to the 3' end of the U-sensitive promoter. In other embodiments, the reporter gene is not contiguous with the promoter, such that one or more nucleotides are located between the 3' end of the U-sensitive promoter and the 5' end of the reporter gene. For example, in some embodiments, a ribosome binding site can be inserted between the 3' end of the U-sensitive promoter (downstream of the TSS) and the 5' end of the reporter gene.

In some embodiments, the U biosensors described herein comprise any non-pathogenic member of Caulobacteridae. In some embodiments described herein, the U biosensor comprises Caulobacteridae such as *C. crescentus* strains NA1000, CB15, and OR37, an environmental isolate from a U-contaminated site that exhibits high heavy metal tolerance [97]. In Examples provided herein, an exemplary host organism is *C. crescentus* strain NA1000.

In some embodiments of the U biosensor described herein, the cell can be any Caulobacteridae having a genome that natively comprises promoters having 1362 binding sites, such as exemplary promoters $P_{1361}$ or $P_{phyt}$, or a homolog thereof.

In the $UO_2F_2$-biosensor of the instant disclosure, the U biosensor herein described is further engineered to include an F-sensing riboswitch.

The term "riboswitch" in the sense of the disclosure indicates a regulatory segment of a messenger RNA molecule that is configured to bind a target compound and to provide upon binding with the target compound a change in production of the proteins encoded by the mRNA. Accordingly, a riboswitch sense concentrations of the target compound. [98].

Riboswitches in the sense of the disclosure comprise an aptamer domain which is configured to specifically and selectively bind the target compound and an expression platform domain configured for genetic control of the mRNA expression. In particular, a riboswitch is configured so that in absence of the target compound the aptamer domain and the expression platform domain are configured to inhibit the expression of the mRNA. In a riboswitch in the sense of the disclosure upon binding of the target compound with the aptamer domain the riboswitch changes configuration and in the expression platform domain's inhibition of the mRNA expression is removed, thus providing in metabolite-dependent allosteric control of gene expression.

In particular, aptamer domains are typically configured to form a stem structure in absence of the target compound. The hybridizing strands forming the stem are referred to as the aptamer strand and the control strand which are configured to complementarily bind to each other. In a riboswitch the stem structure which is either formed or be disrupted in absence of target compound is an aptamer domain-control strand stem structure.

In a riboswitch, expression platform domains generally have at least a portion identified as regulated strand configured to complementarily bind with the control strand of a linked aptamer domain to form a control strand-regulated strand structure, which can be a control strand-regulated strand stem. This control strand regulated strand structure will either form or be disrupted upon binding of the target compound.

Thus, the control strand of the aptamer domain can complementarily bind to with the aptamer strand and the regulated strand to form alternative stem structures with the aptamer strand and the regulated strand of the expression platform domain depending on the presence of the target domain.

The term 'complementary bind", "base pair", "complementary base pair" as used herein with respect to nucleic acids indicates the two nucleotides on opposite polynucleotide strands or sequences that are connected via hydrogen bonds. For example, in the canonical Watson-Crick DNA base pairing, adenine (A) forms a base pair with thymine (T) and guanine (G) forms a base pair with cytosine (C). In RNA base paring, adenine (A) forms a base pair with uracil (U) and guanine (G) forms a base pair with cytosine (C). Accordingly, the term "base pairing" as used herein indicates formation of hydrogen bonds between base pairs on opposite complementary polynucleotide strands or sequences following the Watson-Crick base pairing rule as will be applied by a skilled person to provide duplex polynucleotides. Accordingly, when two polynucleotide strands, sequences or segments are noted to be binding to each other through complementarily binding or complementarily bind to each other, this indicate that a sufficient number of bases pairs forms between the two strands, sequences or segments to form a thermodynamically stable double-stranded duplex, although the duplex can contain mismatches, bulges and/or wobble base pairs as will be understood by a skilled person.

In particular, in the riboswitch, complementary binding between the aptamer strand and the control strand is more or less thermodynamically stable than complementary base paring between the aptamer strand and other sequences of the riboswitch, and complementary binding between the control strand with the regulated strand of the riboswitch, depending on the presence of the target compound.

The term "thermodynamic stability" as used herein indicates a lowest energy state of a chemical system. Thermodynamic stability can be used in connection with description of two chemical entities (e.g. two molecules or portions thereof) to compare the relative energies of the chemical entities. For example, when a chemical entity is a polynucleotide, thermodynamic stability can be used in absolute terms to indicate a conformation that is at a lowest energy state, or in relative terms to describe conformations of the polynucleotide or portions thereof to identify the prevailing conformation as a result of the prevailing conformation being in a lower energy state. Thermodynamic stability can be detected using methods and techniques identifiable by a skilled person. For example, for polynucleotides thermodynamic stability can be determined based on measurement of melting temperature $T_m$, among other methods, wherein a higher $T_m$ can be associated with a more thermodynamically stable chemical entity as will be understood by a skilled person. Contributors to thermodynamic stability can include, but are not limited to, chemical compositions, base compositions, neighboring chemical compositions, and geometry of the chemical entity.

Typically, in a riboswitch, the formation of the control strand-regulated strand structure affects expression of the RNA molecule containing the riboswitch.

The stem structure generally either is, or prevents formation of, an expression regulatory structure. An expression regulatory structure is a structure that allows, prevents, enhances or inhibits expression of an RNA molecule containing the structure. Examples include Shine-Dalgarno sequences, initiation codons, transcription terminators, and stability and processing signals, such as splice sites and sequences.

Riboswitches in the sense of the disclosure can be naturally occurring, isolated and recombinant riboswitches. Microbes, in particular, bacteria and archea, have evolved riboswitches to selectively detect over a dozen small molecules/metabolites (e.g., purine nucleobases) [99], several of which have been exploited for the construction of whole-cell biosensors [100].

Riboswitches in the sense of the disclosure can be comprised in sequences encoding proteins or peptides of interest, including reporter proteins or peptides, which can naturally occurring or synthetic as well as endogenous or heterologous to the host cell.

The term "F-sensing riboswitch" as used herein indicates a riboswitch for which Fluoride is the target compound. Accordingly, F-sensing riboswitches in the sense of the disclosure function as riboswitches that sense fluoride ions. These F-sensing riboswitches increase expression of downstream genes when fluoride levels are elevated, and the downstream genes can modulate the toxic effects of high levels of fluoride.

An F-sensing riboswitch comprises a fluoride aptamer domain which is configured to specifically and selectively bind fluoride and an expression platform domain configured for genetic control of the mRNA expression. An F-sensing riboswitch in accordance with the disclosure is configured so that in the absence of fluoride the fluoride aptamer domain and the expression platform domain are configured to inhibit the expression of the mRNA. Upon binding of fluoride with the aptamer domain the F-sensing riboswitch changes configuration and the inhibition of the mRNA expression imposed by the expression platform domain is thus removed.

In embodiments herein described the fluoride aptamer is expected to bind fluoride anions with a dissociation constant of between 50 M and 60 μM, inclusive and to be able to detect an amount of fluoride in the environment, which can be calculated accordingly. In particular, the dissociation constant is particularly useful for determining the amount of fluoride detectable in the environment if the fluoride export capability of the host is abolished (when fluoride is retained inside the cell rather than pumped back out) as will be understood by a skilled person.

Fluoride detection capability of specific riboswitches is expected to be identified using approaches such as the ones exemplified in Example 20 and Example 22 as will be understood by a skilled person. In an example, following identification of a suitable host, the host genome can be searched to identify presence or absence of a native fluoride riboswitch such as a CrcB or EricF homolog. If a native fluoride riboswitch is present, the detection limit for a biosensor of the disclosure is expected to be close to 1 mM. In those instances, deletion of the fluoride transporter will likely enable a 100-fold decrease in the detection limit. Accordingly, host cell not expressing a native fluoride riboswitch or with a deleted native riboswitch is expected to be able to detect about 10 μM or higher. It is expected that levels such as 50 μM and 60 μM fluoride will not substantially affect the viability of cells lacking fluoride efflux activity and that toxicity for a host will require mM levels of Fluoride depending on the host as will be understood by a skilled person.

As used herein, "fluoride aptamer domains" or "fluoride aptamers" indicate nucleic acid molecules that can specifically bind to fluoride ions. In an F-sensing riboswitch the fluoride aptamer domain is typically configured in a stem structure formed by the fluoride aptamer strand complementarily binding the control strand of the fluoride sensing riboswitch or in an alternative stem structure with the fluoride regulated strand of the expression platform domain or other sequences designed to complementarily bind the fluoride control strand depending on the presence of absence or fluoride according to the riboswitch design.

In particular, Fluoride aptamers typically are configured to form a stem structure in absence of fluoride. Fluoride aptamers include nucleic acid molecules that bind fluoride as the anion alone or fluoride with a counterion. Fluoride aptamers generally can be naturally occurring fluoride aptamers, such as fluoride aptamers in naturally-occurring F-sensing riboswitches, and fluoride aptamers derived from naturally-occurring fluoride aptamers.

A general sequence for F-sensing riboswitches is (SEQ ID NO: 2509)

$N_1N_2N_3N_4N_5N_6N_7N_8N_9G_{10}G_{11}N_{12}R_{13}A_{14}U_{15}G_{16}R_{17}N_{18}U_{19}R_{20}U_{21}Y_{22}C_{23}Y_{24}$ $N_{25}C_{26}C_{27}N_{28}R_{29}N_{30}N_{31}N_{32}N_{33}N_{34}N_{35}C_{36}C_{37}A_{38}U_{39}C_{40}N_{41}R_{42}R_{43}N_{44}S_{45}N_{46}$ $N_{47}N_{48}N_{49}N_{50}N_{51}N_{52}N_{53}N_{54}N_{55}N_{56}N_{57}N_{58}N_{59}N_{60}W_{61}N_{62}N_{63}N_{64}N_{65}N_{66}N_{67}N_{68}$ $M_{69}N_{70}R_{71}R_{72}N_{73}N_{74}M_{75}U_{76}G_{77}M_{78}Y_{79}R_{80}G_8 \cdot C_{82}M_{83}R_{84}Y_{85}M_{86}W_{87}R_{88}A_{89}A_{90}$ $S_{91}N_{92}N_{93}N_{94}N_{95}N_{96}N_{97}N_{98}N_{99}N_{100}N_{101}N_{102}N_{103}N_{104}N_{105}M_{106}N_{107}N_{108}N_{109}$ $N_{110}N_{111}N_{112}N_{113}Y_{114}N_{115}N_{116}A_{117}A_{118}U_{119}U_{120}C_{121}C_{122}G_{123}C_{124}Y_{125}N_{126}$ $N_{127}N_{128}N_{129}N_{130}N_{131}N_{132}G_{133}N_{134}A_{135}G_{136}N_{137}N_{138}N_{139}N_{140}N_{141}N_{142}N_{143}$ $N_{144}N_{145}N_{146}N_{147}N_{148}N_{149}N_{150}N_{151}N_{152}N_{153}N_{154}W_{155}N_{156}N_{157}N_{158}N_{159}N_{160}$ $N_{161}M_{162}N_{163}N_{164}A_{165}N_{166}N_{167}N_{168}N_{169}N_{170}N_{171}N_{172}N_{173}N_{174}N_{175}N_{176}N_{177}$ $N_{178}N_{179}N_{180}N_{181}N_{182}N_{183}N_{184}N_{185}N_{186}N_{187}N_{188}N_{189}N_{190}N_{191}N_{192}C_{193}U_{194}$ $W_{195}M_{196}N_{197}N_{198}N_{199}N_{200}N_{201}N_{202}N_{203}N_{204}N_{205}N_{206}N_{207}N_{208}N_{209}N_{210}N_{211}$ $N_{212}N_{213}R_{214}G_{215}C_{216}U_{217}R_{218}A_{219}U_{220}G_{221}R_{222}Y_{223}Y_{224}Y_{225}C_{226}U_{227}R_{228}$ $Y_{229}N_{230}N_{231}N_{232}N_{233}N_{234}N_{235},$ wherein
    any one of $N_2$, $N_3$, $N_4$, $N_5$, $N_6$, $N_7$, $N_8$, $N_9$, $N_{31}$, $N_{32}$, $N_{33}$, $N_{34}$, $N_{35}$, $N_{47}$, $N_{48}$, $N_{49}$, $N_{50}$, $N_{51}$, $N_{52}$, $N_{53}$, $N_{54}$, $N_{55}$, $N_{56}$, $N_{57}$, $N_{58}$, $N_{59}$, $N_{60}$, $N_{63}$, $N_{64}$, $N_{65}$, $N_{66}$, $N_{67}$, $N_{68}$, $N_{93}$, $N_{94}$, $N_{95}$, $N_{96}$, $N_{97}$, $N_{98}$, $N_{99}$, $N_{100}$, $N_{101}$, $N_{102}$, $N_{103}$, $N_{104}$, $N_{105}$, $N_{108}$, $N_{109}$, $N_{110}$, $N_{111}$, $N_{112}$, $N_{13}$, $N_{127}$, $N_{128}$, $N_{129}$, $N_{130}$, $N_{131}$, $N_{132}$, $N_{138}$, $N_{139}$, $N_{140}$, $N_{141}$, $N_{142}$, $N_{143}$, $N_{144}$, $N_{145}$, $N_{146}$, $N_{147}$, $N_{148}$, $N_{149}$, $N_{150}$, $N_{151}$, $N_{152}$, $N_{153}$, $N_{154}$, $N_{167}$, $N_{168}$, $N_{169}$, $N_{170}$, $N_{171}$, $N_{172}$, $N_{173}$, $N_{174}$, $N_{175}$, $N_{176}$, $N_{177}$, $N_{178}$, $N_{179}$, $N_{180}$, $N_{181}$, $N_{182}$, $N_{183}$, $N_{184}$, $N_{185}$, $N_{186}$, $N_{187}$, $N_{188}$, $N_{189}$, $N_{190}$, $N_{191}N_{192}$, $N_{231}$, $N_{232}$, $N_{233}$, $N_{234}$, and $N_{235}$ indicated in the sequence in bold fonts, can be independently present or absent;
    R indicates a purine (A or G).
    Y indicates a pyrimidine (C or U).
    N indicates any nucleotide
    W indicates a weak nucleotide (A or U).

S, indicates a strong nucleotide (G or C).

M, indicates an amino nucleotide (A or C).

Figure 43:
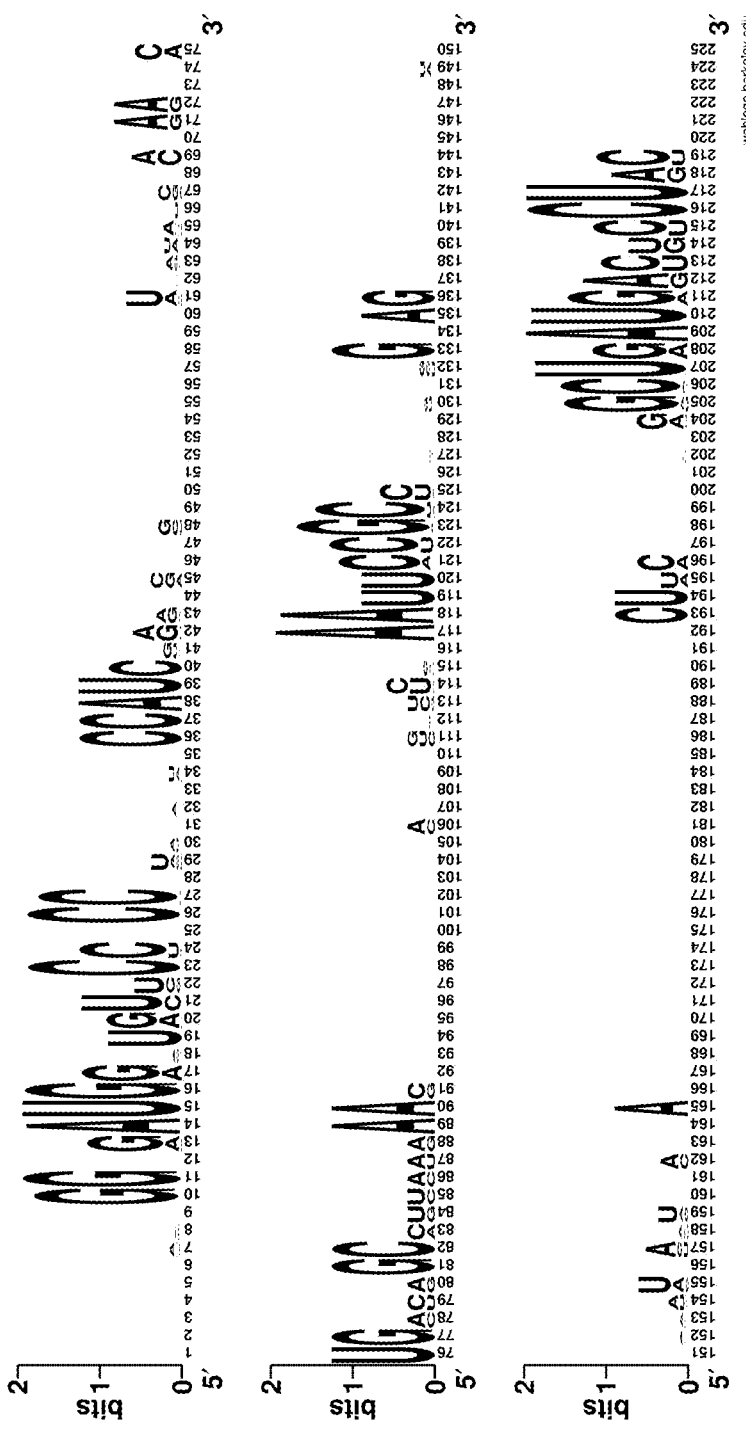
FIG. 43 shows the conserved nucleotides in naturally occurring Fluoride sensing riboswitchs from a gapped alignment of the 2138 fluoride riboswitch sequences from the Rfam database

K, Keto (G or U).

as also illustrated in FIG. 43, This sequence, like any other riboswitch, is encoded by a corresponding DNA sequence wherein U is replaced by T as will be understood by a skilled person. This sequence further provides an indication of the conserved nucleotides in naturally occurring Fluoride sensing riboswitches as will be understood by a skilled person.

Exemplary F-sensing riboswitches in the sense of the disclosure comprise a fluoride-sensing riboswitch called a 'crcB motif' [102, 103]. crcB motif RNAs are typically located upstream of genes encoding proteins of diverse functions and presumably regulate these genes. Some of the gene products are annotated as ion transporters (for example, chloride, sodium, proton) and some others are involved in various physiological (e.g., universal stress adaptation, DNA repair) or metabolic (e.g., enolase, formate-hydrogen lyase) processes. The crcB riboswitch, in particular, enables a mechanism for sensing and detoxifying environmental fluoride by coupling fluoride binding [104] with the activation of genes encoding enzymes that mitigate fluoride toxicity, most commonly a fluoride exporter (CrcB) that expels internal fluoride anions [102, 105](see Example 26). A key feature of the crcB motif is the high fluoride selectivity; binding has not been observed for other halides (including concentrations of chloride up to 2.5 M), small anions, gases and 36 other relevant cellular metabolites [102]. Furthermore, examination of crcB riboswitch function within a modified *Escherichia coli* strain revealed a fluoride detection limit below 10 $\mu$M (sub-500 ppb) and a dynamic range that spanned two orders of magnitude [102](see Example 26). Collectively, these data support the conclusion that crcB motif can be applied toward the environmental detection of fluoride, and ultimately, function as an integral detection component within a whole-cell $UO_2F_2$ compound sensor.

Exemplary fluoride riboswitches, as well as related structures functions and locations in genomes are described in U.S. Pat. No. 9,580,713 incorporated herein by reference in its entirety. [102] as well as in the papers Zao et al, 2017 [106], Ren et al 2012 [104] and Park and Taffet 2019 [107] each of which is herein also incorporated by reference in its entirety.

Figure 48A:
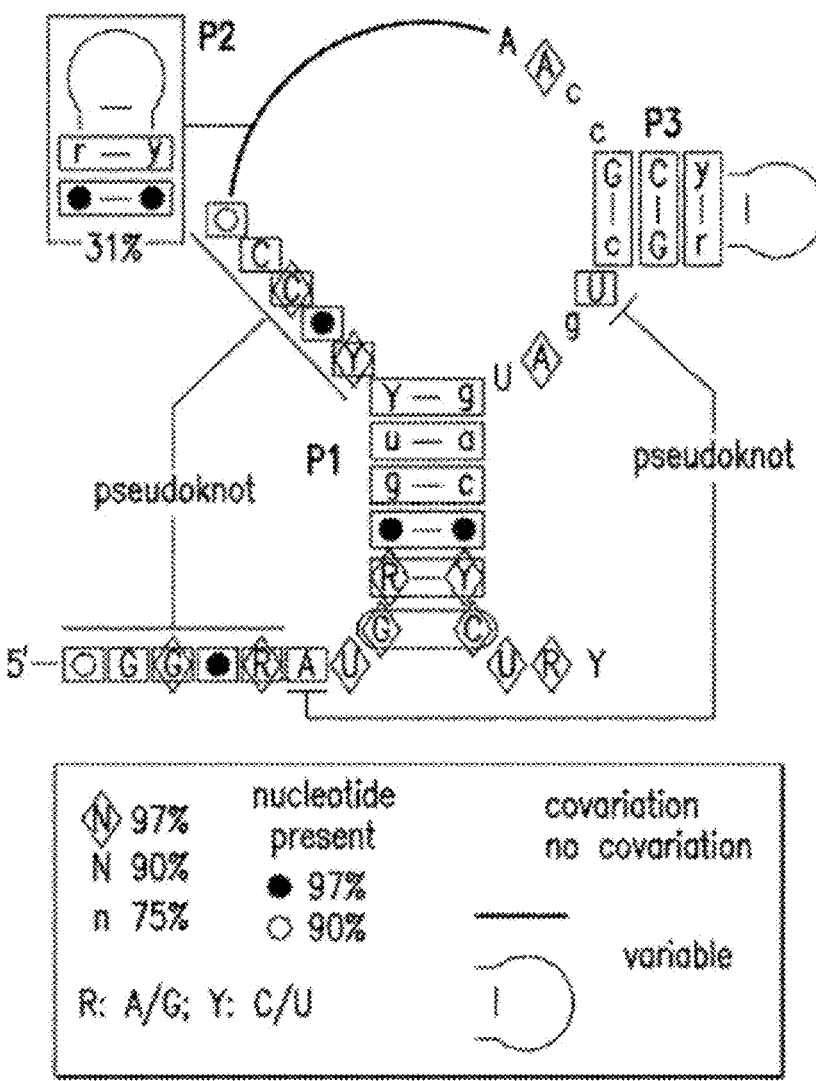
FIG. 48A is FIG. 1A of U.S. Pat. No. 9,580,713 and, as indicated in U.S. Pat. No. 9,580,713 shows a schematic representation of "the consensus sequence and structural model based on the comparison of 2188 representatives from bacterial and archaeal species". As indicated in U.S. Pat. No. 9,580,713 incorporated herein by reference in its entirety "P1, P2, P3 and pseudoknot labels identify base-paired substructures. Note that the bottom of P1 carries a possible G-C pair. However, because noncomplementary nucleotides occur in these positions in some representatives, these nucleotides are depicted as unpaired."

In particular, an exemplary consensus sequence and structure for crcB motif RNAs is shown in FIG. 48A which reproduces FIG. 1A of U.S. Pat. No. 9,580,713 [102] incorporated herein by reference in its entirety.

In particular, FIG. 48A shows a consensus sequence and structural model based on the comparison of 2188 representatives from bacterial and archaeal species. P1, P2, P3 and pseudoknot labels of FIG. 1A of U.S. Pat. No. 9,580,713 [102] identify base-paired substructures. As used herein, a pseudoknot is a nucleic acid secondary structure containing at least two stem-loop structures in which half of one stem is intercalated between the two halves of another stem as will be understood by a person skilled in the art.

Exemplary F-sensing riboswitches with a consensus sequence and structure schematically illustrated in FIG. 48A has sequence (SEQ ID NO: 2510)

$N_1G_2\ G_3\ N_4\ R_5\ A_6\ U_7\ G_8\ R_9\ N_{10}\ G_{11}\ U_{12}\ Y_{13}\ Y_{14}\ N_{15}\ C_{16}\ G_{30}$ $C_{17}\ N_{18}\ A_{19}\ A_{20}\ C_{21}\ C_{22}\ G_{23}\ C_{24}\ Y_{25}\ R_{26}\ G_{27}\ C_{28}\ U_{29}\ A_{31}\ U_{32}$ $G_{33}\ A_{34}\ C_{35}\ N_{36}\ Y_{37}\ C_{38}\ U_{39}\ R_{40}\ Y_{41}$ wherein $N_1\ N_4\ N_{10}\ N_{15}\ N_{15}\ N_{18}$ and $N_{36}$ are independently any amino acid;

$N_1\ N_4\ N_{10}N_{15}\ N_{18}\ N_{18}$ and $N_{36}$ are independently present or absent;

anyone of $N_1G_2\ G_3\ N_4\ R_5$ is linked with any one of $Y_{14}$ $N_{15}\ C_{17}\ C_{17}\ N_{18y}$ by a pseudoknot $A_6$ is linked with $U_{29}$ by a pseudoknot a first insertion segment of variable length is located between $N_{18}$ and $A_{19}$, the first insertion segment comprising a stem loop structure of variable length and having sequence starting with NR and ending with YN in a 5' to 3' direction a second insertion segment of variable length is located between $Y_{25}$ and $K_{26}$; second insertion segment configured to form a stem loop structure R is A or G; and Y is C or U as also indicated in FIG. 48A

In F-sensing riboswitches of sequence SEQ ID NO: 2510, any one of nucleotides $G_3$, $R_5$, $U_7$, $G_8$, $R_9$, $Y_{14}$, $C_{16}$, $A_{20}$, $A_{31}$, $Y_{37}$, $C_{38}$, $U_{39}$, and $R_{40}$ is a 97% conserved nucleotide (present in 97% of the F-sensing riboswitches encompassed by SEQ ID NO: 2510)

In F-sensing riboswitches of sequence SEQ ID NO: 2510, any one of nucleotides $G_2$, $G_3\ R_5$, $A_6$, $U_7$, $G_8$, $R_9$, $Y_{14}$, $C_{16}$, $C_{17}$, $A_{19}$, $A_{20}$, $G_{23}$, $C_{24}$, $G_{27}$, $U_{29}$, $A_{31}$, $Y_{37}$, $C_{38}$, $U_{39}$, $R_{40}$ and $Y_{41}$ is a 90% conserved nucleotide (present in 90% of the F-sensing riboswitches encompassed by SEQ ID NO: 2510)

In F-sensing riboswitches of sequence SEQ ID NO: 2510, any one of nucleotides $G_{11}$, $U_{12}$, $Y_{13}$, $C_{21}$, $C_{22}$, $Y_{25}$, $R_{26}$, $C_{28}$, $G_{30}$, $G_{33}$, $A_{34}$, and $C_{35}$ is a 75% conserved nucleotide (present in 75% of the F-sensing riboswitches encompassed by SEQ ID NO: 2510W)

Figure 48B:
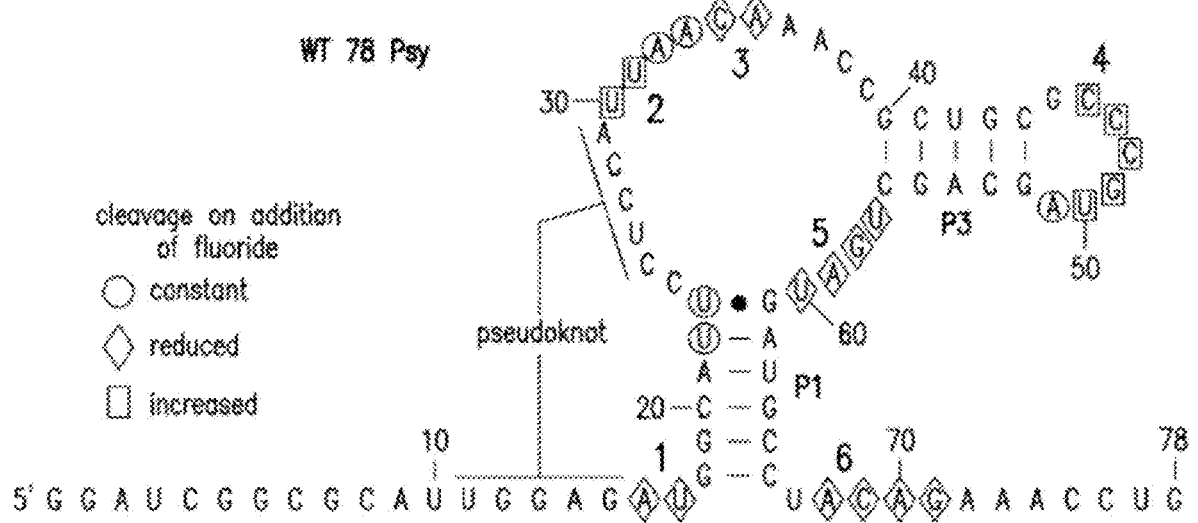
FIG. 48B is FIG. 1B of U.S. Pat. No. 9,580,713 and, as indicated in U.S. Pat. No. 9,580,713 shows the "[s]equence and secondary structure model for the WT 78 Psy RNA (SEQ ID NO:349). Numbers 1, 2, 3, 4, 5, and 6 depict the sites of the in-line probing analysis; results presented in C. The two G residues preceding nucleotide 1 $_{35}$ were added to facilitate RNA production by in vitro transcription."

An additional, exemplary consensus sequence and structure for crcB riboswitches is reported in FIG. 48. FIG. 48B reproduces FIG. 1B of U.S. Pat. No. 9,580,713 [102] and shows an exemplary sequence and secondary structure model for the WT 78 Psy RNA comprising a crcB motif sequence. The 78-nucleotide RNA encompasses the crcB motif from *Pseudomonas syringae*.

An additional exemplary F-sensing riboswitch that is schematically illustrated in FIG. 48B has sequence (SEQ ID NO: 2511)

$G_1G_2A_3U_4C_5G_6G_7C_8G_9C_{10}A_{11}U_{12}U_{13}G_{14}G_{15}A_{16}G_{17}A_{18}U_{19}G_{20}G_{21}C_{22}A_{23}$ $U_{24}U_{25}C_{26}C_{27}U_{28}C_{29}C_{30}A_{31}U_{32}U_{33}A_{34}A_{35}C_{36}A_{37}A_{38}A_{39}C_{40}G_{41}C_{42}U_{43}$ $G_{44}C_{45}G_{46}C_{47}C_{48}C_{49}G_{50}U_{51}A_{52}G_{53}C_{54}A_{55}G_{56}C_{57}U_{58}G_{59}A_{60}U_{61}G_{62}A_{63}$ $U_{64}G_{65}C_{66}C_{67}U_{67}A_{68}C_{69}A_{70}G_{71}A_{72}A_{73}A_{74}C_{75}C_{76}U_{77}G_{78}$ wherein anyone of $_2U_{13}G_{14}G_{15}A_{16}G_{17}$ is linked with any one of $C_{27}U_{28}C_{29}C_{30}A$ by a pseudoknot and the F-sensing riboswitch Additional exemplary sequences are indicated in U.S. Pat. No. 9,580,713. In particular as indicated in U.S. Pat. No. 9,580,713 exemplary crcB motifs are described in (WO 2011/088076 and in [108]) also describing related structure and locations in organisms. Comparative genomics reveals 104 candidate structured RNAs from bacteria, archaeal, and their metagenomes as described in WO 2011/088076 and in [108] which are both hereby incorporated by reference in their entirety. In particular, incorporated by reference in its entirety is section 24 of the Additional File 3 of [108], which shows the sequences of numerous crcB motifs, as well as related genes, organisms, alignments, and consensus structures that can be used in connection with the biosensors herein described.

In some embodiments, the crcB RNA motif sequences herein described is a crcB RNA motif of the RF01734 family annotated by Rfam database which includes 2138 crcB RNA motif sequences of this family, their secondary and 3-D structures, and predicted phylogenetic tree for the sequence alignment (see http://rfam.org/family/RF01734 at the date of filing of the present disclosure which is also incorporated herein by reference in its entirety).

Additional consensus sequence and structures for F-sensing riboswitches are identifiable by a skilled person upon reading of the disclosure. In particular, similar to the consensus sequence and structure of FIG. 1A of U.S. Pat. No. 9,580,713, a consensus secondary structure of the crcB RNA motif sequences of the RF01734 family is illustrated in FIG. 48C. 8 out of 10 base pairs shown in FIG. 48C are significant at E-value=0.05.

An F-sensing riboswitch with a consensus sequence and structure schematically illustrated in FIG. 48C has sequence (SEQ ID NO: 2512)
$N_1N_2G_3G_4N_5G_6A_7U_8G_9R_{10}N_{11}G_{12}U_{13}Y_{14}C_{15}N_{16}C_{16}C_{17}N_{18}N_{19}A_{20}A_{21}C_{22}$ $C_{23}G_{24}C_{25}Y_{26}R_{27}G_{28}C_{25}U_{26}G_{27}A_{28}U_{29}G_{30}A_{231}C_{32}N_{33}Y_{34}C_{35}U_{36}R_{37}C_{38}$ wherein $N_1$ $N_2$ $N_5$ $N_{11}$ $N_{15}$ $N_{18}$ $N_{19}$ and $N_{37}$ are independently any amino acid;

$N_1$ $N_2$ $N_5$ $N_{11}$ $N_{15}$ $N_{18}$ $N_{19}$ and $N_{37}$ are independently present or absent;

anyone of $N_1N_2G_3G_4N_5G_6A_7$ can be linked with any one of $C_{15}N_{16}C_{16}C_{17}N_{18}$ $N_{19}$ by a pseudoknot of sequence NNCCNC a first insertion segment of 0 to 48 nucleotides is located between $N_{19}$ and $A_{20}$, wherein when the first insertion segment is >12 nucleotides long, the first insertion comprises a stem loop structure of variable length having sequence starting with NRR and ending with YYN in a 5' to 3' direction a second insertion segment of variable length structure is located between $Y_{26}$ and $R_{26}$, the second insertion segment configured to form a stem loop;

R is A or G; and

Y is C or U, as also indicated in FIG. 48C.

In F-sensing riboswitches of sequence SEQ ID NO: 2512, any one of $N_1$ $N_2$ $N_8$ $N_{11}$ $N_{18}$ $N_{18}$ and $N_{37}$ is a 97% conserved nucleotide (present in 97% of the F-sensing riboswitches encompassed by sequence SEQ ID NO: 2512), and $N_{19}$ is a 50% conserved nucleotide (present in 50% of the riboswitches encompassed by sequence SEQ ID NO: 2512) (FIG. 48C)

In particular, exemplary F-sensing riboswitch sequence in the sense of the disclosure can have sequence (SEQ ID NO: 2513)
$N_1$ $N_2$ $N_3$ $N_4$ $N_5$ $N_6$ $N_7$ $N_8$ $N_9$ $G_{10}$ $G_{11}$ $N_{12}$ $G_{13}$ $A_{14}$ $U_{15}$ $G_{16}$ $G_{17}$ $N_{18}$ $G_{19}$ $U_{20}$ $Y_{21}$ $C_{22}$ $N_{23}$ $C_{24}$ $C_{25}$ $N_{26}$ $N_{27}$ $N_{28}$ $A_{29}$ $A_{30}$ $C_{31}$ $C_{32}$ $G_{33}$ $C_{34}$ $Y_{35}$ $N_{36}$ $N_{37}$ $N_{38}$ $N_{39}$ $N_{40}$ $N_{41}$ $N_{42}$ $R_{43}$ $G_{44}$ $C_{45}$ $U_{46}$ $G_{47}$ $A_{48}$ $U_{49}$ $G_{50}$ $A_{51}$ $C_{52}$ $N_{53}$ $Y_{54}$ $C_{55}$ $U_{56}$ $R_{57}$ $C_{58}$ $N_{59}$ $N_{60}$ $N_{61}$ $N_{62}$ $N_{63}$ $N_{64}$ wherein $N_1$, $N_2$, $N_3$, $N_4$, $N_5$, $N_6$, $N_7$, $N_8$, $N_9$, $N_{12}$, $N_{18}$, $N_{23}$, $N_{26}$, $N_{27}$, $N_{28}$, $N_{36}$, $N_{37}$, $N_{38}$, $N_{39}$, $N_{40}$, $N_{41}$, $N_{42}$, $N_{53}$, $N_{59}$, $N_{60}$, $N_{61}$, $N_{62}$, $N_{63}$, $N_{64}$ are interdependently any amino acid;

R is A or G; and

Y is C or U.

Figure 48D:
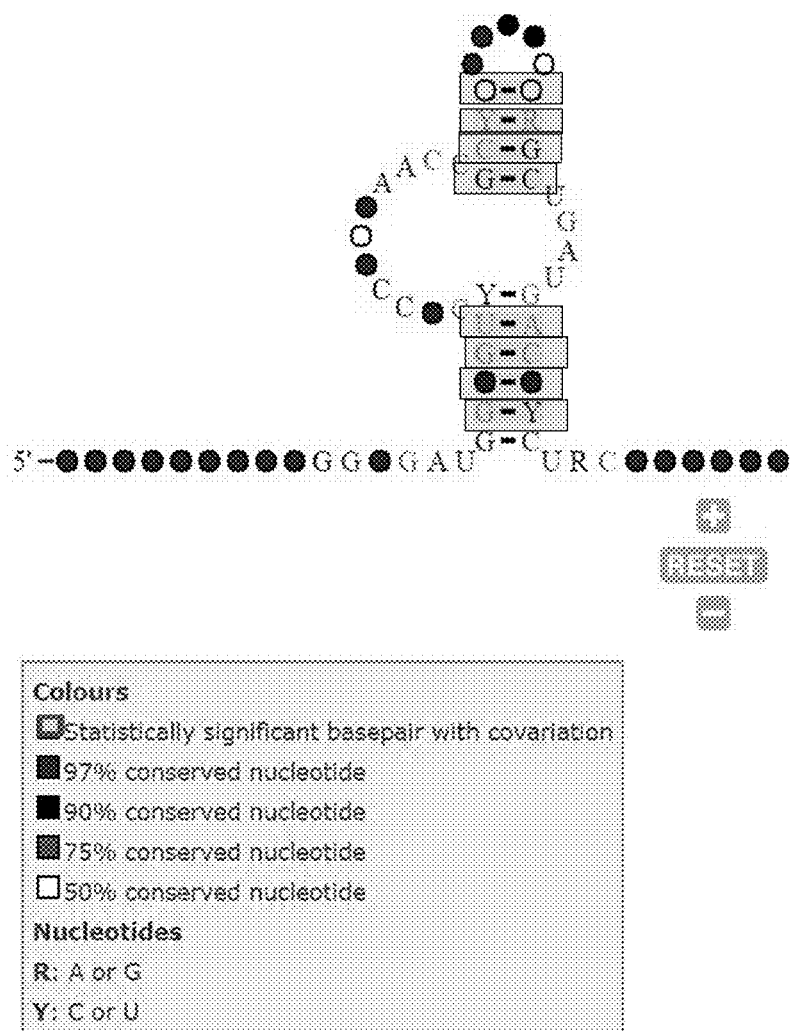
FIG. 48D shows a schematic representation of an exemplary fluoride sensing riboswitch herein described which correspond to a grayscale version of of schematic reported in https://rfam.xfam.org/family/RF01734#tabview=tab3 at the filing date of the present application.

In particular, in F-sensing riboswitches of sequence SEQ ID NO: 2513, each of nucleotides $N_1$, $N_2$, $N_3$, $N_4$, $N_5$, $N_6$, $N_7$, $N_8$, $N_9$, $G_{11}N_{12}$, $A_{14}$ $U_{15}$ $G_{16}$, $N_{18}$, $N_{23}$, $C_{24}$, $N_{26}$ $N_{28}$, $A_{29}$ $A_{30}$, $N_{37}$ $N_{38}$ $U_{46}$ $A_{48}$ $U_{49}$ $N_{83}$ $Y_{54}$ $C_{55}$ $U_{56}$ $C_{58}$ $N_{59}$ $N_{60}$ $N_{61}$ $N_{62}$ $N_{63}$ $N_{64}$ is a 97% conserved nucleotide (conserved in 97% of the F-sensing riboswitches)

each of nucleotides $G_{10}$, $Y_{21}$, $C_{25}$, $G_{33}$ $N_{39}$ $N_{40}$ $R_{57}$ is a 90% conserved nucleotide (conserved in 90% of the F-sensing riboswitches)

each of nucleotides $G_{13}$ $G_{17}$ $G_{19}$ $C_{22}$ $U_{20}$ $C_{31}$ $C_{32}$ $C_{34}$ $Y_{35}$ $R_{43}$ $G_{44}$ $C_{45}$ $G_{47}$ $G_{50}$ $A_{51}$ $C_{52}$ is a 75% conserved nucleotide (conserved in 75% of the F-sensing riboswitches); and each of nucleotides $N_{27}$ $N_{36}$ $N_{41}$ $N_{42}$ is a 50% conserved nucleotide (conserved in 50% of the F-sensing riboswitches) as illustrated in FIG. 48D In particular, F-sensing riboswitches of sequence SEQ ID NO: 2513 and FIG. 48D the positions of the riboswitch $N_1$, $N_2$, $N_3$, $N_4$, $N_5$, $N_6$, $N_7$, $N_8$, $N_9$, $G_{11}N_{12}$, $A_{14}$ $U_{15}$ $G_{16}$, $N_{18}$, $N_{23}$, $C_{24}$, $N_{26}$ $N_{28}$, $A_{29}$ $A_{30}$, $N_{37}$ $N_{38}$ $U_{46}$ $A_{48}$ $U_{49}$ $N_{53}$ $Y_{54}$ $C_{55}$ $U_{56}$ $C_{58}$ $N_{59}$ $N_{60}$ $N_{61}$ $N_{62}$ $N_{63}$ $N_{64}$ [are at least 97% conserved nucleotides, positions $G_{10}$, $Y_{21}$, $C_{25}$, $G_{33}$ $N_{39}$ $N_{40}$ $R_{57}$ are at least 90% conserved nucleotides, positions $G_13$ $G_{17}$ $G_{19}$ $C_{22}$ $U_{20}$ $C_{31}$ $C_{32}$ $C_{34}$ $Y_{35}$ $R_{43}$ $G_{44}$ $C_{45}$ $G_{47}$ $G_{50}$ $A_{51}$ $C_{52}$ are at least 75% conserved nucleotides, and positions $N_{27}$ $N_{36}$ $N_{41}$ $N_{42}$ are at least 50% conserved nucleotides. It has been shown that the most highly conserved nucleotides of the RF01734 family undergo structural change on addition of fluoride, which suggests that these nucleotides help form a ligand-binding aptamer for fluoride [102]. Mutations that alter the aptamer's conserved substructures or conserved nucleotides adversely affect fluoride binding, suggesting that the features common to all crcB motif RNAs are necessary for the selective recognition of fluoride.

In some embodiments, the crcB RNA motif of the RF01734 family can have a dissociation constant ($K_D$) of ~60 µM with respect to binding of fluoride. [102]

Exemplary F-sensing riboswitches in the sense of the disclosure also comprise a fluoride sensing riboswitch that can be found in regulatory regions of a fluoride efflux pump called $Eric^F$, a $F^-/H^+$ antiporter), performing an function (F–efflux) of CrcB efflux pump. that is commonly associated with fluoride riboswitches. CrcB and $Eric^F$ are expected to carryout the same function-fluoride export. It seems that organisms have one or the other.

Figure 53:
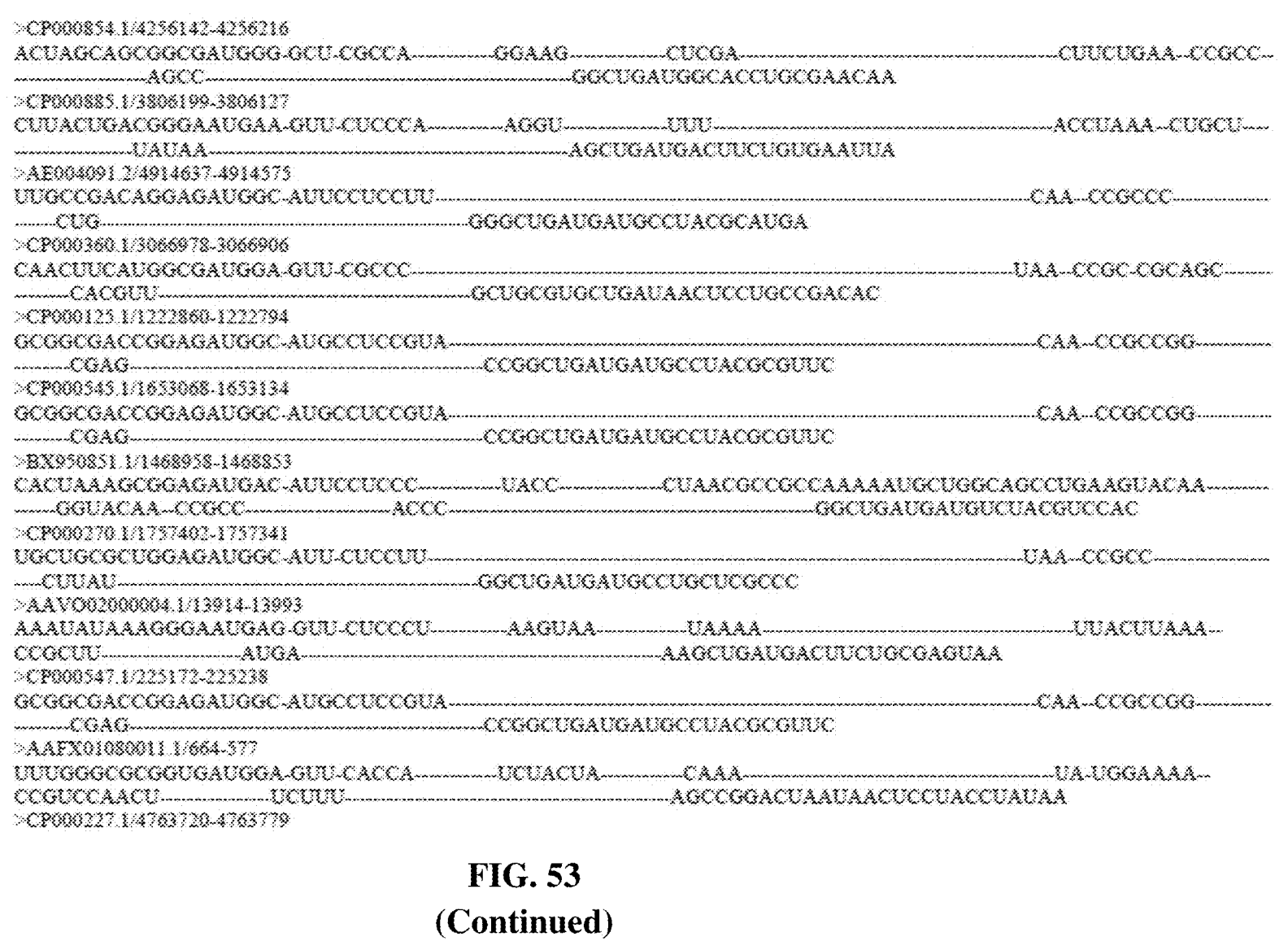
Figure 53:
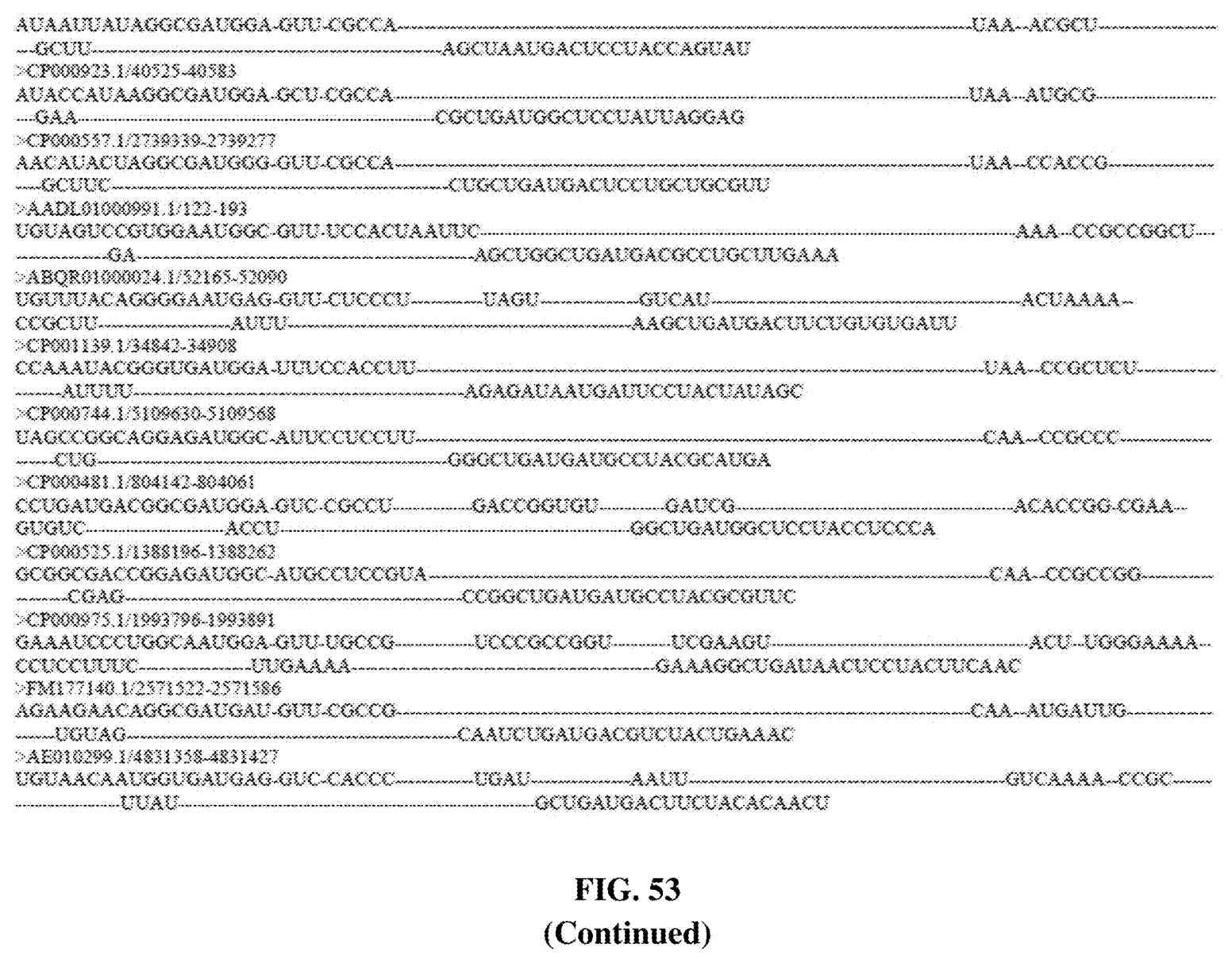
Figure 53:
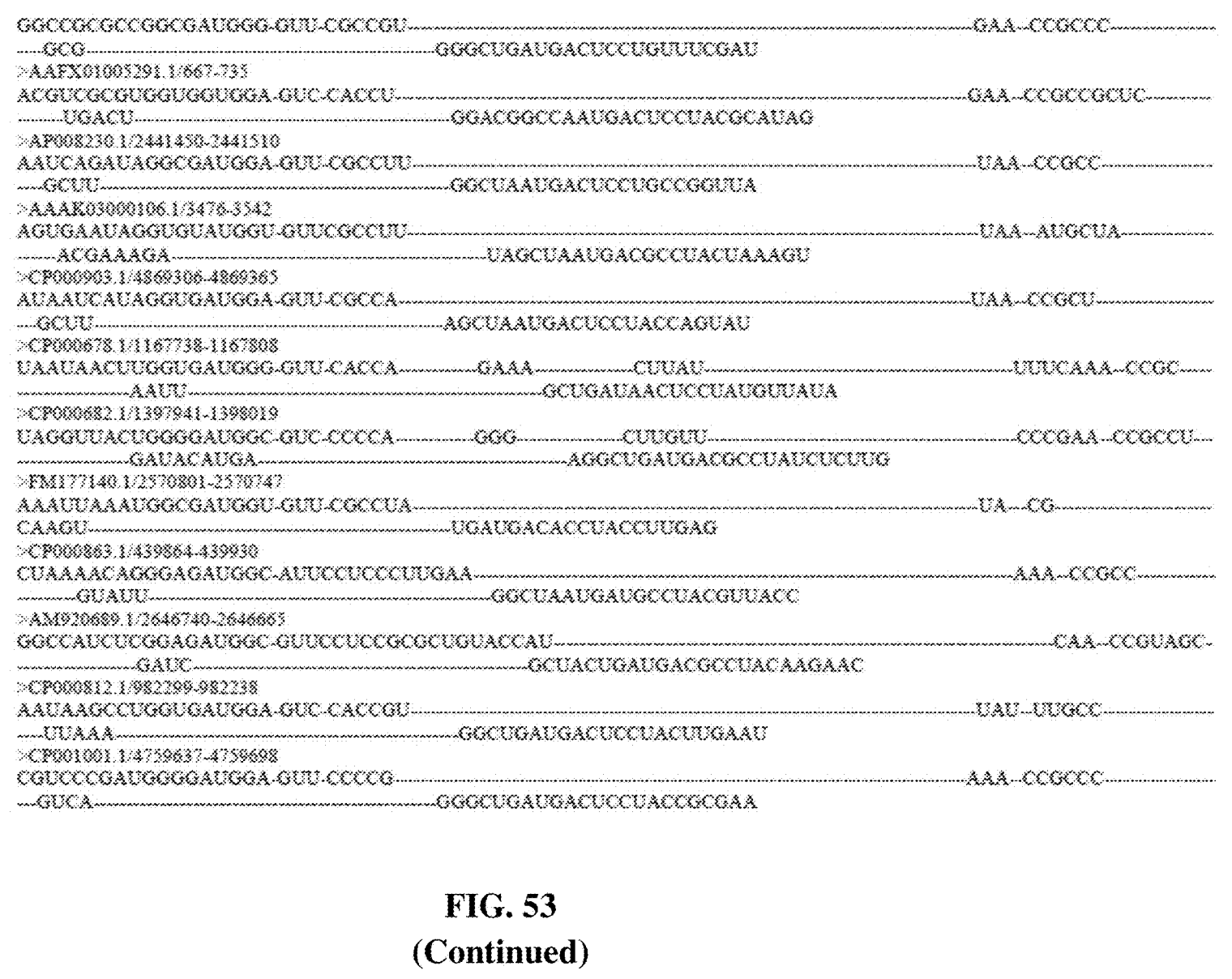
Figure 53:
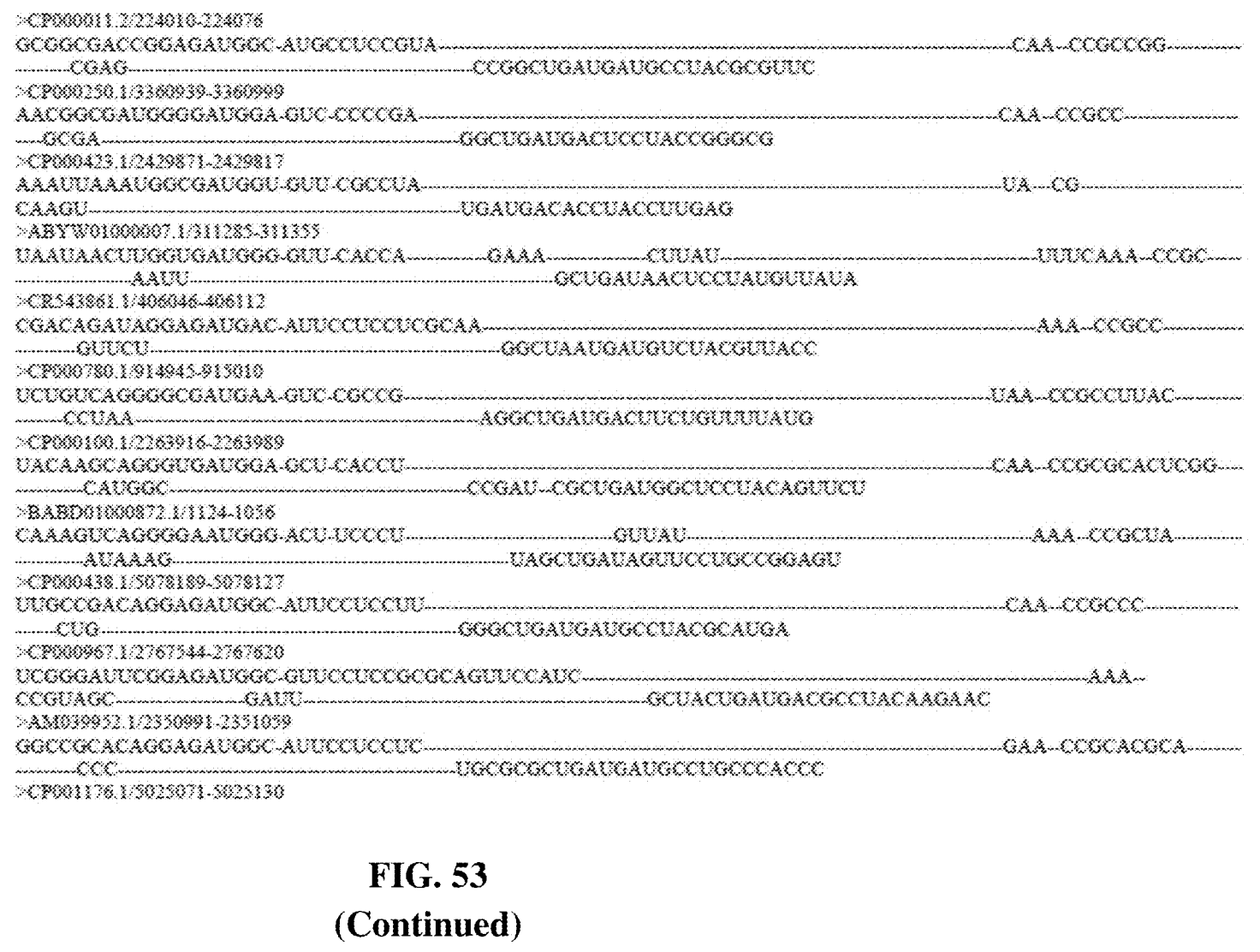
Figure 53:
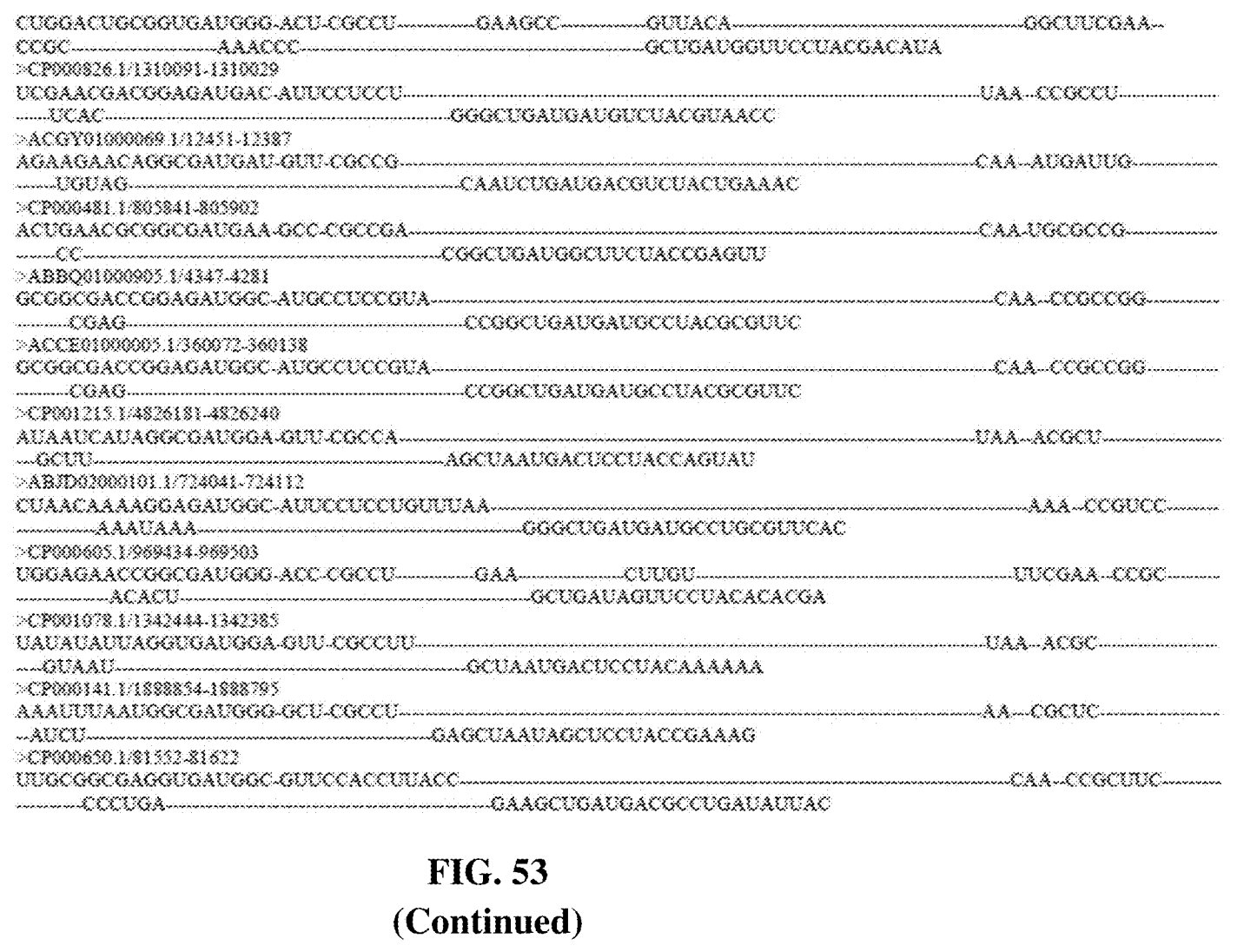
Figure 53:
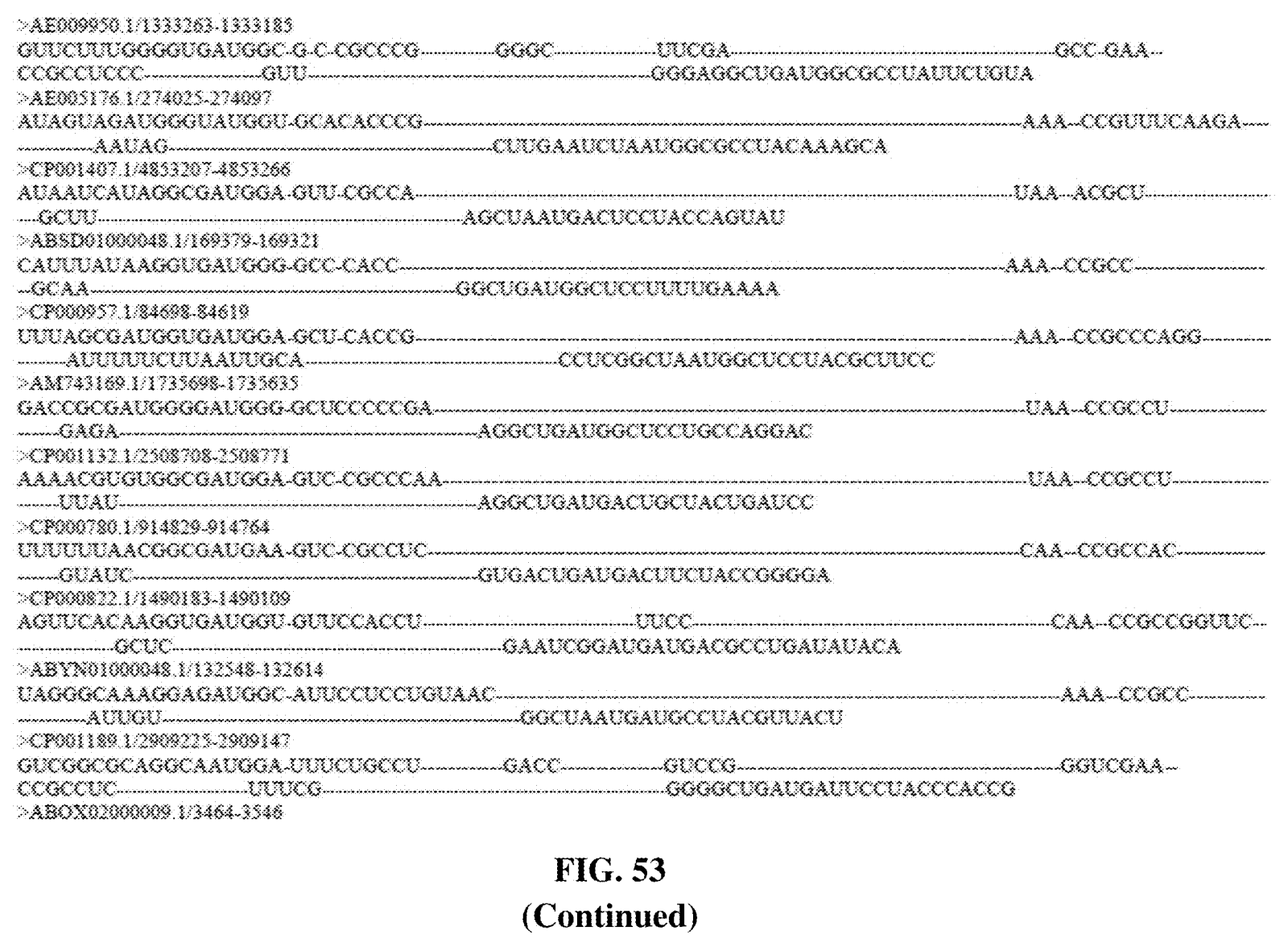
Figure 53:
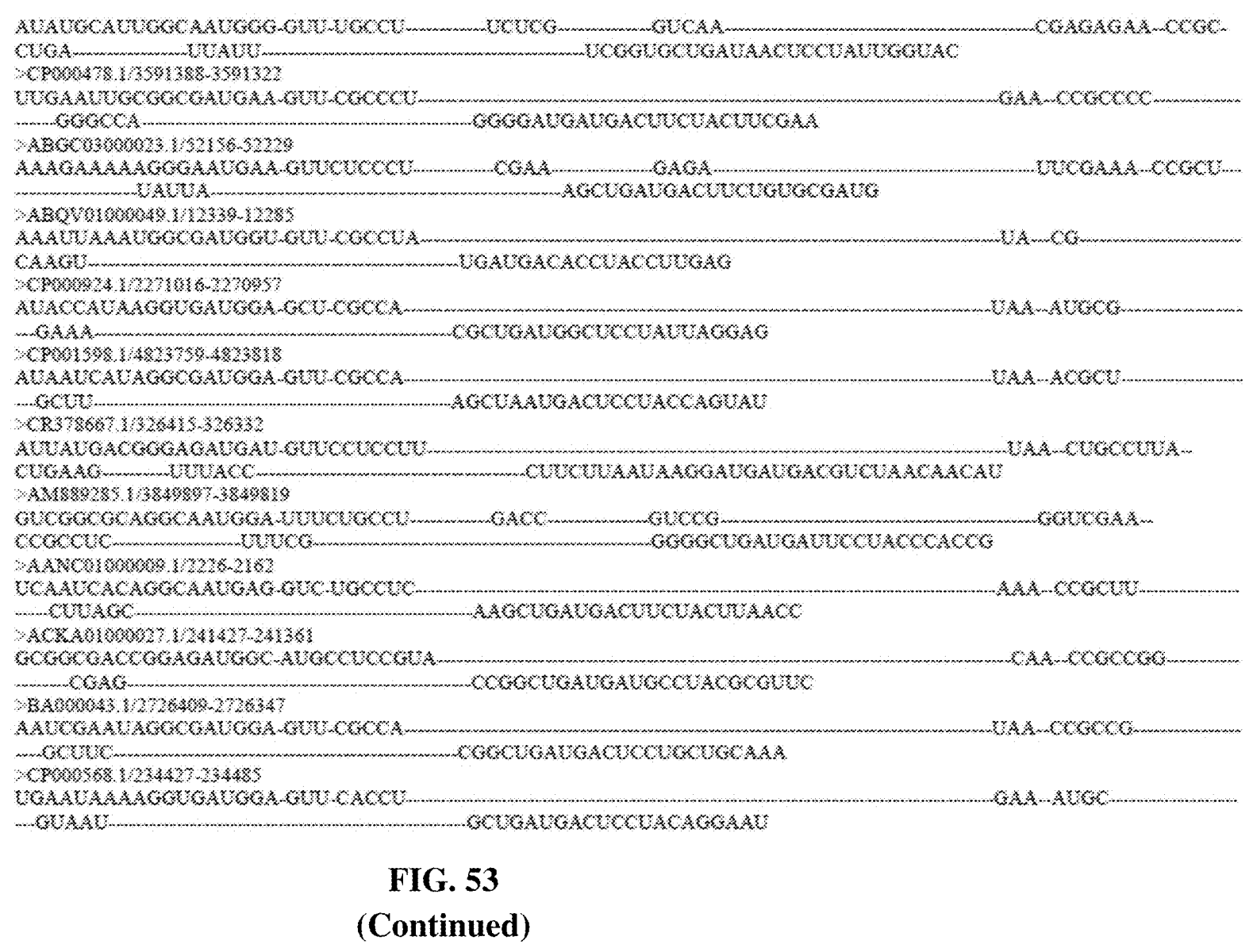
Figure 53:
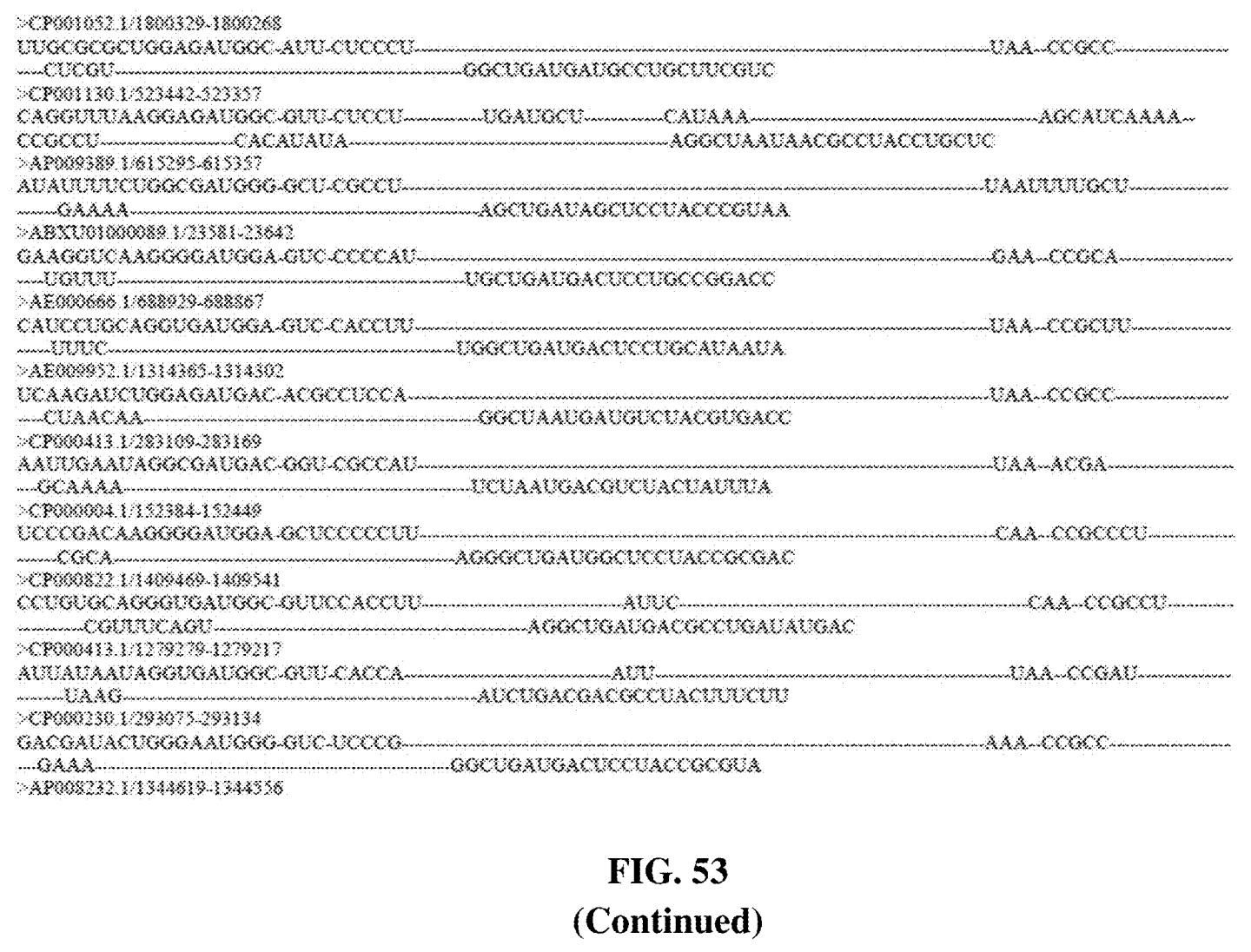
Figure 53:
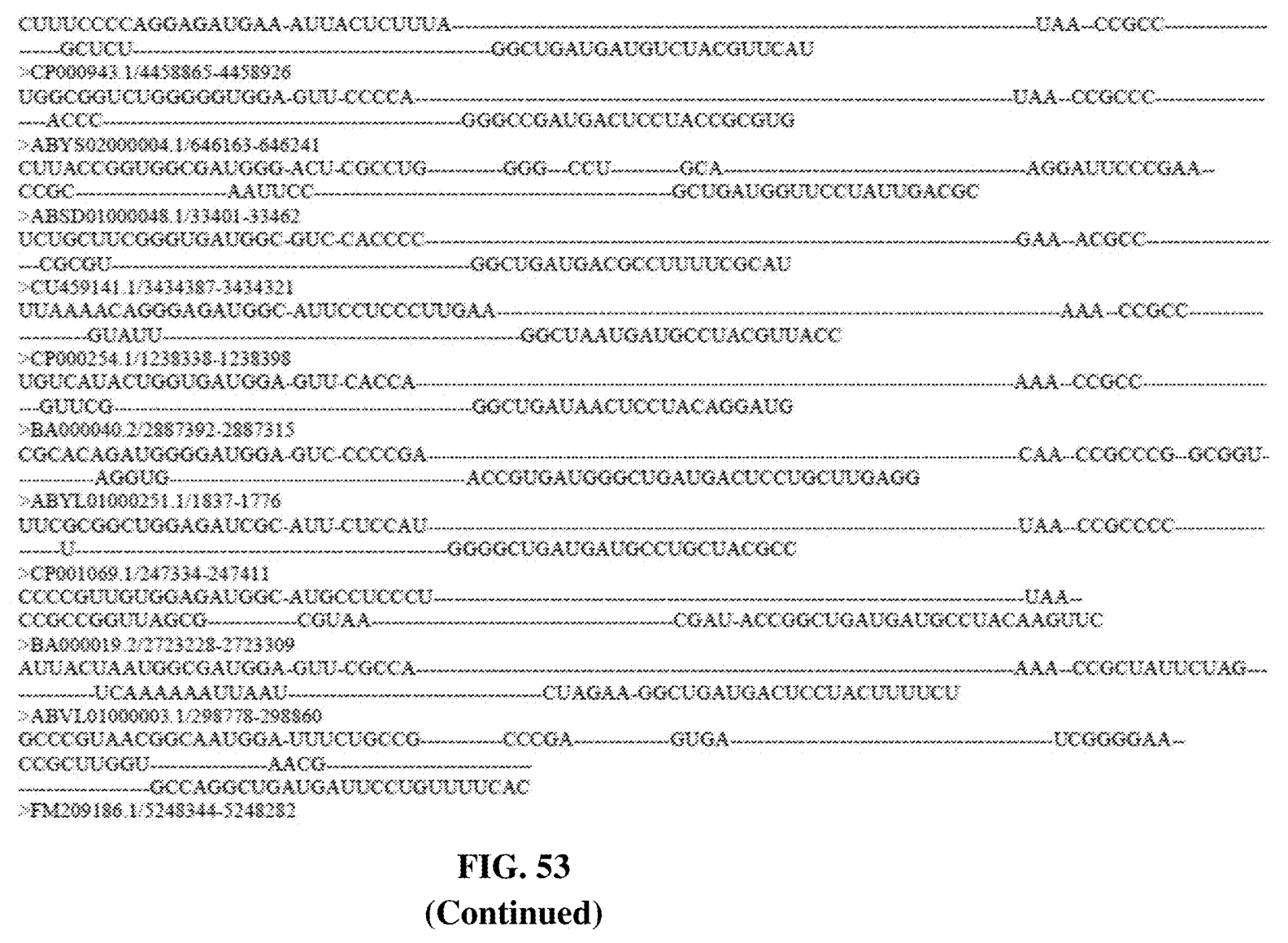
Figure 53:
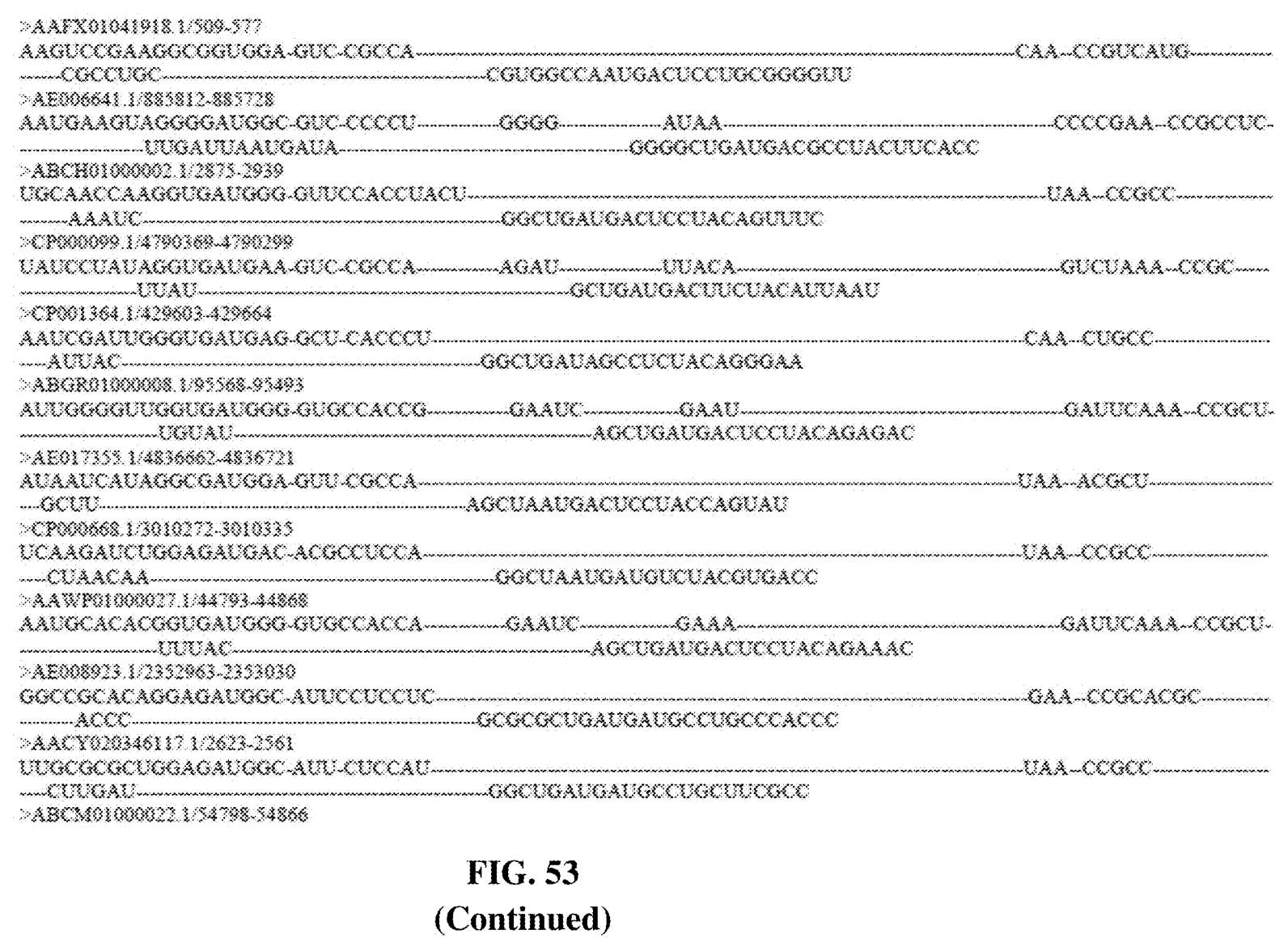
Figure 53:
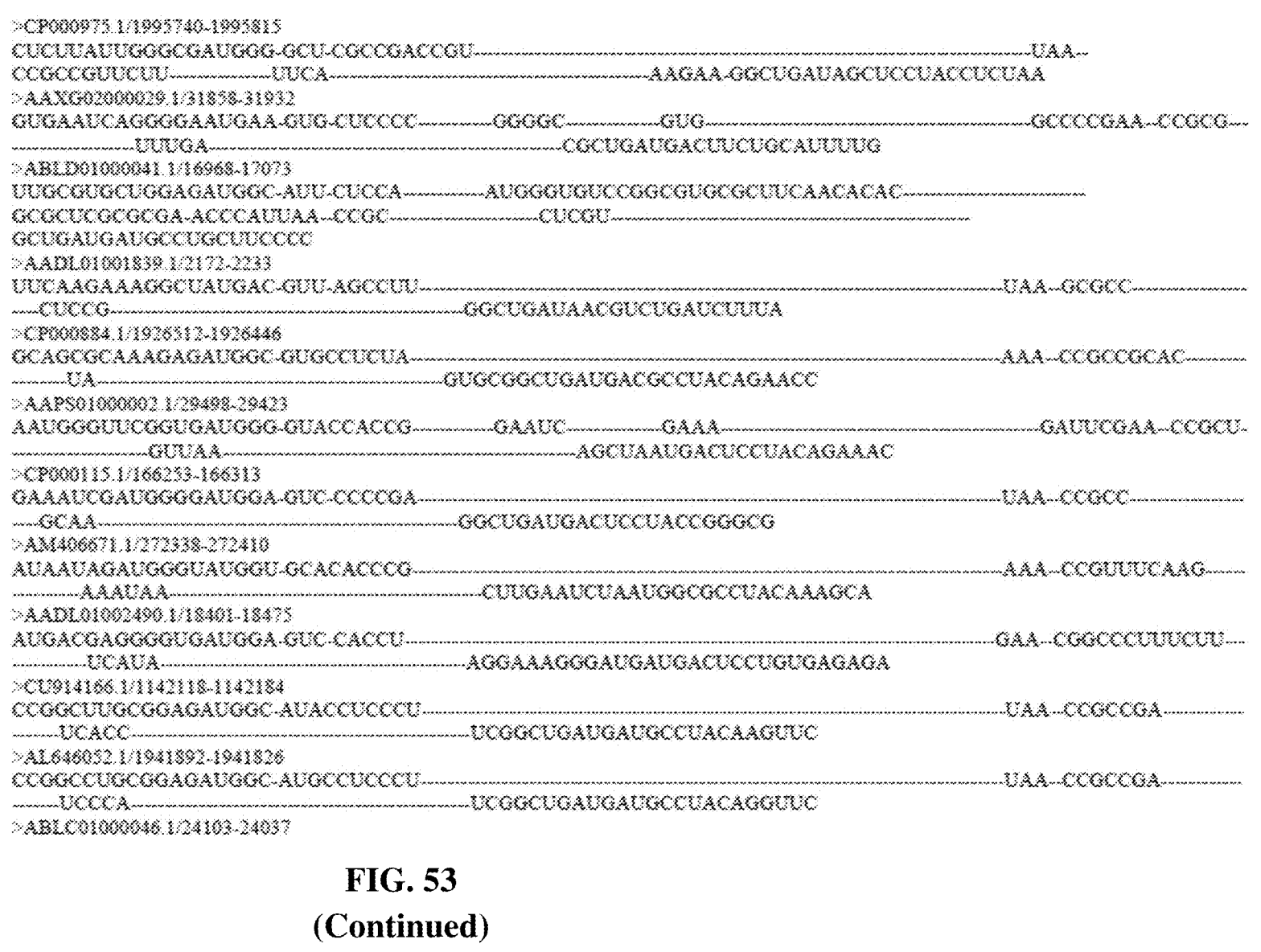
Figure 53:
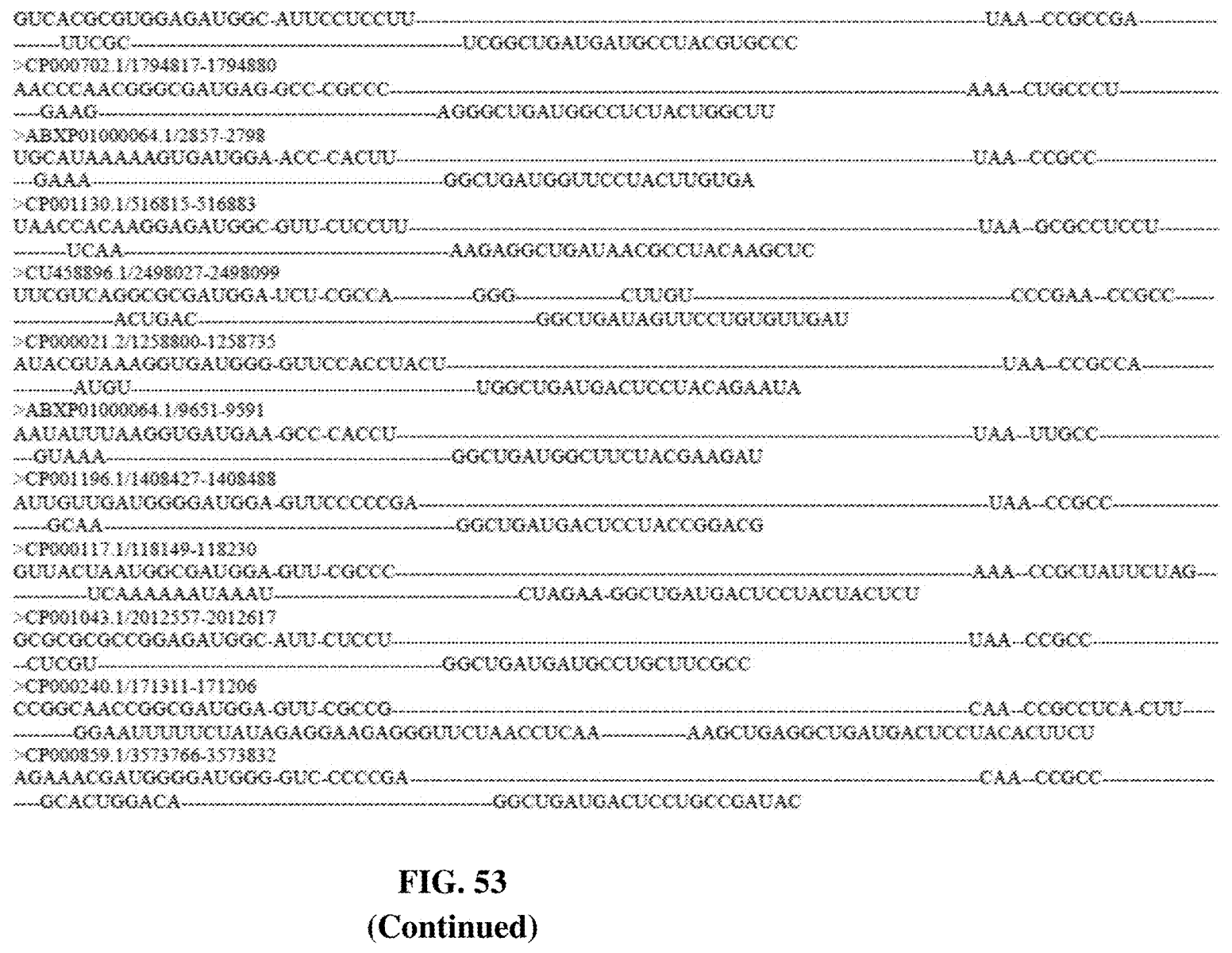
Figure 53:
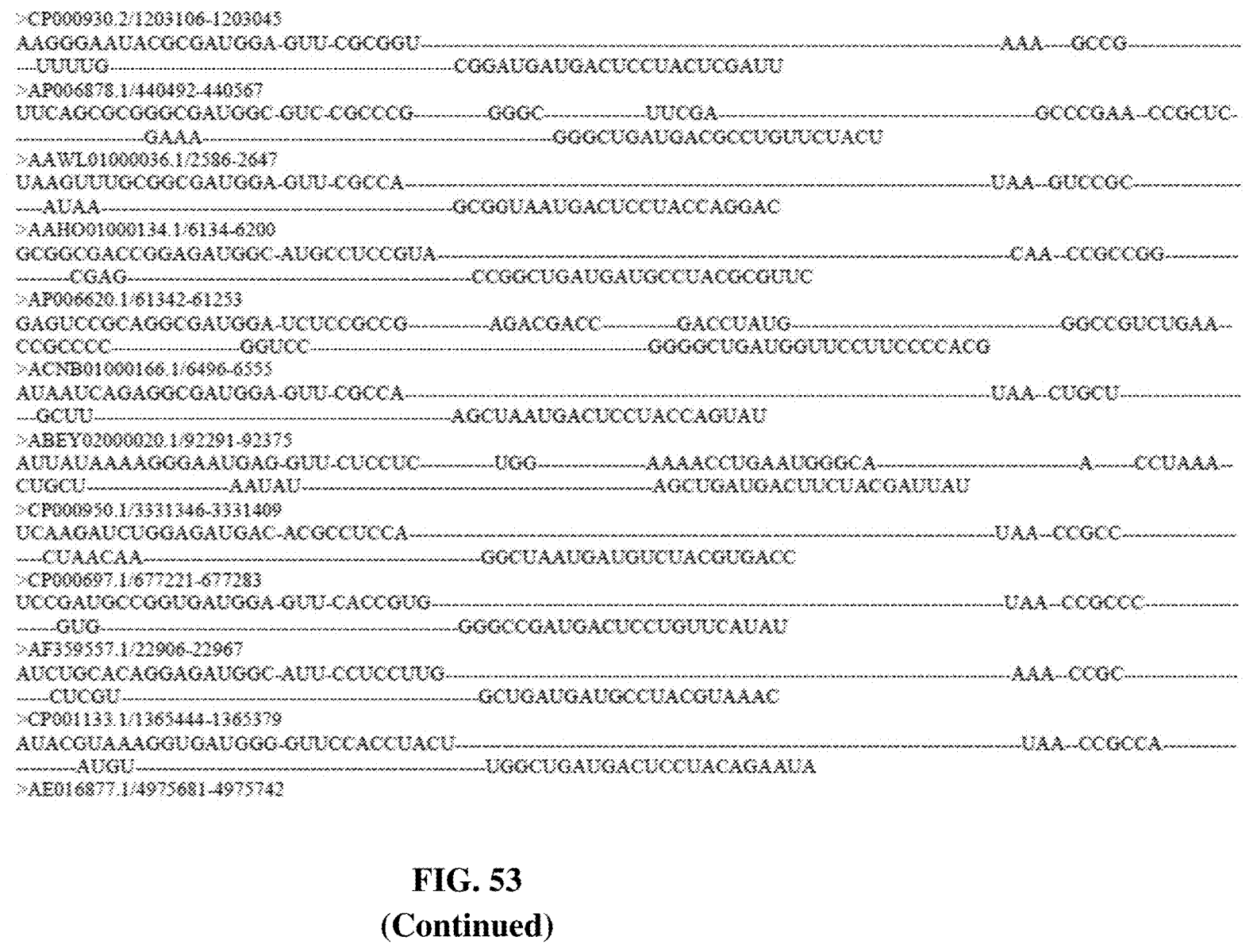
Figure 53:
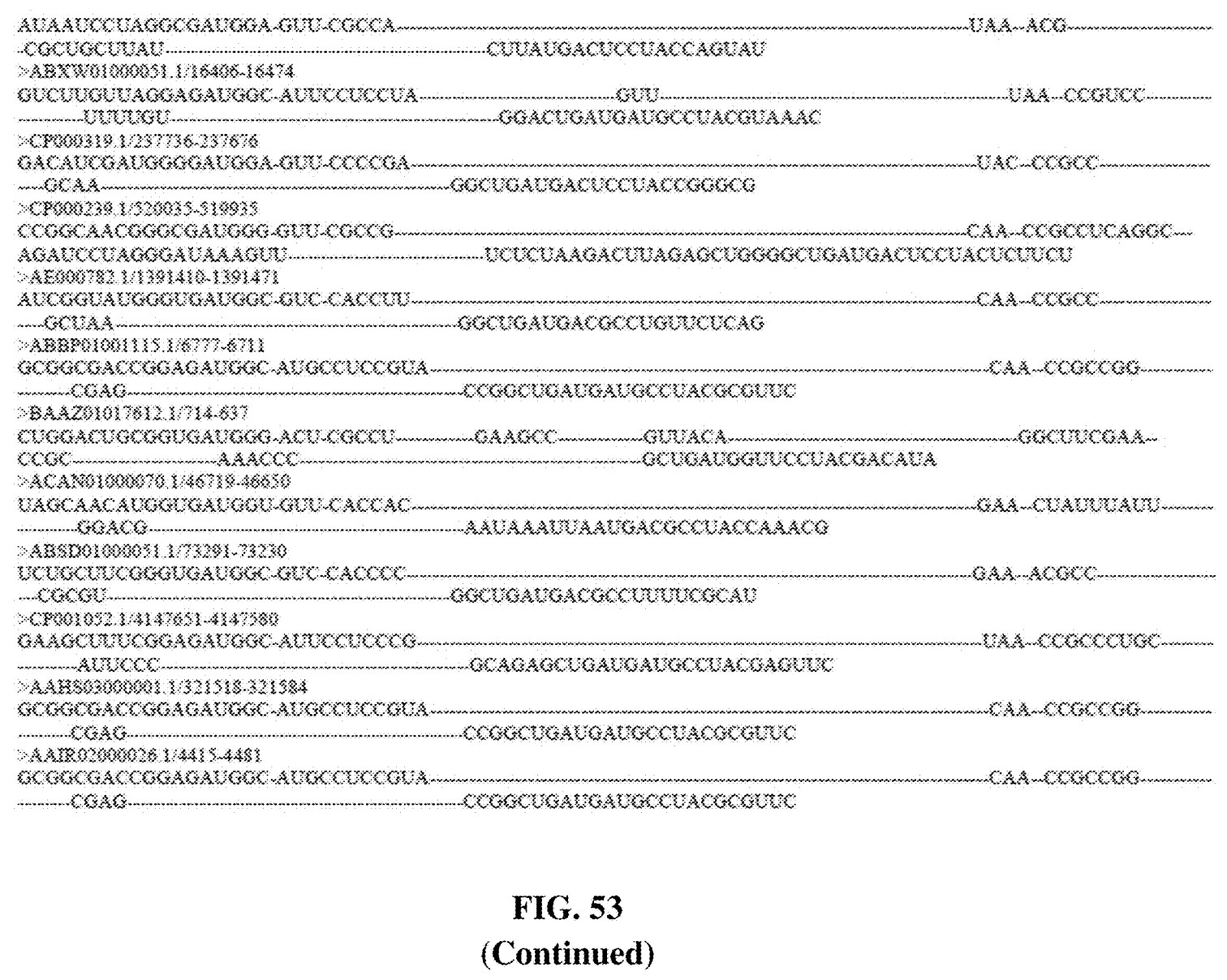

Additional exemplary Fluoride sensing riboswitches are sequences from SEQ ID NO: 205 to SEQ ID NO; 1988 and SEQ ID No: 1999 to SEQ ID NO: 2231 reported in Appendix I of U.S. provisional application No. 62/801,077 and SEQ ID NO: 1989-1998 and SEQ ID NO: 2232-2508 in FIG. 53 of the disclosure which are incorporated herein by reference in its entirety, which contains 2017 exemplary F-sensing riboswitch sequences. An alignment of 287 sequences from the 2017 exemplary F-sensing riboswitch sequences is shown in FIG. 53 (SEQ ID NO: 1989-1998 and SEQ ID NO: 2232-2508) wherein the nucleotide sequences shown are sequences forming a same structure in corresponding aligned sequences and the symbols "--" indicates gaps between the aligned sequences shown (see Example 20) is also for further guidance concerning sequences and structures of F-sensing riboswitches suitable in constructs in accordance with the present disclosure.

In another, preferred embodiment the F-sensing ribo-switch is the F-sensing riboswitch from *Sphingomonas* sp, 67-36 encoded by (SEQ ID NO: 2525)
CATGGTGACGGGGATGGAGTTCCCCGATAACCGCCGTTCCGGGCTGATGA

CTCCTACCAACAC.

In another, preferred embodiment the F-sensing ribo-switch is the F-sensing riboswitch from *Pseudomonas Syringae* encoded by (SEQ ID NO: 2526)
CGGCGCATTGGAGATGGCATTCCTCCATTAACAAACCGCTGCGCCCGTAG

CAGCTGATGATGCCTACAGAAAC.

In a more preferred embodiment, the F-sensing riboswitch is MM-1 from *Sphingomonas* encoded by (SEQ ID NO: 2514)
GTCGGCAACGGCAATGGATTCCTGCCGGGCCTCGCGCCGAACCGCCATTG

AGGGCTGATGATTCCTACCTGCGG (See Example 27 and Example 28).

In some embodiments of the UO$_2$F$_2$-biosensors herein described an F-sensing riboswitch can be comprised within any one of the U-sensing genetic molecular components herein described.

In some embodiments of the UO$_2$F$_2$-biosensors herein described an F-sensing riboswitch can be comprised in an F-sensing molecular component which is a genetically engi-neered polynucleotide construct configured to regulate expression of one or more RNA and/or protein-encoding genes through one or more promoter in combination with one or more F-sensing riboswitches. For example, an F-sensing riboswitch can be comprised in an F-sensing genetic reportable molecular component such as the one exemplified in Example 21.

In embodiments, herein described, any fluoride sensing riboswitch is expected to be functional in the host bacterium of interest. The well-characterized fluoride riboswitches from *P. syringae* DC3000 and *Bacillus subtilis* [102] repre-sent exemplary riboswitches for fluoride sensor construc-tion.

In some embodiments the native fluoride riboswitch from the host bacterium (if present) or a closely related bacterium can be used in the biosensors herein described, particularly if the promoter associated with the fluoride riboswitch is to be employed.

The relatedness among bacteria is defined based on taxo-nomic rank as will be understood by a person skilled in the art. In this connection relatedness among bacteria suitable to be used in biosensor of the present disclosure can be from the following groups Group 1: From the species of interest (e.g., *Caulobacter crescentus*)
Group 2: From the genus of interest (e.g., *Caulobacter*)
Group 3: From the family of interest (e.g., Caulobacter-aceae)
Group 4: From the order of interest (e.g. Caulobacterales)
Group 5 From the subclass of interest (e.g., Caulobacte-ridae)

Group 6: From the class of interest (e.g. Alphaproteobac-teria)

"Closely related" bacteria encompass bacteria within a same subclass of interest (group 5) preferably within a same order of interest (Group 2) and more preferably within a same family of interest (Group 2) and more preferably within the same genus/species of interest (Group I).

For example, while *C. crescentus*, a preferred host strain for the U sensor, lacks a native fluoride riboswitch, the uncharacterized fluoride riboswitch from *Sphingomonas* sp. MM-1 are also expected to be usable. This bacterium is closely related to *C. crescentus* and possesses similarly high genomic G+C content, minimizing compatibility risks with *C. crescentus*. Additionally, despite the lack of biochemical characterization, the function of the *Sphingomonas* sp. crcB motif in fluoride sensing is supported by its homology with characterized crcB riboswitches [Pfam database [109]] and its genomic location upstream of a fluoride exporter.

In some embodiments, the genetically modified bacteria are bacteria incapable of natively expressing an F-sensing riboswitch. In some embodiments, the genetically modified bacteria are bacteria capable of natively expressing an F-sensing riboswitch. In some of those embodiments, the endogenous F-sensing riboswitch, are preferably knocked out or disabled through mutagenesis of conserved nucleo-tides critical for riboswitch function. [102](see Example 26)

In particular in some embodiment where the native CrcB fluoride exporter functions are maintained the detection limit of the colorimetric crcB reporter (~1 mM) can be adversely affected. In those embodiments, abolishing fluoride export by deletion of the crcB gene yielded a 100-fold improve-ment in the fluoride detection limit (sub 10 μM) [102]. Achieving a low fluoride detection limit will likely require deletion of the crcB gene or the analogous eriC$^F$ gene in the host organism.[102]

The utility of a fluoride riboswitch for applications in a whole-cell fluoride sensor is supported by the finding that the crcB motif can be appended to the lacZ reporter gene in both *E. coli* and *B. subtilis*, enabling a colorimetric output response over a 100-fold range of fluoride concentrations. [102]. Additional elements and configuration of F-sensing components herein described (including U-sensing F-sens-ing reportable genetic molecular component, an F-sensing reportable genetic molecular component) can be identified by a skilled person based on the component and the host bacterial cell.

Any fluoride sensing riboswitch and in particular any fluoride sensing riboswitch reported in Appendix I of U.S. provisional application No. 62/801,077, or encompassed by any one of SEQ ID NO: 2509 to SEQ ID NO: 2520, is expected to be employed for fluoride sensor construction, assuming that the promoter and ribosome binding sequence (RBS) are optimized for the organism of interest Any promoter and Ribosome Binding Sequence from a bacteria from the above Groups 1 to Group 6 which is encompassed by a known consensus and has a location upstream of crcB/eric$^F$ can be used in connection with each riboswitch sequence from all groups, with preference for promoters from bacteria closely related to the host bacteria of the UO$_2$F$_2$-biosensors herein described.

An F-sensing riboswitch can be included in any F-sensing molecular component herein described in combination with promoter and RBS in a configuration identifiable by a skilled person. Reference is made in this connection to the sche-matic of FIG. 52 which shows a schematic representation of the primary genetic parts involved in the construction of a fluoride sensing reporter include a (2) promoter to initiate transcription, a (1) fluoride riboswitch to terminate transcription in the absence of fluoride, a (3) ribosome binding site (RBS) to initiate translation, and a (5) reporter for detection. A portion of the (4) native crcB or eric$^F$ gene may be required for riboswitch function (i.e., coupling fluoride binding with transcriptional termination) of some fluoride riboswitches. The crcB gene is not required for the function of the *Sphingomonas* MM-1 fluoride riboswitch (Example 28).

In embodiments, herein described a skilled person will be able to identify a combination and configuration of an F sensing riboswitch based on the host bacteria by selecting the promoter and ribosome binding sequence (RBS) that are functional, and preferably optimized, for the host, such as a promoter and RBS native to the selected host bacterial cell or the closely related bacteria.

An example of closely related bacteria is provided by *C. crescentus*, and *Sphingomonas* sp. Accordingly, in an exemplary embodiments, a biosensor can be engineered in the preferred host strain for the U sensor *C. crescentus*, which lacks a native fluoride riboswitch with the uncharacterized fluoride riboswitch from *Sphingomonas* sp. MM-1. *Sphingomonas* sp is closely related to *C. crescentus* and possesses similarly high genomic G+C content, minimizing compatibility risks with *C. crescentus*.

Following identification of a promoter and RBS functional for the host bacteria, a suitable F-sensing riboswitch and the related configuration to obtain a desired F-sensitivity in a selected host bacteria can be identified with a method wherein the F-sensing riboswitch, promoter and RBS are tested in the host bacteria to identify a functional F-sensing construct to be used in F-sensing genetic molecular components herein described.

The method comprises selecting an F-sensing riboswitch from the host bacteria or from a closely related bacteria; selecting a promoter native to the selected host bacterial cell or the closely related bacteria, selecting a ribosome binding sequence (RBS) native to the selected host bacteria or the closely related bacteria, and selecting a portion of the crcB/eric$^F$ coding region. The method further comprises providing a candidate F-sensing construct wherein the selected F-sensing riboswitch, the selected native promoter, the selected RBS, and the selected portion of the crcB/eric$^F$ coding region are included in an gene expression cassette together with a reporter in a candidate configuration allowing expression of the reporter in the host bacteria in presence of Fluoride (see configuration schematically illustrated in FIG. 52) The method further comprises introducing the candidate F-sensing construct in the host bacteria for a time and under condition to allow expression of the reporter; and detecting expression of the reporter in presence of a selected F amount to identify an F-sensitivity of the candidate F-sensing construct. The method can further comprise performing the method with additional candidate F-sensing constructs and selecting the candidate F-sensing construct having the desired F-sensitivity.

In embodiments herein described, testing of different F-sensing riboswitches in F-sensing construct according to methods herein described can be performed to identify the combination of F-sensing riboswitches promoter and RSB sequence, number of riboswitches, length of the construct, presence of spacers and additional structural features of the configuration of the construct, resulting in an F-sensing cassette with a desired F sensitivity to the U-biosensor over additional combinations with less desired or no F-sensitivity (see e.g. testing of Examples 27-33).

For example, in some embodiments, an F-sensing construct in *C. crescentus* preferably comprises the *Sphingomonas* MM-1 fluoride riboswitch module which outperformed an analogous module from the more distantly related strain *Pseudomonas syringae* in terms of both signal amplitude and dynamic range (see Example 27 and Example 28).

In another exemplary application, an F-sensing in *C. crescentus* comprises the fluoride riboswitch from the closely related *Sphingomonas* 67-36 in combination with a xylose-inducible promoter (see Example 27 and Example 28).

In some embodiments, an F-sensing construct can comprise two or more F-sensing riboswitches (see Example 29).

In some embodiment, the F-sensing riboswitch can be comprised in an F-sensing construct in combination with the Pxyl promoter. In some of those embodiments the F-sensing riboswitch can be anyone of the F-riboswitches from *Sphingomonas* SP., in particular MM-1 (see e.g. SEQ ID NO: 2514) and *Sphingomonas* 67-36 (see e.g. SEQ ID NO: 2525). In some of these embodiments the F-sensing riboswitch can also be anyone of the F-riboswitches from *Pseudomonas Syringae*. In some of embodiments the F-sensing construct can have sequences SEQ ID NO: 2528, SEQ ID NO: 2519 or SEQ ID NO: 2520, preferably SEQ ID NO2518 (see e.g. Example 28).

In some embodiments, the F-sensing riboswitch can be comprised in an F-sensing construct in combination with a promoter native to the host bacteria, In those embodiments, the F-sensing riboswitch can preferably be an F-sensing riboswitch MM-1 from *Sphingomonas* Sp. (see e.g. SEQ ID NO: 2514).

In some embodiments, the F-sensing riboswitch can be comprised in an F-sensing construct in combination with Pphyt promoter. In those embodiments, the F-sensing riboswitch can preferably be an F-sensing riboswitch MM-1 from *Sphingomonas* Sp. (see e.g. SEQ ID NO: 2514).

In embodiments, herein described, preferably an F-sensing riboswitch is comprised together with other elements such promoters, RBS, Shine Dalgarno sequences and others identifiable by a skilled person in F-sensing constructs in a configuration that has a high signal amplitude (e.g. 25,000-200,000 for a normalized fluorescence signal) and large dynamic range with respect to fluorescence (higher than 100, preferably higher then 1000 and more preferably higher than 10,000)).

The wording "signal amplitude" as used herein with respect to a construct, cassette or component herein described, indicates the difference between the maximum (concentration of analyte such as U or F− that yields the highest signal) and minimum (no analyte, in particular no U and/or F) signal produced by the construct, cassette or component herein described For signal amplitude detected by fluorescence a high signal amplitude is typically a normalized fluorescence signal of 25,000-200,000, wherein the wording normalized fluorescence indicates the fluorescence signal (in arbitrary units)/cell density (OD600).

The wording "dynamic range" as used herein with respect to a construct, cassette or component herein described, indicates is defined as the ratio between the maximum (concentration of analyte such as U and/or F− that yields highest signal) and minimum (no analyte, in particular no U and/or F) signal produced by the construct, cassette or component herein described. A high value for the dynamic range are 100, 1000, or 10,000, wherein a higher dynamic range indicates a better analyte detection as will be understood by a skilled person.

In some embodiments, at least one Fluoride sensing riboswitch herein described can be comprised in combination of at least one a U-sensing genetic molecular component herein described, in a U-sensitive F-sensitive genetic circuit together with a reporter molecular component and/or a U-neutralizing molecular component. In addition or in the alternative, a Fluoride sensing riboswitch can be comprised in an F-sensitive genetic circuit together with a reporter molecular component, the F-sensing genetic circuit to be comprise in a biosensor herein described in combination with a U-sensitive genetic circuit and/or component as will be understood by a skilled person upon reading of the present disclosure.

In particular, in a U-sensitive genetic circuit, the U-sensing genetic molecular component, the reporter molecular component, and/or the U-neutralizing molecular components as well as possibly other components are connected one to another in accordance to a circuit design by activating, inhibiting, binding or converting reactions to form a fully connected network of interacting components.

Similarly for an F-sensing genetic circuit an F-sensing genetic molecular component comprising a fluoride sensing riboswitch and a reporter molecular component (as well as possibly other components) are connected one to another in accordance to a circuit design by activating, inhibiting, binding or converting reactions to form a fully connected network of interacting components when the genetic circuit operates according to the circuit design in presence of bioavailable Fluoride.

In a U-sensitive genetic circuit herein described, at least one molecular component is a U-sensing genetic molecular component in which a U-sensitive promoter having a regulator direct repeat sequence of SEQ ID NO: 1 or any of SEQ ID NO:7-28) is activated or repressed in presence of bioavailable U. In a U-sensitive genetic circuit herein described at least one molecular component is a reportable molecular component and/or a U-neutralizing molecular component when the genetic circuit operates according to the circuit design in presence of bioavailable U. In embodiments wherein at least one of the genetic molecular components of the U-sensitive genetic circuit herein described comprises a Fluoride sensing riboswitch the genetic circuit operates according to the circuit design in presence of bioavailable U and in presence of bioavailable Fluoride.

The term "genetic circuit" as used herein indicates a collection of molecular components connected one to another by biochemical reactions according to a circuit design. In particular, in a genetic circuit the molecular components are connected one to another by the biochemical reactions so that the collection of molecular components is capable to provide a specific output in response to one or more inputs.

In genetic circuits in the sense of the present disclosure, the molecular components forming parts of the genetic circuit can be genetic molecular components or cellular molecular components.

The term "cellular molecular component" indicates a molecular component not encoded by a gene, or indicates a molecular component transcribed and/or translated by a gene but comprised in the circuit without the corresponding gene. Exemplary cellular components comprise polynucleotides, polypeptides, polysaccharides, small molecules and additional chemical compounds that are present in a cellular environment and are identifiable by a skilled person.

Polysaccharides, small molecules, and additional chemical compounds can include, for example, NAD, FAD, ATP, GTP, CTP, TTP, AMP, GMP, ADP, GDP, Vitamin B1, B12, citric acid, glucose, pyruvate, 3-phosphoglyceric acid, phosphoenolpyruvate, amino acids, PEG-8000, FiColl 400, spermidine, DTT, b-mercaptoethanol maltose, maltodextrin, fructose, HEPES, Tris-Cl, acetic acid, aTc, IPTG, 3OC12HSL, 3OC6HSL, vanillin, malachite green, Spinach, succinate, tryptophan, and others known to those skilled in the art. Polynucleotides can include RNA regulatory factors (small activating RNA, small interfering RNA), or "junk" decoy DNA that either saturates DNA-binding enzymes (such as exonuclease) or contains operator sites to sequester activator or repressor enzymes present in the system (for example, as in [110]). Polypeptides can include those present in the genetic circuit but not produced by genetic components in the circuit, or those added to affect the molecular components of the circuit.

In some embodiments of genetic circuits herein described, one or more molecular components is a recombinant molecular component that can be provided by genetic recombination (such as molecular cloning) and/or chemical synthesis to bring together molecules or related portions from multiple sources, thus creating molecular components that would not otherwise be found in a single source.

In embodiments herein described, a genetic circuit comprises at least one genetic molecular component or at least two genetic molecular components, and possibly one or more cellular molecular components, connected one to another in accordance to a circuit design by activating, inhibiting, binding or converting reactions to form a fully connected network of interacting components.

The term "activating" as used herein in connection with a molecular component of a genetic circuit refers to a reaction involving the molecular component which results in an increased presence of the molecular component in the cellular environment. For example, activation of a genetic molecular component indicates one or more reactions involving the gene, RNA and/or protein of the genetic molecular component resulting in an increased presence of the gene, RNA and/or protein of the genetic molecular component (e.g. by increased expression of the gene of the molecular component, and/or an increased translation of the RNA). An example of "activating" described herein comprises the initiation of expression of a gene regulated by a UzcRS-regulated promoter by a UzcR protein (e.g., see Example 2).

Activation of a molecular component of a genetic circuit by another molecular component of the circuit can be performed by direct or indirect reaction of the molecular components. Examples of a direct activation of a genetic molecular component comprised in a circuit the production of an alternate sigma factor (molecular component of the circuit) that drives the expression of a gene controlled by the alternate sigma factor promoter (other molecular component of the circuit), or the production of a small ribonucleic acid (molecular component of the circuit) that increases expression of a riboregulator-controlled RNA (molecular component of the circuit). Specific examples of this include the activity of sigma28 or sigma54 as demonstrated in [111]. Examples of indirect activation of a genetic molecular component comprise the production of a first protein that inhibits an intermediate transcriptional repressor protein, wherein the intermediate transcriptional repressor protein represses the production of a target gene, such that the first protein indirectly activates expression of the target gene.

The term "inhibiting" as used herein in connection with a molecular component of a genetic circuit refers to a reaction involving the molecular component of the genetic circuit and resulting in a decreased presence of the molecular component in the cellular environment. For example, inhibition of a genetic molecular component indicates one or more reactions involving the gene, RNA and/or protein of the genetic molecular component resulting in a decreased presence of the gene, RNA and/or protein (e.g. by decreased expression of the gene of the molecular component, and/or a decreased translation of the RNA). Inhibition of a cellular molecular component indicates one or more reactions resulting in a decreased production or increased conversion, sequestration or degradation of the cellular molecular components (e.g. a polysaccharide or a metabolite) in the cellular environment.

Inhibition can be performed in the genetic circuit by direct reaction of a molecular component of the genetic circuit with another molecular component of the circuit or indirectly by reaction of products of a reaction of the molecular components of the genetic circuit with another molecular component of the circuit.

The term "binding" as used herein in connection with molecular components of a genetic circuit refers to the connecting or uniting two or more molecular components of the circuit by a bond, link, force or tie in order to keep two or more molecular components together, which encompasses either direct or indirect binding where, for example, a first molecular component is directly bound to a second molecular component, or one or more intermediate molecules are disposed between the first molecular component and the second molecular component another molecular component of the circuit. Exemplary bonds comprise covalent bond, ionic bond, van der Waals interactions and other bonds identifiable by a skilled person.

In some embodiments, the binding can be direct, such as the production of a polypeptide scaffold that directly binds to a scaffold-binding element of a protein. In other embodiments, the binding may be indirect, such as the co-localization of multiple protein elements on one scaffold. In some instances, binding of a molecular component with another molecular component can result in sequestering the molecular component, thus providing a type of inhibition of said molecular component. In some instances, binding of a molecular component with another molecular component can change the activity or function of the molecular component, as in the case of allosteric interactions between proteins, thus providing a type of activation or inhibition of the bound component. An example of "binding" as described herein comprises the binding of UzcR to an m_5 site in a UzcRS-regulated promoter (e.g., see Example 2).

The term "converting" as used herein in connection with a molecular component of the circuit refers to the direct or indirect conversion of the molecular component into another molecular component. An example of this is the conversion of chemical X by protein A to chemical Y that is then further converted by protein B to chemical Z. An example of "converting" as described herein comprises the cleavage of o-nitrophenyl-$\beta$-D-galactoside (ONPG) by beta-galactosidase encoded by the lacZ gene (e.g. see Example 1).

In embodiments of the U-sensitive and/or F-sensitive genetic circuits described herein, the molecular components are connected one with another according to a circuit design in which a molecular component is an input and another molecular component is an output. In particular, a genetic circuit typically has one or more input or start molecular component which activates, inhibits, binds and/or convert another molecular component, one or more output or end molecular component which are activated, inhibited, bound and/or converted by another molecular component, and intermediary molecular components each inhibiting, binding and/or converting another molecular component and being activated, inhibited, bound and/or converted by another molecular component. In embodiments of the U-sensitive and/or F-sensitive genetic circuits herein described, the input is bioavailable U and/or bioavailable F and the output is a reportable molecular component and/or a U-neutralizing molecular component.

In some embodiments of the $UO_2F_2$ biosensor herein described the U-sensitive and/or F-sensitive genetic circuits can be comprised together within a same biosensor to detect or to detect and neutralize bioavailable $UO_2F_2$.

In some embodiments of the $UO_2F_2$ biosensor herein described the U-sensitive and/or F-sensitive genetic circuits can be comprised in combination with a U-sensing genetic molecular component and/or a F-sensing genetic molecular component of the disclosure to the detect or to detect and neutralize bioavailable $UO_2F_2$.

In some embodiments of the $UO_2F_2$ biosensor described herein, the U-sensitive F-sensitive genetic circuit can comprise at least one F-sensing genetic molecular component in which RNA is expressed in presence of bioavailable F, and at least one U-sensing genetic molecular component in which a U-sensitive promoter is activated or repressed in presence of bioavailable U, the U sensitive promoter comprising a U-sensitive transcriptional 1362 binding site or a U-sensitive transcriptional UzcR binding site. In addition or in the alternative, in the U-sensing F-sensing genetic circuit, a U-sensing genetic molecular component comprises at least one Fluoride sensing riboswitch. In these embodiments, in the U-sensitive F-sensitive genetic circuit at least one molecular component is a reportable molecular component and/or a U-neutralizing molecular component when the genetic circuit operates according to the circuit design in presence of bioavailable U and bioavailable Fluoride.

Exemplary configurations of an F-sensing bioswitch and a U-sensing genetic molecular component in a $UO_2F_2$ biosensors are shown in Examples 23 to 25.

In some embodiments, the $UO_2F_2$ comprise a U-sensing genetic molecular component and/or a U-sensing genetic circuit in combination with a separate F-sensing genetic molecular component and/or a F-sensing genetic circuit to provide a dual output configuration wherein one or more fluoride riboswitches control the expression of a reportable molecular component configured to be independent of U. Exemplary dual output configurations of the $UO_2F_2$ biosensor herein described are showing in Example 25.

In some embodiments, the $UO_2F_2$ biosensor comprise a U-sensing genetic molecular component and/or a U-sensing genetic circuit in combination with a F-sensing riboswitch integrated in the U-sensing genetic molecular component and/or a U-sensing genetic circuit to provide a single output configuration wherein one or more fluoride riboswitches control the output of the U-sensing genetic molecular component and/or the U-sensing genetic circuit. In particular in those embodiments, the fluoride riboswitch functions to prematurely terminate transcription from a U-activated promoter in the absence of fluoride. Fluoride binding mitigates this termination, enabling gene expression thus providing an output in presence of bioavailable U and Fluoride. Exemplary single output configurations of the $UO_2F_2$ biosensor herein described are shown in Example 24.

Exemplary configurations of $UO_2F_2$ biosensors herein described are reported below and in the Examples sections.

In particular, an exemplary genetic circuit described herein comprises, a U sensing genetic molecular component in which a U-sensitive promoter such as $P_{phyt}$ or a $P_{1361}$ is configured to initiate expression of a lacZ gene encoding the beta-galactosidase enzyme (U-sensing genetic molecular component), wherein the beta-galactosidase enzyme converts the substrate ONPG (cellular molecular component) to yield galactose and o-nitrophenol which has a yellow color (reportable molecular component). In some of these embodiments, the genetic molecular components can further comprise a Fluoride sensing riboswitch (e.g. any one of the crcB riboswitches herein described) in a configuration which allows the expression of the lacZ gene in presence of an effective amount of bioavailable fluoride in a single output configuration as will be understood by a skilled person. In addition or in the alternative, the $UO_2F_2$ biosensor can further comprise the F-sensing riboswitch in a separate F-sensing reportable genetic molecular component and/or a separate F-sensing genetic circuit to provide a dual output configuration.

In some embodiments of the $UO_2F_2$ biosensor, the U-sensitive genetic circuit comprises at least one U-sensing genetic molecular component in which a U-sensitive promoter is activated or repressed in presence of bioavailable U, the U sensitive promoter comprising a U-sensitive transcriptional 1362 binding site and the U sensitive genetic circuit is comprised in the biosensor together with an F-sensitive reportable genetic molecular component comprising an F-sensitive riboswitch herein described configured to be expressed in presence of an effective amount of bioavailable Fluoride in a dual output configuration. In these embodiments, in the U-sensitive genetic circuit at least one molecular component is a reportable molecular component and/or a U-neutralizing molecular component when the genetic circuit operates according to the circuit design in presence of bioavailable U as will be understood by a skilled person. In some embodiments, the U-sensitive genetic circuit further comprises at least one genetic molecular component in which a UzcRS two-component system regulated promoter is activated or repressed in presence of bioavailable U.

In an exemplary embodiment of the U-sensitive genetic circuit described herein, at least one U-sensitive genetic molecular component comprises a U-sensitive promoter such as $P_{phyt}$ or a $P_{1361}$ configured to initiate expression of a uzcS gene (CCNA_02842) and a uzcR gene (CCNZ_02485), encoding proteins UzcS and UzcR, respectively (first U-sensing genetic molecular component) and further comprises a second U-sensing genetic molecular component in which a UzcRS two-component system regulated promoter is configured to initiate expression of a reporter gene (e.g. GFP, an exemplary reportable molecular component), in which binding of UzcR protein to the UzcRS-regulated promoter activates the UzcRS-regulated promoter (see Example 2). As understood by those skilled in the art, uzcS and uzcR are genes that are natively comprised in a uzcRS operon in *Caulobacter* and other alphaproteobacteria, as described in Park et al., 2017 [3].

The term "uzcRS operon" as used herein refers to the genetically encoded UzcRS two-component system, comprising the uzcS gene (CCNA_02842) and the uzcR gene (CCNZ_02485), and operatively linked promoters and regulatory elements [3]. In an exemplary *C. crescentus* NA1000 genome, uzcR and uzcS are physically separated by genes $parD_3$ and $parE_3$ encoding the ParDE3 toxin antitoxin (TA) system, together forming a putative four-gene operon [3, 112]. Although uzcR and uzcS are conserved throughout alphaproteobacteria, the insertion of parDE3 between uzcR and uzcS is unique to a subset of the *Caulobacter* genus; uzcR and uzcS are adjacently located in the majority of closely related alphaproteobacteria [3] including *C. crescentus* OR37, an environmental isolate from a U-contaminated site [97].

Accordingly, in some embodiments of the $UO_2F_2$ biosensors described herein, the U biosensor can be any genetically engineered proteobacteria and in particular a genetically engineered Caulobacteridae which comprises a UzcRS two component system.

In some preferred embodiments, a U-sensitive genetic circuit further comprises one or more genetic molecular components comprising one or more negative regulators of UzcRS that function to maintain UzcRS in an OFF state in absence of metal (see Example 9). In particular, in some exemplary embodiments, the $UO_2F_2$ biosensor described herein comprises a chromosomal copy of UzcRS negative regulators 1 and 2 (Example 9) under transcriptional regulation of their native promoters. In other embodiments, one or more genetic molecular components comprising exemplary UzcRS negative regulators 1 and 2 are placed under control of inducible transcriptional regulatory elements in order to desensitize UzcS to a particular signal. For example, overexpression of CCNA_03680-CCNA_03681 reduces the sensitivity of UzcRS for Zn and Cu. In some embodiments, the MarR-type regulators CCNA_03498 and/or CCNA_02289 can be deleted in the host Caulobacteridae genome to increase sensitivity of uzcRS for U.

In some of the embodiments of the U-sensitive genetic circuit in which at least one U-sensitive genetic molecular component comprises a U-sensitive promoter such as $P_{phyt}$ or a $P_{1361}$ configured to initiate expression of a uzcS gene (CCNA_02842) and a uzcR gene (CCNZ_02485), a fluoride riboswitch can be integrated between the UzcRS-regulated promoter and the GFP gene and/or between the $P_{phyt}$ or $P_{1361}$ promoter and the uzcS ATG to provide a U-sensing F-sensing genetic circuit in a single output configuration. In addition or in the alternative, a riboswitch can be comprised in the $UO_2F_2$ biosensor in a separate F-sensing reportable genetic molecular component and/or in a separate F-sensing genetic circuit herein described in a dual output configuration.

In some cases of these embodiments or other embodiments herein described, riboswitch performance is expected to be adversely affected by changes in genomic context, such as fusing the riboswitch to a reporter gene. Accordingly, in any embodiments herein described, if an initial transcriptional fusion to a reporter (such as GFP) fails, a Riboattenuator, a recently developed genetic element that insulates the riboswitch from genomic context and enhances the tunability (e.g., sensitivity, cell-to-cell variability, etc.), will be used to build a riboswitch reporter (e.g. a CrcB reporter). This approach was successfully applied with various elements such as in construction of GFP fusions with the addA (2-aminopurine) and btuB (adenosylcobalamin) riboswitches [113].

In an exemplary embodiment of the U-sensitive F-sensitive genetic circuits described herein, the U-sensitive genetic circuit comprises a U-sensitive promoter such as $P_{phyt}$ or a $P_{1361}$ configured to initiate expression of a hrpS gene encoding an HrpS protein (first U-sensing genetic molecular component) and further comprises a second U-sensing genetic molecular component in which a UzcRS two-component system regulated promoter is configured to initiate expression of an hrpR gene encoding an HrpR protein. The U-sensitive F-sensitive genetic circuit further comprises a fourth genetic molecular component comprising a hrpL promoter ($P_{hrpL}$) configured to initiate expression of a reporter gene (e.g. GFP, an exemplary reportable molecular component), in which binding of both HrpS and HrpR are required for $\sigma^{54}$ dependent activation of the $P_{hrpL}$ and expression of HrpS or HrpR alone is not sufficient for transcriptional activation. (see Example 3). In these embodiments a fluoride riboswitch could be integrated in three positions 1) Between the $P_{phyt}$ or $P_{1361}$ promoter and hrpS; 2); 2) between the UzcRS-regulated promoter and the hrpR; and/or between the PhrpL promoter and gfp to provide a U-sensitive F-sensitive genetic circuit with a single output configuration. In the addition or in the alternative, a riboswitch can be comprised in the $UO_2F_2$ biosensor in a separate F-sensing reportable genetic molecular component and/or in a separate F-sensing genetic circuit herein described in a dual output configuration.

As understood by those skilled in the art, hrpR and hrpS refer to genes that are natively comprised in a $\sigma^{54}$ dependent hrpR/hrpS hetero-regulation module from the hrp (hypersensitive response and pathogenicity) system for Type III secretion in *Psuedomonas syringae* [114-116], wherein both HrpS and HrpR are required for $\sigma^{54}$ dependent activation of the hrpL promoter ($P_{hrpL}$) and expression of HrpS or HrpR alone is not sufficient for transcriptional activation.

In some embodiments of the U-sensitive and/or F-sensitive genetic circuits described herein, at least two genetic molecular components comprise complementary protein fragments of a transcription factor, which are configured to associate together to form a functional transcription factor, such as those based on a bacterial two-hybrid system.

As would be understood by those skilled in the art, the term "bacterial two-hybrid" as used herein refers to a technique used to detect protein-protein interactions and protein-DNA interactions by testing for physical interactions (such as binding) between two proteins or a single protein and a DNA molecule, respectively. As understood by those skilled in the art, the bacterial two-hybrid system relies on the activation of downstream reporter gene(s) upon binding of a transcription factor onto an upstream activating sequence (UAS), wherein the transcription factor is split into two separate fragments, called the binding domain (BD) and activating domain (AD). The BD is a domain configured to bind to the UAS and the AD is a domain configured to activate transcription of the operatively linked gene. Thus, the bacterial two-hybrid system is a protein-fragment complementation assay that requires both the BD and the AD for reporter expression. An exemplary bacterial two-hybrid system utilizes an *E. coli* omega protein, which copurifies with RNA polymerase, and can function as a transcriptional activator when linked covalently to a DNA-binding protein. The *E. coli* omega protein can function as an activation target when this covalent linkage is replaced by a pair of interacting polypeptides fused to the DNA-binding protein and to omega, respectively [117].

Accordingly, in an exemplary embodiment of a U-sensitive genetic circuits described herein, the U-sensitive genetic circuit comprises a U-sensitive promoter such as $P_{phyt}$ or a $P_{1361}$ configured to initiate expression of a BD gene encoding an BD protein (first U-sensing genetic molecular component), and further comprises a second U-sensing genetic molecular component in which a UzcRS two-component system regulated promoter is configured to initiate expression of an AD gene encoding an AD protein. The U-sensitive genetic circuit further comprises a fourth genetic molecular component comprising a promoter comprising binding sites for the BD and the AD, configured to activate expression of the reporter gene, e.g. GFP or the U-neutralizing gene (third genetic molecular component), in which binding of both BD and AD are required activation of the third genetic molecular component and expression of the reportable molecular component and/or the U-neutralizing molecular component (see Example 5). For example, it is expected that a 1363/1362 regulated promoter (e.g., $P_{phyt}$) can be used to initiate expression of alpha-gal11$^P$ (an exemplary AD), and a UzcRS regulated promoter (e.g., $P_{urcB}$) can be used to initiate expression of $\lambda$-gal4 (an exemplary BD) and $P_{lacOR2-62}$ that contains the UAS to initiate expression of a reporter gene, such as GFPmut3 (see Example 5). In those embodiments a fluoride riboswitch could be integrated in three positions: 1) Between the $P_{phyt}$ or $P_{1361}$ promoter and BD; 2) Between the UzcRS-regulated promoter and AD and/or 3)) Between the BD/AD-regulated promoter and gfp to provide a U-sensitive F-sensitive genetic circuit with a single output configuration. In the addition or in the alternative, a riboswitch can be comprised in the $UO_2F_2$ biosensor in a separate F-sensing reportable genetic molecular component and/or in a separate F-sensing genetic circuit herein described in a dual output configuration.

In some embodiments of the U biosensor, the U-sensitive genetic circuit comprises at least one U-sensing genetic molecular component in which a U-sensitive promoter is activated or repressed in presence of bioavailable U, the U sensitive promoter comprising a U-sensitive transcriptional 1362 binding site and/or a UzcR binding site together. In these embodiments, in the U-sensitive genetic circuit at least one molecular component is a reportable molecular component and/or a U-neutralizing molecular component when the genetic circuit operates according to the circuit design in presence of bioavailable U, wherein the reportable genetic component and/or a U-neutralizing molecular component is formed by an assembly of two or more subunits of the reportable molecular component and/or a U-neutralizing molecular component. In some embodiments where a 1362 binding site is present, the U-sensitive genetic circuit further preferably comprises at least one genetic molecular component in which an UzcRS two-component system regulated promoter is activated or repressed in the presence of bioavailable U and bioavailable F. In those embodiments, a Fluoride riboswitch could be integrated in two positions: 1) between the $P_{phyt}$ or $P_{1361}$ promoter and U neutralizing gen; and/or 2) Between the UzcRS-regulated promoter and U neutralizing gene to provide a U-sensitive F-sensitive genetic circuit with a single output configuration. In the addition or in the alternative, a riboswitch can be comprised in the $UO_2F_2$ biosensor in a separate F-sensing reportable genetic molecular component and/or in a separate F-sensing genetic circuit herein described in a dual output configuration.

In an exemplary embodiment of the U-sensitive genetic circuits described herein (see Example 4), the U-sensitive F-sensitive genetic circuit comprises a U-sensitive promoter such as $P_{phyt}$ or a $P_{1361}$ configured to initiate expression of a gfp10-K1 fusion gene encoding a GFP10-K1 fusion protein (first U-sensing genetic molecular component) and further comprises a second U-sensing genetic molecular component in which a UzcRS two-component system regulated promoter is configured to initiate expression of an E1-gfp11 gene encoding E1-GFP11 fusion protein. The U-sensitive genetic circuit further comprises a third genetic molecular component comprising a gfp1-9 gene regulated by a non-U-responsive, xylose inducible promoter ($P_{xyl}$), a constitutively active promoter (e.g., $P_{rsaA}$) or by $P_{phyt}/P_{1361}$. In some of those embodiments, a Fluoride riboswitch can be integrated in three positions: 1) between the $P_{phyt}$ or $P_{1361}$ promoter and gfp10-K1; 2) between the UzcRS-regulated promoter and E1-gfp11; and/or 3) Between constitutive promoter and gfp-1-9 to provide a U-sensitive F-sensitive genetic circuit with a single output configuration. In the addition or in the alternative, a riboswitch can be comprised in the $UO_2F_2$ biosensor in a separate F-sensing reportable genetic molecular component and/or in a separate F-sensing genetic circuit herein described in a dual output configuration.

Accordingly, the term "tripartite GFP" as used herein refers to a GFP reporter that requires expression and assembly of GFP10, GFP11 and GFP1-9 together for GFP reporter function [5]. As understood by those skilled in the art, tripartite GFP assembly and reporter function is based on tripartite association between two twenty amino-acids long GFP tags, GFP10 and GFP11, which are fused to interacting protein partners, in addition to a complementary GFP1-9 detector. When the interacting protein partners interact, GFP10 and GFP11 self-associate with GFP1-9 to form a functional GFP [5]. In embodiments described herein, any protein interaction pair can be used for the tripartite system. Exemplary interacting protein partners comprise oppositely charged K1/E11 coiled coils, FKBP12-FRB rapamycin inducible protein interaction [5], or the leucine zipper of GCN4 [118] among others known to those skilled in the art.

In some embodiments of the $UO_2F_2$ biosensor, a U-sensitive genetic circuit can comprise at least one U-sensing genetic molecular component in which a U-sensitive promoter is activated or repressed in the presence of bioavailable U, the U sensitive promoter comprising a U-sensitive transcriptional 1362 binding site and/or a UzcR binding site. In these embodiments, in the U-sensitive genetic circuit at least one molecular component is a reportable molecular component and/or a U-neutralizing molecular component when the genetic circuit operates according to the circuit design in the presence of bioavailable U, wherein the reportable molecular component and/or the U-neutralizing molecular component is post-transcriptionally and/or post-translationally converted by the U-sensitive F-sensitive genetic circuit in presence of bioavailable U. In some embodiments wherein at least one of the U sensing promoter is 1362 binding sites, the U-sensitive genetic circuit further preferably comprises at least one genetic molecular component in which a UzcRS two-component system regulated promoter is activated or repressed in presence of bioavailable U and bioavailable F.

Accordingly, in an exemplary embodiment of the U sensing genetic molecular components described herein, the U-sensitive genetic molecular component comprises a U-sensitive promoter such as $P_{phyt}$ or a $P_{1361}$ configured to initiate expression of a protease configured to cleave at a cleavage sequence comprised in a linker peptide in a Förster resonance energy transfer (FRET) sensor protein (first U-sensing genetic molecular component), and further comprises a second U-sensing genetic molecular component in which a UzcRS two-component system regulated promoter is configured to initiate expression of the FRET sensor protein. Thus, in presence of bioavailable U, the U-sensitive genetic circuit is configured to express and cleave the FRET sensor protein. In those embodiments, a fluoride sensing riboswitch can be integrated in two positions: 1) between the $P_{phyt}$ or $P_{1361}$ promoter and FRET protein 1 and/or 2) between the UzcRS-regulated promoter and FRET protein 2 to provide a U-sensitive F-sensitive genetic circuit with a single output configuration. In the addition or in the alternative, a riboswitch can be comprised in the $UO_2F_2$ biosensor in a separate F-sensing reportable genetic molecular component and/or in a separate F-sensing genetic circuit herein described in a dual output configuration.

As understood by those skilled in the art, the terms "Förster resonance energy transfer", "FRET", "fluorescence resonance energy transfer", "resonance energy transfer", "RET" or "electronic energy transfer", and "EET" as used herein refers to a mechanism describing energy transfer between two light-sensitive molecules (chromophores) [119]. A donor chromophore, initially in its electronic excited state, can transfer energy to an acceptor chromophore through nonradiative dipole-dipole coupling [120]. The efficiency of this energy transfer is inversely proportional to the sixth power of the distance between donor and acceptor, making FRET extremely sensitive to small changes in distance. Measurements of FRET efficiency can be used to determine if two fluorophores are within a certain distance of each other [121]. Such measurements can be used as a research tool in fields such as biology and chemistry. For example, one common pair fluorophores for biological use is a cyan fluorescent protein (CFP)-yellow fluorescent protein (YFP) pair [122]. Both are color variants of green fluorescent protein (GFP). Thus, for example, a genetically-encoded fusion of CFP and YFP covalently linked by a protease cleavage sequence can be used as a cleavage assay, wherein if the linker is intact, excitation at the absorbance wavelength of CFP (414 nm) causes emission by YFP (525 nm) due to FRET. If the linker is cleaved by a protease, FRET is abolished and emission is at the CFP wavelength (475 nm) [123].

In some embodiments, a $UO_2F_2$ biosensor herein described comprises two or more U-sensitive genetic molecular components and/or U-sensitive genetic circuits, wherein each of the U-sensitive genetic molecular components expresses a different reporter gene and/or a U-neutralizing gene, and/or each of the U-sensitive genetic circuits comprise a different reportable molecular component and/or U-neutralizing molecular component, in presence of bioavailable U. For example, exemplary different reportable molecular components can comprise a first genetically-encoded reporter (e.g., GFP) and a second, different genetically-encoded reporter (e.g., dsRED). In those embodiments, a Fluoride riboswitch can be integrated in two positions: 1) between the $P_{phyt}$ or $P_{1361}$ promoter and reportable molecular component 1 and/or U-neutralizing molecular component 1; and/or 2) between the UzcRS-regulated promoter and reportable molecular component 2 and/or U-neutralizing molecular component 2 to provide a U-sensitive F-sensitive genetic circuit with a single output configuration. In the addition or in the alternative, a riboswitch can be comprised in the $UO_2F_2$ biosensor in a separate F-sensing reportable genetic molecular component and/or in a separate F-sensing genetic circuit herein described in a dual output configuration.

In some embodiments, the $UO_2F_2$ biosensors described herein can comprise a UzcRS U-sensitive genetic molecular component comprising a reporter gene or a U-neutralizing gene operatively connected to a UzcRS-regulated promoter, such as $P_{ucA}$, $P_{ucB}$, and others identifiable by those skilled in the art, such as those described in Park et al., (2017) [3]. In those embodiments, the UzcRS U-sensitive genetic molecular component can be comprised in the biosensor alone or in combination with a 1363/1362 U sensitive genetic molecular component comprising a reporter gene or a U neutralizing gene operatively connected to a 1362 regulated promoter. In those embodiments, a Fluoride riboswitch can be integrated in two positions: 1) Between the $P_{phyt}$ or $P_{1361}$ promoter and reportable molecular component 1 and/or U-neutralizing molecular component; and/or 2) Between the UzcRS-regulated promoter and reportable molecular component 2 and/or U-neutralizing molecular component 2.

In the $UO_2F_2$ biosensors described herein, one or more genetic molecular components of the U-sensitive F-sensitive genetic circuits described herein can comprise genomic DNA of the proteobacterial cell and in particular of the Caulobacteridae cell. The one or more genetic molecular components can comprise native genomic DNA in the Caulobacteridae cell or can be introduced into the genome of the Caulobacteridae cell through genetic engineering, or comprised in the Caulobacteridae cell in one or more extra-genomic polynucleotides or vectors, using standard genetic engineering methods known to those skilled in the art and described herein.

In embodiments described herein, the $UO_2F_2$ biosensors—can detect uranium in a range dependent on the composition of the growth media since media components influence bioavailability. The bioavailability of both compounds will be dictated by the composition of the growth media/the chemical composition of the environmental sample In the $UO_2F_2$ biosensors herein described comprising one or more U-sensitive genetic molecular components, in the absence of bioavailable U, 1362 is not bound to the 1362 binding site of a 1362 U-sensitive genetic molecular component and/or UzcR is not bound to an m_5 site of the UczR U-sensitive genetic molecular component, and reporter gene and/or U-neutralizing gene is not expressed. In a second target range, in presence of bioavailable U, 1362 is bound to the 1362 binding site of the U-sensitive genetic molecular component and/or UzcR is not bound to an m_5 site of the U-sensitive genetic molecular component, and the reporter gene and/or U-neutralizing gene is expressed.

In the $UO_2F_2$ biosensors herein described comprising one or more F-sensitive genetic molecular components, in the absence of bioavailable F, the fluoride riboswitch will not bind F and transcription will be prematurely terminated. In the presence of bioavailable F, the fluoride riboswitch will bind F and transcription initiation will occur.

In some embodiments, a U-sensing genetic molecular component and/or U sensing genetic circuits herein described comprising UzcR binding site and a UzcRS TCS can detect Uranium in ~1 micromolar concentrations as will be understood by a skilled person upon reading of the present disclosure. In some embodiments a U-sensing genetic molecular component and/or U sensing genetic circuits herein described comprising 1362 binding site and a 1363/1362 TCS can detect Uranium at ~500 nM in aqueous conditions lacking Pi or glycerol-phosphate as will be understood by a skilled person upon reading of the present disclosure. In embodiments herein described wherein the U-sensing genetic circuit is integrated with a F-sensing riboswitch in a single output configuration and/or an F sensing molecular component or circuit in a dual output configuration, the biosensor U sensitivity is expected to be about the same and therefore can detect Uranium at ~500 nM in aqueous conditions lacking Pi or glycerol-phosphate as will be understood by a skilled person upon reading of the present disclosure In the $UO_2F_2$ biosensors herein described comprising a U-sensitive and/or F-sensitive genetic circuit comprising one or more F sensing riboswitches activated in presence of bioavailable F, one or more U-sensing genetic molecular components in which a U-sensitive promoter is activated or repressed in presence of bioavailable U, the U sensitive promoter comprising a U-sensitive transcriptional 1362 binding site and/or a UczR binding site, in a first target range of bioavailable U the endogenous proteobacteria U-sensitive transcriptional regulator is not bound to the 1362 binding site and/or the UczR binding site of the U-sensitive promoter and the U-sensitive F-sensitive genetic circuit does not comprise a reportable molecular component and/or a U-neutralizing molecular component, when the genetic circuit operates according to the circuit design. In a second target range of bioavailable U and bioavailable F, the endogenous proteobacteria U-sensitive transcriptional regulator is bound to the 1362 binding site and/or to the UzcR binding site of the U-sensitive promoter and the U-sensitive genetic circuit comprises a reportable molecular component and/or a U-neutralizing molecular component when the genetic circuit operates according to the circuit design. In those embodiments, the fluoride riboswitch will not bind F and transcription will be prematurely terminated. In the presence of bioavailable F, the fluoride riboswitch will bind F and transcription initiation will occur, resulting in activation of the reportable element and the single output of the circuit.

In some of those embodiments, a U-sensitive genetic circuit which comprises a 1362 binding site further comprises at least one genetic molecular component comprising a UzcRS-regulated promoter comprising a UzcR binding site. In these embodiments, in the second target range of bioavailable U concentration, activation or repression of the UzcRS-regulated promoter is also required as an input for the U-sensitive genetic circuit to comprise a reportable molecular component and/or a U-neutralizing molecular component when the genetic circuit operates according to the circuit design, wherein activation or repression of the U-sensitive promoter comprising the regulator direct repeat together with activation or repression of the UzcRS-regulated promoter is herein referred to as an "AND gate", wherein the term "AND" is an operation of Boolean logic.

As would be understood by persons skilled in the art, Boolean logic is a branch of algebra in which the values of the variables are the truth values 'true' and 'false', usually denoted by the digital logic terms '1' and '0' respectively. Instead of elementary algebra where the values of the variables are numbers, and the main operations are addition and multiplication, the main operations of Boolean logic are the conjunction 'AND', the disjunction 'OR', and the negation 'NOT'. As understood by those skilled in the art, it is thus a formalism for describing logical relations in the same way that ordinary algebra describes numeric relations. The term "AND gate" refers to a digital logic gate that implements logical conjunction—it behaves according to the truth table shown in Table 1. A 'true' output (1) results only if both the inputs to the AND gate are 'true' (1). If neither or only one input to the AND gate is 'true' (1), a 'false' (0) output results. Therefore, the output is always 0 except when all the inputs are 1.

TABLE 1

| 'AND gate' truth table: | | |
|---|---|---|
| Input | | Output |
| A | B | A AND B |
| 0 | 0 | 0 |
| 0 | 1 | 0 |
| 1 | 0 | 0 |
| 1 | 1 | 1 |

In particular, the term "AND gate" as used herein refers to the logical relation between two genetic molecular components in a U-sensitive genetic circuit, wherein inputs 'A' and 'B' in Table 1 are two independently activated or repressed genetic molecular components, wherein a first independently activated or repressed genetic molecular component comprises a first promoter having a U-sensitive transcriptional 1362 binding site, and a second independently activated or repressed genetic molecular component comprises a UzcRS-two-component system regulated promoter, and the output 'A AND B' in Table 1 is the reportable molecular component and/or a U-neutralizing molecular component of the U-sensitive genetic circuit.

As would be understood by those skilled in the art, any 'AND gate' genetic system can be employed in the U-sensitive genetic circuits described herein, such as those described in [124, 125].

In some embodiments, the U-sensitive genetic circuits described herein comprise U-sensing genetic molecular components whose expression is regulated independently by (1) a U-sensitive promoter comprising a 1362 binding site, such as $P_{phyt}$ or $P_{1361}$ and (2) UzcRS two-component system, and comprise an AND gate wherein 'inputs' of activation or repression of both (1) a U-sensitive promoter comprising a 1362 binding site, such as $P_{phyt}$ or $P_{1361}$ and (2) UzcRS two-component system-regulated promoter is required for the reportable molecular component 'output' and/or the U-neutralizing molecular component 'output' according to the U-sensitive genetic circuit design (FIG. 3).

In some embodiments of the U-sensitive and/or F-sensing genetic circuit, an F-sensing component and/or a U-sensing genetic molecular component, independently activated or repressed, are arranged 'in series' in the U-sensitive genetic circuit. In an 'in-series' AND gate of a U-sensitive F-sensitive genetic circuit, output of the reportable molecular component and/or the U-neutralizing molecular component according to the genetic circuit design requires two or more of the independently activated or repressed F-sensing genetic molecular component and U-sensing genetic molecular components to be activated or repressed in temporal succession, wherein the activation or repression of the F-sensing genetic molecular component precedes the activation or representation of a first independently activated or repressed U-sensing genetic molecular component which on its turn can precede the activation or repression of a second independently activated or repressed U-sensing genetic molecular component.

The term "in series" as used herein refers to a genetic circuit in which genetic molecular components are connected through biochemical reactions along a single linear circuit path. With regard to Table 1, in an 'in series' AND gate, the temporal sequence of the activation or repression of the independently activated U-sensing genetic molecular components denoted by inputs 'A' and 'B' is such that the second input 'B' is dependent on a prior activation or repression of the first input 'A' in linear succession according to the genetic circuit design.

In exemplary embodiments described herein, an in-series AND gate comprised in a U-sensitive genetic circuit comprises, a first U-sensing genetic molecular component comprising a U-sensitive promoter having a 1362 binding site, such as a $P_{1361}$ promoter or a $P_{phyt}$ promoter, and optionally further comprises a UzcRS two component system-dependent promoter, wherein expression of a uzcR and uzcS genes are under the transcriptional control of a U-sensitive promoter comprising a 1362 binding site, such as a $P_{1361}$ promoter or a $P_{phyt}$ promoter (see Example 2).

In some embodiments of the U-sensitive and/or F-sensing genetic circuits herein described, at least two independently activated or repressed U-sensing genetic molecular components are arranged 'in parallel' in the U-sensitive genetic circuit, herein referred to as an 'in parallel' AND gate. With regard to Table 1, in contrast to the 'in series' AND gate, in an 'in parallel' AND gate, the temporal sequence of inputs 'A' and 'B' is such that a second input 'B' is not dependent on a prior first input 'A' in linear succession, but rather inputs 'A' and 'B' can occur simultaneously. In other words, the term "in parallel" as used herein refers to a genetic circuit in which genetic molecular components are connected through biochemical reactions along more than one circuit path.

In an 'in parallel' AND gate system, output of the reportable molecular component and/or the U-neutralizing molecular component according to the genetic circuit design requires two or more of the independently activated or repressed F-sensing genetic molecular component and/or one or more U-sensing genetic molecular components to be activated or repressed in parallel.

In several embodiments herein described, the in-parallel AND gate comprised in a U-sensitive genetic circuit comprises at least two independently activated or repressed U-sensing genetic molecular components, each comprising a different promoter, (1) a U-sensitive promoter comprising a 1362 direct repeat binding site, such as a $P_{1361}$ or $P_{phyt}$, and (2) a UzcRS-regulated promoter, wherein promoters (1) and (2) act as independently activated or repressed parallel inputs into the U-sensitive genetic circuit, functioning as two independent points of U-sensing in response to their respective U-sensitive transcriptional regulators. In these embodiments, the reportable molecular component output and/or a U-neutralizing molecular component output of the U-sensitive F-sensitive genetic circuit is present only when both of the two independently activated or repressed F-sensing genetic molecular component and U-sensing genetic molecular component are activated or repressed according to the U-sensing genetic circuit design.

Thus, in several embodiments, a U-sensitive F-sensitive genetic circuit comprising an 'in parallel' AND gate for more than one U sensing genetic molecular component, can provide improved selectivity for U, as output of the reportable molecular component and/or the U-neutralizing molecular component is dependent on two independent points of U-sensing in response to two different U-sensitive transcriptional regulators. Persons skilled in the art will recognize that this also reduces the probability of a false positive output, in the first target range of bioavailable U concentration, such as in response to non-U stimuli (such as Zn or Cu).

Figure 6A:
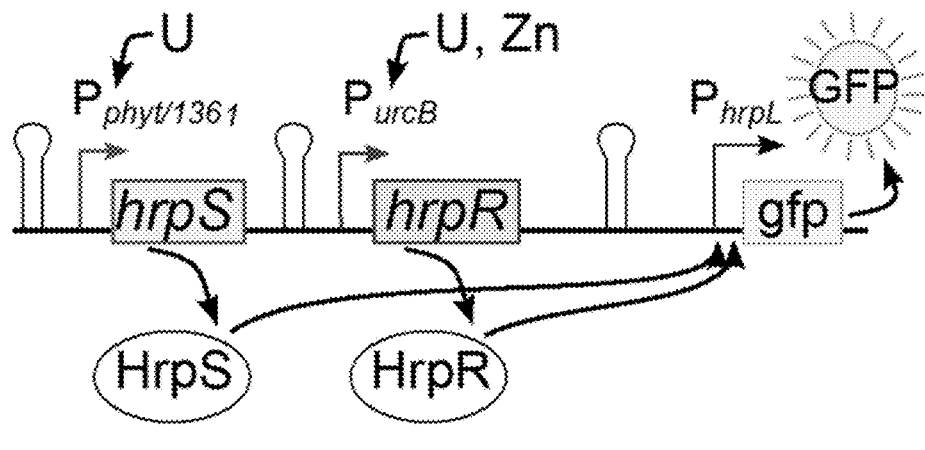
FIG. 6A and FIG. 6B show schematics of two exemplary U-sensitive genetic circuits with 'in parallel' AND gates comprising two points of U-sensing by (1) 1363/1362 two-component system (exemplified by U-sensitive transcriptional regulator direct repeat-containing promoters $P_{phyt}$ or $P_{1361}$) and (2) UzcRS two component system (exemplified by UzcRS-responsive promoter $P_{urcB}$).
Figure 6B:
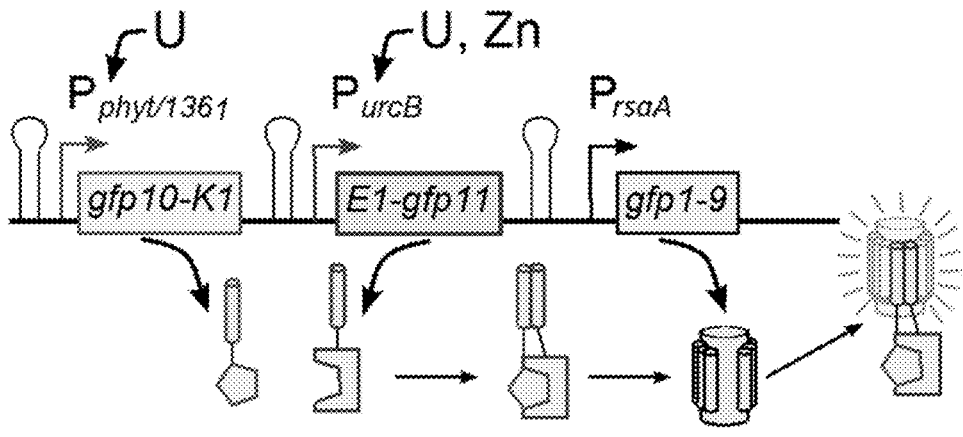
Figure 6C:
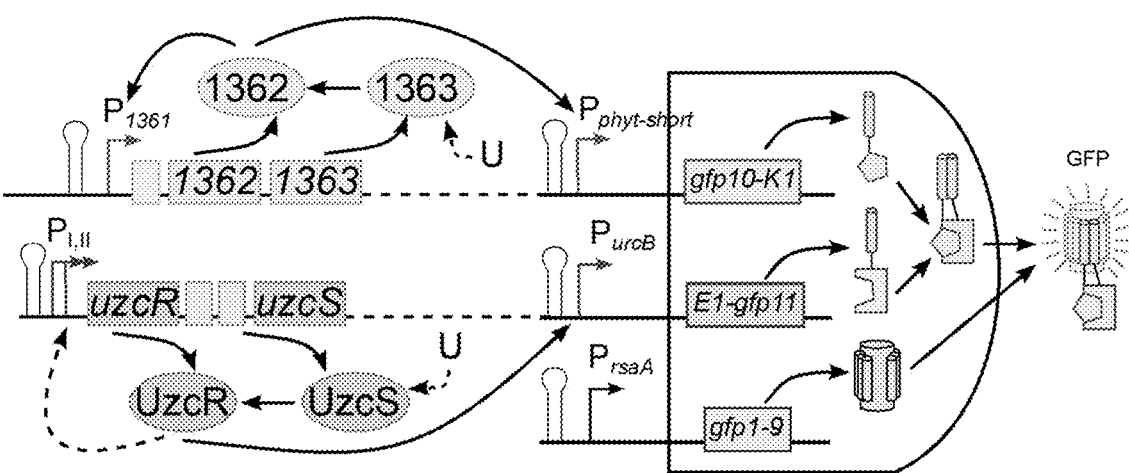
FIG. 6C shows a more detailed version of FIG. 6B, depicting how the two independent U sensing systems are integrated into the AND gate.

In some embodiments described herein, an 'in parallel' AND gate comprises an HRP AND gate. The term "HRP AND gate" as used herein refers to an AND gate system from *Pseudomonas syringae* that was developed in *E. coli* [126]. The HRP AND gate system comprises an orthogonal $\sigma^{54}$ dependent hrpR/hrpS hetero-regulation module from the hrp (hypersensitive response and pathogenicity) system for Type III secretion in Psuedomonas *syringae* [114-116], as described above. In the HRP AND gate system, both HrpS and HrpR are required for $\sigma^{54}$ dependent activation of the hrpL promoter ($P_{hrpL}$) and expression of HrpS or HrpR alone is not sufficient for transcriptional activation. In exemplary embodiments described herein, two different promoters, (1) a U-sensitive promoter comprising a 1362 binding site, such as a $P_{1361}$ or Pphyt, and (2) a UzcRS-regulated promoter, act as independently activated inputs to initiate the transcription of hrpR and hrpS, respectively, functioning as two independent points of U-sensing in response to their respective U-sensitive transcriptional regulators (FIG. 6 Panel A). In exemplary embodiments described herein, transcription of the output hrpL promoter is activated only when both proteins HrpR and HrpS bind the upstream activator sequence to remodel a closed $\sigma$54-RNAP-hrpL transcription complex to an open one through ATP hydrolysis [126]. In an exemplary HRP AND gate described herein, the output shown is GFP reporter expression (FIG. 6 Panel A).

The performance of the HRP AND gate can be described using a Hill function for the promoter steady-state input-output response (transfer function) in the form:

$$f([I]) = k\left(\alpha + [I]^{n_1}/\left(K_1^{n_1} + [I]^{n_1}\right)\right) \qquad \text{Eq. (1)}$$

where [I] is the concentration of the inducer, such as bioavailable U; $K_1$ and $n_1$ are the Hill constant and coefficient, respectively, relating to the promoter-regulator/inducer interaction; k is the maximum expression level due to induction; and a is a constant relating to the basal level of the promoter due to leakage [126] and further in the form:

$$f([R], [S]) = [G]/[G]_{max} = \qquad \text{Eq. (2)}$$
$$\left([R]/K_R\right)^{n_R}\left([S]/K_S\right)^{n_S}/\left(\left(1 + \left([R]/K_R\right)^{n_R}\right)\left(1 + \left([S]/K_S\right)^{n_S}\right)\right)$$

which describes the normalized output of the AND gate as a function of the levels of the two activator proteins ([R] for HrpR, [S] for HrpS) at steady state. $[G]_{max}$ is the maximum activity observed for the output. $K_R$, $K_S$ and $n_R$, $n_S$ are the Hill constants and coefficients for HrpR and HrpS, respectively [126].

In an exemplary HRP AND gate (see Example 3), the expression of hrpS is placed under the control of a U-sensitive promoter comprising a 1362 binding site, such as a $P_{Phyt}$ or $P_{1361}$, while hrpR is placed under the control of $P_{urcB}$, a UzcRS-dependent promoter that has lower basal activity compared to $P_{ucA}$ [3]. In Example 3, the $P_{hrpL}$ promoter regulating gfp expression requires $P_{Phyt}/P_{1361}$ and $P_{urcB}$ to be active to generate a fluorescent signal.

In some embodiments, an 'in parallel' AND gate comprises a tripartite GFP AND gate. As described herein, in the tripartite GFP AND gate system, reporter function is based on tripartite association between two twenty amino-acids long GFP tags, GFP10 and GFP11, which are fused to interacting protein partners, in addition to a complementary GFP1-9 detector. When the interacting protein partners interact, GFP10 and GFP11 self-associate with GFP1-9 to form a functional GFP [5].

In an exemplary tripartite GFP AND gate (see Example 4), expression of a gfp10-K1 fusion gene is placed under control of a U-sensitive promoter comprising a 1362 direct repeat binding site, such as a $P_{phyt}$ or $P_{1361}$, expression of a E1-gfp11 fusion gene is placed under control of a UzcRS-responsive promoter, such as $P_{urcB}$, and expression of gfp1-9 is placed under control of a non-U-responsive, strong, constitutively active promoter, $P_{rsaA}$. Thus, in Example 4, assembly and function of tripartite GFP requires both U binding and activation independently of a U-sensitive promoter comprising a 1362 binding site, such as a $P_{phyt}/P_{1361}$ and a UzcRS-responsive promoter.

In some embodiments, an 'in parallel' AND gate system comprises a bacterial two-hybrid AND gate.

In an exemplary bacterial two-hybrid AND gate (see Example 5). In some embodiments, an 'in parallel' AND gate system comprises a FRET sensor AND gate.

In some embodiments, the U-sensitive genetic circuits described herein comprise a combination of two or more 'in series' and/or 'in parallel' AND gates as described herein, wherein the two or more AND gates are connected by activating, inhibiting, binding or converting reactions.

For example, FIG. 14 shows an exemplary combination of an 'in series' AND gate and an 'in parallel' AND gate (see Example 8). In this exemplary embodiment, the exemplary 'in series' AND gate shown in FIG. 4 Panel C and the exemplary 'in parallel' tripartite GFP AND gate shown in FIG. 6 Panel B are connected, such that the $P_{phyt}$-regulated UzcR no longer activates expression of GFP regulated by $P_{1968}$ as in FIG. 4 Panel C, but rather activates expression of E1-gfp]] regulated by $P_{urcB}$ within the tripartite GFP 'in parallel' AND gate. As a result, in the exemplary combined configuration shown in FIG. 14 is that activation of $P_{urcB}$ in the 'in parallel' tripartite GFP AND gate is restricted to U-selective activation of UzcR and UzcS expression by $P_{phyt}$ in the 'in series' AND gate, whereas in the 'in parallel' tripartite GFP AND gate shown in FIG. 6 Panel B $P_{urcB}$ can be activated by U, Zn or Cu. Thus, an advantage of the combination of these exemplary AND gates is increased selectivity for U.

In particular in some embodiments, circuit contains the native uzcRS genes placed under the control of the Pphyt promoter—the chromosomal P1 and P2 promoters are swapped with Pphyt as described herein. This could be done by deleting uzcRS and using a plasmid-based system to reintroduce these genes into the circuit. In those embodiments, the circuit leverages the improved selectivity of U over Zn observed in the sensor depicted in FIG. 4 Panel C-A U/Zn ratio of 5.5.

In any one of the above embodiments a Fluoride sensing riboswitch can be included within any one of the genetic molecular components of any one of the U-sensitive genetic circuit. The fluoride riboswitch will not bind F and transcription will be prematurely terminated. In the presence of bioavailable F, the fluoride riboswitch will bind F and transcription initiation will occur, resulting in activation of the reportable element of the circuit and in providing the single output of the circuit. In the addition or in the alternative, a F sensing riboswitch can be included within a separate F-sensing reportable genetic molecular component and/or F-sensing genetic circuit. In those embodiments in the presence of bioavailable F, the fluoride riboswitch will bind F and transcription initiation will occur, resulting in activation of the separate F-sensing reportable genetic molecular component and/or the separate F-sensing genetic circuit to provide the F-sensing output of the dual output configuration of the $UO_2F_2$ biosensors herein described.

As would be understood by persons skilled in the art, in order for the $UO_2F_2$-biosensor s described herein to operate in response to bioavailable U, the U-sensitive and/or F-sensitive genetic circuits described herein comprise one or more genetic molecular components that are orthogonal to the proteobacteria cell of the $UO_2F_2$ biosensor.

In some embodiments, the circuit components of U-sensing and/or F-sensing circuit herein described are stably integrated in the host. In some embodiments, the 'in series' AND gate described herein was constructed using the native uzcR and uzcS genes. In some of these embodiments the chromosomal P1 and P2 promoters have been replaced with Pphyt.

Figure 13:
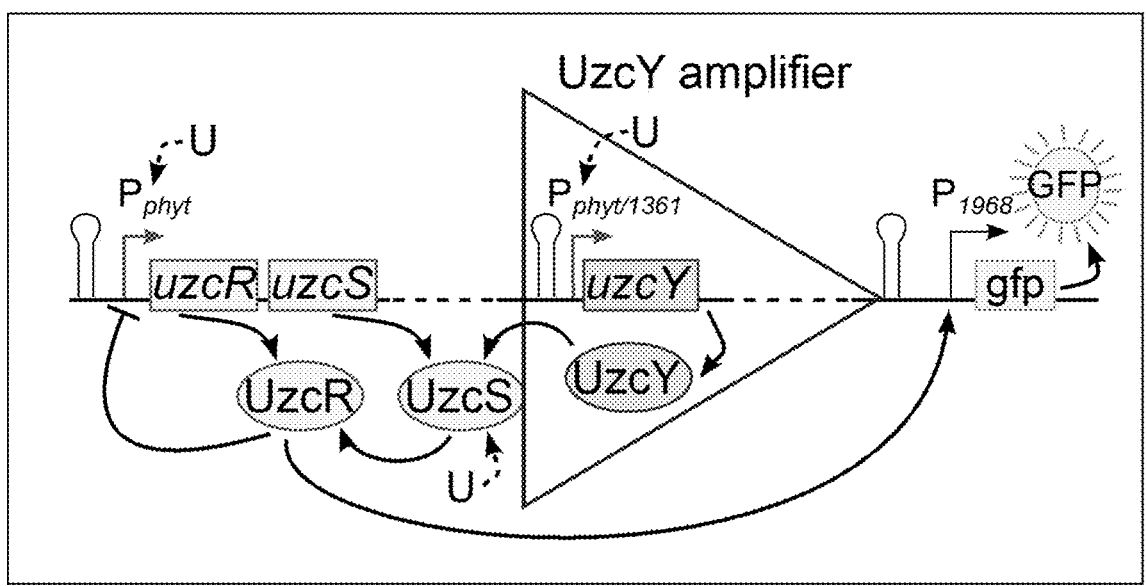
FIG. 13 shows a schematic of an exemplary signal amplifier module incorporated within a U sensing circuit. The signal amplifier uzcY is placed under the control of the U-specific promoters $P_{phyt}$/P1361 such that signal amplification is restricted to conditions of U exposure.

In some embodiments of the U-sensitive genetic molecular components and/or U-sensitive genetic circuit herein described comprising UzcR binding and a UzcRS TCS, the U-sensing genetic molecular component and/or U-sensing genetic circuit can further comprise an amplifier genetic molecular component comprising a U-sensitive promoter and/or a controllable promoter operatively connected to the UzcY and/or UzcZ in a configuration wherein the U-sensitive promoter and/or a controllable promoter directly initiates expression of the amplifier molecular component (see FIG. 13).

The term "UzcY" as used herein indicates a protein having the amino acid sequence:

```
                                   (SEQ ID NO: 33)
MTRDQDTLRMLAEVEAANADLARRAKAPLWYHPALGLLVGALIAVQGQPT

SILLVFYAAYIAGLALLVRAYKRHTGLWVSGYRAGRTRWVALGLATLTMI

GGVIAVWLLRERGLTAAPLIFGAIVAVIVTVGGFVWEAAFRADLRDGRPL
``` or a sequence that when aligned with sequence SEQ ID NO: 33 has a BLAST score has a BLAST score greater than 50 and less than 100, or preferably greater than 100 and less than 200, or more preferably a BLAST score greater than 200 and a homology with SEQ ID NO: 33 less than 100%, or even more preferably BLAST score of 289 and an homology of 100% with SEQ ID NO: 33.

The term "UzcZ" as used herein indicates a protein having the amino acid sequence:

```
                                   (SEQ ID NO: 34)
MRRGSQPMHAPISATERSTIAQIGGRNAPIGALRAFVTLLVIAHHTVLAY

TPNPPPIGDFSQAPYLWQAFPVRDPQKFELFGLLTLINDLFFMSLMFFIS

GLFVADGLRAKGNGGLLSGRAARLGVPFVLAAGLLAPLAYFPAWLQAGGD

VSIAGFASAWLDLPSWPSGPAWFLWVLLAFGAIVTLLNLIAPGVIDALGR

LVRGADRKPGLFFLGLVIASAVAYIPMSATFTFMHWTQLGPFTVQTSRVV

HYFVYFLAGVAVGAAGVGQGLTDSEGKLAKRWWAWQAAPILPVVGVIAVI

IMAFSPKPPPRVALDIGGGVMFALACATLSFAALATFLRFVKKTGPVAAS

LQANAYGMYLTHYVFTTWLAWLLLPQAWGGLAKGAAVFVGATLLSWILTM

ALRRLPLLGRIL
``` or a sequence that when aligned with sequence SEQ ID NO: 34 has a BLAST score has a BLAST score greater than 200 and less than 475, or preferably greater than 470 and less than 700, or more preferably a BLAST score greater than 700 and a homology with SEQ ID NO: 34 less than 100%, or even more preferably BLAST score of 801 and an homology of 100% with SEQ ID NO: 34.

In particular, in U-biosensors herein described comprising UzcR binding and a UzcRS TCS, the amplifier molecular component acts as a 'genetic signal amplifier' configured to increase an output, e.g. expression or levels of a reportable molecular component and/or a U-neutralizing molecular component at a given bioavailable U concentration, thus enabling more sensitive detection and reporting and/or neutralizing of bioavailable U at lower concentrations.

Genes encoding activators UzcY and UczZ herein described are herein also indicated as uzcY gene or uzcY and uczZ gene or uczZ, respectively as will be understood by a skilled person.

In particular, in some embodiments the U-sensitive genetic circuit comprises one or more amplifier genetic molecular components comprising uzcY gene CCNA_03497 encoding *Caulobacter Crescentus* N100 UzcY (SEQ ID NO: 33) and/or uzcZ gene CCNA_02291 encoding for *Caulobacter Crescentus* N100 UzcZ (SEQ ID NO: 34) under a promoter that can be either a constitutively active promoter or an inducible promoter. In preferred embodiments, the promoter is constitutively active.

In some embodiments the uzcY and/or uzcZ gene are under the transcriptional regulation of a promoter comprising a regulator direct repeat, such as exemplary promoters $P_{phyt}$ or $P_{1361}$. In an exemplary embodiment described herein, the U-sensitive genetic circuit comprises CCNA_03497 placed under the control of $P_{phyt}$ so that U exposure enhances the sensitivity of UzcRS for U (see Example 7).

In some embodiments of the U-sensitive genetic molecular components, and/or U-sensitive genetic circuit herein described comprising UzcR binding and a UzcRS TCS, the bacteria are capable of natively expressing endogenous MarR family repressors such as marR1 and/or marR2 genes.

The term "MarR1" as used herein indicates a protein of amino acid sequence:

```
                                   (SEQ ID NO: 35)
MSAALDPVIHAPNRLQMCCMLAAVDTIDFATVREALDVSESVLSKHVKTL

EEAGYVKVKKAASDGRQRTWLSLSKPGREALKGHLAALKAMMAGVPEA
``` or a sequence that when aligned with sequence SEQ ID NO: 35 has a BLAST score greater than 65 and less than 100, or preferably greater than 100 and less than 150, or more preferably a BLAST score greater than 150 and a homology with SEQ ID NO: 35 less than 100%, or even more preferably BLAST score of 199 and a homology of 100% with SEQ ID NO: 35.

The term "MarR2" as used herein indicates a protein having amino acid sequence:

```
                                   (SEQ ID NO: 36)
MAPRFDISGLDDVIHGRVRLGIVAYLASAEVADFTELKDVLEVTQGNLSI

HLRKLEEAGYVSIDKSFVGRKPLTRVRLTDTGRAAFSSYLRAMGQLVEQA

GGG
``` or a sequence that when aligned with sequence SEQ ID NO: 36 has a BLAST score has a BLAST score greater than 75 and less than 100, or preferably greater than 100 and less than 150, or more preferably a BLAST score greater than 150 and a homology with SEQ ID NO: 36 less than 100%, or even more preferably BLAST score of 206 and a homology of 100% with SEQ ID NO: 36.

Figure 12:
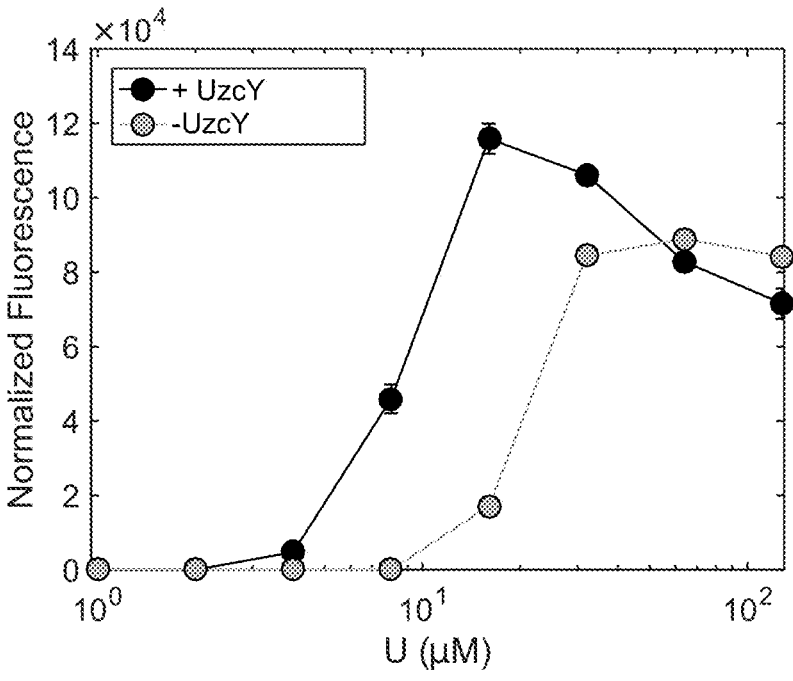
FIG. 12 shows a graph reporting data showing activity of an exemplary native signal amplifier module for UzcRS. The graph shows increase in fluorescence at various U concentrations in a CCNA_03499 mutant (+UzcY) or in wild type cells (−UzcY), relative to conditions in absence of metal. Fluorescence was normalized to cell density ($OD_{600}$).
Figure 26:
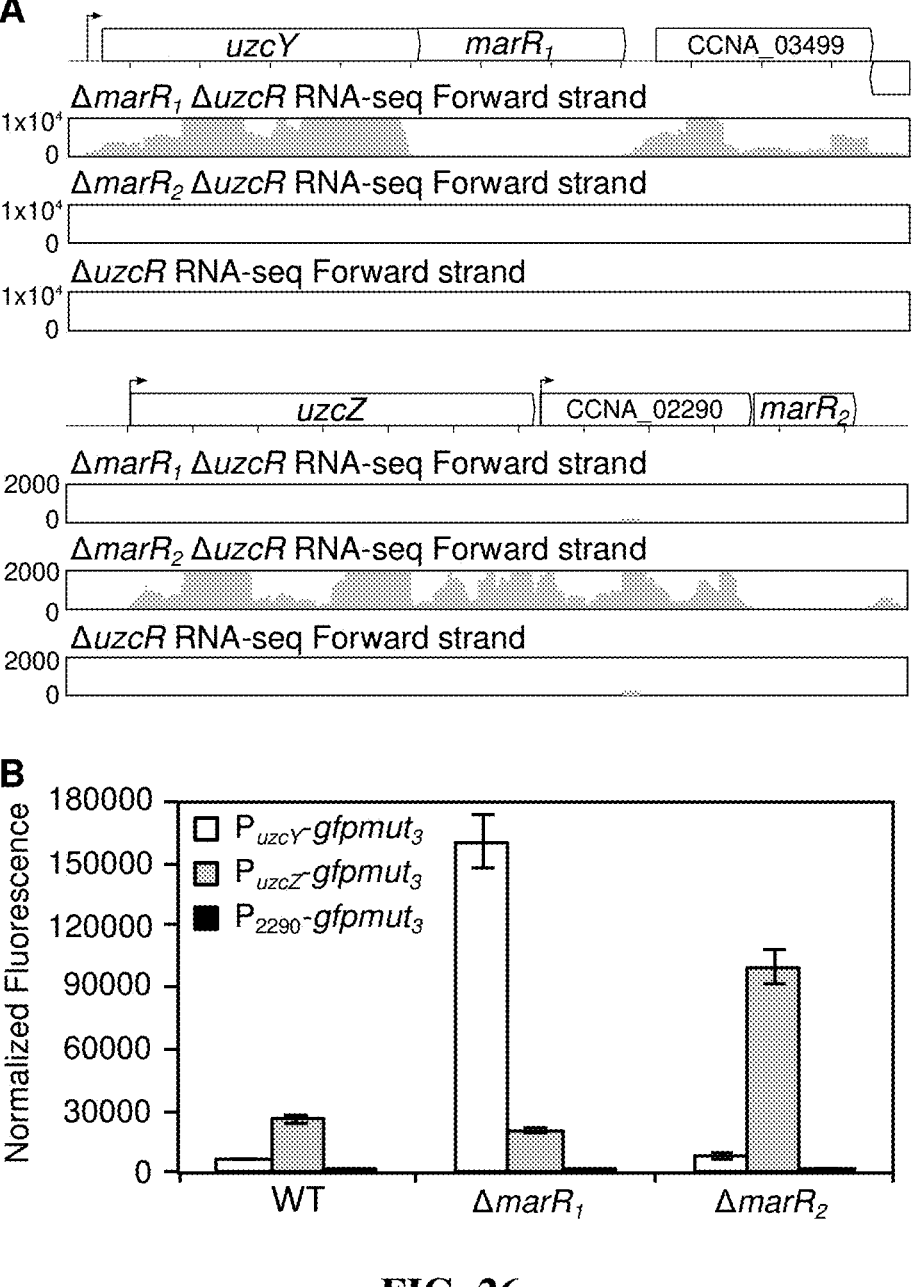
FIG. 26 shows exemplary MarR regulators repressing expression of the membrane proteins UzcY and UzcZ according to some embodiments herein described. Panel (A): Operon diagram and RNA-seq expression profile of the autoregulatory $marR_I$ (top) and $marR_2$ (bottom) operons. The RNA-seq data for a $ΔmarR_1$ ΔuzcR (top), $ΔmarR_2$ ΔuzcR (middle) and ΔuzcR (bottom) is depicted for each operon. The black arrows depict the location of the $P_{uzcY}$ and $P_{uzcZ}$ transcription start sites. Panel (B): Effect of $marR_1$ and $marR_2$ deletions on the expression of the uzcY, uzcZ and CCNA_02290 promoters. The Fluorescence of promoter-gfp fusions was quantified at mid-exponential phase and normalized to the $OD_{600}$. Error bars represent the standard deviation of biological triplicates.

In preferred embodiments, of $UO_2F_2$-biosensors herein described comprising UzcR binding and a UzcRS TCS, wherein the host is capable of natively expressing endogenous MarR family repressors such as marR1 and/or marR2 genes, at least one gene of the endogenous MarR family, preferably all genes of the endogenous MarR family, is knocked out to provide an amplified U-biosensor configured to provide an amplified signal following activation of the U-sensitive genetic circuit (see Example 7 and FIG. 12). In particular, by deleting MarR family repressor, uzcY expression is induced (see FIG. 26), thus leading to the stimulation of UzcS activity and causing a hypersensitive output in response to low metal concentration.

Genes encoding for repressors MarR1 and MarR2 herein described are herein also indicated as marR1 gene or MarR1 and marR2 gene or MarR2, respectively as will be understood by a skilled person.

In some embodiments, wherein the host is *Caulobacter crescentus* NA1000 the protein MarR1 and MarR2 are the protein encoded by marR1 gene CCNA_03498 found in *Caulobacter crescentus* NA1000 (SEQ ID NO: 35) and protein encoded by marR2 gene CCNA_02289 found in *Caulobacter crescentus* NA1000 (SEQ ID NO: 36) respectively.

In some embodiments of the U-sensitive genetic molecular components and/or U-sensitive genetic circuit herein described comprising UzcR binding and a UzcRS TCS, the bacteria are capable of natively expressing an UzcRS Regulating Transporter Atpase aminoPeptidase (herein also urtAP).

In particular, UrtAP is an ATP-binding cassette transporter (ABC transporters) comprising UrtA an ATPase and UrtP a peptidase which contains 13 transmembrane domains and a C-terminal peptidase domain.

The term "UrtA" as used herein indicates a protein encoded by a gene having a protein coding region adjacent in the genome and cotranscribed with urtP, the protein having amino acid sequence:

```
                                    (SEQ ID NO: 143)
MLIIENLTHVYGNGTRALDEVSLTIPRGMYGLLGPNGAGKSTLMRTIATL

QAPTSGHIRFGDIDVLKHPEELRKTLGYLPQDFGVYPRVSAYDMLDHMAV

LKGISGGKERKATVEHLLNQVNLWDVRKKAIAGFSGGMRQRFGIAQALIG

DPRLIIVDEPTAGLDPEERNRFLNLLAEIGENVVVILSTHIVEDVSDLCP

AMAIICNGAIVREGAPADLVAQLKGRIWKKIIDKAELEAAKARYKVISTR

LLAGRTVIHIESETDPGDGFTAVEGGLEDVYFSTLSSTRSRQAA
``` or a sequence that when aligned with sequence SEQ ID NO: 143 has a BLAST score greater than 250 and less than 500, or preferably greater than 500 and less than 599, and a homology with SEQ ID NO: 143 less than 100%, or even more preferably BLAST score of 599 and a homology of 100% with SEQ ID NO: 143. The term "urtP" as used herein indicates a protein of amino acid sequence:

```
                                    (SEQ ID NO: 144)
MFGKIAGFELRYQLKSPVFWVVAVIFFLMTFGAATIDQIRIGGGGNIHKN

APYAIAQTHLILAIFYMFVTTAFVANVVVRDDETGFGPILRSTRIRKFDY

LYGRFTGAFLAAAISFLVVPLAIFVGSFMPWVDPERLGPNDLNAYLFSYF

ALALPAILLTSAIFFALATVTRSMMWTYVGVIAFLVLYIIAGIALDRPEY

EKGAALWEPLGTAAFGLATKYWTASERNSLTPPLAGALLFNRVFVLVLAA

GFLALAYSLFRFQSAELSGQRKSAKKTKAAPTEAAPAASGPLPTPVFDRR

TAWAQLVVRTRLDMGQVFKSPAFFVLLFLGLANAMGALWFATEAGRYGGV

VYPVTRILLFPLLGSFGLIPIIIAIYYSGELVWREREKKTHEIIDATPVP

DWAFVAPKTLAISLVLISTLLISVVAAMLSQVFHGYFNFELEKYLLWYVL

PQALDFILLAVLAVFLQTISPHKFIGWALMVIYIVSTITFTNLGFEHKLY

NYGATTETPFSDMNGLGKFWMGAWWLRAYWTAFALVLLVLAYGLWRRGTE

SRLLPRLRRLPLRLNGGAGALMGVSLVAFAGLGGFIYVNTNVWNEYRTNI
```

-continued
```
DGEKWQAEYEKTLLPFENTPQPKIIAQTLDIDIQPHAPSLETKGSYVLEN

KTGAALKEIHVRFDRDLEVKGLSIEGARPKKTFEKFNYRIFAFDTPMAPG

EQRKMSFITLRAQRGFPNSGAETRVVDNGTFVNNLEIAPILGMSRDGLLT

DRAKRRKYGLPPEQRMAKLGDVSSMQFNGLRKDADFIQSDITVTTVADQT

PIAPGYKVSDSVRNGRRTARFVTEAPIMPFVSIQSARYKVAEETYKGVQL

AVYYDPQHAWNIDRMKTSMKRSLDYMGTNFSPYQFRQLRYQEFPDYAQFA

QSFANTIPWSEGMFFISDYRDPTKIDMVTYVGAHEIGHQWWAHQVIGANQ

QGGAMLSETFAQYSALMVMKHTYGEDQIRKFLKFELDSYLRARGGDVIDE

QPLYKVENQPYIYYRKGSLVMYRLQDQIGEEAVNRALRKLIADHAFKGAP

YPTTLDFMAALRAEAPADKQALITDLFEKITLYDLKTKSAAVKKRADGKF

DVTVVVEAQKKYADGKGKETVAALNETMEIGLFTAKPGDKGFVAKNVVLY

QRRPIRSGENTFTFIVDKAPTFAGIDPYNTVIDRNGDDNTVKVGG
``` or a sequence that when aligned with sequence SEQ ID NO: 144 has a BLAST score greater than 600 and less than 800, or preferably greater than 800 and less than 1200 or greater than 1000 and less than 1200, or more preferably a BLAST score greater than 1200 and less than 2000, or more preferably a BLAST score equal to or higher than 2000 or even more preferably BLAST score of 2436 and a homology of 100% with UrtP sequence from *Caulobacter crescentus* NA1000 or *Caulobacter crescentus* CB15 and in particular with SEQ ID NO: 144.

In preferred embodiments, of $UO_2F_2$-biosensors herein described comprising UzcR binding and a UzcRS TCS, wherein the host is capable of natively expressing endogenous urtAP, at least one gene of the endogenous urtAP, preferably all genes of the endogenous urtAP, is knocked out to provide an amplified U-biosensor configured to provide an amplified signal following activation of the U-sensitive genetic circuit. In particular, by deleting the endogenous urtAP, it is expected that the UzcRS TCS will be stimulated and exhibit greater uranium sensitivity.

Genes encoding for UrtA and UrtP herein described are herein also indicated as urtA gene or UrtA and urtP gene or UrtP, respectively as will be understood by a skilled person.

Detection of a host capable of expressing endogenous urtAP can be performed by detecting UrtP or urtP as urtA is more conserved as will be understood by a skilled person.

In some embodiments, wherein the host is *Caulobacter crescentus* NA1000 the protein UrtA and UrtP are the protein encoded by UrtA gene CCNA_03681 found in *Caulobacter crescentus* NA1000 (SEQ ID NO: 143) and protein encoded by UrtP gene CCNA_03680 found in *Caulobacter crescentus* NA1000 (SEQ ID NO: 144) respectively.

Additional features of the $UO_2F_2$ which are derived from whole cell biosensors in the sectors of heavy metal detection in aqueous systems [127-130], pathogen detection and eradication [131], organic pollutant detection [132], and standoff detection of landmines [133, 134] comprise genetic modification to boost sensor performance (sensitivity, detection limit, etc. [135, 136]), a microfluidic chemostat platform that maintains cell viability and sensor function for at least a week [137], optical transducer components that convert cell fluorescence into an electronic signal that is transmitted on a mobile phone network [138], and an automated water-sampling feature [138].

Additional exemplary features comprise standoff detection functions [133, 134] and couples sensor cells, which are encapsulated within a polymeric matrix and placed in proximity of a suspicious region, with a novel optical scanning system to enable remote detection at a distance of up to 50 meters in optically noisy aqueous and soil environments [133, 134].

In some embodiments herein described, a method to provide a U biosensor is provided, the method comprising genetically engineering a bacterial cell capable of natively and/or heterologously expressing a histidine kinase 1363 and/or histidine kinase UzcS, and U sensitive response regulator 1362 and/or U sensitive response regulator UzcR in combination with a heterologous F-sensing riboswitch, the genetically engineering performed by introducing into the one or more U-sensing genetic molecular components configured to report and/or neutralize U herein described, an F-sensitive riboswitch within the one or more U-sensing genetic molecular components configured to report U, an F-sensitive riboswitch within an F-sensing reportable genetic molecular component;

one or more genetic molecular components of an F sensitive genetic circuit described herein, and/or one or more genetic molecular components of the U-sensitive F-sensitive genetic circuits described herein, to provide a $UO_2F_2$-biosensor according to any one of the embodiments herein described as will be understood by a skilled person upon reading of the present disclosure, and optionally operatively connecting one or more of the U biosensors to an electronic signal transducer adapted to convert a U biosensor reportable molecular component output into an electronic output.

Polynucleotide and protein molecules as described herein can be genetically engineered using recombinant techniques known to those of ordinary skill in the art. In particular, in some embodiments, Fluoride sensing riboswitch, a promoter comprising the U-sensitive 1362 binding site and/or an UzcR binding site can be genetically engineered by introducing into a polynucleotide comprising a promoter DNA sequence a polynucleotide comprising the Fluoride sensing riboswitch, the U-sensitive 1362 binding site and/or a UzcR binding site, as described herein. In other embodiments, a Fluoride sensing riboswitch, a U-sensitive promoter comprising the 1362 binding site and/or a UzcR binding site can be genetically engineered by de novo designing a synthetic promoter DNA sequence comprising the Fluoride sensing riboswitch, the 1362 binding site and/or the UzcR binding site.

Production and manipulation of the polynucleotides described herein are within the skill in the art and can be carried out according to recombinant techniques described, for example, in Sambrook et al. 1989. *Molecular Cloning: A Laboratory Manual*, 2d ed., Cold Spring Harbor Laboratory Press, Cold Spring Harbor, N.Y. [139] and Innis et al. (eds). 1995. *PCR Strategies, Academic Press, Inc., San Diego*, [140] which are incorporated herein by reference.

It is understood that terms herein referring to nucleic acid molecules such as "polynucleotide" and "nucleotide sequence" comprise any polynucleotides such as DNA and RNA molecules and include both single-stranded and double-stranded molecules whether it is natural or synthetic in origin.

The term "polynucleotide" as used herein indicates an organic polymer composed of two or more monomers including nucleotides, or analogs thereof. The isoelectric point of a polynucleotide in the sense of the disclosure is less than 7 as will be understood by a skilled person. The term "nucleotide" refers to any of several compounds that consist of a ribose or deoxyribose sugar joined to a purine or pyrimidine base and to a phosphate group and that is the basic structural unit of nucleic acids. The term "nucleotide analog" refers respectively to a nucleotide in which one or more individual atoms have been replaced with a different atom or with a different functional group. Accordingly, the term "polynucleotide" includes nucleic acids of any length, and in particular DNA, RNA, analogs and fragments thereof. A polynucleotide of three or more nucleotides is also called "nucleotidic oligomer" or "oligonucleotide". In particular, polynucleotides in the sense of the disclosure comprise biological molecules comprising a plurality of nucleotides. Exemplary nucleic acids include deoxyribonucleic acids, ribonucleic acids, and synthetic analogues thereof, including peptide nucleic acids. Polynucleotides can typically be provided in single-stranded form or double-stranded form and in liner or circular form as will be understood by a person of ordinary skill in the art.

In some embodiments herein described, the polynucleotide is a DNA molecule that can be in a linear or circular form, and encodes one or more proteins under the control of a promoter recognizable by an enzyme such as an RNA polymerase, that is capable of transcribing the encoded DNA.

The term "protein" as used herein indicates a polypeptide with a particular secondary and tertiary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full-length proteins and peptides, as well as analogs and fragments thereof. A polypeptide of three or more amino acids is also called a protein oligomer, peptide, or oligopeptide. In particular, the terms "peptide" and "oligopeptide" usually indicate a polypeptide with less than 100 amino acid monomers. In particular, in a protein, the polypeptide provides the primary structure of the protein, wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds, and additional bonds identifiable by a skilled person. Polypeptides in the sense of the present disclosure are usually composed of a linear chain of alpha-amino acid residues covalently linked by peptide bond or a synthetic covalent linkage. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated, counting of residues in a polypeptide is performed from the N-terminal end ($NH_2$— group), which is the end where the amino group is not involved in a peptide bond to the C-terminal end (—COOH group) which is the end where a COOH group is not involved in a peptide bond. Proteins and polypeptides can be identified by x-ray crystallography, direct sequencing, immunoprecipitation, and a variety of other methods as understood by a person skilled in the art. Proteins can be provided in vitro or in vivo by several methods identifiable by a skilled person. In some instances where the proteins are synthetic proteins in at least a portion of the polymer two or more amino acid monomers and/or analogs thereof are joined through chemically-mediated condensation of an organic acid (—COOH) and an amine (—NH$_2$) to form an amide bond or a "peptide" bond.

As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—NH2) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers.

In some embodiments, the sequence of a polynucleotide encoding a genetic molecular component described herein can be homologous to the polynucleotide sequence of the genetic molecular component described herein. For purposes of the present disclosure, two polynucleotide (RNA or DNA) sequences are substantially homologous when at least 80% (preferably at least 85% and most preferably at least 90%) of the nucleotides match over the defined length of the sequence using algorithms such as CLUSTAL or PHILIP. Sequences that are substantially homologous can be identified in a polynucleotide hybridization experiment under stringent conditions as is known in the art. See, for example, Sambrook et al. [139]. Sambrook et al. describe highly stringent conditions as a hybridization temperature 5-10° C. below the T$_m$ of a perfectly matched target and probe; thus, sequences that are "substantially homologous" would hybridize under such conditions. Stringency conditions can be adjusted to screen for moderately similar fragments, such as homologous sequences from distantly related organisms, to highly similar fragments, such as genes that duplicate functional enzymes from closely related organisms. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

As used herein, "substantially similar" refers to polynucleotides wherein changes in one or more nucleotide bases can result in substitution of one or more amino acids, but do not affect the functional properties of the polypeptide or protein encoded by the nucleotide sequence. "Substantially similar" also refers to modifications of the nucleic acid fragments of the instant disclosure such as deletion or insertion of nucleotides that do not substantially affect the functional properties of the resulting polynucleotide or transcript. It is therefore understood that the disclosure encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Methods of alignment of sequences for comparison are well known in the art. Thus, the determination of percent identity between any two sequences can be accomplished using a mathematical algorithm. Non-limiting examples of such mathematical algorithms are the algorithm of Myers and Miller [141], the local homology algorithm of Smith et al. [142]; the homology alignment algorithm of Needleman and Wunsch [143]; the search-for-similarity-method of Pearson and Lipman [144]; the algorithm of Karlin and Altschul [145], modified as in Karlin and Altschul [146].

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence homology", "homology", "sequence identity" or "identity" in the context of two nucleic acid or polypeptide sequences makes reference to the nucleotides or residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage homology" "percentage of sequence identity" means the value determined by comparing two optimally aligned sequences over a comparison window, wherein the portion of the polynucleotide sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a part of a full-length cDNA or partial genomic DNA sequence, or the complete cDNA or gene sequence. A reference sequence can comprise, for example, a sequence identifiable a database such as GenBank and others known to those skilled in the art.

The term "substantial homology" or "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial homology or identity of amino acid sequences for these purposes normally means sequence identity of at least 80%, preferably at least 85%, more preferably at least 90%, and most preferably at least 95%.

The polypeptides and proteins of the disclosure can be altered in various ways including amino acid substitutions, deletions, truncations, and insertions. Novel proteins having properties of interest can be created by combining elements and fragments of proteins of the present disclosure, as well as with other proteins. Methods for such manipulations are generally known in the art. Thus, the polynucleotides described herein comprise both the naturally occurring sequences as well as genetically engineered forms. Likewise, the proteins of the disclosure encompass naturally occurring proteins as well as variations and modified forms thereof.

It is furthermore to be understood that the polynucleotides of the present disclosure comprise both synthetic molecules and molecules obtained through recombinant DNA techniques known in the art.

The bacterial cells described herein can be genetically engineered using methods known to those skilled in the art. The polynucleotides, genetic molecular components and molecular components comprised in vectors described herein can be introduced into the cells using transformation techniques such as electroporation, heat shock, and others known to those skilled in the art and described herein. In some embodiments, the U-sensitive genetic molecular components and/or genetic molecular components of the U-sensitive genetic circuits are introduced into the organism to persist as a plasmid or integrate into the genome. In some embodiments, the cells can be engineered to chromosomally integrate a polynucleotide comprising one or more U-sensitive genetic molecular components and/or genetic molecular components comprised in the U-sensitive genetic circuits described herein, using methods such as sacB counterselection procedure [147]. For example, in some embodiments described herein, the U-sensitive genetic molecular components or genetic circuit components are inserted into the *Caulobacter* chromosome (see Examples). In some exemplary embodiments, a custom designed low copy vector, such as with a pBBR1 oriV origin and a cat (chloramphenicol acetyltransferase) gene can be used for reporter expression or to introduce the signal amplifier gene (CCNA_03497) (see Examples).

In embodiments herein described, a system is provided. The system comprises a plurality of proteobacterial cells and one or more vectors comprising one or more U-sensitive genetic molecular components and/or one or more genetic molecular components of a U-sensitive genetic circuit. The one or more vectors are configured to introduce one or more U-sensitive genetic molecular components and/or one or more genetic molecular components of a U-sensitive genetic circuit into an alphaproteobacterial cell.

As understood by those skilled in the art, vectors comprising a U-sensitive genetic molecular components or genetic molecular components such as promoters or RNA- or protein-coding genes described herein or fragments thereof can be engineered using techniques such as In-Fusion cloning and other methods identifiable by those skilled in the art, to generate vectors suitable for genetically engineering the proteobacterial cells described herein. Polynucleotides encoding genetic molecular components such as promoters and genes encoding RNA and proteins described herein can be isolated from genomic DNA or cDNA comprising the polynucleotides of interest, such as polynucleotides isolated from organisms such as *Caulobacter* or other Caulobacteridae, using standard Polymerase Chain Reaction (PCR)-based methods known in the art. Plasmids comprising reporter genes and/or U-neutralizing genes described herein are commercially available from vendors such as Thermo-Fisher and Clontech, and other sources such as Addgene, among others known to those skilled in the art. Polynucleotides can also be designed and synthesized de novo, such as using gBlock synthesis (IDT Technologies) as described herein.

In embodiments herein described, a composition is provided. The composition comprises one or more $UO_2F_2$-biosensor or vectors herein described together with a suitable vehicle.

The term "vehicle" as used herein indicates any of various media acting usually as solvents, carriers, binders or diluents for the one or more U-sensitive genetic molecular components, vectors, or cells herein described that are comprised in the composition as an active ingredient. In particular, the composition including the one or more U-sensitive genetic molecular components, vectors, or cells herein described can be used in one of the methods or systems herein described.

In embodiments herein described, a system comprising an electronic signal transducer adapted to convert a $UO_2F_2$-biosensor reportable molecular component output into an electronic output is provided. The system comprises an electronic signal transducer and one or more U biosensors herein described operatively connected to the electronic signal transducer. In some embodiments, the system comprises an electronic signal transducer and one or more U biosensors herein described comprised in a composition together with a suitable vehicle.

The term "electronic signal transducer" as used herein refers to an electronic device typically comprising a bio-recognition component, a biotransducer component, and an electronic system which can comprise a signal amplifier, processor, data display, and data communicator. Transducers and electronics can be combined, such as in CMOS-based microsensor systems [148].

Figure 41:
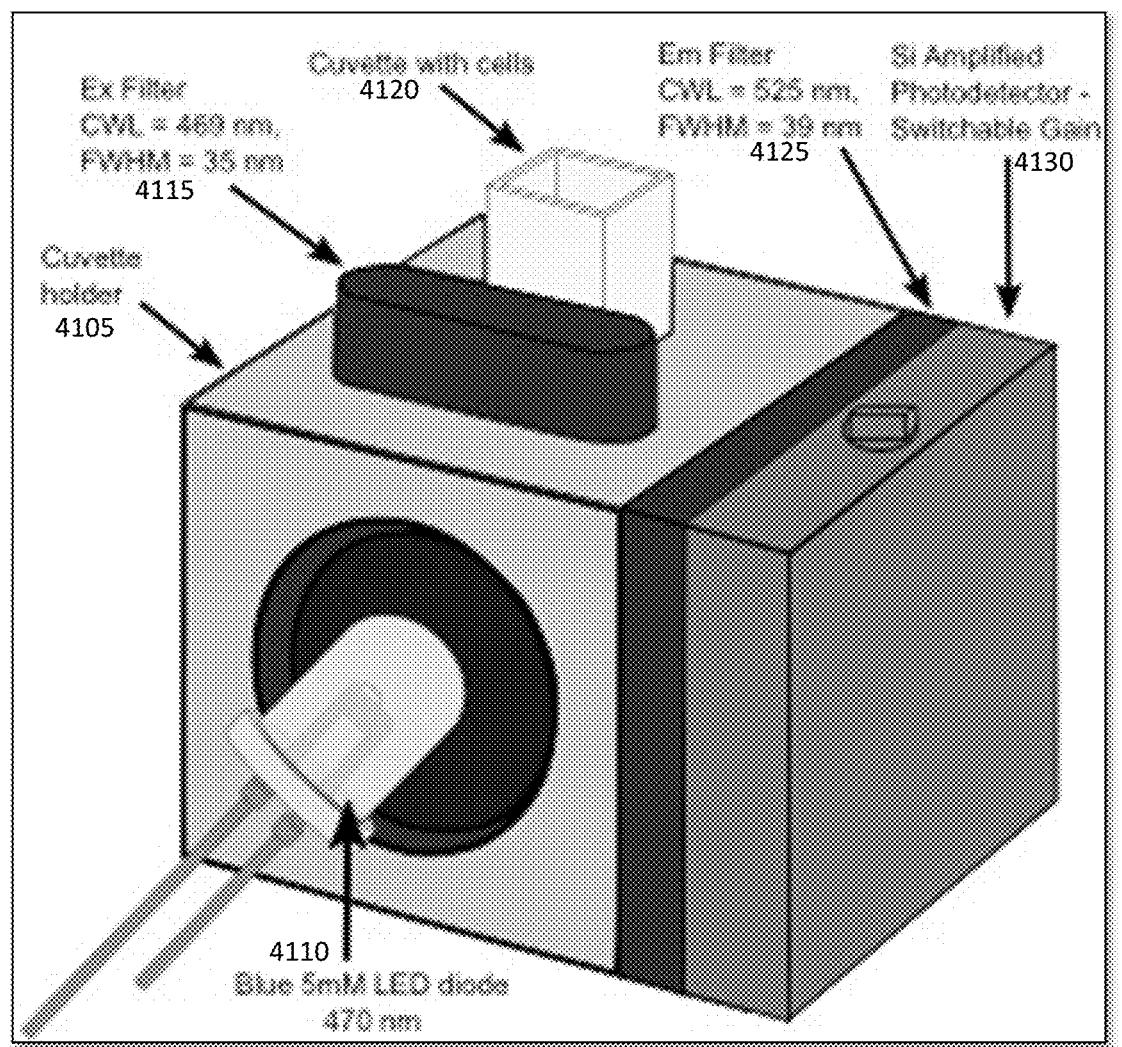
FIG. 41 shows a schematic illustration of an exemplary transducer device configured to convert an optical signal from a biosensor herein described into an electrical current using inexpensive, commercially available components (e.g., a blue LED for excitation, optical filters configured for excitation/emission of GFP, and a photodiode for detection).
Figure 42:
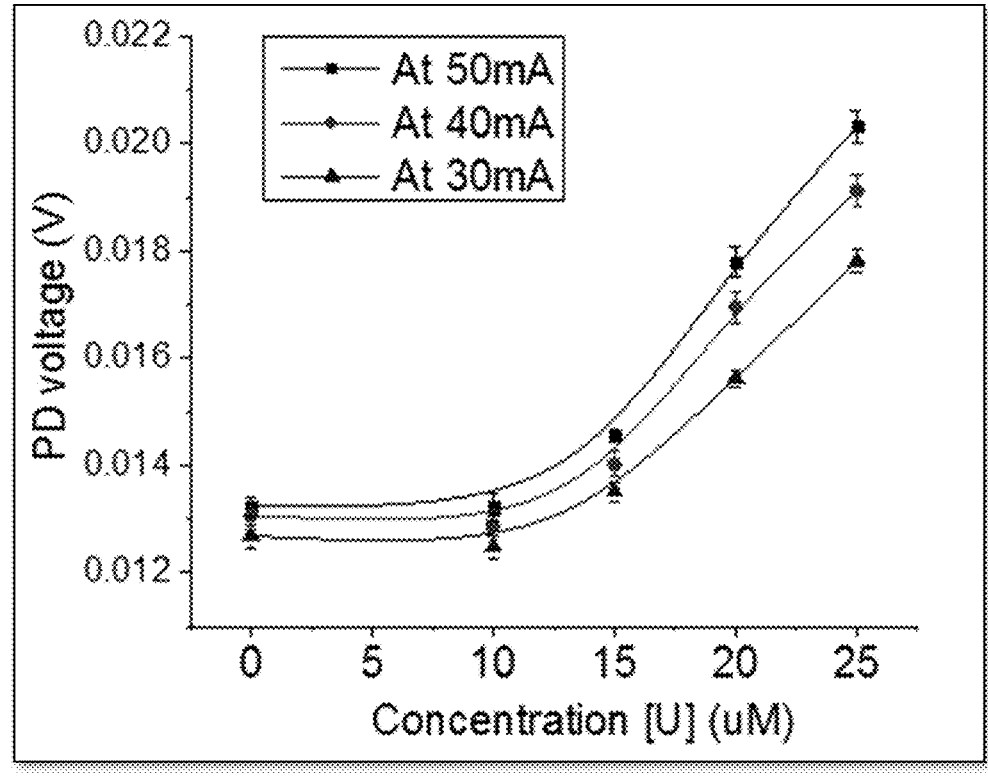
FIG. 42 shows the output voltage as a function of U concentration at three different currents using the exemplary transducer device depicted in FIG. 41. Measurements were taken two hours after uranium exposure.

As shown in FIG. 41, the transducer can be exemplarily fashioned with a blue LED (light emitting diode) (ex. 5 mM, emitting excitation light centered at 470 nm wavelength) 4110 that shines excitation light into a cuvette holder 4105. A cuvette holder is a containing device for the filters and curvette, opaque so that the only light in is from the LED and the only light striking the photodetector is the filtered emission light). The blue light passes through an excitation filter (ex filter) 4115 with a center wavelength (CWL) at 469 nm (blue) and a full width at half maximum of 35 nm (narrow bandwidth). This causes a narrow spectrum of excitation light to hit upon the sample in the cuvette 4120. The cuvette is a transparent container for the sample (cells). The emitted light (emission light) from the sample, caused by excitation from the excitation light, passes through an emission filter (em filter) 4125 that has a CWL of 525 nm and a FWHM of 39 nm (a narrow bandwidth of green light). This emission light is read by a silicon amplified photodetector 4130 (with switchable gain for sensitivity control), turning the emission light into an electrical signal for analysis. In some embodiments, the recognition component, often called a bioreceptor, can use biomolecules from organisms or receptors modeled after biological systems to interact with the reportable molecular component output comprising a target analyte of interest. This interaction is measured by the biotransducer which outputs a measurable signal proportional to the presence of the target analyte in the sample. A biotransducer is the recognition-transduction component of the device. In some embodiments, it can comprise a bio-recognition layer and a physicochemical transducer, which acting together converts a biochemical signal to an electronic or optical signal. The bio-recognition layer typically can contain an enzyme or another binding protein such as antibody. For example, polynucleotides, sub-cellular fragments such as organelles (e.g. mitochondria) and receptor carrying fragments (e.g. cell wall), single whole cells, or a plurality of cells optionally on synthetic scaffolds, can also comprise the bio-recognition layer. The physicochemical transducer is typically in contact with the recognition layer. In some embodiments, as a result of the presence and biochemical action of the target analyte of interest, a physico-chemical change is produced within the biorecognition layer that is measured by the physicochemical transducer producing a signal that is proportionate to the concentration of the analyte. The physicochemical transducer can be electrochemical, optical, electronic, gravimetric, pyroelectric or piezoelectric, as understood by those skilled in the art.

In some embodiments, a quantitative, field-portable $UO_2F_2$-biosensor system comprises one or more $UO_2F_2$-biosensors described herein coupled with an electronic signal transducer to convert the cellular output reportable molecular component signal (e.g., fluorescence) into an electronic output signal. In some embodiments, one or more $UO_2F_2$-biosensors described herein are coupled in conjunction with established, inexpensive, commercially available transducer devices known to those skilled in the art, using one of several immobilization methods such as those utilizing carbon nanotubes or nanoparticles to adhere a $UO_2F_2$-biosensor host organism cells to the transducer. In particular embodiments, wherein the $UO_2F_2$-biosensor host organism is *C. crescentus*, the holdfast organelle that facilitates irreversible adhesion to surfaces can be used to couple the cells to the electronic signal transducer, eliminating the need for exogenous immobilization substrates.

In embodiments herein described, a method of detecting and reporting and/or neutralizing bioavailable $UO_2F_2$ is provided. The method comprises:

contacting one or more $UO_2F_2$ biosensors, or a system comprising an electronic transducer operatively connected to one or more $UO_2F_2$ biosensors, with a target environment comprising one or more target ranges of bioavailable U concentration and bioavailable F for a time and under conditions to detect and report and/or neutralize bioavailable $UO_2F_2$ in the target environment.

In some embodiments, a method to detect bioavailable $UO_2F_2$ with an F-sensing and a U-sensing genetic reportable molecular component and/or with a U sensing and/or F-sensing genetic circuit genetic including a fluorescent label such as GFP is with a fluorometer to quantify GFP or other fluorophore's fluorescence. This can be accomplished with high sensitivity in the laboratory using a microplate reader or in the field using a mini-fluorometer. In some of those embodiments, the method can comprise adding an environmental sample to a 96-well plate or cuvette containing a U-biosensor herein described.

The term "target environment" as used herein indicates the aggregate of components and related conditions wherein a U biosensor can be operated.

In some embodiments, the target environment comprises a sample obtained from a field site. In some embodiments, the sample is provided by means of an operator, such as a human or a machine, to the host organism optionally operatively connected to the electronic transducer. In other embodiments, the sample is provided, in absence of an operator, to the host organism optionally operatively connected to the electronic transducer. In some embodiments, the host organism, optionally operatively connected to the electronic transducer, can be in situ in a field site comprising the target environment.

In an exemplary embodiment, wherein the host is *Caulobacter crescentus* NA1000 the biosensor is expected to work within a pH range of 6-8, temperature range of ~RT-~37 C.

Additional growth nutrients other than inorganic phosphate can be added. In some embodiments, the host can be *Caulobacter crescentus* OR37 strain isolated from the Oak Ridge Field site as an environmentally robust host: including a greater pH, heavy metal, and U tolerance with respect to *Caulobacter crescentus* NA1000.

In some embodiments, the reporting of bioavailable $UO_2F_2$ can be observed directly, such as by visualizing the output of a reportable molecular component, such as fluorescence of a reportable molecular component, e.g., GFP, wherein the expression and/or function of the reportable molecular component is activated by the $UO_2F_2$ biosensor. In some embodiments, the reporting of bioavailable $UO_2F_2$ can be observed indirectly and/or remotely, such as through transduction of reportable molecular component output into an electronic output, which can be quantified by a computer, and which can optionally be communicated to a location at a distance from the target environment by a data communicator, either through wired or wireless communication.

Therefore, in several embodiments $UO_2F_2$ biosensors herein described provide selective and sensitive detection and reporting of $UO_2F_2$ which is a bioavailable product of environmental decomposition of UF6, a toxic form of U.

In several embodiments, the $UO_2F_2$ biosensors, and related U-sensitive F-sensitive genetic molecular components, genetic circuits, compositions, methods and systems described herein provide a cost-effective, selective, sensitive, portable, easy to use, high-throughput measurement of bioavailable U, with little or no sample preparation required.

Additionally, in some embodiments $UO_2F_2$ biosensors described herein can be used in the construction of consolidated bioremediators comprising bacterial systems that possess all the necessary components for deployment in environmental cleanup efforts. Applications of the U biosensors described herein comprise uses in biodefense (e.g., to be used for non-proliferation purposes), environmental monitoring, and mining (for toxicology and safety concerns), among other uses identifiable by those skilled in the art.

EXAMPLES

The U biosensors, and related U-sensitive genetic molecular components, genetic circuits, compositions, methods and systems herein disclosed are further illustrated in the following examples, which are provided by way of illustration and are not intended to be limiting.

In particular, the following examples illustrate exemplary methods and protocols for providing and using U biosensors, and related U-sensitive genetic molecular components, genetic circuits, compositions, methods and systems. A person skilled in the art will appreciate the applicability and the necessary modifications to adapt the features described in detail in the present section, to additional U biosensors, and related U-sensitive genetic molecular components, genetic circuits, compositions, methods and systems according to embodiments of the present disclosure.

The following methods were used:

Bacterial strains, media, and materials. All strains were derived from wild type *C. crescentus* strain NA1000 (ATCC 19089) and listed in Table 2.

TABLE 2

| Strain and Plasmid Table | | |
|---|---|---|
| Strain or plasmid | Description | Source or reference |
| Strains: | | |
| NA1000 | Wild-type *C. crescentus*, a derivative of CB15 capable of being synchronized | [149] |
| JOE2321 | *C. crescentus* CB15N ΔCC_1634 | [150] |
| DMP912 | NA1000 ΔCCNA_01362 (urpR) | Present Disclosure |
| DMP913 | NA1000 ΔCCNA_01363 (urpS) | Present Disclosure |
| DMP470 | JOE2321 P$_{phyt}$-lacZ | Present Disclosure |
| DMP899 | DMP470 CCNA_01362::tn5 (1478156) | Present Disclosure |
| DMP898 | DMP470 CCNA_01362::tn5 (1478165) | Present Disclosure |
| DMP900 | DMP470 CCNA_01362::tn5 (1479640) | Present Disclosure |
| DMP901 | DMP470 CCNA_01362::tn5 (1479738) | Present Disclosure |
| DMP791 | P$_{phyt}$-gfp10_m2_K1, P$_{urcB}$-E1_gfp11_m4, P$_{rsaA}$-gfp1-9 | Present Disclosure |
| | NA1000 ΔuzcR | [151] |
| DMP213 | NA1000 ΔuzcS | [3] |
| DMP683 | NA1000 P$_{phyt}$-gfp10_m2_K1, P$_{urcB}$_E1_gfp11_m4, P$_{xyl}$-gfp1-9 | Present Disclosure |
| DMP804 | NA1000 P$_{phyt}$-gfp10_m2_K1, P$_{urcB}$_E1_gfp11_m4, P$_{rsaA}$-gfp1-9 | Present Disclosure |
| DMP895 | NA1000 P$_{phyt-short}$-gfp10_m2_K1, P$_{urcB}$-E1_gfp11_m4, P$_{rsaA}$-gfp1-9 | Present Disclosure |
| DMP877 | NA1000 P$_{phyt}$-gfp10_m2_K1, P$_{urcB}$_E1_gfp11_m4, P$_{phyt\ short}$-gfp1-9 | Present Disclosure |
| DMP911 | NA1000 P$_{urcB}$-gfp10_m2_K1, P$_{urcB}$_E1_gfp11_m4, P$_{rsaA}$-gfp1-9 | Present Disclosure |
| DMP994 | NA1000 P$_{phyt}$-gfp10_m2_K1, P$_{1361}$-E1_gfp11_m4, P$_{rsaA}$-gfp1-9 | Present Disclosure |
| DMP863 | NA1000 ΔCCNA_03498-3499 | Present Disclosure |
| DMP993 | DMP863 P$_{phyt-short}$-gfp10_m2_K1, P$_{urcB}$-E1_gfp11_m4, P$_{rsaA}$-gfp1-9 | Present Disclosure |
| DMP1009 | DMP863 P$_{phyt-short}$-CCNA_03497, P$_{phyt-short}$-gfp10_m2_K1, P$_{urcB}$-E1_gfp11_m4, P$_{rsaA}$-gfp1-9 | Present Disclosure |
| DMP1011 | NA1000 ΔuzcR P$_{phyt-short}$-gfp10_m2_K1, P$_{urcB}$_E1_gfp11_m4, P$_{rsaA}$-gfp1-9 | Present Disclosure |
| DMP910 | NA1000 P$_{phyt}$-DR1 GTCA->CAGT-gfp10_m2_K1, P$_{urcB}$-E1_gfp11_m4, P$_{rsaA}$-gfp1-9 | Present Disclosure |
| Plasmids: | | |
| VMCS2::Tn5Pvan | Contains the transposon Tn5Pvan | [152] |
| pNPTS138 | Non-replicating vector for integration and allelic replacement; oriT, kan (Km$^R$), sacB | M. R. K. Alley, unpublished |
| pDMP450 | Cat gene from pR9TT and pBBR ori and rep from pPROBE'-gfp[LVA], P$_{mrC}$-gfp mut$_3$ | Unpublished |
| pDMP460 | P$_{phyt}$-gfp mut$_3$ | Present Disclosure |
| pDMP463 | P$_{1361}$-gfp mut$_3$ | Present Disclosure |
| pDMP745 | P$_{phyt}$-DR2 GTCA->CAGT- gfpmut$_3$ | Present Disclosure |
| pDMP746 | P$_{phy-short}$-gfpmut$_3$ | Present Disclosure |
| pDMP747 | P$_{1361}$- DR2 GTCA->CAGT-gfpmut$_3$ | Present Disclosure |
| pDMP786 | P$_{phyt}$ -DR1 GT->CA-gfpmut$_3$ | Present Disclosure |
| pDMP787 | P$_{phyt}$ -DR2 GT->CA-gfpmut$_3$ | Present Disclosure |
| pDMP788 | P$_{1361}$-DR2 GT->CA-gfpmut$_3$ | Present Disclosure |
| pDMP789 | P$_{1361-short}$-gfpmut$_3$ | Present Disclosure |
| pDMP1118 | pET52b-urpR | Present Disclosure |
| DMP791 | Pphyt-gfp10_m2_K1, PurcB_E1_gfp11_m4, PrsaA-glp1-9 | Present Disclosure |
| pDMP82 | pNPTS138 P$_{urcA}$-lacZ | [3] |
| pDMP82 | pNPTS138 P$_{urcA}$-lacZ | [3] |
| pDMP792 | pNPTS138-P$_{phyt}$-gfp10_m2_K1, P$_{urcB}$-E1_gfp11_m4, P$_{rsaA}$-gfp1-9 | Present Disclosure |
| pDMP883 | pNPTS138-P$_{phyt-short}$-gfp10_m2_K1, P$_{urcB}$-E1_gfp11_m4, P$_{rsaA}$-gfp1-9 | Present Disclosure |
| pDMP664 | pNPTS138-P$_{phyt}$-gfp10_m2_K1, P$_{urcB}$_E1_gfp11_m4, P$_{xyl}$-gfp1-9 | Present Disclosure |
| pDMP712 | P$_{phyt}$-gfp10_m2_K1, P$_{urcB}$_E1_gfp11_m4, P$_{xyl}$-gfp1-9 | Present Disclosure |
| pDMP932 | pNPTS138-P$_{urcB}$-gfp10_m2_K1, P$_{urcB}$-E1_gfp11_m4, P$_{rsaA}$-gfp1-9 | Present Disclosure |
| pDMP952 | pNPTS138-P$_{phyt}$-gfp10_m2_K1, P$_{1362}$-E1_gfp11_m4, P$_{rsaA}$-gfp1-9 | Present Disclosure |
| pDMP808 | pNPTS138-P$_{phyt}$-gfp10_m2_K1, P$_{phyt}$-E1_gfp11_m4, P$_{phyt-short}$-gfp1-9 | Present Disclosure |
| pDMP1113 | pNPTS138-P$_{phyt}$-CCNA_03497 | Unpublished |
| pDMP1114 | pNPTS138-P$_{phyt-short}$-CCNA_03497 | Present Disclosure |

Cell growth and fluorescence characterization experiments were performed in modified M5G medium (10 mM PIPES, pH 7, 1 mM NaCl, 1 mM KCl, 0.05% NH$_4$Cl, 0.01 mM Fe/EDTA, 0.2% glucose, 0.5 mM MgSO$_4$, 0.5 mM CaCl$_2$)) supplemented with 5 mM glycerol-2-phosphate as the phosphate source (M5G-G2P) to facilitate uranium solubility at the start of growth assays. U stocks were prepared in nitric acid as previously described [153]. A 10,000 ppm ThCl$_4$ stock was prepared in 5% nitric acid. 50-100 mM stock solutions of Pb(NO$_3$)$_2$, NiSO$_4$, ZnCl$_2$, CuSO$_4$, CaCl$_2$), MnCl$_2$, MgSO$_4$, K$_2$CrO$_4$, Na$_2$SeO$_3$, FeCl$_3$, CoCl$_2$, FeSO$_4$, NaAsO$_2$ were prepared in Milli-Q H$_2$O and a 1 g l$^{-1}$ AlCl$_3$ ICP-MS standard in HCl was used for Al addition. All strains were grown at 30° C. with shaking at 220 RPM in Erlenmeyer flasks or at 1000 RPM in 96-well plates in a PHMP-4 Thermoshaker (Grant Instruments). Strain manipulation was performed in PYE medium, containing 0.2% (wt/vol) Bacto peptone (Difco), 0.1% yeast extract (Difco), 1 mM MgSO$_4$, and 0.5 mM CaCl$_2$) and appropriate antibiotics. *Escherichia coli* HST08 (Clontech) was used for cloning following standard procedures.

Clean deletions and site-directed mutagenesis. In frame deletions of CCNA_01362 and CCNA_01363 were obtained by a two-step sacB counterselection procedure [154] as described previously[3] using the primers depicted in Table 3.

TABLE 3

Primers and qblocks

| Primer name | Primer sequence | SEQ ID NO |
|---|---|---|
| Phyt-138_F | TAACCCTTTGCAAACCGGACGGTGACCGGCAAAC | 145 |
| Phyt-138_R | GATGAACTTGCGCATGGCGGAGCCCCTCGTTTTc | 146 |
| 138_PurcA_F | ATGCGCAAGTTCATCATGAGCC | 147 |
| 138_PurcA_R | GTTTGCAAAGGGTTAATCGACGCC | 148 |
| pNTPS138_urcR_F | gGAACGATAGCGCCGGACGGTGACCGGCAAAC | 149 |
| pNTPS138_urcR_R | CGCACAAAATCCTCATCCTGAGC | 150 |
| BamHI_Pphyt_F | GACGGATCCCGGACGGTGACCGGCAAAC | 151 |
| EcoRI_Pphyt_R | GACGAATTCCCTCGTTTTcatGTCTCGCAGCTAGC | 152 |
| BamHI_P1362 | GACGGATCCAACGATAGCGCCGCCTGC | 153 |
| EcoRI_P1362 | GACGAATTCGGAAAGATCGGGACTGGGTGATGGCGCTTAGGATTCCACAG | 154 |
| Pphyt_EMSA_R | CGTTTTcatGTCTCGCAGCTAGC | 155 |
| 1362_gene_F | CTCTTTCAGGGACCCTTGATGCGCGCGCTCGTC | 156 |
| 1362_gene_R_GC | CACCAGAGCGAGCTCTCACGCCGTCCCGCCGGC | 157 |
| pET52_F | GAGCTCGCTCTGGTGCCAC | 158 |
| pET52_R | GGGTCCCTGAAAGAGGACTTCAAG | 159 |
| urcR_UR_F | caattgaagccggctCAGAAGGTCGACGCCCTGG | 160 |
| urcR_UR_R | CGCACAAAATCCTCATCCTGAGC | 161 |
| Pphyt_urcR-loc_F | gGAACGATAGCGCCGGACGGTGACCGGCAAAC | 162 |
| Pphyt_urcR-loc_R | AATCAGAATGCGcatGGCGGAGCCCCTCG | 163 |
| Pphyt-uzcR_vect_F | atgCGCATTCTGATTATCGAGGACG | 164 |
| Pphyt-uzcR_vect_R | CGGCGCTATCGTTCcctagg | 165 |
| Pphyt_rsaFb_F | GTGAAAAAAGCTTAACTCGAGGGGCTCCGCCatgC | 166 |
| Pphyt_rsaFb_R | TTAAGCTTTTTTCACGCAGTCTCGCAGCTAGCTTAGCCG | 167 |
| P1362_rsaFb_F | GTGAAAAAAGCTTAACTCCGAGCTCCCTAACTAACTAAtcATCT | 168 |
| P1362_rsaFb_R | TTAAGCTTTTTTCACGCAGTGATGGCGCTTAGGATTCCACAG | 169 |
| gfp19_amp_for_pxyl_F | tggggagacgaccaTATGCGTAAGGGCGAAGAGCTG | 170 |
| gfp19_amp_for_pxyl_R | cacggctggctgcagGCCGAATTTCAGGGGTACAGCA | 171 |
| Pphyt_TR_elim_F | GATCCCGGGGATTTCTCTTCGCGCCACC | 172 |
| Pphyt_promoter_shorten_R | GAAATCCCCGGGATCCCTGTGCTCTAGA | 173 |
| XbaI_PurcB | GACTCTAGACGAAGACTGGGCGGGCAG | 174 |
| BglII_PurcB_R | GACAGATCTCGGTTTGGGTGGTCGCTTGG | 175 |
| PrsaA_frag_F | Ttgtcgacgtatgacgtttgctctatagc | 176 |
| PrsaA_frag_R | CGTTCACATCGCCATCCAGCTC | 177 |
| gfp_for_PrsaA_F | ATGGCGATGTGAACGGCCATAAG | 178 |
| gfp_for_PrsaA_R | gtcatacgtcgacaaGCCGAATTTCAGGGGTACAGCA | 179 |
| Pphyt_SD_amp_R | ATGTTTTTCCTCCTTATAAAGTAGATCTTTAGTTAGTTAGGG | 180 |
| gfp1-9_for_pphyt-short_F | AAGGAGGAAAAACATATGCGTAAGGGCGAAGAGCTG | 181 |

TABLE 3-continued

Primers and qblocks

| Primer name | Primer sequence | SEQ ID NO |
|---|---|---|
| gfp1-9_for_phyt_R | GAAATCCCCGGGATCGCCGAATTTCAGGGGTACAGCA | 72 |
| urcA_loc_DR_F | GGTCGCTACCATTACCAGTTGGTC | 182 |
| urcA_loc_UR_R | TGCTTGGGTCGTTTGAGTATATGGT | 183 |
| HRP_chrom_int_F | CAAACGACCCAAGCAGGTGTCGCCCTTCGCTGAAC | 184 |
| HRP_chrom_int_R | GTAATGGTAGCGACCCCAAGCTCAGCTAATTAAGCCTCGAG | 185 |
| PurcA_UR_F | ggctggcgccaagctTGGCCGGCCGCACGCAAGGGCAGA | 186 |
| PurcA_UR_R | TTATTTTTGACACCAGACCAACTGG | 187 |
| PurcA_DR_F | TGGTGTCAAAAATAATCGCACAGGCGACCGC | 188 |
| PurcA_DR_R | gcgaattcgtggatcCAGGCGTCGAGGTGAAGTA | 189 |
| kan_elim_F | ATTCTTCCTTTTTCAATATTATTGAAGCATTTATCAG | 190 |
| kan_elim_R | AAGCTTAATAAGATGATCTTCTTGAGATCG | 191 |
| KpnI_P1362 | GACggtaccGAACGATAGCGCCGCCTGC | 192 |
| AvrII_P1362 | GACcctaggGGAAAGATCGGGACTGGGTGATGGCGCTTAGGATTCCACAG | 193 |
| 3497_for_Pphyt_plas_F | GGAAGATCTACTTTATAAGGAGGAAAAACATATGACCCGAGACCAAGACAC | 194 |
| 3497_for_Pphyt_plas_R | GACCTCGAGTCATAGGGGGCGTCC | 195 |
| 3497_for_Pphyt_short_chrome_R | TCATAGGGGGCGTCCGTCG | 196 |
| Pphyt_short_for_chrom_3497 | GGGATTTCTCTTCGCGCCACC | 197 |
| Chrome_3497_vect_amp_F | GGACGCCCCCTatgAGCG | 198 |
| chrome_vector_amp_R | GCGAAGAGAAATCCCATCATCGCCAGCCCTAGCG | 199 |
| Tripartite GFP gblock* | CAGAGATCTACTTTATAAGGAGGAAAAACATATGGA TCTGCCCGACGATCATTACCTGTCCACCCAGACCATC CTGTCGAAGGATCTGAATGGCACCGACGTGGGCTCC GGTGGCGGGAGTGGTGGTGGCGGGAGCAAGGTCTC CGCCCTCAAGGAGAACGTTAGCGCCCTGAAAGAGA AAGTCTCGGCCCTGACCGAAAAGGTCTCCGCCCTTA AGGAAAAGGTGAGCGCTCTCAAAGAGTAAccaggcatca aataaaacgaaaggctcagtcgaaagactgggcctttcgtttttatctgttgtttgtcggtg aacgctctctactagagtcacactggctcaccttcgggtgggcctttctgcgtttataggt accCGAAGACTGGGCGGGCAGCAGCCCACTCCCAAGC GCCCACCAATTATGACTTCTTTTTCATAGACTTAATT CGACGTCATGAAGCAGTCGTAACGGGTGTTCGCCAT CCGACCGCTCTACATCCTCGATCAACGGATCGCCAA GCGACCACCCAAACCGcctaggtaactaaagattaactttataaggagg aaaaacatATGAAGGTCTCCGCCCTTGAAAATGAGGTCT CGGCTCTCGAAAAGGAGGTGTCGGTCCTGGAGAAAG AAGTCAGCGCGCTTGAGAAGGAGGTCCGTGCCCTGG AGAAGAGTGGCGGTGGGGGGTCTGGGGGCGGTTCT GGGGGCGGCTCCACCTCGGAGAAGCGTGACCACATG GTGCTGCTCGAATATGTCACCGCCGCCGGGATCACC GATGCCTCCTAAgactcctgttgatagatccagtaatgacctcagaactccat ctggatttgttcagaacgctcggttgccgccgggcgtttttttattggtgagaatGAAA AATGCTGTACCCCTGAAATTCGGCTAttgtcgacgtatgacgtt tgctctatagccatcgctgctcccatgcgcgccactcggtcgcaggggtgtgggatt ttttgggagACAATCCTCATGCGTAAGGGCGAAGAGCTG TTCACGGGCGTCGTCCCCATCCTCATCGAGCTGGAT GGCGATGTGAACGGCCATAAGTTCTTCGTCCGTGGG GAAGGCGAGGGGGATGCCACCATCGGCAAGCTGAG CCTCAAGTTCATCTGCACCACCGGCAAGCTCCCGGT CCCCTGGCCGACGCTCGTCACGACCCTCACCTACGG GGTGCAGTGCTTTTCCCGTTACCCCGACCACATGAA GCGGCACGACTTCTTTAAGTCGGCCATGCCCGAAGG CTACGTGCAGGAGCGCACCATCTCTATTTTAAGGACGA TGGCACGTATAAGACCCGCGCGGAGGTCAAGTTCGA AGGGGATACCCTGGTCAACCGTATCGAGCTGAAGGG | 200 |

TABLE 3-continued

Primers and gblocks

| Primer name | Primer sequence | SEQ ID NO |
|---|---|---|
| | CATCGACTTTAAGGAAGATGGCAACATCCTCGGGCA | |
| | CAAGCTCGAATATAATTTTAACTCCCATAAGGTCTA | |
| | CATCACCGCCGACAAGCAAAACAACGGCATCAAGG | |
| | CGAACTTTACGATCCGTCACAATGTGGAGGACGGCA | |
| | GCGTCCAGCTCGCGGATCATTATCAACAGAATACCC | |
| | CCATCGGCGATGGTCCCGTCCTCCTCCCGTAGCTCGA | |
| | GATT | |

**Synthesized (Integrated DNA Technologies, gBlock) with the following components listed in 5' to 3' orientation: promoterless gfp10-m2_k1 (bolded), rrnBT1 and T7Te transcription terminators (BBa_B0015; (lowercase)), $P_{urcB}$ (uppercase)-untraslated region and RBS (lowercase) E1-gfp11-M4 (bolded), lamda $T_0$ terminator (lowercase), the rsaA promoter ($P_{rsaA}$[4]; lowercase) controlling expression of gfp1-9 (bolded). This DNA region is visually depicted in FIG. 31.

Site-directed mutagenesis was performed by amplifying the entire plasmid with the primer sets listed in Table 3. Chromosomal integration and counter selection were performed as described above, and successful substitutions were confirmed by sequencing.

Transposon screen for regulators of $P_{phyt}$. A chromosomally integrated $P_{phyt}$-laCZ fusion was constructed using the two-step sacB counterselection procedure[147] to swap the $P_{urcA}$promoter in pDMP82[3] with $P_{phyt}$. To accomplish this, a $P_{phyt}$ fragment was amplified from the *C. crescentus* genome with the primer pair Phyt-138_F/Phyt-138_R (Table 3) and cloned into pDMP82 that was linearized using the primers 138_PurcA_F and 138_PurcA_F using In-Fusion cloning. The $P_{phyt}$-lacZ fusion was integrated at the chromosomal urcA locus in lacA mutant strain JOE2321, yielding strain DMP470. For the transposon screen, DMP470 was electroporated with VMCS2::Tn5Pvan[152] and plated onto PYE agar plates containing 25 µg ml$^{-1}$ kanamycin. ~12,000 colonies were scraped into a PYE master solution that was frozen and stored at −80° C. The Transposon library was diluted and spread on M5G-G2P agar containing 40 µg ml$^{-1}$ Xgal and 25 µM uranyl nitrate, yielding a total of ~36,000 colonies. Colonies exhibiting a white colony phenotype were selected and nested semi-arbitrary PCR was used to map the location of each transposon as described previously. [152]

Construction of promoter-gfp transcriptional fusions. Plasmid-borne $P_{phyt}$-gfp and $P_{1361}$-gfp fusions were generated by amplifying $P_{phyt}$ and $P_{1361}$ fragments from the *Caulobacter* genome with the primer pairs BamHI_Pphyt_F/EcoRI_Pphyt_R and BamHI_P1362/EcoRI_P1362, respectively, digested with BamHI and EcoRI and cloned into the similarly digested pDMP450, generating pDMP460 and pDMP463. The promoter-gfp fusions were shortened and/or mutated by amplifying pDMP460 and pDMP463 with the primer pairs described in Table 3 and re-ligating using infusion cloning.

Tripartite GFP AND gate sensor construction. A gblock (Tripartite GFP gblock; Table 6) was synthesized (Integrated DNA Technologies, gBlock) with the following components listed in 5' to 3' orientation: promoterless gfp10-m2_k1, rrnBT1 and T7Te transcription terminators (BBa_B0015), $P_{urcB}$-E1-gfp11-M4, lamda $T_0$ terminator, and gfp1-9 under the control of the rsaA promoter ($P_{rsaA}$[4]). gfp10-m2_k1 was placed under the control of $P_{phyt}$ by digesting the Tripartite GFP gblock with BglII and XhoI and ligating into the similarly digested pDMP460 to form pDMP791. DNA sequence encompassing the entire tripartite DNA and an insulating upstream rrnbT1 transcription terminator was amplified with primers HRP_chrome_int F and HRP_chrome_int R and cloned into pDMP82 that was amplified with the primers urcA_loc_DR_F and urcA-loc_UR_R using infusion cloning to form pDMP792. A variant containing GFP10-m2_k1 under the control of a shortened version of $P_{phyt}$ (i.e., the core sensor) was constructed by amplifying pDMP792 with Pphyt_TR_elim_F and Pphyt_promoter_shorten_R and re-ligating using infusion cloning, forming pDMP883. A variant of this AND gate containing gfp1-9 under the control of the xylose inducible promoter (Pxyl [6]) was constructed by amplifying the 360 bp $P_{xyl}$ fragment using Pxyl_F and Pxyl_R and cloning into pDMP792 that were amplified with gfp1-9_amp_for_pxyl_F gfp1-9_amp_for_pxyl_R using infusion cloning to form pDMP664. All tripartite GFP AND gate variants were then integrated into the chromosomal urcA locus using a two-step sacB counterselection procedure,[155] forming DMP804, DMP895, and DMP683

A control tripartite variant containing both GFP10-m2_k1 and E1-GFP11-M4 under the control of $P_{urcB}$ was constructed by directionally cloning a $P_{urcB}$ fragment, generated with primers XbaI_PurcB and BglII_PurcB_R and digested with XbaI and BglII, into the similarly digested pDMP712. Similarly, a tripartite variant containing both GFP10-m2_k1 and E1-GFP11-M4 under the control of UrtAP was constructed by directionally cloning a $P_{1362}$ fragment, generated with primers KpnI_P1362 and AvrII_P1362 and digested with KpnI and AvrII, into the similarly digested pDMP712. Both control AND gates were cloned into the pNPTS138 double recombination plasmid by amplifying with primers HRP_chrome_int F and R and cloning into pDMP82 that was amplified with the primers urcA_loc_DR_F and urcA-loc_UR_R using Infusion cloning. Finally, the $P_{xyl}$ promoter in both constructs was swapped for $P_{rsaA}$ by cloning $P_{rsaA}$, amplified with PrsaA_frag_F and PrsaA_frag_R, into the template vectors that were linearized with the primers gfp_for_PrsaA_F and gfp_for_PrsaA_R, forming pDMP932 and pDMP952. These tripartite GFP AND gate variants were then integrated into the chromosomal urcA locus using a two-step sacB counterselection procedure,[155] to form DMP911 and DMP994.

A U sensing AND gate strain (DMP993) with constitutive UzcY expression was generated by integrating the core sensor (pDMP 883) into the urcA locus of a strain deleted for CCNA_03498 and CCNA_03499 (DMP863). UzcY expression was restricted to conditions of U exposure by placing uzcY expression under the control of $P_{phyt-short}$ as follows. uzcY was amplified from the *C. crescentus* chromosome with primers 3497_for_Pphyt_plas_F and 3497_for_Pphyt_ plas_R, digested with BglII and XhoI, and cloned into the similarly digested pDMP746. The DNA containing the $P_{phyt-short}$-CCNA_03497 fusion was then amplified with 3497_for_Pphyt_short_chrome_R and Pphyt_short_ for_chrom_3497 and cloned into pDMP1113 that was linearized using the primers chrome_3497_vect_amp_F and chrome_vector_amp_R to The resulting suicide vector (form pDMP1114) was used to integrate $P_{phyt-short}$-uzCY into DMP993 to form DMP1009.

Metal induction experiments. Unless otherwise specified, all metal induction experiments were performed with M5G-G2P. Cells were grown to early-exponential phase, washed once with M5G-G2P, and then resuspended in the same volume of fresh M5G-G2P. Washed cells were added in 195 µl aliquots to black 96-well clear bottom plates containing 5 µl of the appropriate metal solution. Cell fluorescence and $OD_{600}$ were determined using a Biotek plate reader (Ex: 480/Em: 516) 2-3 hours post-metal exposure. The mean fluorescence and $OD_{600}$ value for each data point was subtracted by the respective values for a M5G-$G_2$P blank and then the fluorescence was normalized to the $OD_{600}$. The relationship between the U concentration and the GFP output rate was modeled using a Hill function:

$$y = y_{min} + \frac{Y_{max} - Y_{min}}{1 + \left(\frac{x}{K}\right)^{\eta}}$$

where $y_m$ in represents basal normalized fluorescence, $y_{max}$ is the maximum normalized fluorescence, x represents the U concentration, f is the Hill coefficient, and K is the concentration of U required for half maximal fluorescence expression. The best fit values were found by using the lsqcurvefit function in Matlab.

Cloning, overexpression, and purification of Strep-UrpR. urpR was amplified with primers 1362_gene_F and 1362_gene_R_GC and cloned into pET 52-b that was amplified with pET52b_F and pET52b_R using infusion cloning to generate plasmid pDMP1118. E. coli BL21(DE3) plys, containing pDMP1118, was grown at 37° C. until an $OD_{600}$ of 0.5 was reached. Isopropyl-1-thio-b-D-galactopyranoside (IPTG) was added to 0.5 mM, and the cells were shifted to 30° C. for four hours of induction. Cells were harvested and stored at −20° C. The cells pellet was thawed and resuspended in 1.4 ml B-PER™ Complete Bacterial Protein Extraction Reagent (ThermoFisher), followed by addition of EDTA to 1 mM, and rocking for 15 min at room temperature. Insoluble cell debris was pelleted via centrifugation (20, 000×g, 10 min at 4° C.). Strep-UrpR was isolated from cell lysates using a Strep-tactin column as described in the manufacturer's protocol (IBA Lifesciences). The protein concentration of UrpR (reported here as monomers) was determined using a Bradford protein assay (Biorad) with lysozyme as a standard.

Electrophoretic mobility shift assays. A $P_{phyt}$ promoter fragment containing the region from 13 to 245 with respect to the translation initiation site was amplified from pDMP460 and pDMP475 with primers BamHI_Pphyt_F and Pphyt_EMSA_R, the latter of which was labeled with fluorescein on the 5' end. Prior to the EMSA, the Strep Tag was removed from UzrpR using HRV 3C protease (Thermo Fisher) according to the manufacturer's protocol. UrpR was phosphorylated by incubation in phosphorylation buffer (50 mM Tris, pH 7.9, 150 mM NaCl, 10 mM MgCl2) with 50 mM disodium carbamyl phosphate (Sigma-Aldrich) for 1 h at 30° C. (Lynch and Lin, 1996) and immediately used in the binding assays. EMSAs were performed by incubating phosphorylated UrpR with $P_{phyt}$ DNA (50 nM) for 10 min at 37° C. in buffer containing 50 mM Tris-HCl (pH 7.9), 200 mM NaCl, 10 mM MgCl2, 0.1 mg ml$^{-1}$ BSA, 5% glycerol, 1 mM DTT, and 50 µg ml$^{-1}$ poly-dI-dC. A 5% TBE mini-protean polyacrylamide gel was pre-run with 0.5×TBE at 120 V for 30 min in a Mini-PROTEAN tetra cell (Bio-Rad) prior to loading samples. Samples were run at 100V for 45 min, and the reaction products were visualized using a Biorad Gel Doc XR1 System.

Site 300 sample collection. Standard operating procedures for sampling and sample handling at LLNL Site 300 have been described in detail [156] and are consistent with the guidance and requirements of the U.S. EPA. The groundwater samples used in this study were collected from each well with either an electrical submersible pump or a bailer. Well samples were placed on ice, filtered using a 0.2 D m filter, and stored at 4° C.

Inductively coupled—plasma mass spectrometry/optical emission spectrometry. Site 300 samples were diluted in 2% (v/v) nitric acid (trace metal grade) and spiked with an internal holmium standard. U was quantified using a Thermo XSeriesII ICP-MS run in standard mode. The sample introduction system was an ESI PFA-ST nebulizer pumped at 120 l/min. Zn, Pb, Cu, Cd, and Cr were quantified using a Thermo iCAP 7400 radial ICP-OES in standard operating mode. Standard curves were generated using a 100 mM uranyl nitrate stock solution and 10 ppm Zn, Pb, Cu, Cd, and Cr ICP-MS standards (Inorganic Ventures).

$P_{phyt}$-lacZ and $P_{1361}$-lacZ reporter constructs. Chromosomally integrated $P_{phyt}$-lacZ and $P_{1361}$-lacZ translational fusions were constructed using a two-step sacB counterselection procedure [147] to swap the $P_{ucA}$ promoter in pDMP82[3] with either $P_{phyt}$ or $P_{1361}$. pDMP82 contains the necessary sequence to generate a translational $P_{ucA}$-lacZ fusion at the $P_{ucA}$ locus in which the sequence 24 nt downstream of the urcA start codon is fused to E. coli lacZ. To accomplish this, the $P_{phyt}$ and $P_{1361}$ fragments were amplified from the Caulobacter genome with the primer pairs Phyt-138_F/Phyt-138R and 1362_138_F/1362_138_R (Table 4), respectively and cloned into pDMP82 that was linearized using the primers 138_PurcA_F and 138PurcA_F (Table 4) using In-Fusion cloning.

TABLE 4

| DNA primers: | | |
|---|---|---|
| Primer name | Primer sequence | SEQ ID NO: |
| Phyt-138_F | TAACCCTTTGCAAACCGGACGGTGACCGGCAAAC | 37 |
| Phyt-138_R | GATGAACTTGCGCATGGCGGAGCCCCTCGTTTTc | 38 |
| 1362_138_F | TAACCCTTTGCAAACGAACGATAGCGCCGCCTGC | 39 |

TABLE 4-continued

| Primer name | Primer sequence | SEQ ID NO: |
|---|---|---|
| 1362_138_R | TCCCTCTGGCTGGGCGGAAAGATCGGGACTGGGTGATGG CGCTTAGGATTCCACAG | 40 |
| 138_PurcA_F | ATGCGCAAGTTCATCATGAGCC | 41 |
| 138_PurcA_R | GTTTGCAAAGGGTTAATCGACGCC | 42 |
| pNTPS138_urcR_F | gGAACGATAGCGCCGGACGGTGACCGGCAAAC | 43 |
| pNTPS138_urcR_R | CGCACAAAATCCTCATCCTGAGC | 44 |
| urcR_UR_F | caattgaagccggctCAGAAGGTCGACGCCCTGG | 45 |
| urcR_UR_R | CGCACAAAATCCTCATCCTGAGC | 46 |
| Pphyt_urcR-loc_F | gGAACGATAGCGCCGGACGGTGACCGGCAAAC | 47 |
| Pphyt_urcR-loc_R | AATCAGAATGCGcatGGCGGAGCCCCTCG | 48 |
| Pphyt-uzcR_vect_F | atgCGCATTCTGATTATCGAGGACG | 49 |
| Pphyt-uzcR_vect_R | CGGCGCTATCGTTCcctagg | 50 |
| Pphyt_rsaFb_F | GTGAAAAAAGCTTAACTCGAGGGGCTCCGCCatgC | 51 |
| Pphyt_rsaFb_R | TTAAGCTTTTTTCACGCAGTCTCGCAGCTAGCTTAGCCG | 52 |
| P1362_rsaFb_F | GTGAAAAAAGCTTAACTCCGAGCTCCCTAACTAACTAAt cATCT | 53 |
| P1362_rsaFb_R | TTAAGCTTTTTTCACGCAGTGATGGCGCTTAGGATTCCA CAG | 54 |
| gfp19_amp_for_pxyl_F | tggggagacgaccaTATGCGTAAGGGCGAAGAGCTG | 55 |
| gfp19_amp_for_pxyl_R | cacggctggctgcagGCCGAATTTCAGGGGTACAGCA | 56 |
| Pphyt_TR_elim_F | GATCCCGGGGATTTCTCTTCGCGCCACC | 57 |
| Pphyt_promoter_shorten_R | GAAATCCCCGGGATCCCTGTGCTCTAGA | 58 |
| XbaI_PurcB | GACTCTAGACGAAGACTGGGCGGGCAG | 59 |
| BglII_PurcB_R | GACAGATCTCGGTTTGGGTGGTCGCTTGG | 60 |
| PrsaA_frag_F | TtgtcgacgtatgacgtttgctctatagC | 61 |
| PrsaA_frag_R | CGTTCACATCGCCATCCAGCTC | 62 |
| gfp_for_PrsaA_F | ATGGCGATGTGAACGGCCATAAG | 63 |
| gfp_for_PrsaA_R | gtcatacgtcgacaaGCCGAATTTCAGGGGTACAGCA | 64 |
| Pphyt_SD_amp_R | ATGTTTTTCCTCCTTATAAAGTAGATCTTTAGTTAGTTA GGG | 65 |
| gfp1-9_for_pphyt-short_F | AAGGAGGAAAAACATATGCGTAAGGGCGAAGAGCTG | 66 |
| gfp1_9_for_phyt_R | GAAATCCCCGGGATCGCCGAATTTCAGGGGTACAGCA | 67 |
| urcA_loc_DR_F | GGTCGCTACCATTACCAGTTGGTC | 68 |
| urcA_loc_UR_R | TGCTTGGGTCGTTTGAGTATATGGT | 69 |
| HRP_chrom_int_F | CAAACGACCCAAGCAGGTGTCGCCCTTCGCTGAAC | 70 |
| HRP_chrom_int_R | GTAATGGTAGCGACCCCAAGCTCAGCTAATTAAGCCTCG AG | 71 |

TABLE 4-continued

| | DNA primers: | |
|---|---|---|
| Primer name | Primer sequence | SEQ ID NO: |
| PurcA_UR_F | ggctggcgccaagctTGGCCGGCCGCACGCAAGGGCAGA | 73 |
| PurcA_UR_R | TTATTTTTGACACCAGACCAACTGG | 74 |
| PurcA_DR_F | TGGTGTCAAAAATAATCGCACAGGCGACCGC | 75 |
| PurcA_DR_R | gcgaattcgtggatcCAGGCGTCGAGGTGAAGTA | 76 |
| kan_elim_F | ATTCTTCCTTTTTCAATATTATTGAAGCATTTATCAG | 131 |
| kan_elim_R | AAGCTTAATAAGATGATCTTCTTGAGATCG | 132 |
| Cat_R | CATCTTATTAAGCTTTTACGCCCCGCCCTGCCAC | 133 |
| Cat_F | TGAAAAAGGAAGAATATGGAGAAAAAAATCACTGGATAT ACCACCGTTG | 134 |
| pBBR1-rep_F | GACGCTAGCctgcgcaacccaagtgctacc | 135 |
| pBBR1-rep_R | CAGAAGCTTggatatgtggacgatggccgc | 136 |
| P1968_BamHI_F | GACGGATCCGAGTCAGTTGAGCCAGGCGTG | 137 |
| P1968_EcoRI_R | GACGAATTCCGTIVAGTCCATACGCGACIGIG | 138 |
| P1968_HS1_mut_F | ATAGCGCAATTTAAGTGGTCTCTGGCC | 139 |
| P1968_HS1_mut_R | CTTAAATTGCGCTATTGACGGGGATTTAACGGCAGC | 140 |
| P1968_HS2_mut_F | AATGTGGTCTCTGGCCCTCCG | 141 |
| P1968_HS1_mut_R | GCCAGAGACCACATTAATTGCGGTAATGACGGGGAT | 142 |

Both fragments were cloned into the HindIII and BamHI-digested pNPTS138 (Table 5) using In-Fusion cloning and integrated into the chromosome of a *Caulobacter crescentus* lacA mutant strain JOE2321 (Table 5) or NA1000 strain (Table 5) using the double-crossover allele replacement as described above, yielding strains DMP89 and DMP90, respectively (Table 5), integrated at the P$_{urcA}$ locus.

TABLE 5

| | *Caulobacter crescentus* strains and plasmids: | |
|---|---|---|
| Strain or plasmid | Description | Source or reference |
| Strains: | | |
| JOE2321 | *C. crescentus* CB15N ΔCC_1634 | [157] |
| DMP89 | JOE2321 P$_{urcA}$-lacZ | Unpublished |
| DMP90 | NA1000 P$_{urcA}$-lacZ | Unpublished |
| DMP470 | JOE2321 P$_{phyt}$-lacZ | Unpublished |
| DMP471 | JOE2321 P$_{1361}$-lacZ | Unpublished |
| | NA1000 ΔuzcR | [151] |
| DMP701 | NA1000 ΔparDE$_3$ P$_{1968}$-gfp mut$_3$ | [158] |
| DMP702 | NA1000 ΔparDE$_3$ Pphyt-uzcRS P$_{1968}$-gfp mut$_3$ | Unpublished |
| DMP703 | NA1000 ΔparDE$_3$ Pphyt$_{m\_5}$-uzcRS P$_{1968}$-gfp mut$_3$ | Unpublished |
| DMP674 | pNPTS138 ΔparDE$_3$ P2844 elim | Unpublished |
| DMP690 | ΔparDE3 P1362-uzcRS | Unpublished |
| DMP679 | ΔparDE3 P1362-rsafB-BS-uzcRS | Unpublished |
| DMP643 | Pphyt-rsafB-BS-uzcRS | Unpublished |
| DMP601 | ΔparDE3 Pphyt-uzcRS | Unpublished |
| DMP681 | NA1000 Pphyt-hrpS, PurcB-hrpR, PhrpL-gfpmut3 | Unpublished |
| DMP683 | NA1000 P$_{phyt}$-gfp10_m2_K1, P$_{urcB}$_E1_gfp11_m4, P$_{rsaA}$-gfp1-9 | Unpublished |
| DMP804 | NA1000 P$_{phyt}$-gfp10_m2_K1, P$_{urcB}$_E1_gfp11_m4, P$_{xyl}$-gfp1-9 | Unpublished |
| DMP877 | NA1000 P$_{phyt}$-gfp10_m2_K1, P$_{urcB}$_E1_gfp11_m4, P$_{phyt\ short}$-gfp1-9 | Unpublished |
| DMP878 | NA1000 P$_{1361}$-gfp10_m2_K1, P$_{urcB}$_E1_gfp11_m4, P$_{phyt\ short}$-gfp1-9 | Unpublished |
| DMP895 | NA1000 P$_{phyt-short}$-gfp10_m2_K1, P$_{urcB}$_E1_gfp11_m4, P$_{rsaA}$-gfp1-9 | Unpublished |
| DMP213 | NA1000 ΔuzcS | [3] |
| DMP561 | NA1000 pDMP558 | [3] |
| DMP562 | NA1000 ΔuzcR pDMP558 | [3] |
| DMP563 | NA1000 pDMP559 | [3] |

TABLE 5-continued

| | _Caulobacter crescentus_ strains and plasmids: | |
|---|---|---|
| Strain or plasmid | Description | Source or reference |
| DMP564 | NA1000 pDMP560 | [3] |
| DMP911 | NA1000 $P_{urcB}$ -gfp10_m2_K1, $P_{urcB}$_E1_gfp11_m4, $P_{rsaA}$-gfp1-9 | Unpublished |
| DMP912 | NA1000 ΔCCNA_01362 | Unpublished |
| DMP913 | NA1000 ΔCCNA_01363 | Unpublished |
| Plasmids: | | |
| pNPTS138 | Non-replicating vector for integration and allelic replacement; oriT, kan (Km$^R$), sacB | M. R. K. Alley, unpublished |
| pDMP450 | Cat gene from pR9TT and pBBR ori and rep from pPROBE'-gfp[LVA], $P_{mrC}$-gfp mut3 | Unpublished |
| pDMP460 | $P_{phyt}$-gfp mut3 | Unpublished |
| pDMP463 | $P_{1361}$-gfp mut3 | Unpublished |
| pDMP462 | Synthetic promoter probe vector containing gfpmut3 | Unpublished |
| pDMP460 | Cat gene from pR9TT and pBBR ori and rep from pPROBE'-gfp[LVA] | [3] |
| pDMP558 | $P_{1968}$-gfpmut3 | [3] |
| pDMP559 | $P_{1968}$(5'-CAATAG-3')-gfpmut3 | [3] |
| PDMP560 | $P_{1968}$(5'-TAAT-3')-gfpmut3 | [3] |
| pDMP499 | pNPTS138 derived vector for D51A substitution in UzcR | [3] |
| pDMP614 | pNPTS138 derived vector for $P_{phyt}$-lacZ integration into urcA locus | Unpublished |
| pDMP609 | pNPTS138 derived vector for $P_{1361}$-lacZ integration into urcA locus | Unpublished |
| pDMP610 | $P_{hrpL}$- gfp mut3 | Unpublished |
| pDMP621 | pNPTS138-Pphyt$_{m\_5}$-uzcRS | Unpublished |
| pDMP673 | pNPTS138-P1361$_{m\_5}$-uzcRS | Unpublished |
| pDMP460 | $P_{phyt}$-gfpmut3 | Unpublished |
| pDMP463 | $P_{1362}$- gfpmut3 | Unpublished |
| pDMP791 | Pphyt-gfp10_m2_K1, PurcB_E1_gfp11_m4, PrsaA-gfp1-9 | Unpublished |
| pDMP881 | P1362-gfp10_m2_K1, PurcB_E1_gfp11_m4, PrsaA-gfp1-9 | Unpublished |
| pDMP82 | pNPTS138 $P_{urcA}$-lacZ | [3] |
| pDMP792 | pNPTS138-Pphyt-gfp10_m2_K1, PurcB_E1_gfp11_m4, PrsaA-gfp1-9 | Unpublished |
| pDMP883 | pNPTS138-Pphyt-short-gfp10_m2_K1, PurcB_E1_gfp11_m4, PrsaA-gfp1-9 | Unpublished |
| pDMP932 | pNPTS138-PurcB-gfp10_m2_K1, PurcB_E1_gfp11_m4, PrsaA-gfp1-9 | Unpublished |
| pDMP692 | pNPTS138-P1362-gfp10_m2_K1, PurcB_E1_gfp11_m4, PrsaA-gfp1-9 | Unpublished |
| pDMP664 | pNPTS138-$P_{phyt}$-tripartite-GFP | Unpublished |
| pDMP665 | pNPTS138-$P_{1362}$-tripartite-GFP | Unpublished |
| pDMP712 | $P_{phyt}$-gfp10_m2_K1, $P_{urcB}$_E1_gfp11_m4, Pxyl-gfp1-9 | Unpublished |
| pDMP713 | P1361-gfp10_m2_K1, $P_{urcB}$_E1_gfp11_m4, Pxyl-gfp1-9 | Unpublished |
| pDMP808 | pNPTS138-$P_{phyt}$-gfp10_m2_K1, Pphyt_E1_gfp11_m4, Pphyt-short-gfp1-9 | Unpublished |
| pDMP809 | pNPTS138-P1362-gfp10_m2_K1, Pphyt_E1_gfp11_m4, Pphyt-short-gfp1-9 | Unpublished |
| pDMP745 | $P_{phyt}$ -DR1 GTCA->CAGT- gfpmut3 | Unpublished |
| pDMP746 | $P_{phyt}$-large-TR-elim-gfpmut3 | Unpublished |
| pDMP747 | P1361- DR1 GTCA->CAGT-gfpmut3 | Unpublished |
| pDMP786 | $P_{phyt}$ -DR1 GT->CA-gfpmut3 | Unpublished |
| pDMP787 | $P_{phyt}$ -DR2 GT->CA-gfpmut3 | Unpublished |
| pDMP788 | $P_{1361}$-DR2 GT->CA-gfpmut3 | Unpublished |
| pDMP789 | $P_{1361}$ shorten- gfpmut3 | Unpublished |
| pDMP748 | pNPTS138-PurcB-gfp10_m2_K1, PurcB_E1_gfp11_m4, Pxyl-gfp1-9 | Unpublished |
| pDMP741 | PurcB-gfp10_m2_K1, PurcB_E1_gfp11_m4, Pxyl-gfp1-9 | Unpublished |
| pDMP558 | $P_{1968}$-gfpmut3 | [3] |

$P_{phyt}$-gfp and P1361-gfp constructs. Plasmid-borne $P_{phyt}$-gfp and $P_{1361}$-gfp fusions were generated by amplifying $P_{phyt}$ and $P_{1361}$ fragments from the _Caulobacter_ genome with the primer pairs Phyt-138_F/Phyt-138_R and 1362_138_F/1362_138_R (Table 4), respectively, digested with BamHI and EcoRI and cloned into the similarly digested pDMP450 (Table 5), generating pDMP460 and pDMP463 (Table 5).

Construction of a CCNA_01968 promoter-gfp transcriptional fusion. A synthetic vector with a P15A origin, kanamycin resistance cassette and gfpmut3 gene insulated with an upstream rrnB terminator 1 (DNA2.0) was used as a template to construct promoter-gfp fusions. First, the cat gene (chloramphenicol acetyltransferase) from pNJH123 was amplified with the primers cat_F and cat_R and cloned into pDMP462 that was linearized with the primers kan_elim_F and kan_elim_R using infusion cloning. The p15A origin was then swapped with a pBRR-rep1 origin that was amplified from pPROBE-GFP' using the primers pBBR1-rep_F and pBBR1-rep_R and the restriction enzymes NheI and HindIII, generating pDMP460. The DNA sequence region from 170 to −9 with respect to the translation initiation site of CCNA_01968 was amplified with P1968_BamHI_F and P1968_EcoRI_R, digested with EcoRI and BamHI, and cloned into the similarly digested pDMP460 to construct a CCNA_01968-promoter gfp fusion (pDMP558). Site directed mutagenesis was performed with the primers P1968_HS1_mut_F and P1968_HS1_mut_R to mutate UzcR half site one from 5'-CATTAC-3' to 5'-CAATAG-3' and primers P1968_HS2_mut_F and P1968_HS2_mut_R and to mutate the half site two from 5'-TTAA-3' to 5'-TAAT-3', generating pDMP559 and pDMP560, respectively.

Engineering of constructs to place the uzcRS operon under the transcriptional control of $P_{phyt}$/$P_{1361}$. The two mapped promoters of uzcR were replaced with $P_{1361}$ and $P_{phyt}$ as follows. First, a synthetic DNA containing the rrnb T1 and T7Te transcription terminators (BBA_0B0015) followed by a $P_{1361}$ fusion with the first 168 nucleotides of uzcR was prepared (Integrated DNA Technologies, Inc.) Then, pDMP499 (Table 5), a pNPTS138-based vector containing the DNA sequence for substituting the aspartate residue at position 51 for alanine was amplified with primers pNTPS138_urcR_F and pNTPS138_urcR_R (Table 4) and the 531 bp region upstream of the uzcR promoters was amplified with urcR_UR_F and urcR_UR_R (Table 4). All three DNAs were ligated together to make pDMP610 (Table 5). $P_{phyt}$ was swapped for $P_{1361}$ using infusion cloning with the fragments generating by amplifying pDMP610 (Table 5) with Pphyt-uzcR_vect_F/Pphyt-uzcR_vect_R and pDMP614 with Pphyt_urcR-loc_F/Pphyt_urcR-loc_R (Tables 4 and 5).

The resulting suicide vectors pDMP609 and pDMP614 (Table 5) were electroporated into FC922 (Table 5) and the P1361-uzcRS (DMP690) and Pphyt-uzcRS strains (DMP601) (Table 5) were obtained by a two-step sacB counterselection procedure [147]. The UzcR binding site from the rsaFb promoter TGCGTGAAAAAAGCTTAACT (SEQ ID NO: 201) was inserted downstream of the transcriptional start site of $P_{phyt}$ and $P_{1361}$ as follows. Plasmids pDMP609 and pDMP614 and were amplified with the primer pairs P1362_rsaFb_F/P1362_rsaFb_F and Pphyt_r- saFb_F/Pphyt_rsaFb_F, respectively (Table 5) and re-ligated using InFusion cloning. The resulting suicide vectors pDMP673 and pDMP621 (Table 5) were electroporated into *Caulobacter* strain FC922 and the P1361m_5-uzcRS (DMP679) and Pphytm_5-uzcRS (DMP643) strains (Table 5) were obtained by the two-step sacB counterselection procedure. All strains were transformed with pDMP558, encoding a CCNA_01968 promoter gfpmut3 fusion (Table 5).

Engineering of constructs to place expression of hrpS under control of $PPh_yt$ or P1361, and hrpR under control of $P_{urcB}$. $P_{hrpL}$ DNA (SEQ ID 80) was synthesized (IDT), then digested with BamHI and BglII and ligated into the similarly digested pDMP450, generating pDMP610. Next, the synthetic Pphyt-hrpS_PurcB-hrpR DNA fragment was digested with XbaI and BamHI and cloned into the similarly digested pDMP610 to generate pDMP612. pDMP612 was cloned into NA1000 to produce DMP681.

TABLE 6

| DNA sequences of genetic molecular components: | | |
|---|---|---|
| Genetic molecular component | DNA sequence | SEQ ID NO: |
| $P_{1361}$ promoter | GAACGATAGCGCCGCCTGCGAGCGCGACCTCAGGCCTCGGACGAAGCGCGT CCGGGGCCTTTTCTTGTCGATGTTCAGCGCCTGGTTACCGGCGATGGCGCG GTGTCAGCGTTCGGGCGTTGCGATGCGTCAGGAGCGTGTCAGGATGCCTGT GGAATCCTAAGCGCCATCACCCAGTCCCGATCTTTCC | 77 |
| $P_{phyt}$ promoter | CCGGACGGTGACCGGCAAACCACCGCTGTCATGAATGCGTTTTGAAGCTTC GCCATAACGCGCCTTGGGTATCCGGTTCGGAACGCGGCGCTTTCGTTGACC TCTGGCCACGGAGAATTCTCCATCCCAAAGAGGGTGTGGCCCAAAGAGGGT GTGGATTTCTCTTCGCGCCACCCGTTTCGTCAGCCGGACGTCAGGTCCAGA CGGCTAAGCTAGCTGCGAGACatgAAAACGAGGGGCTCCGCC | 78 |
| rrnBT1-T7T3-P1361-uzcr (1-168 nt) | TGAGGATTTTGTGCGccaggcatcaaataaaacgaaaggctcagtcgaaag actgggcctttcgttttatctgttgtttgtttgtcggtgaacgctctctactaga gtcacactggctcaccttcgggtgggcctttctgcgtttatacctaggGAA CGATAGCGCCGCCTGCGAGCGCGACCTCAGGCCTCGGACGAAGCGCGTCCG GGGCCTTTTCTTGTCGATGTTCAGCGCCTGGTTACCGGCGATGGCGCGGTG TCAGCGTTCGGGCGTTGCGATGCGTCAGGAGCGTGTCAGGATGCCTGTGGA ATCCTAAGCGCCATCACCCAGTCCCGATCTTTCCGAGCTCCCTAACTAACT AAtcATCTACTTTATAAGGAGGAAAAACATatgCGCATTCTGATTATCGAG GACGACCTGGAAGCCGCCGGCGCCATGGCGCACGGGCTCAAGGAAGCCGGC TACGACGTCGCCCACGCGCCGGACGGCGAGGCGGGCCTGGCCGAGGCCCAG AAGGGCGGCTGGGACGTGCTGGTCGTCGCCCGGATGATGCCCAAG | 79 |
| PhrpL | GACGGATCCGCCGGATTATGTCCGCTGAGTGGGTCACGGTCCCGGATCAGT TCCCTTGCGAAGCTGACCGATGTTTTTGTGCCAAAAGCTGTTGTGGCAAAA AACGGTTTGCGCAAAGTTTTGTATTACAAAGAATTTCACATTTTAAAATAT CTTTATAAATCAATCAGTTATTTCTATTTTTAAGCTGGCATGGTTATCGCT ATAGGGCTTGTACAGATCTGTC | 80 |
| Tripartite GFP gblock | CAGAGATCTACTTTATAAGGAGGAAAAACATATGGATCTGCCCGACGATCA TTACCTGTCCACCCAGACCATCCTGTCGAAGGATCTGAATGGCACCGACGT GGGCTCCGGTGGCGGGAGTGGTGGTGGCGGGAGCAAGGTCTCCGCCCTCAA GGAGAACGTTAGCGCCCTGAAAGAGAAAGTCTCGGCCCTGACCGAAAAGGT CTCCGCCCTTAAGGAAAAAGGTGAGCGCTCTCAAAGAGTAAccaggcatcaa ataaaacgaaaggctcagtcgaaagactgggcctttcgttttatctgttgt ttgtcggtgaacgctctctactagagtcacactggctccttcgggtggg cctttctgcgtttataggtaccCGAAGACTGGGCGGGCAGCAGCCCACTCC CAAGCGCCCACCAATTATGACTTCTTTTTCATAGACTTAATTCGACGTCAT GAAGCAGTCGTAACGGGTGTTCGCCATCCGACCGCTCTACATCCTCGATCA ACGGATCGCCAAGCGACCACCCAAACCGcctaggtaactaaagattaactt tataaggaggaaaaacatATGAAGGTCTCCGCCCTTGAAAATGAGGTCTCG GCTCTCGAAAAGGAGGTGTCGGTCCTGGAGAAAGAAGTCAGCGCGCTTGAG AAGGAGGTCCGTGCCCTGGAGAAGAGTGGCGGTGGGGGGTCTGGGGGCGGT TCTGGGGGCGGCTCCACCTCGGAGAAGCGTGACCACATGGTGCTGCTCGAA TATGTCACCGCCGCCGGGATCACCGATGCCTCCTAAGactcctgttgatag atccagtaatgacctcagaactccatctggatttgttcagaacgctcggtt gccgcgggcgttattattggtgagaatGAAAAATGCTGTACCCCTGAAAT TCGGCTAttgtcgacgtatgacgtttgctctatagccatcgctgctcccat gcgcgccactcggtcgcaggggtgtgtgggattttttttgggagACAATCCT CATGCGTAAGGGCGAAGAGCTGTTCACGGGCGTCGTCCCCATCCTCATCGA GCTGGATGGCGATGTGAACGGCCATAAGTTCTTCGTCCGTGGGGAAGGCGA | 81 |

TABLE 6-continued

DNA sequences of genetic molecular components:

| Genetic molecular component | DNA sequence | SEQ ID NO: |
|---|---|---|
| | GGGGGATGCCACCATCGGCAAGCTGAGCCTCAAGTTCATCTGCACCACCGG<br>CAAGCTCCCGGTCCCCTGGCCGACGCTCGTCACGACCCTCACCTACGGGGT<br>GCAGTGCTTTTCCCGTTACCCCGACCACATGAAGCGGCACGACTTCTTTAA<br>GTCGGCCATGCCCGAAGGCTACGTGCAGGAGCGCACCATCTATTTTAAGGA<br>CGATGGCACGTATAAGACCCGCGCGGAGGTCAAGTTCGAAGGGGATACCCT<br>GGTCAACCGTATCGAGCTGAAGGGCATCGACTTTAAGGAAGATGGCAACAT<br>CCTCGGGCACAAGCTCGAATATAATTTTAACTCCCATAAGGTCTACATCAC<br>CGCCGACAAGCAAAACAACGGCATCAAGGCGAACTTTACGATCCGTCACAA<br>TGTGGAGGACGGCAGCGTCCAGCTCGCGGATCATTATCAACAGAATACCCC<br>CATCGGCGATGGTCCCGTCCTCCTCCCGTAGCTCGAGATTTGAGGATTTTG | |
| Pphyt-<br>hrpS_PurcB-<br>hrpR | TGCGccaggcatcaaataaaacgaaaggctcagtcgaggctcaccttcggg<br>aagactgggcctttcgttttatctgttgtttgtcggtgaacgctctctact<br>agagtcacacttgggcctttctgcgtttatacctaggGAACGATAGCGCCG<br>CCTGCGAGCGCGACCTCAGGCCTCGGACGAAGCGCGTCCGGGGCCTTTTCT<br>TGTCGATGTTCAGCGCCTGGTTACCGGCGATGGCGCGGTGTCAGCGTTCGG<br>GCGTTGCGATGCGTCAGGAGCGTGTCAGGATGCCTGTGGAATCCTAAGCGC<br>CATCACCCAGTCCCGATCTTTCCGAGCTCCCTAACTAACTAAtcATCTACT<br>TTATAAGGAGGAAAAACATatgCGCATTCTGATTATCGAGGACGACCTGGA<br>AGCCGCCGGCGCCATGGCGCACGGGCTCAAGGAAGCCGGCTACGACGTCGC<br>CCACGCGCCGGACGGCGAGGCGGGCCTGGCCGAGGCCCAGAAGGGCGGCTG<br>GGACGTGCTGGTCGTCGACCGGATGATGCCCAAG | 82 |

Example 1: Identification of U-Selective Promoters P1361 and $P_{Phyt}$ in *Caulobacter crescentus*

The highest U-induced gene urcA (uranium response in *Caulobacter*) has been exploited as a U sensor that can detect micromolar U concentrations in contaminated ground water [55]. However, previously the molecular mechanisms governing $P_{urcA}$ regulation were not examined, nor its cross-reactivity with environmentally relevant metal cations. To address this, the specificity was characterized and the transcriptional regulatory mechanism governing expression of the $P_{urcA}$ was identified [3]. Although most metals failed to induce $P_{urcA}$, significant induction was observed with the metal ions Zn and Cu and to a lesser degree, Cd (FIG. 2 Panel A).

The UzcRS two-component system was identified as the regulatory system responsible for U, Zn, and Cu-dependent activation of $P_{urcA}$ and 41 other promoters in the *Caulobacter* genome [3]. Together, these data suggest that the $P_{urcA}$ does not have satisfactory selectivity to function as a standalone sensor of environmental U. Nevertheless, since UzcRS exhibits a U-concentration dependence in a wide range of media conditions, a sensor that incorporates UzcRS as one component within a more advanced U-sensitive genetic circuit comprising an additional point of U sensing that is independent of the UzcRS system could produce an effective U sensor.

To identify additional U responsive genes that are not cross-reactive with other metal cations, gene expression was monitored in the presence of U and Zn using RNA-seq (FIG. 1). Two additional promoters ($P_{1361}$ (promoter of operon containing CCNA_01362) and $P_{phyt}$(promoter of CCNA_01353)) that are strongly responsive to U but not to Zn. To further characterize the specificity of these promoters, the DNA sequences corresponding to each promoter were cloned upstream of lacZ and gfpmut3 reporter genes and reporter expression was monitored following exposure to 10 different metals. Surprisingly, the data revealed that both promoters lack cross-reactivity with metal ions commonly encountered in the environment (FIG. 2 Panels B-C).

Furthermore, U-dependent induction of these promoters was not dependent on UzcRS; $P_{1361}$-gfp expression was induced 10.5 (±0.8) for wild type and 9.6 (±0.5) for a strain deleted for uzc during exposure to 20 M U, suggesting that that regulation of these promoters is governed by a regulatory mechanism distinct from $P_{urcA}$. In other words, U-sensing by $P_{phyt}/P_{1361}$ and $P_{urcA}$ is mediated through independent mechanisms. As such, these sensors are suitable for U sensor construction.

Figure 4:
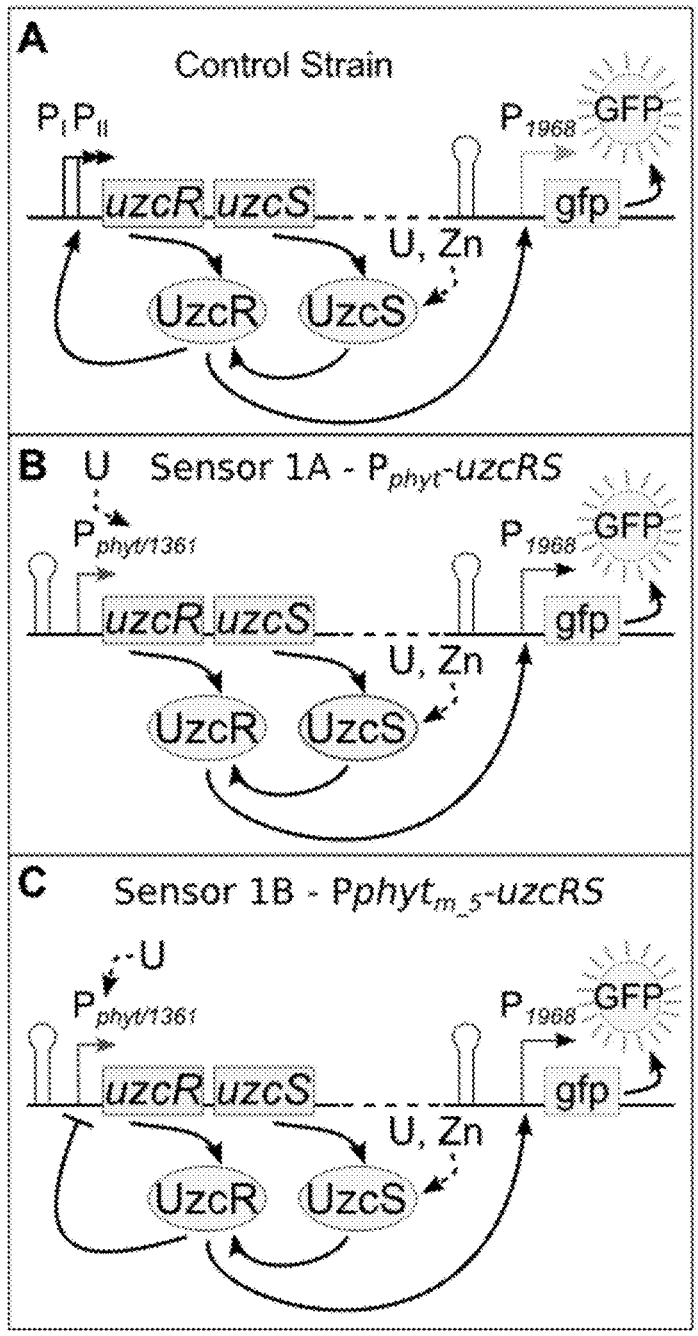
FIG. 4 Panels A-C shows schematics illustrating the stepwise genetic engineering of an exemplary U-sensitive genetic circuit with incremental improvements from Panel A to Panel C to enhance specificity for U, resulting in a genetic circuit comprising an 'in series' AND gate comprising two points of U-sensing by (1) P$_{phyt}$ or P$_{1361}$ and (2) UzcRS two component system. Panel A shows a schematic of a U-sensitive genetic circuit comprising uzcRS under the control of the native P$_{uzcR}$ promoters P1 and P2 and GFP expression under the control of UzcR-regulated promoter P$_{1968}$. In this genetic circuit, binding of U directly or through indirect stimulation of UzcS causes the UzcS-mediated phosphorylation and activation of UzcR, leading to the homodimerization of UzcR and DNA binding of the UzcR dimer at the m_5 binding sites in the P$_{1968}$ promoter. The genetic circuit shown in Panel A only requires one point of U sensing, by UzcRS. As expected, this genetic circuit produces a high fluorescence signal in response to U, Zn, and Cu, as shown in FIG. 5. Incremental improvements of this circuit are shown in Panel B and Panel C to enhance selectivity for U. Panel B shows a schematic of a U-sensitive genetic circuit where $P_I$ and $P_{II}$ are replaced with $P_{phyt}$ or $P_{1361}$ such that uzcRS expression is now dependent on activation by these U-specific promoters. This construct requires two points of U sensing for reporter activation, (1) activation of uzcRS transcription by $P_{phyt}$ or $P_{1361}$ and (2) stimulation of UzcRS transcriptional regulatory activity. This sensor shows greater signal in response to U compared to the genetic circuit shown in Panel A, as shown in FIG. 5 Panel A. Importantly, in the genetic circuit shown in FIG. 4 Panel B, Cu-sensing has been completely abolished while Zn induction with the range of inducing Zn concentrations narrowed compared to the UzcRS sensor alone; also, the ratio of the U signal output to that of Zn has been increased from 1.6 to 3.5 as shown in FIG. 5 Panel B.

Example 2: Engineering of a U-Sensitive Genetic Circuit Comprising an 'in Series' AND Gate Wherein the uzcRS Operon is Placed Under the Transcriptional Control of $P_{phyt}/P_{1361}$ In the *C. crescentus* NA1000 genome, uzcR and uzcS are physically separated by genes encoding the ParDE3 toxin anti-toxin (TA) system, together forming a putative four-gene operon [112]. Although uzcR and uzcS are conserved throughout much of alphaproteobacteria, the insertion of parDE3 between uzcR and uzcS is unique to a subset of the *Caulobacter* genus; uzcR and uzcS are adjacently located in the majority of closely related alphaproteobacteria [3] including *C. crescentus* strain OR37, an environmental isolate from a U-contaminated site [97]. The $parDE_3$ system does not contribute to the metal-dependent regulation by UzcRS [3]. Given this result and the potential toxicity associated with $parDE_3$ overexpression, the $parDE_3$ TA system was deleted, so that uzcR and uzcS are adjacently located. The expression of uzcR is controlled by two promoters ($P_1$ and $P_2$) in *C. crescentus* [3], which enables sufficient basal expression of uzcRS to activate transcription in response to metal (U, Zn, Cu). There is also a putative UzcR binding site located upstream of $P_1$ that likely yields a positive feedback loop. Indeed, UzcR protein levels increase in a uzcS-dependent manner in response to metal sensing. Deletion of the $parDE_3$ TA system and the parD promoter places uzcS expression under the exclusive control of $P_1$ and $P_2$ (FIG. 4 Panel A). A "control strain" of *Caulobacter* was generated comprising a U-sensitive genetic circuit in which uzcR is under the control of $P_1$ and $P_2$ and uzcS under the control of $P_1$ and $P_2$, (FIG. 4 Panel A). As expected, this strain produces a high fluorescence signal in response to U, Zn, Cu (FIG. 5 Panel A left, middle, right graphs, respectively). Incremental improvements were made to this circuit to enhance specificity, as described below.

Figure 5:
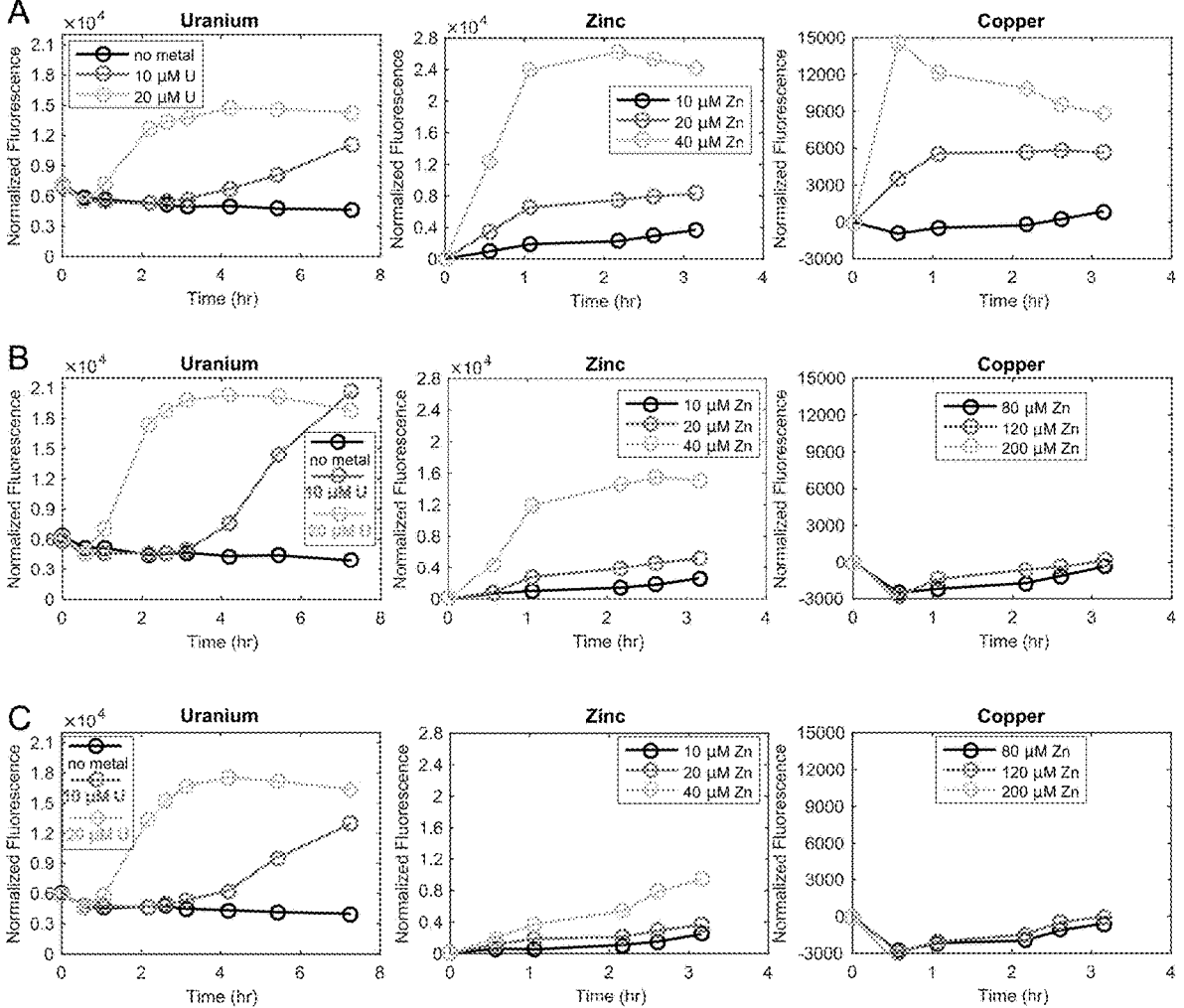
FIG. 5 shows graphs of exemplary GFP reporter fluorescence produced by the U-sensitive genetic circuits shown in FIG. 4, comprised in the host organism *C. crescentus* NA1000, upon exposure to U, Zn or Cu.

To enhance the selectivity of UzcRS for U, P1 and P2 were replaced with $P_{phyt}$ or $P_{1361}$ such that uzcRS expression is dependent on activation by these U-specific promoters (FIG. 4 Panel B). This genetic circuit requires two points of U sensing for reporter activation, (1) activation of uzcRS transcription by $P_{phyt}$ or $P_{1361}$ and (2) stimulation of UzcRS transcriptional activity. *Caulobacter* comprising this sensor showed greater reporter expression signal in response to U (FIG. 5 Panel B, left graph) compared to the control (FIG. 5 Panel A, left graph). Importantly, Cu-sensing has been completely abolished (FIG. 5 Panel B, right graph) while Zn induction with the range of inducing Zn concentrations narrowed (FIG. 5 Panel B, middle graph) compared to the $P_{urcA}$ sensor alone (FIG. 5 Panel A, middle graph). The ratio of the U signal output to that of Zn has been increased from 1.6 to 3.5 (FIG. 5 Panel B, left and right graphs).

To further improve specificity of U sensing, a negative feedback loop was incorporated into the circuit, whereby UzcR represses its own expression from $P_{phyt}$ or $P_{1361}$, in order to minimize the basal expression of the uzcRS operon. Specifically, a UzcR binding site was placed downstream of the $P_{phyt}$ or $P_{1361}$ transcription start site (FIG. 4 Panel C). Although the UzcR binding site from the rsaFb promoter was used, any m_5 site is suitable. *Caulobacter* comprising this sensor showed strong responsiveness to U (FIG. 5 Panel C, left graph) and further shifted ratio of U response to that of Zn to 5.5 (FIG. 5 Panel C, left and right graphs).

Example 3: Engineering of a U-Sensitive Genetic Circuit Comprising an 'in Parallel' HRP AND Gate This Example describes the engineering of a U-sensitive genetic circuit comprising an 'in parallel' AND gate that utilizes the HRP AND gate system from *Pseudomonas syringae* that was recently developed in *E. coli* [126]. In this system, both HrpS and HrpR are required for $\sigma^{54}$ dependent activation of the hrpL promoter ($P_{hrpL}$). Expression of HrpS or HrpR alone is not sufficient for transcriptional activation.

The genetic circuit described in this Example contains genetic components whose expression is controlled independently by (1) $P_{phyt}$ or $P_{1361}$ and (2) UzcRS systems, and reporter expression requires both HrpS and HrpR to be expressed.

To generate this U-sensing AND gate, the expression of hrpS was placed under the control of $P_{Phyt}$ or $P_{1361}$, while hrpR was placed under the control of $P_{urcB}$, a UzcRS-dependent promoter that was recently identified that has lower basal activity compared to $P_{urcA}$ [3](FIG. 6 Panel A). A $P_{hrpL}$-gfp fusion was generated as a reporter and requires $P_{Phyt}/P_{1361}$ and $P_{urcB}$ to be active to generate a fluorescent signal.

Example 4: Engineering of a U-Sensitive Genetic Circuit Comprising an 'in Parallel' Tripartite GFP AND Gate This Example describes the engineering of a U-sensitive genetic circuit comprising an 'in parallel' AND gate that utilizes the tripartite GFP system [5], which requires expression of gfp10, gfp11 and gfp1-9 for reporter expression (FIG. 6 Panel B).

To construct an in parallel AND gate comprising the tripartite GFP system a gblock (Tripartite GFP gblock) was synthesized (Integrated DNA Technologies, gBlock) with the following components listed in 5' to 3' orientation: GFP10-m2_k1, rrnBT1 and T7Te transcription terminators, E1-GFP11-M4 under the control of the UzcRS promoter ($P_{urcB}$), lamdaT$_0$ terminator, gfp1-9 under the control of the rsaA promoter ($P_{rsaA}$ [4]). GFP10-m2_k1 was placed under the control of $P_{phyt}$ or $P_{1361}$ by digesting Tripartite GFP gblock with BglII and XhoI and ligating into the similarly digested pDMP460 and pDMP463, respectively, to form pDMP791 and pDMP881. DNA sequence encompassing the entire $P_{phyt}/P_{1361}$ tripartite DNA and an insulating upstream rrnbT1 transcription terminator was amplified with primers HRP_chrome_int F and R and cloned into pDMP82 that was amplified with the primers urcA_loc_DR_F and urcA-loc_UR_R using infusion cloning to form pDMP792 and pDMP692. A variant of this AND gate containing gfp1-9 under the control of the xylose inducible promoter (Pxyl [6]) was constructed by amplifying the 360 bp $P_{xyl}$ fragment using Pxyl_F and Pxyl_R and cloning into pDMP792 ($P_{phyt}$ version) and pDMP692 ($P_{1361}$ version) that were amplified with gfp1-9_amp_for_pxyl_F gfp1-9_amp_for_pxyl_R using infusion cloning to form pDMP664 and pDMP 665, respectively. A variant of this AND gate containing gfp1-9 under the control of the shortened $P_{phyt}$ promoter was constructed by amplifying pDMP736 with Pphyt_TR_e-lim_F and Pphyt_SD_amp_R and cloning this 137 bp fragment into pDMP712 ($P_{phyt}$ version) or pDMP713 ($P_{1361}$ version) that was amplified with gfp1-9_for_pphyt-short_F and gfp1-9_for_phyt_R using infusion cloning to form pDMP808 and pDMP809. A variant containing GFP10-m2_k1 under the control of a shortened version of $P_{phyt}$ and gfp1-9 under the control of $P_{rsaA}$ was constructed by amplifying pDMP792 with Pphyt_TR_elim_F and Pphyt_promoter_shorten_R and re-ligating using infusion cloning, forming pDMP883. Lastly, a control tripartite variant containing both GFP10-m2_k1 and E1-GFP11-M4 under the control of $P_{urcB}$ was constructed in three parts. First, a $P_{urcB}$ fragment generated with primers XbaI_PurcB and BglII_PurcB_R was digested with XbaI and BglII and directionally cloned into the similarly digested pDMP712, forming pDMP741. Next, DNA sequence encompassing the entire $P_{urcB}$ tripartite DNA and an insulating upstream rrnbT1 transcription terminator was amplified with primers HRP_chrome_int F and R and cloned into pDMP82 that was amplified with the primers urcA_loc_DR_F and urcA-loc_UR_R using infusion cloning to form pDMP748. Finally, the $P_{xyl}$ promoter was swapped for $P_{rsaA}$ by cloning PrsaA, amplified with PrsaA_frag_F and PrsaA_frag_R, into pDMP748 that was amplified with gfp_for_PrsaA_F and gfp_for_PrsaA_R, forming pDMP932. These tripartite GFP AND gate variants were then integrated into the chromosomal urcA locus using a two-step sacB counterselection procedure [155].

Figure 11:
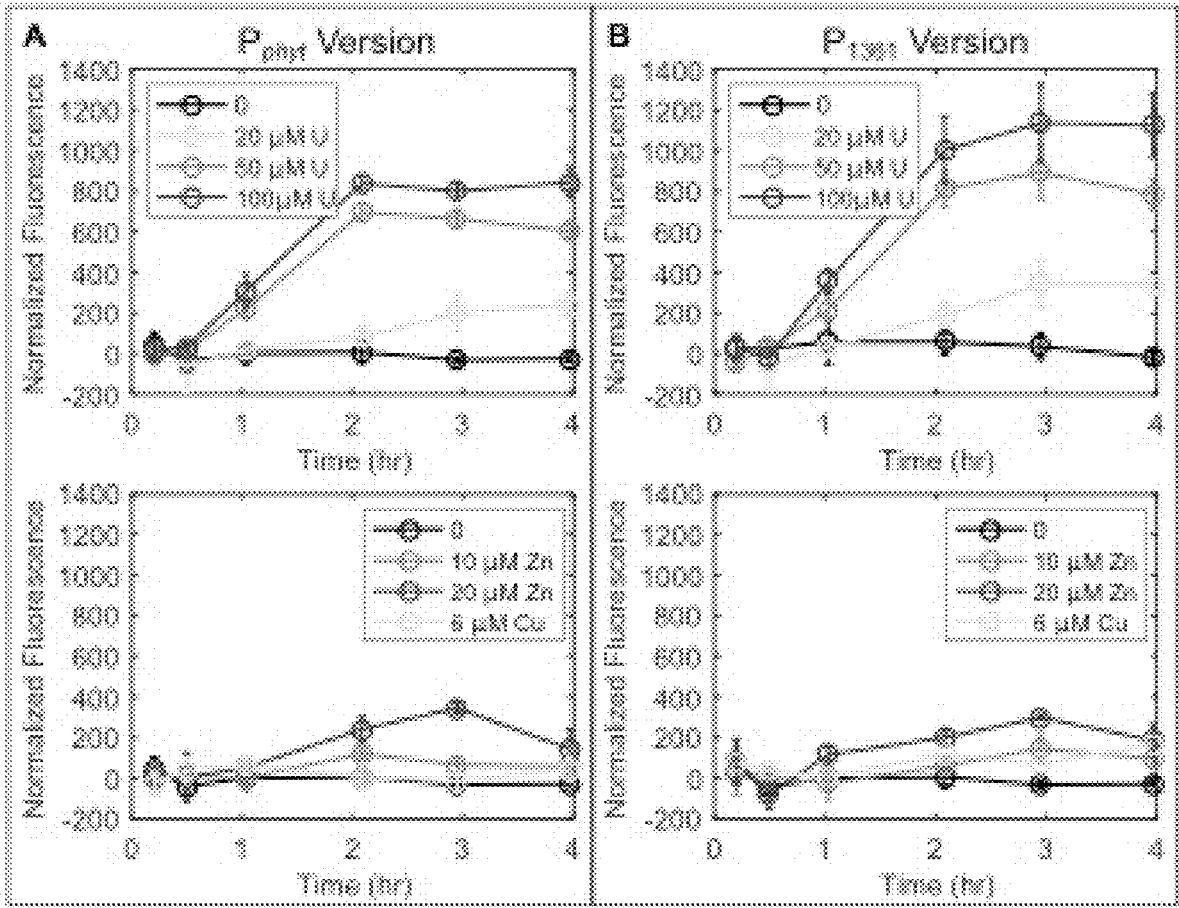
FIG. 11 shows graphs reporting exemplary data corresponding to the exemplary U-sensitive genetic circuit in FIG. 6 Panel B. Graphs reporting quantification of GFP fluorescence produced by *C. crescentus* NA1000 comprising the U-sensitive genetic circuit shown in FIG. 6 Panel B with gfp10 under the control of $P_{phyt}$ (Panel A) or $P_{1361}$ (Panel B) in response to exposure to 20, 50, and 100 μM U (FIG. 11 Panels A and B, upper graphs), or 10, 20 μM Zn and 6 μM Cu (FIG. 11 Panels A and B, lower graphs). In this version of the circuit, gfp1-9 is controlled by $P_{xyl}$ and gfp1-9 expression is induced with 10 mM xylose. Fluorescence output for both $P_{phyt}$ and $P_{1361}$ sensor variants is plotted as a function of time following metal exposure and was normalized to the fluorescence of a strain lacking the UzcR regulator. Cells were grown to mid-exponential phase in M5G-G2P media, washed once with fresh media, then resuspended in fresh media containing the indicated metal concentration.

FIG. 11 shows graphs reporting exemplary data corresponding to the exemplary U-sensitive tripartite GFP genetic circuit.

Tripartite GFP system with PrsaA-gfp1-9: Can detect U in the 2-20 uM range. When a growth media containing Glycerol-2-phosphate as the P source is used, the signal amplitude is higher but the responsive range is shifted to 8 uM-30 uM. Higher concentrations have a diminished signal output. The shifted range likely reflects U coordination by glycerol-2-phosphate that reduces the bioavailability.

Figure 22:
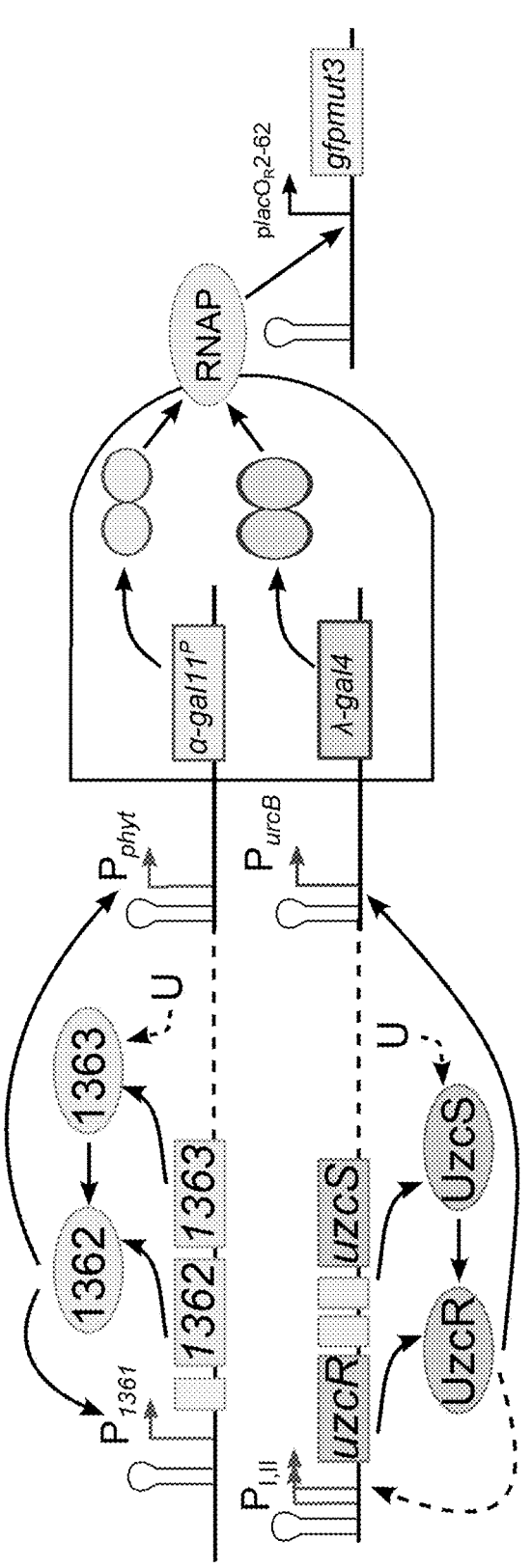
FIG. 22 shows a schematic showing an exemplary AND gate comprised in a U-sensitive genetic circuit wherein an alpha-gal11P fusion and a lambda repressor-gal4 fusion are expected to be driven by a combination of $P_{phyt}$/P1361 and any UzcRS regulated promoter.
Figure 23:
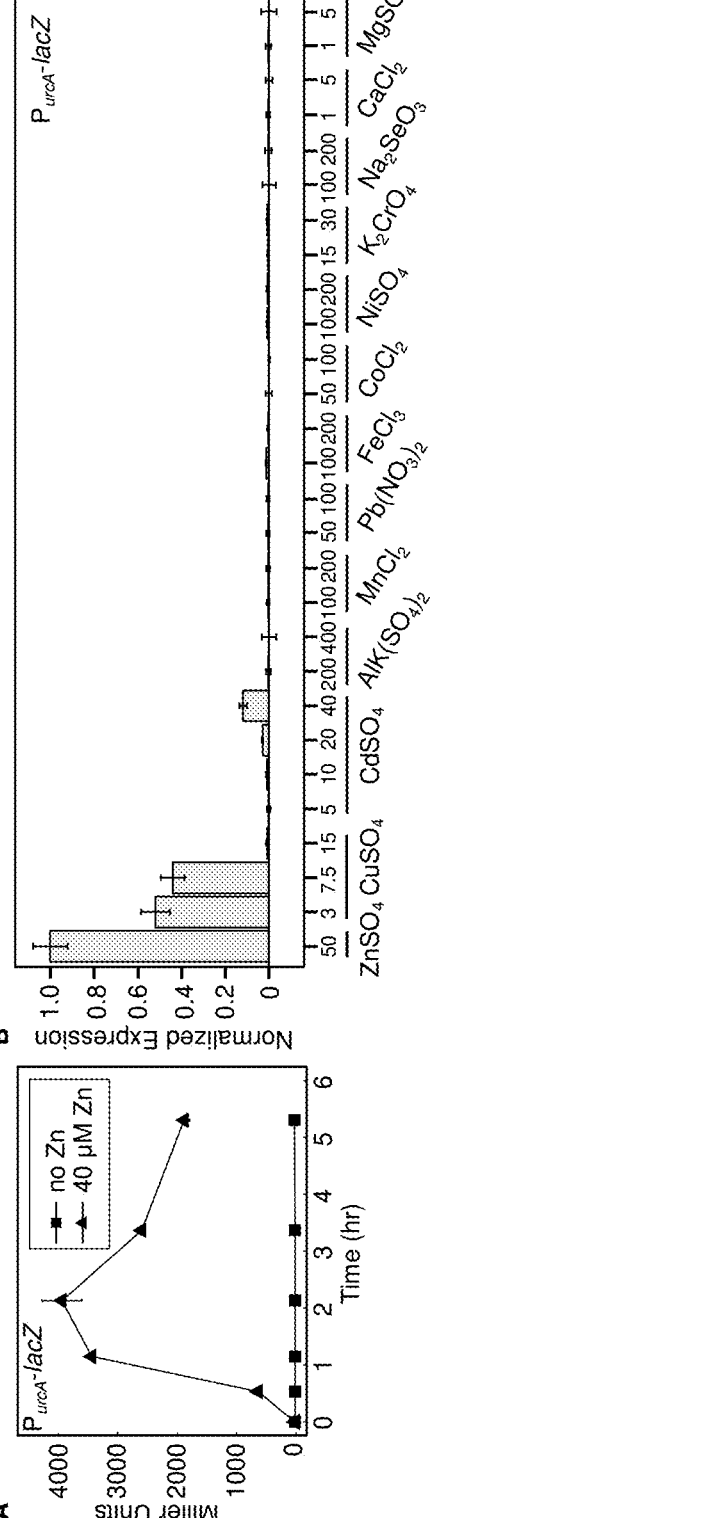
FIG. 23 shows in some embodiments the determination of metal specificity of $P_{urcA}$. Panel (A): Time course of chromosomal $P_{urcB}$ A-lacZ induction after treatment of early exponential phase cells with or without Zn. Cells were grown in PYE and the β-galactosidase activity at each time point is depicted. Error bars represent the standard deviation of biological triplicates. Panel (B): Metal specificity of $P_{urcA}$ was determined by treating mid-exponential phase cells with various metal cations in modified M5G media supplemented with 1.3 mM inorganic phosphate for two hours before determining β-galactosidase activity. Expression values were normalized to the level of expression with 50 M Zn and error bars represent that standard deviation calculated using a formula for propagation of standard error [20]. The depicted metal concentrations are in units of μM except for $CaCl_2$ and $MgSO_4$ that were added at mM concentrations.
Figure 24:
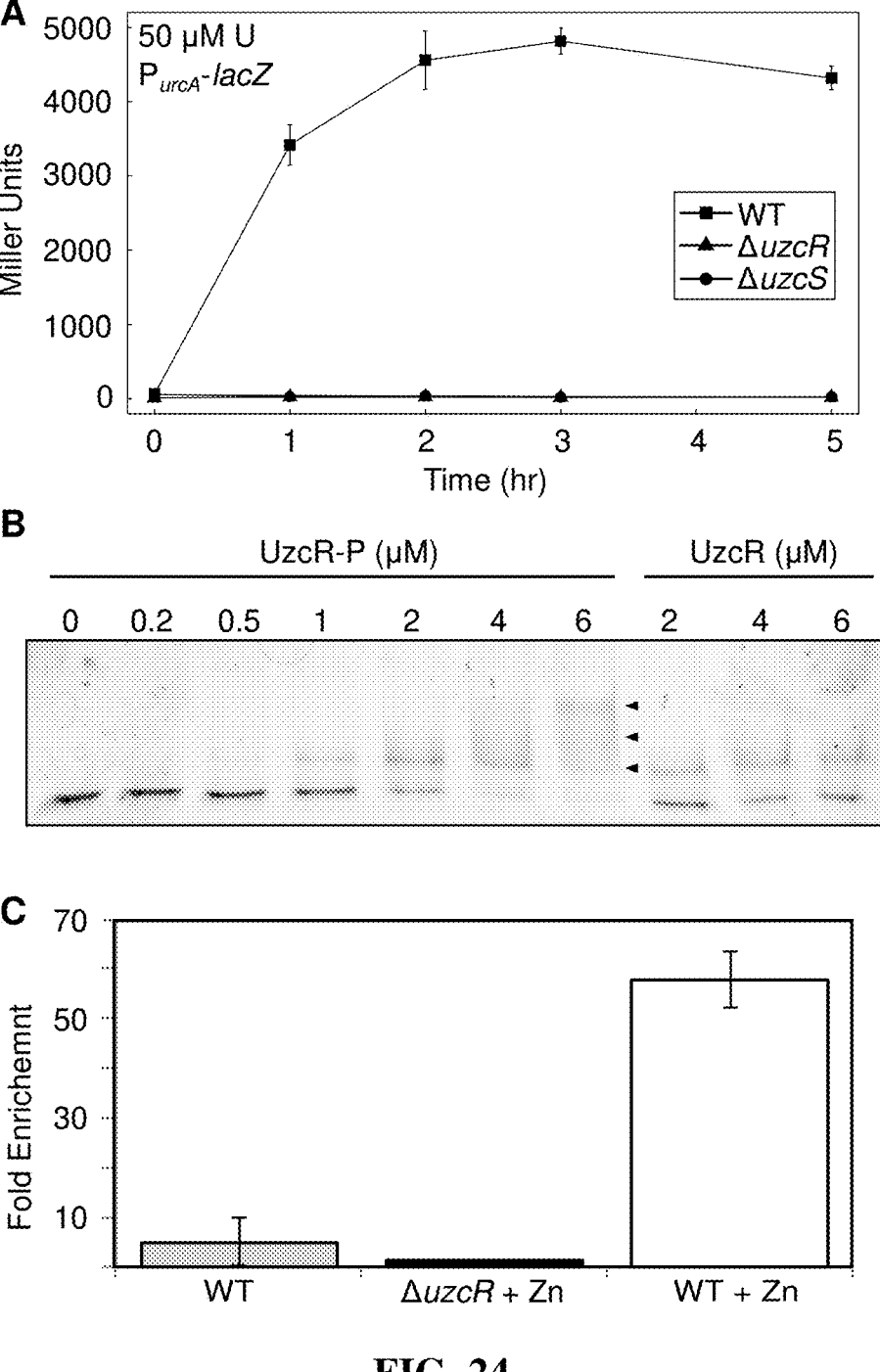
FIG. 24 shows an exemplary direct activation of $P_{urcA}$ by UzcRS according to some embodiments herein described. Panel (A): Time course of $P_{urcA}$-lacZ expression following treatment with uranyl nitrate in M5G media supplemented with 5 mM glycerol-2-phosphate as the phosphate source media for wild type (WT), ΔuzcR and ΔuzcS. Panel (B): EMSA assay of UzcR binding to a 5' 6-FAM (Fluorescein)-labeled urcA promoter fragment. UzcR-P was phosphorylated with carbamoyl phosphate and the concentrations indicate the total UzcR used in the assay. Arrows depict shifted complexes. Panel (C): In vivo binding of UzcR to $P_{urcA}$ using ChIP-qRT PCR. Data are plotted as the fold enrichment at $P_{urcA}$ relative to the control region (sodA) for wild type (WT) with or without 40 M Zn and ΔuzcR with 40 M Zn.

Example 5: Engineering of a U-Sensitive Genetic Circuit Comprising an 'in Parallel' Bacterial Two-Hybrid System AND Gate This Example describes the engineering of a U-sensitive genetic circuit comprising an 'in parallel' AND gate that utilizes the bacterial two-hybrid system [117]. In such an embodiment, the alpha-gal11P fusions and lamda repressor-gal4 fusion are expected to be driven by a combination of $P_{phyt}/P_{1361}$ and any UzcRS regulated promoter (see FIG. 22).

Example 6. Identification of a Putative U-Sensitive Transcriptional Regulatory DNA Binding Site in Pphyt and P1361 Promoter Sequences Using a bioinformatic approach, a putative regulator binding site was identified in proximity to the transcription start site in $P_{phyt}$ and $P_{1361}$ that is comprised of two direct repeat elements (e.g., CGTCAGC (SEQ ID NO: 202)); FIG. 7 Panels A and B). This binding site is conserved amongst Caulobacteridae Bradyrhizobiaceae, Sphingomonadaceae, Hyphomicrobiaceae, and Rhodobacteracea, facilitating a phylogenetic footprinting approach to construct a putative regulator DNA-binding motif (FIG. 7 Panel C), using 26 DNA sequences of $P_{phyt}$ and $P_{1361}$ from *Caulobacter* sp. Root342, *Phenylobacterium* sp. Root700, *Caulobacter crescentus* NA1000, *Caulobacter* sp. Root1455, *Caulobacter* sp. Root487D2Y, *Paracoccus* sp. 228, Caulobacteraceae bacterium OTSz_A_272, Novosphingobium sp. AP12 PMI02, *Hyphomicrobium* sp. MCi, *Hyphomicrobium denitrificans*, *Brevundimonas* sp. Root1279, *Sphingopyxis* sp. Root1497, *Afipia* sp. P52-10, *Caulobacter* sp. Root342, *Hyphomicrobium denitrificans*, Sphingobium sp. YBL2, *Sphingobium baderi* LL03, Sphingobium indicum B90A, and *Roseovarius indicus* strain DSM 26383.

The functional role of the putative regulator site within each promoter was tested by mutating conserved nucleotides within each direct repeat away from consensus, as shown in FIG. 8 Panels B, C, D, G and H. Mutations within either direct repeat abrogated U-dependent activation of both the $P_{phyt}$ and $P_{1361}$ promoters in the host organism *C. crescentus* NA1000 suggesting that the U-responsive regulator is natively a transcriptional activator (FIG. 9 Panels A and B).

$P_{phyt}$ (but not $P_{1361}$) also contains a large tandem repeat (TR;32 bp) located further upstream from the putative regulator site (FIG. 8 Panel A). To test the function of this TR in U-dependent induction of $P_{phyt}$ the size of the $P_{phyt}$ DNA was reduced from 238 bp to 81 bp, eliminating the TR and all upstream DNA (FIG. 8 Panel C). The data shown in FIG. 9 Panel A indicate that the TR is not required for U induction. Similarly, a shortened version of $P_{1361}$ that included only nine bp upstream of the regulator binding site (FIG. 8 Panel I) retained U-dependent regulation (FIG. 9 Panel B). Collectively, these data indicate that the DNA sequence extending beyond the regulator binding site within $P_{1361}$ and $P_{phyt}$ are not required for U-dependent activation.

To create a synthetic uranium repressed promoter, the consensus direct repeat UrpR binding site can be integrated within a promoter region, such that UrpR DNA binding will interfere with RNA polymerase binding and/or transcription. The UrpR binding site should be integrated at a location that overlaps, but does not alter the sequence of the −35 and/or −10 promoter elements or the TSS; disturbing −35 and/or −10 promoter elements will yield a promoter with low basal activity. Ideally, multiple locations will be tested to optimize results. While this promoter can be used to control transcription of any biological reporter, destabilized gfp (e.g., GFP-LVA[159]) is expected to yield the best results given the enhanced degradation rate. Highly stable reporters (e.g., GFP) will require several rounds of cell division to observe a uranium (e.g. UrpR) dependent decrease in reporter activity.

Example 7. Signal Amplifier Module

A positive regulator protein UzcY, encoded by CCNA_03497, was identified, which functions as a "natural" signal amplifier for the UzcRS system. Under normal growth conditions, uzcY is repressed by the MarR family transcription factor (CCNA_03498), and thus has no effect on UzcRS activity. However, when UzcY expression is induced through relief of CCNA_03498 repression or by ectopic expression, it stimulates UzcS activity through a direct interaction, causing a hypersensitive output in response to the metal inducers U, Zn, and Cu. This has the effect of dramatically increasing the output signal amplitude in response to low U (or Zn/Cu) concentrations, thus increasing sensitivity, and lowering the U detection limit of UzcRS by over 4-fold (FIG. 12).

To enhance the sensitivity of U sensors, this "natural" signal amplifier module can be integrated into U sensor circuitry. To accomplish this, in an exemplary circuit the U-specific promoter $P_{phyt}$ or $P_{1361}$ is used to drive expression of uzcY (e.g., see FIG. 13) such that UzcY levels are modulated in a U-concentration dependent manner. The low U detection limit of $P_{phyt}$ and $P_{1361}$ (~500 nM) is expected to allow signal amplification at environmentally relevant U concentrations, which is expected to improve U sensitivity and lower the detection limit in view of exemplary data demonstrating that both of these properties can be achieved with the native UzcRS system (e.g., see FIG. 12). Additionally, by restricting UzcY-mediated signal amplification to conditions of U exposure (e.g. by placing UzcY under regulatory control of a U-selective promoter such as $P_{1361}$ or $P_{phyt}$, the selectivity for U is expected to be further enhanced.

Example 8. Combination of 'in Parallel' and 'in Series' AND Gate Circuits

An example of combining 'in series' and 'in parallel' AND gate circuits within the same cell to enhance selectivity is shown in FIG. 14. An advantage of this exemplary circuit is that the UzcRS input is U selective whereas in the original 'in parallel' circuit as shown in FIG. 6 Panel B, the UzcRS-regulated promoter $P_{urcB}$ is cross-reactive with Zn and Cu.

Example 9. Negative Regulators of UzcRS

The following four different negative regulators of UzcRS that are encoded in the *Caulobacter* chromosome were identified (see FIG. 27). None of these regulators are required for U sensing by UzcRS, however, their levels modulate the sensitivity to U.

Negative regulator 1: CCNA_03681 and CCNA_03680 encode an ABC transporter ATPase and an ABC-2 family transporter fused to a C-terminal aminopeptidase N domain, respectively (urtAP). Together these proteins form an ABC transporter with a C-terminal aminopeptidase domain.

Negative regulator 2: CCNA_02866 (also referred to herein as uzcX), encodes a membrane protein of unknown function that is located within a prophage region of the genome and part of the UzcR direct regulon (~8-fold activated by UzcR (Park et al., 2017) [3].

Negative regulator 3: A MarR family regulator CCNA_03498 that represses expression of an operon containing CCNA_03497, CCNA_03498 and CCNA_03499 (see FIG. 26). Expression of CCNA_03497 (occurs when repression mediated by CCNA_03498 is lifted) hypersensitizes UzcS to metal inducers.

Negative regulator 4: A second, paralogous MarR family regulator CCNA_02289 that represses expression of an operon containing CCNA_02291, CCNA_02290 and CCNA_02289 (see FIG. 26). Expression of CCNA_02291 (occurs when repression mediated by CCNA_02289 is lifted) hypersensitizes UzcS to metal inducers.

Example 10. U Biosensor Having U-Neutralization Output

This Example describes a U biosensor having exemplary U-neutralization outputs in response to bioavailable U.

Figure 21:
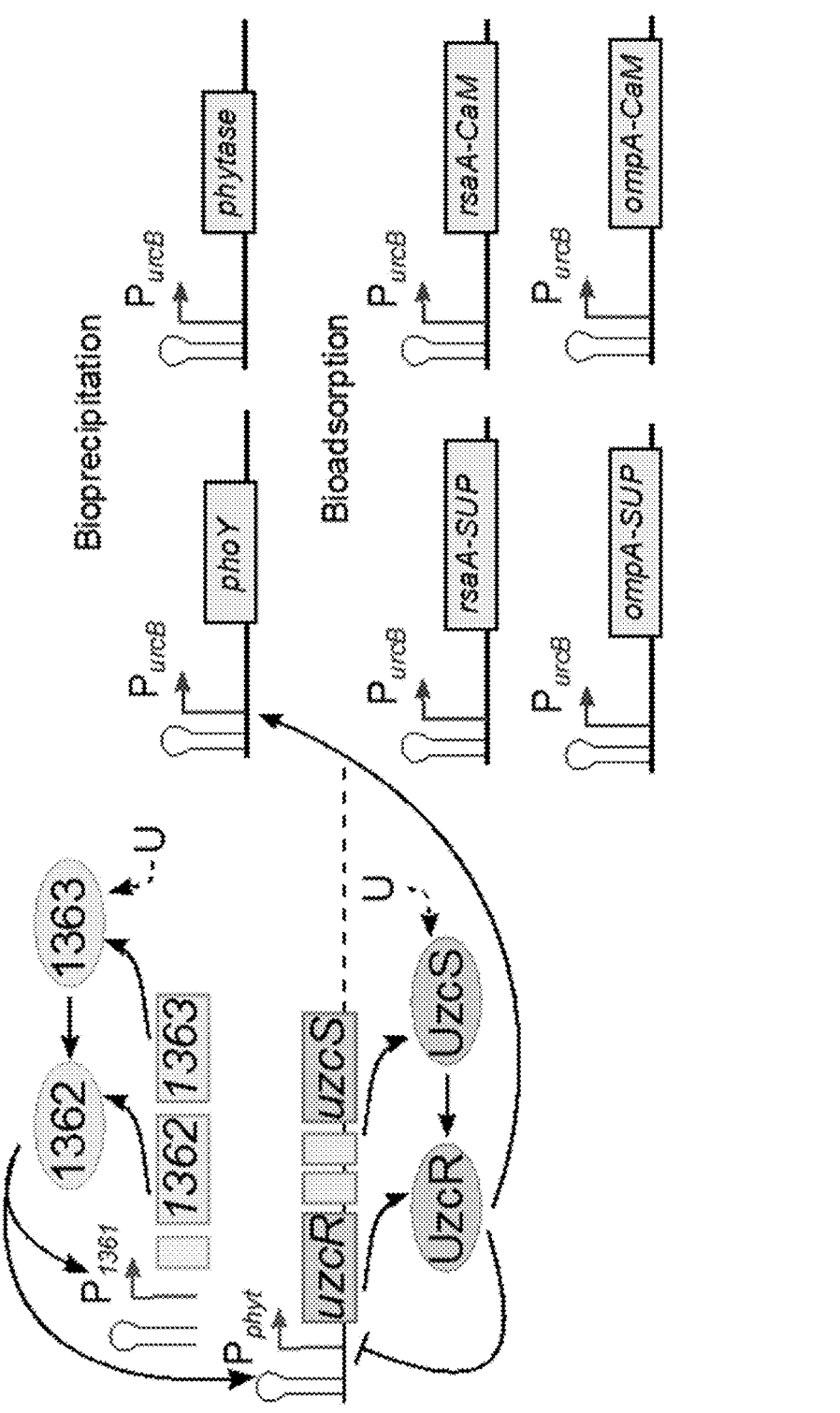
FIG. 21 shows a schematic showing exemplary U-sensitive genetic circuits having exemplary U-neutralizing outputs to allow U bioprecipitation or bioadsorption.

FIG. 21 shows a schematic showing exemplary U-sensitive genetic circuits having exemplary U-neutralizing outputs to allow U bioprecipitation or bioadsorption. In the exemplary U-sensitive genetic circuits, an exemplary AND gate comprises a $P_{phyt}$ promoter configured to initiate expression of UzcR and UzcS in presence of bioavailable U, and a $P_{urcB}$ promoter (activated by UzcR) configured to initiate expression of exemplary U-neutralizing genes phoY or phytase (to provide a U bioprecipitation output), or fusion genes of rsaA-SUP, rsaA-CaM, ompA-SUP, or ompA-CaM (to provide a bioadsorption output).

Example 11. UzcR Regulated Promoter

Table 7 shows a list of UzcR regulated promoters. Bolded regions are putative UzcR m_5 sites and single boded nucleotide is TSS.

TABLE 7

| Exemplary UzcR regulated promoters | | |
|---|---|---|
| Promoter | Promoter sequence | SEQ ID NO |
| CCNA_03 906 (PurcA) | CCCTTTGCAAACCATATACTCAAACGACCCAAGCAATATGGTCAC AAAAACTTCAAACATTACAGACTGTTTAGAATATTAAAGCCCC GTAATTCTCTTAATTACGCGTCATGACTGAGGTGTAACGAGACT TCGCGAGAACCCGAATGTATCCAATATTCATCGGCGCAGCGAAC AGCGCCCAGCCAGAGGGATACTTCA | 84 |
| CCNA_01 185 (PurcB) | GAAGACCCAAGTTTTGCGGTTAATCATTTACGAAGACTGGGCGGG CAGCAGCCCACTCCCAAGCGCCCACCAATTATGACTTCTTTTTC ATAGACTTAATTCGACGTCATGAAGCAGTCGTAACGGGTGTTCG CCATCCGACCGCTCTACATCCTCGATCAACGGATCGCCAAGCGAC CACCCAAACCGAGGATCAAGACA | 85 |
| CCNA_R 0078 | ACCTGCGCCTGGGCCCCACGGCGGACGGGTCGCGGCCCGGCGCC ACCTTGCAAAGGTTTAATCCACCTGTCCGGCTTGTAACTTCCCTCA AGGGGAGCCGAGAGGCACCGTCGAACCCA | 86 |
| CCNA_00 224 | GGAGCGGCGGTCTCAGAAAGGTGGCGAAAATAAAGCACTGATCA TAAGTAAATCGCGATCATCCAAGTAATGACGCCGGGCAATCGATT GTAGAAAGATGAAAATCTCGTAATGCTATCGGATATGTAATCTA CATGTCAGGCTTGTAACTTGAGATGAATGTTCGGGGCGTTCAGAC CTGTCGCCACTGAGGGGAACCAG | 87 |
| CCNA_03 098 | TCACGCGTCTTCATGGGGCTGCTCCTTGCGACATCGGCGACGAAA CACGCCGTAGACGCCCAGATGGGGGTCGCCCGGAGGCGCGACAA TGGTCGAACCGCATCACCGGGGCAGGCGCCCGTGAAGATTACAGT CAATTAAATTGAACGCCGTTCTTCCTTTTCGGAAAGTGCCTTGGG AACTTCCGGACCGAGGGACGTGG | 88 |
| CCNA_00 858 | CAGACACGCGCGGGTTTCCGCGACGGAAGAGTGTCGAGGCGGGC GCATACGCCTGTGGCGCGAATGCCACTTGGAGTCCCTCACCCGCA ACATTGCCGAAAAGAAATTTGTCCCGGCGCGTCGGAGCGTCTTT ACGGCTGGGGGTCGAGACCGCGCGGACGTCCGCAGCGTATCGCT CGACACTTGAAGTTGAGGTCTCCC | 89 |
| CCNA_03 762 | ATGCAGGCCGCCTCAGGGGACAAAGTTTCTCACGAAACGGCCTTG TGCGATCACATTACACCGCTGTAACCTCGATTACGCGCGTCAAC GTTCCTTAAATCGGCGTCATGAAGCAAGAGTAACGTGTAATAAC CATGGGCGGACCTATATCCCTCTCATCGGACGCCAACGGGGCGG CCGAAGAAAAAAGGGATCAAGAC | 90 |
| CCNA_02 172-02174 | TAACCAGACCGCAAGGCGCCTAAGTCATAAGCCTCTTACCGCCGA GGCCGCGCGCCGGCTGGCGAGCGACGAGGTCTGCCCTTCAGCGA GGCCGGCCCCGACTATTTCATGCCTGAAACGCGCCCTTACCCCGA TTTAACTTGGCCACTCGTCGATCGGCGTTCATTGCTGCAACCGTC GATTGGGGGAGCACGAGTCCGCA | 91 |
| CCNA_01 968 (P1968) | GCGGAGATGGATCGCGCGACGGGTCTGAAACAGAGTCAGTTGAG CCAGGCGTGCGGCGATGACTCCACGTTGTTGCCCCGCGGACTTTC CATTCCGCGCTGCCGTTAAATCCCCGTCATTACCGCAATTTAAGT GGTCTCTGCCCTCCGTCGGTCCAAACCGTAACTCACACAGTCGC GTATGGACTGAACGGAGTAGTC | 92 |

TABLE 7-continued

Exemplary UzcR regulated promoters

| Promoter | Promoter sequence | SEQ ID NO |
|---|---|---|
| CCNA_03 396 | ACCCTTATGGCATCGGCGGTGGATCCGCGCCTCTTGAAGGATGAC CAGCATGCGGATGCGCGGCTGGAAAAGCCGATCACCCCTGGACG TCTTCTGCAGACGGTGCGCGCGCTGGAAAGCCCACGCAGCCGT GACAGAACTTTAAGCTGACCCCGACCACTTCGCGCCCCTAGGGT GTGACGCGTTTTTGGGGAGCTCAC | 93 |
| CCNA_02 758 | GCTCGACCCGGCGTTCGCGGCGGGGCTGGAGGCGGCGGCCAAGG CCGGGGTGGAGGTGCTGGTCTATGCGTGTGAAATGGGGACGCAG GCGGTGCGGATCGCGCGGCGCATTTTGTGGAGCCACGCCCACCT AACAGCGATTTAAGCTGCATTTCGCGCCCGCTGAGCTAACCCTT CTGCAGGCTCGCGAAATGGGGATCG | 94 |
| CCNA_01 551 | GAAAGAGTGTTCAGGCGCAACCTGGGGGAAGGTCCCAAGGCCTA GACTGGCACCTAGGGCCGAGCGACGCTTGCGACAACCGTCGGAA TTCTAAGGGTGCTGTCAGATGTCGTGGAGCCCCCTTGCAAGACCA TCGGCCCTTCATGACCAAAAGTTCACTCGCCTGCTTTGCGAAAT GCTCGCATAACGCCGCTATGGGAT | 95 |
| CCNA_03 997- CCNA_03 786-03788 | GGTTCGCCGCGCGATCGCATGGCGTGACGACCATGACTAGAGGG GCCAAGCGCCAGAACCTGTCAGCTAAGCCGCCCAGCGACGCCGA ACGCCGTTACCGCGATGGGCAAACCTGTAGAATTGTTCATGAAC CCGGACATTTTCGCGCCATAACCGCGTGGCCAAGCTCCAGGCTCG GACTACGACAGGGAGCTCACAAC | 96 |
| CCNA_00 147-00149 | CCTCGATGATCGCGACCGACCCCTCCACGGCCTGAGTGTGCGCCG ATAGCGCGGGCGACACGCCGCCGCCGATCATTGCCAAAGTTTAA TATCGTTTCTCGATAAACGACATTGGCGGAACCGCAAACCCGGCC TATCTGTTCAGTGTGGCGAAGGGGCGAATGTTTCGGCCCTGGCCA TGTCTCTCAAACTGGAAAAAGC | 97 |
| CCNA_03 324 | TCGTACGGCGATGGTCGATGTGCATGGCCAGTTGGATGAAACTCG CTTGCGCCTTGGCGTTAGGACCCGCATGGGCGGCTCGCTCAAGCC GATCGAGGAAACCACGCGTGGGTTGAAGGAAGTCGGCTGAGCAA CGATCAACCGGACATTGCGATAGTTTAATAACCTTGGGCCTCTA ATTTAGGTTAGAGGCCCAAGTCA | 98 |
| CCNA_01 303 | CTCGCGACGCTCGCTCGCCGCTATCCCCGGCTGGGCGCGGCGCTG GGCCTCGGCTTCGGCCTGGTGGGTCTGGCGATGATGGTGGACTAG CCTGACCCCAACATGACTTCGCGGTCATGACCTCGAATTAAGTC GAAACCTTGTCGGCCCCTCGGTAGCCTCTCCTCATCGAATTTCAA CACGCGTCCTTGGGGAGACACT | 99 |
| CCNA_00 913-00911 | GGTACGAACGCCGCGGCTACCGCCTGACCGGCGAAACCCAGCCC TTCCCCTATGGCGACGACCGCTTCGGCCTGCCCGCAGCGGGATGAT CTGGCGTTCGTGGTGATGGAGAAGGGGCTGTAGGGCCCCATTAC CGAACCTTAAGTAGCTCCGTCCGGGCCGACGCGTTCAGATGCCG CGTCTTCGGCTCAGGGACTCTCCA | 100 |
| CCNA_03 699 | CCTGACCGATCGGGTCTATGACTGGGTCGCCGCGAACCGCTATCG GATCTTCGGCAAGCATGACCAGTGCCGGATCCCGACGCCGGCGC AACGGGCGCGCTTTCTGATCGACTAGCCCCGCCCCTATATGAACT CTCGGTAAGGTTTCCCGGCGAACCGGCGGTGCTAGGGTCCCGCGC AAACATTCAGGAGACTCTCGCG | 101 |
| CCNA_02 196 | GTCGTGGGCGCTGATCATCTCCGGCTCGGTCGTCTATGCCGGAAT CTACCTGCTGGCGCTGGCGCCGGTGGGCAAGAGCCGCTGGGCGC GCCGCTGGCAGCTTCTGAAGTAGGGCGGTGAATTCGGCGTAATC CGCGTCGAATCCCCTTCACAGCGACGCCTTGCGGAGCCACCTCTA GGGTCTCTTCCTGGGGCAGCACA | 102 |
| CCNA_01 521 | CTGCATGGCGCGCTGCTGAAAAACGAGCAGGACGTCCATCTGTTC GAACGTCTGGCGTTCCTCGCCCGCCGCGAAGGCTCGGGCACTCGT CCGGGCCAGTAAGGCGTCTGCGGCGAAACGGCCGTTACCGGGA TTTCACTGGACGCGCGCCAGACGCGCGGCCACCTTCCCGCCCATC AGGGGACGGCCGAGGAAACACCA | 103 |
| CCNA_01 379-01380 | GTCGGCCGTCGCGCCGCGTTCGACGCTTCGCCGCCGCTGCTCGCC GGCTTCGAGGCTGAGACGGGCTTCAGCTTCTGACGATCTGGGCCC GATGGACCGTCGCAACGTTTGCGTGAAAAAAGCTTAACTGGCGA CGACTGGCGGAGCGCACTTACACGCGATCATATTGTGGCCGGCGC GAGCTTCGCGTGATTGGGGATAG | 104 |

TABLE 7-continued

| Promoter | Promoter sequence | SEQ ID NO |
|---|---|---|
| CCNA_01 335-01334 | ACCAGGGACAGCAGGCGGCGCAGGATCATCTTCGGGCTCGACTT GGAACGACGGTTCCAGCGGTCATCCATGGCCCAGATTGCAGGCGT ATGACGACCGGCGGTCTCCGAGGCATGACACCCTCTTAACTTGG CGTGGGCGGGCGCGCTCGCCATAGTCTTCGCGTCGAGTCGACTCA GGTCGGCGTCCGGAACCGCTCCA | 105 |
| CCNA_02 866 | TGCAGCCGAACGCCAGGCGCGCGGGCAGGCGCGCCTCATGGAAC TCGCTCATCAAGCGATCCTTCTGGAAAGTCGAGAAAAGGTTTGAG GAAAAGCAAGACGGCGCGCTTAGTCGACGCCATTAAGACGACGTC ATGACCCGCTTTTCACTTCTTGCGCGGGACATCGGTCTCTAGGTT AGGGATCGAGATTGGAGACCACGA | 106 |
| CCNA_R 0100 | GAAGAACAGCGGATTCTTAATTCGCATCCATGAAAGGGCCCCGC AGCGATTCGCCATGGTCTCGCCACAGAGTGGCGGCGAGCTTGGC CGCG | 107 |
| CCNA_00 851-00849 | GGTCTCGTCAGTTATGGAAGTCCTGTGCGGCATTACATTTCCGTT AGGTCAGCCAAACGCGCGGCGCCGGAGGTTGACTTGCGACACTC CAGCTCTTATGTCCAGCCCACATGAGAATGAACGTTCATTCTCAA ATCGTTCATCATAGTGGCCGCGTCAAGGGTAAGAGCCCGCGCGAC CCTCGCCTCCCGGGGTCAAACA | 108 |
| CCNA_03 619 | AACCCGGGCAAATCCTTTCCCGGCCCGGATCCCCTGCAAGGCCGC CGCACGTTCCCCAACGTCGGCGGCCTTTTTGCGTCGCTTCTCGCGC CGAGGCCCGACCCGCCCTGTAAAAAATGGGTCACATGAACTTTT TTTAAGGGGGTAAAGTTTTCGCGCCGTTGCAGATTGCCGGCGGCT CACACCAACGGATGCGAATTC | 109 |
| CCNA_02 933 | CCTGGCGATAACGCCGGTCTTCGCGCCAAAACCTGCCCAAGGATTA CAAAACGTTCAGACTCCCCCGTCTCGACAAGCTGTCACAGGCTC GACATGGTTCGCCGCCGTCGCGGACTTGGGGGTCTGCGGTGCGGG GATTGGGGCGGTCGCGCCTCCAACACCAAACATAATTTTGGCTAC ACGCCCGAGGAGCGTCTCAAGT | 110 |
| CCNA_02 597 | CGGCCGCCTAGCAACAGCGACGCTCCGGGAGTTGGTCGTCGTTCC ACCCTATGTGATCCGCTATTATGTGGCTGACGGTCTGGTGCATAT CGTCCGCATCCGGCACGCCGCCCGGTTGTGACTTTTTCGTAATT CATCCTGGGTTCAGGCGGCGAGCGGTCCTCTCACGGTCAAGCTGA CCAAAAAGAGGGGACACCAGCA | 111 |
| CCNA_01 139 | AAGGACGCCGCCGAGCAGTCAGGGACCTATCTGGCGACCTGGAA GAAGGTCACGGGCCAGTGGGTGATCGAGAACGAGCTTTTCGTGA CGCTGGCTTGAGCGACGGGCCTCTTCCCAGCGAGTATGACGCGG AATTAATTAAGCCCAAACAGGGGCGGGGCTTACGCCTTCGTCCTT CAATGCGCCTCTGGGGAGGAAAAC | 112 |
| CCNA_03 816-03814 | CGCCTGGGGCAGACGCTGCACGAGGGCGCGGTGGACCGAGAGGC CGCCCACGCCAGAGTCAAAGACGCCGATCATGGGCCAAGCTGTA GCCGCCAAAGCGGGGCGCGTCCACGCACTGGGGAAGGTTACAGT CCTGTCATGTGACAGGTCGGCCGCCCATATCCTAGGGTCACGGC CAACACTTTCACCGGAGATCCTCCG | 113 |
| CCNA_02 588 | GCGACCAGGCGGGCTTCGAGCGCGCGTGAGACATGGGCACGGG ACAGCTACTCCGATCCTTCAACGACCTATGTGACCGGGATTCCTT AAAAACGGCCATACCCCGGGCCCACAGGTTACAACCCTAGTTATA AAACCACTCATCGTTATGACCGAGAATTAATTGAATGTGGCGCC CGCTCCGGGCCATGTAGCGCCCA | 114 |
| CCNA_02 218 | GGCGCCGTATCGGCCGCCAAGCGGAGCCATAGCCACTCGAAGCG CGTTCGGCTCCTTGGCGGTATTGGTGCGGGCTCTCGCCGCATTGC ACTAAAGTCATGTGAACGATCATTCTCATTGTGCTAGAAGCGCG GAATGAGGTGATCCGGTCGCTTTGTCGTGCGTATCTCTCCTGTCCG TTGCTGGTTTCGAGGCGACCCA | 115 |
| CCNA_03 097 | CGTCATCGCCATGCCACGTCCCTCGGTCCGGAAGTTCCCAAGGCA CTTTTCCGAAAAGGAAGAACGGCGTTCAATTTAATTGACTGTAAT CTTCACGGCGCCTGCCCCGGTGATGCGGTTCGACCATTGTCGCGC CTCCGGGCGACCCCCATCTGGGCGTCTACGGCGTGTTTCGTCGCC GATGTCGCAAGGAGCAGCCCCA | 116 |
| CCNA_00 419 | GTCGTCCTGCAGCGTCGGCGGGACGGCGGTGTCTGGGGTGGGGTC GGTCACGGTTGAGCCTGGAATAGTCTTGTTATCCAGATCGTCGCG CTGATCAGGCCGTGATGCAAAATGAAGGTGGCGTCATGAAGGCG ATGTCACGTTGGGCGCGTCCGCCGGAACCTTACAAAAAAGTCATC | 117 |

TABLE 7-continued

Exemplary UzcR regulated promoters

| Promoter | Promoter sequence | SEQ ID NO |
|---|---|---|
| | TCCTCGGATCGATCCGGCGCCGACGCCGGGCCGTAATCATCATCA GACCGCGCGCCGTCGACCGCTTCAGATCCCCCAACCCGAAGACTT GATGGAAGGTTTCAGACAATGATGCGTTCGATGC | |
| CCNA_00 417-00416 | GTCGTCCTGCAGCGTCGGCGGGACGGCGGTGTCTGGGGTGGGGTC GGTCACGGTTGAGCCTGGAATAGTCTTGTTATCCAGATCGTCGCG CTGATCAGGCCGTGATGCAAATGAAGGTGGCGTCATGAAGGCG ATGTCACGTTGGGCGCGTCCGCCGGACCTTACAAAAAAGTCATC TCCTCGGATCGATCCGGCGCCGACGCCGGGCCGTAATCATCATCA GACCGCGCGCCGTCGACCGCTTCAGATCCCCCAACCCGAAGACTT GATGGAAGGTTTCAGACAATGATGCGTTCGATGC | 118 |
| CCNA_02 914-02917 | AAGGACGAGGATTTCCAGCCGGCCTCGCGCCGAAATCTTGGCGA CGAAGCCTTTTCCCCGGGGGAAGGCACGTTTGCAGCCGGATCGGT AGCGAAATGCGTCACGCGTGCAAACACCGCGCGCTGAAACATTA CATCTGAGAAATATTTGACCTCAGACGCCAGTCTGCGTCAGAAC TTCGCTCGCGTGAGATTCCGGCCGATCCGGAACGGGCGAGACCGT GCCCCAATCGCGGGCCACTGGGAGGAGAGACCTTGGATAGACGA CAGTTCCTCGCGGCCTGCGGCATCGGCGCCGGGGG | 119 |
| CCNA_00 976 | CATGCGAAACGCCAAGCGCCGCTTTCGCGGCGCCGAGGGCTTTGA TTTTAGAGGATTTTCCCGCCTCTGGCTGGCGGGGAGGAAATGGTC GGAGTGGCAGGATTTGAACCTGCGACCCCTGCGTCCCGAACGCA GTGCTCTACCAGACTGAGCCACACTCCGACTTGGAGGCCGGCCTT ATAGGTGGGTGTTCCGGGGGGCGCAAGCGCCTTTTTGCAGGTTGG TCGGGAGGCCTGAAAAAAGTTCTGAAAAGGTCGTTGCATCCATCC GAGTCGTGAGCTATCTCCACCGCCTCGCCGGG | 120 |
| CCNA_03 893- CCNA_01 721 | CGCGCCGGTGCTGAACGTGCTGATCGGCGCGCTGGCGCCGGGTCT CGCCCCCGCTGCGGCGGCGCTGGCCCTGGTGGCGGCCACGCTGCT GGTCAGCAGTCCCTCGGTCCGGCGGCGACTGGGCTTGGCCGCCGT TTAGCGCCTTACGAAAGTTTCATGGCGAGCGGCGGCGCCTCCAAACG GGGGCGTGAGCGCCTCTTACCAGTGAAGGCGGCGCGCTGTGGCGTC GTTCACCGAACTGGAGGATTTGAGAATGGGTCCCGAAATCATCGT CCCGGTCGCGCTCTTCGCGATGATCTGCGCCGT | 121 |
| CCNA_03 456 | TTCTCGTGGCGCGCCTGCGCCGAGGAGTTCTTCCGCAACCTGCAG CCCTATCCGGAACCGGAAAAGACCCGCTTCTGGCGCCGGCTGCGG CGCCTGGCGCGCCTGCGCAAGAAGACGGCGGCGTAGTCGCTTCCT GTCCGCATTGTAATTGGCGCGGCGCGCAGACCTCGGATAACGCTG GTCTCTCGATAGGGAGGGCGGCATGAAGCTCATCATGATCGTCAT GGGACTGTGTCTGGCGGTCAGCGCCGCCCAGGCCCAAACGAGCA CGCCCGCGCCCGTCATCGAGACCTACAAGACA | 122 |
| CCNA_03 519-03521 | CGCGCATCGCTAGCCCTTGCCAAGCGCCAGAGCCCACGCGCTGAG CATGGGAACAGCCCGTAACCCCCGCCCCGAGGGGGTTCAGTCGC GAATGCCTCTCAGAAACCCCCGAATTCGGCGTCCGGATCATTAC GTATCATTCATGAGTAGGTACCTTGCACCACTCAGTACCGGGCG GTACAAGGGAGCATCAACGGAGGCAAGGACGCCGTGCCGGAAAC AATTGAAATCCAACTGAAGAAAGGCGTGCTGGCGCTCTGTGTGCT GGCTCTGCTCTCGCACGCCGACAGCTACGCCTACG | 123 |
| CCNA_01 712-01710 | CCAGCACCTCCTCGGCCGGCTTGGGGCTGTCGGCCCCAGAGCACCT TCATGACTTCGCTCTCGGCGCCGCTGATACGTTGTGATGTCGTTTC CATGAGCGAACGATTACGCACGTAAACGTTTCCGTCAAGTGATCG ATTACGCACGTAAACGAAATGTAATGCAGCGTTGGAGGCGTAAG CGAAGCGGCTTAACGCTCGAGAGCGGAGGAGTCGTACATGCCAG ACACGCTTCAGCTTGGCCTGCCGGGCCTTGAGTCGCCCACGCCGA CGGATCGGCTGATGTTCCTGCTGTATCCTGAC | 124 |
| CCNA_03 195 | GCCCGGGACGATCTGGGTCGCCAGCCACAAGCCGAAGGCGGCGA TCAGCAGGCGAAAAATGAGACGGACCCATGACTTCTCTCCAACTTC AGCCGCAACGCGTCCAAACCATCGCCGCATTCGTACAATATCCGA GCCCGAAACTCGGACATTACAAATGCGTTACCGCTCTTCAAACT GCCGCAGCGTGAACTATCTACCCTCCTGTGTGGGGGATGATCGCG CGCGATTGGCGAGCGGATCCGCACGCAAGGGGATATGAGTAAGA TGGCCGTGAATTCTCTATCGGTGATGTCGCCGGA | 125 |
| CCNA_03 640 | CTCGTCCCCGATCAGGACAATCCGACCCTCGTGACCATACTGGCG CAGGAACGCGGCGACCGAGCCGCCCGCGTGACCCGCGCCGACGA TGACGACGCATGCGTTCTGATTAACTTCAGCGCTCAATGACGCCC TCCCTTTCGTCAAAAATGACGCCGGCGTCACCTATTGGCAAGCGC CTTCGACAGAGGCGGATACGGAATGGGGCGGCTCGTTTCCGAAG CCGCCCCACATTTATCGCTCTGCAGCGTGCGTCAGACGACGCGCT CGACCATCATCTTCTTGATTTCGGCGATGGCCT | 126 |

TABLE 7-continued

| Promoter | Promoter sequence | SEQ ID NO |
|---|---|---|
| CCNA_02 421-02419 | TGAATAGTCCGCCTGGAGCTCGATAGCTCTCCCCCCCAGCGGACC CGCTTCGCTGCGCTCGACCCGTTACGCCCCTCACGAGGACCAGCC TCCAGAAGGATCGTTTCGAAGCGCGTGCAACCGACGCCCTTTTGG GGCTCCGGTCTTACCGCAATGTTAGAATTGCGGCTGGGGTCCTTT GGCAACCCCTTTTCGTACCGTCAAGGGTCTCATTTGGGCACAAAT TCATCGTCACGCCCCCGCCCCCCTGGCGTTTGCCGCAGTGCACAA AACGGTTTTCCGGATTTCGGGGCGGTTTTTC | 127 |
| CCNA_00 974 | GTTTCGGGAGCGGAAAATAGCCTAGAAAAAACAGCCTCATGTTT GTGAGCGCGTGCTGTTTTCGATGCTTGCGTATCCATATTGAGCAA TGATTTTCCGAAAAGCGTTCCTCCTGTGGCGATTTTGCGACAGGG GGGTCGGGATAATGATTACTTTTTTGCAATCAGAATTGACCCTCG CCCGATCCACCCCCTAACGTCGCTGCAACCGGAAGAGTTTGTTCC GGGACACATGTGATCGCGTGGTGGATTTACAGCGGATTTCGGCTC GAAAACGGACAGGTCGCTGAGGGGCTTCTTGT | 128 |
| CCNA_02 370 | AGCCCGATTGGCAACCTGTCAATCCGTCAACTTGGGGGGATTTGC GCACCTAGCGCCCACCAGCATGGGCGATAAGTGGCGCAAAGAAG ACACACATCGCCCGTTTCGAGCCGCCTCGCCGCACCGAACGGTCA TCGTTTGCAGATTTTTGTGTTGATTACGGTCCGTTAATTTGCAGTA ATTTGCAGCAACGGCCCGCCGCATGACCTCAACAGCGCAGAGCC GGACAGGGAGGGAACTCGTATGAACACCCAATTTTCGCGCCGTC GCGCCTGGCTGATGGCCGGCGGGGCCACGGGCC | 129 |
| CCNA_02 287-02288 | GATGACAAGGAAATAGCCGGCGGCCATGCGGTCGAAGGCGGTTT CAAAGGCGTTCAGCGTGCGGTTCATGATGGAAGTCCCTCATTTTG GCTTGCCCCGACCCCCTGTGGGTCATCGCCCTCGAAAGTTACGAG GCGATCTGGACAGTGCTTAGATAGCACCAATCTGAACGCCGTCAA GATGGTCTTTACAGCGTTTAGATGAAATTTTAGAAAGCTATGGTT AGAGTGAGGCCGATGAGCACAGCGACCGCCGAATCCCGCCCCTA TCACCATGGCGATCTGAGCCGCGCCCTGATCGA | 130 |

Example 12: Application of a Combinatorial Input Logic Towards U Detection

A combinatorial sensor approach using multiple regulators with broad specificity profiles can be adopted for the selective detection of compounds lacking specific regulators (e.g., butanol).

To apply the combinatorial input logic towards U detection, an AND gate circuit was developed by integrating two functionally independent, native U-responsive regulatory pathways into a single synthetic pathway in *Caulobacter crescentus*. Prior studies revealed that *C. crescentus* tolerates high U concentrations [160, 161] and exhibits a robust and specific gene expression response following U exposure. [160, 162, 163] Using the promoter of the highest U-induced gene, urcA,(P$_{urcA}$) to drive expression of UV-excitable gfp, Hillson et al generated a whole-cell U sensor that was responsive to sub-micromolar U concentrations and successfully detected U in a groundwater sample. [163] Subsequent genetic and biochemical analyses revealed that the majority of U-dependent gene induction in this bacterium, including regulation of P$_{urcA}$, is mediated by the TCS UzcRS,[153] supporting a role for UzcRS as a U-responsive master regulator. However, characterization of the specificity of UzcRS revealed strong cross-reactivity with the common environmental metals Zn and Cu. [3]

To improve upon the selectivity of the UzcRS system, the selectivity of a second U-responsive regulatory system (UrpRS) in *C. crescentus* was identified and characterized. Leveraging the distinct selectivity profiles of the UzcRS and UrpRS TCS and the tripartite GFP genetic framework,[164] an AND gate circuit that integrates signaling input from both pathways was constructed and characterized.

Example 13: Identification of the U-Responsive UrpRS TCS

Examination of U and Zn transcriptomic data [3, 160] in *C. crescentus* revealed a small subset of highly U-induced genes that are not regulated by UzcRS and only weakly induced by Zn (FIG. 1). Two operons (CCNA_01361-CCNA_01362-CCNA_01363 and CCNA_01353-CCNA_01352-CCNA_01351) were of particular interest based on several observations. First, both operons are highly induced by U in minimal and complex media, but lack induction by other known stress responses (e.g., DNA damage, heat shock, heavy metals; Table 8A to Table 8C).

TABLE 8A

| | Fold change in CCNA_01361 and CCNA_01362 expression under various stress conditions | | | | |
|---|---|---|---|---|---|
| gene | Function | U - PYE | U - M2G[160] | Zn - PYE[160] | Cd - M2G[160] |
| CCNA_01361 | PepSY superfamily protein | 91.8 | 7.4 | 1.1 | no DE |
| CCNA_01362 | two-component response regulator | 103.3 | 9.7 | 2.3 | no DE |
| CCNA_01363 | two-component sensor histidine kinase | 74.4 | 7.7 | 3.4 | no DE |

TABLE 8A-continued

| | Fold change in CCNA_01361 and CCNA_01362 expression under various stress conditions | | | | |
|---|---|---|---|---|---|
| gene | Function | U - PYE | U - M2G[160] | Zn - PYE[160] | Cd - M2G[160] |
| CCNA_01353 | myo-inositol-hexaphosphate 3-phosphohydrolase (phytase) | 115.1 | 5.5 | 2.4 | no DE |
| CCNA_01352 | two component sensor histidine kinase | 7.2 | 6.6 | 1.3 | no DE |
| CCNA_01351 | two-component response regulator protein | 4.4 | 9.5 | 1.6 | no DE |

TABLE 8B

| | Fold change in CCNA_01361 and CCNA_01362 expression under various stress conditions | | | | |
|---|---|---|---|---|---|
| gene | Function | $CrO_4^{2-}$ - M2G[160] | $Cr_2O_7^{-2[160]}$ | $^2SeO_3^{2-[160]}$ | starvation (Britos) [165] |
| CCNA_01361 | PepSY superfamily protein | no DE | no DE | no DE | 2.9 |
| CCNA_01362 | two-component response regulator | no DE | no DE | no DE | no DE |
| CCNA_01363 | two-component sensor histidine kinase | no DE | no DE | no DE | no DE |
| CCNA_01353 | myo-inositol-hexaphosphate 3-phosphohydrolase (phytase) | no DE | no DE | no DE | no DE |
| CCNA_01352 | two component sensor histidine kinase | no DE | no DE | no DE | no DE |
| CCNA_01351 | two-component response regulator protein | no DE | no DE | no DE | no DE |

TABLE 8C

| | Fold change in CCNA_01361 and CCNA_01362 expression under various stress conditions | | | |
|---|---|---|---|---|
| gene | Function | heat shock (DnaK/J depleted) [166] | DNA Damage [167] | Fe limitation [168] |
| CCNA_01361 | PepSY superfamily protein | 1.0 | 1.1 | no DE |
| CCNA_01362 | two-component response regulator | 0.8 | 1.1 | no DE |
| CCNA_01363 | two-component sensor histidine kinase | 0.6 | 1.0 | no DE |
| CCNA_01353 | myo-inositol-hexaphosphate 3-phosphohydrolase (phytase) | 2.1 | 1.1 | no DE |
| CCNA_01352 | two component sensor histidine kinase | 1.8 | 1.3 | no DE |
| CCNA_01351 | two-component response regulator protein | 0.8 | 1.3 | no DE |

The operons are furthermore likely regulated by the same transcription factor based on the presence of nearly identical DNA sites comprised of two tandem direct repeats (5'-GTCAG-3'; FIG. 7A-B) with 11-bp center-to-center (ctc) spacing within the CCNA_01353 ($P_{phyt}$) and CCNA_01361 promoters ($P_{1361}$). This direct repeat site is conserved within the promoters of closely related alpha proteobacteria (FIG. 7C) and required for U-dependent induction of $P_{phyt}$ and $P_{1361}$; mutations away from consensus in both $P_{phyt}$- and $P_{1361}$-gfp fusions abrogate U-induction (FIG. 9A-B). The CCNA_01353-CCNA_01352-CCNA_01351 operon encodes a phytase enzyme that confers U tolerance[162] and an uncharacterized response regulator and histidine kinase pair, while the CCNA_01361-CCNA_01362-CCNA_01363 operon encodes a PepSY superfamily protein and another uncharacterized response regulator and histidine kinase pair.

Figure 17:
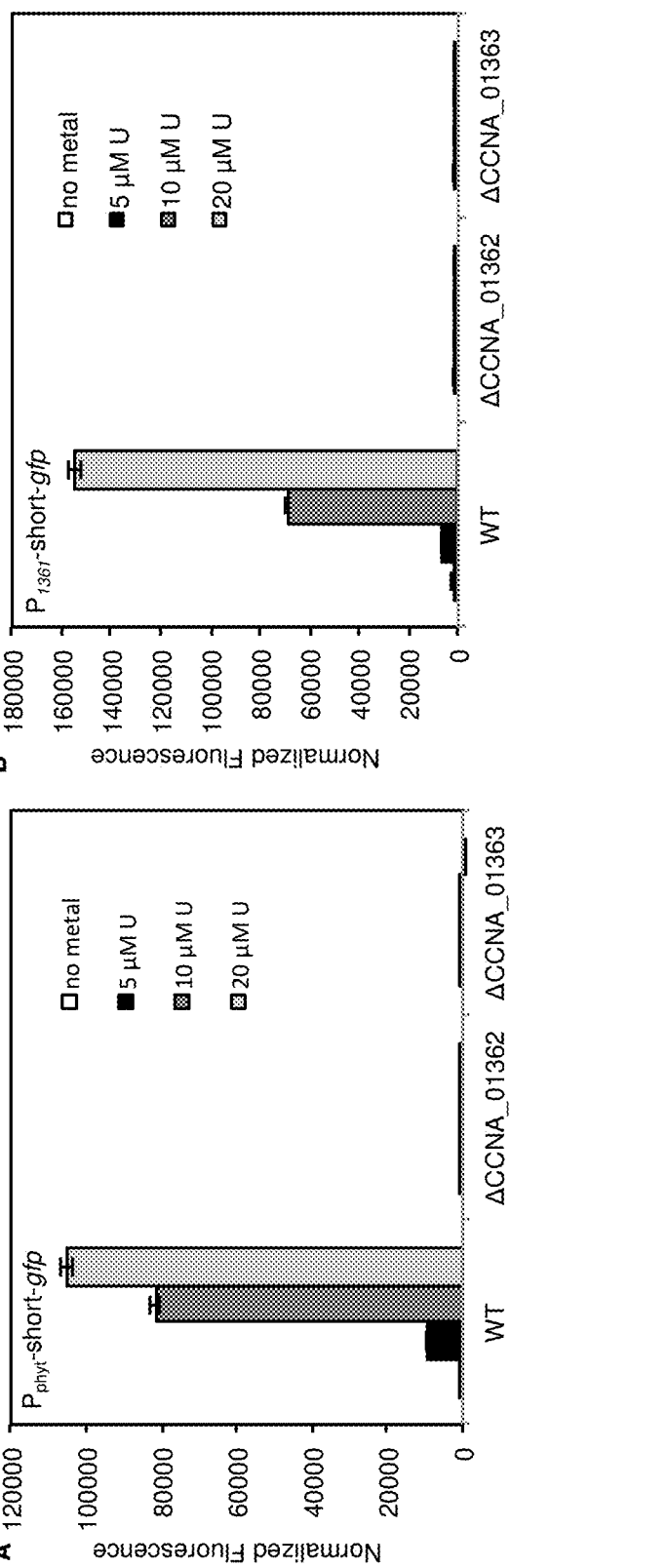
FIG. 17 shows graphs reporting quantification of exemplary fluorescence levels of a shortened $P_{phyt}$-gfp (FIG. 17 Panel A) and shortened $P_{1361}$-gfp (FIG. 17 Panel B) variants in response to U at 5 μM, 10 M or 20 M.
Figure 18:
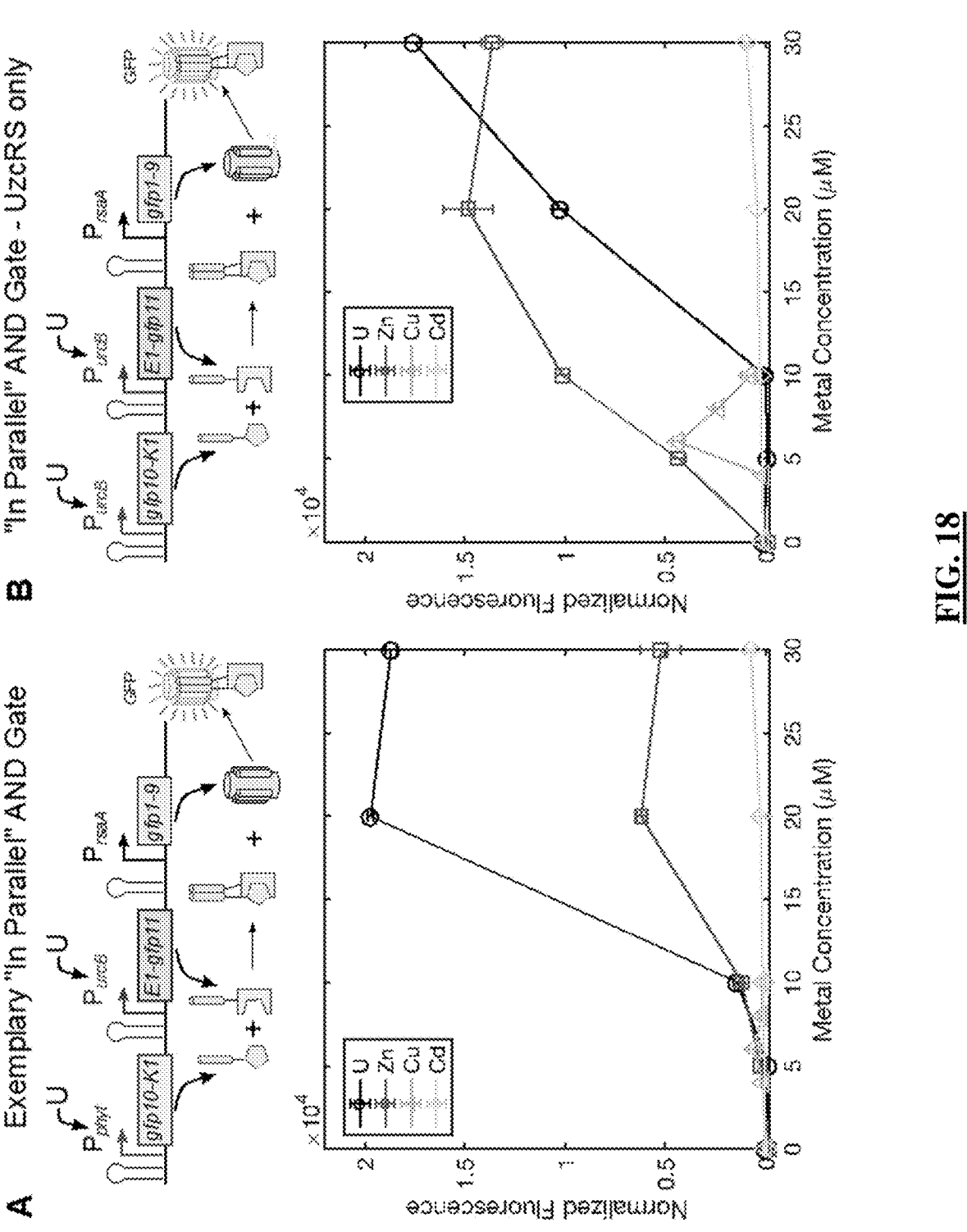
FIG. 18 shows schematics illustrating exemplary tripartite GFP U-sensitive genetic circuits together with graphs reporting quantification of exemplary GFP reporter fluorescence produced by the respective genetic circuits under the conditions indicated. In particular, FIG. 18 Panel A shows a schematic of the U-sensitive genetic circuit shown in FIG. 6 Panel B and FIG. 18 Panel B shows a schematic of a control circuit that incorporates input from only the UzcRS TCS, comprised in the host organism *C. crescentus* NA1000, upon exposure to U, Zn, Cu or Cd.
Figure 19:
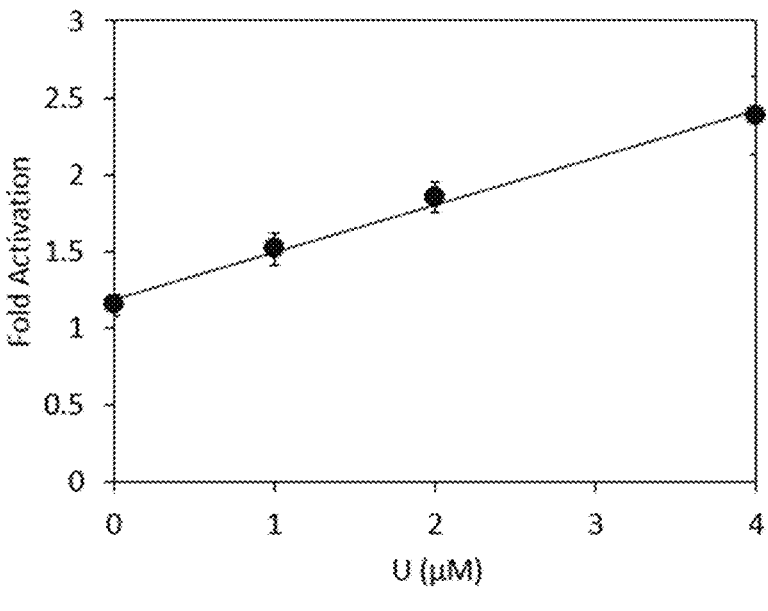
FIG. 19 shows a graph reporting exemplary data indicating the limit of U detection for the U biosensor described in FIG. 4 Panel B. Mid-exponential phase cells were washed twice in 10 mM Pipes pH 7 and then resuspended in 10 mM Pipes pH 7 containing uranyl nitrate. As shown in the graph, a linear response was observed for U concentrations in the low micromolar range.
Figure 20:
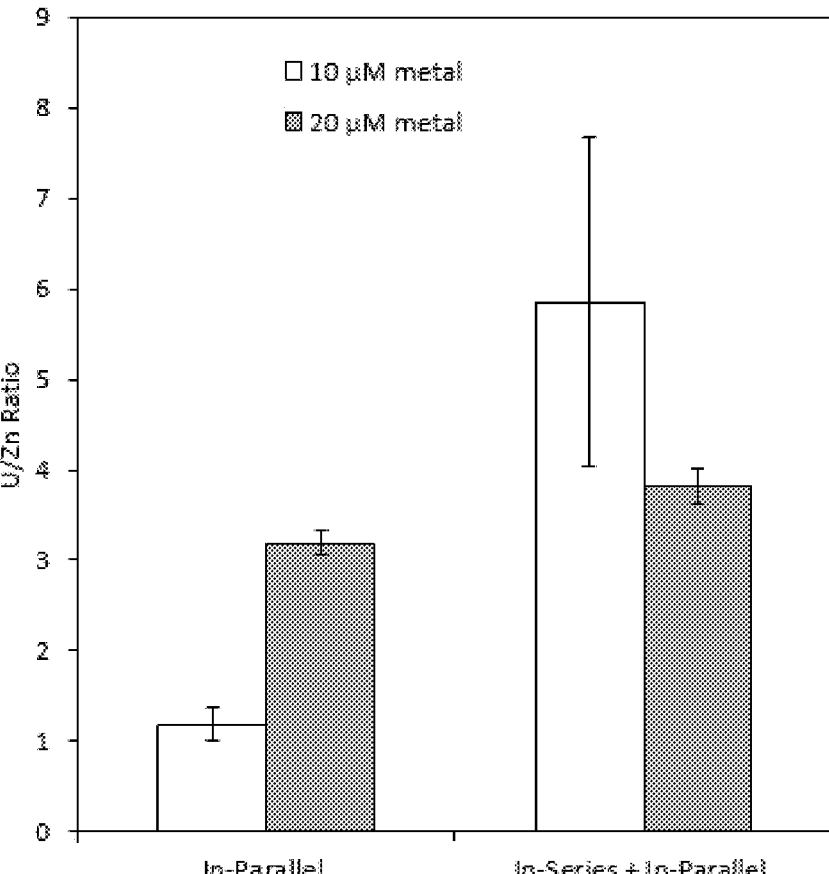
FIG. 20 shows a graph reporting exemplary data showing the ratio of the fluorescence output in response to 10 and 20 M of U and Zn for the "In-parallel" AND-gate shown in FIG. 6 Panel C and the combined "In-series" plus "in-parallel" genetic circuit shown in FIG. 14. Cells were grown to mid-exponential phase in M5G-G2P media, washed once with fresh media, then resuspended in fresh media containing the indicated metal concentration. Fluorescence was quantified following a three-hour exposure of cells to each metal concentration and normalized to the $OD_{600}$. The U/Zn ratio was calculated by dividing the normalized fluorescence with U by that with Zn.

This direct repeat binding site bears striking resemblance to the binding sites of OmpR/PhoB family response regulators. [169, 170] As such, the OmpR/PhoB-family response regulators CCNA_01351 and CCNA_01362, whose expression is governed by $P_{phyt}$ and $P_{1361}$, respectively, are potential candidates for the U-responsive regulator. Deletion of CCNA_01351 or the histidine kinase CCNA_01352 had no effect on U-dependent induction of either promoter (data not shown), consistent with the results of transcriptomics performed with both mutants during U exposure.[160] In contrast, deletion of CCNA_01362 or the histidine kinase CCNA_01363 abolished U-dependent induction of both promoters (FIG. 17A-B).

Figure 28:
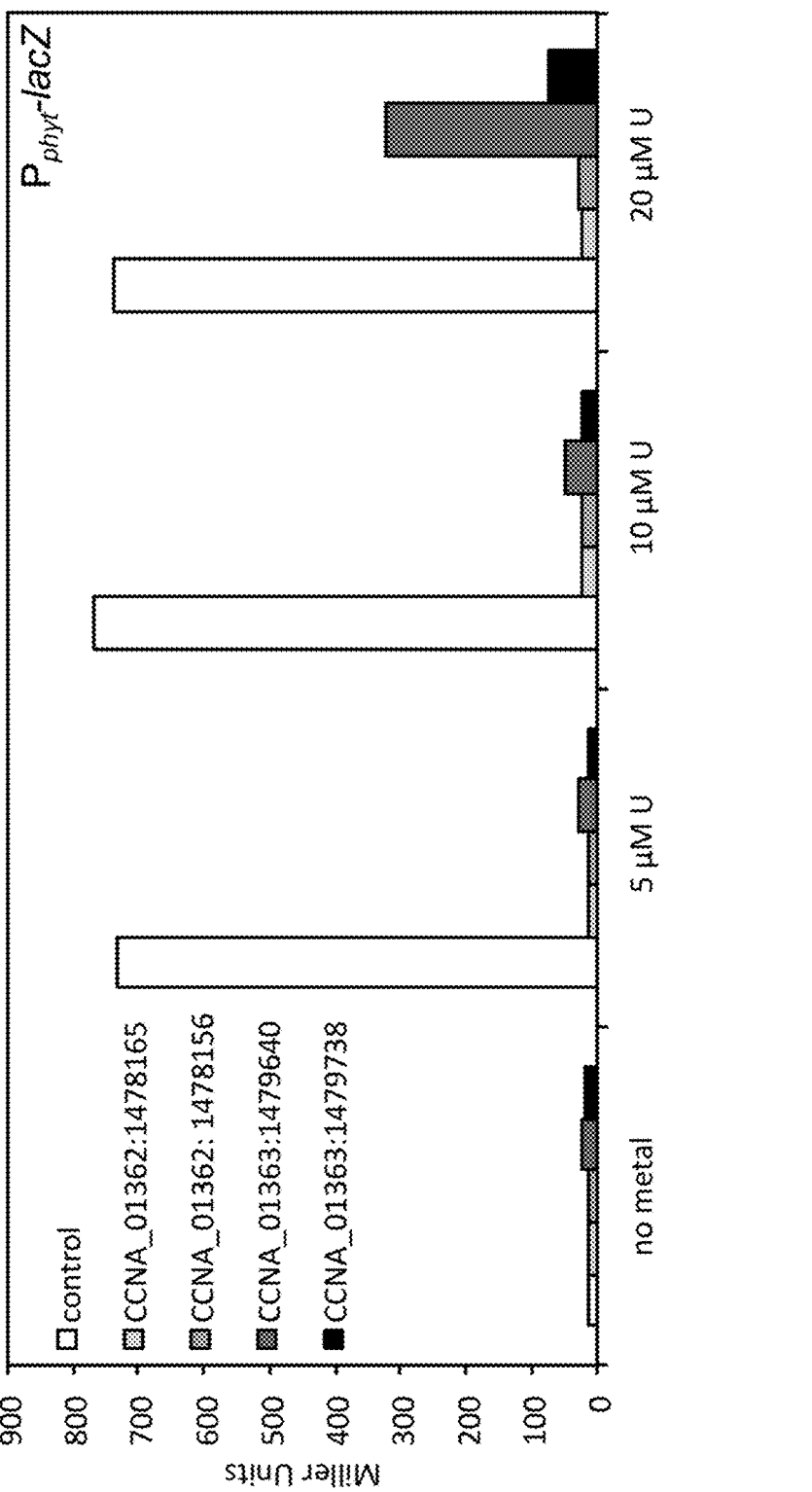
FIG. 28 shows diagrams illustrating the results of experiments showing that transposon insertions within CCNA_01362 and CCNA_01363 abrogate U-dependent induction of $P_{phyt}$. $P_{phyt}$-lacZ activity was assayed in strains containing transposons inserted within CCNA_01362 and CCNA_01363 using β-galactosidase assays. Error bars represent the standard deviation of triplicate measurements.

Furthermore, a forward genetic screen for mutants that failed to induce $P_{phyt}$-lacZ in response to U resulted in five transposons that mapped to unique locations within CCNA_01362 and CCNA_01363 (FIG. 28; Table 9), providing independent validation for a functional role of both proteins in U-dependent stimulation of $P_{phyt}$.

TABLE 9

| Transposons in CCNA_01362 and CCNA_01363 that abolished U-dependent induction of $P_{phyt}$-lacZ | | |
|---|---|---|
| Gene location | Chromosomal location | Number isolated |
| CCNA_01362 | 1478156 | 1 |
| CCNA_01362 | 1478165 | 4 |
| CCNA_01363 | 1479640 | 3 |
| CCNA_01363 | 1479645 | 3 |
| CCNA_01363 | 1479738 | 1 |

These proteins have been putatively named UrpR and UrpS (Uranium Responsive Phytase Regulator and Sensor, respectively), since this TCS strongly activates a gene encoding a phytase enzyme.

Figure 10:
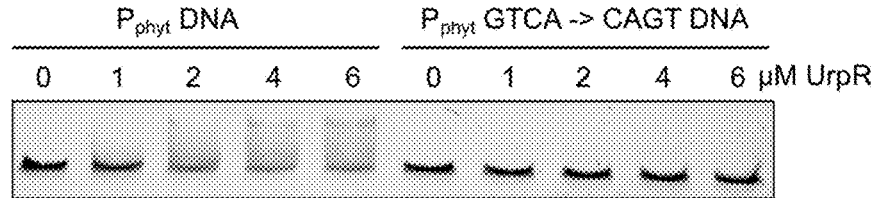
FIG. 10 illustrates the results of an electrophoretic mobility assay (EMSA) showing UrpR binding to wild type and mutant $P_{phyt}$ fragments. The mutant $P_{phyt}$ DNA ($P_{1361}$) contains a GTCA→CAGT mutation of DR2 (see FIG. 7B). The assays were performed with 50 nM 6-FAM-labeled DNA and UrpR, phosphorylated with carbamoyl phosphate. The concentrations indicate the total UrpR used in the assay. A representative example of three biological replicates is depicted.

To confirm that regulation by UrpR is direct, UrpR was purified, and its binding to $P_{phyt}$ was tested using an electrophoretic mobility shift assay. As expected, UrpR bound to $P_{phyt}$ in a concentration-dependent manner (FIG. 10). Binding was not observed to a $P_{phyt}$ fragment containing a 5'-GTCA-3' to 5'-CAGT-3' mutation at DR2 (FIG. 10), supporting the functional role of the direct repeat site in UrpR DNA binding. Collectively, these data suggest that the TCS comprised of UrpR and UrpS is the U-dependent activator of $P_{phyt}$ and $P_{1361}$, revealing a positive feedback loop within this regulatory system.

Example 14: UrpRS Exhibits Improved Metal Selectivity Compared to UzcRS

To test whether UrpRS functions independently of UzcRS with respect to U perception (a property that is important for its dual integration with UzcR in a synthetic U sensing pathway), the expression of $P_{phyt}$ and the UzcR-regulated promoter $P_{urcB}$ were tested in strains lacking the non-cognate TCS. The U-induction profile of a shortened $P_{phyt}$ reporter ($P_{phyt-short}$; diagrammed in FIG. 7A-B) was largely unaffected by deletion of uzcR or uzcS (FIG. 29A; FIG. 30), while the U-induction profile for $P_{urcB}$-gfp was unaffected by deletion of urpR or urpS (FIG. 29A; FIG. 30). Collectively, these data indicate that C. crescentus possesses at least two independent U-responsive TCS.

Figure 29:
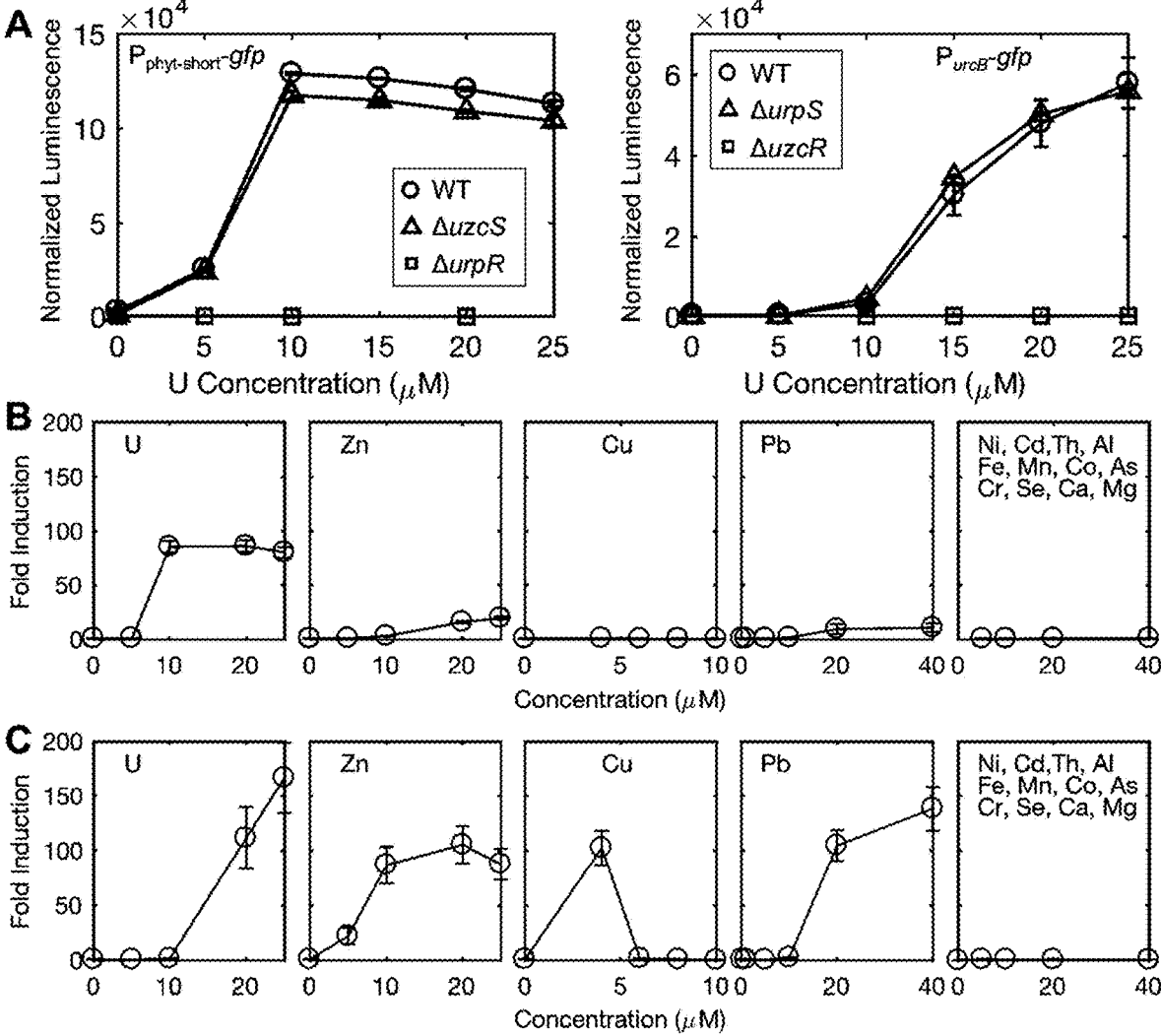
FIG. 29 shows diagrams illustrating the results of experiments showing metal selectivity of UrpRS and UzcRS in an exemplary embodiment. Panel A) Functional independence of UrpRS and UzcRS. U response curves of $P_{phyt}$-short-gfp and $P_{urcB}$-gfp reporters were determined by quantifying fluorescence following a two-hour exposure to a range of U concentrations in wild type *C. crescentus* and strains deleted for uzcS, urpS and the cognate response regulator. Error bars represent the average of biological triplicates. Metal selectivity profiles for $P_{phyt-short}$-gfp (panel B) and $P_{urcB}$-gfp (panel C). Reporter fluorescence was quantified following exposure to 16 metals. The furthest right plot depicts representative data for metals that failed to induce either promoter. Raw fluorescence values can be found in Table 10. Error bars represent the average of biological triplicates.
Figure 30:
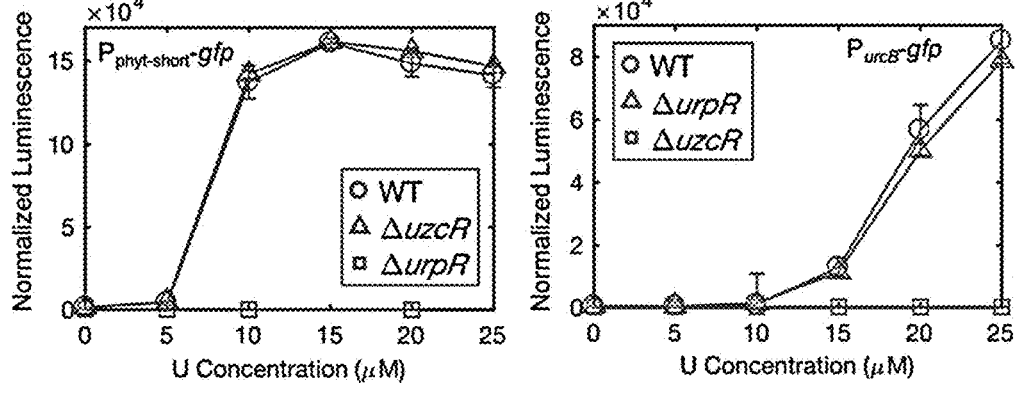
FIG. 30 shows diagrams illustrating the results of experiments showing in an exemplary embodiment functional independence of UrpRS and UzcRS. Fluorescence of a $P_{phyt-short}$-gfp and $P_{urcB}$-gfp were quantified following a two-hour exposure to a range of U concentrations in wild type *C. crescentus* and strains deleted for uzcR and urpR. Error bars represent the average of biological triplicates.

To determine the metal selectivity of UrpRS, $P_{phyt-short}$-gfp fluorescence was quantified following exposure to 16 metals of environmental relevance (FIG. 29B). To encourage metal solubility and thus bioavailability, minimal media containing glycerol-2-phosphate (G$_2$P) was employed as the sole source of phosphate. As a control, the metal selectivity of the $P_{urcB}$-gfp reporter was also tested (FIG. 29C). For both promoters, the strongest induction was observed in response to U; however, $P_{phyt-short}$ exhibited greater U sensitivity, resembling a switch-like activation response (FIG. 29A) that can likely be attributed to the strong positive auto-regulation within the UrpRS system. Most metals, including Th, a radionuclide that is part of the U decay chain and likely co-occurs with U, failed to induce either reporter (Table 10).

TABLE 10

Metal selectivity of UrpRS and UzcRS

| Metal | $P_{phyt}$-gfp Fold Induction | $P_{phyt}$-gfp std dev | $P_{urcB}$-gfp Fold Induction | $P_{urcB}$-gfp std dev |
|---|---|---|---|---|
| 5 μM U | 1.3 | 0.2 | 0.8 | 0.1 |
| 10 μM U | 85.7 | 5.1 | 1.7 | 0.3 |
| 20 μM U | 86.4 | 5.3 | 111.5 | 28.3 |
| 25 μM U | 80.5 | 5.0 | 166.7 | 32.0 |
| 5 μM Zn | 1.2 | 0.1 | 22.2 | 7.4 |
| 10 μM Zn | 3.2 | 0.3 | 87.0 | 16.7 |
| 20 μM Zn | 16.1 | 1.0 | 105.5 | 17.0 |
| 25 μM Zn | 19.7 | 1.3 | 87.6 | 14.0 |
| 4 μM Cu | 1.3 | 0.1 | 102.5 | 15.5 |
| 6 μM Cu | 0.9 | 0.2 | 1.8 | 0.5 |
| 8 μM Cu | 0.8 | 0.1 | 0.9 | 0.2 |
| 10 μM Cu | 0.8 | 0.1 | 0.4 | 0.3 |
| 20 μM Ni | 1.1 | 0.1 | 0.9 | 0.1 |
| 40 μM Ni | 1.3 | 0.1 | 0.7 | 0.3 |
| 20 μM Cd | 1.0 | 0.1 | 1.6 | 0.6 |

TABLE 10-continued

Metal selectivity of UrpRS and UzcRS

| Metal | $P_{phyt}$-gfp Fold Induction | $P_{phyt}$-gfp std dev | $P_{urcB}$-gfp Fold Induction | $P_{urcB}$-gfp std dev |
|---|---|---|---|---|
| 40 μM Cd | 0.9 | 0.1 | 1.9 | 0.4 |
| 5 μM Th(IV) | 1.0 | 0.1 | 0.8 | 0.1 |
| 10 μM Th(IV) | 1.0 | 0.1 | 1.1 | 0.3 |
| 20 μM Th(IV) | 1.0 | 0.1 | 0.8 | 0.1 |
| 40 μM Th(IV) | 1.0 | 0.1 | 1.0 | 0.2 |
| 1 μM Pb | 1.0 | 0.1 | 1.0 | 0.2 |
| 5 μM Pb | 1.1 | 0.1 | 0.6 | 0.3 |
| 10 μM Pb | 1.8 | 0.5 | 2.7 | 0.4 |
| 20 μM Pb | 9.6 | 4.7 | 104.7 | 14.2 |
| 40 μM Pb | 11.1 | 4.1 | 138.5 | 20.1 |
| 20 μM Al | 2.4 | 0.3 | 1.0 | 0.3 |
| 40 μM Al | 2.5 | 0.4 | 1.0 | 0.1 |
| 20 μM Fe(III) | 1.0 | 0.1 | 1.1 | 0.1 |
| 40 μM Fe(III) | 1.1 | 0.1 | 1.1 | 0.1 |
| 20 μM Fe(II) | 1.0 | 0.1 | 0.9 | 0.4 |
| 40 μM Fe(II) | 1.1 | 0.1 | 0.7 | 0.1 |
| 20 μM Mn | 1.0 | 0.1 | 1.1 | 0.4 |
| 40 μM Mn | 1.0 | 0.1 | 1.0 | 0.1 |
| 20 μM Co | 0.7 | 0.1 | 0.4 | 0.1 |
| 40 μM Co | 0.7 | 0.1 | 0.2 | 0.1 |
| 20 μM As | 1.0 | 0.1 | 1.0 | 0.2 |
| 40 μM As | 1.1 | 0.1 | 0.9 | 0.2 |
| 100 μM As | 1.0 | 0.1 | 1.2 | 0.3 |
| 20 μM Cr(VI) | 1.5 | 0.1 | 3.2 | 0.7 |
| 40 μM Cr(VI) | 1.5 | 0.1 | 2.6 | 0.6 |
| 20 μM Se | 0.9 | 0.1 | 0.9 | 0.1 |
| 40 μM Se | 0.9 | 0.1 | 0.8 | 0.1 |

Importantly, $P_{phyt-short}$ was unresponsive to Cu and only minimally responsive to Zn or Pb (FIG. 29B). In contrast, strong $P_{urcB}$ induction was observed with Zn, Pb, and within a narrow Cu range. The Pb-dependent induction of $P_{urcB}$ was surprising and contrasts with prior reports.[153, 163] It is suspected that the Pb induction likely reflects the higher initial Pb bioavailability in the presence of G2P compared to orthophosphate, given the low solubility of lead phosphate. [171] These data suggest that while UrpRS is not exclusively selective for U, it exhibits an improved metal selectivity profile compared to UzcRS.

Example 15: Construction of a U-Responsive AND Gate Pathway in C. crescentus

Given the distinct metal selectivity profiles and functional independence of UzcRS and UrpRS, it is expected that a combinatorial approach that incorporates the U-responsive functionality of both UrpRS and UzcRS will yield a whole-cell U sensor with enhanced specificity. Accordingly, the recently developed Tripartite GFP system[164] was used as a template to construct a U sensing AND gate. In this system, GFP is split into three parts (gfp10, gfp11 and gfp1-9) that interact to reconstitute active GFP when co-expressed; the synthetic K1 and E1 coiled-coils[172] were fused to the C-terminus of gfp10 and the N-terminus of gfp11, respectively, to mediate dimerization.[164] An advantage of the tripartite system is the low basal level of GFP fluorescence, ensuring a robust OFF state.

Figure 31:
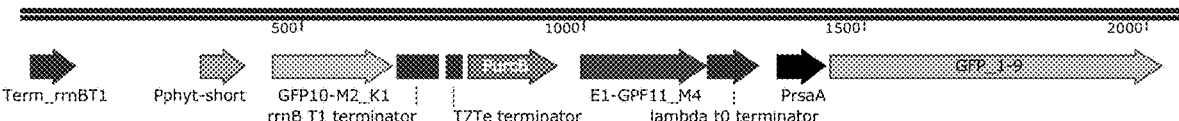
FIG. 31 illustrates a schematic of U-sensing AND gate configuration that was integrated at the chromosomal urcA locus. Details of AND gate construction and chromosomal integration are outlined in the methods sections.
Figure 32:
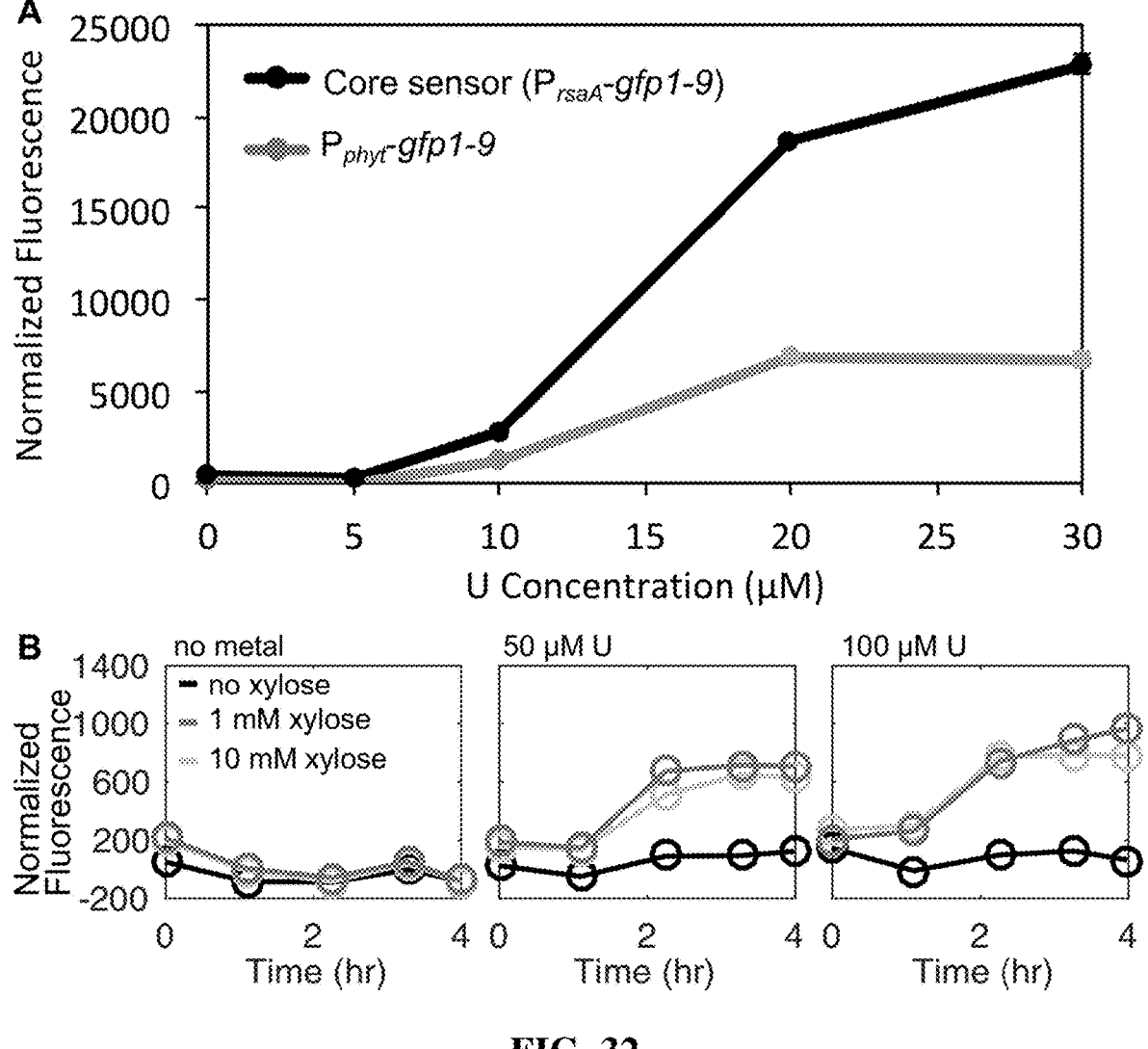
FIG. 32 shows diagrams illustrating the results of experiments showing in an exemplary embodiment U sensing AND gate variants with different mechanisms of gfp1-9 expression. Panel A shows the fluorescence output profile of the core sensor and a sensor variant with gfp1-9 expression driven by $P_{phyt}$ following a three-hour exposure to the indicated U concentration. Panel B shows the fluorescence output of a U-sensor variant with gfp1-9 expression driven by the xylose-inducible promoter $P_{xyl}$ as a function of time.

$P_{phyt-short}$ and $P_{urcB}$, which both exhibit low basal activity and a large U-dependent fold change, were used to drive expression of gfp]0-K1 and E1-gfp11, respectively. The expression of gfp1-9 was driven by the strong, constitutive rsaA promoter ($P_{rsaA}$)[4] in order to produce high GFP1-9 levels at all stages of growth (FIG. 14A; diagrammed in FIG. 31). Hereafter, this sensor configuration in an otherwise wild type (WT) strain background is referred to as the core sensor. Sensor variants where gfp1-9 expression was driven by the xylose-inducible promoter $(P_{xyl})$[6] or the UrpR-regulated $P_{phyt}$ were also tested, but exhibited a lower signal amplitude and were not pursued further (FIG. 32). Additionally, attempts to employ the hrp (hypersensitive response and pathogenicity) amplifier from *Pseudomonas syringae* as the AND gate template for U sensor construction by placing hrpR and hrpS under the control of $P_{phyt}$-short and $P_{urcB}$, respectively, and using $P_{hrpL}$ to drive gfp expression, did not result in a functional sensor.

Figure 33:
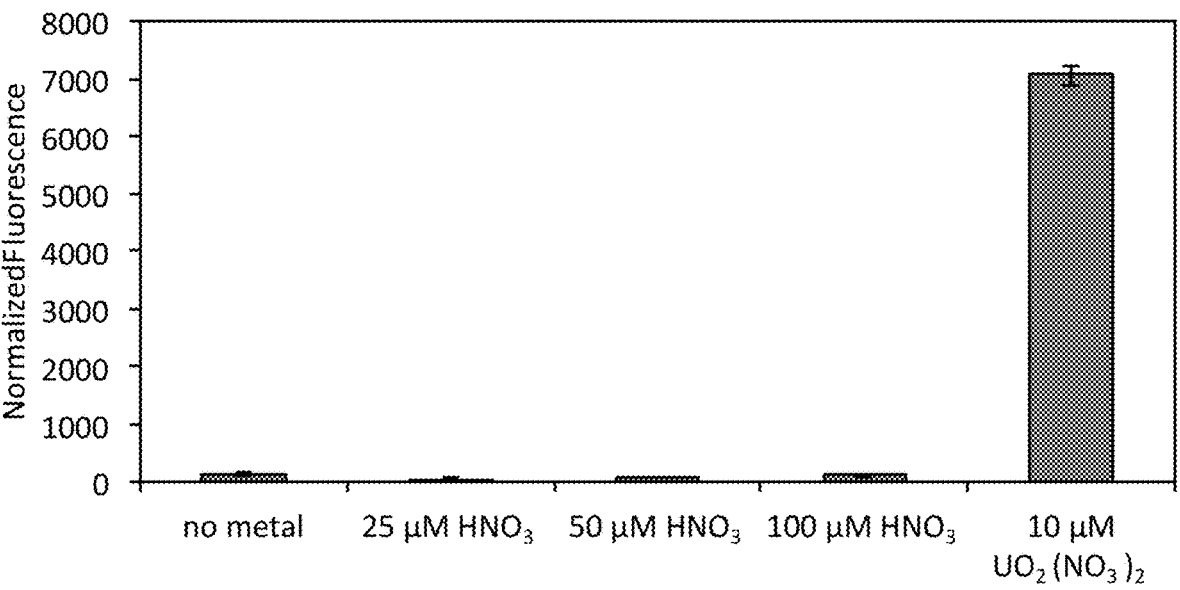
FIG. 33 shows a graph reporting that core sensor is not responsive to nitrate. Given the use of a uranyl nitrate stock in $HNO_3$ (100 mM $UO_2NO_3$ in 100 mM $HNO_3$) to characterize the U sensing performance of the core sensor, control experiments were conducted with $HNO_3$ nitrate alone. Relevant concentrations of $HNO_3$ failed to induce fluorescence, confirming that nitrate alone is not responsible for the core sensor output signal.

Initial characterization of the tripartite U sensor was performed in M5G $G_2P$, given the robust U-dependent induction of both $P_{phyt}$ and $P_{urcB}$ under these conditions and the lack of induction in growth media containing orthophosphate, where U bioavailability is low as a result of uranyl phosphate mineralization.[161, 173] Notably, the basal fluorescence output of the sensor was indistinguishable from a control strain lacking GFP1-9 expression, supporting a very low OFF state (FIG. 14B). Addition of uranyl nitrate, but not nitrate alone (FIG. 33), yielded a nonlinear fluorescence response curve that deviated from background at concentrations as low as 5 µM and plateaued at ~15 µM (FIG. 14B). The hypersensitivity of the U response curve was quantified by fitting the data with a Hill function. It is noted that this approach is semiempirical, and it is not used as a basis to derive insight on the mechanisms of the reactions occurring in the system. The model revealed a hill coefficient hypersensitive nature of the U response curve suggests that the core sensor is well poised as a qualitative YES/NO digital sensor of environmental U.

Importantly, U-dependent fluorescence was not observed with control sensor variants that lacked either a functional UrpR binding site in $P_{phyt-short}$ or gfp1-9 expression (FIG. 14B). Additionally, deletion of uzcR severely impaired, but did not completely abolish, U-dependent fluorescence (FIG. 14B). Since the data in FIG. 29A indicate that $P_{urcB}$ activity is abolished by uzcR deletion, the minor induction of sensor fluorescence in the ΔuzcR strain may reflect low-level transcriptional read-through of the transcription terminator separating $P_{phyt-short}$-gfp10-K1 and $P_{urcB}$-E1-gfp11 modules (diagramed in FIG. 31). Collectively, these data highlight the requirement for expression from all three promoters for a U-dependent fluorescent output.

Figure 34:
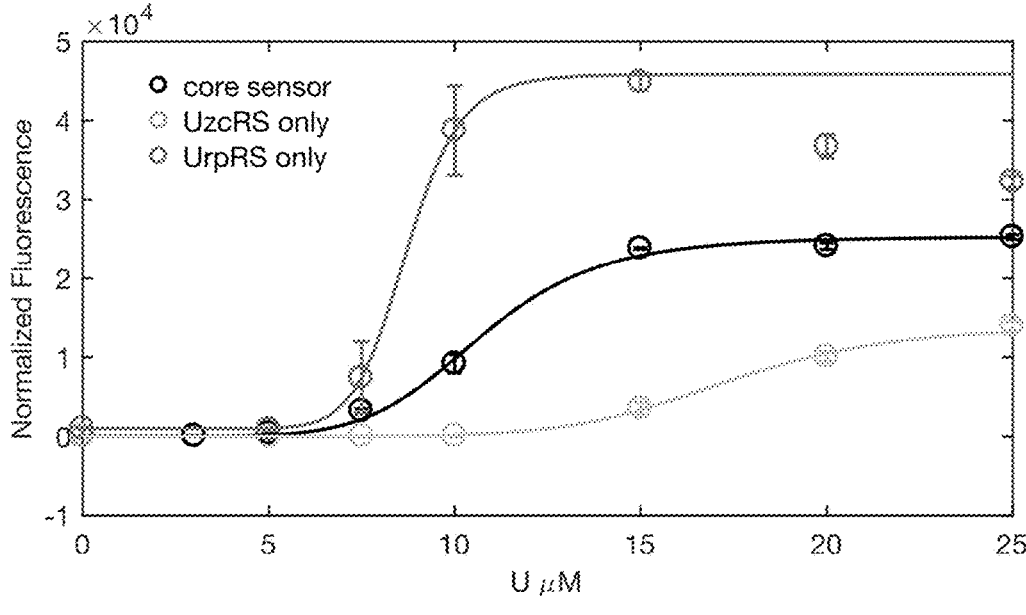
FIG. 34 shows in a graph the U response curves for the core sensor and control variants in which the expression of gfp10-K1 and E1-gfp11 components is driven by UzcRS or UrpRS alone. Fluorescence was quantified following a three-hour exposure to a range of U concentrations. The data were fit with a Hill equation to determine the U concentration that yields half-maximal fluorescence induction and the hill slope as an indicator of U sensitivity. Data points with diminished fluorescence output were not included in the curve fitting.
Figure 40:
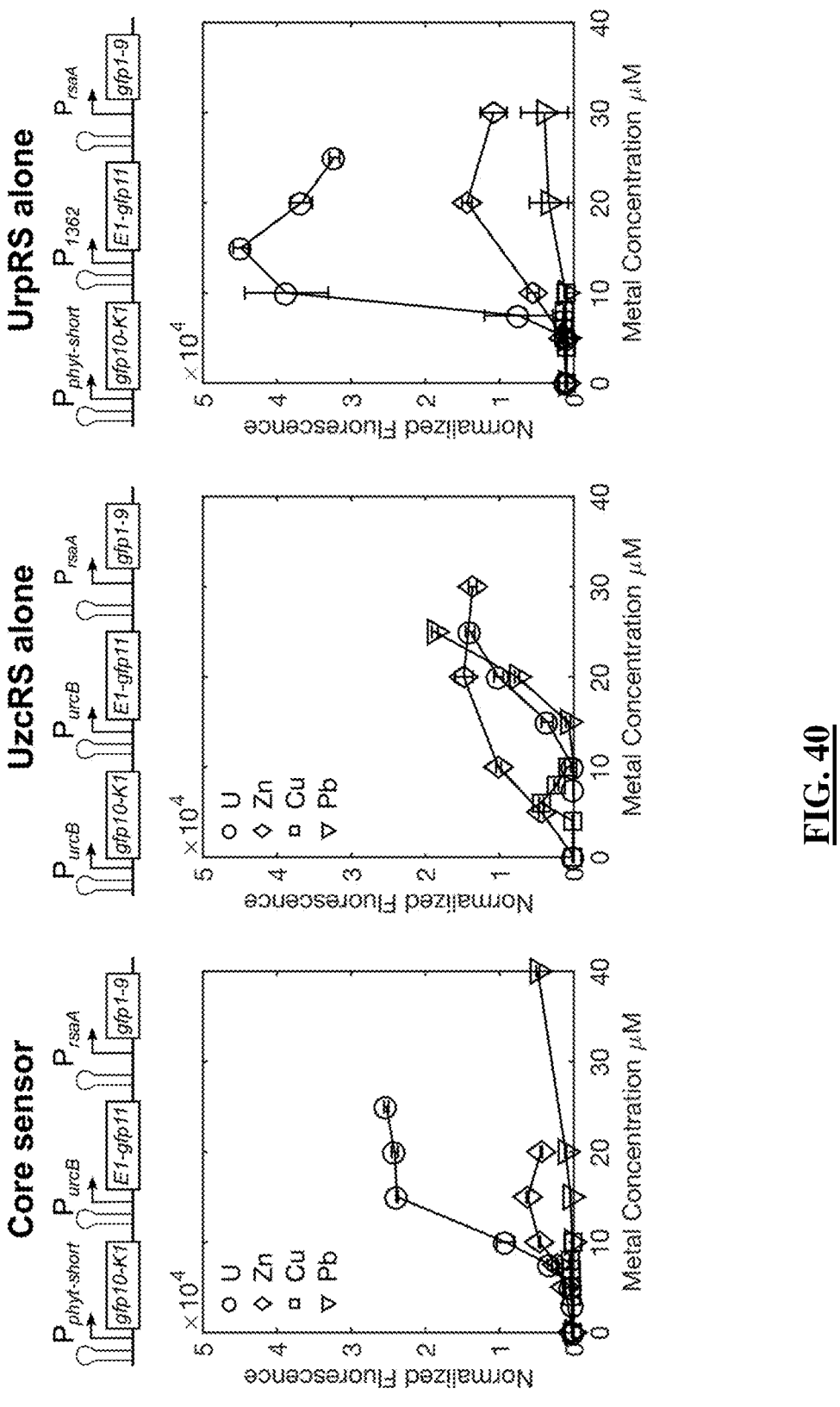
FIG. 40 shows a metal selectivity profile of core sensor and control variants. The top panel depicts simplified schematics of the core sensor and control variants in which the expression of gfp10-K1 and E1-gfp11 components is driven by UzcRS or UrpRS alone. The bottom panel depicts the U/Zn/Cu/Pb response curves for the core sensor and control variants. Fluorescence was quantified following a three-hour exposure to a range of metal concentrations. Error bars represent the average of biological triplicates.

Example 16: U-Sensing AND Gate Exhibits Improved Selectivity Relative to UzcRS Alone To characterize the selectivity of the core sensor, fluorescence was quantified in response to known inducers of either TCS and compared to results obtained with control sensor variants where either UzcRS or UrpRS governs the expression of both gfp10 and gfp11 (FIG. 40). Consistent with the U response curves for $P_{phyt-short}$- and $P_{rcB}$-gfp fusions (FIG. 29A), the control sensor driven by UrpRS alone yielded a U response curve with greater sensitivity compared to the sensor driven by UzcRS alone ($n^H$ of 12.5, K of 8.8 M compared to $n^H$ of 7.9 and K of 17.4 µM; Table 11; FIG. 34).

TABLE 11

| | Hill function fitting | | |
|---|---|---|---|
| Sensor Variant | Half maximal fluorescence (K) | Hill coefficient | $R^2$ |
| core sensor | 9.9 (0.1) | 7.6 (0.3) | 0.996 |
| constitutive UzcY | 6.3 (0.0) | 11.0 (0.6) | 1 |

TABLE 11-continued

| | Hill function fitting | | |
|---|---|---|---|
| Sensor Variant | Half maximal fluorescence (K) | Hill coefficient | $R^2$ |
| $P_{phyt}$-uzcY | 8.4 (0.1) | 9.5 (0.2) | 1 |
| UzcRS only | 17.4 (0.6) | 7.9 (0.3) | 0.995 |
| UrpRS only | 8.8 (0.7) | 12.5 (1.1) | 0.999 |

Figure 35:
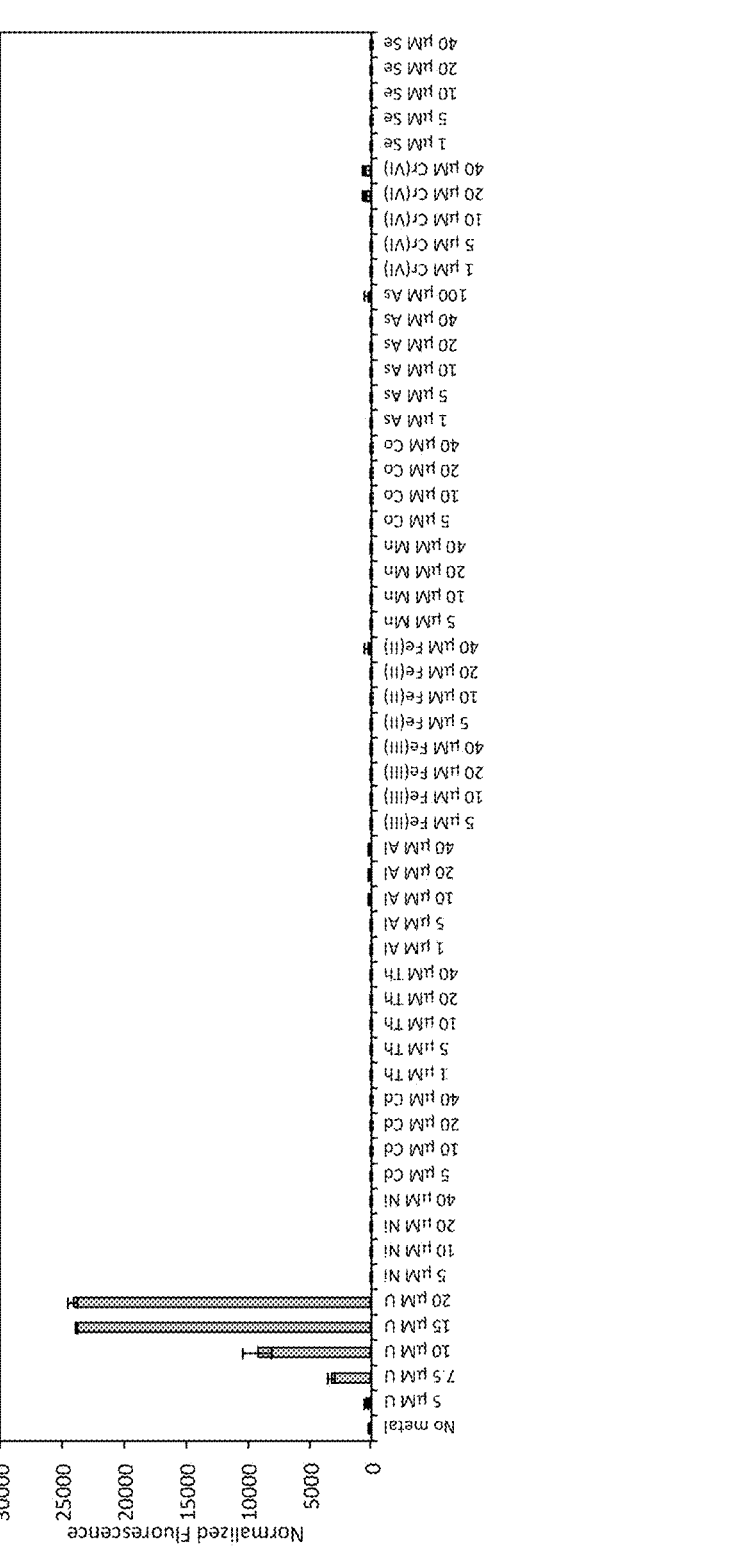
FIG. 35 shows diagrams illustrating the results of experiments showing metal selectivity profile of a core sensor. Fluorescence was quantified following a two-hour exposure to each metal. Error bars represent the average of biological triplicates.
Figure 37:
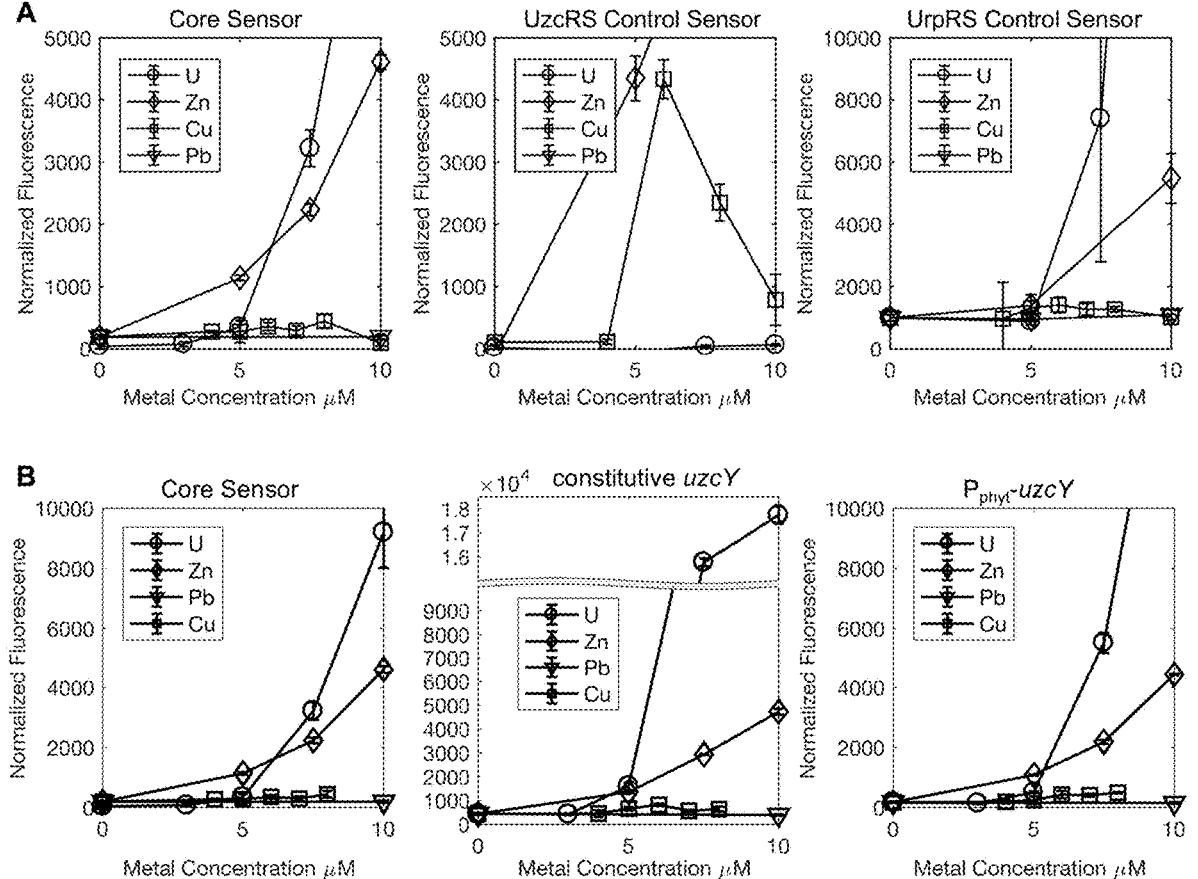
FIG. 37 shows a zoomed in version of the U/Zn/Cu/Pb response curves for the core sensor, control variants, and uzcY amplifier variants. In particular, FIG. 37 Panel A shows the curves for the Core Sensor, UzcRS Control Sensor and UrpRS control Sensor.

As expected, the core sensor was unresponsive to Ni, Cd, Th, Al, Fe(III), Fe(II), Mn, Co, arsenate, Se, and chromate (FIG. 35). The core sensor and the sensor variant driven by UrpRS alone were also unresponsive to Cu, in contrast to the sensor driven exclusively by UzcRS (FIG. 40). Critically, the sensitivity of the core sensor to Zn and Pb was significantly diminished relative to the UzcRS control; high Pb concentrations (greater than 20 uM) were required for weak fluorescence induction while the Zn-induced fluorescence was reduced relative to U for every tested concentration. Despite the improved selectivity for U, low Zn concentrations (5 µM Zn) yielded a fluorescence response in the core sensor that exceeded the U response (FIG. 37). Nevertheless, the lack of Cu responsiveness and the weakened Zn/Pb responsiveness of the core sensor relative to a sensor constructed with UzcRS alone highlights the selectivity improvement of the AND gate approach.

Example 17: Integration of UzcY Signal Amplifier Improves U Sensitivity and Selectivity A notable limitation of this AND gate approach is that the improved selectivity comes at a cost to U sensitivity in the low micromolar range; incorporation of the less sensitive UzcRS TCS yielded a sensor with lower sensitivity compared to the control sensor driven by UrpRS alone (FIG. 34). Notably, swapping the UzcRS-regulated $P_{urcB}$ promoter with $P_{urcA}$, a promoter that is highly induced by UzcR and sensitive to low UzcR-P concentrations, failed to significantly improve sensor sensitivity (Data not shown). This suggests that simply swapping $P_{urcB}$ with an alternative UzcR-regulated promoter is unlikely to remedy the sensitivity limitation.

As an alternative approach to improve the coupling and matching of the UzcRS and UrpRS inputs, the use of a signal amplifier module was considered to boost the sensitivity of UzcRS. While the hrp (hypersensitive response and pathogenicity) amplifier from *Pseudomonas syringae* appeared to be a logical choice given its impressive ability to increase the sensitivity and output dynamic range of the ArsR-based arsenic sensor, it was unable to generate a functional U sensor using hrpR, hrpS, and $P_{hrpL}$ components in *C. crescentus*. Instead, the recently identified membrane protein UzcY that functions as a native signal amplifier for the UzcRS system was leveraged. Under normal growth conditions, uzcY expression is silenced by the MarR family regulator $MarR_1$ (CCNA_03498) and has no effect on UzcRS activity. However, when UzcY expression is induced by deleting $marR_1$, the sensitivity of UzcRS to its metal inducers is enhanced. The signal amplification mechanism was incorporated within the core sensor by either deleting $marR_1$, which yields a constitutive amplifier function, or by swapping the native uzcY promoter with the UrpRS-regulated $P_{phyt-short}$ (FIG. 36A), such that UzcY levels are modulated in a U-concentration dependent manner.

Figure 36:
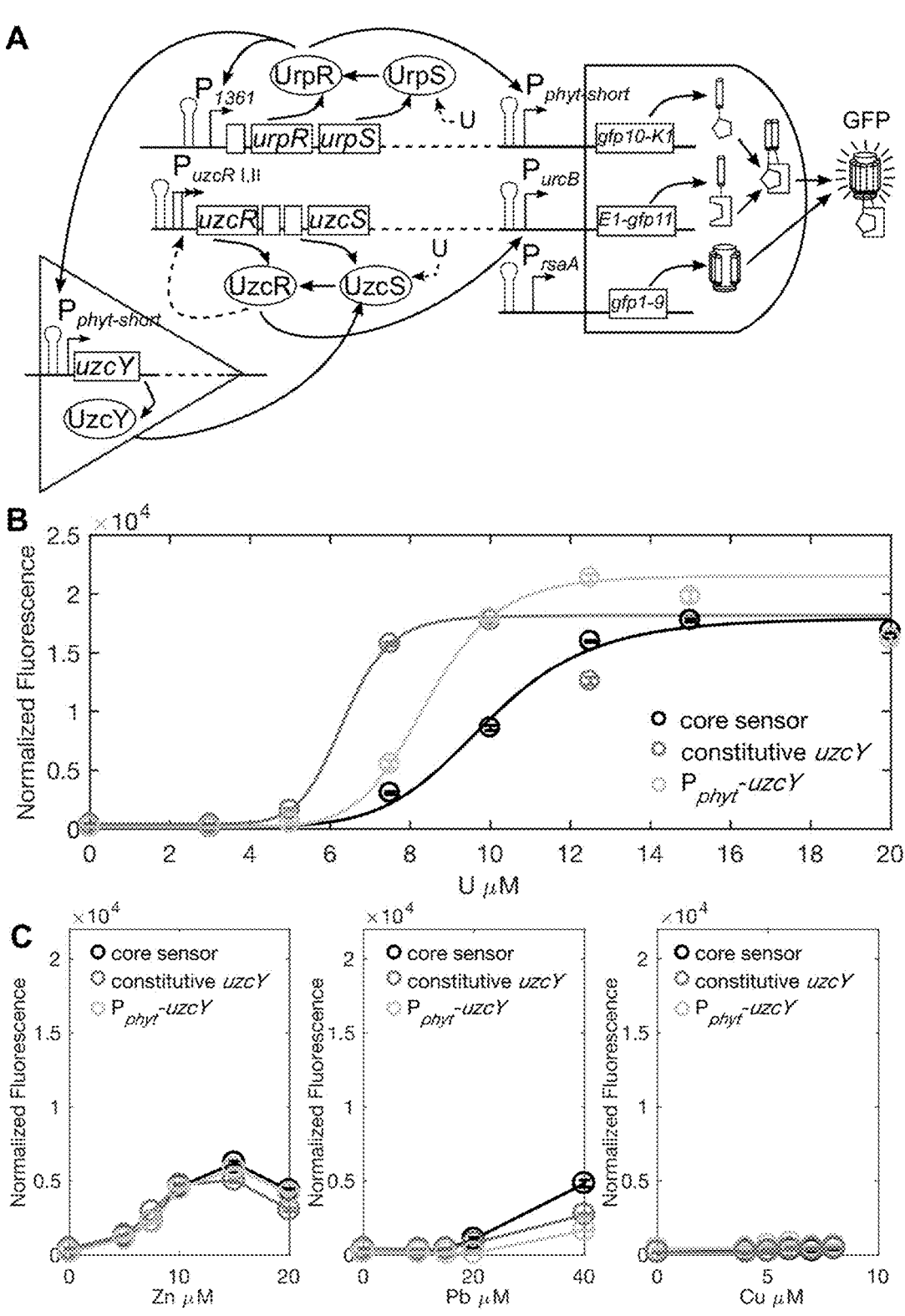
FIG. 36 shows graphs reporting incorporation of a signal amplifier module within the core sensor circuitry. Panel A: schematic for the integration of the UzcY signal amplifier within the U-sensing AND gate. In this variant, uzcY is placed under the control of the U-specific promoter $P_{phyt}$-short such that the signal amplification is restricted to conditions of U exposure. Panel B: The fluorescence output of the core sensor and signal amplifier variants following a three-hour exposure to a range of U concentrations. The data were fit with a Hill equation to determine the U concentration that yields half-maximal fluorescence induction and the hill slope as an indicator of U sensitivity. Signal amplifier data points with diminished fluorescence output were not included in the curve fitting. Panel C: The fluorescence output of the core sensor and signal amplifier variants following a three-hour exposure to a range of Zn, Pb, and Cu concentrations. Error bars represent the average of biological triplicates.

Constitutive UzcY expression significantly enhanced the U sensitivity of the core sensor in the low U concentration range (5-10 μM), yielding a U-dependent fluorescence profile with comparable sensitivity ($n^H$ of 11, K of 6.3 μM; FIG. 36B; Table 11) to the sensor driven exclusively by UrpRS alone ($n^H$ of 12.5; K of 8.8 μM). A diminished fluorescence output was observed at U concentrations above 10 μM, and may reflect reduced tolerance of the $\Delta marR_1$ strain to U toxicity compared to WT as was previously observed for Zn. Placing uzcY under the control of $P_{phyt-short}$, and, thus, conditionally restricting UzcY function to conditions of UrpRS stimulation, improved sensitivity ($n^H$ of 9.5, K of 8.4) in the 7.5-12.5 M range, but not to the same degree as constitutive uzcY expression (FIG. 36B). Importantly, neither amplifier configuration altered the Zn-, Cu-, or Pb-dependent induction profile of the core sensor (FIG. 36C). By enhancing U sensitivity without affecting Zn sensitivity, the expression of UzcY significantly improved the U to Zn output ratio in the low concentration range (5-10 μM; FIG. 37).

Collectively, these data suggest that in M5G G2P, integration of the UzcRS-specific signal amplifier UzcY overcame the sensitivity limitations of the UzcRS TCS, and enhanced the selectivity for U compared to the core sensor. While the sensitivity and selectivity of this amplified sensor are comparable to the sensor driven by UzcRS alone, the use of a combinatorial sensing approach is expected to be beneficial for minimizing core sensor cross-reactivity with yet unidentified inducers of UrpRS. This is based on the expectation that UrpRS is directed to detect a stress that is likely to be encountered in the oligotrophic freshwater environment of this bacterium.

Example 18: Whole-Cell U Sensor Detects as Low as 1.0 PM in Groundwater

To test the efficacy of the sensor to detect U in ground water, samples from three distinct locations were obtained from LLNL site-300, a high-explosives test facility in the Altamont Hills of California where ground water concentrations of U exceed the EPA MCL. Quantification of the heavy metal content of each sample using ICP-MS or ICP-OES revealed U concentrations that range from 1.0 to 1.24 μM (238-295 ppb; Table 12), representing a challenging test for the whole-cell sensor given the ~5 μM detection limit observed in M5G G2P medium. The trace metals Zn, Pb, Cu, Cd, and Cr were either undetectable or in the low nanomolar range in all samples (Table 12), and thus not expected to affect sensor performance.

TABLE 12

Heavy metal concentrations in ground water samples

| Sample Site | U (μM) | Zn | Pb | Cu | Cd | Cr |
|---|---|---|---|---|---|---|
| Well W-815-2621 | 1.01 (0.02) | <150 nM | 6 nM | 13 nM | <9 nM | <19 nM |
| Well W-812-01 | 1.24 (0.02) | <150 nM | 5 nM | 11 nM | <9 nM | <19 nM |
| Well W-6C | 1.09 (0.00) | <150 nM | <5 nM | 8 nM | <9 nM | <19 nM |

Figure 38:
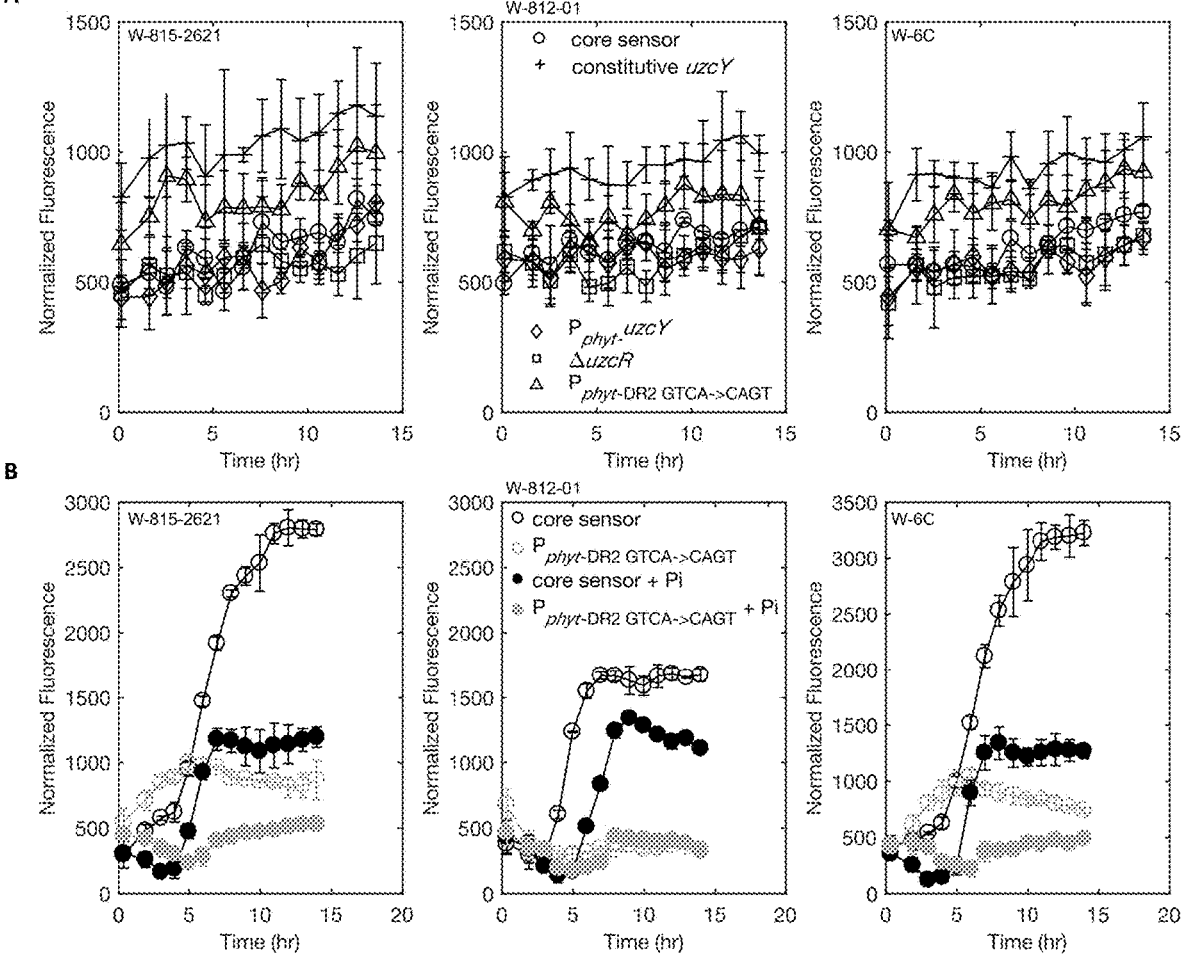
FIG. 38 shows graphs reporting fluorescence output of sensor variants in ground water samples without nutrient supplementation.
Figure 39:
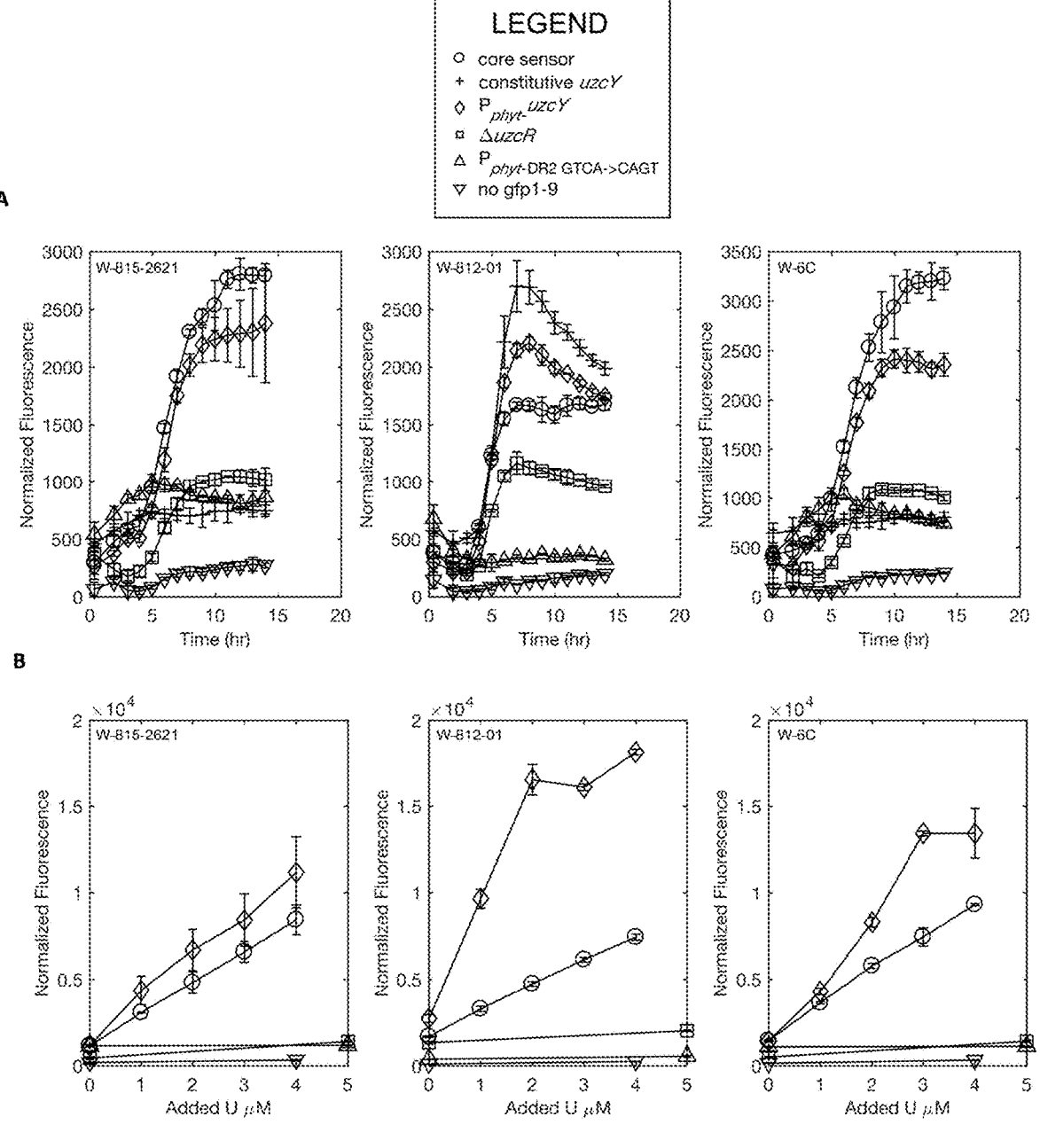
FIG. 39 shows detection of U in ground water samples in an exemplary embodiment.

The fluorescence output of the core sensor, UzcY amplifier variants, and negative controls lacking UzcRS, UrpRS, or gfp1-9 input were monitored as a function of time in the site-300 samples with and without growth nutrient supplementation. Exposure of the sensor strains to unmodified site-300 samples yielded no detectable increase in fluorescence and no cell growth (FIG. 38A; Data not shown). In contrast, supplementation with glucose, glycerol-2-phosphate (P source), and ammonium chloride (N source) together, but not glucose alone (data not shown), enabled cell growth and yielded a detectable increase in fluorescence for the core sensor within six hours of exposure to each sample (FIG. 39A). The fluorescence induction of the core sensor was significantly reduced in all samples when G2P was replaced with orthophosphate, which reduces U bioavailability (FIG. 38B). For samples 1 and 3 (~1 μM U), the $P_{phyt-short}$-uzCY amplifier variant yielded a fluorescence induction profile with slightly lower amplitude compared to the core sensor, while the constitutive amplifier failed to produce an output that differed from the negative controls (FIG. 39A). Future efforts will seek to optimize the constitutive level of UzcY to improve this sensor variants performance in environmental samples. In contrast, in sample 2 (~1.24 μM U), both signal amplifier variants yielded a fluorescence output signal that exceeded that of the core sensor (FIG. 39A), suggesting that UzcRS is limiting U sensor sensitivity in sample 2. Lastly, compared to the negative controls lacking a UrpR binding site or gfp1-9 expression, the $\Delta uzcR$ mutant yielded a fluorescence induction profile with similar kinetics, but lower signal amplitude compared to the core sensor. This result suggests that while $P_{urcB}$-E1-gfp11 is incompletely insulated from upstream UrpRS-mediated transcriptional activity, the function of both TCS is required to produce the fluorescence response of the core sensor in the ground water samples.

To further confirm U detectability in the ground water samples, uranyl nitrate was added in small, incremental amounts (1 uM increments), and fluorescence was quantified following a six-hour exposure (FIG. 39B). The rational is that if U is responsible for the fluorescence induction of the whole-cell sensors then small, incremental U additions should further boost sensor fluorescence. A nearly identical linear increase in fluorescence as a function of U concentration was observed for the core sensor in all three ground water samples. The $P_{phyt-short}$-uzCY amplifier variant yielded a comparable fluorescence output as the core sensor in sample 1, but enhanced the signal amplitude for all U concentrations in samples 2 and 3, supporting its ability to increase sensitivity in an environmental context. Collectively, these data confirm the functionality of the AND gate sensor to detect U in environmental samples and support a lower limit of detection for U of ~1 M (~238 ppb). This result is in agreement with the ~0.5 M detection limit reported for the UzcRS-regulated $P_{urcA}$-gfpUV sensor[163] and comparable with other field-portable U detection methodologies such as gamma spec and X-ray fluorescence. While additional work will be required to achieve a detection limit on par with the EPA MCL (30 ppb), the current sensitivity of the AND gate sensor is well suited as a screening mechanism (e.g., yes/no) for elevated U concentrations in regions with known or suspected anthropogenic activities.

The finding that cell growth and U solubility are required for robust U detection has important implications for further sensor development. The inability of the biosensor to detect insoluble forms of uranyl (e.g., uranyl phosphate minerals) may be exploited as a mechanism to distinguish natural from anthropogenic U since natural U commonly occurs in the form of insoluble minerals,[37] and aqueous phosphate concentrations are typically very low (<10 ppb).[34] To circumvent the U-Pi incompatibility, the organophosphate G2P was employed that serves the dual function of providing a phosphate source for cell growth while maintaining initial U solubility through complexation.[161, 173] Since the physicochemical form—or speciation of U—is dependent on the geochemical conditions and strongly influences bioavailability, and consequently the detectability by this biosensor, addition of G2P may be an effective means of conditioning the environmental samples for U detection. Evaluating this hypothesis, and ultimately, the utility of the sensor for environmental monitoring, will require systematic characterization of the solution matrix composition. Nevertheless, given the requirement for nutrient supplementation, it is expected that the path toward a fieldable sensor will entail encapsulation of the whole-cell sensor within an integrated detection device that maintains cells in an active state of growth and automates sampling and solution conditioning (e.g., addition of G2P) for detection. Recent efforts have yielded promising results for integrating cell sensors into field-applicable autonomous devices.[137, 138, 174]

By identifying and integrating two independent, U-responsive TCS within a synthetic AND gate circuit, a selective U-sensing functionality was developed in *C. crescentus*. The results highlight the value of a combinatorial approach for selective detection of compounds for which there are no known evolved regulators. This approach is expected to be generalizable and to drive the development of additional, bio-based modules for environmental toxin detection.

Example 19: Naturally Occurring Fluoride Sensing Riboswitches and Related Consensus Sequence The Rfam database was queried to identify naturally occurring F-sensing riboswitches comprising a crcB motif. [00528]2138 fluoride riboswitch sequences were identified and aligned and conserved nucleotides identified from a gapped alignment as illustrated in FIG. 43, which shows the conserved nucleotides in naturally occurring Fluoride sensing riboswitches.

The sequences of the exemplary fluoride sensing riboswitches from the Rfam database are reported in Appendices I and II incorporated herein by references in their entirety.

Example 20: Establishing a Fluoride-Detection Capability in *C. crescentus*

Environmental detection of UF6- or the more stable hydrolysis product $UO_2F_2$, which is rapidly formed when atmospheric $UF_6$ reacts with water vapor [29] strongly suggests an enrichment program. A bacteria-based $UO_2F_2$- sensor will be developed by integrating and optimizing a fluoride-sensing functionality within the engineered whole-cell U biosensor.

Figure 44:
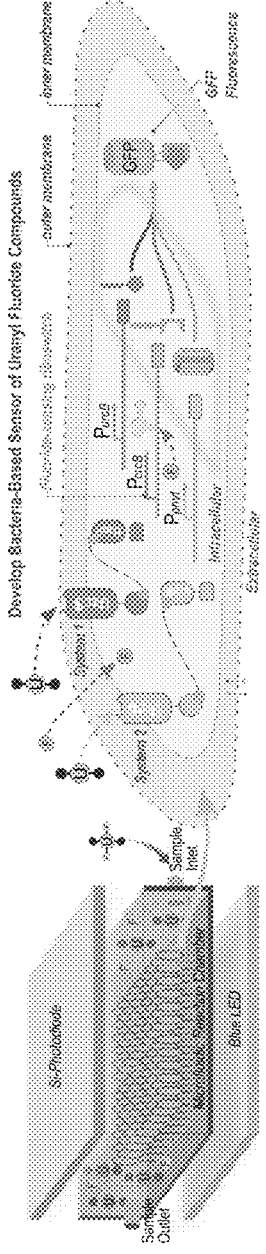
FIG. 44 shows a schematic illustration of a design of a bacteria-based sensor of uranyl fluoride products.

FIG. 44 shows a schematic illustration of an approach which will be used to develop a bacteria-based sensor of uranyl fluoride products. Using a synthetic biology approach, uranium- and fluoride-detection components are expected to be integrated and optimized within *C. crescentus* (right panel) and the $UO_2F_2$ detection performance under aqueous conditions systematically characterized. The left schematic depicts a foreseeable application of the whole cell sensor: autonomous environmental monitoring for aqueous $UO_2F_2$ species by a *C. crescentus* monolayer biofilm.

Example 21: Construction of a crcB-mCherry Fusion and Test Performance in *C. crescentus*

To establish a fluoride detection capability in *C. crescentus*, the fluoride sensing crcB riboswitch [102] will be engineered to control the expression of a fluorescent reporter (e.g., mCherry) such that fluoride perception leads to cell fluorescence. Initial sensor strains will be built with the crcB motifs from three distinct bacteria, including the well-characterized crcB motifs in *P. syringae* DC3000 and *Bacillus subtilis* [102] and an uncharacterized crcB motif from *Sphingomonas* sp. MM-1. *Sphingomonas* sp. MM-1 represents a particularly promising option since this bacterium is closely related to *C. crescentus* and possesses similarly high genomic G+C content (6×%), minimizing compatibility risks with the *C. crescentus* transcriptional machinery. Additionally, despite the lack of biochemical characterization, the function of the *Sphingomonas* sp. crcB motif in fluoride sensing is supported by its homology with characterized crcB riboswitches [Pfam database [109]] and its genomic location upstream of a fluoride exporter.

To accomplish a targeted integration of crcB riboswitches within *C. crescentus*, all crcB-mCherry reporters will be integrated within the *C. crescentus* chromosome. mCherry fluorescence will be quantified in a high-throughput (96-well format) manner over a range of NaF concentrations. Then, the fluoride selectivity will be characterized using commonly encountered anions (e.g., $Cl^-$, $NO_3^-$, $SO_4^{2-}$, $PO_4^{3-}$).

Based on prior biochemical characterization of the *P. syringae* crcB riboswitch [102], we expect the crcB-mCherry reporters to exhibit high fluoride selectivity. Each sensor will be evaluated based on the detection limit, sensitivity, selectivity, dynamic range, and signal amplitude with the best performing crcB-mCherry reporter used for subsequent studies.

Figure 45:
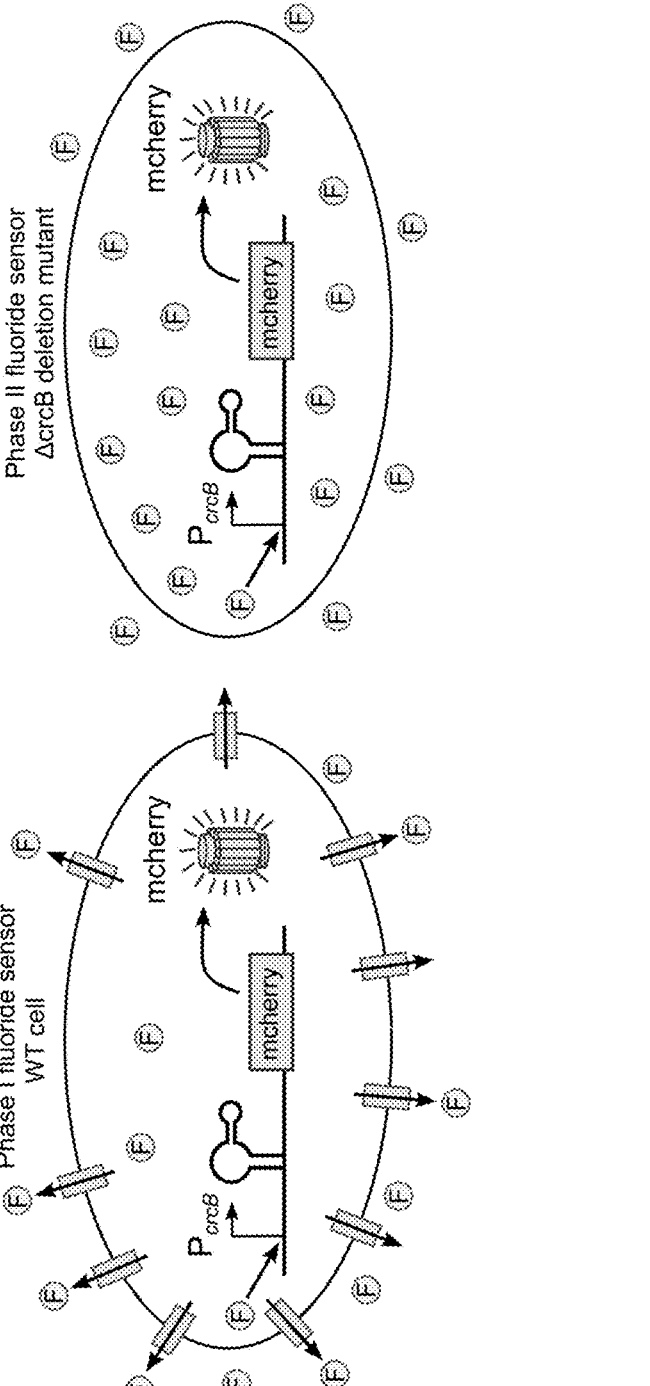
FIG. 45. shows a schematic illustration of a design to integrate and optimize a fluoride-detection capability in *C. crescentus* to provide a $UO_2F_2$ biosensor herein described.

FIG. 45 shows a schematic illustration of the approach. (Left) Phase I fluoride sensor: crcB-mCherry fusion built in wild type strain (Right). Phase II fluoride sensor: crcB-mCherry fusion built in strain deleted for fluoride export (ΔcrcB). Deletion of the crcB gene in *E. coli* improved the detection limit of a crcB-lacZ reporter by over 100-fold [102]. As such, this approach is expected to yield a fluoride-sensing capability that, when coupled with a U-sensing component herein described, will enable $UO_2F_2$ detection by *C. crescentus*.

Example 22 Reduction of the Fluoride Detection Limit by Manipulating the Expression Levels of the Native Fluoride Detoxification System/s in *C. crescentus*

*C. crescentus* possesses a putative fluoride ion transporter (CrcB) and withstands high mM concentrations of fluoride, suggesting native mechanism/s of fluoride detoxification. Prior data in *E. coli* indicate that the CrcB fluoride exporter functions to maintain low intracellular fluoride concentrations, adversely affecting the detection limit of the colorimetric crcB reporter (~1 mM). As such, the detection limit of phase 1 fluoride sensors development is expected to be significantly higher than the detection limit of our U sensor (~2 μM), and thus unlikely to be acceptable for nuclear effluent detection.

Accordingly, an analogous approach will be implemented as what allowed *E. coli* to yield a 100-fold improvement in the fluoride detection limit (sub 10 μM) [102]. Specifically, the function of the fluoride ion exporter will be abolished by deleting the crcB gene (encodes the CrcB fluoride exporter) in a strain containing the crcB-mCherry reporter (FIG. 45). Subsequently, crcB-mCherry fluorescence will be quantified over a range of NaF concentrations.

An analogous reduction in the F– detected limit in *C. crescentus* or other potential host organisms is expected be achieved through deletion of the crcB homolog or eriC$^F$, an analogous fluoride exporter. Both the CrcB and Eric$^F$ proteins have been previously defined.[102]

If deletion of crcB fails to improve crcB-mCherry performance or reduces the ability of *C. crescentus* to withstand high fluoride concentrations, the genes responsible for fluoride tolerance will be experimentally identified using one of two unbiased whole genome approaches: 1) RNA-seq to identify genes that increase in expression following fluoride exposure, and 2) transposon mutagenesis to screen for genes that, when inactivated, enhance the fluoride sensitivity of the crcB-mCherry reporter. The team successfully applied both approaches to identify the U-responsive regulators that form the basis of the whole-cell sensor [175].

One caveat of eliminating the native mechanism of fluoride efflux in *C. crescentus* is the reduced tolerance of cells to environmental fluoride. For example, the minimal inhibitory concentration of fluoride was reduced from 200 to slightly above 1 mM in an analogous *E. coli* crcB mutant. Since fluoride levels in groundwater, sea, and soil are typically in the 10-100 M range [176], the reduced tolerance is not expected to be problematic except in the most highly concentrated environments.

If the *C. crescentus* crcB mutant will be too sensitive to fluoride (MIC <1 mM), the fluoride tolerance will be partly rescued by expressing the crcB fluoride exporter over a range of concentrations to identify levels that yield a desirable balance between the organism's fluoride tolerance and the sensitivity of the crcB-mCherry.

Example 23, Integration of Uranyl- and Fluoride-Sensing Components and Evaluate Detection Performance Under Aqueous Conditions A U-sensing AND gate circuit will be integrated with the optimal performing crcB-mCherry circuit within *C. crescentus* to enable $UO_2F_2$ detection. Two distinct configurations will be constructed and further characterized.

Figure 47:
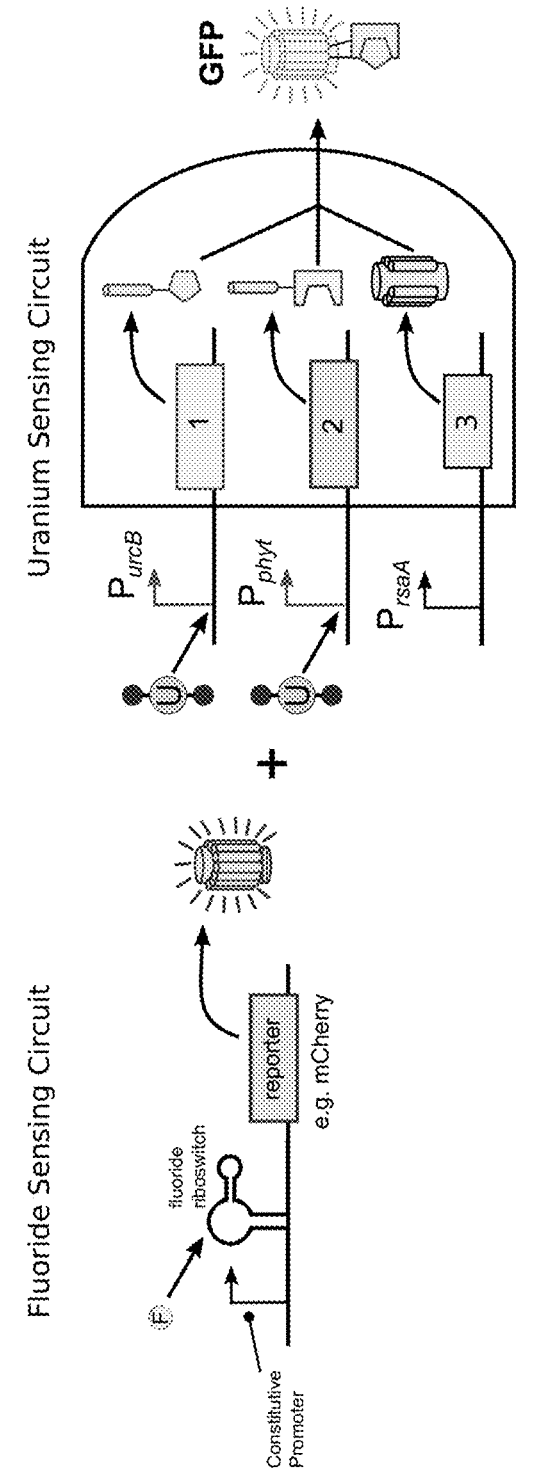
FIG. 47 shows a schematic representation of an exemplary dual output configurations of a $UO_2F_2$ biosensor herein described.

FIGS. 46 and 47 show a schematic illustration of the related approach.

The configurations of the exemplary $UO_2F_2$-biosensors of FIG. 46 and FIG. 47 will provide an individual readout of uranium and fluoride levels and provides a safeguard for environments where natural uranium or fluoride occur at elevated levels. Uranium occurs naturally at concentrations of ~10-100 ppb in soils and ~5-100s of ppb in ground water [37] while fluoride levels in groundwater, sea, and soil are typically in the 10-100 μM range [176].

Continuous environmental monitoring with the biosensor is expected to identify significant deviations from background levels for either or both analytes that it is expected to signify an anthropogenic release. This circuit configuration also enables the flexibility to individually adjust the sensitivity of the U and F detection components to suit the specific application or region of interest and in particular a lower fluoride detection limit (compared to U) may be acceptable if the whole cell sensor is integrated with an air-sampling device that collects $UO_2F_2$ aerosols and HF formed from atmospheric hydrolysis of $UF_6$.

Specific configurations are exemplified in Example 24 and 25.

Example 24: $UO_2F_2$ Single Output Biosensor Configuration: Integrated Uranium- and Fluoride-Sensing Components within an AND Gate Circuit A $UO_2F_2$ sensor 2 will be constructed with an integrated uranium- and fluoride-sensing components within an AND gate circuit such that GFP fluorescence is produced only when the cell perceives both U and fluoride.

In particular, uranium- and fluoride-sensing components can be integrated within a configuration such that a single reporter molecule (e.g., mCherry, GFP) is produced only when the cell perceives both U and fluoride.

Examples of single output $UO_2F_2$ biosensor configuration are shown in FIG. 46

In particular in FIG. 46 panel A a configuration is schematically illustrated wherein uranium- and fluoride-sensing components are integrated in series. The promoter can be any UzcR- or UrpR-regulated promoter (defined in prior patent app) such that U-dependent transcription is initiated by UzcR or UrpR. In this circuit, transcription will be prematurely terminated by the fluoride sensing riboswitch in the absence of fluoride (i.e., not detectable output). Binding of fluoride to the riboswitch will mediate transcriptional read-through and ultimately, production of the reporter.

In FIG. 46 panel B a configuration is schematically illustrated wherein uranium- and fluoride-sensing components integrated in series where U-dependent transcriptional activation requires the function of both UrpR and UzcR. Will provide greater selectivity for uranium compared to the sensors described in panel A. However, in this configuration, the sensitivity for U would be limited by the UzcRS component.

In FIG. 46 panel C a configuration is schematically illustrated wherein integration of the fluoride riboswitch within the AND gate circuit such that expression of component three requires fluoride exposure. In this configuration, reconstitution of GFP fluorescence requires activation of the two uranium-responsive pathways and fluoride binding to the fluoride riboswitch. Transcription of component three can theoretically be controlled by any constitutive promoter. The assignment of each component with the given regulatory promoter is arbitrary and easily swapped. For example, the fluoride riboswitch could be used to control expression of component one or two.

The single output of this configuration simplifies detection and will be most useful for an all-or-none screening function that fluoresces when threshold U and fluoride levels are encountered. The sensitivity of detection would be theoretically limited by the least sensitive component.

The single output of this configuration also simplifies standoff detection and will be most useful for an all-or-none screening function that fluoresces when threshold U and fluoride levels are encountered.

While the sensitivity of detection would be theoretically limited by the least sensitive component, this configuration will focus on improving the sensitivity of the U and fluoride components. To construct the $UO_2F_2$ sensor 2, the crcB riboswitch will be integrated within the state-of-the art AND gate circuit exemplified in the present disclosure such that expression of component three requires fluoride exposure.

In this configuration, reconstitution of GFP fluorescence requires activation of the two uranium-responsive pathways and fluoride binding to the crcB riboswitch.

Example 25 $UO_2F_2$ Dual Output Biosensor Configuration with Uranium and Fluoride-Sensing Riboswitch in Separate Circuits with Different Output Reporter Uranium- and fluoride-sensing components can be integrated within a configuration such that integrated uranium- and fluoride-sensing components are provided as separate components or separate circuits with different output reporters (Dual Output UO$_2$F$_2$ Sensor)

Exemplary configurations of a dual output UO$_2$F$_2$ biosensor are shown in FIG. 47

In particular, in FIG. 47 an exemplary sensor 1 is schematically described in comprising a U-sensing genetic circuit and a separate a Fluoride sensing reportable genetic molecular components.

In the illustration of FIG. 47, the U-sensing genetic circuit comprises a reportable genetic molecular component which is expressed when the genetic circuit operates according to the circuit design in presence of bioavailable U. in the exemplary illustration of FIG. 47, the reportable component is the GFP protein which is expressed upon expression of a first U-sensing genetic molecular component comprising a PUzcrB promoter encoding for a first component of the GFP protein, a second U sensing component comprising a Pphyt promoter and encoding for a second component of the GFP protein and a genetic molecular component a third component of the GFP protein under an exemplary active constitutive promoter (rsA).

In the illustration of FIG. 47, the Fluoride sensing reportable genetic molecular component is a genetic reportable molecular component expresses the fluorescent reporter mCherry within a gene comprising a Fluoride sensing riboswitch under the control of an crcB promoter to provide a Fluoride sensing component.

To construct the biosensor in the output configuration schematically illustrated in exemplary FIG. 47, the optimal performing crcB-mCherry fusion will be integrated into the chromosome of a *C. crescentus* strain that already contains the tripartite GFP U-sensing AND gate.

As such, mCherry and GFP fluorescence can be quantified to provide a separate readout of environmental fluoride and U levels.

In particular the variation of the biosensor described therein is shown in FIG. 47 wherein in the fluoride sensing reportable genetic molecular component the fluorescent reporter mCherry within a gene comprising a Fluoride sensing riboswitch is under the control of an active constitutive promoter to provide a Fluoride sensing component.

This configuration will provide an individual readout of uranium and fluoride levels and provides a safeguard for environments where natural uranium or fluoride occur at elevated levels. Uranium occurs naturally at concentrations of ~10-100 ppb in soils and ~5-100s of ppb in ground water [37] while fluoride levels in groundwater, sea, and soil are typically in the 10-100 μM range.

Continuous environmental monitoring with the biosensor could identify significant deviations from background levels for either or both analytes that could signify an anthropogenic release. This circuit configuration also enables the flexibility to individually adjust the sensitivity of the U and F detection components to suit the specific application or region of interest—a lower fluoride detection limit (compared to U) may be acceptable if the whole cell sensor is integrated with an air-sampling device that collects UO$_2$F$_2$ aerosols and HF formed from atmospheric hydrolysis of UF$_6$. To construct this sensor, the fluoride riboswitch will be placed downstream of a constitutive promoter and upstream of a reporter (e.g., mCherry), such that transcription of the reporter occurs only in the presence of fluoride. This crcB-mCherry fusion will be employed in tandem with the tripartite GFP U-sensing AND gate. As such, mCherry and GFP fluorescence can be quantified to provide a separate readout of environmental fluoride and U levels.

Example 26: F-Sensing Riboswitch of Host Bacteria Knocked Out

To mitigate fluoride toxicity, many bacteria employ a fluoride export protein (e.g., CrcB or Eric$^F$ that functions to maintain low cytoplasmic fluoride concentrations.

Prior data in *E. coli* indicate that this CrcB-mediated fluoride exporter adversely affects the detection limit of the colorimetric crcB reporter (~1 mM) as a consequence of the low intracellular fluoride concentrations.

A similar fluoride export activity is expected in *C. crescentus* since *C. crescentus* possesses an annotated CrcB transporter with high amino acid sequence similarity to previously characterized CrcB fluoride-specific ion channels [177] and tolerates high mM concentrations of fluoride.

Accordingly, to achieve a fluoride detection limit on par with the U detection limit of our sensor (~1 μM), we will implement an analogous approach as that in *E. coli*, which yielded a 100-fold improvement in the fluoride detection limit (sub 10 μM) and maintained a dynamic range that spanned two orders of magnitude. [102].

Figure 49:
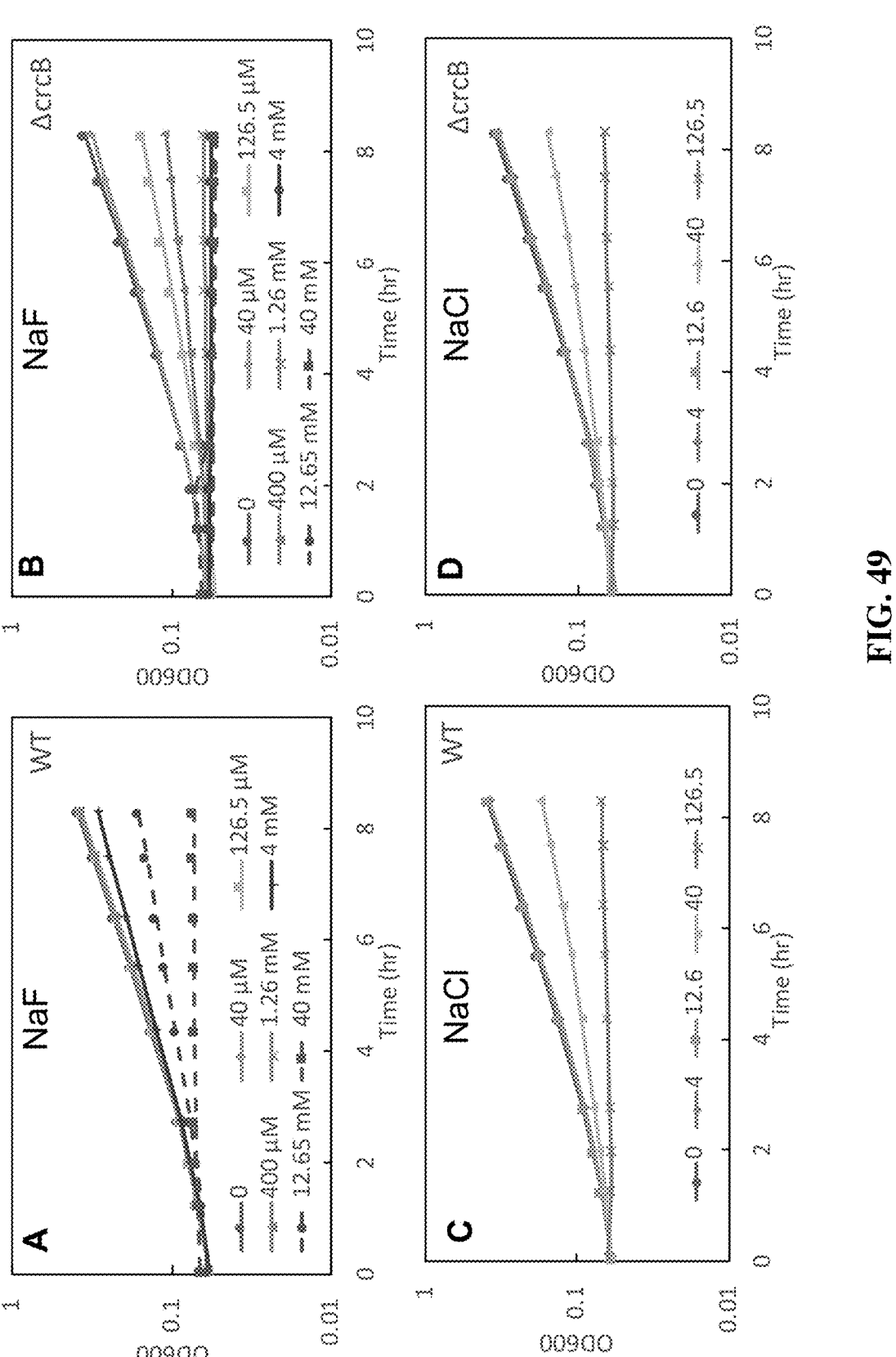
FIG. 49 shows charts reporting the effect of crcB deletion on the growth of *Caulobacter crescentus* in the presence of NaF and NaCl.

Specifically, the function of the fluoride ion exporter in *C. crescentus* was tested by monitoring the growth of a strain deleted for crcB in the presence of NaF and NaCl (FIG. 49).

The results illustrated in FIG. 49 panels A and B show growth defect is observed for WT at NaF concentrations above 4 mM and for the crcB deletion strain at concentrations above 126.5 μM, marking a greater than 30-fold reduction in Fluoride tolerance in the absence of the fluoride efflux pump.

The results illustrated in FIG. 49 panels C and D show that growth of *C. crescentus* in the presence of NaCl is unaffected by deletion of crcB. These data confirm the role of *C. crescentus* CrcB in fluoride efflux.

Importantly, the growth profile of the crcB deletion strain was indistinguishable from WT over a range of NaCl concentrations (FIG. 49 panel B), supporting a specific role for *C. crescentus* CrcB in fluoride efflux.

Figure 55:
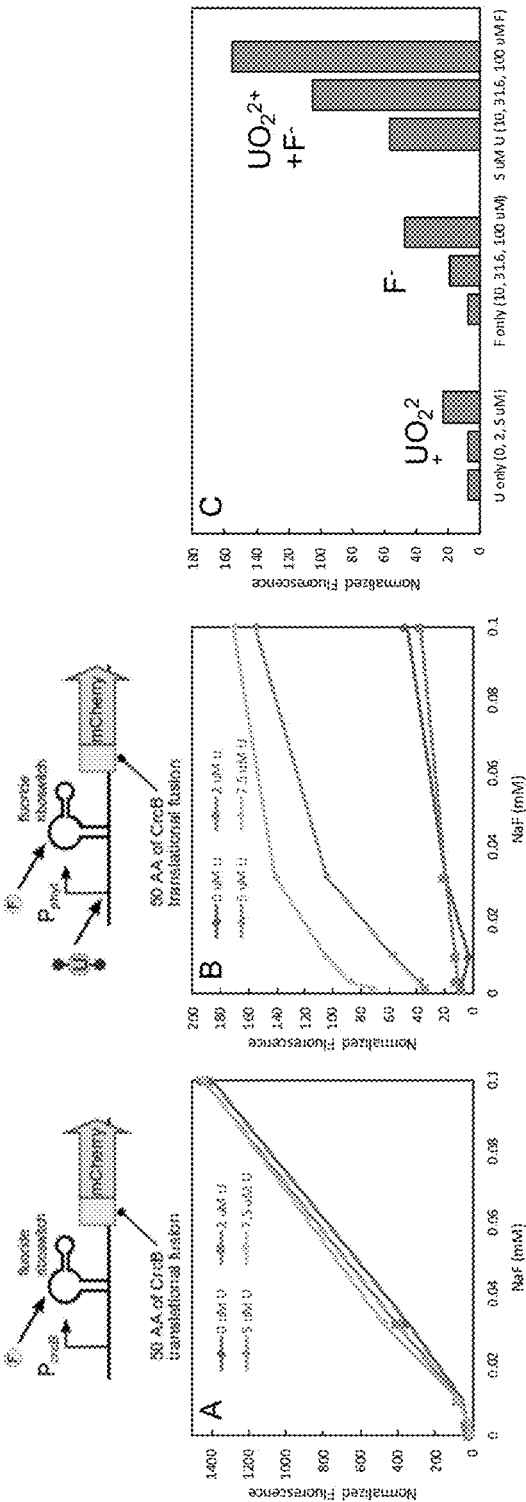
FIG. 55 shows charts reporting the testing of an in-series uranyl fluoride sensing circuit, FIG. 55 Panel A shows fluoride detection performed with a control, MM-1 fluoride sensing circuit with native crcB promoter not responsive to U.

Example 27: Comparison of Riboswitches Performance in a LacZ Fusion Construct To enable detection of fluoride in *C. crescentus*, a fluoride sensing riboswitch [102] will be employed to control the expression of a fluorescent reporter (e.g., mCherry) such that fluoride detection results in cell fluorescence (FIG. 55).

Figure 50:
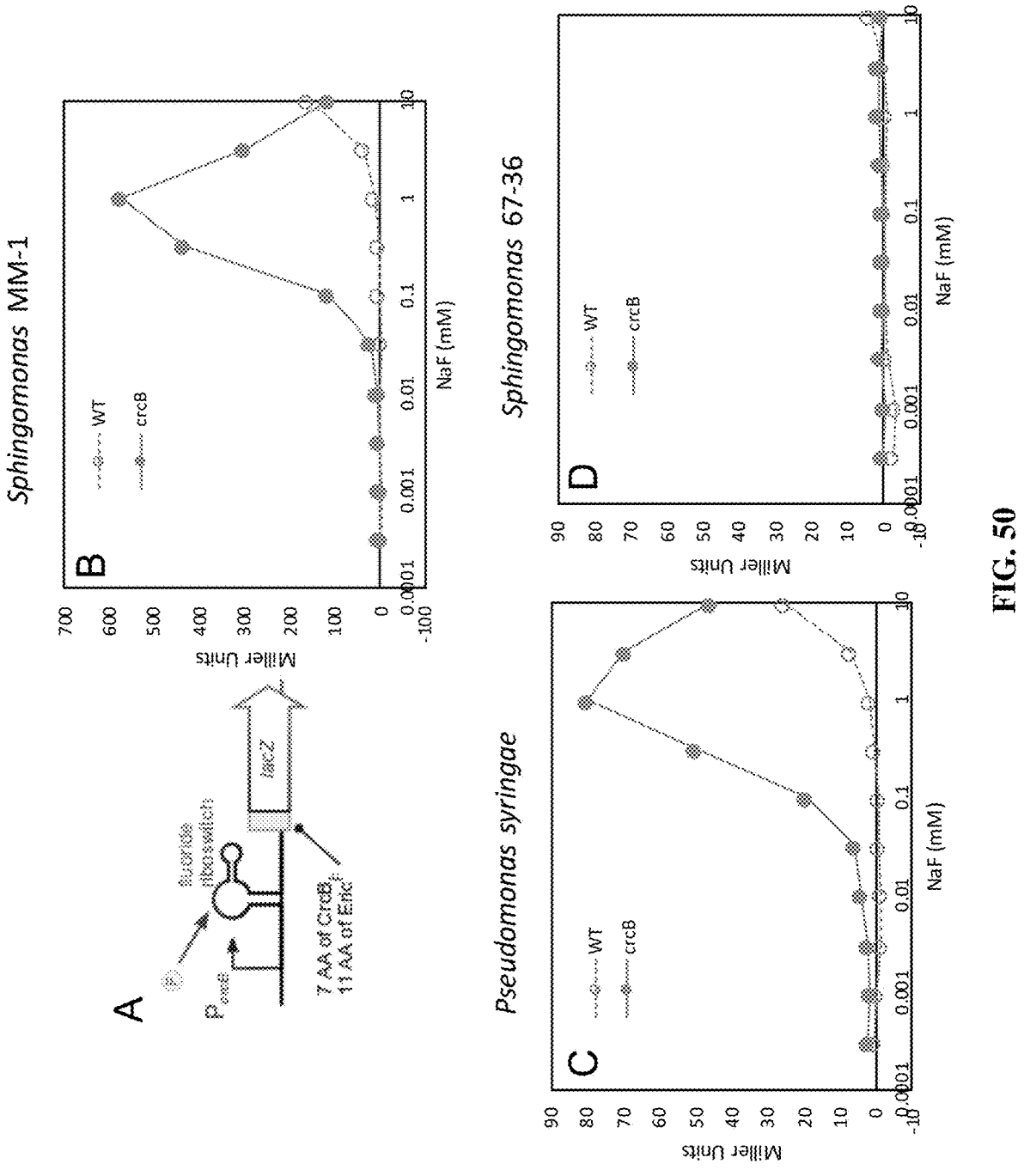
FIG. 50 shows a schematic and charts illustrating the result of testing the function of fluoride riboswitches from three different bacteria in *Caulobacter crescentus*.

Since *C. crescentus* lacks a native fluoride riboswitch, a library of riboswitch reporters (transcriptional fusions to mCherry) was built and screened that included the well-characterized fluoride riboswitches from *P. syringae* DC3000 [102] and previously uncharacterized fluoride riboswitches from *Sphingomonas* sp. MM-1 and *Sphingomonas* sp. 67-36, which are closely related to *C. crescentus* and possesses similarly high genomic G+C content (66%) (FIG. 50 Panels A to D).

The sequences of the riboswitches and related constructs are reported in Table 13 below.

TABLE 13

Sequences of tested riboswitches

| Construct including Riboswitch | Sequence | SEQ ID NO |
|---|---|---|
| Translational lacZ fusion comprising a *Sphingomonas* MM-1 riboswitch | CAGAGATCTAACGCCAGTTACAGCACGCG TGGCGAAGGGCGCGATCGAGGTGGCCGCG CCGGCTGGGTGACGGGCTGCCATTGACGC GCTGCCCCACCCCCGCCATATCGTCGGCA ACGGCAATGGATTCCTGCCGGGCCTCGCG CCGAACCGCCATTGAGGGCTGATGATTCC TACCTGCGGCCGCCCTGCGGCAAGGAGGA ATCATGCGTTCGGTATTTCTCGTCTTGGT ACCTGC | 2515 |
| Translational lacZ fusion comprising *Sphingomonas* 67-36 riboswitch sequence | CAGAGATCTGCCGACAAGGCCAAGAAGCT CGGCATCCCGGTCTGGAGGTTCGGCGGCG CGTAAGCGCCGCCCCGACCTCTACCAAGA GCCGATCTCTTTCGATATCATGCATGGTG ACGGGGATGGAGTTCCCCGATAACCGCCG TTCCGGGCTGATGACTCCTACCAACACAG GCAACCCGCCCGTCGATGGTAGGTGTTCG CCTTCGACTGGTACCTGC | 2516 |
| Translational lacZ fusion comprising *Pseudomonas syringae* riboswitch sequence | CAGAGATCTTTTGGCCCTCTTTCGTAAGC GGTGACTCGAAGACGCCTTCGCTTGCCTC GTACTCCGAAACACGATTTTACATTTTGG ACAGACCTAGCTAAGATCGGCGCATTGGA GATGGCATTCCTCCATTAACAAACCGCTG CGCCCGTAGCAGCTGATGATGCCTACAGA AACCTGATCAAACCAGGTCTGTAGGCGTT CGCGCTTAGAATCCCTTCTTTGGTCAGGC CCACTTATTTTTTGTGGCTGGCCAAATGT CTAAATTTCGACGACCTGAGGTACCTGC | 2517 |

The function of the fluoride riboswitches was tested in *C. crescentus* initially using translational lacZ fusions with the associated native crcB or eric$^F$ promoters schematically illustrated in FIG. 50 panel A.

In particular the function of fluoride riboswitches from three different bacteria was tested in *Caulobacter crescentus* with a construct in which each riboswitch was included between a Pcrcb and a LacZ reporter (FIG. 50 Panel A)

In particular, DNA sequence spanning from 197 and 180 nucleotides upstream of the start codon for *Sphingomonas* MM-1 and 67-36, respectively, through the first 7 amino acids of the crcB gene was fused to lacZ to produce a translational fusion. A DNA sequence range from 236 nucleotides upstream of the start codon through the first 11 amino acids of the Eric$^F$ efflux pump was used for *Pseudomonas syringae*.

The results reported in FIG. 50 Panels B to D indicate a difference in performance of the different riboswitches in the construct schematically described in FIG. 50, Panel A.

In particular, the fluoride riboswitch from *Sphingomonas* MM-1 was responsive to fluoride and had the largest dynamic range and signal amplitude (FIG. 50 Panel B), while the riboswitch from *Sphingomonas* 67-36 was non-responsive to fluoride (FIG. 50 Panel D).

In particular, the construct for *Sphingomonas* 67-36 lacked fluoride induction, which is expected to reflect a lack of a promoter sequence in the construct or weak promoter activity in *C. crescentus*.

The riboswitch from *Pseudomonas syringae* was also fluoride responsive, but had a lower dynamic range compared to the riboswitch from MM-1 (FIG. 50 Panel C).

Importantly, this set of experiments further evidenced that the crcB deletion strain significantly improved the F$^-$ sensitivity compared to WT with induction occurring at almost two orders of magnitude lower F$^-$ concentration.

An additional LacZ fusion including *Sphingomonas* MM-1 riboswitch sequence with a reduced G+C content is (SEQ ID NO: 2527)
CAGAGATCTAACGCCGGTGACGGCGCGCGTGGCGAAGGGCGCGATCGAGGT

GGCCGCGCCGGCTGGGTGACGGGCTGCCATTGACGCGCTGCCCCACCCCCG

CCATATCGTCGGCAACGGCAATGGATTCCTGCCGGGCCTCGCGCCGAACCG

CCATTGAGGGCTGATGATTCCTACCTGCGGCCGCCCTGCGGCAAGGAGGAA

TCATGCGTTCGGTATTTCTCGTCTTGGTACCTGC.

Example 28: Modularity of Exemplary Riboswitches

The function of each riboswitch outside of the context of the native promoter was tested to determine the modularity with respect to the promoter sequence.

Modularity with respect to the promoter is critical feature for a fluoride riboswitch-based sensor since this would allow the use of a strong constitutive promoter (to improve the signal amplitude) and a U-sensitive promoter to enable detection of $UO_2F_2$.

Figure 51:
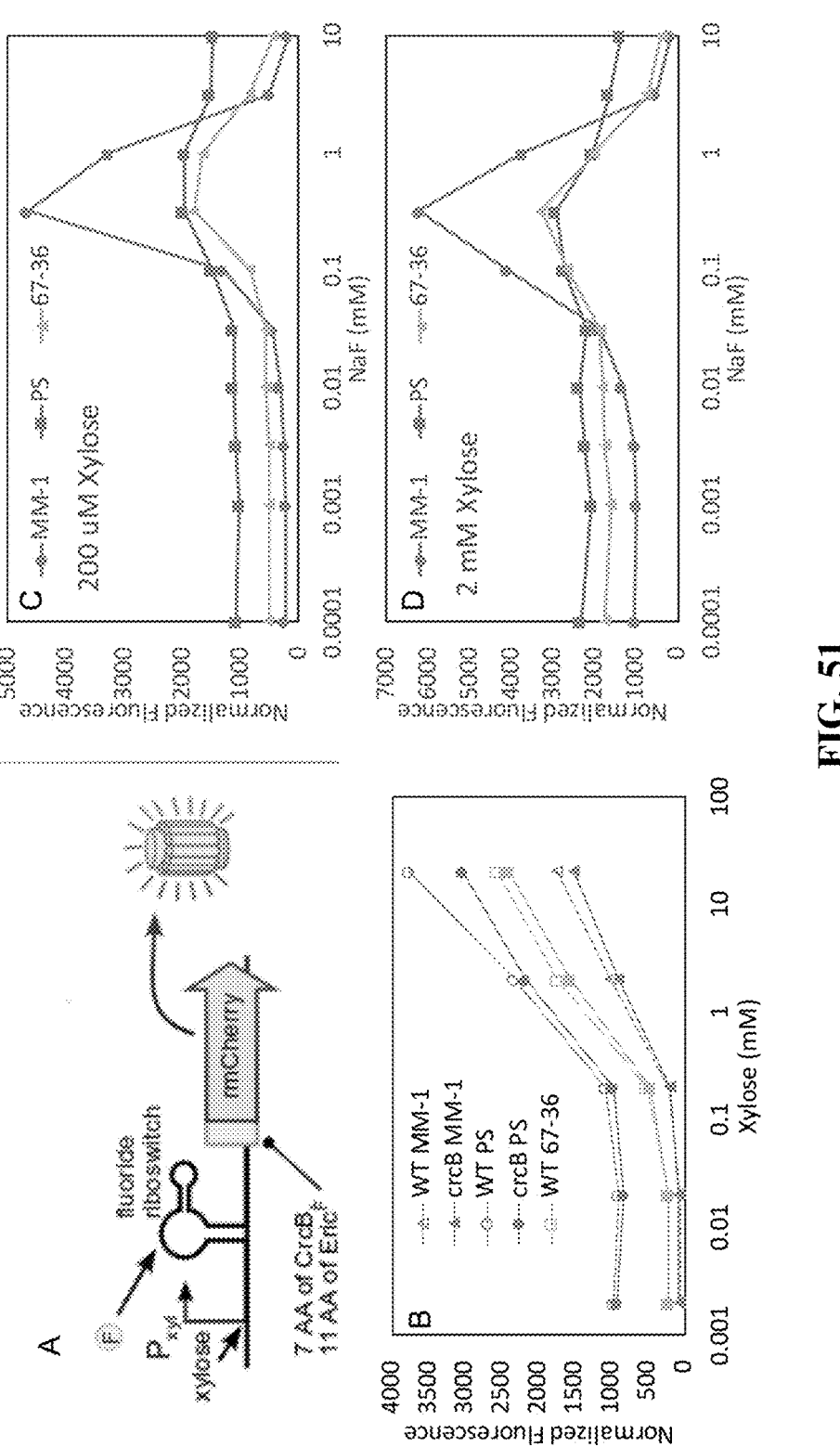
FIG. 51 shows a schematic and charts illustrating fluoride responsiveness of fluoride riboswitches from three different bacteria tested in *C. crescentus* using the xylose inducible promoter.
Figures 51, 52:
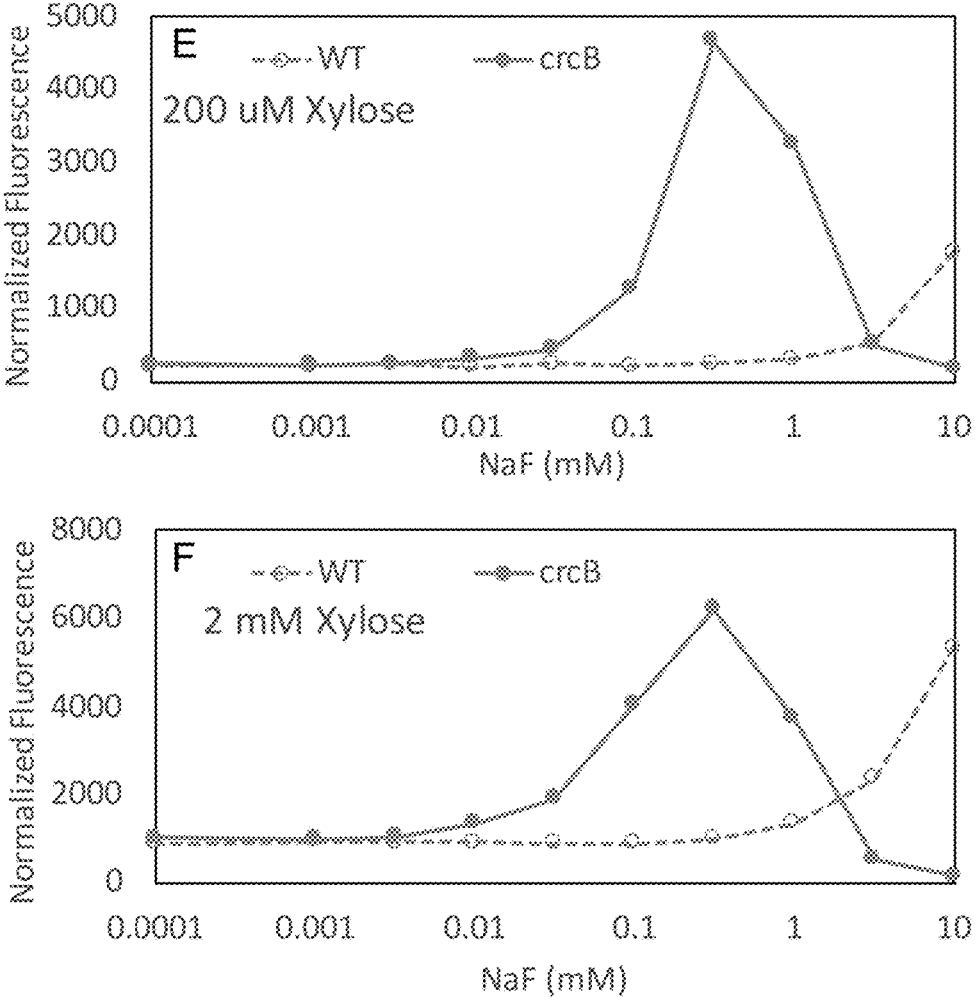
FIG. 52 shows a schematic representation of the primary genetic parts involved in the construction of a fluoride responsive reporter.

To this end, DNA sequence 97, 146, and 80 bp upstream of the start codon for *Sphingomonas* MM-1, *Pseudomonas syringae*, and *Sphingomonas* 67-36, respectively was fused to the xylose inducible promoter (Pxyl) and to mCherry in a construct schematically illustrated in FIG. 51 Panel A. P$_{xyl}$ was employed since it allows a wide range of promoter activities to be assayed (FIG. 51 Panel A).

The sequences of each riboswitch is reported in Table 14 below

TABLE 14

Sequences of tested riboswitches

| Construct including Riboswitch | Sequence | SEQ ID NO |
|---|---|---|
| Pxyl regulated translational mCherry fusion comprising *Sphingomonas* MM-1 riboswitch sequence | tgccgacgaacgcgcATATCGTCGGCAA CGGCAATGGATTCCTGCCGGGCCTCGCG CCGAACCGCCATTGAGGGCTGATGATTC CTACCTGCGGCCGCCCTGCGGCAAGGAG GAATCATGCGTTCGGTATTTCTCGTCAT GGTGAGCAAGGGG | 2518 |
| Pxyl regulated translational mCherry fusion comprising *Sphingomonas* 67-36 riboswitch sequence | tgccgacgaacgcgcTCATGCATGGTGA CGGGGATGGAGTTCCCCGATAACCGCCG TTCCGGGCTGATGACTCCTACCAACACA GGCAACCCGCCCGTCGATGGTAGGTGTT CGCCTTCGAATGGTGAGCAAGGGG | 2519 |
| Pxyl regulated translational mCherry fusion comprising *Pseudomonas syringae* riboswitch sequence | tgccgacgaacgcgcAAGATCGGCGCAT TGGAGATGGCATTCCTCCATTAACAAAC CGCTGCGCCCGTAGCAGCTGATGATGCC TACAGAAACCTGATCAAACCAGGTCTGT AGGCGTTCGCGCTTAGAATCCCTTCTTT GGTCAGGCCCACTTATTTTTTGTGGCTG GCCAAATGTCTAAATTTCGACGACCTAT GGTGAGCAAGGGG | 2520 |

The fluoride responsiveness of the fluoride riboswitches in such construct was tested in *C. crescentus* to test the compatibility of each riboswitch with a non-native promoter to test the modularity of the riboswitch.

Fluorescence was monitored as a function of xylose and NaF concentrations.

The results illustrated in FIG. 51 Panel B show that expression of mCherry remains low in the absence of fluoride at xylose concentrations up to 200 uM. However, high concentrations of xylose (2-20 mM) lead to partial fluoride-independent activation. This result suggests that a single fluoride riboswitch is insufficient to halt all transcription initiation events when promoter activity is high.

The results illustrated in FIG. 51 Panels C and D show that while all three riboswitches were responsive to fluoride, the riboswitch from *Sphingomonas* MM-1 exhibited the largest dynamic range, which is in agreement with the lacZ fusion data reported in Example 27 and FIG. 50.

These results suggest that the fluoride riboswitch from *Sphingomonas* MM-1 is modular with respect to the promoter sequence and the most suitable for application in *C. crescentus*. It is expected that a further optimization of the native Shine Dalgarno sequence will enhance the dynamic range and signal amplitude of the *Pseudomonas syringae* riboswitch construct.

The results of the experiments related to placement of the MM-1 riboswitch downstream of the xylose-inducible promoter (Pxyl), also indicated that at high concentrations of xylose (2-20 mM) lead to partial fluoride-independent activation.

This result suggests that a single fluoride riboswitch can be insufficient to halt all transcription initiation events when promoter activity is high. In those cases, a second MM-1 riboswitch, added in tandem, is expected to increase the probability of terminating transcription in the absence of fluoride, which will reduce the level of fluoride-independent activation and is also expected to increase the dynamic range. Preferably, when two riboswitches are placed in tandem, the first riboswitch does not contain the native RBS or downstream protein coding sequence.

In addition, it is also expected that addition of a spacer DNA region between the DNA region encoding each riboswitch will increase performance of the F-sensing element with MM-1 riboswitches. A non-structured DNA of 10-50 bp is expected to be sufficient (preferably with a shorter sequence to minimize the length of the this 5' untranslated region). If the RBS and downstream protein coding sequence cannot be removed without losing fluoride binding activity, then the DNA encoding the first 50 amino acids can be fused to the first riboswitch and terminated with a stop codon.

The results illustrated in FIG. 51 Panels E and F further show that the crcB deletion strain has significantly improved F− sensitivity compared to WT. These results further confirm that the crcB deletion background can be employed for all subsequence experiments to maximize fluoride sensitivity.

The above results support the use of the *Sphingomonas* MM-1 fluoride riboswitch in a crcB deletion background for subsequent experiments.

Example 29: Effects of Different Fusion Lengths and Attenuators on Fluoride Detection of F Sensing Riboswitches In order to test the length of the fusion including a fluorescence protein [113] further experiment have been performed to identify the lengths and associated fluoride detection to identify an optimized length.

In particular, the effect of two different translational fusion lengths (7 and 50 amino acids) and two so-called ribo-attenuators (ATT2 and ATT3) [113], which are genetic elements designed for increased ribosome modularity through predictable tuning, insulation from contextual changes, and a reduction in expression variation.

Accordingly, the DNA encoding 0, 7, and 50 amino acids of *Sphingomonas* MM-I CrcB was fused to mCherry and the native crcB promoter was used to drive expression of the riboswitch reporter construct A transcriptional mCherry fusion was also tested, where the crcB gene and the shine Dalgarno sequence were deleted from the construct.

Figure 54:
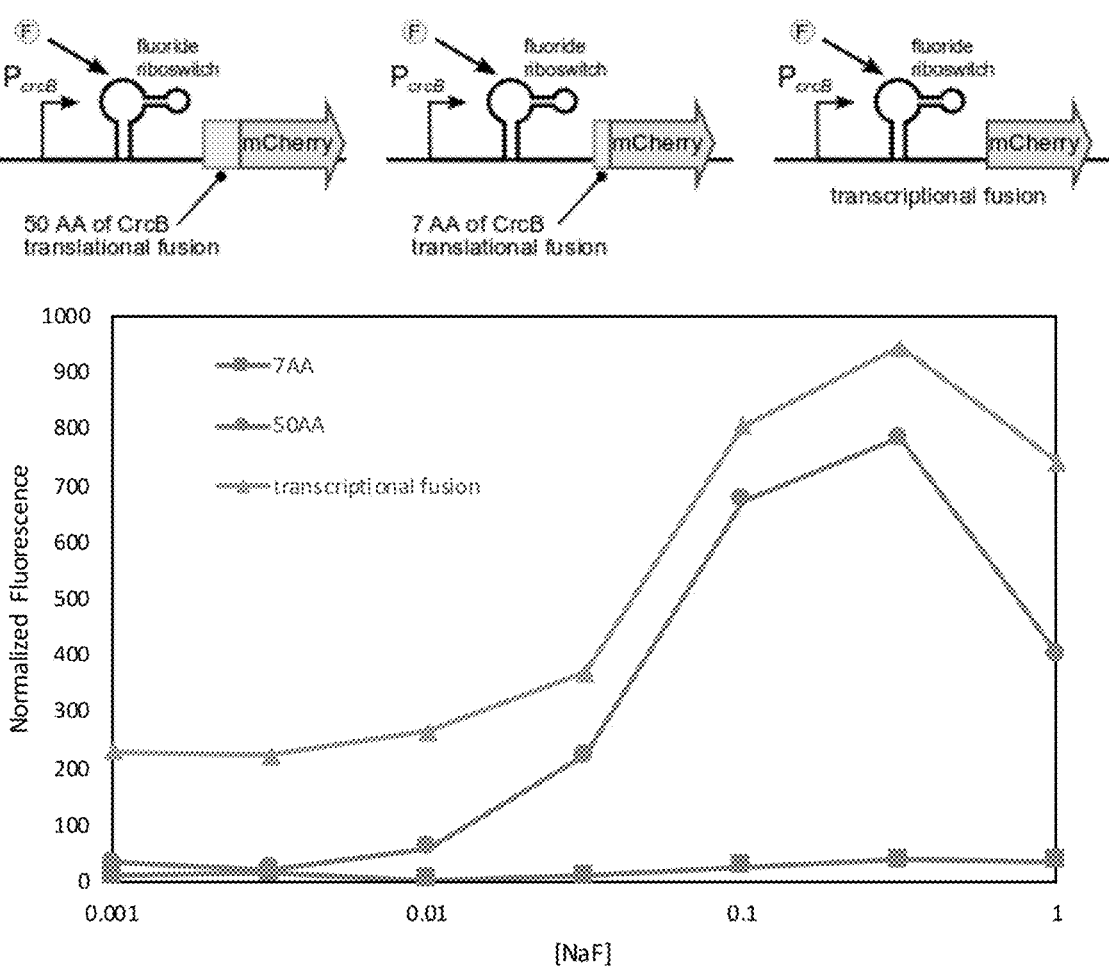
FIG. 54 show tbc effect of translational fusion length on Sphingomonas MM-1 fluoride riboswitch function.

The results reported in FIG. 54 show that the constructs containing either a 50 AA translational fusion or a transcriptional fusion exhibited a fluoride-dependent increase in fluorescence, whereas the 7 AA translational fusion was only very weakly responsive to fluoride (FIG. 54).

These data suggest that the MM4 riboswitch can function independently of its native crcB gene and that a longer transnational fusion with mCherry is preferred vs a shorter fusion in the context of MM-I riboswitch function.

Example 30: Selection of Promoters and F Sensing Riboswitches for an F-Sensing Genetic Reportable Molecular Component To develop a uranyl fluoride sensor, the UrpRS regulated promoter $_{P\ Phyt-short}$ was integrated upstream of the MM4 riboswitch, replacing the native crcB promoter. The native shine Dalgarno sequence for the crcB gene was not modified and a translational mCherry promoter was constructed with the first 150 nucleotides (50 amino acids) of the crcB gene. While the presence of U or fluoride alone yielded a minor increase in fluorescence, the presence of both U and fluoride yielded the highest fluorescence increase, confirming the intended functionality of the circuit (FIG. 55 Panels B and C). In contrast, the control fluoride sensor containing the native crcB promoter was unresponsive to uranium MM-1 fluoride sensing circuit with native crcB promoter is not responsive to U. (B) A uranyl fluoride sensing circuit constructed by combining the UrpRS-responsive Pphyt promoter with the MM-1 riboswitch. (C) Depicts the fluorescence of the uranyl fluoride sensing circuit in the presence of U alone, F alone, and both U and F. Tests-were performed with F−, added as NaF, and uranyl, added as uranyl nitrate. The presence of both U and fluoride yields the highest signal amplitude.

Example 31: Selection of Promoters and F Sensing Riboswitches for an F-Sensing Genetic Reportable Molecular Component The following approach can be followed to optimize promoter for a bacterial host and application of interest for cassettes where U and F sensing components are placed in different circuits (e.g., FIG. 46C; FIG. 47).

The consensus promoter sequence for the housekeeping sigma factor (sigma73) in *Caulobacter crescentus* has been previously determined [178].

For optimal fluoride riboswitch reporter function, mutating the native crcB/eric$^F$ promoter toward the *C. crescentus* consensus is recommended. For example, it is expected that mutating the −10 region of the *Sphingomonas* MM-1 crcB promoter from 5'-GCCATATC-3' (SEQ ID NO: 2521) to 5'GCTATATC-3' (SEQ ID NO: 2522) will enhance the signal amplitude of the fluoride sensing reporter. The optimal functional fluoride reporter can be integrated within a *C. crescentus* strain containing a U-sensing promoter (any from prior patent app) for a two-color output (e.g., FIG. 47) or integrated within the U sensing AND gate (two U-responsive components and one F-responsive component (e.g., FIG. 46C)) for a single-color output.

Example 32: Selection of Promoters and F Sensing Riboswitches for a U Sensing F-Sensing Genetic Reportable Molecular Component For application wherein the optimization is desired when combining a U-responsive promoter with a fluoride riboswitch (e.g., FIG. 46B-C) to place the U-responsive and F-responsive components within a single circuit, the native crcB promoter can be replaced with a uranium responsive promoter (any UzcRS or UrpRS promoter). For example, The Pphyt-short promoter was added upstream of the *Sphingomonas* sp MM-1 fluoride riboswitch and exhibited the highest fluorescent output signal in the presence of uranyl and fluoride. It is anticipated that the signal amplitude can be further improved by optimizing the RBS as described below. Furthermore, the F-independent output signal is expected be reduced by adding a second riboswitch sequence, resulting in an improve dynamic range.

Example 33: Selection of RBS Sequence for Inclusion in F-Sensing Component and U-Sensing F-Sensing Components Since the fluoride riboswitch has been shown to function through a mechanism of transcriptional termination, the ribosome binding site is likely amenable to optimization. The RBS can be optimized using the standard registry of parts (http://parts.igem.org/Main_Page at the date of filing of the instant application), which contains several well-characterized RBS sequences that are likely to work in a broad range of host organisms. For example, it is expected that swapping the native *Sphingomonas* crcB RBS (5'-AAGGAGGAATCATG-3') (SEQ ID NO: 2523) with the potent 5'-AAGGAGGAAAAACATATG-3' RBS (SEQ ID NO; 2524) will improve the dynamic range.

In summary described herein are U biosensors, and related U-sensing genetic molecular components, genetic circuits, compositions, methods and systems are described, which in several embodiments can be used to detect and/or neutralize uranium and in particular bioavailable U.

The examples set forth above are provided to give those of ordinary skill in the art a complete disclosure and description of how to make and use the embodiments of the U biosensors, and related U-sensitive genetic molecular components, genetic circuits, compositions, methods and systems of the disclosure, and are not intended to limit the scope of what the inventors regard as their disclosure. Those skilled in the art will recognize how to adapt the features of the exemplified U biosensors, and related U-sensitive genetic molecular components, genetic circuits, compositions, methods and systems herein disclosed to additional U biosensors, and related U-sensitive genetic molecular components, genetic circuits, compositions, methods and systems, and related genetic molecular components, sets of polynucleotides, polypeptides, proteins, and/or metabolites, in according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible sub-combinations of the group are intended to be individually included in the disclosure. Every combination of components or materials described or exemplified herein can be used to practice the disclosure, unless otherwise stated. One of ordinary skill in the art will appreciate that methods, system elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the genetic circuits, genetic molecular components, and methods steps set forth in the present description. As will be obvious to one of skill in the art, methods and systems useful for the present methods and systems may include a large number of optional composition and processing elements and steps.

In particular, it will be understood that various modifications may be made without departing from the spirit and scope of the present disclosure. Accordingly, other embodiments are within the scope of the following claims.

REFERENCES

1. Miller, J., *Experiments in molecular genetics. Cold Spring Laboratory Press.* 1972, Cold Spring Harbor, NY.
2. Ku, H., *Notes on the use of propagation of error formulas.* Journal of Research of the National Bureau of Standards, 1966. 70(4).
3. Park, D. M., et al., *Identification of a U/Zn/Cu responsive global regulatory two-component system in Caulobacter crescentus.* Mol Microbiol, 2017.
4. Fisher, J. A., J. Smit, and N. Agabian, *Transcriptional analysis of the major surface array gene of Caulobacter crescentus.* J Bacteriol, 1988. 170(10): p. 4706-13.
5. Cabantous, S., et al., *A new protein-protein interaction sensor based on tripartite split-GFP association.* Scientific reports, 2013. 3: p. 2854.
6. Meisenzahl, A. C., L. Shapiro, and U. Jenal, *Isolation and characterization of a xylose-dependent promoter from Caulobacter crescentus.* J Bacteriol, 1997. 179(3): p. 592-600.
7. Newsome, L., K. Morris, and J. R. Lloyd, *The biogeochemistry and bioremediation of uranium and other priority radionuclides.* Chemical Geology, 2014. 363: p. 164-184.
8. Langmuir, D., *Aqueous environmental geochemistry.* 1997.
9. Ewing, R. C., *Environmental impact of the nuclear fuel cycle.* Geological Society, London, Special Publications, 2004. 236(1): p. 7-23.
10. Bernier-Latmani, R., et al., *Non-uraninite products of microbial U (VI) reduction. Environmental science & technology,* 2010. 44(24): p. 9456-9462.
11. Brutinel, E. D. and J. A. Gralnick, *Shuttling happens: soluble flavin mediators of extracellular electron transfer in Shewanella.* Applied microbiology and biotechnology, 2012. 93(1): p. 41-48.
12. Lovley, D. R. and E. J. Phillips, *Microbial reduction of uranium.* Nature, 1991. 350(6317): p. 413.
13. Williams, K. H., et al., *Bioremediation of uranium-contaminated groundwater: a systems approach to subsurface biogeochemistry.* Current opinion in biotechnology, 2013. 24(3): p. 489-497.
14. Beazley, M. J., et al., *The effect of pH and natural microbial phosphatase activity on the speciation of uranium in subsurface soils.* Geochimica et Cosmochimica Acta, 2011. 75(19): p. 5648-5663.
15. Macaskie, L. E., et al., *Enzymically mediated bioprecipitation of uranium by a Citrobacter sp.: a concerted role for exocellular lipopolysaccharide and associated phosphatase in biomineral formation.* Microbiology, 2000. 146(8): p. 1855-1867.
16. Macaskie, L. E., et al., *Uranium Bioaccumulation by a Citrobacter sp. as a Result of Enzymically Mediated Growth of Polycrystalline HUO_2 PO_4.* Science, 1992: p. 782-784.
17. Beveridge, T. and R. Murray, *Sites of metal deposition in the cell wall of Bacillus subtilis.* Journal of bacteriology, 1980. 141(2): p. 876-887.
18. Gadd, G. M., *Biosorption: critical review of scientific rationale, environmental importance and significance for pollution treatment.* Journal of Chemical Technology and Biotechnology, 2009. 84(1): p. 13-28.

19. Choudhary, S. and P. Sar, *Uranium biomineralization by a metal resistant Pseudomonas aeruginosa strain isolated from contaminated mine waste.* Journal of hazardous materials, 2011. 186(1): p. 336-343.
20. Ku, H. H., *Notes on the use of propagation of error formulas.* Journal of Research of the National Bureau of Standards—C. Engineering and Instrumentation, 1966. 70C(4): p. 263-273.
21. Bailey, T. L. and C. Elkan, *Fitting a mixture model by expectation maximization to discover motifs in biopolymers.* Proc Int Conf Intell Syst Mol Biol, 1994. 2: p. 28-36.
22. Zhou, B., et al., *The global regulatory architecture of transcription during the Caulobacter cell cycle.* PLoS Genet, 2015. 11(1): p. e1004831.
23. McGrath, P. T., et al., *High-throughput identification of transcription start sites, conserved promoter motifs and predicted regulons.* Nat Biotechnol, 2007. 25(5): p. 584-92.
24. Markich, S. J., *Uranium speciation and bioavailability in aquatic systems: an overview. The Scientific World Journal,* 2002. 2: p. 707-729.
25. Focazio, M. J., et al., *The Chemical Quality of Self-Supplied Domestic Well Water in the United States.* Groundwater Monitoring & Remediation, 2006. 26(3): p. 92-104.
26. Hoover, J., et al., *Elevated Arsenic and Uranium Concentrations in Unregulated Water Sources on the Navajo Nation, USA.* Exposure and Health, 2016: p. 1-12.
27. Kemp, R. S., *Environmental Detection of Clandestine Nuclear Weapon Programs.* Annual Review of Earth and Planetary Sciences, 2016. 44(1): p. 17-35.
28. Kemp, R. S., *Initial Analysis of the Detectability of UO2F2 Aerosols Produced by UF6 Released from Uranium Conversion Plants.* Science & Global Security, 2008. 16(3): p. 115-125.
29. Bostick, W., et al., *Sampling and characterization of aerosols formed in the atmospheric hydrolysis of UF/sub 6.* 1983.
30. Wogman, N. A., *Prospects for the introduction of wide area monitoring using environmental sampling for proliferation detection.* Journal of Radioanalytical and Nuclear Chemistry, 2013. 296(2): p. 1071-1077.
31. Kips, R. S. and M. J. Kristo, *Investigation of chemical changes in uranium oxyfluoride particles using secondary ion mass spectrometry.* Journal of Radioanalytical and Nuclear Chemistry, 2009. 282(3): p. 1031.
32. Myers, W. L., *A literature review on the chemical and physical properties of uranyl fluoride (UO sub 2 Fsub 2).* 1990: United States.
33. Langmuir, D., *Uranium solution-mineral equilibria at low temperatures with applications to sedimentary are deposits.* Geochimica et Cosmochimica Acta, 1978. 42(6, Part A): p. 547-569.
34. Markich, S. J., *Uranium speciation and bioavailability in aquatic systems: an overview. ScientificWorldJournal,* 2002. 2: p. 707-29.
35. Sheng, L. and J. B. Fein, *Uranium adsorption by Shewanella oneidensis MR-1 as a function of dissolved inorganic carbon concentration.* Chemical Geology, 2013. 358: p. 15-22.
36. Bencheikh-Latmani, R. and J. O. Leckie, *Association of uranyl with the cell wall of Pseudomonas fluorescens inhibits metabolism.* Geochimica et Cosmochimica Acta, 2003. 67(21): p. 4057-4066.

149

37. Nolan, J. and K. A. Weber, *Natural Uranium Contamination in Major U.S. Aquifers Linked to Nitrate.* Environmental Science & Technology Letters, 2015. 2(8): p. 215-220.

38. Ferla, M. P., et al., *New rRNA gene-based phylogenies of the Alphaproteobacteria provide perspective on major groups, mitochondrial ancestry and phylogenetic instability.* PLoS One, 2013. 8(12): p. e83383.

39. Slonczewski JL, F. J., *Microbiology: An Evolving Science* W. W. Norton & Company, 2014: p. 742-3.

40. Dworkin M, F. S., Rosenberg E, Schleifer KH, Stackebrandt E, *The Prokaryotes: Proteobacteria: Alpha and Beta Subclasses.* 2006. 5: p. 15-18.

41. Stock, A. M., V. L. Robinson, and P. N. Goudreau, *Two-component signal transduction.* Annual review of biochemistry, 2000. 69(1): p. 183-215.

42. Mascher, T., J. D. Helmann, and G. Unden, *Stimulus perception in bacterial signal-transducing histidine kinases.* Microbiology and Molecular Biology Reviews, 2006. 70(4): p. 910-938.

43. Capra, E. J. and M. T. Laub, *Evolution of two-component signal transduction systems. Annual review of microbiology,* 2012. 66: p. 325-347.

44. Sanders, D., et al., *Phosphorylation site of NtrC, a protein phosphatase whose covalent intermediate activates transcription.* Journal of bacteriology, 1992. 174 (15): p. 5117-5122.

45. Sanders, D. A., et al., *Identification of the site of phosphorylation of the chemotaxis response regulator protein, CheY.* Journal of Biological Chemistry, 1989. 264(36): p. 21770-21778.

46. Datsenko, K. A. and B. L. Wanner, *One-step inactivation of chromosomal genes in Escherichia coli K-12 using PCR products.* Proc Natl Acad Sci USA, 2000. 97(12): p. 6640-5.

47. Sharma, C. M., et al., *The primary transcriptome of the major human pathogen Helicobacter pylori.* Nature, 2010. 464(7286): p. 250.

48. Carey, M. F., C. L. Peterson, and S. T. Smale, *The primer extension assay.* Cold Spring Harbor Protocols, 2013. 2013(2): p. pdb. prot071902.

49. Wade, J. T., *Where to begin? Mapping transcription start sites genome-wide in Escherichia coli.* Journal of bacteriology, 2015. 197(1): p. 4-6.

50. Poindexter, J. S., *The caulobacters: ubiquitous unusual bacteria.* Microbiological reviews, 1981. 45(1): p. 123.

51. Hu, P., et al., *Whole-genome transcriptional analysis of heavy metal stresses in Caulobacter crescentus.* Journal of bacteriology, 2005. 187(24): p. 8437-8449.

52. Park, D. M. and Y. Jiao, *Modulation of medium pH by Caulobacter crescentus facilitates recovery from uranium-induced growth arrest.* Applied and environmental microbiology, 2014.80(18): p. 5680-5688.

53. Bollmann, A., et al., *Isolation and physiology of bacteria from contaminated subsurface sediments.* Applied and environmental microbiology, 2010. 76(22): p. 7413-7419.

54. Yung, M. C. and Y. Jiao, *Biomineralization of uranium by PhoY phosphatase activity aids cell survival in Caulobacter crescentus.* Applied and environmental microbiology, 2014. 80(16): p. 4795-4804.

55. Hillson, N. J., et al., *Caulobacter crescentus as a whole-cell uranium biosensor.* Applied and environmental microbiology, 2007. 73(23): p. 7615-7621.

56. Cormack, B. P., R. H. Valdivia, and S. Falkow, *FACS-optimized mutants of the green fluorescent protein (GFP).* Gene, 1996. 173(1): p. 33-38.

57. Lovley, D. R. and E. Phillips, *Reduction of uranium by Desulfovibrio desulfuricans.* Applied and environmental microbiology, 1992. 58(3): p. 850-856.

58. Francis, A. J., et al., *XPS and XANES studies of uranium reduction by Clostridium sp.* Environmental science & technology, 1994. 28(4): p. 636-639.

59. Shelobolina, E. S., et al., *Isolation, characterization,* and *U (VI)-reducing potential of a facultatively anaerobic, acid-resistant Bacterium from Low-pH, nitrate-and U (VI)- contaminated subsurface sediment* and *description of Salmonella subterranea sp. nov.* Applied and Environmental Microbiology, 2004. 70(5): p. 2959-2965.

60. Wu, Q., R. A. Sanford, and F. E. Löffler, *Uranium (VI) reduction by Anaeromyxobacter dehalogenans* strain 2CP-C. Applied and environmental microbiology, 2006. 72(5): p. 3608-3614.

61. Begg, J. D., et al., *Bioreduction behavior of U (VI) sorbed to sediments.* Geomicrobiology Journal, 2011. 28(2): p. 160-171.

62. Istok, J., et al., *In situ bioreduction of technetium and uranium in a nitrate-contaminated aquifer.* Environmental Science & Technology, 2004. 38(2): p. 468-475.

63. Law, G. T., et al., *Uranium redox cycling in sediment and biomineral systems.* Geomicrobiology Journal, 2011. 28(5-6): p. 497-506.

64. Wilkins, M., et al., *The influence of microbial redox cycling on radionuclide mobility in the subsurface at a low-level radioactive waste storage site.* Geobiology, 2007. 5(3): p. 293-301.

65. Williams, K. H., et al., *Acetate availability and its influence on sustainable bioremediation of uranium-contaminated groundwater.* Geomicrobiology Journal, 2011. 28(5-6): p. 519-539.

66. Wu, W.-M., et al., *In situ bioreduction of uranium (VI) to submicromolar levels and reoxidation by dissolved oxygen.* Environmental Science & Technology, 2007. 41(16): p. 5716-5723.

67. Lovley, D. R., et al., *Geobacter metallireducens gen. nov. sp. nov., a microorganism capable of coupling the complete oxidation of organic compounds to the reduction of iron* and *other metals.* Archives of microbiology, 1993. 159(4): p. 336-344.

68. Richter, K., M. Schicklberger, and J. Gescher, *Dissimilatory reduction of extracellular electron acceptors in anaerobic respiration.* Applied and environmental microbiology, 2012. 78(4): p. 913-921.

69. Lovley, D. R., D. E. Holmes, and K. P. Nevin, *Dissimilatory fe (iii) and mn (iv) reduction.* Advances in microbial physiology, 2004. 49: p. 219-286.

70. Marsili, E., et al., *Shewanella secretes flavins that mediate extracellular electron transfer.* Proceedings of the National Academy of Sciences, 2008. 105(10): p. 3968-3973.

71. Suzuki, Y., et al., *Flavin mononucleotide mediated electron pathway for microbial U (VI) reduction.* Physical Chemistry Chemical Physics, 2010. 12(34): p. 10081-10087.

72. Von Canstein, H., et al., *Secretion of flavins by Shewanella species and their role in extracellular electron transfer.* Applied and environmental microbiology, 2008. 74(3): p. 615-623.

73. Anderson, R. T., et al., *Stimulating the in situ activity of Geobacter species to remove uranium from the groundwater of a uranium-contaminated aquifer.* Applied and environmental microbiology, 2003. 69(10): p. 5884-5891.

74. Senko, J. M., et al., *The effect of U (VI) bioreduction kinetics on subsequent reoxidation of biogenic U (IV).* Geochimica et Cosmochimica Acta, 2007. 71(19): p. 4644-4654.

75. Martinez, R. J., et al., *Aerobic uranium (VI) bioprecipitation by metal-resistant bacteria isolated from radionuclide-and metal-contaminated subsurface soils.* Environmental microbiology, 2007. 9(12): p. 3122-3133.

76. Basnakova, G., et al., *The use of Escherichia coli bearing a phoN gene for the removal of uranium and nickel from aqueous flows.* Applied microbiology and biotechnology, 1998. 50(2): p. 266-272.

77. Powers, L. G., et al., *Introduction of a plasmid-encoded phoA gene for constitutive overproduction of alkaline phosphatase in three subsurface Pseudomonas isolates.* FEMS microbiology ecology, 2002. 41(2): p. 115-123.

78. Thomas, R. A. and L. Macaskie, *Biodegradation of tributyl phosphate by naturally occurring microbial isolates and coupling to the removal of uranium from aqueous solution.* Environmental science & technology, 1996. 30(7): p. 2371-2375.

79. Siuda, W. and R. Chróst, *Utilization of selected dissolved organic phosphorus compounds by bacteria in lake water under non-limiting orthophosphate conditions.* Polish Journal of Environmental Studies, 2001. 10(6): p. 475-484.

80. Lim, B. L., et al., *Distribution and diversity of phytate-mineralizing bacteria.* The ISME journal, 2007. 1(4): p. 321.

81. Ko, W.-h. and F. K. Hora, *Production of phospholipases by soil microorganisms.* Soil Science, 1970. 110(5): p. 355-358.

82. Kazy, S. K., S. F. D'Souza, and P. Sar, *Uranium and thorium sequestration by a Pseudomonas sp.: mechanism and chemical characterization.* J Hazard Mater, 2009. 163(1): p. 65-72.

83. Vanengelen, M. R., et al., *UO(2) 2+ speciation determines uranium toxicity and bioaccumulation in an environmental Pseudomonas sp. isolate.* Environ Toxicol Chem, 2010. 29(4): p. 763-9.

84. Choudhary, S. and P. Sar, *Uranium biomineralization by a metal resistant Pseudomonas aeruginosa strain isolated from contaminated mine waste.* J Hazard Mater, 2011. 186(1): p. 336-43.

85. Renninger, N., et al., *Uranyl precipitation by Pseudomonas aeruginosa via controlled polyphosphate metabolism.* Appl Environ Microbiol, 2004. 70(12): p. 7404-12.

86. Zhou, L., et al., *A protein engineered to bind uranyl selectively and with femtomolar affinity.* Nat Chem, 2014. 6(3): p. 236-41.

87. Pardoux, R., et al., *Modulating uranium binding affinity in engineered calmodulin EF-hand peptides: effect of phosphorylation.* PLoS One, 2012. 7(8): p. e41922.

88. Nomellini, J. F., et al., *S-layer-mediated display of the immunoglobulin G-binding domain of streptococcal protein G on the surface of Caulobacter crescentus: development of an immunoactive reagent.* Appl Environ Microbiol, 2007. 73(10): p. 3245-53.

89. Park, D. M., et al., *Bioadsorption of Rare Earth Elements through Cell Surface Display of Lanthanide Binding Tags.* Environ Sci Technol, 2016. 50(5): p. 2735-42.

90. Choppin, G., J. Liljenzin, and J. Rydberg, *Behavior of Radionuclides in the Environment. Radiochemistry and Nuclear Chemistry,* 1995.

91. Hsi, C.-k.D. and D. Langmuir, *Adsorption of uranyl onto ferric oxyhydroxides: application of the surface com-*

152

*plexation site-binding model.* Geochimica et Cosmochimica Acta, 1985. 49(9): p. 1931-1941.

92. Koch-Steindl, H. and G. Pröhl, *Considerations on the behaviour of long-lived radionuclides in the soil.* Radiation and environmental biophysics, 2001. 40(2): p. 93-104.

93. Davis, J. A., et al., *Approaches to surface complexation modeling of uranium (VI) adsorption on aquifer sediments.* Geochimica et Cosmochimica Acta, 2004. 68(18): p. 3621-3641.

94. Pabalan, R. T., et al., *Uranium (VI) sorption onto selected mineral surfaces: Key geochemical parameters.* 1996, American Chemical Society, Washington, DC (United States).

95. Siegel, M. and C. Bryan, *Radioactive Contamination.* Environmental Geochemistry, 2005. 9: p. 205.

96. Bargar, J. R., et al., *Uranium redox transition pathways in acetate-amended sediments. Proceedings of the National Academy of Sciences,* 2013. 110(12): p. 4506-4511.

97. Utturkar, S. M., et al., *Draft genome sequence for Caulobacter sp. strain OR37, a bacterium tolerant to heavy metals.* Genome announcements, 2013. 1(3): p. e00322-13.

98. Garst, A. D., A. L. Edwards, and R. T. Batey, *Riboswitches: structures and mechanisms.* Cold Spring Harb Perspect Biol, 2011. 3(6).

99. Breaker, R. R., *Riboswitches and the RNA world.* Cold Spring Harb Perspect Biol, 2012. 4(2).

100. Hallberg, Z. F., et al., *Engineering and In Vivo Applications of Riboswitches.* Annu Rev Biochem, 2017. 86: p. 515-539.

101. !!!INVALID CITATION !!![101].

102. Baker, J. L., et al., *Widespread genetic switches and toxicity resistance proteins for fluoride.* Science, 2012. 335(6065): p. 233-235.

103. Breaker, R. R., *New insight on the response of bacteria to fluoride.* Caries Res, 2012. 46(1): p. 78-81.

104. Ren, A., K. R. Rajashankar, and D. J. Patel, *Fluoride ion encapsulation by Mg2+ ions and phosphates in a fluoride riboswitch.* Nature, 2012. 486(7401): p. 85-9.

105. Stockbridge, R. B., et al., *Fluoride resistance and transport by riboswitch-controlled CLC antiporters.* Proc Natl Acad Sci USA, 2012. 109(38): p. 15289-94.

106. Zhao, B., et al., *An excited state underlies gene regulation of a transcriptional riboswitch.* Nat Chem Biol, 2017. 13(9): p. 968-974.

107. Park, D. M. and M. J. Taffet, *Combinatorial Sensor Design in Caulobacter crescentus for Selective Environmental Uranium Detection.* ACS Synth Biol, 2019. 8(4): p. 807-817.

108. Weinberg, Z., et al., *Comparative genomics reveals 104 candidate structured RNAs from bacteria, archaea, and their metagenomes.* Genome Biol, 2010. 11(3): p. R31.

109. Finn, R. D., et al., *The Pfam protein families database: towards a more sustainable future.* Nucleic Acids Res, 2016. 44(D1): p. D279-85.

110. Brewster, R. C., et al., *The transcription factor titration effect dictates level of gene expression.* Cell, 2014. 156(6): p. 1312-23.

111. Shin, J. and V. Noireaux, *An E. coli cell-free expression toolbox: application to synthetic gene circuits and artificial cells.* ACS Synth Biol, 2012. 1(1): p. 29-41.

112. Procaccini, A., et al., *Dissecting the specificity of protein-protein interaction in bacterial two-component signaling: orphans and crosstalks.* PLoS one, 2011. 6(5): p. e19729.

113. Folliard, T., et al., *Ribo-attenuators: novel elements for reliable and modular riboswitch engineering*. Sci Rep, 2017. 7(1): p. 4599.

114. Büttner, D. and U. Bonas, *Who comes first?How plant pathogenic bacteria orchestrate type III secretion*. Current opinion in microbiology, 2006. 9(2): p. 193-200.

115. Hutcheson, S. W., et al., *Enhancer-Binding Proteins HrpR and HrpS Interact To Regulate hrp-Encoded Type III Protein Secretion in Pseudomonas syringae* Strains. Journal of Bacteriology, 2001. 183(19): p. 5589-5598.

116. Jin, Q., et al., *Type III protein secretion in Pseudomonas syringae*. Microbes and Infection, 2003. 5(4): p. 301-310.

117. Dove, S. L. and A. Hochschild, *Conversion of the ω subunit of Escherichia coli RNA polymerase into a transcriptional activator or an activation target*. Genes & development, 1998. 12(5): p. 745-754.

118. Blondel, A. and H. Bedouelle, *Engineering the quaternary structure of an exported protein with a leucine zipper*. Protein Eng, 1991. 4(4): p. 457-61.

119. Cheng, P.-C., *The contrast formation in optical microscopy*, in *Handbook of Biological Confocal Microscopy*. 2006, Springer. p. 162-206.

120. Helms, V., *Principles of computational cell biology*. 2008: John Wiley & Sons.

121. Zheng, J., *Spectroscopy-based quantitative fluorescence resonance energy transfer analysis*. Ion channels: methods and protocols, 2006: p. 65-77.

122. Periasamy, A., *Fluorescence resonance energy transfer microscopy: a mini review. Journal of biomedical optics*, 2001. 6(3): p. 287-291.

123. Nguyen, A. W. and P. S. Daugherty, *Evolutionary optimization of fluorescent proteins for intracellular FRET*. Nature biotechnology, 2005. 23(3): p. 355.

124. Buchler, N. E., U. Gerland, and T. Hwa, *On schemes of combinatorial transcription logic. Proceedings of the National Academy of Sciences*, 2003. 100(9): p. 5136-5141.

125. Silva-Rocha, R. and V. de Lorenzo, *Mining logic gates in prokaryotic transcriptional regulation networks*. FEBS letters, 2008. 582(8): p. 1237-1244.

126. Wang, B., et al., *Engineering modular and orthogonal genetic logic gates for robust digital-like synthetic biology*. Nature communications, 2011. 2: p. 508.

127. Park, M., S. L. Tsai, and W. Chen, *Microbial biosensors: engineered microorganisms as the sensing machinery*. Sensors (Basel), 2013. 13(5): p. 5777-95.

128. Yagi, K., *Applications of whole-cell bacterial sensors in biotechnology and environmental science*. Appl Microbiol Biotechnol, 2007. 73(6): p. 1251-8.

129. Dai, C. and S. Choi, *Technology and Applications of Microbial Biosensor*. Open Journal of Applied Biosensor, 2013. 2(3).

130. Bereza-Malcolm, L. T., G. Mann, and A. E. Franks, *Environmental Sensing of Heavy Metals Through Whole Cell Microbial Biosensors: A Synthetic Biology Approach*. ACS Synth Biol, 2014.

131. Hwang, I. Y., et al., *Engineered probiotic Escherichia coli can eliminate and prevent Pseudomonas aeruginosa gut infection in animal models*. Nature Communications, 2017. 8: p. 15028.

132. King, J. M., et al., *Rapid, sensitive bioluminescent reporter technology for naphthalene exposure and biodegradation*. Science, 1990. 249(4970): p. 778-81.

133. Belkin, S., et al., *Remote detection of buried landmines using a bacterial sensor*. Nat Biotechnol, 2017. 35(4): p. 308-310.

134. Kabessa, Y., et al., *Standoff detection of explosives and buried landmines using fluorescent bacterial sensor cells*. Biosensors and Bioelectronics, 2016. 79: p. 784-788.

135. Wang, B., M. Barahona, and M. Buck, *Engineering modular and tunable genetic amplifiers for scaling transcriptional signals in cascaded gene networks*. Nucleic Acids Res, 2014. 42(14): p. 9484-92.

136. Berset, Y., et al., *Mechanistic Modeling of Genetic Circuits for ArsR Arsenic Regulation. ACS Synth Biol*, 2017. 6(5): p. 862-874.

137. Buffi, N., et al., *An automated microreactor for semi-continuous biosensor measurements*. Lab Chip, 2016. 16(8): p. 1383-92.

138. Truffer, F., et al., *Compact portable biosensor for arsenic detection in aqueous samples with Escherichia coli bioreporter cells*. Rev Sci Instrum, 2014. 85(1): p. 015120.

139. Sambrook, J., E. Fritsch, and T. Maniatis, *Molecular cloning: a laboratory manual, 2nd edn*. Cold Spring Laboratory Press. New York, 1989.

140. Innis, M. A., D. H. Gelfand, and J. J. Sninsky, *PCR strategies*. 1995: Academic Press.

141. Myers, E. W. and W. Miller, *Optimal alignments in linear space*. Computer applications in the biosciences: CABIOS, 1988. 4(1): p. 11-17.

142. Smith, T. F. and M. S. Waterman, *Comparison of biosequences*. Advances in applied mathematics, 1981. 2(4): p. 482-489.

143. Needleman, S. B. and C. D. Wunsch, *A general method applicable to the search for similarities in the amino acid sequence of two proteins*. Journal of molecular biology, 1970. 48(3): p. 443-453.

144. Pearson, W. R. and D. J. Lipman, *Improved tools for biological sequence comparison. Proceedings of the National Academy of Sciences*, 1988. 85(8): p. 2444-2448.

145. Karlin, S. and S. F. Altschul, *Methods for assessing the statistical significance of molecular sequence features by using general scoring schemes*. Proceedings of the National Academy of Sciences, 1990. 87(6): p. 2264-2268.

146. Karlin, S. and S. F. Altschul, *Applications and statistics for multiple high-scoring segments in molecular sequences*. Proceedings of the National Academy of Sciences, 1993. 90(12): p. 5873-5877.

147. Stephens, C., et al., *A cell cycle-regulated bacterial DNA methyltransferase is essential for viability*. Proceedings of the National Academy of Sciences, 1996. 93(3): p. 1210-1214.

148. Hierlemann, A. and H. Baltes, *CMOS-based chemical microsensors*. Analyst, 2003. 128(1): p. 15-28.

149. Evinger, M. and N. Agabian, *Envelope-associated nucleoid from Caulobacter crescentus stalked and swarmer cells*. J Bacteriol, 1977. 132(1): p. 294-301.

150. Arellano, B. H., et al., *Identification of a dehydrogenase required for lactose metabolism in Caulobacter crescentus*. Appl Environ Microbiol, 2010. 76(9): p. 3004-14.

151. Skerker, J. M., et al., *Two-component signal transduction pathways regulating growth and cell cycle progression in a bacterium: a system-level analysis*. PLoS Biol, 2005. 3(10): p. e334.

152. Christen, B., et al., *High-throughput identification of protein localization dependency networks*. Proc Natl Acad Sci USA, 2010. 107(10): p. 4681-6.

153. Park, D. M., et al., *Identification of a U/Zn/Cu responsive global regulatory two-component system in Caulobacter crescentus*. Mol Microbiol, 2016.

154. Stephens, C., et al., *A cell cycle-regulated bacterial DNA methyltransferase is essential for viability*. Proc Natl Acad Sci USA, 1996. 93(3): p. 1210-4.

155. Fiebig, A., et al., *Interaction specificity, toxicity and regulation of a paralogous set of ParE/RelE-family toxin-antitoxin systems*. Mol Microbiol, 2010. 77(1): p. 236-51.

156. Goodrich, R., Lorega, G., *LLNL Livermore Site and Site 300 Environmental Restoration Project Standard Operating Procedures (SOPs)*. Lawrence Livermore National Laboratory Livermore, Calif, 2016. (UCRL-MA-109115 Rev. 15).

157. Arellano, B. H., et al., *Identification of a dehydrogenase required for lactose metabolism in Caulobacter crescentus*. Applied and environmental microbiology, 2010. 76(9): p. 3004-3014.

158. Fiebig, A., et al., *Interaction specificity, toxicity and regulation of a paralogous set of ParE/RelE-family toxin-antitoxin systems*. Molecular microbiology, 2010. 77(1): p. 236-251.

159. Andersen, J. B., et al., *New unstable variants of green fluorescent protein for studies of transient gene expression in bacteria*. Appl Environ Microbiol, 1998. 64(6): p. 2240-6.

160. Hu, P., et al., *Whole-genome transcriptional analysis of heavy metal stresses in Caulobacter crescentus*. J Bacteriol, 2005. 187(24): p. 8437-49.

161. Park, D. M. and Y. Jiao, *Modulation of medium pH by Caulobacter crescentus facilitates recovery from uranium-induced growth arrest*. Appl Environ Microbiol, 2014. 80(18): p. 5680-8.

162. Yung, M. C., et al., *Shotgun proteomic analysis unveils survival and detoxification strategies by Caulobacter crescentus during exposure to uranium, chromium, and cadmium*. J Proteome Res, 2014. 13(4): p. 1833-47.

163. Hillson, N. J., et al., *Caulobacter crescentus as a whole-cell uranium biosensor*. Appl Environ Microbiol, 2007. 73(23): p. 7615-21.

164. Cabantous, S., et al., *A new protein-protein interaction sensor based on tripartite split-GFP association*. Sci Rep, 2013. 3: p. 2854.

165. Britos, L., et al., *Regulatory response to carbon starvation in Caulobacter crescentus*. PLoS One, 2011. 6(4): p. e18179.

166. Jonas, K., et al., *Proteotoxic stress induces a cell-cycle arrest by stimulating Lon to degrade the replication initiator DnaA*. Cell, 2013. 154(3): p. 623-36.

167. Modell, J. W., A. C. Hopkins, and M. T. Laub, *A DNA damage checkpoint in Caulobacter crescentus inhibits cell division through a direct interaction with FtsW*. Genes Dev, 2011. 25(12): p. 1328-43.

168. da Silva Neto, J. F., R. F. Lourenco, and M. V. Marques, *Global transcriptional response of Caulobacter crescentus to iron availability*. BMC Genomics, 2013. 14: p. 549.

169. Blanco, A. G., et al., *Tandem DNA Recognition by PhoB, a Two-Component Signal Transduction Transcriptional Activator*. Structure, 2002. 10(5): p. 701-713.

170. Park, D. M. and P. J. Kiley, *The influence of repressor DNA binding site architecture on transcriptional control*. MBio, 2014. 5(5): p. e01684-14.

171. Nriagu, J. O., *Lead orthophosphates. I. Solubility and hydrolysis of secondary lead orthophosphate*. Inorganic Chemistry, 1972. 11(10): p. 2499-2503.

172. Tri pet, B., et al., *Engineering a de novo designed coiled-coil heterodimerization domain for the rapid detection, purification and characterization of recombinantly expressed peptides and proteins*. Protein Eng, 1997. 10(3): p. 299.

173. Yung, M. C. and Y. Jiao, *Biomineralization of uranium by PhoY phosphatase activity aids cell survival in Caulobacter crescentus*. Appl Environ Microbiol, 2014. 80(16): p. 4795-804.

174. Roggo, C. and J. R. van der Meer, *Miniaturized and integrated whole cell living bacterial sensors infield applicable autonomous devices*. Curr Opin Biotechnol, 2017. 45: p. 24-33.

175. Park, D. M., et al., *Identification of a U/Zn/Cu responsive global regulatory two-component system in Caulobacter crescentus*. Mol Microbiol, 2017. 104(1): p. 46-64.

176. Weinstein, L. H. and A. Davison, *Fluorides in the Environment: Effect on Plants and Animals*. 2004.

177. Stockbridge, R. B., et al., *A family of fluoride-specific ion channels with dual-topology architecture*. Elife, 2013. 2: p. e01084.

178. Malakooti, J., S. P. Wang, and B. Ely, *A consensus promoter sequence for Caulobacter crescentus genes involved in biosynthetic and housekeeping functions*. J Bacteriol, 1995. 177(15): p. 4372-6.

SEQUENCE LISTING

The patent contains a lengthy sequence listing. A copy of the sequence listing is available in electronic form from the USPTO web site (https://seqdata.uspto.gov/docdetail?docId=US12571058B2). An electronic copy of the sequence listing will also be available from the USPTO upon request and payment of the fee set forth in 37 CFR 1.19(b)(3).

The invention claimed is:

1. A $UO_2F_2$-biosensor comprising a genetically engineered bacterial cell capable of heterologously and/or natively expressing histidine kinase 1363, and U-sensitive transcriptional regulator 1362; the cell further capable of natively and/or heterologously expressing histidine kinase UzcS, and response regulator UzcS, wherein the bacterial cell is an engineered bacterial cell including a U-sensing genetic reportable molecular component and/or a U-sensing/U-neutralizing genetic molecular component, each comprising a U-sensitive promoter in a configuration wherein the U-sensitive promoter initiates expression of the U-sensing reportable molecular component and/or of the U-sensing U-neutralizing molecular component in presence of bioavailable U;

wherein the U-sensitive promoter of at least one U-sensing genetic reportable molecular component and/or a U-sensing/U-neutralizing genetic molecular component comprises a U-sensitive transcriptional 1362 binding site having a DNA sequence $$N_1N_2N_3N_4N_5N_6N_7N_8N_9N_{10}N_{11}N_{12}N_{13}N_{14}N_{15}N_{16}N_{17}N_{18},$$ (SEQ ID NO: 1)

in which $N_1$ is C or T; $N_2$ is G or A; $N_3$ is T or C; $N_4$ is C; $N_5$ is A or G; $N_6$ is G or C; $N_7$ is C or G; $N_8$ is any nucleotide; $N_9$ is any nucleotide; $N_{10}$ is any nucleotide; $N_{11}$ is any nucleotide; $N_{12}$ is T or C; $N_{13}$ is G; $N_{14}$ is T or C; $N_{15}$ is C; $N_{16}$ is A or C; $N_{17}$ is G; and $N_{18}$ is C or G, and in which $N_1$ to $N_{17}$ selected independently wherein the U-sensitive promoter of at least one U-sensing genetic reportable molecular component and/or a U-sensing/U-neutralizing genetic molecular component comprises a U-sensitive transcriptional UzcR binding site having a DNA sequence:

$$CATTACN_7N_8N_9N_{10}N_{11}N_{12}TTAA$$ (SEQ ID NO: 2)

wherein $N_7$-$N_{12}$ is independently any nucleotide, the UzcR binding site inserted at a location downstream of a transcription start site of the U sensitive promoter and wherein the genetically modified bacterial cell is an engineered bacterial cell further comprising an F-sensing riboswitch within at least one of the U-sensing reportable genetic molecular component in a configuration wherein the U-sensing reportable genetic molecular component, is transcribed in presence of an effective amount of bioavailable fluoride, an F-sensing reportable genetic molecular component in a configuration wherein the F-sensing reportable genetic molecular component is transcribed in presence of an effective amount of bioavailable fluoride, and an F sensitive genetic circuit in which at least one molecular component is a reportable molecular component (and in particular one or more reportable genetic molecular component and/or one or more reportable cellular molecular component), the reportable molecular component expressed when the genetic circuit operates according to the circuit design in presence of bioavailable F.

2. The $UO_2F_2$ biosensor of claim 1, further comprising a UzcY gene and/or UzcZ gene inserted at a location downstream of a transcription start site of the UzcR U-sensitive promoter.

3. The $UO_2F_2$ biosensor of claim 1, wherein the bacteria are capable of natively expressing endogenous MarR family repressors and at least one gene of the endogenous MarR family, is knocked out.

4. The $UO_2F_2$ biosensor of claim 1, wherein the bacteria are capable of natively expressing endogenous urtAP genes and at least one gene of the endogenous urtAP is knocked out.

5. A $UO_2F_2$ biosensor of claim 1, wherein the F-sensing riboswitch comprises a crcB motif or an $eric^F$ motif.

6. A $UO_2F_2$ biosensor of claim 1, wherein the F-sensing riboswitch comprises a F-sensing riboswitch having sequence SEQ ID NO: 2509.

7. A $UO_2F_2$ biosensor of claim 1, wherein the F-sensing riboswitch comprises a F-sensing riboswitch having sequence SEQ ID NO: 2510 or SEQ ID NO: 2512.

8. A $UO_2F_2$ biosensor of claim 1, wherein the F-sensing riboswitch comprises a F-sensing riboswitch having sequence SEQ ID NO: 2511 or SEQ ID NO: 2513.

9. A $UO_2F_2$ biosensor of claim 1, wherein the F-sensing riboswitch comprises a F-sensing riboswitch having any one of SEQ ID NO: 205 to SEQ ID NO: 1988 and from SEQ ID NO: 1999 to SEQ ID NO: 2231.

10. The $UO_2F_2$ biosensor of claim 1, wherein the F-sensing riboswitch comprises a F-sensing riboswitch Sphingomonas sp. MM-1, having sequence SEQ ID NO: 2514 or an F-sensing riboswitch from Sphingomonas sp, 67-36 having sequence SEQ ID NO: 2525 or the F-sensing riboswitch is the F-sensing riboswitch from Pseudomonas Syringae having sequence SEQ ID NO: 2526.

11. A $UO_2F_2$ biosensor of claim 1, wherein the bacterial cell comprises an endogenous F-sensing riboswitch and the endogenous F-sensing riboswitch is knocked out.

12. The $UO_2F_2$ biosensor of claim 1, wherein in the sequence SEQ ID NO:1:

$N_1$ is C; $N_2$ is G; $N_3$ is T; $N_5$ is A; $N_6$ is G; $N_{14}$ is T; and/or $N_{16}$ is A.

13. The $UO_2F_2$ biosensor of claim 1, wherein the U-sensitive transcriptional 1362 binding site has a sequence selected from the group consisting of SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26 and SEQ ID NO:27.

14. The $UO_2F_2$ biosensor of claim 1, wherein the U-sensitive promoter comprising the U-sensitive transcriptional 1362 binding site further comprises nucleotides $N_{19}N_{20}N_{21}$, downstream of SEQ ID NO: 1 wherein $N_{19}$ is any nucleotide; $N_{20}$ is any nucleotide; and $N_{21}$ is G (SEQ ID NO: 83).

15. The $UO_2F_2$ biosensor of claim 14, wherein $N_{18}$ of the regulator direct repeat is located about −17 to about −40 upstream of a transcription start site.

16. The $UO_2F_2$ biosensor of claim 1, wherein the U-sensitive promoter is $P_{1361}$ or $P_{phyt}$.

17. The $UO_2F_2$ biosensor of claim 1, wherein the F-sensing reportable genetic molecular component the U-sensing genetic reportable molecular component and/or the U-sensing/U-neutralizing genetic molecular component, are operatively connected to a same or a different reportable molecular component in U-sensing genetic circuit.

18. The $UO_2F_2$ biosensor of claim 17, wherein the U-sensitive genetic circuit comprises one or more AND gates.

19. The $UO_2F_2$ biosensor of claim 18, wherein at least one of the AND gates is an in-series AND gate.

20. The $UO_2F_2$ biosensor of claim 18, wherein at least one of the AND gates is an in-parallel AND gate.

21. The $UO_2F_2$ biosensor of claim 18, wherein two or more in series AND gates and/or in parallel AND gates are connected by activating, inhibiting, binding, or converting reactions.

22. The $UO_2F_2$ biosensor of claim 18, wherein at least one of the AND gates is selected from the group consisting of an HRP AND gate, a bacterial two-hybrid AND gate, a tripartite GFP AND gate, and a FRET sensor AND gate.

23. The $UO_2F_2$ biosensor of claim 1, wherein the $UO_2F_2$ biosensor is configured to detect and/or neutralize bioavailable U present in a target environment at a concentration of 100 nM or greater, between 100 nM and 1 µM, or greater than 1 µM.

24. The method of claim 1, wherein the $UO_2F_2$ biosensor is configured to detect bioavailable F present in a target environment at a concentration 10 µM, or greater, between 50 µM and 60 µM, greater than 1 nanomolar and between 100 nanomolar and 1 mM.

25. The $UO_2F_2$ biosensor of claim 1, wherein the reportable molecular component is capable of being detected using fluorescence, luminescence, chemiluminescence, colorimetric analysis, radioactivity, or electrical.

26. The $UO_2F_2$ biosensor of claim 1, wherein the U-neutralizing molecular component is configured to decrease or eliminate toxicity of U by bioreduction, biomineralization, bioaccumulation, and/or biosorption.

27. The $UO_2F_2$ biosensor of claim 1, wherein the bacterial cell is a proteobacterial cell.

28. The $UO_2F_2$ biosensor of claim 27, wherein the proteobacterial cell is an alphaproteobacteria, a betaproteobacteria, or a gammaproteobacteria.

29. The $UO_2F_2$ biosensor of claim 27, wherein the proteobacterial cell is a Caulobacteridae cell.

30. The $UO_2F_2$ biosensor of claim 27, wherein the proteobacterial cell is a *Caulobacter crescentus* cell.

31. The $UO_2F_2$ biosensor of claim 30 wherein the *Caulobacter crescentus* cell is a member of a strain selected from the group consisting of NA1000, CB15, and OR37.

32. A $UO_2F_2$-sensing system comprising:
one or more of the $UO_2F_2$— biosensors of claim 1 operatively connected to an electronic signal transducer adapted to convert a $UO_2F_2$— biosensor reportable molecular component output into an electronic output.

33. A method of detecting and reporting and/or neutralizing bioavailable U comprising:
contacting one or more of the $UO_2F_2$ biosensors of claim 1, with a target environment comprising one or more target ranges of U concentration, the contacting performed for a time and under conditions to detect and report and/or neutralize bioavailable U in the target environment.

34. A $UO_2F_2$-sensing genetic reportable component comprising:
one or more U sensitive promoters comprising
a U-sensitive transcriptional 1362 binding site having a DNA sequence (SEQ ID NO: 1)

$N_1N_2N_3N_4N_5N_6N_7N_8N_9N_{10}N_{11}N_{12}N_{13}N_{14}N_{15}N_{16}N_{17}N_{18}$, in which
$N_1$ is C or T;
$N_2$ is G or A;
$N_3$ is T or C;
$N_4$ is C;
$N_5$ is A or G;
$N_6$ is G or C;
$N_7$ is C or G;
$N_8$ is any nucleotide;

$N_9$ is any nucleotide;
$N_{10}$ is any nucleotide;
$N_{11}$ is any nucleotide;
$N_{12}$ is T or C;
$N_{13}$ is G;
$N_{14}$ is T or C;
$N_{15}$ is C;
$N_{16}$ is A or C;
$N_{17}$ is G; and
$N_{13}$ is C or G,
and in which $N_1$ to $N_{17}$ selected independently
the one or more U sensitive promoters further comprising
a U sensitive transcriptional UzcR binding site, having a DNA sequence:

(SEQ ID NO: 2)

$CATTACN_7N_8N_9N_{10}N_{11}N_{12}TTAA$ wherein $N_7$-$N_{12}$ is independently any nucleotide together with
a U-sensing reportable molecular component,
wherein at least one of the one or more U-sensitive promoters and the U-sensing reportable molecular component, comprises an F-sensing riboswitch in a single output configuration wherein the U-sensing reportable genetic molecular component, is transcribed in presence of an effective amount of bioavailable fluoride,
and wherein the one or more U sensitive promoters and the U-sensing reportable molecular component are in a configuration wherein the one or more U sensitive promoters directly initiate expression of the U-sensing reportable molecular component in presence of bioavailable U and bioavailable Fluoride.

35. A $UO_2F_2$-sensing genetic reportable component of claim 34 wherein the one or more U-sensitive promoters and the U-sensing reportable molecular component are configured to provide a $UO_2F_2$-sensing gene cassette, a $UO_2F_2$-sensing gene cassette being an expression cassette.

36. A $UO_2F_2$-sensing genetic reportable component of claim 35, wherein the $UO_2F_2$-sensing gene cassette is comprised within a vector.

37. The $UO_2F_2$ biosensor of claim 1, wherein the U-sensitive 1362 binding site and the UzcR binding site, are on a same U-sensing genetic reportable molecular component and/or U-sensing/U-neutralizing genetic molecular component.

38. The $UO_2F_2$ biosensor of claim 3, wherein all genes of the endogenous MarR family, are knocked out.

39. The $UO_2F_2$ biosensor of claim 4, wherein all genes of the endogenous urtAP are knocked out.

40. The $UO_2F_2$ biosensor of claim 1, wherein the bacterial cell natively expresses a fluoride efflux pump and the gene encoding the native efflux pump is deleted.

41. The $UO_2F_2$ biosensor of claim 40, wherein the fluoride efflux pump is crcB.

42. The $UO_2F_2$ biosensor of claim 41, wherein the fluoride efflux pump is ericF.

43. The $UO_2F_2$ biosensor of claim 27, wherein the bacterial cell natively expresses a fluoride efflux pump and the gene encoding the native efflux pump is deleted.

* * * * *